United States Patent
Schurpf et al.

(10) Patent No.: US 12,173,059 B2
(45) Date of Patent: Dec. 24, 2024

(54) LTBP COMPLEX-SPECIFIC INHIBITORS OF TGFβ AND USES THEREOF

(71) Applicant: Scholar Rock, Inc., Cambridge, MA (US)

(72) Inventors: Thomas Schurpf, Cambridge, MA (US); Justin W. Jackson, Cambridge, MA (US); George Coricor, Cambridge, MA (US); Abhishek Datta, Boston, MA (US); Stefan Wawersik, Westborough, MA (US); Christopher Littlefield, Marblehead, MA (US); Adam Fogel, Watertown, MA (US); Caitlin Stein, Lebanon, NH (US); Julia McCreary, Lebanon, NH (US); Matthew Salotto, Lebanon, NH (US); Frederick Streich, Jr., Newton, MA (US)

(73) Assignee: Scholar Rock, Inc., Cambridge, MA (US)

( * ) Notice: Subject to any disclaimer, the term of this patent is extended or adjusted under 35 U.S.C. 154(b) by 393 days.

(21) Appl. No.: 17/746,325

(22) Filed: May 17, 2022

(65) Prior Publication Data
US 2022/0363741 A1    Nov. 17, 2022

Related U.S. Application Data

(63) Continuation of application No. 17/530,786, filed on Nov. 19, 2021, now Pat. No. 11,365,245, which is a continuation of application No. 16/997,438, filed on Aug. 19, 2020, now Pat. No. 11,214,614, which is a continuation of application No. PCT/US2020/015915, filed on Jan. 30, 2020.

(60) Provisional application No. 62/798,927, filed on Jan. 30, 2019.

(51) Int. Cl.
| | |
|---|---|
| A61K 39/00 | (2006.01) |
| A61P 1/16 | (2006.01) |
| A61P 13/12 | (2006.01) |
| C07K 16/22 | (2006.01) |
| C07K 16/28 | (2006.01) |

(52) U.S. Cl.
CPC ............ *C07K 16/22* (2013.01); *A61P 1/16* (2018.01); *A61P 13/12* (2018.01); *C07K 16/2863* (2013.01); *A61K 2039/505* (2013.01); *C07K 2317/32* (2013.01); *C07K 2317/56* (2013.01); *C07K 2317/565* (2013.01); *C07K 2317/76* (2013.01); *C07K 2317/92* (2013.01); *C07K 2317/94* (2013.01)

(58) Field of Classification Search
CPC .................................................. A61K 39/395
See application file for complete search history.

(56) References Cited

U.S. PATENT DOCUMENTS

| | | |
|---|---|---|
| 11,214,614 B2 | 1/2022 | Schurpf et al. |
| 11,365,245 B2 | 6/2022 | Schurpf et al. |
| 2011/0165063 A1 | 7/2011 | Hsieh et al. |
| 2015/0337034 A1 | 11/2015 | Schurpf et al. |
| 2020/0231682 A1 | 7/2020 | Schurpf et al. |

FOREIGN PATENT DOCUMENTS

| | | |
|---|---|---|
| CN | 108350067 A | 7/2018 |
| CN | 108424451 A | 8/2018 |
| CN | 109071646 A | 12/2018 |
| WO | 2011/102483 A1 | 8/2011 |
| WO | 2014/074532 A2 | 5/2014 |
| WO | 2014/182676 A2 | 11/2014 |
| WO | 2017/156500 A8 | 9/2017 |
| WO | 2018/043734 A1 | 3/2018 |
| WO | 2018/129329 A1 | 7/2018 |
| WO | 2019/023661 A1 | 1/2019 |

OTHER PUBLICATIONS

Bostrom et al., Improving antibody binding affinity and specificity for therapeutic development. Methods Mol Biol. 2009;525:353-76, xiii.
Gonzales et al., Minimizing the immunogenicity of antibodies for clinical application. Tumour Biol. Jan.-Feb. 2005;26(1):31-43.
Kunik et al., Structural consensus among antibodies defines the antigen binding site. PLoS Comput Biol. 2012;8(2):e1002388, 12 pages.
Wark et al., Latest technologies for the enhancement of antibody affinity. Adv Drug Deliv Rev. Aug. 7, 2006;58(5-6):657-70.
U.S. Appl. No. 16/997,438, filed Aug. 19, 2020, U.S. Pat. No. 11,214,614, Issued.
U.S. Appl. No. 17/530,786, filed Nov. 19, 2021, U.S. Pat. No. 11,365,245, Issued.
Maccallum et al., Antibody-antigen interactions: contact analysis and binding site topography. J Mol Biol. Oct. 11, 1996;262(5):732-45.
Rudikoff et al., Single amino acid substitution altering antigen-binding specificity. Proc Natl Acad Sci U S A. Mar. 1982;79(6):1979-83.
Sela-Culang et al., The structural basis of antibody-antigen recognition. Front Immunol. Oct. 8, 2013;4:302.
Vajdos et al., Comprehensive functional maps of the antigen-binding site of an anti-ErbB2 antibody obtained with shotgun scanning mutagenesis. J Mol Biol. Jul. 5, 2002;320(2):415-28.

(Continued)

*Primary Examiner* — Prema M Mertz
(74) *Attorney, Agent, or Firm* — McCarter & English, LLP; Marcie B. Clarke

(57) ABSTRACT

Disclosed herein are inhibitors, such as antibodies, and antigen-binding portions thereof, that selectively bind complexes of LTBP1-TGFβ and/or LTBP3-TGFβ. The application also provides methods of use of these inhibitors for, for example, inhibiting TGFβ activation, and treating subjects suffering from TGFβ-related disorders, such as fibrotic conditions. Methods of selecting a context-dependent or context-independent isoform-specific TGFβ inhibitor for a subject in need thereof are also provided.

20 Claims, 29 Drawing Sheets

Specification includes a Sequence Listing.

(56) References Cited

OTHER PUBLICATIONS

Wu et al., Humanization of a murine monoclonal antibody by simultaneous optimization of framework and CDR residues. J Mol Biol. Nov. 19, 1999;294(1):151-62.
Invitation to Pay Additional Fees for Application No. PCT/US2020/015915, dated Jun. 3, 2020, 14 pages.
International Search Report and Written Opinion or Application No. PCT/US2020/015915, dated Sep. 18, 2020, 19 pages.

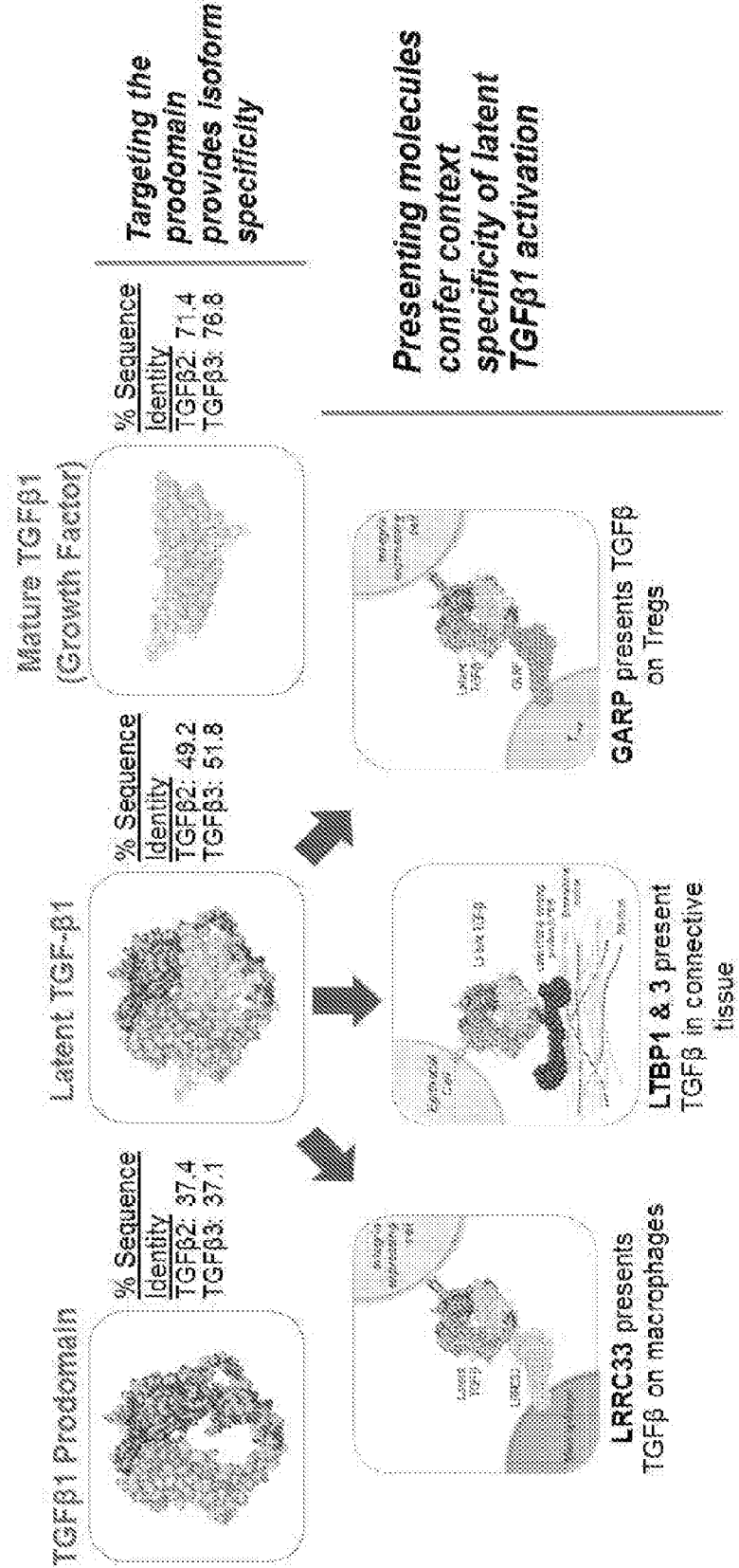
FIG. 1: Targeting the latent form of TGFβ1 provides isoform and context specificity

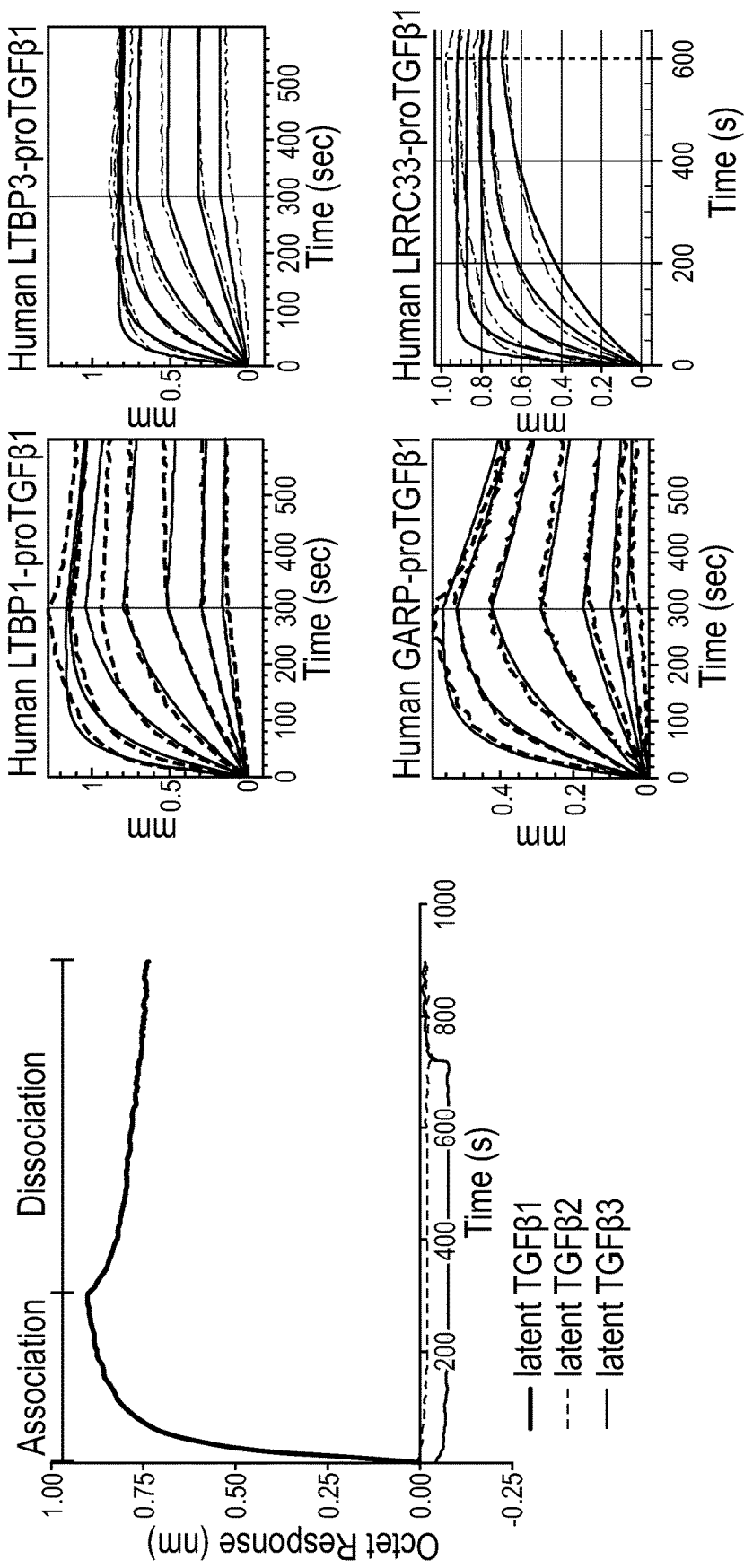
FIG. 2A: In Vitro Binding Profile of a Context-Independent Antibody (SR-AB1) Against proTGFβ1

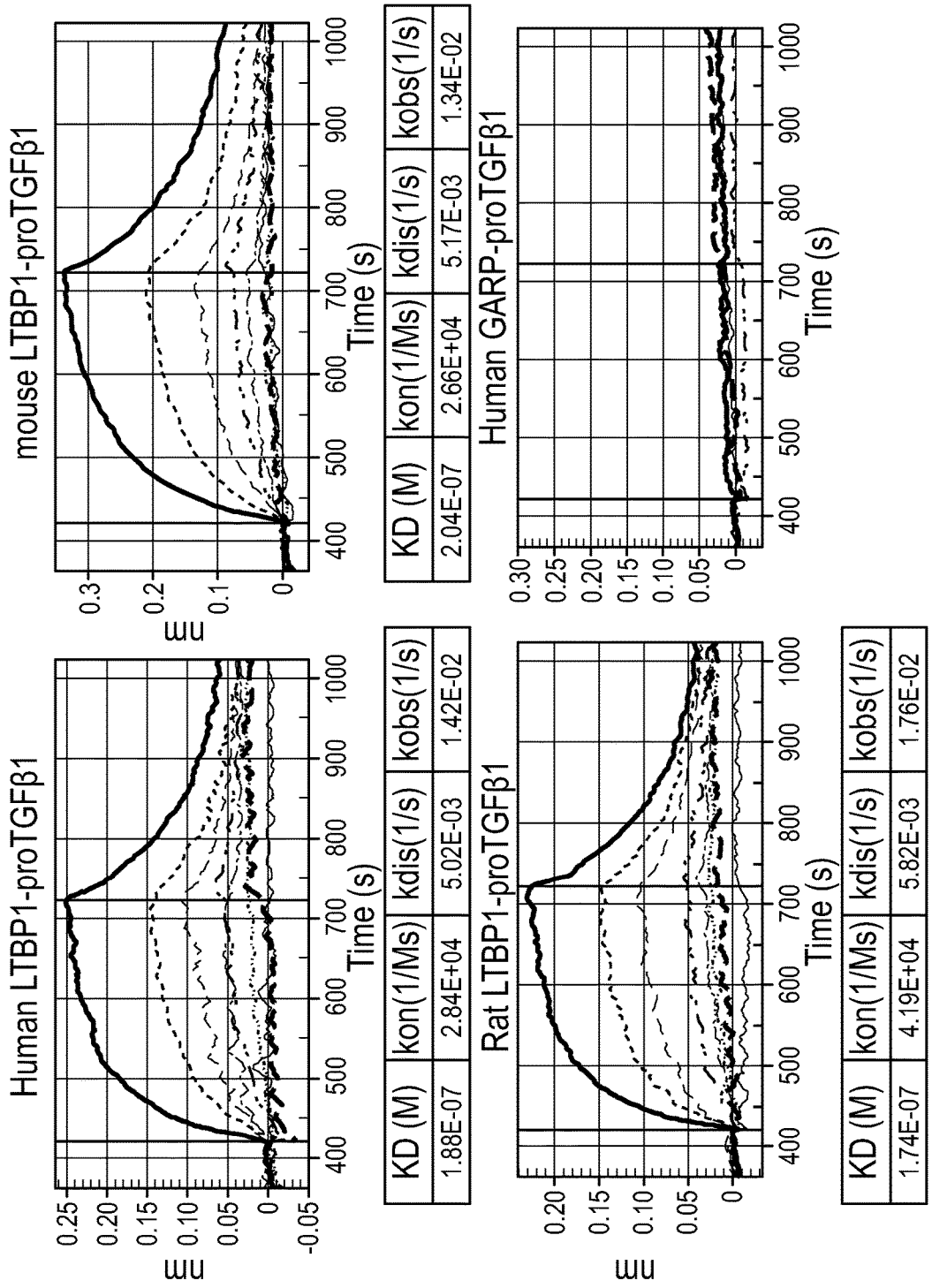
FIG. 2B: In Vitro Binding Profile of a Context-Selective Antibody (SR-AB2) Against LTBP1-proTGFβ1

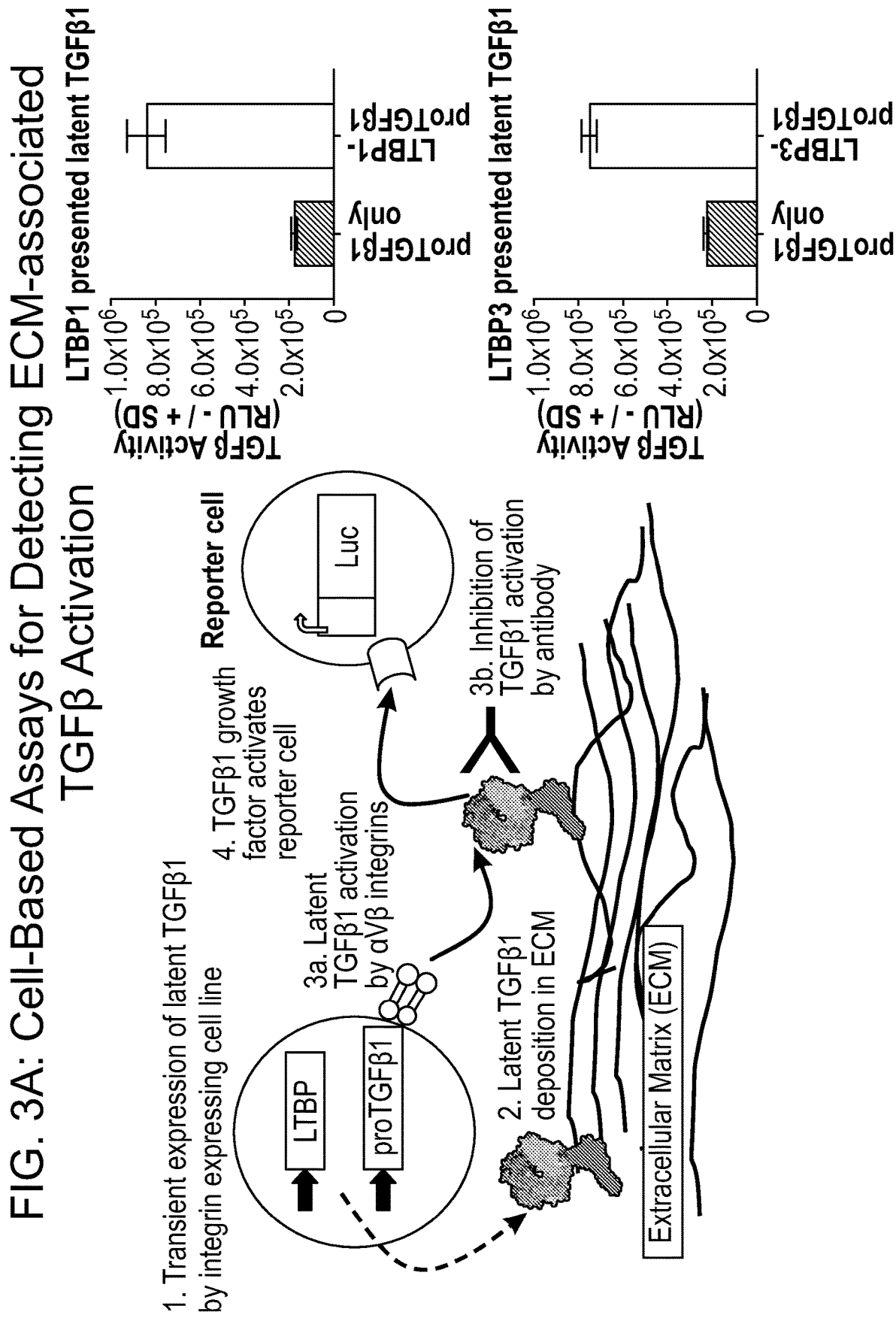
FIG. 3A: Cell-Based Assays for Detecting ECM-associated TGFβ Activation

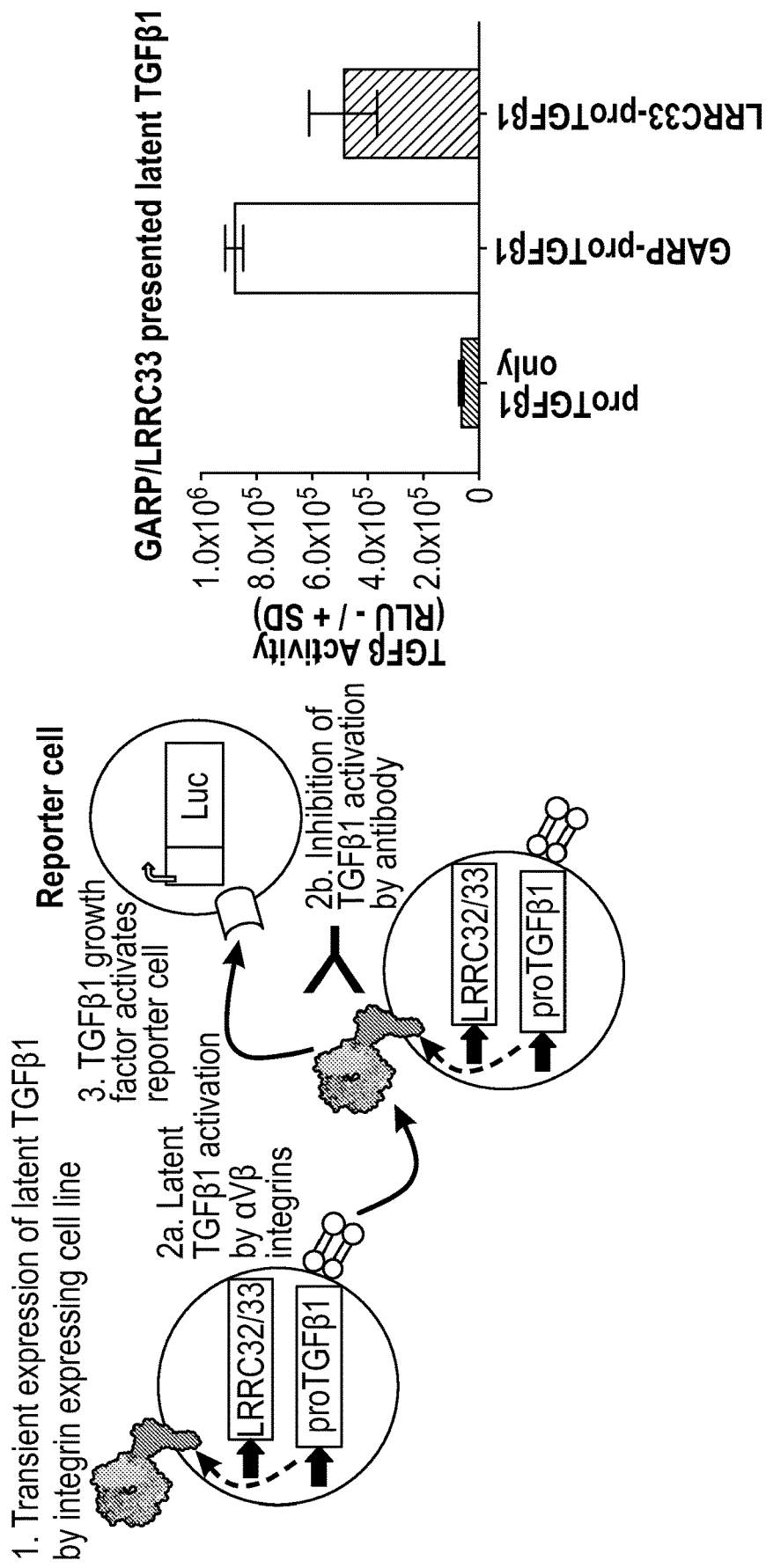
FIG. 3B: Cell-based Assays for Detecting Cell Surface TGFβ Activation

Optimization of Cell-Based Potency Assays

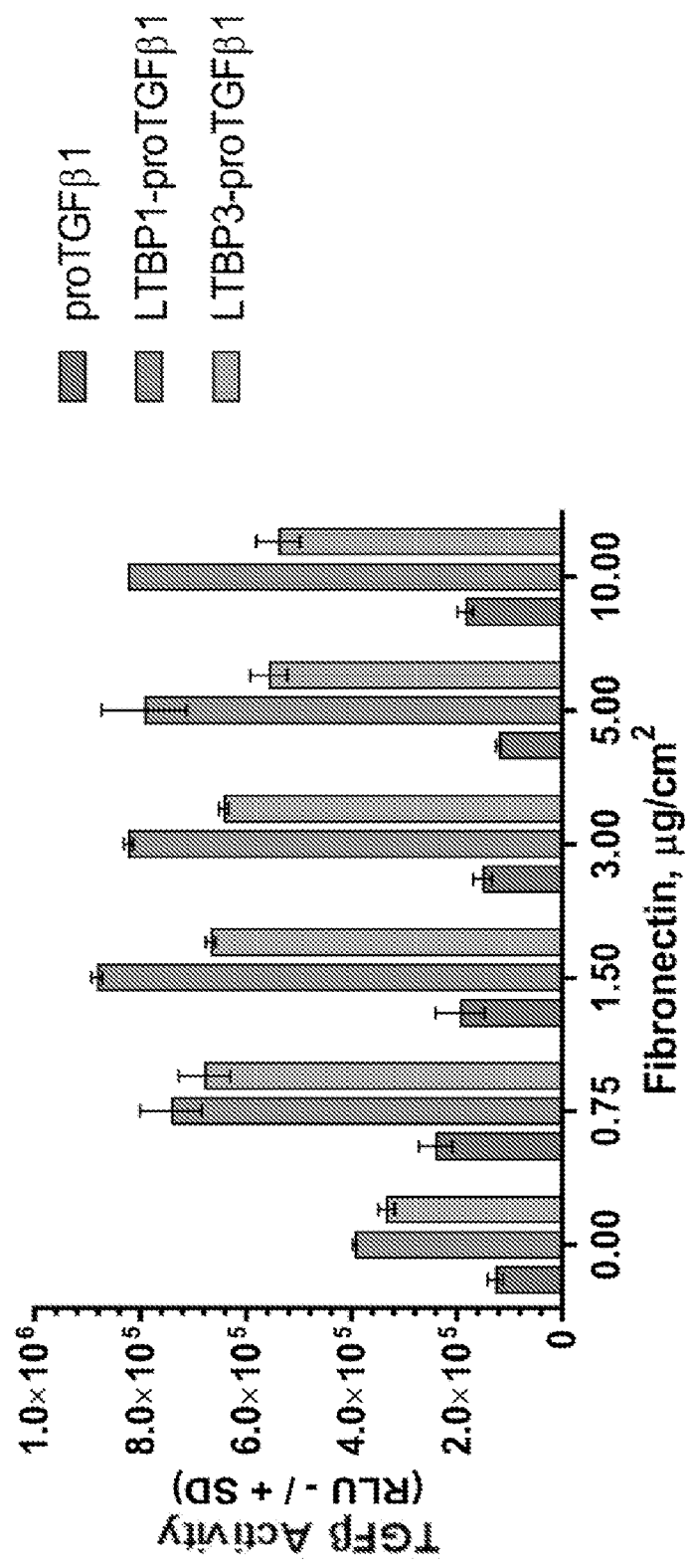
FIG. 5: Fibronectin promotes integrin activation of LTBP-presented latent TGFβ1

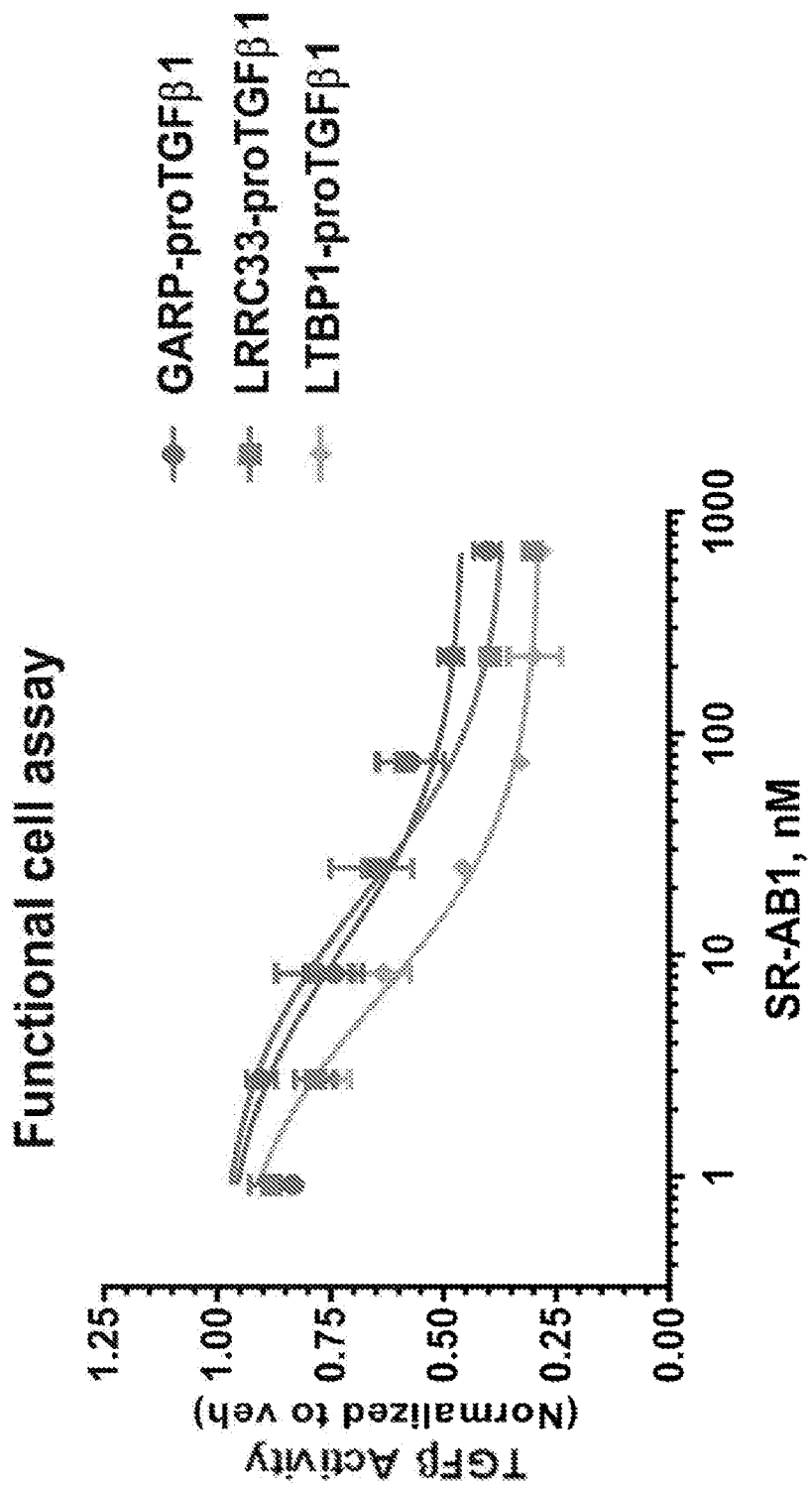
FIG. 6: SR-AB1 Inhibits Integrin-Mediated Activation of Matrix-Associated and Cell-Associated TGFβ1

FIG. 8: SR-AB2 Variable Region Sequence

VH:

CDRH1 CDRH2 CDRH3

QVQLVQSGAEVKKPGASVKVSCKASGYTFTSYGISWVRQAPGQGLEWMGWISAYNGNTNYAQKLQGRVTMTTDTSTSTAYMELRSLRSDDTAVYYCARAPLGNFDSWGQGTMVTVSS

VLambda:

CDRL1 CDRL2 CDRL3

NFMLTQPHSVSESPGKTVTISCTRSSGSIASNYVQWYQQRPGSSPTTVIYEDNQRPSGVPDRFSGSIDSSSNSASLTISGLKTEDEADYYCQSYDSSNHPVVFGGGTKLTVL

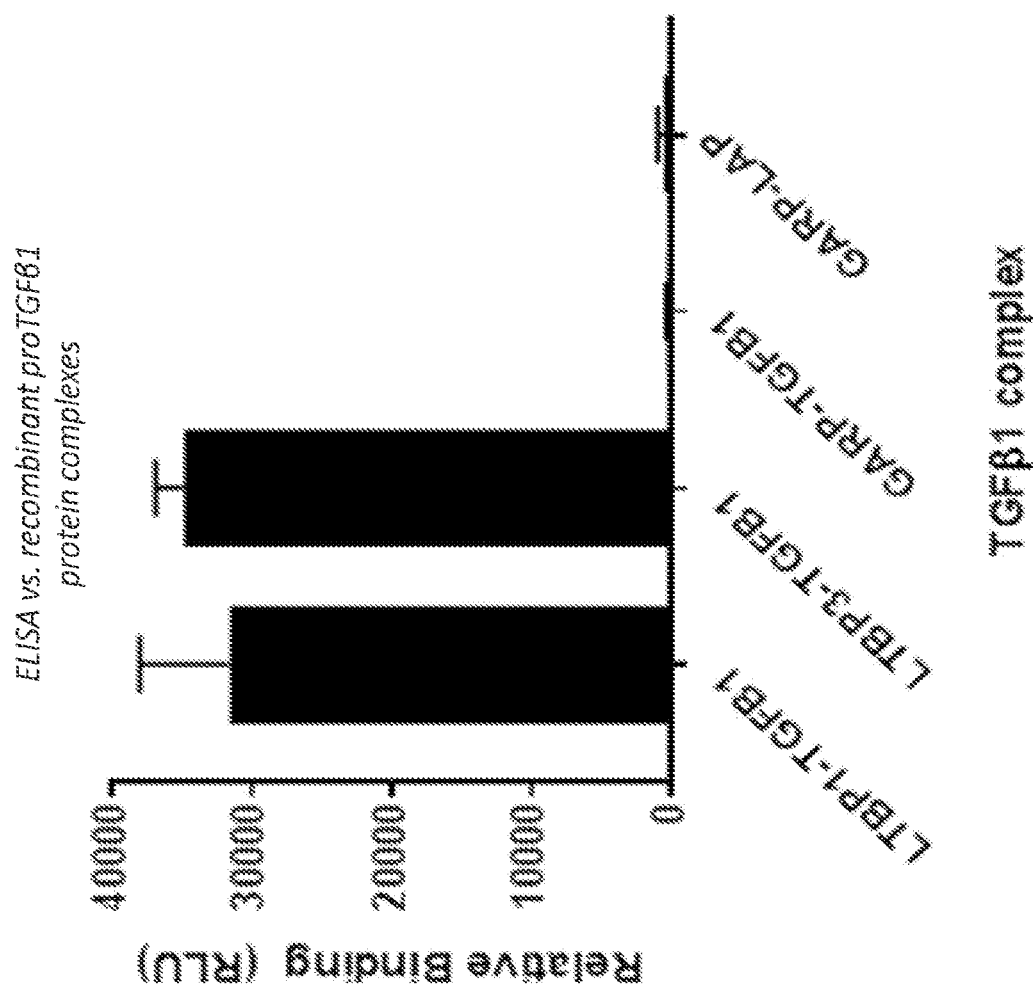
FIG. 9: SR-AB2 Specifically Binds to proTGFβ1:LTBP1 & 3 Complexes

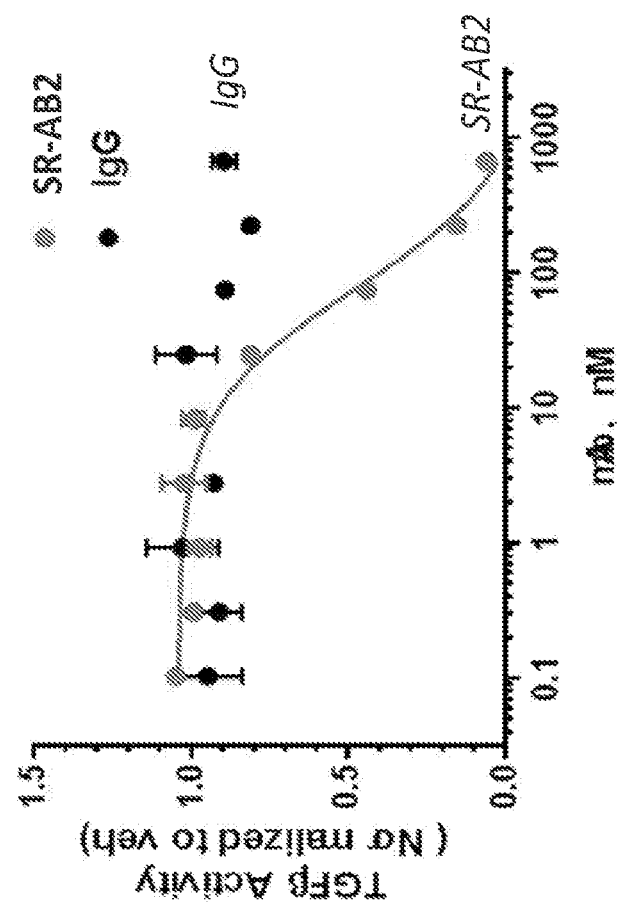
FIG. 10A: SR-AB2 Selectively Inhibits Activation of Matrix-Associated, but not GARP-Associated, proTGFβ1

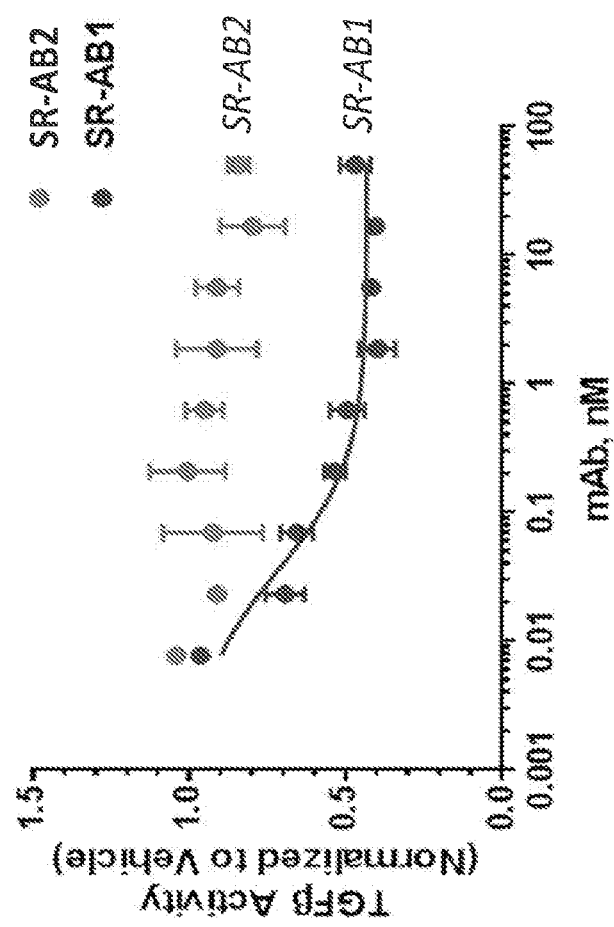
FIG. 10B: SR-AB2 Selectively Inhibits Activation of Matrix-Associated, but not GARP-Associated, proTGFβ1
SR-AB2 Does Not Inhibit GARP-proTGFβ proTGFβ1 presented by overexpressed GARP LN229 cells, αVβ8 activation

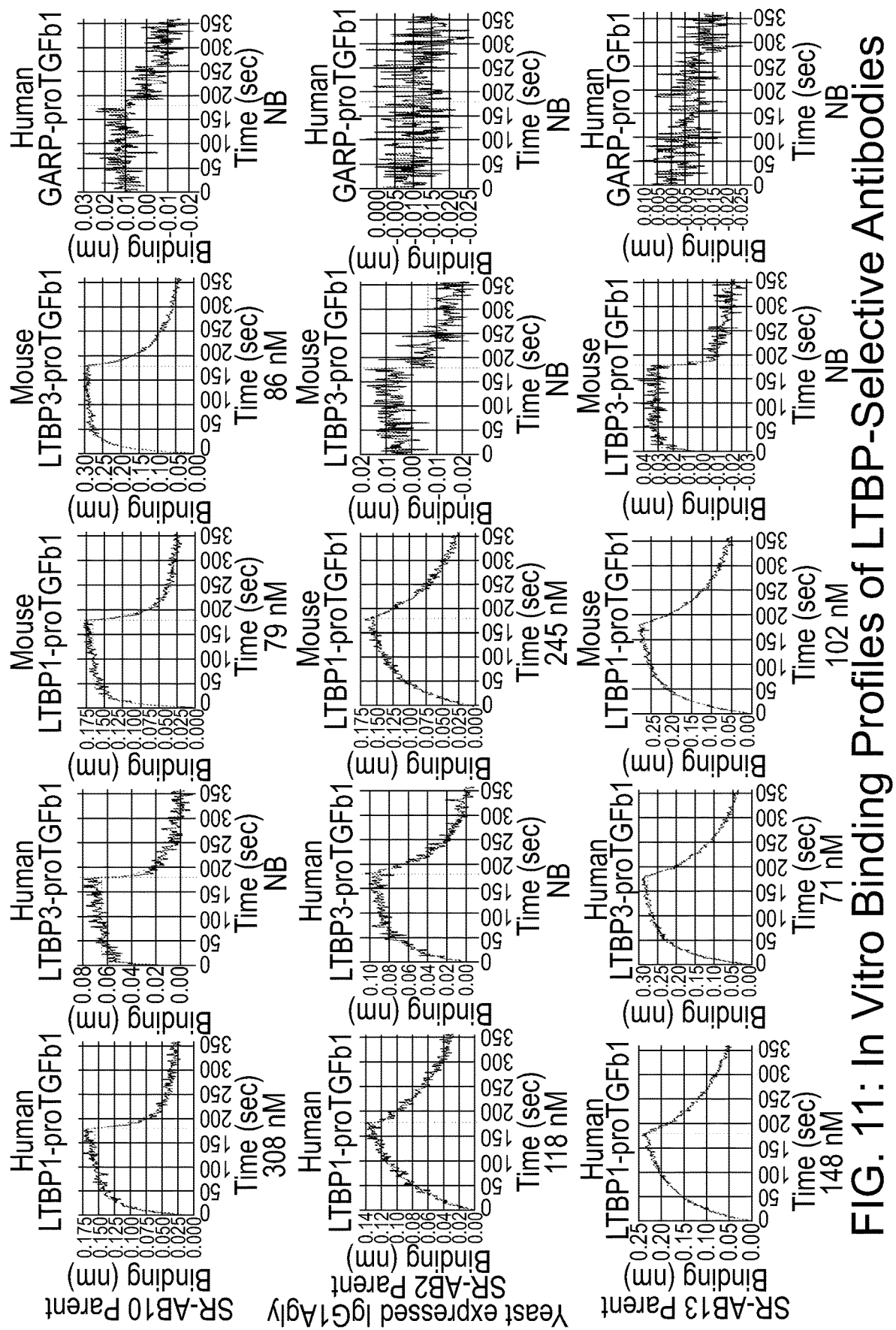
FIG. 11: In Vitro Binding Profiles of LTBP-Selective Antibodies

Initial Optimization (i.e., CDR H1/H2 diversification) of LTBP-Specific Antibodies SR-AB10 and SR-AB13 Improves Potency Second Round of Optimization (i.e., CDR-H3 mutagenesis) Further Improves Potency of AB10-related antibodies Second Round of Optimization (i.e., CDR-H3 mutagenesis) Further Improves Potency of AB13-related antibodies

* = cycle 1 optimized antibody

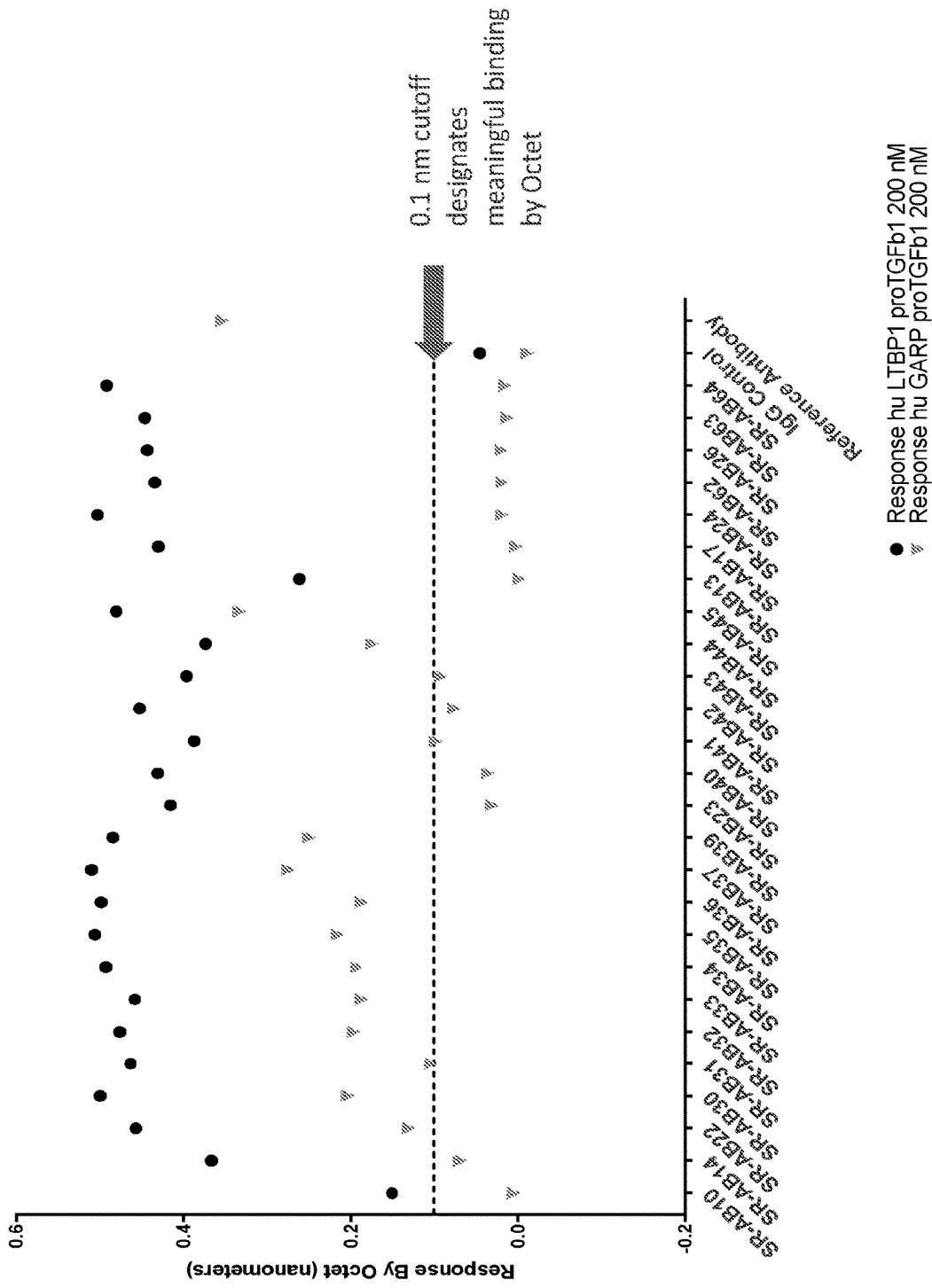

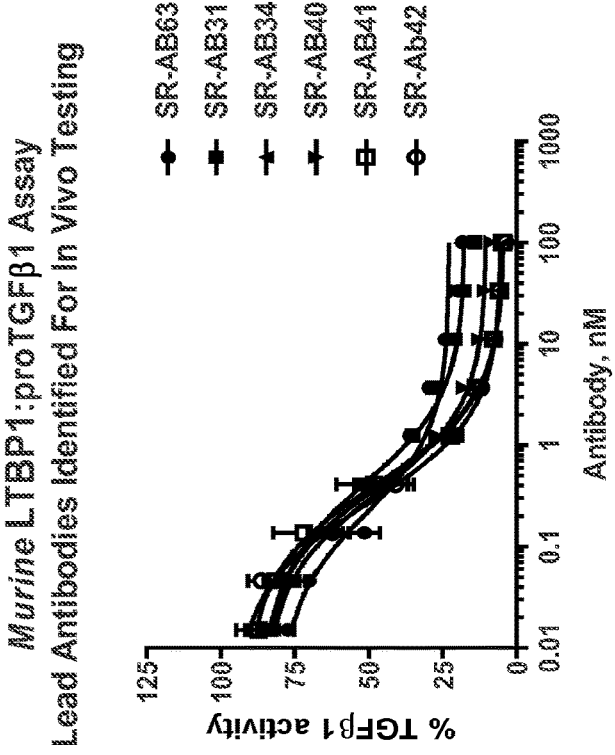
FIG. 16: Functional Activity of LTBP Complex Specific Antibodies

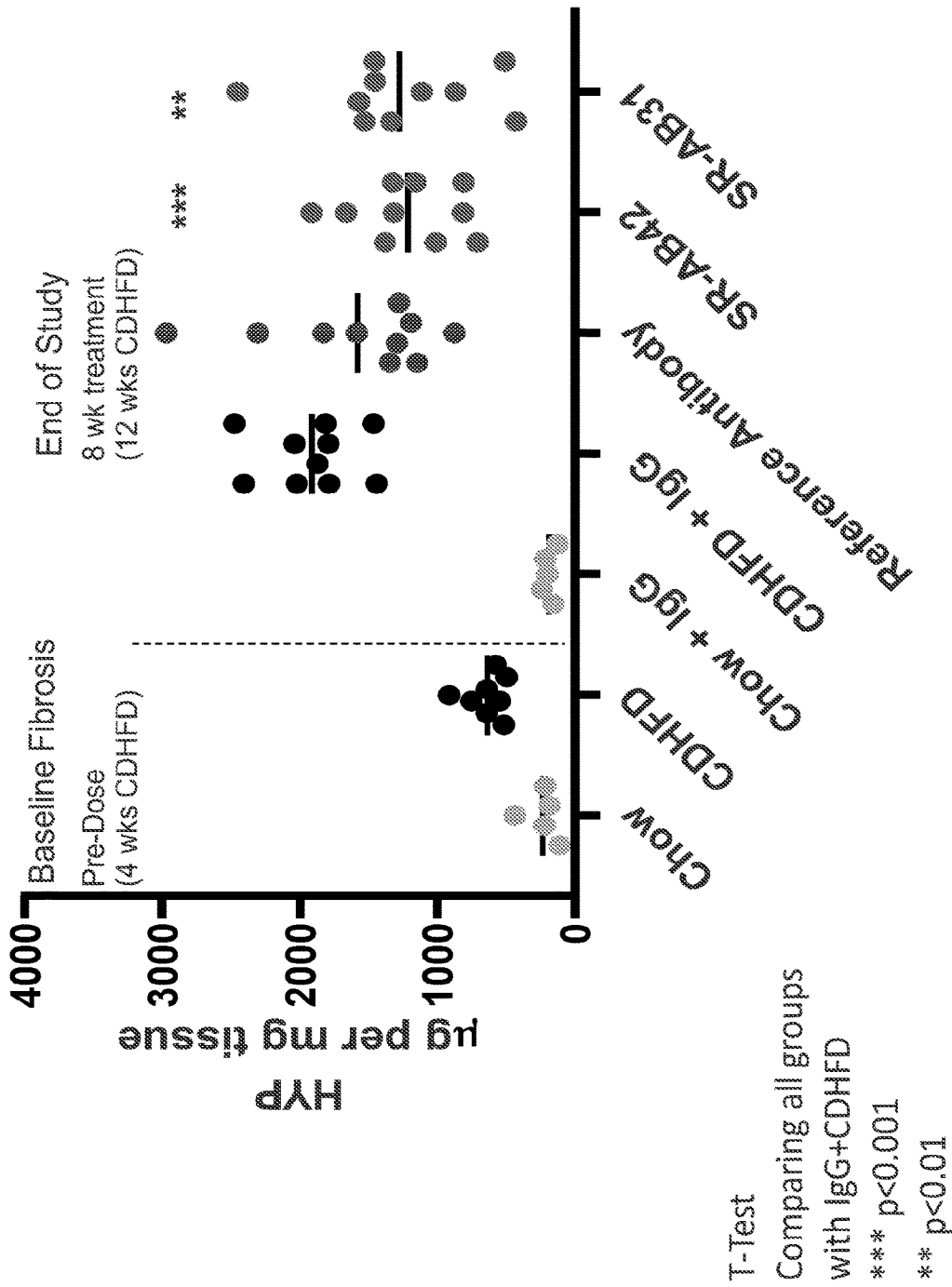
FIG. 19: LTBP Specific Antibodies Reduce Hydroxyproline Content in Mouse CDHFD Liver Tissue

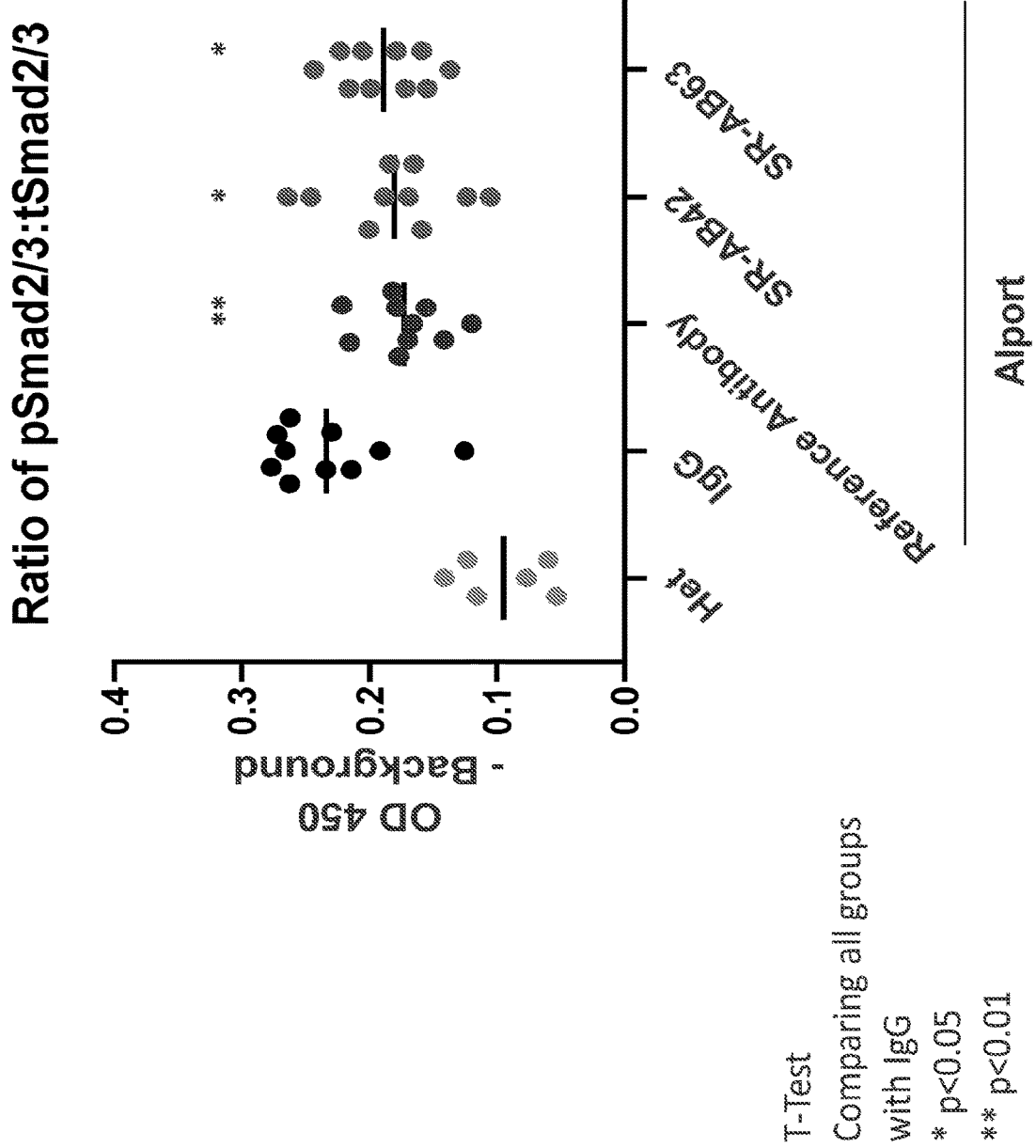

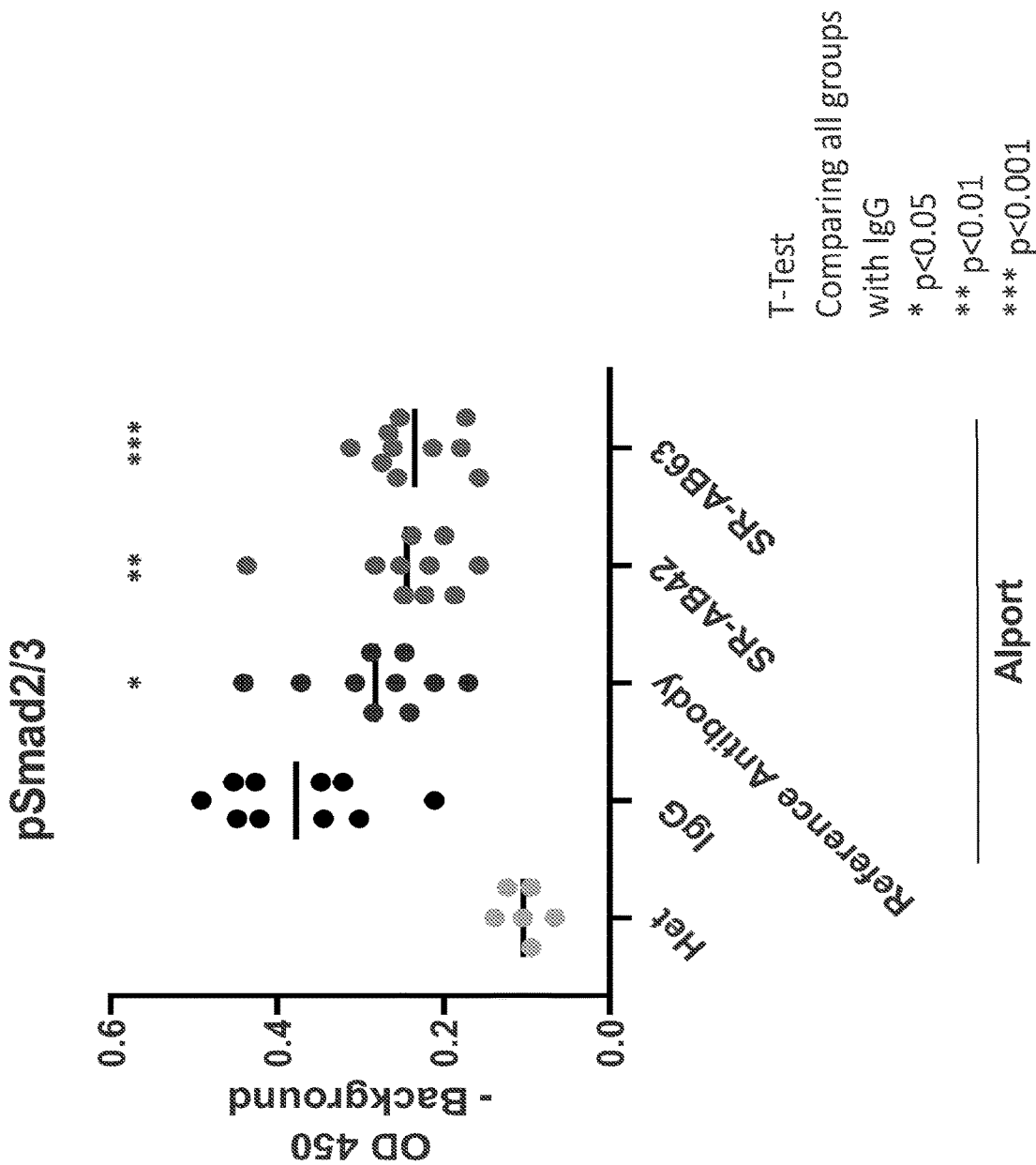

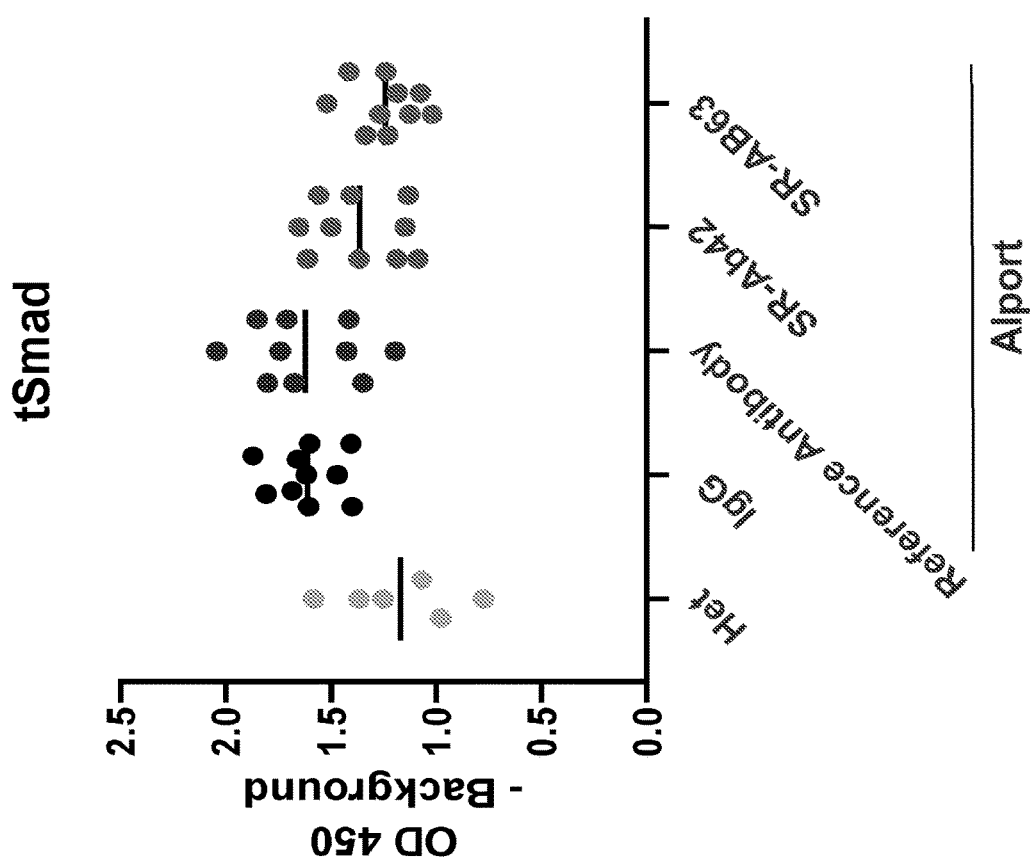

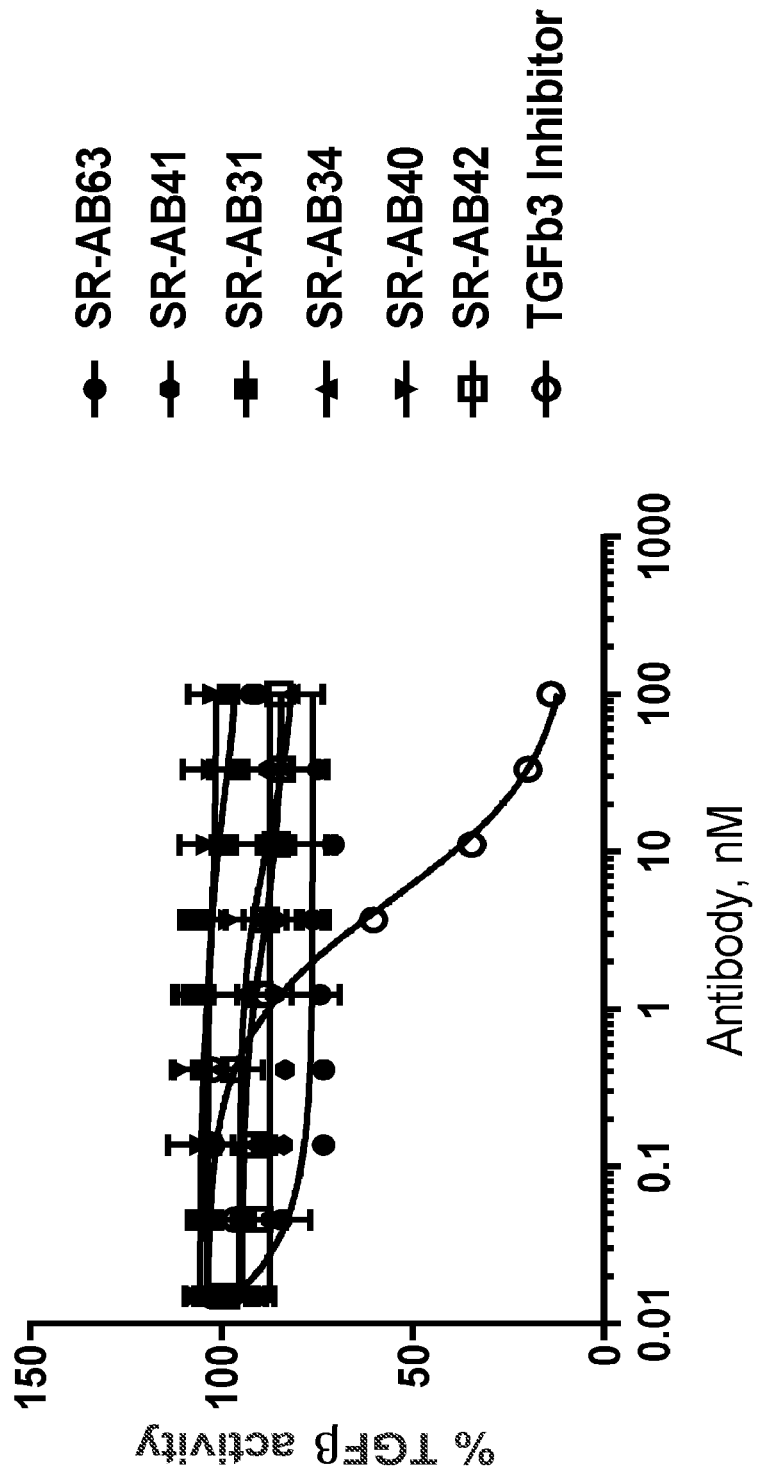
FIG. 21: Human LTBP:proTGFB3 Counterscreen

TGFβ3-selective inhibitor exacerbates fibrosis and suppresses anti-fibrotic effects of TGFβ1-selective inhibitor in mouse CDHFD model

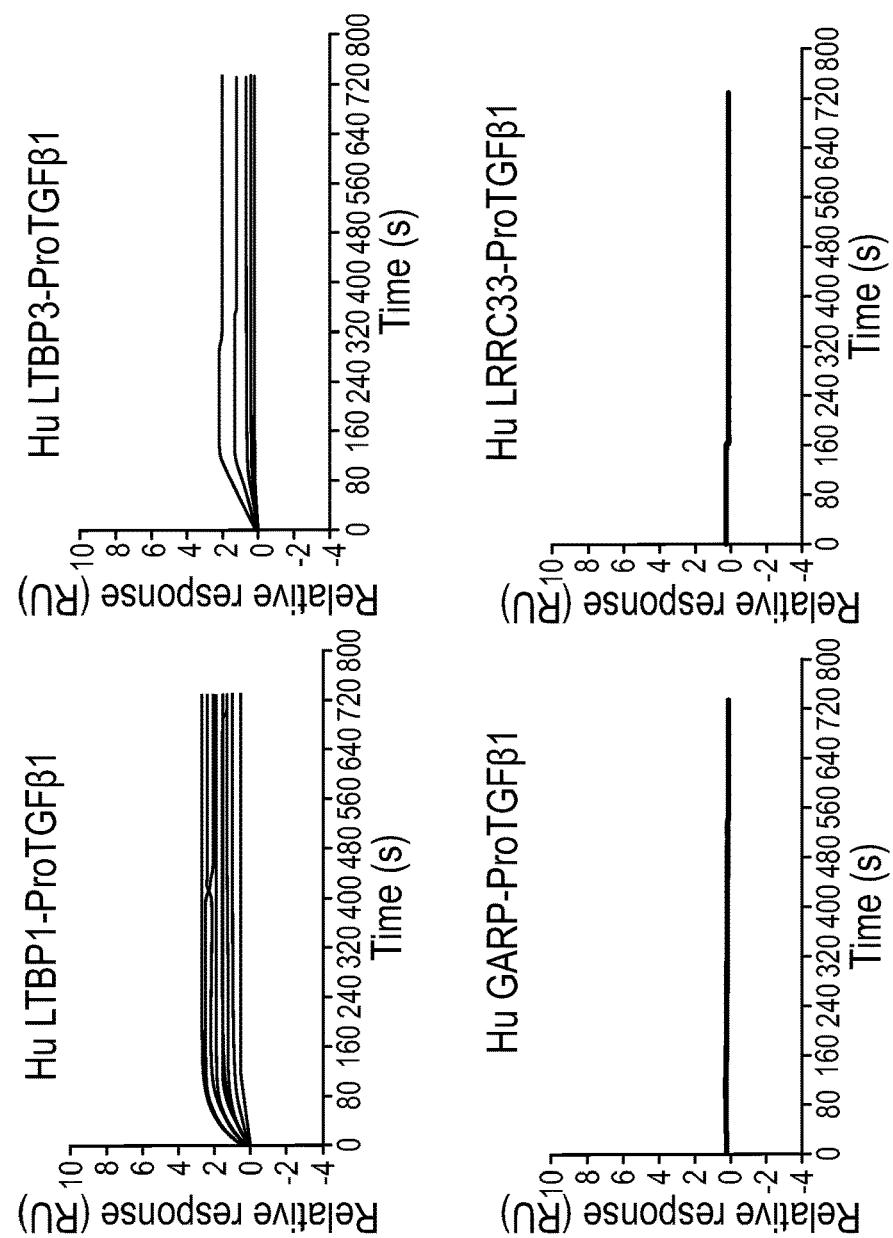
FIG. 23: LTBP Antibodies Are Highly Specific and Have Picomolar Monovalent Affinities

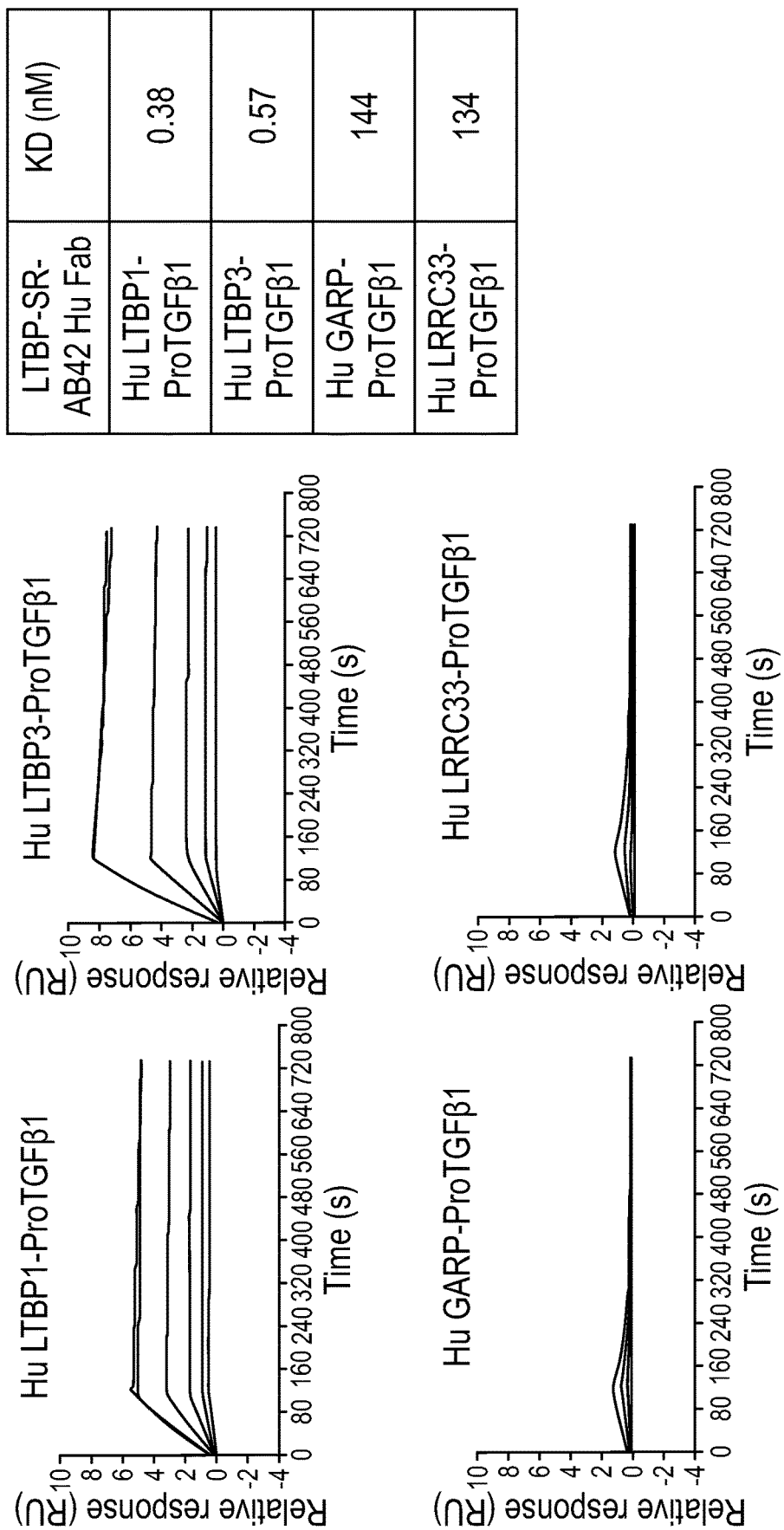
FIG. 24: LTBP Antibodies Are Highly Specific and Have Picomolar Monovalent Affinities

US 12,173,059 B2

LTBP COMPLEX-SPECIFIC INHIBITORS OF TGFβ AND USES THEREOF

RELATED APPLICATIONS

This application is a continuation of U.S. patent application Ser. No. 17/530,786, filed Nov. 19, 2021, allowed, which is a continuation of U.S. patent application Ser. No. 16/997,438, filed Aug. 19, 2020, issued as U.S. Pat. No. 11,214,614, which is a continuation application filed under 35 U.S.C. § 111 (a) of International Application No. PCT/US2020/015915, filed on Jan. 30, 2020, which in turn claims the benefit of and priority to U.S. Provisional Application No. 62/798,927, filed Jan. 30, 2019, the contents of each of which are expressly incorporated herein by reference in their entireties.

SEQUENCE LISTING

The instant application contains a Sequence Listing which has been submitted electronically in ASCII format and is hereby incorporated by reference in its entirety. Said ASCII copy, created on May 17, 2022, is named 127036 03007SL.txt and is 376,925 bytes in size.

BACKGROUND

Transforming growth factor beta (TGFβ) superfamily of growth factors are involved in a number of signaling cascades that regulate diverse biological processes including, but not limited to: inhibition of cell growth, tissue homeostasis, extracellular matrix (ECM) remodeling, endothelial to mesenchymal transition, cell migration and invasion, and immune modulation/suppression, as well as mesenchymal to epithelial transition. In relation to ECM remodeling, TGFβ signaling may increase fibroblast populations and ECM deposition (e.g., collagen). In the immune system, TGFβ ligand modulates T regulatory cell function and maintenance of immune precursor cell growth and homeostasis. In normal epithelial cells, TGFβ is a potent growth inhibitor and promoter of cellular differentiation. However, as tumors develop and progress, they frequently lose their negative growth response to TGFβ. In this setting, TGFβ may become a promoter of tumor development due to its ability to stimulate angiogenesis, alter the stromal environment, and induce local and systemic immunosuppression. For these and other reasons, TGFβ has been a therapeutic target for a number of clinical indications. Despite much effort made to date by a number of groups, clinical development of a TGFβ therapeutic has been challenging.

Observations from preclinical studies, including in rats and dogs, have revealed certain toxicities associated with inhibition of TGFβ in vivo. Moreover, although several TGFβ inhibitors have been developed to date, most clinical programs targeting TGFβ have been discontinued due to side effects or risk of toxicity.

For example, Anderton et al. (Toxicology Pathology, 39: 916-24, 2011) reported that small molecule inhibitors of TGFβ type I (ALK5) receptor induced heart valve lesions characterized by hemorrhage, inflammation, degeneration and proliferation of valvular interstitial cells in a preclinical animal model. The toxicity was observed in all heart valves at all doses tested. Frazier et al. (Toxicology Pathology, 35: 284-295, 2007) reported that administration of the small molecule inhibitor of TGFβ type I (ALK5) receptor GW788388 induced physeal dysplasia in rats. Stauber et al. (J. Clin. Practice 4:3, 2014) reported that a chronic (≥3 months) administration of the inhibitor of TGFβ receptor I kinase, LY2157299, which is being investigated for certain cancer treatments, caused multiple organ toxicities involving the cardiovascular, gastrointestinal, immune, bone/cartilage, reproductive, and renal systems, in rats and dogs.

Fresolimumab (GC1008), a "pan" TGFβ antibody capable of neutralizing all human isoforms of TGFβ, has been reported to induce an epithelial hyperplasia of the gingiva, bladder, and of the nasal turbinate epithelium after multiple administrations in studies with cynomolgus macaques (Lonning et al., Current Pharmaceutical Biotechnology 12: 2176-89, 2011). Similarly, a variety of skin rashes/lesions, gingival bleeding and fatigue have been reported in clinical trials after administration of multiple doses of the drug. The most notable adverse reaction to fresolimumab includes the induction of cutaneous keratoacanthomas and/or squamous cell carcinomas in human cancer patients (see, for example: Lacouture et al., 2015, Cancer Immunol Immunother, 64: 437-46; Stevenson et al., 2013, Oncolmmunology, 2:8, e26218; and Lonning et al., 2011). Additional evidence from a clinical trial suggests that in some cases this antibody may accelerate tumor progression (Stevenson et al., 2013, Oncolmmunology, 2:8, e26218).

Thus, new methods and compositions for modulating TGFβ signaling are necessary that can be used to effectively and safely treat diseases and disorders involving TGFβ, including, for example, cancer, fibrosis and inflammation.

With an increasing recognition of potentially dangerous adverse effects associated with broad inhibition of TGFβ, a number of groups have more recently turned to identifying inhibitors that target a subset—but not all—of the isoforms and still retain sufficient efficacy. For example, WO 2016/161410 discloses neutralizing antibodies that bind both TGFβ1 and TGFβ2 (i.e., TGFβ1/2 inhibitors). WO 2006/116002 provides neutralizing antibodies that bind both TGFβ1 and TGFβ3 (i.e., TGFβ1/3 inhibitors), albeit preferentially to the former. In addition to traditional monoclonal antibodies, some groups are developing engineered fusion proteins that function as so-called "ligand traps" (see, for example, WO 2018/158727, WO 2018029367 and WO 2018129331), at least some of which may be selective for TGFβ1/3. Another class of TGFβ1/3 inhibitors include inhibitors of alpha-V (αv) integrins such as antibodies against αvβ6, which is an integrin known to activate both TGFβ1 and TGFβ3 (i.e., TGFβ1/3). Yet others continue to pursue "better" pan-inhibitors that inhibit all three isoforms (i.e., TGFβ1/2/3 or pan-inhibitors) (see, for example, WO 2018/134681).

From an efficacy standpoint, however, the prevailing view of the field remains to be that it is advantageous to inhibit multiple isoforms of TGFβ to achieve therapeutic effects, and to accommodate this, toxicity management by "careful dosing regimen" is suggested as a solution (Brennan et al. (2018) mAbs, 10:1, 1-17).

Recently, Applicant described isoform-selective TGFβ1 inhibitors which were demonstrated to be both safe and efficacious in animal models (see, for example: WO 2017/156500 and WO 2018/129329, incorporated by reference), supporting the notion that selectively targeting the TGFβ1 isoform, as opposed to broadly antagonizing all TGFβ isoforms, may provide an advantageous approach to achieving efficacy with acceptable toxicity.

Whilst the observed safety profile achieved by selective inhibition of TGFβ1 at doses that were shown efficacious in vivo is a promising step towards developing a TGFβ1 inhibitor for clinical applications, identification of TGFβ1 inhibitors that are capable of selectively affecting a defined subset of TGFβ1 effects (e.g., TGFβ inhibitors that are selective to LTBP-presented complexes) remained elusive. More recently, Applicant demonstrated that such "LTBP context-specific" inhibitors can be generated (WO 2019/023661, incorporated herein by reference) using the methods previously described by Applicant (see, for example, WO 2014/074532 and WO 2014/182676). However, the LTBP-selective TGFβ1 inhibitors described in the aforementioned international publication showed modest affinities and inhibitory activities, coupled with suboptimal cross-species reactivity.

SUMMARY OF THE INVENTION

The present disclosure provides improved TGFβ inhibitors capable of selectively targeting matrix-associated proTGFβ complexes, such as LTBP1-proTGFβ1 and LTBP3-proTGFβ1.

These inhibitors bind and inhibit LTBP1- and/or LTBP3-presented proTGFβ at high affinities (at least nanomolar range) but do not bind and inhibit immune cell-associated TGFβ, e.g., GARP- and/or LRRC33-presented proTGFβ1, or the binding is below meaningful levels (e.g., at least 50 times affinities for the LTBP complexes over GARP or LRRC33 complex). Thus, these inhibitors can selectively inhibit activation of TGFβ in a context-dependent manner, such that they selectively bind, thereby inhibiting the TGFβ signaling axis associated with the ECM. In particular, the present disclosure includes selective inhibitors of matrix-associated (e.g., LTBP1 and/or LTBP3-associated) TGFβ activation. In some embodiments, such inhibitors specifically bind a particular isoform of TGFβ (e.g., proTGFβ1, proTGFβ2, and/or proTGFβ3) associated with LTBP1 and/or LTBP3, thus also providing TGFβ isoform specificity. In a particular embodiment, such inhibitors specifically bind to LTBP1/3-proTGFβ1. In any of the embodiments of the present invention, such inhibitors do not inhibit activation of TGFβ1 associated with immune cell function, mediated by GARP and/or LRRC33. The improved antibodies encompassed by the present disclosure have affinities towards human LTBP1-proTGFβ1 and/or human LTBP3-proTGFβ1 in at least a nanomolar range (i.e., $1\times10^9$M to $10\times10^{-9}$M). In some embodiments, such antibodies also have affinities towards murine LTBP1-proTGFβ1 and/or murine LTBP3-proTGFβ1 in at least a nanomolar range (i.e., $1\times10^{-9}$M to $10\times10^{-9}$M).

Rationale for the therapeutic use of a TGFβ1 inhibitor that does not target the GARP-proTGFβ1 complex on regulatory T cells is at least threefold:

First, regulatory T cells play a crucial role in maintaining immune tolerance to self-antigens and in preventing autoimmune disease. Since Tregs generally suppress, dampen or downregulate induction and proliferation of effector T cells, systemic inhibition of this function may lead to overactive or exaggerated immune responses in the host by disabling the "break" that is normally provided by Treg cells. Thus, the approach taken here (e.g., TGFβ1 inhibition without disabling Treg function) is aimed to avoid the risk of eliciting autoimmunity. Furthermore, patients who already have a propensity for developing over-sensitive immune responses or autoimmunity may be particularly at risk of triggering or exacerbating such conditions, without the availability of normal Treg function; and therefore, the inhibitors that selectively target the matrix TGFβ1 may advantageously minimize such risk.

Second, evidence suggests that an alteration in the Th17/Treg ratio leads to an imbalance in pro-fibrotic Th17 cytokines, which correlate with severity of fibrosis, such as liver fibrosis (see, for example, Shoukry et al. (2017) J Immunol 198 (1 Supplement): 197.12). The present inventors reasoned that perturbation of the GARP arm of TGFβ1 function may directly or indirectly exacerbate fibrotic conditions.

Third, regulatory T cells are indispensable for immune homeostasis and the prevention of autoimmunity. It was reasoned that, particularly for a TGFβ1 inhibition therapy intended for a long-term or chronic administration, it would be desirable to avoid potential side effects stemming from perturbation of normal Treg function in maintaining immune homeostasis (reviewed in, for example, Richert-Spuhler and Lund (2015) Prog Mol Biol Transl Sci. 136: 217-243). This strategy is at least in part aimed to preserve normal immune function, which is required, inter alia, for combatting infections.

To this end, the inventors of the present disclosure set out to generate isoform-specific, context-selective inhibitors of TGFβ1 that selectively target matrix-associated TGFβ1 activation but not immune cell-associated TGFβ1 activation.

Technical challenges that exist to date include limited ability to discern and selectively modulate these subpools of TGFβ1 present in various contexts (or "niches") in vivo.

In an effort to address this challenge, the present inventors have identified isoform-specific monoclonal antibodies that bind the latent TGFβ1 prodomain, with no detectable binding to latent TGFβ2 or TGFβ3, and that inhibit integrin-mediated activation of latent TGFβ1 in vitro with the context-dependency as described herein. The discovery and characterization of such antibodies was made possible, at least in part, by the development of context-dependent cell-based assays of TGFβ1 activation. In the process of this novel assay development and validation, it was demonstrated that, like the αVβ6 integrin, αVβ8 can also activate LTBP1-proTGFβ1. It was further demonstrated that, similar to the LTBP1 complex, LTBP3-proTGFβ1 can be activated by αVβ6. Antibodies discovered by screening in these assays revealed a class of antibodies that binds and inhibits TGFβ1 only when presented by LTBP1 or LTBP3. Such LTBP-specific antibodies do not inhibit TGFβ1 in the context of the immune-associated TGFβ1 presenters GARP and LRRC33. Such antibodies are therapeutic candidates for the treatment of disorders including, e.g., fibrotic conditions, and could allow chronic dosing that would avoid TGFβ-related immune system activation. Methods of selecting a context-specific or context-independent TGFβ1 inhibitor for various fibrotic conditions are also provided herein.

Accordingly, in one aspect, the invention provides isoform-specific TGFβ antibodies, or antigen-binding fragments thereof, characterized in that they bind selectively to an LTBP1-TGFβ1 complex and/or a LTBP3-TGFβ1 complex with a $K_D \leq 50$ nM. In one embodiment, the invention provides isoform-specific TGFβ antibodies, or antigen-binding fragments thereof, characterized in that they bind selectively to an LTBP1-TGFβ1 complex and/or a LTBP3-TGFβ1 complex with a $K_D \leq 25$ nM. In one embodiment, the invention provides isoform-specific TGFβ antibodies, or antigen-binding fragments thereof, characterized in that they bind selectively to an LTBP1-TGFβ1 complex and/or a LTBP3-TGFβ1 complex with a $K_D \leq 10$ nM. In one embodiment, the invention provides an isolated antibody, or antigen-binding portion thereof, that selectively binds to a LTBP1-proTGFβ1 complex and a LTBP3-proTGFβ1 complex, wherein the antibody, or antigen-binding portion thereof, does not bind to one or more of the following targets: (a) LTBP1 alone; (b) proTGFβ1 alone; (c) a GARP-proTGFβ1 complex; and (d) a LRRC33-proTGFβ1 complex. In further embodiments, the invention provides isoform-specific TGFβ antibodies, or antigen-binding fragments thereof, characterized in that they bind selectively to an LTBP1-TGFβ1 complex and/or a LTBP3-TGFβ1 complex with a $K_D \leq 5$ nM.

In one aspect, the invention provides inhibitors of extracellular matrix-associated TGFβ activation, which selectively bind a LTBP1/3-presented proTGFβ latent complex. In one embodiment, the inhibitor does not inhibit immune cell-associated TGFβ1 activation, for example, immune cell-associated TGFβ1 activation that results from activation of a GARP-presented proTGFβ1 latent complex. In exemplary embodiments, the inhibitor is an antibody, or antigen-binding portion thereof.

In other aspects, the invention provides TGFβ antibodies, or antigen-binding fragments thereof, characterized in that they bind selectively to an LTBP1-TGFβ complex and/or a LTBP3-TGFβ complex. In some embodiments, the antibodies, or antigen-binding fragments thereof, selectively bind to LTBP1-TGFβ1. In some embodiments, such antibodies bind both human and murine counterparts.

In one aspect, the invention provides an isolated antibody, or antigen-binding portion thereof, that selectively binds an LTBP1-proTGFβ latent complex and/or an LTBP3-proTGFβ latent complex, thereby modulating release of mature TGFβ growth factor from the latent complex, wherein the antibody, or antigen-binding portion thereof, does not bind mature TGFβ1 alone or a GARP-proTGFβ1 latent complex. In one embodiment, the antibody, or antigen-binding portion thereof, does not bind an LRRC33-proTGFβ1 latent complex. Alternatively, in one embodiment, the antibody, or antigen-binding portion thereof, binds an LRRC33-proTGFβ1 latent complex.

In some embodiments, the antibody, or antigen-binding portion thereof, is specific to an LTBP1-proTGFβ1 latent complex. In other embodiments, the antibody, or antigen-binding portion thereof, is specific to an LTBP3-proTGFβ1 latent complex. In one embodiment, the antibody, or antigen-binding portion thereof, binds an LTBP1-proTGFβ1 complex and/or a LTBP3-proTGFβ1 complex with a dissociation constant ($K_D$) of at least about $10^{-8}$ M. In one embodiment, the antibody, or antigen-binding portion thereof, binds a human LTBP1-proTGFβ1 complex and/or a human LTBP3-proTGFβ1 complex with a $K_D$ of <50 nM as measured in a suitable in vitro binding assay such as Bio-Layer Interferometry (BLI). In one embodiment, the antibody, or antigen-binding portion thereof, binds a human LTBP1-proTGFβ1 complex and/or a human LTBP3-proTGFβ1 complex with a $K_D$ of <10 nM as measured in a suitable in vitro binding assay such as Bio-Layer Interferometry (BLI). In one embodiment, the antibody, or antigen-binding portion thereof, binds a mouse LTBP1-proTGFβ1 complex and/or a mouse LTBP3-proTGFβ1 complex with a $K_D$ of <50 nM as measured in a suitable in vitro binding assay such as Bio-Layer Interferometry (BLI). In one embodiment, the antibody, or antigen-binding portion thereof, binds a mouse LTBP1-proTGFβ1 complex and/or a mouse LTBP3-proTGFβ1 complex with a $K_D$ of <10 nM as measured in a suitable in vitro binding assay such as Bio-Layer Interferometry (BLI).

The present disclosure further provides antibodies and antigen binding fragments thereof, which selectively bind an LTBP1-proTGFβ complex and/or an LTBP3-proTGFβ complex and have one or more yet further advantageous properties. Indeed, the inventors surprisingly found that such antibodies could be provided which bind a human LTBP1-proTGFβ complex and a human LTBP3-proTGFβ complex with high affinity, and advantageously slow dissociation rates, while also being cross-reactive with mouse LTBP1-proTGFβ complex and mouse LTBP3-proTGFβ complex and displaying no significant binding to human GARP-proTGFβ complex (or indeed to human LRRC33-proTGFβ complex).

Further still, antibodies disclosed herein (including antibodies having one or more, or even all of the aforementioned advantageous properties) exhibit potent inhibition of TGFβ1 signaling in cell-based assays, and significantly reduce markers of fibrosis and TGFβ signaling in multiple animal models of fibrosis.

Thus, in some embodiments, the antibody, or antigen-binding fragment thereof binds a human LTBP1-proTGFβ1 complex and/or a human LTBP3-TGFβ1 complex with a $K_D$ of <5 nM as measured by BLI, and has one or more of the following properties:

i) is cross-reactive with mouse LTBP1-proTGFβ1 complex;
ii) is cross-reactive with mouse LTBP3-proTGFβ1 complex;
iii) binds a mouse LTBP1-proTGFβ1 complex with a $K_D$ of <10 nM as measured by BLI;
iv) binds a mouse LTBP3-proTGFβ1 complex with a $K_D$ of <10 nM as measured by BLI;
v) binds a human LTBP1-proTGFβ1 complex and/or a human LTBP3-TGFβ1 complex with a $K_D$ that is at least 50 times lower than the $K_D$ when binding to a human GARP-proTGFβ1 complex under the same assay conditions;
vi) does not show detectable binding to a human GARP-proTGFβ1 complex, as measured by BLI, under the same assay conditions as used to measure binding to human LTBP1-proTGFβ1 complex and/or a human LTBP3-TGFβ1 complex;
vii) does not show detectable binding to an LRRC33-proTGFβ1 complex (e.g., a human LRRC33-proTGFβ1 complex) as measured by BLI, under the same assay conditions as used to measure binding to human LTBP1-proTGFβ1 complex and/or human LTBP3-TGFβ1 complex.

In some embodiments, the antibody or antigen-binding fragment has at least properties (i)-(v) above, and optionally (vii). In some embodiments, the antibody or antigen-binding fragment has at least properties (i)-(iv) and (vi) above, and optionally (vii). In some embodiments, the antibody or antigen-binding fragment has at least properties (i), (iii) and (v) above, and optionally (vii). In some embodiments, the antibody or antigen-binding fragment has at least properties (ii), (iv) and (v) above, and optionally (vii). In some embodiments, the antibody or antigen-binding fragment has at least properties (i), (iii) and (vi) above, and optionally (vii). In some embodiments, the antibody or antigen-binding fragment has at least properties (ii), (iv) and (vi) above, and optionally (vii). In some embodiments, the antibody or antigen-binding fragment has at least properties (i)-(iii) and (v) above, and optionally (vii). In some embodiments, the antibody or antigen-binding fragment has at least properties (i)-(iii) and (vi) above, and optionally (vii).

In some preferred embodiments, the antibody or antigen-binding fragment binds a human LTBP1-proTGFβ1 complex and a human LTBP3-TGFβ1 complex with a $K_D$ of <5 nM as measured by BLI, and has all of the above properties (i)-(vii).

The antibody or antigen-binding fragment may selectively bind a LTBP1/3-presented proTGFβ latent complex and inhibit extracellular matrix-associated TGFβ activation.

Further still, further advantageous isoform-selective inhibitors of TGFβ1 activation may include monoclonal antibodies (including immunoglobulins and antigen-binding fragments or portions thereof) that exhibit slow dissociation rates (i.e., off-rates, $k_{OFF}$). Thus, the invention is further based on the recognition that treatment of chronic and progressive disease such as fibrosis may require inhibitors with superior durability, which may be reflected on the dissociation rate of such antibody.

The affinity of an antibody to its antigen is typically measured as the equilibrium dissociation constant, or $K_D$. The ratio of the experimentally measured off- and on-rates ($k_{OFF}/k_{ON}$) can be used to calculate the $K_D$ value. The $k_{OFF}$ value represents the antibody dissociation rate, which indicates how quickly it dissociates from its antigen, whilst the $k_{ON}$ value represents the antibody association rate which provides how quickly it binds to its antigen. The latter is typically concentration-dependent, while the former is concentration-independent. The $K_D$ value relates to the concentration of antibody (the amount of antibody needed for a particular experiment) and so the lower the $K_D$ value (lower concentration) and thus the higher the affinity of the antibody. With respect to a reference antibody, a higher affinity antibody may have a lower $k_{OFF}$ rate, a higher $k_{ON}$ rate, or both.

Both the $k_{OFF}$ and $k_{ON}$ rates contribute to the overall affinity of a particular antibody to its antigen, and relative importance or impact of each component may depend on the mechanism of action of the antibody. For example, neutralizing antibodies, which bind mature growth factors (e.g., soluble, transient TGFβ1 ligand liberated from a latent complex), must compete with the endogenous high-affinity receptors for ligand binding in vivo. Because the ligand-receptor interaction is a local event and because the ligand is short-lived, such antibodies must be capable of rapidly targeting and sequestering the soluble growth factor before the ligand finds its cellular receptor—thereby activating the TGFβ1 signaling pathway—in the tissue. Therefore, for ligand-targeting neutralizing antibodies to be potent, the ability to bind the target growth factor fast, i.e., high association rates ($k_{ON}$), may be especially important.

By contrast, Applicant reasoned that antibodies that inhibit the TGFβ1 signaling by preventing the activation (e.g., release) of mature growth factor from the latent complex ("activation inhibitors") may preferentially benefit from having slow dissociation rates once the antibody is engaged with the target antigen (e.g., proTGFβ1 complexes). Unlike neutralizing antibodies, such antibodies do not directly compete with cellular receptors; rather, they work upstream of the signaling by targeting inactive precursor forms (e.g., latent proTGFβ1 complexes) that remain dormant within a tissue environment thereby preemptively preventing the activation of TGFβ1. Such antibodies may exert their inhibitory activity by preventing mature growth factor from being liberated from the latent complex. For example, such antibodies may function like a "clamp" to lock the active growth factor in the prodomain cage structure to keep it in an inactive (e.g., "latent") state. Indeed, structural analyses, including epitope mapping, provided insight into the molecular mechanism underlining the ability of these antibodies to block TGFβ1 activation. In this regard, the Latency Lasso region of the prodomain may be a particularly useful target.

Upon target engagement, antibodies that are able to remain bound to the target (e.g., dissociate very slowly from the latent complex) are expected to be advantageous in achieving superior in vivo potency, due to enhanced durability of effects and/or avidity. Based on this recognition, Applicant of the present disclosure sought to identify isoform-selective activation inhibitors of TGFβ1 with particularly low $k_{OFF}$ values as compared to previously described antibodies. Thus, according to the invention, preferred antibodies have high affinities primarily attributable to a slow dissociation rate ($k_{OFF}$), as opposed to fast association rate ($k_{ON}$). Accordingly, in some embodiments, the antibody, or antigen-binding fragment thereof binds a human LTBP1-proTGFβ1 complex and/or a human LTBP3-TGFβ1 complex with a $K_D$ of <5 nM as measured by BLI, and has one or more of the following properties (which may be in addition to one of properties (i)-(vii), or combinations thereof set out above):

(viii) low dissociation rates ($k_{OFF}$) of $<5\times10^{-4}$ (1/s), when binding human LTBP1-proTGFβ1 complex and/or human LTBP3-TGFβ1 complex (e.g., as measured by a suitable in vitro binding/kinetics assay, such as by BLI, e.g., Octet-based systems); and/or (ix) long half-binding time (t½) of ≥45 minutes when bound to human LTBP1-proTGFβ1 and/or human LTBP3-proTGFβ1 complex (e.g., as measured by SPR).

In some preferred embodiments, the antibody or antigen binding fragment comprises the following six CDRs:

a) CDR-H1 comprising the amino acid sequence FTFRSYVMH (SEQ ID NO: 166);

b) CDR-H2 comprising the amino acid sequence VISHEGS($X_1$)KYYADSVKG, wherein: $X_1$ is L or G (SEQ ID NO: 366); and c) CDR-H3 comprising the amino acid sequence A($X_1$)PRIAARRGGFG($X_2$), wherein: $X_1$ is V, R or L; and $X_2$ is Y, S or T (SEQ ID NO: 367);

d) CDR-L1 comprising the amino acid sequence TRS($X_1$)G($X_2$)ID($X_3$)NYVQ, wherein, $X_1$ is S or H; $X_2$ is N, L, S or A; and $X_3$ is N, D or Y (SEQ ID NO: 368);

e) CDR-L2 comprising the amino acid sequence ED($X_1$)($X_2$)RPS, wherein: $X_1$ is N, F or A; and $X_2$ is Q, I or V (SEQ ID NO: 369); and f) CDR-L3 comprising the amino acid sequence Q($X_1$)YD($X_2$)($X_3$)($X_4$)Q($X_5$)VV, wherein: $X_1$ is S or G; $X_2$ is S, F, Y, D, H or W; $X_3$ is N, D or S; $X_4$ is N, A, L, E or T; and $X_5$ is G, R, A or L (SEQ ID NO: 370).

In some preferred embodiments, the antibody or antigen-binding fragment thereof competes or cross-competes with an antibody having a heavy chain variable region sequence as set forth in SEQ ID NO: 318 and light chain variable region sequence as set forth in SEQ ID NO: 319 (e.g., Ab42). The antibody may comprise a heavy chain variable region having an amino acid sequence that is at least 90% identical to SEQ ID NO: 318 and a light chain variable region having an amino acid sequence that is at least 90% identical to SEQ ID NO: 319.

The antibody or antigen-binding fragment thereof provided herein may, in some preferred embodiments, comprise the following six CDRs (e.g., those of Ab42):

CDR-H1 comprising the amino acid sequence FTFRSYVMH (SEQ ID NO: 166);

CDR-H2 comprising the amino acid sequence VISHEGSLKYYADSVKG (SEQ ID NO: 167);

CDR-H3 comprising the amino acid sequence ARPRIAARRGGFGY (SEQ ID NO: 168);

CDR-L1 comprising the amino acid sequence TRSSGNIDNNYVQ (SEQ ID NO: 169);
CDR-L2 comprising the amino acid sequence EDNQRPS (SEQ ID NO: 170); and
CDR-L3 comprising the amino acid sequence QSYDYDTQGVV (SEQ ID NO: 171).

The antibody or antigen-binding fragment may further comprise a heavy chain variable region having an amino acid sequence that is at least 95% identical (optionally at least 98% identical) to SEQ ID NO: 318 and a light chain variable region having an amino acid sequence that is at least 95% identical (optionally at least 98% identical) to SEQ ID NO: 319.

In some alternative embodiments, the antibody, or antigen-binding fragment thereof, comprises the following six CDRs:
a) CDR-H1 comprising the amino acid sequence GSIRSSSYYWG (SEQ ID NO: 292);
b) CDR-H2 comprising the amino acid sequence SISYSATTYY (SEQ ID NO: 293);
c) CDR-H3 comprising the amino acid sequence $A(X_1)$DPSYDS$(X_2)$AGM$(X_3)$V, wherein: $X_1$ is S or G; $X_2$ is A or I; and $X_3$ is D or Q (SEQ ID NO: 371);
d) CDR-L1 comprising the amino acid sequence RAS$(X_1)(X_2)$IS$(X_3)$YLN, wherein: $X_1$ is K or Q; $X_2$ is V or S; and $X_3$ is S or Y (SEQ ID NO: 389);
e) CDR-L2 comprising the amino acid sequence $(X_1)$AS$(X_2)(X_3)$QS, wherein: $X_1$ is Y, A or S; $X_2$ is S or N; and $X_3$ is L or R (SEQ ID NO: 390);
f) CDR-L3 comprising the amino acid sequence QQ$(X_1)(X_2)$D$(X_3)$P$(X_4)$T, wherein: $X_1$ is S or G; $X_2$ is F or N; $X_3$ is W or F; and $X_4$ is F or L (SEQ ID NO: 391).

In some embodiments, the antibody or antigen-binding fragment thereof competes or cross-competes with an antibody having a heavy chain variable region sequence as set forth in SEQ ID NO: 360 and light chain variable region sequence as set forth in SEQ ID NO: 361 (e.g., Ab63). The antibody may comprise a heavy chain variable region having an amino acid sequence that is at least 90% identical to SEQ ID NO: 360 and a light chain variable region having an amino acid sequence that is at least 90% identical to SEQ ID NO: 361.

The antibody or antigen-binding fragment thereof provided herein may comprise the following six CDRs (e.g., those of Ab63):
CDR-H1 comprising the amino acid sequence GSIRSSSYYWG (SEQ ID NO: 292);
CDR-H2 comprising the amino acid sequence SISYSATTYY (SEQ ID NO: 293);
CDR-H3 comprising the amino acid sequence AGDPSYDSIAGMQV (SEQ ID NO: 294);
CDR-L1 comprising the amino acid sequence RASQSISSYLN (SEQ ID NO: 295);
CDR-L2 comprising the amino acid sequence AASNLQS (SEQ ID NO: 296); and
CDR-L3 comprising the amino acid sequence QQSFDWPLT (SEQ ID NO: 297).

The antibody or antigen-binding fragment may further comprise a heavy chain variable region having an amino acid sequence that is at least 95% identical (optionally at least 98% identical) to SEQ ID NO: 360 and a light chain variable region having an amino acid sequence that is at least 95% identical (optionally at least 98% identical) to SEQ ID NO: 361.

In one aspect, the invention provides an antibody, or antigen-binding fragment thereof, for use in a method for treating a fibrotic disorder in a subject, wherein the antibody, or antigen-binding fragment thereof, specifically binds a human LTBP1-proTGFβ complex and/or a human LTBP3-proTGFβ complex, and does not bind a human GARP-proTGFβ1 complex; wherein: a) the fibrotic disorder comprises chronic inflammation; b) the subject benefits from immune suppression; c) the subject has or is at risk of developing an autoimmune disease; d) the subject is a candidate for or has received an allograft transplant; e) the subject has an elevated Th17/Treg ratio; and/or, f) the subject is in need of a long-term or chronic administration of the TGFβ1 inhibitor. In some embodiments, the the subject has or is at risk of developing a metabolic disorder (and the subject is optionally a subject according to one or more of a)-f)). In some embodiments, the the antibody, or antigen-binding fragment thereof, is an isoform-specific LTBP1-proTGFβ1 inhibitor and/or LTBP3-proTGFβ1 inhibitor.

The antibodies or antigen-binding fragments thereof provided herein may be used in a method for treating a fibrotic disorder in a subject. The fibrotic disorder may comprise chronic inflammation. The subject may benefit from immune suppression. The subject may have or be at risk of developing an autoimmune disease. The subject may be a candidate for or may have received an allograft transplant.

Alternatively, or in addition, the subject may have an elevated Th17/Treg ratio. The subject may be in need of a long-term or chronic administration of the TGFβ1 inhibitor.

Alternatively, or in addition, the subject may have or be at risk of developing a metabolic disorder.

In another aspect, the invention provides a method for making a composition comprising an antibody, or antigen-binding fragment thereof, that specifically binds a human LTBP1-proTGFβ complex and/or a human LTBP3-proTGFβ complex, and does not bind a human GARP-proTGFβ1 complex; wherein the antibody, or antigen-binding fragment thereof, inhibits TGFβ1 but does not inhibit TGFβ2 or TGFβ3, the method comprising steps of i) providing at least one antigen comprising LTBP1-proTGFβ1 and/or LTBP3-proTGFβ1, ii) selecting a first pool of antibodies, or antigen-binding fragments thereof, that specifically bind the at least one antigen of step (i) so as to provide specific binders of LTBP1-proTGFβ1 and/or LTBP3-proTGFβ1; iii) selecting a second pool of antibodies, or antigen-binding fragments thereof, that inhibit activation of TGFβ1, so as to generate specific inhibitors of TGFβ1 activation; iv) formulating an antibody, or antigen-binding fragment thereof, that is present in the first pool of antibodies and the second pool of antibodies into a pharmaceutical composition, thereby making the composition comprising the antibody, or antigen-binding fragment thereof.

In one embodiment, the method further comprises a step of removing from the first pool of antibodies, or antigen-binding fragments thereof, any antibodies, or antigen-binding fragments thereof, that bind GARP-proTGFβ1, LRRC33-proTGFβ1, mature TGFβ1, GARP-proTGFβ2, LRRC33-proTGFβ2, mature TGFβ2, GARP-proTGFβ3, LRRC33-proTGFβ3, mature TGFβ3, or any combinations thereof. In one embodiment, the method further comprises a step of determining or confirming isoform-specificity of the antibodies, or antigen-binding fragments thereof, selected in steps (ii) and/or (iii). In one embodiment, the method further comprises a step of selecting for antibodies, or antigen-binding fragments thereof, that are cross-reactive to human and rodent antigens. In one embodiment, the method further comprises a step of generating a fully human or humanized antibody, or antigen-binding fragment thereof, of the antibody, or antigen-binding fragment thereof, that is present in the first pool of antibodies and the second pool of antibodies.

In one embodiment, the method further comprises a step of subjecting the antibody, or antigen-binding fragment thereof, that is present in the first pool of antibodies and the second pool of antibodies to affinity maturation and/or optimization, so as to provide an affinity matured and/or optimized antibody or fragment thereof. In one embodiment, the affinity maturation/optimization comprises a step of subjecting the antibody, or antigen-binding fragment thereof, that is present in the first pool of antibodies and/or the second pool of antibodies to light chain shuffling as described herein. In one embodiment, the affinity maturation/optimization comprises the step of subjecting the antibody, or antigen-binding fragment thereof, that is present in the first, second, and/or third pool of antibodies to CDR H1/H2 diversification as described herein. In one embodiment, the affinity maturation/optimization comprises the step of subjecting the antibody, or antigen-binding fragment thereof, to CDR-H3 mutagenesis as described herein. In one embodiment, the affinity maturation/optimization comprises the step of subjecting the antibodies, or antigen-binding fragment thereof, to light chain CDR mutagenesis as described herein. In one embodiment, the affinity maturation/optimization comprises the step of subjecting the antibodies, or antigen-binding fragment thereof, to light chain CDR L1/L2 diversification as described herein.

In one embodiment, the method further comprises a step of determining affinity of the antibodies, or antigen-binding fragments thereof, from the first and/or second pools of antibodies to human LTBP1-proTGFβ1 and/or human LTBP3-proTGFβ1. In some embodiments, the method further comprises a step of removing from the first and/or second pools of antibodies, or antigen-binding fragments thereof, any antibodies, or antigen-binding fragments thereof, that bind to human LTBP1-proTGFβ1 and/or human LTBP3-proTGFβ1 with a $K_D$ of >100 nM, >50 nM, >25 nM, or >10 nM, as measured in a suitable in vitro binding assay such as Bio-Layer Interferometry (BLI).

In one embodiment, the method further comprises a step of determining affinity of the antibodies, or antigen-binding fragments thereof, from the first and/or second pools to mouse LTBP1-proTGFβ1 and/or mouse LTBP3-proTGFβ1. In some embodiments, the method further comprises a step of removing from the first and/or second pools of antibodies, or antigen-binding fragments thereof, any antibodies, or antigen-binding fragments thereof, that bind to mouse LTBP1-proTGFβ1 and/or mouse LTBP3-proTGFβ1 with a $K_D$ of >100 nM, >50 nM, or >10 nM, as measured in a suitable in vitro binding assay such as Bio-Layer Interferometry (BLI).

In one embodiment, the method further comprises a step of removing from the first and/or second pools of antibodies, or antigen-binding fragments thereof, any antibodies, or antigen-binding fragments thereof, that do not bind mouse LTBP1-proTGFβ1 and/or mouse LTBP3-proTGFβ1.

In one embodiment, the method further comprises a step of determining the $IC_{50}$ of the antibodies, or antigen-binding fragments thereof, from of the first and/or second pools of antibodies, or antigen-binding fragments thereof, as measured by a suitable functional in vitro cell-based assay such as a caga assay, as described herein. In some embodiments, the method comprises the step of removing antibodies, or antigen-binding fragments thereof, from the first and/or second pools of antibodies, or antigen-binding fragments thereof, that have an $IC_{50}$ of greater than 100 nM, 50 nM, 25 nM, 10 nM, or 5 nM as measured by a cell-based assay (such as a caga assay) as described herein.

In some embodiments, the method comprises the step of removing antibodies, or antigen-binding fragments thereof, from the first and/or second pools, antibodies, or antigen-binding fragments thereof, that have an $IC_{50}$ of greater than 50 nM or 10 nM as measured by an endogenous LTBP caga assay as described herein.

In some embodiments, the method comprises the step of removing antibodies, or antigen-binding fragments thereof, from the first and/or second pools, antibodies, or antigen-binding fragments thereof, that have an $IC_{50}$ of greater than 50 nM, 25 nM, or 10 nM, as measured by a human LTBP overexpression caga assay as described herein.

In some embodiments, the method comprises the step of removing antibodies, or antigen-binding fragments thereof, from the first and/or second pools, antibodies, or antigen-binding fragments thereof, that have an $IC_{50}$ of greater than 50 nM, 25 nM, 10 nM, or 5 nM, as measured by a murine LTBP overexpression caga assay as described herein.

Processes and methods for identifying or selecting TGFβ1-selective inhibitors suitable for therapeutic use are encompassed by the invention, as are methods for making a composition comprising a TGFβ1-selective inhibitor. In preferred embodiments, a TGFβ1 inhibitor (e.g., a selected inhibitor) includes one or more antibodies or antigen-binding fragments with particularly advantageous kinetics criteria characterized by: i) high affinities to each of human LTBP1/3-proTGFβ1 complexes (e.g., $K_D \leq 5$ nM), and, ii) low dissociation rates ($k_{OFF}$), e.g., $\leq 5 \times 10^{-4}$ (1/s), as measured by a suitable in vitro binding/kinetics assay, such as by BLI, e.g., Octet-based systems. The low dissociation rate criterion may be reflected in long dissociation half-time t½), e.g., >45 minutes from human LTBP1-proTGFβ1 and/or human LTBP3-proTGFβ1 complexes. Preferably, the long dissociation half-time of an antibody or antigen-binding fragment thereof for the matrix-associated complex(es) is coupled with short dissociation half-time with respect to cell-associated complexes, e.g., human GARP-proTGFβ1 and/or human LRRC33-proTGFβ1 complexes. In particular, preferred antibodies or fragments dissociate from human GARP-proTGFβ1 complex with t½ of no more than 10 minutes, more preferably no more than 5 minutes. Likewise, methods for making a composition comprising a TGFβ1-selective inhibitor as described herein may further include a step of selecting such antibodies. The selected antibody or the plurality of antibodies are evaluated in preclinical studies comprising an efficacy study and a toxicology/safety study, employing suitable preclinical models. Effective amounts of the antibody or the antibodies determined in the efficacy study are below the level that results in undesirable toxicities determined in the toxicology/safety study. Preferably, the antibody or antibodies are selected which has/have at least 3-fold, 6-fold, and more preferably 10-fold therapeutic window. Effective amounts of the antibodies according to the present disclosure may be between about 0.1 mg/kg and about 30 mg/kg when administered weekly. In preferred embodiments, the maximally tolerated dose (MTD) of the antibodies according to the present disclosure is >100 mg/kg when dosed weekly for at least 4 weeks. In some embodiments, in a preclinical toxicology study, the antibodies show a NOAEL of >100 mg/kg/week, >200 mg/kg/week or >300 mg/kg/week, wherein optionally the toxicology study is a 4-week study, 8-week study, or a 12-week study. For example, the NOAEL is >100 mg/kg/week in a 12-week sub-chronic dosing regimen in healthy mice or rats.

The present disclosure also includes a surprising finding that inhibition of TGFβ3 with a TGFβ3-selective inhibitor produced pro fibrotic effects in mice. Similarly, concurrent inhibition of both TGFβ1 and TGFβ3 in the same model with a combination of a TGFβ1-selective inhibitor and a TGFβ3-selective inhibitor resulted in attenuated anti-fibrotic effects of the TGFβ1 inhibitor. These observations raise the possibility that non-selective TGFβ inhibitors (such as pan-inhibitors and TGFβ1/3 inhibitors) may in fact exacerbate fibrosis. Advantageously, the antibodies disclosed herein (e.g., Ab42 and variants thereof, as described herein) are isoform-selective in that they specifically target the latent TGFβ1 complex and do so with low dissociation rates. Thus, the invention includes the recognition that when selecting a particular TGFβ inhibitor for patients with a fibrotic condition (e.g., disease involving ECM dysregulation), isoform selectivity should be carefully considered so as to avoid risk of exacerbating ECM dysregulation. Accordingly, the present disclosure includes therapeutic methods comprising selecting a TGFβ inhibitor that does not inhibit TGFβ3 to treat a subject with a fibrotic condition, (including preferred fibrotic conditions, as described herein).

The isoform-selective LTBP1/3-proTGFβ1 complex-selective inhibitor as used herein may in some embodiments be selected from Ab31, Ab34, Ab37, Ab38, Ab39, Ab40, Ab41, Ab42, Ab43, Ab44, Ab45, Ab62, Ab63, and Ab64 (optionally Ab42 or Ab63) (i.e., an antibody or antigen-binding fragment having the heavy and light chain variable regions of the corresponding Ab, as provided herein), a variant/derivative or antigen-binding fragment thereof, or an engineered molecule comprising an antigen-binding fragment thereof. In some preferred embodiments, the LTBP1/3-proTGFβ1 complex-selective inhibitor inhibitor is Ab42, a variant/derivative or antigen-binding fragment thereof, or an engineered molecule comprising an antigen-binding fragment thereof. In preferred embodiments, the LTBP1/3-proTGFβ1 complex-selective inhibitor is Ab42 or an antigen-binding fragment thereof.

BRIEF DESCRIPTION OF THE FIGURES

FIG. 1 graphically depicts that targeting of the latent form of TGFβ1 provides isoform and context specificity.

FIGS. 2A-2B demonstrate the identification of isoform-specific and LTBP complex-specific binders of latent TGFβ1. FIG. 2A demonstrates that SR-AB1 binds latent TGFβ1, independent of the presenting molecule. SR-AB1 is a human monoclonal antibody that was discovered by yeast display, which selectively binds latent TGFβ1, without detectable binding to latent TGFβ2, TGFβ3, or mature TGFβ1. SR-AB1 cross-reacts with mouse, rat, and cynomolgus monkey proteins and binds to all four latent TGFβ1 complexes. FIG. 2B demonstrates that SR-AB2, an anti-LTBP1-proTGFβ1 antibody, does not bind GARP-proTGFβ1 or mature TGFβ1. SR-AB2 cross-reacts with rodent LTBP1-proTGFβ1.

FIGS. 3A-3B demonstrate functional assays (potency assays) to detect the inhibition of activated recombinant latent TGFβ1. FIG. 3A depicts the activation of latent TGFβ1 deposited in the extracellular matrix (ECM). In this assay, presenting molecules are co-transfected with proTGFβ1 in integrin-expressing cells. Transiently transfected cells are seeded in assay plates in the presence of inhibitors. Latent LTBP-proTGFβ1 complex is embedded in the ECM. TGFβ reporter cells are then added to the system; free growth factor (released by integrin) signals and is detected by luciferase assay. FIG. 3B depicts the activation of latent TGFβ1 presented on the cell surface. Presenting molecules are co-transfected with proTGFβ1 in integrin-expressing cells. Latent TGFβ1 is expressed on the cell surface by GARP or LRRC33. TGFβ reporter cells and inhibitors are then added to the system; free growth factor (released by integrin) signals and is detected by luciferase assay.

FIG. 4A depicts the relative contribution of presenting molecule and/or proTGFβ1 activation upon co-transfection of presenting molecule and proTGFβ1. FIG. 4B depicts the optimization of co-transfection: the ratio of plasmid DNAs for presenting molecule and proTGFβ1. Equivalent amounts of each plasmid were optimal for co-transfection.

FIG. 5 demonstrates that fibronectin promotes integrin activation of LTBP-presented latent TGFβ1. Assay plates were pre-coated with fibronectin purified from human plasma. Fibronectin increases integrin-mediated activation of latent TGFβ1 presented by LTBP1 and/or LTBP3.

FIG. 6 is a graph demonstrating that SR-AB1 is a context-independent inhibitor of TGFβ1 activation. SR-AB1 was shown to inhibit integrin-dependent activation of TGFβ1 independent of the presenting molecule.

FIG. 7A demonstrates that SR-AB2 specifically binds LTBP-proTGFβ1 complex; it does not bind proTGFβ1 or LTBP1 alone. SR-AB2 also does not bind GARP-proTGFβ1. FIG. 7B depicts that SR-AB2 inhibits integrin activation of LTBP1-proTGFβ1 (human and mouse complexes). FIG. 7C depicts that SR-AB2 inhibits integrin activation of LTBP3-proTGFβ1.

FIG. 8 presents the heavy chain and light chain variable region sequences of SR-AB2 (SEQ ID NOs: 7-8, respectively, in order of appearance). Complementary determining regions (CDRs) are underlined.

FIG. 9 is a graph demonstrating the binding specificity of SR-AB2 to LTBP1-proTGFβ1 and LTBP3-proTGFβ1 complexes.

FIGS. 10A-10B provide data showing context-selective inhibition of matrix-associated TGFβ1 activation by SR-AB2. FIG. 10A demonstrates that SR-AB2 inhibits LTBP-proTGFβ, wherein the transfected proTGFβ1 is presented by endogenous LTBP1/3. FIG. 10B demonstrates that SR-AB2 does not inhibit GARP-presented TGFβ1 activation. These assays were performed in LN229 cells, which express high LTBP3 mRNA, low LTBP1 mRNA, undetectable GARP, and undetectable LRRC33. TGFβ activity, normalized to vehicle, is shown on the y-axis.

FIG. 11 presents binding profiles and affinity data for LTBP complex-specific antibodies SR-AB10, SR-AB2, and SR-13.

FIGS. 12A and 12B are graphs showing improved potency of optimized LTBP complex-specific antibodies. FIG. 12A provides a graph showing improved inhibitory potency of SR-AB14 (an optimized SR-AB10) as measured by cell-based TGFβ reporter assays. FIG. 12B provides a graph showing improved inhibitory potency of SR-AB15 (an optimized SR-AB13) as measured by cell-based TGFβ assays.

FIGS. 14A and 14B are graphs showing improved potency of optimized LTBP complex-specific antibodies after CDR-H3 mutagenesis (i.e., SR-AB24, SR-AB25, SR- AB26, SR-AB27, SR-AB28, and SR-AB29), as measured by cell-based TGFβ reporter assays.

FIG. 15 is a graph that shows affinity matured antibodies show specific binding to the LTBP-proTGFβ1 complex.

FIG. 16 is a graph showing improved potency of optimized LTBP complex-specific antibodies after cycles 1, 2 and 3 of antibody optimization as measured by cell-based TGFβ reporter assays.

FIG. 19 is a graph showing treatment with SR-AB42 and SR-AB31 inhibited the increase in hydroxyproline (HYP) (μg/mg tissue) in liver tissue in animals on a choline-deficient high fat diet (CDHFD).

FIG. 20A is a graph showing relative ratios of phosphorylated versus total (phosphorylated and unphospohrylated) Smad2/3 (pSMAD2/3:tSMAD2/3) in an Alport mouse model. A single dose of SR-AB42 or SR-AB63 was sufficient to significantly inhibit pSmad2/3 signaling in whole kidney lysates. FIG. 20B is a graph showing the amount of phosphorylated SMAD2/3 (pSMAD2/3) as determined by ELISA, and FIG. 20C is a graph showing the amount of total SMAD2/3 (tSMAD2/3) protein as determined by ELISA. As shown by FIG. 20B and FIG. 20C, reduction of pSMAD is contributing to the change in ratio shown in FIG. 20A.

FIG. 21 is a graph showing that the lead cycle 3 antibodies show no inhibition in the LTBP-TGFβ33 assay.

FIG. 23 shows LTBP-complex antibodies such as SR-AB63 are highly specific and have picomolar monovalent affinities.

FIG. 24 shows LTBP-complex antibodies such as SR-AB42 are highly specific and have picomolar monovalent affinities.

DETAILED DESCRIPTION OF CERTAIN EMBODIMENTS

Figure 4A:
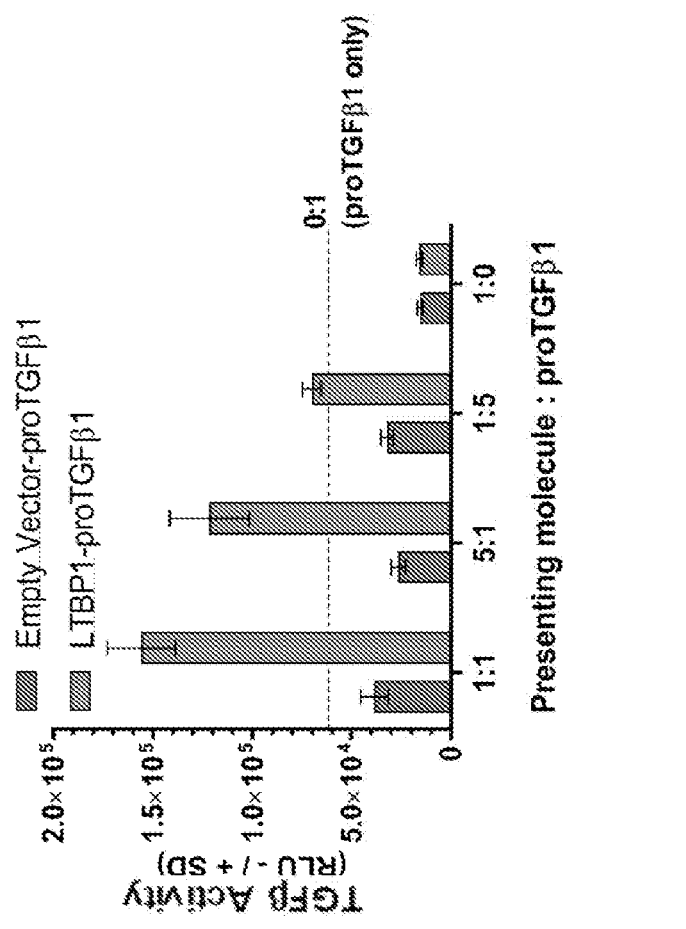
FIGS. 4A-4B depict the optimization of the recombinant functional assays.

The present invention provides compositions that are useful for reducing activation of TGFβ. Inhibitors that target latent proTGFβ complexes, upstream of growth factor-receptor interaction, are generally referred to as activation inhibitors of TGFβ.

To date, four presenting molecules for TGFβ have been identified: latent TGF beta-binding protein 1 ("LTBP1"), latent TGF beta-binding protein 3 ("LTBP3"), glycoprotein A repetitions predominant ("GARP") and leucine-rich repeat-containing protein 33 ("LRRC33"). Each of these presenting molecules can form disulfide bonds with a homodimeric pro-protein complex of the TGFβ precursor, i.e., proTGFβ. The proTGFβ complex remains dormant (latent) in the respective extracellular niche (e.g., ECM and immune cell surface) until activation events trigger the release of soluble growth factor from the complex.

As compared to the TGFβ growth factors and the receptors, which are expressed broadly, the presenting molecules show more restricted or selective (e.g., tissue-specific) expression patterns, giving rise to functional compartmentalization of TGFβ activities by virtue of association. The four presenting molecule-proTGFβ complexes, namely, LTBP1-proTGFβ, LTBP3-proTGFβ, GARP-proTGFβ and LRRC33-proTGFβ3, therefore, provide discrete "contexts" of TGFβ signaling within the tissue in which the presenting molecules are expressed. These contexts may be divided into two broad categories: i) TGFβ signaling associated with the ECM (e.g., matrix-associated TGFβ function); and ii) TGFβ signaling associated with cells (particularly certain immune cell function). The LTBP1-proTGFβ3 and LTBP3-proTGFβ complexes fall under the first category, while GARP-proTGFβ and LRRC33-proTGFβ complexes fall under the second category. Thus, disclosed herein are inhibitors of TGFβ that are capable of selectively inhibiting the activation of TGFβ that is associated with the ECM. In some embodiments, the inhibitors are also selective for a particular TGFβ isoform (e.g., proTGFβ1, proTGFβ2, and/or proTGFβ33).

In exemplary embodiments, the compositions described herein are useful for selectively reducing activation of TGFβ1 in the context of an LTBP protein, e.g., a LTBP1 and/or a LTBP3 protein. Such compositions advantageously inhibit activation of extracellular matrix-associated TGFβ1, without inhibiting TGFβ1 in the context of the immune-associated TGFβ1 presenting molecules GARP and LRRC33. The compositions described herein are useful for treating disorders associated with TGFβ1 activation, e.g., fibrotic disorders. Accordingly, in embodiments, the invention provides compositions for reducing activation of TGFβ1, methods of use thereof, methods of manufacture, and treatment methods. Methods of selecting a TGFβ1 inhibitor for subjects exhibiting symptoms of a fibrotic disorder are also provided.

Definitions

In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

Affinity: Affinity is the strength of binding of a molecule (such as an antibody) to its ligand (such as an antigen). It is typically measured and reported by the equilibrium dissociation constant ($K_D$). $K_D$ is the ratio of the antibody dissociation rate ("off rate" or $K_{off}$), how quickly it dissociates from its antigen, to the antibody association rate ("on rate" or $K_{on}$) of the antibody, how quickly it binds to its antigen. For example, an antibody with an affinity of ≤1 μM has a $K_D$ value that is 1 μM or lower (i.e., 1 μM or higher affinity) determined by a suitable in vitro binding assay. Suitable in vitro assays, such as Biolayer Interferometry (e.g., Octet) or surface plasmon resonance (e.g., Biacore System) can be used to assess affinities, as measured by $K_D$ values based on well-known methods.

Affinity maturation: Affinity maturation is a type of antibody optimization and is a process of improving the affinity of an antibody or a fragment to its antigen and typically involves making one or more changes to the amino acid sequence of the antibody or the fragment to achieve greater affinity. Typically, a parental antibody and an affinity-matured counterpart retain the same epitope. Affinity maturation may include diversification and/or mutagenesis of one or more CDR sequences.

Antibody: The term "antibody" encompasses any naturally-occurring, recombinant, modified or engineered immunoglobulin or immunoglobulin-like structure or antigen-binding fragment or portion thereof, or derivative thereof, as further described elsewhere herein. Thus, the term refers to an immunoglobulin molecule that specifically binds to a target antigen, and includes, for instance, chimeric, humanized, fully human, and bispecific antibodies. Unless otherwise specified to the contrary, the term "antibody" as used herein shall encompass antigen-binding fragments and variants thereof. An intact antibody will generally comprise at least two full-length heavy chains and two full-length light chains, but in some instances can include fewer chains such as antibodies naturally occurring in camelids which can comprise only heavy chains. Antibodies can be derived solely from a single source, or can be "chimeric," that is, different portions of the antibody can be derived from two different antibodies. Antibodies, or antigen-binding portions thereof, can be produced in hybridomas, by recombinant DNA techniques, or by enzymatic or chemical cleavage of intact antibodies. The term antibodies, as used herein, includes monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), respectively. In some embodiments, the term also encompasses peptibodies.

Antigen: The term "antigen" broadly includes any molecules comprising an antigenic determinant within a binding region(s) to which an antibody or a fragment specifically binds. An antigen can be a single-unit molecule (such as a protein monomer or a fragment) or a complex comprised of multiple components. An antigen provides an epitope, e.g., a molecule or a portion of a molecule, or a complex of molecules or portions of molecules, capable of being bound by a selective binding agent, such as an antigen-binding protein (including, e.g., an antibody). Thus, a selective binding agent may specifically bind to an antigen that is formed by two or more components in a complex. In some embodiments, the antigen is capable of being used in an animal to produce antibodies capable of binding to that antigen. An antigen can possess one or more epitopes that are capable of interacting with different antigen-binding proteins, e.g., antibodies. In the context of the present disclosure, a suitable antigen is a complex (e.g., multimeric complex comprised of multiple components in association) containing a proTGF dimer ("small latent complex" or SLC) preferably in association with a presenting molecule (together "large latent complex" or LLC). Each monomer of the proTGF dimer comprises a prodomain and a growth factor domain, separated by a furin cleavage sequence. Two such monomers form the proTGF dimer complex. This in turn is covalently associated with a presenting molecule via disulfide bonds, which involve a cysteine residue present near the N-terminus of each of the proTGF monomer. This multi-complex formed by a proTGF dimer bound to a presenting molecule is generally referred to as a large latent complex. An antigen complex suitable for screening antibodies or antigen-binding fragments, for example, includes a presenting molecule component of a large latent complex. Such presenting molecule component may be a full-length presenting molecule or a fragment(s) thereof. Minimum required portions of the presenting molecule typically contain at least 50 amino acids, but more preferably at least 100 amino acids of the presenting molecule polypeptide, which comprises two cysteine residues capable of forming covalent bonds with the proTGFβ1 dimer.

Antigen-binding portion/fragment: The terms "antigen-binding portion" or "antigen-binding fragment" of an antibody, as used herein, refers to one or more fragments of an antibody that retain the ability to specifically bind to an antigen (e.g., LTBP1-proTGFβ1 and LTBP3-proTGFβ1). Antigen-binding portions include, but are not limited to, any naturally occurring, enzymatically obtainable, synthetic, or genetically engineered polypeptide or glycoprotein that specifically binds an antigen to form a complex. In some embodiments, an antigen-binding portion of an antibody may be derived, e.g., from full antibody molecules using any suitable standard techniques such as proteolytic digestion or recombinant genetic engineering techniques involving the manipulation and expression of DNA encoding antibody variable and optionally constant domains. Non-limiting examples of antigen-binding portions include: (i) Fab fragments, a monovalent fragment consisting of the VL, VH, CL and CH1 domains; (ii) F(ab')2 fragments, a bivalent fragment comprising two Fab fragments linked by a disulfide bridge at the hinge region; (iii) Fd fragments consisting of the VH and CH1 domains; (iv) Fv fragments consisting of the VL and VH domains of a single arm of an antibody; (v) single-chain Fv (scFv) molecules (see, e.g., Bird et al. (1988) SCIENCE 242:423-426; and Huston et al. (1988) PROC. NAT'L. ACAD. SCI. USA 85:5879-5883); (vi) dAb fragments (see, e.g., Ward et al. (1989) NATURE 341: 544-546); and (vii) minimal recognition units consisting of the amino acid residues that mimic the hypervariable region of an antibody (e.g., an isolated complementarity determining region (CDR)). Other forms of single chain antibodies, such as diabodies are also encompassed. The term antigen-binding portion of an antibody includes a "single chain Fab fragment" otherwise known as an "scFab," comprising an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids.

Advanced fibrosis: As used herein, a subject suffers from advanced fibrosis if s/he has an advanced stage of a fibrotic disorder, particularly organ fibrosis, which renders the patient a candidate for receiving, or in need of, an allograft transplant.

As needed: In the context of dosing regimens, the term "as needed" refers to a dosing regimen that is not based on a predetermined dosing schedule but instead based on one or more parameters or markers measured or monitored periodically during treatment, which provides information or guidance as to whether additional doses should be beneficial to the subject/patient. For instance, a pharmaceutical composition comprising a TGFβ inhibitor such as TGFβ1/2/3 inhibitors ("pan" inhibitors), TGFβ1/2 inhibitors and TGFβ1/3 inhibitors, may be administered, intermittently, on an "as needed" basis in a therapeutically effective amount sufficient to achieve and/or maintain clinical benefit (e.g., reduction of one or more clinical markers of fibrosis). In some embodiments, administration of a LTBP1/3-complex selective TGFβ inhibitor such as any one of the antibodies disclosed herein (e.g., Ab31, Ab34, Ab37, Ab38, Ab39, Ab40, Ab41, Ab42, Ab43, Ab44, Ab45, Ab62, Ab63, or Ab64 (optionally Ab42)) may be used in combination with a method of determining or monitoring therapeutic efficacy. In some embodiments, the LTBP1/3-complex selective TGFβ inhibitor is administered in patients only when clinical benefit from additional doses of the TGFβ inhibitor is expected. It is contemplated that, in order to manage toxicities, intermittent or "as-needed" dosing regimen may be required more frequently with isoform-non-selective inhibitors of TGFβ, as compared to TGFβ1-selective inhibitors, such as those disclosed herein.

Bias: In the context of the present disclosure, the term "bias" refers to skewed or uneven affinity towards or against a subset of antigens to which an antibody is capable of specifically binding. For example, an antibody is said to have bias when the affinity for one antigen complex and the affinity for another antigen complex are not equivalent (e.g., more than five-fold difference in affinity). Antibodies characterized as "unbiased" have approximately equivalent affinities towards such antigen complexes (e.g., less than five-fold difference in affinity). Antibodies of the present disclosure "selectively" bind EMC-associated complexes (LTBP1-proTGFβ1 and LTBP3-proTGFβ). Such selective binding may in some embodiments comprise binding such that relative affinities between at least one of the matrix-associated complexes and at least one (preferably both) of the cell-associated complexes (GARP-proTGFβ1 and/or LRRC33-proTGFβ1 complexes) is greater than fifty-fold.

Biolayer Interferometry (BLI): BLI is a label-free technology for optically measuring biomolecular interactions, e.g., between a ligand immobilized on the biosensor tip surface and an analyte in solution. BLI provides the ability to monitor binding specificity, rates of association and dissociation, or concentration, with precision and accuracy. BLI platform instruments are commercially available, for example, from ForteBio and are commonly referred to as the Octet® System. BLI can be employed in carrying out in vitro binding assays as described herein.

Autoimmune disease: An autoimmune disease is a condition arising from an abnormal or overactive immune response to a normal body part Immunostimulating agents administered to such patients with autoimmune conditions may exacerbate the condition.

Cell-associated proTGFβ1: The term refers to TGFβ1 or its signaling complex (e.g., pro/latent TGFβ1) that is membrane-bound (e.g., tethered to cell surface). Typically, such cell is an immune cell. TGFβ1 that is presented by GARP or LRRC33 is a cell-associated TGFβ1. GARP and LRRC33 are transmembrane presenting molecules that are expressed on cell surface of certain cells. GARP-proTGFβ1 and LRRC33-proTGFβ1 may be collectively referred to as "cell-associated" (or "cell-surface") proTGFβ1 complexes, that mediate cell-associated (e.g., immune cell-associated) TGFβ1 activation/signaling.

Chronic inflammation: In the context of the present disclosure, fibrotic disorders that involve chronic inflammation are characterized by continuous or persistent injury to a tissue such that it does not resolve in normal healing after an initial injury. Chronic inflammation refers to a prolonged inflammatory response that involves a progressive change in the type of cells present at the site of inflammation (e.g., fibrotic tissues). It is characterized by the simultaneous destruction and repair of the tissue from the inflammatory process. It can follow an acute form of inflammation or be a prolonged low-grade form.

Clinical benefit: As used herein, the term "clinical benefits" is intended to include both efficacy and safety of a therapy. Thus, therapeutic treatment that achieves a desirable clinical benefit is both efficacious and safe (e.g., with tolerable or acceptable toxicities or adverse events).

Combinatory or combinatorial epitope: A combinatorial epitope is an epitope that is recognized and bound by a combinatorial antibody at a site (i.e., antigenic determinant) formed by non-contiguous portions of a component or components of an antigen, which, in a three-dimensional structure, come together in close proximity to form the epitope. Thus, antibodies of the invention may bind an epitope formed by two or more components (e.g., portions or segments) of a pro/latent TGFβ1 complex. A combinatory epitope may comprise amino acid residue(s) from a first component of the complex, and amino acid residue(s) from a second component of the complex, and so on. Each component may be of a single protein or of two or more proteins of an antigenic complex. A combinatory epitope is formed with structural contributions from two or more components (e.g., portions or segments, such as amino acid residues) of an antigen or antigen complex.

Complementary determining region: As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The exact boundaries of these CDRs have been defined differently according to different systems. The system described by Kabat (Kabat et al. (1987; 1991) Sequences of Proteins of Immunological Interest (National Institutes of Health, Bethesda, Md.) not only provides an unambiguous residue numbering system applicable to any variable region of an antibody, but also provides precise residue boundaries defining the three CDRs on each of the heavy and light chains. These CDRs may be referred to as Kabat CDRs.

Conformational epitope: A conformational epitope is an epitope that is recognized and bound by a conformational antibody in a three-dimensional conformation, but not in an unfolded peptide of the same amino acid sequence. A conformational epitope may be referred to as a conformation-specific epitope, conformation-dependent epitope, or conformation-sensitive epitope. A corresponding antibody or fragment thereof that specifically binds such an epitope may be referred to as conformation-specific antibody, conformation-selective antibody, or conformation-dependent antibody. Binding of an antigen to a conformational epitope depends on the three-dimensional structure (conformation) of the antigen or antigen complex.

Context-specific: Context-specific (or context-selective) antibodies of the invention (as opposed to "context-independent" antibodies) are capable of binding selectively to a subset, but not all, of proTGFβ1 complexes associated with a particular biological context. For example, matrix-selective targeting enables specific inhibition of TGFβ1 function associated with the ECM. ECM-selective inhibition can be achieved by the use of antibodies or fragments thereof that selectively target the ECM components, LTBP1-proTGFβ1 and/or LTBP3-proTGFβ1. Antibodies and fragments disclosed herein therefore represent a class of context-specific antibodies. LTBP1-specific and LTBP3-specific inhibitors of TGFβ1 activation are also context-specific antibodies.

Cross-block/cross-blocking: a first antibody or antigen-binding portion thereof and a second antibody or antigen-binding portion thereof cross-block with each other with respect to the same antigen, for example, as assayed by as measured by Biolayer Interferometry (such as Octet) or surface plasmon resonance (such as Biacore System), using standard test conditions, e.g., according to the manufacturer's instructions (e.g., binding assayed at room temperature, —20-25° C.). The first antibody or fragment thereof and the second antibody or fragment thereof may have the same epitope; may have non-identical but overlapping epitopes; or, may have separate (different) epitopes which are in close proximity in a three-dimensional space, such that antibody binding is cross-blocked via steric hindrance. "Cross-block" means that binding of the first antibody to an antigen prevents binding of the second antibody to the same antigen, and similarly, binding of the second antibody to an antigen prevents binding of the first antibody to the same antigen.

Dissociation rate: The term dissociation rate as used herein has the meaning understood by the skilled artisan in the pertinent art (e.g., antibody technology) as refers to a kinetics parameter measured by how fast/slow a ligand (e.g., antibody or fragment) dissociates from its binding target (e.g., antigen). Dissociation rate is also referred to as the "off" rate ("$k_{OFF}$"). Relative on/off rates between an antibody and its antigen (i.e., $k_{ON}$ and $k_{OFF}$) determine the overall strength of the interaction, or affinity, typically expressed as a dissociation constant, or $K_D$. Therefore, equivalent affinities (e.g., $K_D$ values) may be achieved by having fast association (high $k_{ON}$), slow dissociation (low $k_{OFF}$), or contribution from both factors. Monovalent interactions may be measured by the use of monovalent antigen-binding molecules/fragments, such as fAb (Fab), whilst divalent interactions may be measured by the use of divalent antigen-binding molecules such as whole immunoglobulins (e.g., IgGs). Dissociation kinetics may be expressed in terms of dissociation half-time (sometimes referred to as half binding time), or t½, defined as a duration of time it takes for one half the number of antibody molecules (e.g., mAb, Fab, etc.) to dissociate from bound antigen. Thus, antibodies with slow dissociation rates have long dissociation half-time, and antibodies with fast dissociation rates have short dissociation half-time.

Dosage: As used herein, typical therapeutic dosage of an antibody of the present invention ranges between about 1-30 mg/kg per dose. A typical dosing regimen may include once a week, every 2 weeks, every 3 weeks, every 4 weeks, once a month, every 6 weeks, etc.

ECM-associated (or "matrix-associated") TGFβ1: The term refers to TGFβ1 or its signaling complex (e.g., pro/latent TGFβ31) that is a component of (e.g., deposited into) the extracellular matrix. TGFβ1 that is presented by LTBP1 or LTBP3 is an ECM-associated TGFβ1.

Effective amount: An "effective amount" (or therapeutically effective amount) is a dosage or dosing regimen that achieves statistically significant clinical benefits in a patient population.

Fibrotic disorder: The term "fibrosis" or "fibrotic condition/disorder" refers to the process or manifestation characterized by the pathological accumulation of extracellular matrix (ECM) components, such as collagens, within a tissue or organ. Fibrosis can include primary fibrosis, as well as secondary fibrosis that are associated with a disease or disorder.

GARP-proTGFβ1: As used herein, the term "GARP-proTGFβ1" refers to a protein complex comprising a pro-protein form or latent form of a transforming growth factor-β1 (TGFβ1) protein associated with a glycoprotein-A repetitions predominant protein (GARP) or fragment or variant thereof. The proTGFβ1 homodimer is capable of forming covalent association with a single molecule of GARP via disulfide bonds. The term "GARP-TGFβ1" may be used interchangeably. GARP-proTGFβ1 expression is limited to certain cell types, such as regulatory T cells (Treg).

Human antibody: The term "human antibody," as used herein, is intended to include antibodies having variable and constant regions derived from human germline immunoglobulin sequences. The human antibodies of the present disclosure may include amino acid residues not encoded by human germline immunoglobulin sequences (e.g., mutations introduced by random or site-specific mutagenesis in vitro or by somatic mutation in vivo), for example in the CDRs and in particular CDR3 (e.g., CDR-H3 or CDR-L3 mutagenesis).

Humanized antibody: The term "humanized antibody" refers to antibodies, which comprise heavy and light chain variable region sequences from a non-human species (e.g., a mouse) but in which at least a portion of the VH and/or VL sequence has been altered to be more "human-like," i.e., more similar to human germline variable sequences. One type of humanized antibody is a CDR-grafted antibody.

Immune suppression/immunosuppression: The term immunosuppression refers to suppression or reduction of the strength of the body's immune system. Patients who "benefit from immunosuppression" include those who have advanced stages of organ fibrosis and are candidates for, being considered for, or have undergone transplantation.

Isoform-specific: The term "isoform specificity" refers to an agent's ability to discriminate one isoform over other structurally related isoforms (i.e., selectivity). An isoform-specific TGFβ inhibitor exerts its inhibitory activity towards one isoform of TGFβ but not the other isoforms of TGFβ at a given concentration. For example, an isoform-specific TGFβ1 antibody selectively binds TGFβ1. A TGFβ1-specific inhibitor (antibody) preferentially targets (binds thereby inhibits) the TGFβ1 isoform over TGFβ2 or TGFβ3 with substantially greater affinity. For example, the selectivity in this context may refer to at least a 500-1000-fold difference in respective affinities as measured by an in vitro binding assay such as Octet and Biacor. In some embodiments, the selectivity is such that the inhibitor when used at a dosage effective to inhibit TGFβ1 in vivo does not inhibit TGFβ2 and TGFβ3. Context-specific inhibitors of the present disclosure are also isoform-specific.

Isolated: An "isolated" antibody as used herein, refers to an antibody that is substantially free of other antibodies having different antigenic specificities. In some embodiments, an isolated antibody is substantially free of other unintended cellular material and/or chemicals.

Long-term or chronic administration: As used herein, a therapeutic regimen that involves over six months of treatment is considered long-term. In some patient populations, long-term therapeutic regimens involve administration of a drug (such as context-selective TGFβ1 inhibitors) for an indefinite duration of time.

LRRC33-proTGFβ1: As used herein, the term "LRRC33-TGFβ1 complex" refers to a complex between a pro-protein form or latent form of transforming growth factor-β1 (TGFβ1) protein and a Leucine-Rich Repeat-Containing Protein 33 (LRRC33; also known as Negative Regulator Of Reactive Oxygen Species or NRROS) or fragment or variant thereof. In some embodiments, a LRRC33-TGFβ1 complex comprises LRRC33 covalently linked with pro/latent TGFβ1 via one or more disulfide bonds. In other embodiments, a LRRC33-TGFβ1 complex comprises LRRC33 non-covalently linked with pro/latent TGFβ1. In some embodiments, a LRRC33-TGFβ1 complex is a naturally-occurring complex, for example a LRRC33-TGFβ1 complex in a cell.

LTBP1-TGFβ1: As used herein, the term "LTBP1-TGFβ1 complex" (or "LTBP1-proTGFβ1 complex") refers to a protein complex comprising a pro-protein form or latent form of transforming growth factor-β1 (TGFβ31) protein (may be referred to as "proTGFβ31" herein) and a latent TGF-beta binding protein 1 (LTBP1) or fragment or variant thereof. In some embodiments, a LTBP1-TGFβ1 complex comprises LTBP1 covalently linked with pro/latent TGFβ1 via one or more disulfide bonds. In other embodiments, a LTBP1-TGFβ1 complex comprises LTBP1 non-covalently linked with pro/latent TGFβ1. In some embodiments, a LTBP1-TGFβ1 complex is a naturally-occurring complex, for example a LTBP1-TGFβ1 complex in a cell. An exemplary LTBP1-TGFβ1 complex is shown in FIG. 3.

LTBP3-TGFβ1: As used herein, the term "LTBP3-TGFβ1 complex" (or "LTBP3-proTGFβ1 complex")refers to a protein complex comprising a pro-protein form or latent form of transforming growth factor-β1 (TGFβ31) protein (may be referred to as "proTGFβ31" herein) and a latent TGF-beta binding protein 3 (LTBP3) or fragment or variant thereof. In some embodiments, a LTBP3-TGFβ1 complex comprises LTBP3 covalently linked with pro/latent TGFβ1 via one or more disulfide bonds. In other embodiments, a LTBP3-TGFβ1 complex comprises LTBP1 non-covalently linked with pro/latent TGFβ1. In some embodiments, a LTBP3-TGFβ1 complex is a naturally-occurring complex, for example a LTBP3-TGFβ1 complex in a cell. An exemplary LTBP3-TGFβ1 complex is shown in FIG. 3.

Macrophages: Macrophages are a type of white blood cells of the immune system and includes heterogeneous, phenotypically diverse subpopulations of myeloid cells. Some macrophages differentiate from bone marrow-derived, circulating monocytes, while others are tissue-specific macrophages that reside within particular anatomical or tissue locations ("resident" macrophages). Tissue-specific macrophages include but are not limited to: Adipose tissue macrophages; Kupffer cells (Liver); Sinus histiocytes (Lymph nodes); Alveolar macrophages (or dust cells, Pulmonary alveoli of lungs); Tissue macrophages (histiocytes) leading to giant cells (Connective tissue); Langerhans cells (Skin and mucosa); Microglia (Central nervous system); Hofbauer cells (Placenta); Intraglomerular mesangial cells (Kidney); Osteoclasts (Bone); Epithelioid cells (Granulomas); Red pulp macrophages (or Sinusoidal lining cells, Red pulp of spleen); Peritoneal macrophages (Peritoneal cavity); and, LysoMac (Peyer's patch). Macrophages, e.g., bone-marrow derived monocytes, can be activated by certain stimuli (such as cytokines) resulting in polarized phenotypes, e.g., M1 and M2. M2-biased activated macrophages are further classified into several phenotypically distinct subtypes, such as M2a, M2b, M2c (e.g., pro-fibrotic) and M2d (pro-tumor or TAM-like).

Matrix-associated proTGF LTBP1 and LTBP3 are presenting molecules that are components of the extracellular matrix (ECM). LTBP1-proTGFβ1 and LTBP3-proTGFβ1 may be collectively referred to as "ECM-associated" (or "matrix-associated") proTGFβ1 complexes, that mediate ECM-associated TGFβ1 activation/signaling.

Maximally tolerated dose (MTD): The term MTD generally refers to, in the context of safety/toxicology considerations, the highest amount of a test article (such as a TGFβ1 inhibitor) evaluated with no observed adverse effect level (NOAEL). For example, the NOAEL for Ab2 in rats was the highest dose evaluated (100 mg/kg), suggesting that the MTD for Ab2 is >100 mg/kg, based on a four-week toxicology study.

Myeloid-derived suppressor cell: Myeloid-derived suppressor cells (MDSCs) are a heterogeneous population of cells generated during various pathologic conditions and thought to represent a pathologic state of activation of monocytes and relatively immature neutrophils. MDSCs include at least two categories of cells termed i) "granulocytic" (G-MDSC) or polymorphonuclear (PMN-MDSC), which are phenotypically and morphologically similar to neutrophils; and ii) monocytic (M-MDSC) which are phenotypically and morphologically similar to monocytes. MDSCs are characterized by a distinct set of genomic and biochemical features, and can be distinguished by specific surface molecules. For example, human G-MDSCs/PMN-MDSCs typically express the cell-surface markers CD11b, CD33, CD15 and CD66. In addition, human G-MDSCs/PMN-MDSCs may also express HLA-DR and/or Arginase. By comparison, human M-MDSCs typically express the cell surface markers CD11b, CD33 and CD14. The MDSCs may also express CD39 and CD73 to mediate adenosine signaling involved in organ fibrosis (such as liver fibrosis, and lung fibrosis), cancer and myelofibrosis). In addition, human M-MDSCs may also express HLA-DR. In addition to such cell-surface markers, MDSCs are characterized by the ability to suppress immune cells, such as T cells, NK cells and B cells Immune suppressive functions of MDSCs may include inhibition of antigen-non-specific function and inhibition of antigen-specific function. MDSCs can express cell surface LRRC33 and/or LRRC33-proTGFβ1.

Myofibroblast: Myofibroblasts are cells with certain phenotypes of fibroblasts and smooth muscle cells and generally express vimentin, alpha-smooth muscle actin (α-SMA; human gene ACTA2) and paladin. In many disease conditions involving extracellular matrix dysregulations (such as increased matrix stiffness), normal fibroblast cells become de-differentiated into myofibroblasts in a TGFβ-dependent manner.

Off rate ($k_{OFF}$): The off rate is a kinetic parameter of how fast or how slowly an antibody (such as mAb) or antigen-binding fragment (such as fAb) dissociates from its antigen and may be also referred to as the dissociation rate. Dissociation rates can be experimentally measured in suitable in vitro binding assays, such as BLI (Octet®)- and/or SPR (Biacore)-based systems. In the context of antibody-antigen binding kinetics, the term "half-binding-time" (T½) or "dissociation half-time" refers to the duration of time required for half the number of antibody molecules (e.g., mAb, Fab) to dissociate from the bound antigen (e.g., LTBP1-proTGFβ1, LTBP3-proTGFβ31). Thus, an antibody that dissociates slowly (i.e., low off rates) from its antigen has a long T½. Conversely, an antibody that dissociates rapidly (i.e., high off rates) from its antigen has a short T½.

Pan-TGFβ inhibitor/pan-inhibition of TGFβ: The term "pan-TGFβ inhibitor" refers to any agent that is capable of inhibiting or antagonizing all three isoforms of TGFβ. Such an inhibitor may be a small molecule inhibitor of TGFβ isoforms. The term includes pan-TGFβ antibody which refers to any antibody capable of binding to each of TGFβ isoforms, i.e., TGFβ1, TGFβ2, and TGFβ3. In some embodiments, a pan-TGFβ antibody binds and neutralizes activities of all three isoforms, i.e., TGFβ1, TGFβ2, and TGFβ3 activities.

Potency: The term "potency" as used herein refers to activity of a drug, such as a functional antibody (or fragment) having inhibitory activity, with respect to concentration or amount of the drug to produce a defined effect. For example, an antibody capable of producing certain effects at a given dosage is more potent than another antibody that requires twice the amount (dosage) to produce equivalent effects. Potency may be measured in cell-based assays, such as TGFβ activation/inhibition assays. In some cases, the degree of TGFβ activation, such as activation triggered by integrin binding, can be measured in the presence or absence of test article (e.g., inhibitory antibodies) in a cell-based system. Typically, antibodies with higher affinities tend to show higher potency than antibodies with lower affinities.

Presenting molecule: Presenting molecules are proteins that form covalent bonds with latent pro-proteins (e.g., proTGFβ31) and "present" the inactive complex in an extracellular niche (such as ECM or immune cell surface) thereby maintaining its latency until an activation event occurs. Known presenting molecules for proTGFβ1 include: LTBP1, LTBP3, GARP and LRRC33, which can form presenting molecule-proTGFβ1 complexes, namely, LTBP1-proTGFβ1, LTBP3-proTGFβ1, GARP-proTGFβ1 and LRRC33-proTGFβ1, respectively. LTBP1 and LTBP3 are components of the extracellular matrix (ECM); therefore, LTBP1-proTGFβ1 and LTBP3-proTGFβ1 may be collectively referred to as "ECM-associated" (or "matrix-associated") proTGFβ1 complexes, that mediate ECM-associated TGFβ1 signaling/activities. GARP and LRRC33, on the other hand, are transmembrane proteins expressed on cell surface of certain cells; therefore, GARP-proTGFβ1 and LRRC33-proTGFβ1 may be collectively referred to as "cell-associated" (or "cell-surface") proTGFβ1 complexes, that mediate cell-associated (e.g., immune cell-associated) TGFβ1 signaling/activities.

ProTGFβ1: The term "proTGFβ1" as used herein is intended to encompass precursor forms of inactive TGFβ1 complex that comprises a prodomain sequence of TGFβ1 within the complex. Thus, the term can include the pro-, as well as the latent-forms of TGFβ1. The expression "pro/latent TGFβ1" may be used interchangeably. The "pro" form of TGFβ1 exists prior to proteolytic cleavage at the furin site. Once cleaved, the resulting form is said to be the "latent" form of TGFβ1. The "latent" complex remains associated until further activation trigger, such as integrin-driven activation event. The proTGFβ1 complex is comprised of dimeric TGFβ1 pro-protein polypeptides, linked with disulfide bonds. The latent dimer complex is covalently linked to a single presenting molecule via the cysteine residue at position 4 (Cys4) of each of the proTGFβ1 polypeptides. The adjective "latent" may be used generally to describe the "inactive" state of TGFβ1, prior to integrin-mediated or other activation events. The proTGFβ1 polypeptide contains a prodomain (LAP) and a growth factor domain (SEQ ID NO: 12).

Regulatory T cell (Treg): "Regulatory T cells," or Tregs, are a type of immune cells characterized by the expression of the biomarkers, CD4, forkhead box P3 (FOXP3), and CD25, as well as STAT5. Tregs are sometimes referred to as suppressor T cells and represent a subpopulation of T cells that modulate the immune system, maintain tolerance to self-antigens, and prevent autoimmune disease. Tregs are immunosuppressive and generally suppress or downregulate induction and proliferation of effector T (Teff) cells. Tregs can develop in the thymus (so-called CD4+Foxp3+"natural" Tregs) or differentiate in the periphery upon priming of naïve CD4+ T cells by antigen-presenting cells (APCs), for example, following exposure to TGFβ or retinoic acid. Treg cells produce and secrete cytokines including IL-10 and TGFβ1. Generally, differentiation of Treg and Th17 cells is negatively correlated.

Specific binding: As used herein, the term "specific binding" or "specifically binds" means that the interaction of the antibody, or antigen-binding portion thereof, with an antigen is dependent upon the presence of a particular structure (e.g., an antigenic determinant or epitope). For example, the antibody, or antigen-binding portion thereof, binds to a specific protein rather than to proteins generally. In some embodiments, an antibody, or antigen-binding portion thereof, specifically binds to a target, e.g., TGFβ1, if the antibody has a $K_D$ for the target of at least about $10^{-6}$ M. More preferably, the measured $K_D$ values of such antibody range between 10-100 nM. More preferably, the measured $K_D$ values of such antibody range between 0.1-10 nM.

Subject: The term "subject" in the context of therapeutic applications refers to an individual who receives clinical care or intervention, such as treatment, diagnosis, etc. Suitable subjects include vertebrates, including but not limited to mammals (e.g., human and non-human mammals). Where the subject is a human subject, the term "patient" may be used interchangeably. In a clinical context, the term "a patient population" or "patient subpopulation" is used to refer to a group of individuals that falls within a set of criteria, such as clinical criteria (e.g., disease presentations, disease stages, susceptibility to certain conditions, responsiveness to therapy, etc.), medical history, health status, gender, age group, genetic criteria (e.g., carrier of certain mutation, polymorphism, gene duplications, DNA sequence repeats, etc.) and lifestyle factors (e.g., smoking, alcohol consumption, exercise, etc.).

TGFβ inhibitor: The term "TGFβ inhibitor" refers to any agent capable of antagonizing biological activities or function of TGFβ growth factor (e.g., TGFβ31, TGFβ2 and/or TGFβ3). The term is not intended to limit its mechanism of action and includes, for example, neutralizing inhibitors, receptor antagonists, soluble ligand traps, and activation inhibitors of TGFβ.

T helper 17 cell: T helper 17 cells (Th17) are a subset of pro-inflammatory T helper cells characterized by the markers STAT3 and RORγt and the production of cytokines including interleukin 17 (IL-17A/F) and IL-22. Th17 cells are differentiated when naïve T cells are exposed to TGFβ and IL-6. Th17 cells are generally associated with tissue inflammation, autoimmunity and clearance of certain pathogens. The differentiation of Th17 cells and Treg cells is generally inversely related. Imbalance in Th17-to-Treg ratios (e.g., "Th17/Treg") has been implicated in a number of pathologies, such as fibrotic conditions and autoimmune conditions.

Th17/Treg ratio: Th17-to-Treg ratios refer to measured ratios (relative proportions) of the number of Th17 cells versus the number of Treg cells in a tissue or sample of interest. Typically, known cell markers are used to identify, sort or isolate the cell types. Such markers include cell-surface molecules expressed on the particular cell type; a cytokine or a panel of cytokines produced (e.g., secreted) by the particular cell type, and/or mRNA expression of certain gene markers that serve as a signature/profile of the particular cell type. For example, the Th17/Treg ratio of one (1) means that there is an equal or equivalent number of each of the cell types within the tissue or sample being evaluated. The Th17/Treg ratio of two (2) means that there is approximately twice the number of Th17 cells as compared to Treg cells in the tissue or sample. An elevated Th17/Treg ratio may arise from an increased number of Th17 cells, a decreased number of Treg cells, or combination thereof.

Therapeutic window: The term "therapeutic window" refers to a range of doses/concentrations that produces therapeutic response without causing significant/observable/ unacceptable adverse effect (e.g., within adverse effects that are acceptable or tolerable) in subjects. Therapeutic window may be calculated as a ratio between minimum effective concentrations (MEC) to the minimum toxic concentrations (MTC). To illustrate, a TGFβ1 inhibitor that achieves in vivo efficacy at 10 mg/kg and shows tolerability or acceptable toxicities at 100 mg/kg provides at least a 10-fold (e.g., 10×) therapeutic window. By contrast, a pan-inhibitor of TGFβ that is efficacious at 10 mg/kg but causes adverse effects at 5 mg/kg is said to have "dose-limiting toxicities." For example, the applicants have found that a context-independent TGFβ1 inhibitor antibody is efficacious at dosage ranging between about <3 and 30 mg/kg/week and is free of observable toxicities associated with pan-inhibition of TGFβ at least 100 mg/kg/week for 4 weeks in preclinical models such as rats. Based on this, the context-independent TGFβ1 inhibitor antibody shows at minimum a 3.3-fold and up to 33-fold therapeutic window.

Toxicity: As used herein, the term "toxicity" or "toxicities" refers to unwanted in vivo effects in patients associated with a therapy administered to the patients, such as undesirable side effects and adverse events. "Tolerability" refers to a level of toxicities associated with a therapy or therapeutic regimen, which can be reasonably tolerated by patients, without discontinuing the therapy due to the toxicities (i.e., acceptable level of toxicities). Typically, toxicity/toxicology studies are carried out in one or more preclinical models prior to clinical development to assess safety profiles of a drug candidate (e.g., monoclonal antibody therapy). Toxicity/toxicology studies may help determine the "no observed adverse effect level (NOAEL)" and the "maximally tolerated dose (MTD)" of a test article, based on which a therapeutic window may be deduced. Preferably, a species that is shown to be sensitive to the particular intervention should be chosen as a preclinical animal model in which safety/toxicity study is to be carried out. In case of TGFβ inhibition, suitable species include rats, dogs, and cynos. Mice are reported to be less sensitive to pharmacological inhibition of TGFβ and may not reveal toxicities that are potentially dangerous in other species, including human, although certain studies report toxicities observed with pan-inhibition of TGFβ in mice. To illustrate, the NOAEL for a context-independent TGFβ1 inhibitor antibody in rats was the highest dose evaluated (100 mg/kg), suggesting that the MTD is >100 mg/kg per week, based on a four-week toxicology study.

Treat/treatment: The term "treat" or "treatment" includes therapeutic treatments, prophylactic treatments, and applications in which one reduces the risk that a subject will develop a disorder or other risk factor. Thus the term is intended to broadly mean: causing therapeutic benefits in a patient by, for example, enhancing or boosting the body's immunity; reducing or reversing immune suppression; reducing, removing or eradicating harmful cells or substances from the body; reducing disease burden (e.g., tumor burden); preventing recurrence or relapse; prolonging a refractory period, and/or otherwise improving survival. Treatment does not require the complete curing of a disorder and encompasses embodiments in which one reduces symptoms or underlying risk factors. In the context of combination therapy, the term may also refer to: i) the ability of a second therapeutic to reduce the effective dosage of a first therapeutic so as to reduce side effects and increase tolerability; ii) the ability of a second therapy to render the patient more responsive to a first therapy; and/or iii) the ability to effectuate additive or synergistic clinical benefits.

Variable region: The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. In certain embodiments, variable regions of different antibodies differ extensively in amino acid sequence even among antibodies of the same species. The variable region of an antibody typically determines specificity of a particular antibody for its target.

TGFβ1

In mammals, the transforming growth factor-beta (TGFβ3) superfamily is comprised of at least 33 gene products. These include the bone morphogenetic proteins (BMPs), activins, growth and differentiation factors (GDFs), and the three isoforms of the TGFβ family: TGFβ1, TGFβ2, and TGFβ3. The TGFβ s are thought to play key roles in diverse processes, such as inhibition of cell proliferation, extracellular matrix (ECM) remodeling, and immune homeostasis. The importance of TGFβ1 for T cell homeostasis is demonstrated by the observation that TGFβ1−/− mice survive only 3-4 weeks, succumbing to multiorgan failure due to massive immune activation (Kulkarni, A. B., et al., Proc Natl Acad Sci USA, 1993. 90(2): p. 770-4; Shull, M. M., et al., Nature, 1992. 359(6397): p. 693-9). The roles of TGFβ2 and TGFβ3 are less clear. Whilst the three TGFβ isoforms have distinct temporal and spatial expression patterns, they signal through the same receptors, TGFβRI and TGFβ3, although in some cases, for example for TGFβ2 signaling, type III receptors such as betaglycan are also required (Feng, X. H. and R. Derynck, Annu Rev Cell Dev Biol, 2005. 21: p. 659-93; Massague, J., Annu Rev Biochem, 1998. 67: p. 753-91). Ligand-induced oligomerization of TGFβRI/II triggers the phosphorylation of SMAD transcription factors, resulting in the transcription of target genes, such as Col1al, Col3al, ACTA2, and SERPINE1 (Massague, J., J. Seoane, and D. Wotton, Genes Dev, 2005. 19(23): p. 2783-810). SMAD-independent TGFβ signaling pathways have also been described, for example in cancer or in the aortic lesions of Marfan mice (Derynck, R. and Y. E. Zhang, Nature, 2003. 425(6958): p. 577-84; Holm, T. M., et al., Science, 2011. 332(6027): p. 358-61).

The biological importance of the TGFβ pathway in humans has been validated by genetic diseases. Camurati-Engelman disease results in bone dysplasia due to an autosomal dominant mutation in the TGFB1 gene, leading to constitutive activation of TGFβ1 signaling (Janssens, K., et al., J Med Genet, 2006. 43(1): p. 1-11). Patients with Loeys/Dietz syndrome carry autosomal dominant mutations in components of the TGFβ signaling pathway, which cause aortic aneurism, hypertelorism, and bifid uvula (Van Laer, L., H. Dietz, and B. Loeys, Adv Exp Med Biol, 2014. 802: p. 95-105). As TGFβ pathway dysregulation has been implicated in multiple diseases, several drugs that target the TGFβ pathway have been developed and tested in patients, but with limited success. Most TGFβ inhibitors described to date lack isoform specificity as briefly summarized below.

Fresolimumab, a humanized monoclonal antibody that binds and inhibits all three isoforms of TGFβ has been tested clinically in patients with focal segmental glomerulosclerosis, malignant melanoma, renal cell carcinoma, and systemic sclerosis (Rice, L. M., et al., J Clin Invest, 2015. 125(7): p. 2795-807; Trachtman, H., et al., Kidney Int, 2011. 79(11): p.

1236-43; Morris, J. C., et al., PLoS One, 2014. 9(3): p. e90353). Additional companies have developed monoclonal antibodies against the TGFβ growth factors with varying degrees of selectivity for TGFβ isoforms. Such agents likely elicit toxicities in vivo through residual activity against other TGFβ family members besides TGFβ1. This lack of isoform specificity may be due to the high degree of sequence identity between isoforms.

Other approaches to target the TGFβ pathway include ACE-1332, a soluble TGFβRII-Fc ligand trap from Acceleron (Yung, L. M., et al., A Am J Respir Crit Care Med, 2016. 194(9): p. 1140-1151), or small molecule inhibitors of the ALK5 kinase, such as Eli Lilly's galunisertib. ACE-1332 binds TGFβ1 and TGFβ3 with equally high affinity (Yung, L. M., et al., Am J Respir Crit Care Med, 2016. 194(9): p. 1140-1151), and ALK5 inhibitors block the activity of all growth factors that signal through TGFR1. Substantial toxicities have been found in preclinical studies using ALK5 inhibitors (Anderton, M. J., et al., Toxicol Pathol, 2011. 39(6): p. 916-24; Stauber, A., et al., Clinical Toxicology, 2014. 4(3): p. 1-10), and sophisticated clinical dosing schemes are required to maintain efficacy while reducing adverse events (Herbertz, S., et al., Drug Des Devel Ther, 2015. 9: p. 4479-99). In fact, the question of TGFβ signaling specificity and its possible effect on toxicity observed with the known TGFβ inhibitors has not been raised in most, if not all, of the candidate drugs that attempted to block TGFβ. For example, how much of the toxicities are due to inhibition of TGFβ1 versus TGFβ2 and/or TGFβ3 has not been addressed. Similarly, modes of TGFβ activation have not been taken into account in designing or developing ways to antagonize TGFβ signaling.

Recent structural insights into the activation mechanism of TGFβ1 (Shi, M., et al., Nature, 2011. 474(7351): p. 343-9) have enabled more specific approaches to TGFβ inhibition (see, e.g., PCT/US2017/21972, the entire contents of which are incorporated herein by reference). Unlike other cytokines, TGFβ superfamily members are not secreted as active growth factors, but as dimeric pro-proteins which consist of an N-terminal prodomain and a C-terminal growth factor domain. Cleavage of proTGFβ1 by furin proteases separates the homodimeric growth factor domain from its prodomain, also referred to as latency associated peptide (LAP). However, the growth factor and LAP remain non-covalently associated, forming a latent complex which is unable to bind its receptors and induce signaling. During translation, latent TGFβ1, also called the small latent complex (SLC), becomes linked to "presenting molecules" via disulfide bridges, forming the large latent complex (LLC). These molecules allow proTGFβ1 to be presented in specific cellular or tissue contexts. Two cysteines near the N-terminus of the latent TGFβ1 link to appropriately positioned cysteines on the presenting molecule. The identity of the presenting molecule depends on the environment and cell type producing latent TGFβ1. For example, fibroblasts secrete latent TGFβ1 tethered to latent TGFβ-binding proteins (LTBPs), which then associate with proteins in the extracellular matrix (ECM) (i.e., fibronectin, fibrillin-1) to link latent TGFβ3 to the ECM (Robertson et al. Matrix Biol 47: 44-53 (2015) (FIG. 2A). On the surface of activated regulatory T cells latent TGFβ1 is covalently linked to the transmembrane protein GARP (glycoprotein-A repetitions predominant protein (GARP), and a protein closely related to GARP, LRRC33 (leucine-rich repeat-containing protein 33), serves as a presenting molecule for TGFβ1 on the surface of monocytes, macrophages and microglia (Wang, R., et al., Mol Biol Cell, 2012. 23(6): p. 1129-39 and T. A. Springer, Int. BMP Conference 2016).

A number of studies have shed light on the mechanisms of TGFβ1 activation. Three integrins, αVβ6, αVβ8, and αVβ1 have been demonstrated to be key activators of latent TGFβ1 (Reed, N. I., et al., Sci Transl Med, 2015. 7(288): p. 288ra79; Travis, M. A. and D. Sheppard, Annu Rev Immunol, 2014. 32: p. 51-82; Munger, J. S., et al., Cell, 1999. 96(3): p. 319-28). αV integrins bind the RGD sequence present in TGFβ1 and TGFβ1 LAPs with high affinity (Dong, X., et al., Nat Struct Mol Biol, 2014. 21(12): p. 1091-6). Transgenic mice with a mutation in the TGFβ1 RGD site that prevents integrin binding, but not secretion, phenocopy the TGFβ1−/− mouse (Yang, Z., et al., J Cell Biol, 2007. 176(6): p. 787-93). Mice that lack both 136 and 138 integrins recapitulate all essential phenotypes of TGFβ1 and TGFβ3 knockout mice, including multiorgan inflammation and cleft palate, confirming the essential role of these two integrins for TGFβ1 activation in development and homeostasis (Aluwihare, P., et al., J Cell Sci, 2009. 122(Pt 2): p. 227-32). Key for integrin-dependent activation of latent TGFβ1 is the covalent tether to presenting molecules; disruption of the disulfide bonds between GARP and TGFβ1 LAP by mutagenesis does not impair complex formation, but completely abolishes TGFβ1 activation by αVβ6 (Wang, R., et al., Mol Biol Cell, 2012. 23(6): p. 1129-39). The recent structure of latent TGFβ1 illuminates how integrins enable release of active TGFβ1 from the latent complex: the covalent link of latent TGFβ1 to its presenting molecule anchors latent TGFβ1, either to the ECM through LTBPs, or to the cytoskeleton through GARP or LRRC33. Integrin binding to the RGD sequence results in a force-dependent change in the structure of LAP, allowing active TGFβ1 to be released and bind nearby receptors (Shi, M., et al., Nature, 2011. 474(7351): p. 343-9). The importance of integrin-dependent TGFβ1 activation in disease has also been well validated. A small molecular inhibitor of αVβ1 protects against bleomycin-induced lung fibrosis and carbon tetrachloride-induced liver fibrosis (Reed, N. I., et al., Sci Transl Med, 2015. 7(288): p. 288ra79), and αVβ6 blockade with an antibody or loss of integrin 136 expression suppresses bleomycin-induced lung fibrosis and radiation-induced fibrosis (Munger, J. S., et al., Cell, 1999. 96(3): p. 319-28); Horan, G. S., et al., Am J Respir Crit Care Med, 2008. 177(1): p. 56-65). In addition to integrins, other mechanisms of TGFβ1 activation have been implicated, including thrombospondin-1 and activation by proteases such as matrix metalloproteinases (MMPs), cathepsin D or kallikrein. However, the majority of these studies were performed in vitro using purified proteins; there is less evidence for the role of these molecules from in vivo studies. Knockout of thrombospondin-1 recapitulates some aspects of the TGFβ1−/− phenotype in some tissues, but is not protective in bleomycin-induced lung fibrosis, known to be TGFβ3-dependent (Ezzie, M. E., et al., Am J Respir Cell Mol Biol, 2011. 44(4): p. 556-61). Additionally, knockout of candidate proteases did not result in a TGFβ1 phenotype (Worthington, J. J., J. E. Klementowicz, and M. A. Travis, Trends Biochem Sci, 2011. 36(1): p. 47-54). This could be explained by redundancies or by these mechanisms being critical in specific diseases rather than development and homeostasis.

TGFβ3 has been implicated in a number of biological processes, including fibrosis, immune-modulation and cancer progression. TGFβ1 was the first identified member of the TGFβ3 superfamily of proteins. Like other members of the TGFβ3 superfamily, TGFβ1 and the isoforms TGFβ2 and TGFβ3, are initially expressed as inactive precursor pro-protein forms (termed proTGF(3). TGFβ3 proteins (e.g., TGFβ1, TGFβ2 and TGF(33) are proteolytically cleaved by proprotein convertases (e.g., furin) to yield the latent form (termed latent TGF(3). In some embodiments, a pro-protein form or latent form of a TGFβ3 protein (e.g., TGFβ1, TGFβ2 and TGFβ3) may be referred to as "pro/latent TGFβ3 protein". TGFβ1 may be presented to other molecules in complex with multiple molecules including, for example, GARP (to form a GARP-TGF(31 complex), LRRC33 (to form a LRRC33-TGF(31 complex), LTBP1 (to form a LTBP1-TGF(31 complex), and/or LTBP3 (to form a LTBP3-TGF(31 complex). The TGFβ1 present in these complexes may be in either latent form (latent TGF(31) or in precursor form (proTGF(31).

Isoform Selectivity and Mechanisms of Action of TGF Inhibitors

From a safety standpoint, there has been an increasing recognition that broad inhibition of TGFβ across isoforms may be a cause of observed toxicities, which underscores the fact that no TGFβ inhibitors have been successfully developed to this day. To circumvent potentially dangerous adverse effects, a number of groups have recently turned to identifying inhibitors that target a subset—but not all—of the isoforms and still retain efficacy. From an efficacy standpoint, however, the prevailing view of the field remains to be that it is advantageous to inhibit multiple isoforms of TGFβ3 to achieve therapeutic effects, and to accommodate this, toxicity management by "careful dosing regimen" is suggested as a solution (Brennan et al. (2018) mAbs, 10:1, 1-17). Consistent with this premise, numerous groups are developing TGFβ3 inhibitors that target more than one isoforms. These include low molecular weight antagonists of TGFβ3 receptors, e.g., ALK5 antagonists, such as Galunisertib (LY2157299 monohydrate); monoclonal antibodies (such as neutralizing antibodies) that inhibit all three isoforms ("pan-inhibitor" antibodies) (see, for example, WO 2018/134681); monoclonal antibodies that preferentially inhibit two of the three isoforms (e.g., antibodies against TGFβ1/2 (for example WO 2016/161410) and TGFβ1/3 (for example WO 2006/116002); and engineered molecules (e.g., fusion proteins) such as ligand traps (for example, WO 2018/029367; WO 2018/129331 and WO 2018/158727). Similarly, inhibitors of integrins such as αVβ6 also block integrin-dependent activation of both TGFβ1 and TGFβ3 and therefore may be considered as isoform-non-selective inhibitors of TGFβ signaling. In addition, examples of antibodies that selectively bind and neutralize both TGFβ1 and TGFβ2 (i.e., TGFβ1/2 inhibitors) include XOMA 089 (or NIS793) and variants (see, for example, WO 2016/161410).

Previously, Applicant demonstrated that inhibition of TGFβ1 alone was sufficient to sensitize immunosuppressive tumors to a checkpoint inhibitor therapy even in tumors where both TGFβ1/3 are co-expressed (PCT/US2019/041373). Similarly, TGFβ1-selective inhibitors are shown to mitigate fibrosis in preclinical models, including mouse liver fibrosis model where both the TGFβ1/3 isoforms are co-expressed in the fibrotic tissue, albeit in discrete cell types, as observed by immunohistochemistry (data now shown). Surprisingly, inhibition of TGFβ3 promoted pro fibrotic phenotypes. The exacerbation of fibrosis is observed when the TGFβ3 inhibitor is used alone. In addition, when used in combination with a TGFβ1-selective inhibitor, the TGFβ3 inhibitor attenuated the anti-fibrotic effect of the TGFβ1-selective inhibitor, as evidenced by increased collagen accumulation in the fibrotic liver. These results raise the possibility that inhibitory potency against TGFβ3 may be an undesirable feature of TGFβ inhibitors to be used as therapy in situations where fibrosis is a concern.

Beyond the fibrosis context, there is a broader implication to this unexpected finding since the pro-fibrotic phenotype (e.g., increased collagen deposit into the ECM) is associated not only with fibrosis, but also with aspects of cancer progression, such as tumor invasion and metastasis. See, for example, Chakravarthy et al. (Nature Communications, (2018) 9:4692. "TGF-β-associated extracellular matrix genes link cancer-associated fibroblasts to immune evasion and immunotherapy failure"). Diseased tissues with dysregulated ECM, including fibrotic tissues and stroma of various tumor types, can express both TGFβ1 and TGFβ3. As of today, multiple groups are making effort to develop TGFβ inhibitors that target both of these isoforms, such as ligand traps, neutralizing antibodies and integrin inhibitors. However, the finding presented herein cautions that such approach may in fact exacerbate (e.g., worsen) the disease.

Accordingly, the present disclosure provides the teaching that for the treatment of a disorder involving ECM dysregulation, such as fibrosis and cancer, a TGFβ inhibitor that does not specifically target TGFβ3 should be selected. Preferably, such inhibitor is an isoform-selective inhibitor of TGFβ1, such as inhibitors that selectively target LTBP1/3-associated TGFβ1 (e.g., as disclosed herein). Related methods include a method for selecting a TGFβ inhibitor for use in the treatment of a fibrotic disorder in a subject, wherein the method includes the steps of: testing potency of one or more candidate inhibitors for the ability to inhibit TGFβ1, TGFβ2 and TGFβ3, and selecting an inhibitor that inhibits TGFβ1 but does not inhibit TGFβ3, for therapeutic use. Related treatment methods can further comprise a step of administering to the subject the inhibitor that inhibits TGFβ1 but does not inhibit TGFβ3 in an amount sufficient to treat the fibrotic disorder or treat a subject having or at risk of developing a fibrotic disorder. Preferably, the selected inhibitor is an antibody or fragment thereof that selectively inhibits LTBP1- and/or LTBP3-associated TGFβ1 signaling (e.g., as disclosed herein). In some embodiments, subjects at risk of developing a fibrotic disorder may suffer from a metabolic disorder, such as diabetes, obesity and NASH. The proposed exclusion of the subpopulation of patients is aimed to reduce risk of triggering, facilitating or exacerbating a pro-fibrotic effect.

In addition to the possible concerns of inhibiting TGFβ3 addressed above, Takahashi et al. (Nat Metab. 2019, 1(2): 291-303) recently reported a beneficial role of TGFβ2 in regulating metabolism. The authors identified TGFβ2 as an exercise-induced adipokine, which stimulated glucose and fatty acid uptake in vitro, as well as tissue glucose uptake in vivo; which improved metabolism in obese mice; and, which reduced high fat diet-induced inflammation. Moreover, the authors observed that lactate, a metabolite released from muscle during exercise, stimulated TGFβ2 expression in human adipocytes and that a lactate-lowering agent reduced circulating TGFβ2 levels and reduced exercise-stimulated improvements in glucose tolerance. These observations suggest that therapeutic use of a TGFβ inhibitor with inhibitory activity towards the TGFβ2 isoform may be harmful at least in the metabolic aspect.

Without being bound by particular theory, it is contemplated that it is advantageous to select a TGFβ1-selective inhibitor as a TGFβ inhibitor for use in the treatment of a metabolic disease, such as liver fibrosis associated with NASH. In preferred embodiments, the TGFβ1-selective inhibitor selected for use in the treatment of the metabolic disease selectively inhibits LTBP1/3-associated TGFβ1, such as the antibodies and fragments disclosed herein. Accordingly, the invention includes a a TGFβ inhibitor for use in the treatment of a metabolic disease in a subject, wherein the treatment comprises selection of a TGFβ inhibitor that inhibits TGFβ1 but does not inhibit TGFβ2, optionally wherein the inhibitor is TGFβ1-selective, and administration of the inhibitor to a subject suffering from a metaboic disease. The metabolic disease may be a liver disease, such as liver fibrosis, NASH, NAFLD, optionally accompanied by obesity and/or type 2 diabetes. In preferred embodiments, the TGFβ1-selective inhibitor is an antibody or antigen-binding fragment thereof that selectively targets matrix-associated TGFβ1 (e.g., LTBP1-proTGFβ1 and LTBP3-proTGFβ31), such as those disclosed herein.

In preferred embodiments, a TGFβ inhibitor for use in the treatment of a fibrotic disorder is an isoform-selective activation inhibitor of TGFβ1 (such as the novel antibodies with low $k_{OFF}$ or long $t^{1/2}$ disclosed herein) capable of targeting matrix-associated TGFβ1-containing latent complexes in vivo.

The antibodies of the present disclosure work by preventing the step of TGFβ1 activation. In some embodiments, such inhibitors can inhibit integrin-dependent (e.g., mechanical or force-driven) activation of TGFβ1. In some embodiments, such inhibitors can inhibit protease-dependent or protease-induced activation of TGFβ1. The latter includes inhibitors that inhibit the TGFβ1 activation step in an integrin-independent manner. In some embodiments, such inhibitors can inhibit TGFβ1 activation irrespective of the mode of activation, e.g., inhibit both integrin-dependent activation and protease-dependent activation of TGFβ1. Non-limiting examples of proteases which may activate TGFβ1 include serine proteases, such as Kallikreins, Chemotrypsin, Trypsin, Elastases, Plasmin, thrombin, as well as zinc metalloproteases (MMP family) such as MMP-2, MMP-9, MMP-12, MMP-13 and ADAM proteases (e.g., ADAM10 and ADAM17) Kallikreins include plasma-Kallikreins and tissue Kallikreins, such as KLK1, KLK2, KLK3, KLK4, KLKS, KLK6, KLK7, KLK8, KLK9, KLK10, KLK11, KLK12, KLK13, KLK14 and KLK15.

Latent TGFβ-Binding Proteins (LTBPs)

In mammals there are four known LTBPs, LTBP1-4, each with multiple splice variants (Robertson, I. B., et al., Matrix Biol, 2015. 47: p. 44-53). LTBP2 is the only LTBP that does not associate with latent TGFβ (Saharinen, J. and J. Keski-Oja, Mol Biol Cell, 2000. 11(8): p. 2691-704). While the association between LTBP1 or LTBP3 and latent TGFβ1 has been well validated, the role of LTBP4 in TGFβ presentation is less clear. The complex with LTBP4 and latent TGFβ1 appears to form much less efficiently, potentially due to the absence of several negatively charged residues in the TGFβ-binding domain of LTBP4 (Saharinen, J. and J. Keski-Oja, Mol Biol Cell, 2000. 11(8): p. 2691-704; Chen, Y., et al., J Mol Biol, 2005. 345(1): p. 175-86). Both LTBP4S−/− mice and Urban-Rifkin-Davis syndrome patients, who have null mutations in LTBP4, suffer from disrupted elastic fiber assembly (Urban, Z., et al., Am J Hum Genet, 2009. 85(5): p. 593-605; Dabovic, B., et al., J Cell Physiol, 2015. 230(1): p. 226-36). Additionally, while LTBP4S−/− mice have a lung septation and an elastogenesis defect, transgenic mice with an LTBP4 that cannot form a complex with latent TGFβ1 have no obvious phenotype (Dabovic, B., et al., J Cell Physiol, 2015. 230(1): p. 226-36). Whether LTBP4 is directly involved in regulation of latent TGFβ1 by functioning as a presenting molecule is unclear; LTBP4 may instead be required for proper formation of elastic fibrils in the ECM and its loss indirectly affect latent TGFβ1 activation through defects in the ECM.

In one aspect, the present invention is directed to inhibitors, e.g., immunoglobulins, e.g., antibodies, or antigen-binding portions thereof, that selectively bind to a complex containing a TGFβ pro-protein and a LTBP protein (e.g., LTBP1 or LTBP3). In a preferred embodiment, the TGFβ protein is TGFβ1. In some embodiments, the binding molecules disclosed herein bind selectively to a complex containing pro/latent TGFβ1 and LTBP1 or LTBP3. Such binding molecules can allow TGFβ1 activity to be selectively modulated in a context-dependent manner, i.e., by modulating TGFβ1 in the context of a LTPB protein, without modulating the activity of TGFβ1 complexed with other presenting molecules (e.g., GARP and/or LRRC33).

Antibodies that Selectively Inhibit LTBP-Mediated TGFβ Activation

The present invention provides novel, TGFβ inhibitors that selectively target matrix- or ECM-associated TGFβ activities. More specifically, such inhibitors include isoform-specific, context-selective inhibitors of TGFβ1 activation that specifically bind latent forms of TGFβ1 (e.g., proTGFβ1 complex) within the ECM environment and prevent release of mature growth factor from the complex at the niche. Such matrix-targeting inhibitors are context-specific in that they selectively bind proTGFβ1 associated with ECM presenting molecules, namely, LTBP1 and/or LTBP3. Thus, disclosed herein are monoclonal antibodies and fragments thereof capable of binding an epitope present in an LTBP1-proTGFβ1 complex and/or LTBP3-proTGFβ1 complex, whereas the epitope is not present in a GARP-proTGFβ1 complex and/or LRRC33-proTGFβ1 complex.

In some embodiments, the context-selective inhibitors of the present disclosure are capable of specifically binding both a human LTBP1-proTGFβ1 complex and a human LTBP3-proTGFβ1 complex, with affinities of <5 nM each (measured $K_D$ values) in a suitable in vitro binding assay, such as Octet. In preferred embodiments, such antibodies bind both a human LTBP1-proTGFβ1 complex and a human LTBP3-proTGFβ1 with affinities of <5 nM each (measured $K_D$ values) in a suitable in vitro binding assay, such as Octet. On the other hand, these context-specific antibodies do not show any detectable binding to a human GARP-proTGFβ1 complex or a human LRRC33-proTGFβ1 complex under the same assay conditions. Preferably, such antibody or the fragment binds each of the human LTBP1-proTGFβ1 complex and the human LTBP3-proTGFβ1 complex with KD of less than 1 nM.

In some embodiments, the context-selective inhibitors of the present disclosure are capable of specifically binding either a human LTBP1-proTGFβ1 complex or a human LTBP3-proTGFβ1 complex. Neither shows any detectable binding to a human GARP-proTGFβ1 complex or a human LRRC33-proTGFβ1 complex under the same assay conditions.

The art is familiar with suitable in vitro binding assays, including, for example, BLI-based assays such as Octet and SPR-based assays such as Biacore, which can be used to measure antibody-antigen interactions (e.g., binding kinetics). As used herein, "no binding" in these contexts may refer to no detectable binding by a particular assay, e.g., the binding, if any, is below the sensitivity of the assay. In some embodiments, "no binding" may refer to "no meaningful binding", set by a cutoff, which defines the minimum level required to be considered meaningful as measured by a particular assay system. For example, in a BLI (Octet) assay, 0.1 nm of optical shift measured at predetermined analyte (e.g., target antigen) concentrations (e.g., 100 nM, 200 nM, etc.) may indicate meaningful binding, below which may be considered as no binding (see for example, Example 9). Similarly, in a typical SPR (Biacore) assay, the cutoff level may be 0.2 RU (resonance unit). In some embodiments, the signal at 0 nM antibody (e.g., background noise) is subtracted from all the sensorgrams obtained at higher concentrations. Under these conditions, using SPR (Biacore), 0.2 RUs may be a suitable cutoff.

In some embodiments, the context-selective inhibitors of the present disclosure are capable of specifically binding a human LTBP1-proTGFβ1 complex or a human LTBP3-proTGFβ1 complex without showing detectable binding to a human GARP-proTGFβ1 complex, as measured by BLI, under the same assay conditions as used to measure binding to human LTBP1-proTGFβ1 complex and/or human LTBP3-TGFβ1.

In some embodiments, the context-selective inhibitors of the present disclosure bind a human LTBP1-proTGFβ1 complex or a human LTBP3-proTGFβ1 complex with a $K_D$ that is at least 50 times lower (e.g., at least 75 times lower, at least 100 times lower) than the $K_D$ when binding to a human GARP-proTGFβ1 complex under the same assay conditions. In some embodiments, the $K_D$ is as determined by BLI or SPR. In some embodiments, the $K_D$ is as determined by SPR.

In some embodiments, the context-selective inhibitors of the present disclosure are capable of specifically binding a human LTBP1-proTGFβ1 complex or a human LTBP3-proTGFβ1 complex without showing detectable binding to an LRRC33-proTGFβ1 latent complex, as measured by BLI, under the same assay conditions as used to measure binding to human LTBP1-proTGFβ1 complex and/or human LTBP3-TGFβ1.

In some embodiments, the context-selective inhibitors of the present disclosure bind a human LTBP1-proTGFβ1 complex or a human LTBP3-TGFβ1 complex with a $K_D$ that is at least 50 times lower (e.g., at least 75 times lower, at least 100 times lower) than the $K_D$ when binding to a human LRRC33-proTGFβ1 complex under the same assay conditions. In some embodiments, the $K_D$ is as determined by BLI or SPR. In some embodiments, the $K_D$ is as determined by SPR.

The invention includes the recognition that preferred antibodies (e g, immunoglobulins and antigen-binding fragments such as Fabs, as well as engineered constructs incorporating such fragments), once bound to its target/antigen (e.g., human LTBP1-proTGFβ1, human LTBP3-TGFβ31), dissociates slowly from the antigen. Thus, the novel antibodies of the instant invention are selected not only for their high overall affinities (such as KD of no more than 5 nM) but especially for their low dissociation rates. According to the present disclosure, such antibodies have dissociation rates of $<5\times10$ (1/s), as measured by BLI (e.g., when binding to human LTBP1-proTGFβ1 and/or human LTBP3-TGFβ31). Such dissociation rates of of $<5\times10^{-4}$ (1/s) of the antibodies or antigen-binding fragments may be monovalent dissociation rates or divalent dissociation rates. In some embodiments, the antibody or the fragment dissociates slowly from human LTBP1-proTGFβ1 and/or human LTBP3-TGFβ1, preferably for both human LTBP1-proTGFβ1 and human LTBP3-TGFβ1, with a monovalent dissociation half-time (t½) of at least 45 minutes (e.g., >45, 60, 75, 90 minutes) as measured by SPR. On the other hand, should binding to a human GARP-proTGFβ1 and/or LRRC33-TGFβ1 complex be detectable, such antibody dissociates rapidly from a human GARP-proTGFβ1 and/or human LRRC33-TGFβ1 complex(es), particularly the human GARP-proTGFβ1. In some embodiments, the antibody dissociates from human GARP-proTGFβ1 with t' of less than 5 minutes as measured by SPR. In particularly preferred embodiments, the antibody or the fragments show species cross-reactivity such that they bind murine counterparts with equivalent affinities.

The TGFβ1 present in these complexes may be in either latent form (latent TGFβ31) or in precursor form (proTGFβ31). In one embodiment, the inhibitors do not significantly bind to LTBP1 alone (e.g., when not complexed with TGFβ31). In another embodiment, the inhibitors do not significantly bind to LTBP3 alone (e.g., when not complexed with TGFβ31). In another embodiment, the inhibitors do not significantly bind to TGFβ1 alone (e.g., pro or latent TGFβ1 not complexed with LTBP1 or LTBP3, or mature TGFβ1). In another embodiment, the inhibitors that selectively bind a LTBP1-TGFβ1 complex and/or a LTBP3-TGFβ1 complex do not significantly bind to a complex containing TGFβ1 and another presenting molecule, e.g., a GARP-TGFβ1 complex (e.g., GARP complexed to pro- or latent TGFβ1) and/or a LRRC33-TGFβ1 complex (e.g., LRRC33 complexed to pro- or latent TGFβ31). In one embodiment, the inhibitors that selectively bind LTBP1/3-TGFβ1 do not significantly bind one or more (e.g., two or more, three or more, or all four) of the following: LTBP1 alone, TGFβ1 alone, a GARP-TGFβ1 complex, and a LRRC33-TGFβ1 complex. In addition, in some embodiments, the inhibitors do not significantly bind LTBP3 alone.

As used herein, the term "inhibitor" refers to any agent capable of blocking or antagonizing TGFβ1 signaling. Such agents may include small molecule antagonists of TGFβ1 and biologic antagonists of TGFβ1 (e.g., protein fragments and antibodies). In some embodiments, the inhibitor may be an antibody (including fragments thereof, such as Domain Antibodies (dAbs) as described in, for example, U.S. Pat. Nos. 6,291,158; 6,582,915; 6,593,081; 6,172,197; and 6,696,245), a small molecule inhibitor, an Adnectin, an Affibody, a DARPin, an Anticalin, an Avimer, a Versabody or a gene therapy. Use of inhibitors encompassed by the present invention also includes antibody mimetics, such as monobodies and single-domain antibodies. Monobodies are synthetic binding proteins that typically employ a fibronectin type III domain (FN3) as a molecular scaffold. Monobodies include Adnectins™ which are based on the 10th fibronectin type III domain.

In some aspects, the inhibitors, e.g., antibodies, or antigen-binding portions thereof, selectively bind to an epitope present on a LTBP1/3-TGFβ1 complex, that is not present on a GARP-TGFβ1 complex and/or a LRRC33-TGFβ1 complex. In some embodiments, the epitope is available due to a conformational change in LTBP1/3 and/or TGFβ1 that occurs when LTBP1/3 and TGFβ1 form a complex. In this embodiment, the epitope is not present in LTBP1/3 or TGFβ1 when the proteins are not associated in a complex. In one embodiment, the epitope is present on TGFβ1, when TGFβ1 is in a complex with LTBP1 or LTBP3. In another embodiment, the epitope is present on LTBP1, when LTBP1 is in a complex with TGFβ1. In another embodiment, the epitope is present on LTBP3, when LTBP3 is in a complex with TGFβ1. In another embodiment, the epitope comprises residues from both LTBP1 and TGFβ1. In another embodiment, the epitope comprises residues from both LTBP3 and TGFβ1.

Surprisingly, some of the LTBP1/3 complex-selective antibodies disclosed herein (e.g., Ab14, Ab20, Ab21-23, Ab17, and Ab24-29) are capable of binding to the small latent complex (proTGFβ1 C4S) in the absence of a presenting molecule (e.g., LTBP1/3) and yet exert context-selectivity. Without wishing to be bound by theory, this finding suggests that the antibodies (and variants thereof, or cross-competing antibodies) may bind an epitope that is available in the LTBP1/3-proTGFβ1 complex and in proTGFβ1 alone, but which is not available when an LRRC-type of presenting molecule (GARP or LRRC33) is present. The epitope might be entirely on latent TGFβ1, but gets occluded (directly or indirectly) when GARP or LRRC33 is complexed.

Alternatively, LTBP-selective inhibitors according to the present disclosure may bind a combinatorial epitope that comprises one or more amino acid residues of LTBP1 or LTBP3 and one or more amino acid residues of proTGFβ1, which confer the context-selectivity towards an LTBP-bound complex over GARP/LRRC33-bound complex. In these embodiments, selectivity towards the isoform (TGFβ31) as well as the context (ECM) is attributable to the combined contributions from both elements of the antigen complex.

In some embodiments, the inhibitors, e.g., antibodies, or antigen-binding portions thereof, are selective for the TGFβ1 isoform. In such embodiments, the inhibitors, e.g., antibodies, or antigen-binding portions thereof, do not bind to TGFβ2 and/or TGFβ3. For example, in one embodiment, the inhibitors, e.g., antibodies, or antigen-binding portions thereof, selectively bind a LTBP1/3-TGFβ1 complex, but do not bind TGFβ2, or a complex containing TGFβ2. In another embodiment, the inhibitors, e.g., antibodies, or antigen-binding portions thereof, selectively bind a LTBP1/3-TGFβ1 complex, but do not bind TGFβ3, or a complex containing TGFβ3.

In some embodiments, the inhibitors, e.g., antibodies, or antigen-binding portions thereof, do not prevent TGFβ1 from binding to integrin. For example, in some embodiments, the inhibitors, e.g., antibodies, or antigen-binding portions thereof, do not mask the integrin-binding site of TGFβ1.

In one aspect, the invention provides functional inhibitors, e.g., antibodies, that modulate TGFβ1 activity. In exemplary embodiments, the antibodies described herein are inhibitory antibodies, which inhibit the function or activity of TGFβ1. In some embodiments, the antibodies, or antigen-binding portions thereof, inhibit the activation (release) of TGFβ1 from a LTBP1-TGFβ1 complex and/or a LTBP3-TGFβ1 complex. The present disclosure provides, in exemplary embodiments, "context-specific" or "context-selective" inhibitors of TGFβ1 activation. Such inhibitors can bind a LTBP1/3-TGFβ1 complex and inhibit activation of TGFβ1 that is presented by LTBP1 or LTBP3, without inhibiting the activation of TGFβ1 presented by GARP and/or LRRC33. Accordingly, in some embodiments, the antibodies, or antigen-binding portions thereof, described herein inhibit the release of mature TGFβ1 from a LTBP1-TGFβ1 complex and/or a LTBP3-TGFβ1 complex, but do not inhibit the release of mature TGFβ1 from a GARP-TGFβ1 complex and/or a LRRC33-TGFβ1 complex. Due to the differential localization of LTBP, GARP, and LRRC33, the context-specific inhibitors of TGFβ1 provided by the present invention can block a particular subset of TGFβ1 activity in vivo. In one embodiment, the context-specific antibodies provided herein that inhibit LTBP1/3-TGFβ1 but do not inhibit GARP-TGFβ1 or LRRC33-TGFβ1 can be used to inhibit TGFβ1 localized to the extracellular matrix. In another embodiment, the context-specific antibodies can inhibit TGFβ1 without modulating TGFβ1-associated immune activity or immune response. In another embodiment, the context-specific antibodies can be used to inhibit TGFβ1 activity associated with the extracellular matrix without modulating TGFβ1 activity associated with hematopoietic cells. Accordingly, the context-specific antibodies can be used to inhibit LTBP1/3-associated TGFβ1 activity in applications in which TGFβ1 activation in the context of GARP and/or LRRC33 is undesirable, as described herein.

In some embodiments, the TGFβ1 comprises a naturally occurring mammalian amino acid sequence. In some embodiment, the TGFβ1 comprises a naturally occurring human amino acid sequence. In some embodiments, the TGFβ1 comprises a human, a monkey, a rat or a mouse amino acid sequence.

In some embodiments, an antibody, or antigen-binding portion thereof, described herein selectively binds to a complex comprising a TGFβ1 protein comprising the amino acid sequence set forth in SEQ ID NO: 9, and LTBP1 or LTBP3. In some embodiments, an antibody, or antigen-binding portion thereof, described herein selectively binds to a LTBP1/3-TGFβ1 complex which comprises a non-naturally-occurring TGFβ1 amino acid sequence (otherwise referred to herein as a non-naturally-occurring TGFβ1). For example, a non-naturally-occurring TGFβ1 may comprise one or more recombinantly generated mutations relative to a naturally-occurring TGFβ1 amino acid sequence.

In some embodiments, an antibody, or antigen-binding portion thereof, described herein does not bind TGFβ2 and/or TGFβ3, or to protein complexes containing TGFβ2 and/or TGFβ3. Exemplary TGFβ2 and TGFβ3 amino acid sequences are set forth in SEQ ID NOs: 10 and 11, respectively. In some embodiments, a TGFβ1, TGFβ2, or TGFβ3 amino acid sequence comprises an amino acid sequence as set forth in SEQ ID NOs: 12-23, as shown in Table 1. In some embodiments, a TGFβ1 amino acid sequence comprises an amino acid sequence as set forth in SEQ ID NOs: 24-31, as shown in Table 2.

TGFβ1

(SEQ ID NO: 9)
LSTCKTIDMELVKRKRIEAIRGQILSKLRLASPPSQGEVPPGPLPEAVL

ALYNSTRDRVAGESAEPEPEPEADYYAKEVTRVLMVETHNEIYDKFKQS

THSIYMFFNTSELREAVPEPVLLSRAELRLLRLKLKVEQHVELYQKYSN

NSWRYLSNRLLAPSDSPEWLSFDVTGVVRQWLSRGGEIEGFRLSAHCSC

DSRDNTLQVDINGFTTGRRGDLATIHGMNRPFLLLMATPLERAQHLQSS

RHRRALDTNYCFSSTEKNCCVRQLYIDFRKDLGWKWIHEPKGYHANFCL

GPCPYIWSLDTQYSKVLALYNQHNPGASAAPCCVPQALEPLPIVYYVGR

KPKVEQLSNMIVRSCKCS

TGFβ2

(SEQ ID NO: 10)
SLSTCSTLDMDQFMRKRIEAIRGQILSKLKLTSPPEDYPEPEEVPPEVI

SIYNSTRDLLQEKASRRAAACERERSDEEYYAKEVYKIDMPPFFPSENA

IPPTFYRPYFRIVRFDVSAMEKNASNLVKAEFRVFRLQNPKARVPEQRI

ELYQILKSKDLTSPTQRYIDSKVVKTRAEGEWLSFDVTDAVHEWLHHKD

RNLGFKISLHCPCCTFVPSNNYIIPNKSEELEARFAGIDGTSTYTSGDQ

KTIKSTRKKNSGKTPHLLLMLLPSYRLESQQTNRRKKRALDAAYCFRNV

-continued
QDNCCLRPLYIDFKRDLGWKWIHEPKGYNANFCAGACPYLWSSDTQHSR
VLSLYNTINPEASASPCCVSQDLEPLTILYYIGKTPKIEQLSNMIVKSC
KCS TGFβ3
(SEQ ID NO: 11)
SLSLSTCTTLDFGHIKKKRVEAIRGQILSKLRLTSPPEPTVMTHVPYQV
LALYNSTRELLEEMHGEREEGCTQENTESEYYAKEIHKFDMIQGLAEHN -continued
ELAVCPKGITSKVFRFNVSSVEKNRTNLFRAEFRVLRVPNPSSKRNEQR
IELFQILRPDEHIAKQRYIGGKNLPTRGTAEWLSFDVTDTVREWLLRRE
SNLGLEISIHCPCHTFQPNGDILENIHEVMEIKFKGVDNEDDHGRGDLG
RLKKQKDHHNPHLILMMIPPHRLDNPGQGGQRKKRALDTNYCFRNLEEN
CCVRPLYIDFRQDLGWKWVHEPKGYYANFCSGPCPYLRSADTTHSTVLG
LYNTLNPEASASPCCVPQDLEPLTILYVGRTPKVEQLSNMVVKSCKCS

TABLE 1

Exemplary TGFβ1, TGFβ2, and TGFβ3 amino acid sequences

| Protein | Sequence | SEQ ID NO |
|---|---|---|
| proTGFβ1 | LSTCKTIDMELVKRKRIEAIRGQILSKLRLASPPSQGEVPPGPLPEAVLALYNSTRDR VAGESAEPEPEPEADYYAKEVTRVLMVETHNEIYDKFKQSTHSIYMFFNTSELREAVP EPVLLSRAELRLLRLKLKVEQHVELYQKYSNNSWRYLSNRLLAPSDSPEWLSFDVTGV VRQWLSRGGEIEGFRLSAHCSCDSRDNTLQVDINGFTTGRRGDLATIHGMNRPFLLLM ATPLERAQHLQSSRHRRALDTNYCFSSTEKNCCVRQLYIDFRKDLGWKWIHEPKGYHA NFCLGPCPYIWSLDTQYSKVLALYNQHNPGASAAPCCVPQALEPLPIVYYVGRKPKVE QLSNMIVRSCKCS | 12 |
| proTGFβ1 C4S | LSTSKTIDMELVKRKRIEAIRGQILSKLRLASPPSQGEVPPGPLPEAVLALYNSTRDR VAGESAEPEPEPEADYYAKEVTRVLMVETHNEIYDKFKQSTHSIYMFFNTSELREAVP EPVLLSRAELRLLRLKLKVEQHVELYQKYSNNSWRYLSNRLLAPSDSPEWLSFDVTGV VRQWLSRGGEIEGFRLSAHCSCDSRDNTLQVDINGFTTGRRGDLATIHGMNRPFLLLM ATPLERAQHLQSSRHRRALDTNYCFSSTEKNCCVRQLYIDFRKDLGWKWIHEPKGYHA NFCLGPCPYIWSLDTQYSKVLALYNQHNPGASAAPCCVPQALEPLPIVYYVGRKPKVE QLSNMIVRSCKCS | 13 |
| proTGFβ1 D2G | LSTCKTIDMELVKRKRIEAIRGQILSKLRLASPPSQGEVPPGPLPEAVLALYNSTRDR VAGESAEPEPEPEADYYAKEVTRVLMVETHNEIYDKFKQSTHSIYMFFNTSELREAVP EPVLLSRAELRLLRLKLKVEQHVELYQKYSNNSWRYLSNRLLAPSDSPEWLSFDVTGV VRQWLSRGGEIEGFRLSAHCSCDSRDNTLQVDINGFTTGRRGDLATIHGMNRPFLLLM ATPLERAQHLQSSRHGALDTNYCFSSTEKNCCVRQLYIDFRKDLGWKWIHEPKGYHAN FCLGPCPYIWSLDTQYSKVLALYNQHNPGASAAPCCVPQALEPLPIVYYVGRKPKVEQ LSNMIVRSCKCS | 14 |
| proTGFβ1 C4S D2G | LSTSKTIDMELVKRKRIEAIRGQILSKLRLASPPSQGEVPPGPLPEAVLALYNSTRDR VAGESAEPEPEPEADYYAKEVTRVLMVETHNEIYDKFKQSTHSIYMFFNTSELREAVP EPVLLSRAELRLLRLKLKVEQHVELYQKYSNNSWRYLSNRLLAPSDSPEWLSFDVTGV VRQWLSRGGEIEGFRLSAHCSCDSRDNTLQVDINGFTTGRRGDLATIHGMNRPFLLLM ATPLERAQHLQSSRHGALDTNYCFSSTEKNCCVRQLYIDFRKDLGWKWIHEPKGYHAN FCLGPCPYIWSLDTQYSKVLALYNQHNPGASAAPCCVPQALEPLPIVYYVGRKPKVEQ LSNMIVRSCKCS | 15 |
| proTGFβ2 | SLSTCSTLDMDQFMRKRIEAIRGQILSKLKLTSPPEDYPEPEEVPPEVISIYNSTRDL LQEKASRRAAACERERSDEEYYAKEVYKIDMPPFFPSENAIPPTFYRPYFRIVRFDVS AMEKNASNLVKAEFRVFRLQNPKARVPEQRIELYQILKSKDLTSPTQRYIDSKVVKTR AEGEWLSFDVTDAVHEWLHHKDRNLGFKISLHCPCCTFVPSNNYIIPNKSEELEARFA GIDGTSTYTSGDQKTIKSTRKKNSGKTPHLLLMLLPSYRLESQQTNRRKKRALDAAYC FRNVQDNCCLRPLYIDFKRDLGWKWIHEPKGYNANFCAGACPYLWSSDTQHSRVLSLY NTINPEASASPCCVSQDLEPLTILYYIGKTPKIEQLSNMIVKSCKCS | 16 |
| proTGFβ2 C5S | SLSTSSTLDMDQFMRKRIEAIRGQILSKLKLTSPPEDYPEPEEVPPEVISIYNSTRDL LQEKASRRAAACERERSDEEYYAKEVYKIDMPPFFPSENAIPPTFYRPYFRIVRFDVS AMEKNASNLVKAEFRVFRLQNPKARVPEQRIELYQILKSKDLTSPTQRYIDSKVVKTR AEGEWLSFDVTDAVHEWLHHKDRNLGFKISLHCPCCTFVPSNNYIIPNKSEELEARFA GIDGTSTYTSGDQKTIKSTRKKNSGKTPHLLLMLLPSYRLESQQTNRRKKRALDAAYC FRNVQDNCCLRPLYIDFKRDLGWKWIHEPKGYNANFCAGACPYLWSSDTQHSRVLSLY NTINPEASASPCCVSQDLEPLTILYYIGKTPKIEQLSNMIVKSCKCS | 17 |
| proTGFβ 2C5S D2G | SLSTSSTLDMDQFMRKRIEAIRGQILSKLKLTSPPEDYPEPEEVPPEVISIYNSTRDL LQEKASRRAAACERERSDEEYYAKEVYKIDMPPFFPSENAIPPTFYRPYFRIVRFDVS AMEKNASNLVKAEFRVFRLQNPKARVPEQRIELYQILKSKDLTSPTQRYIDSKVVKTR AEGEWLSFDVTDAVHEWLHHKDRNLGFKISLHCPCCTFVPSNNYIIPNKSEELEARFA GIDGTSTYTSGDQKTIKSTRKKNSGKTPHLLLMLLPSYRLESQQTNRRKGALDAAYCF RNVQDNCCLRPLYIDFKRDLGWKWIHEPKGYNANFCAGACPYLWSSDTQHSRVLSLYN TINPEASASPCCVSQDLEPLTILYYIGKTPKIEQLSNMIVKSCKCS | 18 |
| proTGFβ2 D2G | SLSTCSTLDMDQFMRKRIEAIRGQILSKLKLTSPPEDYPEPEEVPPEVISIYNSTRDL LQEKASRRAAACERERSDEEYYAKEVYKIDMPPFFPSENAIPPTFYRPYFRIVRFDVS AMEKNASNLVKAEFRVFRLQNPKARVPEQRIELYQILKSKDLTSPTQRYIDSKVVKTR AEGEWLSFDVTDAVHEWLHHKDRNLGFKISLHCPCCTFVPSNNYIIPNKSEELEARFA | 19 |

TABLE 1-continued

Exemplary TGFβ1, TGFβ2, and TGFβ3 amino acid sequences

| Protein | Sequence | SEQ ID NO |
|---|---|---|
| | GIDGTSTYTSGDQKTIKSTRKKNSGKTPHLLLMLLPSYRLESQQTNRRKGALDAAYCF<br>RNVQDNCCLRPLYIDFKRDLGWKWIHEPKGYNANFCAGACPYLWSSDTQHSRVLSLYN<br>TINPEASASPCCVSQDLEPLTILYYIGKTPKIEQLSNMIVKSCKCS | |
| proTGFβ3 | SLSLSTCTTLDFGHIKKKRVEAIRGQILSKLRLTSPPEPTVMTHVPYQVLALYNSTRE<br>LLEEMHGEREEGCTQENTESEYYAKEIHKFDMIQGLAEHNELAVCPKGITSKVFRFNV<br>SSVEKNRTNLFRAEFRVLRVPNPSSKRNEQRIELFQILRPDEHIAKQRYIGGKNLPTR<br>GTAEWLSFDVTDTVREWLLRRESNLGLEISIHCPCHTFQPNGDILENIHEVMEIKFKG<br>VDNEDDHGRGDLGRLKKQKDHHNPHLILMMIPPHRLDNPGQGGQRKKRALDTNYCFRN<br>LEENCCVRPLYIDFRQDLGWKWVHEPKGYYANFCSGPCPYLRSADTTHSTVLGLYNTL<br>NPEASASPCCVPQDLEPLTILYYVGRTPKVEQLSNMVVKSCKCS | 20 |
| proTGFβ3 C7S | SLSLSTSTTLDFGHIKKKRVEAIRGQILSKLRLTSPPEPTVMTHVPYQVLALYNSTRE<br>LLEEMHGEREEGCTQENTESEYYAKEIHKFDMIQGLAEHNELAVCPKGITSKVFRFNV<br>SSVEKNRTNLFRAEFRVLRVPNPSSKRNEQRIELFQILRPDEHIAKQRYIGGKNLPTR<br>GTAEWLSFDVTDTVREWLLRRESNLGLEISIHCPCHTFQPNGDILENIHEVMEIKFKG<br>VDNEDDHGRGDLGRLKKQKDHHNPHLILMMIPPHRLDNPGQGGQRKKRALDTNYCFRN<br>LEENCCVRPLYIDFRQDLGWKWVHEPKGYYANFCSGPCPYLRSADTTHSTVLGLYNTL<br>NPEASASPCCVPQDLEPLTILYYVGRTPKVEQLSNMVVKSCKCS | 21 |
| proTGFβ3 C7S D2G | SLSLSTSTTLDFGHIKKKRVEAIRGQILSKLRLTSPPEPTVMTHVPYQVLALYNSTRE<br>LLEEMHGEREEGCTQENTESEYYAKEIHKFDMIQGLAEHNELAVCPKGITSKVFRFNV<br>SSVEKNRTNLFRAEFRVLRVPNPSSKRNEQRIELFQILRPDEHIAKQRYIGGKNLPTR<br>GTAEWLSFDVTDTVREWLLRRESNLGLEISIHCPCHTFQPNGDILENIHEVMEIKFKG<br>VDNEDDHGRGDLGRLKKQKDHHNPHLILMMIPPHRLDNPGQGGQRKGALDTNYCFRNL<br>EENCCVRPLYIDFRQDLGWKWVHEPKGYYANFCSGPCPYLRSADTTHSTVLGLYNTLN<br>PEASASPCCVPQDLEPLTILYYVGRTPKVEQLSNMVVKSCKCS | 22 |
| proTGFβ3 D2G | SLSLSTCTTLDFGHIKKKRVEAIRGQILSKLRLTSPPEPTVMTHVPYQVLALYNSTRE<br>LLEEMHGEREEGCTQENTESEYYAKEIHKFDMIQGLAEHNELAVCPKGITSKVFRFNV<br>SSVEKNRTNLFRAEFRVLRVPNPSSKRNEQRIELFQILRPDEHIAKQRYIGGKNLPTR<br>GTAEWLSFDVTDTVREWLLRRESNLGLEISIHCPCHTFQPNGDILENIHEVMEIKFKG<br>VDNEDDHGRGDLGRLKKQKDHHNPHLILMMIPPHRLDNPGQGGQRKGALDTNYCFRNL<br>EENCCVRPLYIDFRQDLGWKWVHEPKGYYANFCSGPCPYLRSADTTHSTVLGLYNTLN<br>PEASASPCCVPQDLEPLTILYYVGRTPKVEQLSNMVVKSCKCS | 23 |

TABLE 2

Exemplary non-human TGFβ1 amino acid sequences

| Protein | Species | Sequence | SEQ ID NO |
|---|---|---|---|
| proTGFβ1 | Mouse | LSTCKTIDMELVKRKRIEAIRGQILSKLRLASPPSQGEVPPGPLPEAVLALYN<br>STRDRVAGESADPEPEPEADYYAKEVTRVLMVDRNNAIYEKTKDISHSIYMFF<br>NTSDIREAVPEPPLLSRAELRLQRLKSSVEQHVELYQKYSNNSWRYLGNRLLT<br>PTDTPEWLSFDVTGVVRQWLNQGDGIQGFRFSAHCSCDSKDNKLHVEINGISP<br>KRRGDLGTIHDMNRPFLLLMATPLERAQHLSSRHRRALDTNYCFSSTEKNCC<br>VRQLYIDFRKDLGWKWIHEPKGYHANFCLGPCPYIWSLDTQYSKVLALYNQHN<br>PGASASPCCVPQALEPLPIVYYVGRKPKVEQLSNMIVRSCKCS | 24 |
| proTGFβ1 | Cyno | LSTCKTIDMELVKRKRIEAIRGQILSKLRLASPPSQGEVPPGPLPEAVLALYN<br>STRDRVAGESAEPEPEPEADYYAKEVTRVLMVETHNEIYDKFKQSTHSIYMFF<br>NTSELREAVPEPVLLSRAELRLLRLKLKVEQHVELYQKYSNNSWRYLSNRLLA<br>PSDSPEWLSFDVTGVVRQWLSRGGEIEGFRLSAHCSCDSKDNTLQVDINGFTT<br>GRRGDLATIHGMNRPFLLLMATPLERAQHLQSSRHRRALDTNYCFSSTEKNCC<br>VRQLYIDFRKDLGWKWIHEPKGYHANFCLGPCPYIWSLDTQYSKVLALYNQHN<br>PGASAAPCCVPQALEPLPIVYYVGRKPKVEQLSNMIVRSCKCS | 25 |
| TGFβ1 LAP C4S | Mouse | LSTSKTIDMELVKRKRIEAIRGQILSKLRLASPPSQGEVPPGPLPEAVLALYN<br>STRDRVAGESADPEPEPEADYYAKEVTRVLMVDRNNAIYEKTKDISHSIYMFF<br>NTSDIREAVPEPPLLSRAELRLQRLKSSVEQHVELYQKYSNNSWRYLGNRLLT<br>PTDTPEWLSFDVTGVVRQWLNQGDGIQGFRFSAHCSCDSKDNKLHVEINGISP<br>KRRGDLGTIHDMNRPFLLLMATPLERAQHLSSRHRR | 26 |
| TGFβ1 LAP C4S | Cyno | LSTSKTIDMELVKRKRIEAIRGQILSKLRLASPPSQGEVPPGPLPEAVLALYN<br>STRDRVAGESAEPEPEPEADYYAKEVTRVLMVETHNEIYDKFKQSTHSIYMFF<br>NTSELREAVPEPVLLSRAELRLLRLKLKVEQHVELYQKYSNNSWRYLSNRLLA<br>PSDSPEWLSFDVTGVVRQWLSRGGEIEGFRLSAHCSCDSKDNTLQVDINGFTT<br>GRRGDLATIHGMNRPFLLLMATPLERAQHLQSSRHRR | 27 |
| proTGFβ1 C4S D2G | Mouse | LSTSKTIDMELVKRKRIEAIRGQILSKLRLASPPSQGEVPPGPLPEAVLALYN<br>STRDRVAGESADPEPEPEADYYAKEVTRVLMVDRNNAIYEKTKDISHSIYMFF<br>NTSDIREAVPEPPLLSRAELRLQRLKSSVEQHVELYQKYSNNSWRYLGNRLLT | 28 |

TABLE 2-continued

Exemplary non-human TGFβ1 amino acid sequences

| Protein | Species | Sequence | SEQ ID NO |
|---|---|---|---|
| | | PTDTPEWLSFDVTGVVRQWLNQGDGIQGFRFSAHCSCDSKDNKLHVEINGISP<br>KRRGDLGTIHDMNRPFLLLMATPLERAQHLHSSRHGALDTNYCFSSTEKNCCV<br>RQLYIDFRKDLGWKWIHEPKGYHANFCLGPCPYIWSLDTQYSKVLALYNQHNP<br>GASASPCCVPQALEPLPIVYYVGRKPKVEQLSNMIVRSCKCS | |
| proTGFβ1<br>C4S | Mouse | LSTSKTIDMELVKRKRIEAIRGQILSKLRLASPPSQGEVPPGPLPEAVLALYN<br>STRDRVAGESADPEPEPEADYYAKEVTRVLMVDRNNAIYEKTKDISHSIYMFF<br>NTSDIREAVPEPPLLSRAELRLQRLKSSVEQHVELYQKYSNNSWRYLGNRLLT<br>PTDTPEWLSFDVTGVVRQWLNQGDGIQGFRFSAHCSCDSKDNKLHVEINGISP<br>KRRGDLGTIHDMNRPFLLLMATPLERAQHLHSSRHRRALDTNYCFSSTEKNCC<br>VRQLYIDFRKDLGWKWIHEPKGYHANFCLGPCPYIWSLDTQYSKVLALYNQHN<br>PGASASPCCVPQALEPLPIVYYVGRKPKVEQLSNMIVRSCKCS | 29 |
| proTGFβ1<br>C4S | Cyno | LSTSKTIDMELVKRKRIEAIRGQILSKLRLASPPSQGEVPPGPLPEAVLALYN<br>STRDRVAGESAEPEPEPEADYYAKEVTRVLMVETHNEIYDKFKQSTHSIYMFF<br>NTSELREAVPEPVLLSRAELRLLRLKLKVEQHVELYQKYSNNSWRYLSNRLLA<br>PSDSPEWLSFDVTGVVRQWLSRGGEIEGFRLSAHCSCDSKDNTLQVDINGFTT<br>GRRGDLATIHGMNRPFLLLMATPLERAQHLQSSRHRRALDTNYCFSSTEKNCC<br>VRQLYIDFRKDLGWKWIHEPKGYHANFCLGPCPYIWSLDTQYSKVLALYNQHN<br>PGASAAPCCVPQALEPLPIVYYVGRKPKVEQLSNMIVRSCKCS | 30 |
| proTGFβ1<br>C4S D2G | Cyno | LSTSKTIDMELVKRKRIEAIRGQILSKLRLASPPSQGEVPPGPLPEAVLALYN<br>STRDRVAGESAEPEPEPEADYYAKEVTRVLMVETHNEIYDKFKQSTHSIYMFF<br>NTSELREAVPEPVLLSRAELRLLRLKLKVEQHVELYQKYSNNSWRYLSNRLLA<br>PSDSPEWLSFDVTGVVRQWLSRGGEIEGFRLSAHCSCDSKDNTLQVDINGFTT<br>GRRGDLATIHGMNRPFLLLMATPLERAQHLQSSRHGALDTNYCFSSTEKNCCV<br>RQLYIDFRKDLGWKWIHEPKGYHANFCLGPCPYIWSLDTQYSKVLALYNQHNP<br>GASAAPCCVPQALEPLPIVYYVGRKPKVEQLSNMIVRSCKCS | 31 |

In some embodiments, an antibody, or antigen-binding portion thereof, as described herein, is capable of selectively binding to an LTBP-TGFβ1 complex. In some embodiments, antigenic protein complexes (e.g., a LTBP-TGFβ1 complex) may comprise an LTBP protein selected from the following: LTBP1, LTBP2, LTBP3, and LTBP4.

In some embodiments, the antibody, or antigen-binding portion thereof, selectively binds an LTBP1-TGFβ1 complex. In some embodiments, the LTBP1 protein is a naturally-occurring protein. In some embodiments, the LTBP1 protein is a non-naturally occurring protein. In some embodiments, the LTBP1 protein is a recombinant protein. Such recombinant LTBP1 protein may comprise LTBP1, alternatively spliced variants thereof, and/or fragments thereof. Recombinant LTBP1 proteins may also be modified to comprise one or more detectable labels. In some embodiments, the LTBP1 protein comprises a leader sequence (e.g., a native or non-native leader sequence). In some embodiments, the LTBP1 protein does not comprise a leader sequence (i.e., the leader sequence has been processed or cleaved). Such detectable labels may include, but are not limited to biotin labels, polyhistidine tags, myc tags, HA tags and/or fluorescent tags. In some embodiments, the LTBP1 protein is a mammalian LTBP1 protein. In some embodiments, the LTBP1 protein is a human, a monkey, a mouse, or a rat LTBP1 protein. In some embodiments, the LTBP1 protein comprises an amino acid sequence as set forth in SEQ ID NO: 32 in Table 3. In some embodiments, the LTBP1 protein comprises an amino acid sequence as set forth in SEQ ID NOs: 33 or SEQ ID NO: 34 in Table 3.

In some embodiments, an antibody, or antigen-binding portion thereof, as described herein, is capable of binding to a LTBP3-TGFβ1 complex. In some embodiments, the LTBP3 protein is a naturally-occurring protein. In some embodiments, the LTBP3 protein is a non-naturally occurring protein. In some embodiments, the LTBP3 protein is a recombinant protein. Such recombinant LTBP3 protein may comprise LTBP3, alternatively spliced variants thereof and/or fragments thereof. In some embodiments, the LTBP3 protein comprises a leader sequence (e.g., a native or non-native leader sequence). In some embodiments, the LTBP3 protein does not comprise a leader sequence (i.e., the leader sequence has been processed or cleaved). Recombinant LTBP3 proteins may also be modified to comprise one or more detectable labels. Such detectable labels may include, but are not limited to biotin labels, polyhistidine tags, myc tags, HA tags and/or fluorescent tags. In some embodiments, the LTBP3 protein is a mammalian LTBP3 protein. In some embodiments, the LTBP3 protein is a human, a monkey, a mouse, or a rat LTBP3 protein. In some embodiments, the LTBP3 protein comprises an amino acid sequence as set forth in SEQ ID NO: 35. In some embodiments, the LTBP3 protein comprises an amino acid sequence as set forth in SEQ ID NOs: 36 or 37.

TABLE 3

Exemplary LTBP amino acid sequences.

| Protein | Species | Sequence | SEQ ID NO |
|---|---|---|---|
| LTBP1S | Human | NHTGRIKVVFTPSICKVTCTKGSCQNSCEKGNTTTLISENGHAADTLTATNFR<br>VVICHLPCMNGGQCSSRDKCQCPPNFTGKLCQIPVHGASVPKLYQHSQQPGKA<br>LGTHVIHSTHTLPLTVTSQQGVKVKFPPNIVNIHVKHPPEASVQIHQVSRIDG<br>PTGQKTKEAQPGQSQVSYQGLPVQKTQTIHSTYSHQQVIPHVYPVAAKTQLGR | 32 |

TABLE 3-continued

Exemplary LTBP amino acid sequences.

| Protein | Species | Sequence | SEQ ID NO |
|---------|---------|----------|-----------|
| | | CFQETIGSQCGKALPGLSKQEDCCGTVGTSWGFNKCQKCPKKPSYHGYNQMME<br>CLPGYKRVNNTFCQDINECQLQGVCPNGECLNTMGSYRCTCKIGFGPDPTFSS<br>CVPDPPVISEEKGPCYRLVSSGRQCMHPLSVHLTKQLCCCSVGKAWGPHCEKC<br>PLPGTAAFKEICPGGMGYTVSGVHRRRPIHHHVGKGPVFVKPKNTQPVAKSTH<br>PPPLPAKEEPVEALTFSREHGPGVAEPEVATAPPEKEIPSLDQEKTKLEPGQP<br>QLSPGISTIHLHPQFPVVIEKTSPPVPVEVAPEASTSSASQVIAPTQVTEINE<br>CTVNPDICGAGHCINLPVRYTCICYEGYRFSEQQRKCVDIDECTQVQHLCSQG<br>RCENTEGSFLCICPAGFMASEEGTNCIDVDECLRPDVCGEGHCVNTVGAFRCE<br>YCDSGYRMTQRGRCEDIDECLNPSTCPDEQCVNSPGSYQCVPCTEGFRGWNGQ<br>CLDVDECLEPNVCANGDCSNLEGSYMCSCHKGYTRTPDHKHCRDIDECQQGNL<br>CVNGQCKNTEGSFRCTCGQGYQLSAAKDQCEDIDECQHRHLCAHGQCRNTEGS<br>FQCVCDQGYRASGLGDHCEDINECLEDKSVCQRGDCINTAGSYDCTCPDGFQL<br>DDNKTCQDINECEHPGLCGPQGECLNTEGSFHCVCQQGFSISADGRTCEDIDE<br>CVNNTVCDSHGFCDNTAGSFRCLCYQGFQAPQDGQGCVDVNECELLSGVCGEA<br>FCENVEGSFLCVCADENQEYSPMTGQCRSRTSTDLDVDVDQPKEEKKECYYNL<br>NDASLCDNVLAPNVTKQECCCTSGVGWGDNCEIFPCPVLGTAEFTEMCPKGKG<br>FVPAGESSSEAGGENYKDADECLLFGQEICKNGFCLNTRPGYECYCKQGTYYD<br>PVKLQCFDMDECQDSSCIDGQCVNTEGSYNCFCTHPMVLDASEKRCIRPAES<br>NEQIEETDVYQDLCWEHLSDEYVCSRPLVGKQTTYTECCCLYGEAWGMQCALC<br>PLKDSDDYAQLCNIPVTGRRQPYGRDALVDFSEQYTPEADPYFIQDRFLNSFE<br>ELQAEECGILNGCENGRCVRVQEGYTCDCFDGYHLDTAKMTCVDVNECDELNN<br>RMSLCKNAKCINTDGSYKCLCLPGYVPSDKPNYCTPLNTALNLEKDSDLE | |
| LTBP1S | Cyno | NHTGRIKVVFTPSICKVTCTKGSCQNSCEKGNTTTLISENGHAADTLTATNFR<br>VVLCHLPCMNGGQCSSRDKCQCPPNFTGKLCQIPVHGASVPKLYQHSQQPGKA<br>LGTHVIHSTHTLPLTVTSQQGVKVKFPPNIVNIHVKHPPEASVQIHQVSRIDG<br>PTGQKTKEAQPGSQVSYQGLPVQKTQTIHSTYSHQQVIPHVYPVAAKTQLGR<br>CFQETIGSQCGKALPGLSKQEDCCGTVGTSWGFNKCQKCPKKPSYHGYNQMME<br>CLPGYKRVNNTFCQDINECQLQGVCPNGECLNTMGSYRCTCKIGFGPDPTFSS<br>CVPDPPVISEEKGPCYRLVSSGRQCMHPLSVHLTKQLCCCSVGKAWGPHCEKC<br>PLPGTAAFKEICPGGMGYTVSGVHRRRPIHHHVGKGPVFVKPKNTQPVAKSTH<br>PPPLPAKEEPVEALTFSREHGPGVAEPEVATAPPEKEIPSLDQEKTKLEPGQP<br>QLSPGISTIHLHPQFPVVIEKTSPPVPVEVAPEASTSSASQVIAPTQVTEINE<br>CTVNPDICGAGHCINLPVRYTCICYEGYKFSEQQRKCVDIDECTQVQHLCSQG<br>RCENTEGSFLCICPAGFMASEEGTNCIDVDECLRPDVCGEGHCVNTVGAFRCE<br>YCDSGYRMTQRGRCEDIDECLNPSTCPDEQCVNSPGSYQCVPCTEGFRGWNGQ<br>CLDVDECLEPNVCTNGDCSNLEGSYMCSCHKGYTRTPDHKHCKDIDECQQGNL<br>CVNGQCKNTEGSFRCTCGQGYQLSAAKDQCEDIDECQHHLCAHGQCRNTEGS<br>FQCVCDQGYRASGLGDHCEDINECLEDKSVCQRGDCINTAGSYDCTCPDGFQL<br>DDNKTCQDINECEHPGLCGPQGECLNTEGSFHCVCQQGFSISADGRTCEDIDE<br>CVNNTVCDSHGFCDNTAGSFRCLCYQGFQAPQDGQGCVDVNECELLSGVCGEA<br>FCENVEGSFLCVCADENQEYSPMTGQCRSRTSTDLDVEQPKEEKKECYYNLND<br>ASLCDNVLAPNVTKQECCCTSGAGWGDNCEIFPCPVLGTAEFTEMCPKGKGFV<br>PAGESSSEAGGENYKDADECLLFGQEICKNGFCLNTRPGYECYCKQGTYYDPV<br>KLQCFDMDECQDSSCIDGQCVNTEGSYNCFCTHPMVLDASEKRCIRPAESNE<br>QIEETDVYQDLCWEHLSDEYVCSRPLVGKQTTYTECCCLYGEAWGMQCALCPM<br>KDSDDYAQLCNIPVTGRRQPYGRDALVDFSEQYAPEADPYFIQDRFLNSFEEL<br>QAEECGILNGCENGRCVRVQEGYTCDCFDGYHLDTAKMTCVDVNECDELNNRM<br>SLCKNAKCINTEGSYKCLCLPGYVPSDKPNYCTPLNTALNLEKDSDLE | 33 |
| LTBP1S | mouse | NHTGRIKVVFTPSICKVTCTKGNCQNSCQKGNTTTLISENGHAADTLTATNFR<br>VVICHLPCMNGGQCSSRDKCQCPPNFTGKLCQIPVLGASMPKLYQHAQQQGKA<br>LGSHVIHSTHTLPLTMTSQQGVKVKFPPNIVNIHVKHPPEASVQIHQVSRIDS<br>PGGQKVKEAQPGSQVSYQGLPVQKTQTVHSTYSHQQLIPHVYPVAAKTQLGR<br>CFQETIGSQCGKALPGLSKQEDCCGTVGTSWGFNKCQKCPKKQSYHGYTQMME<br>CLQGYKRVNNTFCQDINECQLQGVCPNGECLNTMGSYRCSCKMGFGPDPTFSS<br>CVPDPPVISEEKGPCYRLVSPGRHCMHPLSVHLTKQICCCSVGKAWGPHCEKC<br>PLPGTAAFKEICPGGMGYTVSGVHRRRPIHQHIGKEAVYVKPKNTQPVAKSTH<br>PPPLPAKEEPVEALTSSWEHGPRGAEPEVVTAPPEKEIPSLDQEKTRLEPGQP<br>QLSPGVSTIHLHPQFPVVVEKTSPPVPVEVAPEASTSSASQVIAPTQVTEINE<br>CTVNPDICGAGHCINLPVRYTCICYEGYKFSEQLRKCVDIDECAQVRHLCSQG<br>RCENTEGSFLCVCPAGFMASEEGTNCIDVDECLRPDMCRDGRCINTAGAFRCE<br>YCDSGYRMSRRGYCEDIDECLKPSTCPEEQCVNTPGSYQCVPCTEGFRGWNGQ<br>CLDVDECLQPKVCTNGSCTNLEGSYMCSCHRGYSPTPDHRHCQDIDECQQGNL<br>CMNGQCRNTDGSFRCTCGQGYQLSAAKDQCEDIDECEHHHLCSHGQCRNTEGS<br>FQCVCNQGYRASVLGDHCEDINECLEDSSVCQGGDCINTAGSYDCTCPDGFQL<br>NDNKGCQDINECAQPGLCGSHGECLNTQGSFHCVCEQGFSISADGRTCEDIDE<br>CVNNTVCDSHGFCDNTAGSFRCLCYQGFQAPQDGQGCVDVNECELLSGVCGEA<br>FCENVEGSFLCVCADENQEYSPMTGQCRSRVTEDSGVDRQPREEKKECYYNLN<br>DASLCDNVLAPNVTKQECCCTSGAGWGDNCEIFPCPVQGTAEFTEMCPRGKGL<br>VPAGESSYDTGGENYKDADECLLFGEEICKNGYCLNTQPGYECYCKQGTYYDP<br>VKLQCFDMDECQDPNSCIDGQCVNTEGSYNCFCTHPMVLDASEKRCVQPTESN<br>EQIEETDVYQDLCWEHLSEEYVCSRPLVGKQTTYTECCCLYGEAWGMQCALCP<br>MKDSDDYAQLCNIPVTGRRRPYGRDALVDFSEQYGPETDPYFIQDRFLNSFEE<br>LQAEECGILNGCENGRCVRVQEGYTCDCFDGYHLDMAKMTCVDVNECSELNNR<br>MSLCKNAKCINTEGSYKCLCLPGYIPSDKPNYCTPLNSALNLDKESDLE | 34 |

TABLE 3-continued

Exemplary LTBP amino acid sequences.

| Protein | Species | Sequence | SEQ ID NO |
|---|---|---|---|
| LTBP3S | Human | ETDECRLNQNICGHGECVPGPPDYSCHCNPGYRSHPQHRYCVDVNECEAEPCG<br>PGRGICMNTGGSYNCHCNRGYRLHVGAGGRSCVDLNECAKPHLCGDGGFCINF<br>PGHYKCNCYPGYRLKASRPPVCEDIDECRDPSSCPDGKCENKPGSFKCIACQP<br>GYRSQGGGACRDVNECAEGSPCSPGWCENLPGSFRCTCAQGYAPAPDGRSCLD<br>VDECEAGDVCDNGICSNTPGSFQCQCLSGYHLSRDRSHCEDIDECDFPAACIG<br>GDCINTNGSYRCLCPQGHRLVGGRKCQDIDECSQDPSLCLPHGACKNLQGSYV<br>CVCDEGFTPTQDQHGCEEVEQPHHKKECYLNFDDTVFCDSVLATNVTQQECCC<br>SLGAGWGDHCEIYPCPVYSSAEFHSLCPDGKGYTQDNNIVNYGIPAHRDIDEC<br>MLFGSEICKEGKCVNTQPGYECYCKQGFYYDGNLLECVDVDECLDESNCRNGV<br>CENTRGGYRCACTPPAEYSPAQRQCL | 364 |
| LTBP3 | Human | GPAGERGAGGGGALARERFKVVFAPVICKRTCLKGQCRDSCQQGSNMTLIGEN<br>GHSTDTLTGSGFRVVVCPLPCMNGGQCSSRNQCLCPPDFTGRFCQVPAGGAGG<br>GTGGSGPGLSRTGALSTGALPPLAPEGDSVASKHAIYAVQVIADPPGPGEGPP<br>AQHAAFLVPLGPGQISAEVQAPPPVVNVRVHHPPEASVQVHRIESSNAESAAP<br>SQHLLPHPKPSHPRPPTQKPLGRCFQDTLPKQPCGSNPLPGLTKQEDCCGSIG<br>TAWGQSKCHKCPQLQYTGVQKPGPVRGEVGADCPQGYKRLNSTHCQDINECAM<br>PGVCRHGDCLNNPGSYRCVCPPGHSLGPSRTQCIADKPEEKSLCFRLVSPEHQ<br>CQHPLTTRLTRQLCCCSVGKAWGARCQRCPTDGTAAFKEICPAGKGYHILTSH<br>QTLTIQGESDFSLFLHPDGPPKPQQLPESPSQAPPPEDTEEERGVTTDSPVSE<br>ERSVQQSHPTATTTPARPYPELISRPSPPTMRWFLPDLPPSRSAVEIAPTQVT<br>ETDECRLNQNICGHGECVPGPPDYSCHCNPGYRSHPQHRYCVDVNECEAEPCG<br>PGRGICMNTGGSYNCHCNRGYRLHVGAGGRSCVDLNECAKPHLCGDGGFCINF<br>PGHYKCNCYPGYRLKASRPPVCEDIDECRDPSSCPDGKCENKPGSFKCIACQP<br>GYRSQGGGACRDVNECAEGSPCSPGWCENLPGSFRCTCAQGYAPAPDGRSCLD<br>VDECEAGDVCDNGICSNTPGSFQCQCLSGYHLSRDRSHCEDIDECDFPAACIG<br>GDCINTNGSYRCLCPQGHRLVGGRKCQDIDECSQDPSLCLPHGACKNLQGSYV<br>CVCDEGFTPTQDQHGCEEVEQPHHKKECYLNFDDTVFCDSVLATNVTQQECCC<br>SLGAGWGDHCEIYPCPVYSSAEFHSLCPDGKGYTQDNNIVNYGIPAHRDIDEC<br>MLFGSEICKEGKCVNTQPGYECYCKQGFYYDGNLLECVDVDECLDESNCRNGV<br>CENTRGGYRCACTPPAEYSPAQRQCLSPEEMDVDECQDPAACRPGRCVNLPGS<br>YRCECRPPWVPGSGRDCQLPESPAERAPERRDVCWSQRGEDGMCAGPLAGPA<br>LTFDDCCRQGRGWGAQCRPCPPRGAGSHCPTSQSESNSFWDTSPLLLGKPPR<br>DEDSSEEDSDECRCVSGRCVPRPGGAVCECPGGFQLDASRARCVDIDECRELN<br>QRGLLCKSERCVNTGSFRCVCKAGFARSRPHGACVPQRRR | 35 |
| LTBP3 | CYNO | GPAGERGAGGGGALARERFKVVFAPVICKRTCLKGQCRDSCQQGSNMTLIGEN<br>GHSTDTLTGSGFRVVVCPLPCMNGGQCSSRNQCLCPPDFTGRFCQVPAGGAGG<br>GTGGSGPGLSRAGALSTGALPPLAPEGDSVASKHAIYAVQVIADPPGPGEGPP<br>AQHAAFLVPLGPGQISAEVQAPPPVVNVRVHHPPEASVQVHRIESSNAEGAAP<br>SQHLLPHPKPSHPRPPTQKPLGRCFQDTLPKQPCGSNPLPGLTKQEDCCGSIG<br>TAWGQSKCHKCPQLQYTGVQKPGPVRGEVGADCPQGYKRLNSTHCQDINECAM<br>PGVCRHGDCLNNPGSYRCVCPPGHSLGPSRTQCIADKPEEKSLCFRLVSPEHQ<br>CQHPLTTRLTRQLCCCSVGKAWGARCQRCPADGTAAFKEICPAGKGYHILTSH<br>QTLTIQGESDFSLFLHPDGPPKPQQLPESPSQAPPPEDTEEERGVTTDSPVSE<br>ERSVQQSHPTATTSPARPYPELISRPSPPTMRWFLPDLPPSRSAVEIAPTQVT<br>ETDECRLNQNICGHGECVPGPPDYSCHCNPGYRSHPQHRYCVDVNECEAEPCG<br>PGRGICMNTGGSYNCHCNRGYRLHVGAGGRSCVDLNECAKPHLCGDGGFCINF<br>PGHYKCNCYPGYRLKASRPPVCEDIDECRDPSSCPDGKCENKPGSFKCIACQP<br>GYRSQGGGACRDVNECAEGSPCSPGWCENLPGSFRCTCAQGYAPAPDGRSCVD<br>VDECEAGDVCDNGICTNTPGSFQCQCLSGYHLSRDRSHCEDIDECDFPAACIG<br>GDCINTNGSYRCLCPQGHRLVGGRKCQDIDECTQDPGLCLPHGACKNLQGSYV<br>CVCDEGFTPTQDQHGCEEVEQPHHKKECYLNFDDTVFCDSVLATNVTQQECCC<br>SLGAGWGDHCEIYPCPVYSSAEFHSLCPDGKGYTQDNNIVNYGIPAHRDIDEC<br>MLFGAEICKEGKCVNTQPGYECYCKQGFYYDGNLLECVDVDECLDESNCRNGV<br>CENTRGGYRCACTPPAEYSPAQRQCLSPEEMDVDECQDPAACRPGRCVNLPGS<br>YRCECRPPWVPGSGRDCQLPESPAERAPERRDVCWSQRGEDGMCAGPQAGPA<br>LTFDDCCRQGRGWGAQCRPCPPRGAGSQCPTSQSESNSFWDTSPLLLGKPRR<br>DEDSSEEDSDECRCVSGRCVPRPGGAVCECPGGFQLDASRARCVDIDECRELN<br>QRGLLCKSERCVNTGSFRCVCKAGFARSRPHGACVPQRRR | 36 |
| LTBP3 | Mouse | GPAGERGTGGGGALARERFKVVFAPVICKRTCLKGQCRDSCQQGSNMTLIGEN<br>GHSTDTLTGSAFRVVVCPLPCMNGGQCSSRNQCLCPPDFTGRFCQVPAAGTGA<br>GTGSSGPGLARTGAMSTGLPPLAPEGESVASKHAIYAVQVIADPPGPGEGPP<br>AQHAAFLVPLGPGQISAEVQAPPPVVNVRVHHPPEASVQVHRIEGPNAEGPAS<br>SQHLLPHPKPPHPRPPTQKPLGRCFQDTLPKQPCGSNPLPGLTKQEDCCGSIG<br>TAWGQSKCHKCPQLQYTGVQKPVPVRGEVGADCPQGYKRLNSTHCQDINECAM<br>PGNVCHGDCLNNPGSYRCVCPPGHSLGPLAAQCIADKPEEKSLCFRLVSTEHQ<br>CQHPLTTRLTRQLCCCSVGKAWGARCQRCPADGTAAFKEICPGKGYHILTSHQ<br>TLTIQGESDFSLFLHPDGPPKPQQLPESPSRAPPLEDTEEERGVTMDPPVSEE<br>RSVQQSHPTTTTSPPRPYPELISRPSPPTFHRFLPDLPPSRSAVEIAPTQVTE<br>TDECRLNQNICGHGQCVPGPSDYSCHCNAGYRSHPQHRYCVDVNECEAPCGP<br>GKGICMNTGGSYNCHCNRGYRLHVGAGGRSCVDLNECAKPHLCGDGGFCINFP<br>GHYKCNCYPGYRLKASRPPICEDIDECRDPSTCPDGKCENKPGSFKCIACQPG<br>YRSQGGGACRDVNECSEGTPCSPGWCENLPGSYRCTCAQYEPAQDGLSCIDVD | 37 |

TABLE 3-continued

Exemplary LTBP amino acid sequences.

| Protein | Species | Sequence | SEQ ID NO |
|---|---|---|---|
| | | ECEAGKVCQDGICTNTPGSFQCQCLSGYHLSRDRSRCEDIDECDFPAACIGGD<br>CINTNGSYRCLCPLGHRLVGGRKCKKDIDECSQDPGLCLPHACENLQGSYVCV<br>CDEGFTLTQDQHGCEEVEQPHHKKECYLNFDDTVFCDSVLATNVTQQECCCSL<br>GAGWGDHCEIYPCPVYSSAEFHSLVPDGKRLHSGQQHCELCIPAHRDIDECIL<br>FGAEICKEGKCVNTQPGYECYCKQGFYYDGNLLECVDVDECLDESNCRNGVCE<br>NTRGGYRCACTPPAEYSPAQAQCLIPERWSTPQRDVKCAGASEERTACVWGPW<br>AGPALTFDDCCCRQPRLGTQCRPCPPRGTGSQCPTSQSESNSFWDTSPLLLGK<br>SPRDEDSSEEDSDECRCVSGRCVPRPGGAVCECPGGFQLDASRARCVDIDECR<br>ELNQRGLLCKSERCVNTSGSFRCVCKAGFTRSRPHGPACLSAAADDAAIAHTS<br>VIDHRGYFH | |
| LTBP3S | Mouse | ETDECRLNQNICGHGQCVPGPSDYSCHCNAGYRSHPQHRYCVDVNECEAEPCG<br>PGKGICMNTGGSYNCHCNRGYRLHVGAGGRSCVDLNECTKPHLCGDGGFCINF<br>PGHYKCNCYPGYRLKASRPPICEDIDECRDPSTCPDGKCENKPGSFKCIACQP<br>GYRSQGGGACRDVNECSEGTPCSPGWCENLPGSYRCTCAQGYEPAQDGLSCID<br>VDECEAGKVCQDGICTNTPGSFQCQCLSGYHLSRDRSRCEDIDECDFPAACIG<br>GDCINTNGSYRCLCPQGHRLVGGRKCQDIDECSQDPGLCLPHGACENLQGSYV<br>CVCDEGFTLTQDQHGCEEVEQPHHKKECYLNFDDTVFCDSVLATNVTQQECCC<br>SLGAGWGDHCEIYPCPVYSSAEFHSLCPDGKGYTQDNNIVNYGIPAHRDIDEC<br>ILFGAEICKEGKCVNTQPGYECYCKQGFYYDGNLLECVDVDECLDESNCRNGV<br>CENTRGGYRCACTPPAEYSPAQRQCL | 365 |

In an exemplary embodiment, inhibitors, e.g., antibodies, and antigen-binding portions thereof, that selectively bind LTBP1-TGFβ1 and/or LTBP3-TGFβ1 do not bind to a complex containing TGFβ1 and GARP or LRRC33. In one embodiment, the antibodies, or antigen-binding portions thereof, do not bind a GARP protein having a sequence set forth in SEQ ID NO:38 or SEQ ID NO:39, and do not bind to a complex containing said GARP protein. In another embodiment, the inhibitors, e.g., antibodies, or antigen-binding portions thereof, do not bind a GARP protein having a sequence set forth in SEQ ID NO:40 or SEQ ID NO:41, and do not bind to a complex containing said GARP protein. In one embodiment, the inhibitors, e.g., antibodies, or antigen-binding portions thereof, do not bind a LRRC33 protein having a sequence set forth in SEQ ID NO:42 or SEQ ID NO:43, and do not bind to a complex containing said LRRC33 protein. In one embodiment, the inhibitors, e.g., antibodies, or antigen-binding portions thereof, do not bind a GARP/LRRC33 chimera, e.g., the GARP/LRRC33 chimera set forth in SEQ ID NO:44.

TABLE 4

Exemplary GARP and LRRC33 amino acid sequences.

| Protein | Sequence | SEQ ID NO |
|---|---|---|
| GARP | AQHQDKVPCKMVDKKVSCQVLGLLQVPSVLPPDTETLDLSGNQLRSILASP<br>LGFYTALRHLDLSTNEISFLQPGAFQALTHLEHLSLAHNRLAMATALSAGG<br>LGPLPRVTSLDLSGNSLYSGLLERLLGEAPSLHTLSLAENSLTRLTRHTFR<br>DMPALEQLDLHSNVLMDIEDGAFEGLPRLTHLNLSRNSLTCISDFSLQQLR<br>VLDLSCNSIEAFQTASQPQAEFQLTWLDLRENKLLHFPDLAALPRLIYLNL<br>SNNLIRLPTGPPQDSKGIHAPSEGWSALPLSAPSGNASGRPLSQLLNLDLS<br>YNEIELIPDSFLEHLTSLCFLNLSRNCLRTFEARRLGSLPCLMLLDLSHNA<br>LETLELGARALGSLRTLLLQGNALRDLPPYTFANLASLQRLNLQGNRVSPC<br>GGPDEPGPSGCVAFSGITSLRSLSLVDNEIELLRAGAFLHTPLTELDLSSN<br>PGLEVATGALGGLEASLEVLALQGNGLMVLQVDLPCFICLKRLNLAENRLS<br>HLPAWTQAVSLEVLDLRNNSFSLLPGSAMGGLETSLRRLYLQGNPLSCCGN<br>GWLAAQLHQGRVDVDATQDLICRFSSQEEVSLSHVRPEDCEKGGLKNINLI<br>IILTFILVSAILLTTLAACCCVRRQKFNQQYKA | 38 |
| sGARP | AQHQDKVPCKMVDKKVSCQVLGLLQVPSVLPPDTETLDLSGNQLRSILASP<br>LGFYTALRHLDLSTNEISFLQPGAFQALTHLEHLSLAHNRLAMATALSAGG<br>LGPLPRVTSLDLSGNSLYSGLLERLLGEAPSLHTLSLAENSLTRLTRHTFR<br>DMPALEQLDLHSNVLMDIEDGAFEGLPRLTHLNLSRNSLTCISDFSLQQLR<br>VLDLSCNSIEAFQTASQPQAEFQLTWLDLRENKLLHFPDLAALPRLIYLNL<br>SNNLIRLPTGPPQDSKGIHAPSEGWSALPLSAPSGNASGRPLSQLLNLDLS<br>YNEIELIPDSFLEHLTSLCFLNLSRNCLRTFEARRLGSLPCLMLLDLSHNA<br>LETLELGARALGSLRTLLLQGNALRDLPPYTFANLASLQRLNLQGNRVSPC<br>GGPDEPGPSGCVAFSGITSLRSLSLVDNEIELLRAGAFLHTPLTELDLSSN<br>PGLEVATGALGGLEASLEVLALQGNGLMVLQVDLPCFICLKRLNLAENRLS<br>HLPAWTQAVSLEVLDLRNNSFSLLPGSAMGGLETSLRRLYLQGNPLSCCGN<br>GWLAAQLHQGRVDVDATQDLICRFSSQEEVSLSHVRPEDCEKGGLKNIN | 39 |
| GARP mouse | ISQRREQVPCRTVNKEALCHGLGLLQVPSVLSLDIQALYLSGNQLQSILVSP<br>LGFYTALRHLDLSDNQISFLQAGVFQALPYLEHLNLAHNRLATGMALNSGG<br>LGRLPLLVSLDLSGNSLHGNLVERLLGETPRLRTLSLAENSLTRLARHTFW<br>GMPAVEQLDLHSNVLMDIEDGAFEALPHLTHLNLSRNSLTCISDFSLQQLQ<br>VLDLSCNSIEAFQTAPEPQAQFQLAWLDLRENKLLHFPDLAVFPRLIYLNV | 40 |

TABLE 4-continued

Exemplary GARP and LRRC33 amino acid sequences.

| Protein | Sequence | SEQ ID NO |
|---|---|---|
| | SNNLIQLPAGLPRGSEDLHAPSEGWSASPLSNPSRNASTHPLSQLLNLDLS<br>YNEIELVPASFLEHLTSLRFLNLSRNCLRSFEARQVDSLPCLVLLDLSHNV<br>LEALELGTKVLGSLQTLLLQDNALQELPPYTFASLASLQRLNLQGNQVSPC<br>GGPAEPGPPGCVDFSGIPTLHVLNMAGNSMGMLRAGSFLHTPLTEDLSTN<br>PGLDVATGALVGLEASLEVLELQGNGLTVLRVDLPCFLRLKRLNLAENQLS<br>HLPAWTRAVSLEVLDLRNNSFSLLPGNAMGGLETSLRRLYLQGNPLSCCGN<br>GWLAAQLHQGRVDVDATQDLICRFGSQEELSLSLVRPEDCEKGGLKNVNLI<br>LLLSFTLVSAIVLTTLATICFLRRQKLSQQYKA | |
| sGARP mouse | ISQRREQVPCRTVNKEALCHGLGLLQVPSVLSLDIQALYLSGNQLQSILVS<br>PLGFYTALRHLDLSDNQISFLQAGVFQALPYLEHLNLAHNRLATGMALNSG<br>GLGRLPLLVSLDLSGNSLHGNLVERLLGETPRLRTLSLAENSLTRLARHTF<br>WGMPAVEQLDLSHNVLMDIEDGAFEALPHLTHLNLSRNSLTCISDFSLQQL<br>QVLDLSCNSIEAFQTAPEPQAQFQLAWLDLRENKLLHFPDLAVFPRLIYLN<br>VSNNLIQLPAGLPRGSEDLHAPSEGWSASPLSNPSRNASTHPLSQLLNLDL<br>SYNEIELVPASFLEHLTSLRFLNLSRNCLRSFEARQVDSLPCLVLLDLSHN<br>VLEALELGTKVLGSLQTLLLQDNALQELPPYTFASLASLQRLNLQGNQVSP<br>CGGPAEPGPPGCVDFSGIPTLHVLNMAGNSMGMLRAGSFLHTPLTEDLST<br>NPGLDVATGALVGLEASLEVLELQGNGLTVLRVDLPCFLRLKRLNLAENQL<br>SHLPAWTRAVSLEVLDLRNNSFSLLPGNAMGGLETSLRRLYLQGNPLSCCG<br>NGWLAAQLHQGRVDVDATQDLICRFGSQEELSLSLVRPEDCEKGGLKNVN | 41 |
| LRRC33 (also known as NRROS; Uniprot Accession No. Q86YC3) | MELLPLWLCLGFHFLTVGWRNRSGTATAASQGVCKLVGGAADCRGQSLASV<br>PSSLPPHARMLTLDANPLKTLWNHSLQPYPLLESLSLHSCHLERISRGAFQ<br>EQGHLRSLVLGDNCLSENYEETAAALHALPGLRRLDLSGNALTEDMAALML<br>QNLSSLRSVSLAGNTIMRLDDSVFEGLERLRELDLQRNYIFEIEGGAFDGL<br>AELRHLNLAFNNLPCIVDFGLTRLRVLNVSYNVLEWFLATGGEAAFELETL<br>DLSHNQLLFFPLLPQYSKLRTLLLRDNNMGFYRDLYNTSSPREMVAQFLLV<br>DGNVTNITTVSLWEEFSSSDLADLRFLDMSQNQFQYLPDGFLRKMPSLSHL<br>NLHQNCLMTLHIREHEPPGALTELDLSHNQLSELHLAPGLASCLGSLRLFN<br>LSSNQLLGVPPGLFANARNITTLDMSHNQISLCPLPAASDRVGPPSCVDFR<br>NMASLRSLSLEGCGLGALPDCPFQGTSLTYLDLSSNWGVLNGSLAPLQDVA<br>PMLQVLSLRNMGLHSSFMALDFSGFGNLRDLDLSGNCLTTFPRFGGSLALE<br>TLDLRRNSLTALPQKAVSEQLSRGLRTIYLSQNPYDCCGVDGWGALQHGQT<br>VADWAMVTCNLSSKIIRVTELPGGVPRDCKWERLDLGLLYLVLILPSCLTL<br>LVACTVIVLTFKKPLLQVIKSRCHWSSVY<br>*Native signal peptide is depicted in bold font. | 42 |
| soluble LRRC33 (sLRRC33) | MDMRVPAQLLGLLLLWFSGVLGWRNRSGTATAASQGVCKLVGGAADCRGQS<br>LASVPSSLPPHARMLTLDANPLKTLWNHSLQPYPLLESLSLHSCHLERISR<br>GAFQEQGHLRSLVLGDNCLSENYEETAAALHALPGLRRLDLSGNALTEDMA<br>ALMLQNLSSLRSVSLAGNTIMRLDDSVFEGLERLRELDLQRNYIFEIEGGA<br>FDGLAELRHLNLAFNNLPCIVDFGLTRLRVLNVSYNVLEWFLATGGEAAFE<br>LETLDLSHNQLLFFPLLPQYSKLRTLLLRDNNMGFYRDLYNTSSPREMVAQ<br>FLLVDGNVTNITTVSLWEEFSSSDLADLRFLDMSQNQFQYLPDGFLRKMPS<br>LSHLNLHQNCLMTLHIREHEPPGALTELDLSHNQLSELHLAPGLASCLGSL<br>RLFNLSSNQLLGVPPGLFANARNITTLDMSHNQISLCPLPAASDRVGPPSC<br>VDFRNMASLRSLSLEGCGLGALPDCPFQGTSLTYLDLSSNWGVLNGSLAPL<br>QDVAPMLQVLSLRNMGLHSSFMALDFSGFGNLRDLDLSGNCLTTFPRFGGS<br>LALETLDLRRNSLTALPQKAVSEQLSRGLRTIYLSQNPYDCCGVDGWGALQ<br>HGQTVADWAMVTCNLSSKIIRVTELPGGVPRDCKWERLDLGL<u>HHHHHH</u><br>*Modified human kappa light chain signal peptide is depicted in bold font.<br>**Histidine tag is underlined. | 43 |
| Human LRRC33-GARP chimera | MDMRVPAQLLGLLLLWFSGVLG<u>WRNRSGTATAASQGVCKLVGGAADCRGQS<br>LASVPSSLPPHARMLTLDANPLKTLWNHSLQPYPLLESLSLHSCHLERISR<br>GAFQEQGHLRSLVLGDNCLSENYEETAAALHALPGLRRLDLSGNALTEDMA<br>ALMLQNLSSLRSVSLAGNTIMRLDDSVFEGLERLRELDLQRNYIFEIEGGA<br>FDGLAELRHLNLAFNNLPCIVDFGLTRLRVLNVSYNVLEWFLATGGEAAFE<br>LETLDLSHNQLLFFPLLPQYSKLRTLLLRDNNMGFYRDLYNTSSPREMVAQ<br>FLLVDGNVTNITTVSLWEEFSSSDLADLRFLDMSQNQFQYLPDGFLRKMPS<br>LSHLNLHQNCLMTLHIREHEPPGALTELDLSHNQLSELHLAPGLASCLGSL<br>RLFNLSSNQLLGVPPGLFANARNITTLDMSHNQISLCPLPAASDRVGPPSC<br>VDFRNMASLRSLSLEGCGLGALPDCPFQGTSLTYLDLSSNWGVLNGSLAPL<br>QDVAPMLQVLSLRNMGLHSSFMALDFSGFGNLRDLDLSGNCLTTFPRFGGS<br>LALETLDLRRNSLTALPQKAVSEQLSRGLRTIYLSQNPYDCCGVDGWGALQ<br>HGQTVADWAMVTCNLSSKIIRVTELPGGVPRDCKWERLDLGL</u>*LIIILTFIL<br>VSAILLTTLAACCC*<u><u>VRRQKFNQQYKA</u></u><br>*Modified human kappa light chain signal peptide is depicted in bold font.<br>**LRRC33 ectodomain is underlined.<br># GARP transmembrane domain is italicized.<br>## GARP intracellular tail is double underlined. | 44 |

In another aspect, the invention provides methods of inhibiting TGFβ1 activation in the context of LTBP1 and/or LTBP3. In one embodiment, the method comprises exposing a LTBP1-proTGFβ1 complex or a LTBP3-proTGFβ1 complex an inhibitor, an antibody or antigen-binding portion thereof, and/or a pharmaceutical composition described herein. For example, in one embodiment, the inhibitor is an inhibitor of extracellular matrix-associated TGFβ1 activation, which selectively binds a LTBP1/3-presented proTGFβ1 latent complex. In one embodiment, the inhibitor does not inhibit immune cell-associated TGFβ1 activation, for example, immune cell-associated TGFβ1 activation that results from activation of a GARP-presented proTGFβ1 latent complex. In another embodiment, the antibody, or antigen-binding portion thereof, selectively binds an LTBP1-proTGFβ1 latent complex and/or an LTBP3-proTGFβ1 latent complex, thereby modulating release of mature TGFβ1 growth factor from the latent complex, wherein the antibody, or antigen-binding portion thereof, does not bind mature TGFβ1 alone or a GARP-proTGFβ1 latent complex. In one embodiment, the antibody, or antigen-binding portion thereof, inhibits the release of mature TGFβ1 from the LTBP1-proTGFβ1 complex and/or the LTBP3-proTGFβ1 complex. In one embodiment, the antibody, or antigen-binding portion thereof, does not inhibit the release of mature TGFβ1 from a GARP-proTGFβ1 complex or a LRRC33-proTGFβ1 complex.

In one embodiment, the method is performed in vitro. In another embodiment, the method is performed in vivo. In one embodiment, the LTBP1-proTGFβ1 complex or the LTBP3-proTGFβ1 complex is in an extracellular matrix. The extracellular matrix can comprise, for example, fibrillin and/or fibronectin. In some embodiments, the extracellular matrix comprises a protein comprising an RGD motif.

In some embodiments of the foregoing aspects, the antibody, or antigen-binding portion thereof, does not stimulate immune effector cells. In one embodiment, the antibody, or antigen-binding portion thereof, inhibits the release of mature TGFβ1 from a LTBP1-proTGFβ1 complex and/or a LTBP3-proTGFβ1 complex, and does not inhibit the release of mature TGFβ1 from a GARP-proTGFβ1 complex and/or an LRRC33-proTGFβ1 complex.

In some embodiments, inhibitors, e.g., antibodies, of the present disclosure that selectively bind to a LTBP1-TGFβ1 complex and/or a LTBP3-TGFβ1 complex can bind the complex with relatively high affinity, e.g., with a dissociation constant ($K_D$) less than $10^{-6}$M, $10^{-7}$ M, $10^{-8}$M, $10^{-9}$ M, $10^{-10}$ M, $10^{-11}$ M or lower. In one embodiment, an antibody, or antigen-binding portion thereof, binds a LTBP1-TGFβ1 complex and/or a LTBP3-TGFβ1 complex with a dissociation constant ($K_D$) of about $10^{-8}$M, about $10^{-9}$ M, about $10^{-10}$ M, about $10^{-11}$ M, about $10^{-12}$ M, or about $10^{-13}$ M. For example, antibodies that selectively bind to a LTBP1-TGFβ1 complex and/or a LTBP3-TGFβ1 complex can bind the complex with an affinity between 5 pM and 500 nM, e.g., between 10 pM and 100 nM, e.g., between 50 pM and 50 nM. In one embodiment, the antibody, or antigen-binding fragment thereof, can bind a LTBP1-TGFβ1 complex and/or a LTBP3-TGFβ1 complex with an affinity of less than about 300 nm, for example about 20 nM or lower, about 10 nM or lower, about 500 pM or lower, or about 5 pM or lower. For example, the antibody, or antigen-binding fragment thereof, can bind a LTBP1-TGFβ1 complex and/or a LTBP3-TGFβ1 complex with an affinity of about 1 nm to about 350 nm, from about 10 nm to about 200 nm, from about 15 nm to about 250 nm, from about 20 nm to about 200 nm, about 1 nm, about 20 nm, about 25 nm, about 50 nm, about 100 nm, about 150 nm, about 200 nm, about 250 nm, about 300 nm, or about 500 pm.

The disclosure also includes antibodies or antigen-binding fragments that compete with any of the antibodies described herein for binding to a LTBP1-TGFβ1 complex and/or a LTBP3-TGFβ1 complex. In some embodiments, such antibodies have an affinity for the complex of 50 nM or lower (e.g., 20 nM or lower, 10 nM or lower, 500 pM or lower, 50 pM or lower, or 5 pM or lower). The affinity and binding kinetics of antibodies (or antigen-binding fragments thereof) that selectively bind to a LTBP1-TGFβ1 complex and/or a LTBP3-TGFβ1 complex can be tested using any suitable method, including but not limited to biosensor technology (e.g., OCTET or BIACORE).

In one embodiment, the antibodies, or antigen-binding fragments thereof, of the present disclosure do not compete with antibody SR-Abl for binding to a human LTBP1-proTGFβ1 complex.

Aspects of the disclosure relate to antibodies that compete or cross-compete with any of the antibodies provided herein. The term "compete", as used herein with regard to an antibody, means that a first antibody binds to an epitope (e.g., an epitope of a LTBP1-TGFβ1 complex and/or an epitope of a LTBP3-TGFβ1 complex) in a manner sufficiently similar to the binding of a second antibody, such that the result of binding of the first antibody with its epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its epitope or ligand, whether to the same, greater, or lesser extent, the antibodies are said to "cross-compete" with each other for binding of their respective epitope(s). Both competing and cross-competing antibodies are within the scope of this disclosure. Regardless of the mechanism by which such competition or cross-competition occurs (e.g., steric hindrance, conformational change, or binding to a common epitope, or portion thereof), the skilled artisan would appreciate that such competing and/or cross-competing antibodies are encompassed and can be useful for the methods and/or compositions provided herein.

Aspects of the disclosure relate to antibodies that compete or cross-compete with any of the specific antibodies, or antigen-binding portions thereof, as provided herein, e.g., an antibody having one or more CDR sequences (1, 2, 3, 4, 5, or 6 CDR sequences) set forth in Table 5. In one embodiment, the invention provides antibodies, and antigen-binding fragments thereof, that compete or cross-compete with an antibody having heavy chain CDR sequences comprising SEQ ID NO:1, SEQ ID NO:2, and SEQ ID NO:3 as set forth in Table 5, and/or light chain CDR sequences comprising SEQ ID NO:4, SEQ ID NO:5, and SEQ ID NO:6 as set forth in Table 5. In one embodiment, the invention provides antibodies that compete or cross-compete with an antibody, or antigen-binding portion thereof, having a heavy chain variable region sequence comprising SEQ ID NO:7, and/or a light chain variable region sequence comprising SEQ ID NO:8. In some embodiments, an antibody, or antigen-binding portion thereof, binds at or near the same epitope as any of the antibodies provided herein. In some embodiments, an antibody, or antigen-binding portion thereof, binds near an epitope if it binds within 15 or fewer amino acid residues of the epitope. In some embodiments, any of the antibody, or antigen-binding portion thereof, as provided herein, binds within 1, 2, 3, 4, 5, 6, 7, 8, 9, 10, 11, 12, 13, 14 or 15 amino acid residues of an epitope that is bound by any of the antibodies provided herein.

In another embodiment, provided herein is an antibody, or antigen-binding portion thereof, competes or cross-competes for binding to any of the antigens provided herein (e.g., a LTBP1-TGFβ1 complex and/or a LTBP3-TGFβ1 complex) with an equilibrium dissociation constant, $K_D$, between the antibody and the protein of less than $10^{-6}$ M. In other embodiments, an antibody competes or cross-competes for binding to any of the antigens provided herein with a $K_D$ in a range from $10^{11}$ M to $10^{-6}$ M. In other embodiments, an antibody competes or cross-competes for binding to a human LTBP1-TGFβ1 complex and/or a human LTBP3-TGFβ1 complex with a $K_D$ of <50 nM as determined by a suitable in vitro binding assay, e.g., BLI, such as Octet®. In other embodiments, an antibody competes or cross-competes for binding to a human LTBP1-TGFβ1 complex and/or a human LTBP3-TGFβ1 complex with a $K_D$ of <10 nM as determined by a suitable in vitro binding assay, e.g., BLI, such as Octet.

In some embodiments, the antibody or antigen-binding portion competes or cross-competes with an antibody having a heavy chain variable region sequence and light chain variable region sequence of Ab42, as set forth in Table 6 (e.g., SEQ ID NOs: 318 and 319, respectively). The antibody may compete or cross-compete for binding to a human LTBP1-TGFβ1 complex and/or a human LTBP3-TGFβ1 complex with a $K_D$ of <10 nM as determined by a suitable in vitro binding assay, e.g., BLI, such as Octet. The antibody may compete or cross-compete for binding to a human LTBP1-TGFβ1 complex and/or a human LTBP3-TGFβ1 complex with a $K_D$ of <5 nM as determined by a suitable in vitro binding assay, e.g., BLI, such as Octet. The antibody may bind to a human LTBP1-TGFβ1 complex and a human LTBP3-TGFβ1 complex with a $K_D$ of <5 nM as determined by a suitable in vitro binding assay, e.g., BLI, such as Octet. The antibody may not show any detectable binding to a human GARP-proTGFβ1 complex in a suitable in vitro binding assay, such as BLI (e.g., Octet). The antibody may not show detectable binding to a human GARP-proTGFβ1 complex, as measured by BLI, under the same assay conditions as used to measure binding to human LTBP1-proTGFβ1 complex and/or human LTBP3-TGFβ1 complex. Alternatively, or in addition, the antibody or antigen-binding portion may bind (e.g., selectively bind) a human LTBP1-proTGFβ1 complex and/or a human LTBP3-TGFβ1 complex with a $K_D$ that is at least 50 times lower than the $K_D$ when binding to a human GARP-proTGFβ1 complex (and optionally at least 50 times lower than the $K_D$ when binding to a human LRRC33-proTGFβ1 complex) under the same assay conditions.

In some embodiments, the antibody competes or cross-competes with an antibody having a heavy chain variable region sequence and light chain variable region sequence of Ab63, as set forth in Table 6 (e.g., SEQ ID NOs: 360 and 361, respectively). The antibody may compete or cross-compete for binding to a human LTBP1-TGFβ1 complex and/or a human LTBP3-TGFβ1 complex with a $K_D$ of <10 nM as determined by a suitable in vitro binding assay, e.g., BLI, such as Octet. The antibody may compete or cross-compete for binding to a human LTBP1-TGFβ1 complex and/or a human LTBP3-TGFβ1 complex with a $K_D$ of <5 nM as determined by a suitable in vitro binding assay, e.g., BLI, such as Octet. The antibody may bind to a human LTBP1-TGFβ1 complex and a human LTBP3-TGFβ1 complex with a $K_D$ of <5 nM as determined by a suitable in vitro binding assay, e.g., BLI, such as Octet. The antibody may not show any detectable binding to a human GARP-proTGFβ1 complex in a suitable in vitro binding assay, such as BLI (e.g., Octet). The antibody may not show detectable binding to a human GARP-proTGFβ1 complex, as measured by BLI, under the same assay conditions as used to measure binding to human LTBP1-proTGFβ1 complex and/or human LTBP3-TGFβ1 complex. Alternatively, or in addition, the antibody or antigen-binding portion may bind (e.g., selectively bind) a human LTBP1-proTGFβ1 complex and/or a human LTBP3-TGFβ1 complex with a $K_D$ that is at least 50 times lower than the $K_D$ when binding to a human GARP-proTGFβ1 complex (and optionally at least 50 times lower than the $K_D$ when binding to a human LRRC33-proTGFβ1 complex) under the same assay conditions.

In further embodiments, the antibody which selectively binds a human LTBP1-TGFβ1 complex and/or a human LTBP3-TGFβ1 complex may not show meaningful binding (e.g., may not show a response of more than 0.1 units (nm)) on exposure to a human GARP-proTGFβ1 complex in a BLI assay (e.g., Octet) when the human GARP-proTGFβ1 complex is at a concentration of 200 nM.

In some embodiments, provided herein is an anti-TGFβ1 antibody, or antigen-binding portion thereof, that competes for binding with an antibody, or antigen-binding portion thereof, described herein. In some embodiments, provided herein is an anti-TGFβ1 antibody, or antigen-binding portion thereof, that binds to the same epitope as an antibody, or antigen-binding portion thereof, described herein.

The antibodies provided herein can be characterized using any suitable methods. For example, one method is to identify the epitope to which the antigen binds, or "epitope mapping." There are many suitable methods for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). In some embodiments, the epitope is a TGFβ1 epitope that is only available for binding by the antibody, or antigen-binding portion thereof, described herein, when the TGFβ1 is in a LTBP1-TGFβ1 complex and/or a LTBP3-TGFβ1 complex. In some embodiments, the epitope is present on a LTBP1/3-TGFβ1 complex, and is not present on a GARP-TGFβ1 complex and/or a LRRC33-TGFβ1 complex. In some embodiments, the epitope is available due to a conformational change in LTBP1/3 and/or TGFβ1 that occurs when LTBP1/3 and TGFβ1 form a complex. In this embodiment, the epitope is not present in LTBP1/3 or TGFβ1 when the proteins are not associated in a complex. In one embodiment, the epitope is present on TGFβ1, when TGFβ1 is in a complex with LTBP1 or LTBP3. In another embodiment, the epitope is present on LTBP1, when LTBP1 is in a complex with TGFβ1. In another embodiment, the epitope is present on LTBP3, when LTBP3 is in a complex with TGFβ1. In another embodiment, the epitope comprises residues from both LTBP1 and TGFβ1. In another embodiment, the epitope comprises residues from both LTBP3 and TGFβ1. Peptides of varying lengths (e.g., at least 4-6 amino acids long) can be isolated or synthesized (e.g., recombinantly) and used for binding assays with an antibody. In another example, the epitope to which the antibody binds can be determined in a systematic screen by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen-binding domain, domain swapping experiments and alanine scanning mutagenesis can be performed to identify residues required, sufficient, and/or necessary for epitope binding. For example, domain swapping experiments can be performed using a mutant of a target antigen in which various fragments of the LTBP1-TGFβ1 complex or LTBP3-TGFβ1 complex have been replaced (swapped) with sequences from a closely related, but antigenically distinct protein, such as another member of the TGFβ protein family (e.g., GDF11). By assessing binding of the antibody to the mutant of the LTBP1-TGFβ1 complex and/or LTBP3-TGFβ1 complex, the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art.

Further, the interaction of the any of the antibodies provided herein with one or more residues in a LTBP1-TGFβ1 complex and/or a LTBP3-TGFβ1 complex can be determined by routine technology. For example, a crystal structure can be determined, and the distances between the residues in a LTBP1-TGFβ1 complex and/or a LTBP3-TGFβ1 complex, and one or more residues in the antibody, can be determined accordingly. Based on such distance, whether a specific residue in a LTBP1/3-TGFβ1 complex interacts with one or more residues in the antibody can be determined. Further, suitable methods, such as competition assays and target mutagenesis assays, can be applied to determine the preferential binding of a candidate antibody.

In some embodiments, the antibodies, or antigen-binding portions thereof, of the present invention that selectively bind to a LTBP1-TGFβ1 complex and/or a LTBP3-TGFβ1 complex include one or more of complementary determining regions (CDRs) shown in Table 5. In some embodiments, the invention provides a nucleic acid molecule that encodes an antibody, or antigen-binding portion thereof, that selectively binds to a LTBP1-TGFβ1 complex and/or a LTBP3-TGFβ1 complex, as described herein. In one embodiment, the nucleic acid molecules encode one or more of the CDR sequences shown in Table 5.

TABLE 5

Complementary determining regions of the heavy chain (CDRHs) and the light chain (CDRLs) of SR-AB2, SR-AB10, SR-AB13, SR-AB22, SR-AB23, SR-AB31, SR-AB34, SR-AB37, and SR-AB38 to SR-AB64 as determined using the Kabat numbering scheme.

| Antibody | |
|---|---|
| SR-AB2 | |
| CDRH1 | GYTFTSYG (SEQ ID NO: 1) |
| CDRH2 | ISAYNGNT (SEQ ID NO: 2) |
| CDRH3 | ARAPLGNFDS (SEQ ID NO: 3) |
| CDRL1 | SGSIASNY (SEQ ID NO: 4) |
| CDRL2 | EDN (SEQ ID NO: 5) |
| CDRL3 | QSYDSSNHPVV (SEQ ID NO: 6) |
| SR-AB10 | |
| CDRH1 | FTFNNYPIH (SEQ ID NO: 94) |
| CDRH2 | VMSYDGINKYYADSVKG (SEQ ID NO: 95) |
| CDRH3 | ARPRIAARRGGFDY (SEQ ID NO: 96) |
| CDRL1 | TRSSGNIDNNYVQ (SEQ ID NO: 97) |
| CDRL2 | EDNQRPS (SEQ ID NO: 98) |
| CDRL3 | QSYDSDNQGVV (SEQ ID NO: 99) |
| SR-AB13 | |
| CDRH1 | GSISSSSYYWG (SEQ ID NO: 100) |
| CDRH2 | SISYSGSTYY (SEQ ID NO: 101) |
| CDRH3 | ARDPSYDSIAGMDV (SEQ ID NO: 102) |
| CDRL1 | RASQSISSYLN (SEQ ID NO: 103) |
| CDRL2 | AASNLQS (SEQ ID NO: 104) |
| CDRL3 | QQSFDFPFT (SEQ ID NO: 105) |
| SR-AB22 | |
| CDRH1 | FTFRSYVMH (SEQ ID NO: 108) |
| CDRH2 | VISHEGSLKYYADSVKG (SEQ ID NO: 109) |

TABLE 5-continued

Complementary determining regions of the heavy chain (CDRHs) and the light chain (CDRLs) of SR-AB2, SR-AB10, SR-AB13, SR-AB22, SR-AB23, SR-AB31, SR-AB34, SR-AB37, and SR-AB38 to SR-AB64 as determined using the Kabat numbering scheme.

| Antibody | | |
|---|---|---|
| CDRH3 | AVPRIAARRGGFGY (SEQ ID NO: 110) | |
| CDRL1 | TRSSGNIDNNYVQ (SEQ ID NO: 111) | |
| CDRL2 | EDNQRPS (SEQ ID NO: 112) | |
| CDRL3 | QSYDSDNQGVV (SEQ ID NO: 113) | |
| SR-AB23 | | |
| CDRH1 | FTFRSYVMH (SEQ ID NO: 116) | |
| CDRH2 | VISHEGSLKYYADSVKG (SEQ ID NO: 117) | |
| CDRH3 | ARPRIAARRGGFGY (SEQ ID NO: 118) | |
| CDRL1 | TRSSGNIDNNYVQ (SEQ ID NO: 119) | |
| CDRL2 | EDNQRPS (SEQ ID NO: 120) | |
| CDRL3 | QSYDSDNQGVV (SEQ ID NO: 121) | |
| SR-AB31 | | |
| CDRH1 | FTFRSYVMH (SEQ ID NO: 124) | |
| CDRH2 | VISHEGSLKYYADSVKG (SEQ ID NO: 125) | |
| CDRH3 | AVPRIAARRGGFGY (SEQ ID NO: 126) | |
| CDRL1 | TRSSGNIDNNYVQ (SEQ ID NO: 127) | |
| CDRL2 | EDNQRPS (SEQ ID NO: 128) | |
| CDRL3 | QSYDFNNQGVV (SEQ ID NO: 129) | |
| SR-AB34 | | |
| CDRH1 | FTFRSYVMH (SEQ ID NO: 130) | |
| CDRH2 | VISHEGSLKYYADSVKG (SEQ ID NO: 131) | |
| CDRH3 | AVPRIAARRGGFGY (SEQ ID NO: 132) | |
| CDRL1 | TRSSGNIDNNYVQ (SEQ ID NO: 133) | |
| CDRL2 | EDNQRPS (SEQ ID NO: 134) | |
| CDRL3 | QSYDYDAQGVV (SEQ ID NO: 135) | |
| SR-AB37 | | |
| CDRH1 | FTFRSYVMH (SEQ ID NO: 136) | |
| CDRH2 | VISHEGSLKYYADSVKG (SEQ ID NO: 137) | |
| CDRH3 | AVPRIAARRGGFGY (SEQ ID NO: 138) | |
| CDRL1 | TRSSGLIDDNYVQ (SEQ ID NO: 139) | |
| CDRL2 | EDNQRPS (SEQ ID NO: 140) | |
| CDRL3 | QSYDSDLQRVV (SEQ ID NO: 141) | |
| SR-AB38 | | |
| CDRH1 | FTFRSYVMH (SEQ ID NO: 142) | |
| CDRH2 | VISHEGSLKYYADSVKG (SEQ ID NO: 143) | |
| CDRH3 | AVPRIAARRGGFGY (SEQ ID NO: 144) | |
| CDRL1 | TRSSGSIDNNYVQ (SEQ ID NO: 145) | |
| CDRL2 | EDFIRPS (SEQ ID NO: 146) | |
| CDRL3 | QSYDDDLQGVV (SEQ ID NO: 147) | |
| SR-AB39 | | |
| CDRH1 | FTFRSYVMH (SEQ ID NO: 148) | |
| CDRH2 | VISHEGSLKYYADSVKG (SEQ ID NO: 149) | |
| CDRH3 | AVPRIAARRGGFGY (SEQ ID NO: 150) | |
| CDRL1 | TRSSGLIDDNYVQ (SEQ ID NO: 151) | |
| CDRL2 | EDAQRPS (SEQ ID NO: 152) | |
| CDRL3 | QSYDHDEQGVV (SEQ ID NO: 153) | |
| SR-AB40 | | |
| CDRH1 | FTFRSYVMH (SEQ ID NO: 154) | |
| CDRH2 | VISHEGSLKYYADSVKG (SEQ ID NO: 155) | |
| CDRH3 | ARPRIAARRGGFGY (SEQ ID NO: 156) | |

TABLE 5-continued

Complementary determining regions of the heavy chain (CDRHs) and the light chain (CDRLs) of SR-AB2, SR-AB10, SR-AB13, SR-AB22, SR-AB23, SR-AB31, SR-AB34, SR-AB37, and SR-AB38 to SR-AB64 as determined using the Kabat numbering scheme.

| Antibody | | |
|---|---|---|
| CDRL1 | TRSSGNIDNNYVQ (SEQ ID NO: 157) | |
| CDRL2 | EDNQRPS (SEQ ID NO: 158) | |
| CDRL3 | QSYDYSNQGVV (SEQ ID NO: 159) | |
| SR-AB41 | | |
| CDRH1 | FTFRSYVMH (SEQ ID NO: 160) | |
| CDRH2 | VISHEGSLKYYADSVKG (SEQ ID NO: 161) | |
| CDRH3 | ARPRIAARRGGFGY (SEQ ID NO: 162) | |
| CDRL1 | TRSSGNIDNNYVQ (SEQ ID NO: 163) | |
| CDRL2 | EDNQRPS (SEQ ID NO: 164) | |
| CDRL3 | QSYDYDNQAVV (SEQ ID NO: 165) | |
| SR-AB42 | | |
| CDRH1 | FTFRSYVMH (SEQ ID NO: 166) | |
| CDRH2 | VISHEGSLKYYADSVKG (SEQ ID NO: 167) | |
| CDRH3 | ARPRIAARRGGFGY (SEQ ID NO: 168) | |
| CDRL1 | TRSSGNIDNNYVQ (SEQ ID NO: 169) | |
| CDRL2 | EDNQRPS (SEQ ID NO: 170) | |
| CDRL3 | QSYDYDTQGVV (SEQ ID NO: 171) | |
| SR-AB43 | | |
| CDRH1 | FTFRSYVMH (SEQ ID NO: 172) | |
| CDRH2 | VISHEGSLKYYADSVKG (SEQ ID NO: 173) | |
| CDRH3 | ARPRIAARRGGFGY (SEQ ID NO: 174) | |
| CDRL1 | TRSSGNIDYNYVQ (SEQ ID NO: 175) | |
| CDRL2 | EDNVRPS (SEQ ID NO: 176) | |
| CDRL3 | QSYDSDNQRVV (SEQ ID NO: 177) | |
| SR-AB44 | | |
| CDRH1 | FTFRSYVMH (SEQ ID NO: 178) | |
| CDRH2 | VISHEGSLKYYADSVKG (SEQ ID NO: 179) | |
| CDRH3 | ARPRIAARRGGFGY (SEQ ID NO: 180) | |
| CDRL1 | TRSHGNIDDNYVQ (SEQ ID NO: 181) | |
| CDRL2 | EDNVRPS (SEQ ID NO: 182) | |
| CDRL3 | QSYDSDNQLVV (SEQ ID NO: 183) | |
| SR-AB45 | | |
| CDRH1 | FTFRSYVMH (SEQ ID NO: 184) | |
| CDRH2 | VISHEGSLKYYADSVKG (SEQ ID NO: 185) | |
| CDRH3 | ARPRIAARRGGFGY (SEQ ID NO: 186) | |
| CDRL1 | TRSSGAIDDNYVQ (SEQ ID NO: 187) | |
| CDRL2 | EDFQRPS (SEQ ID NO: 188) | |
| CDRL3 | QSYDDDLQGVV (SEQ ID NO: 189) | |
| SR-AB46 | | |
| CDRH1 | FTFRSYVMH (SEQ ID NO: 190) | |
| CDRH2 | VISHEGSGKYYADSVKG (SEQ ID NO: 191) | |
| CDRH3 | ARPRIAARRGGFGS (SEQ ID NO: 192) | |
| CDRL1 | TRSSGNIDYNYVQ (SEQ ID NO: 193) | |
| CDRL2 | EDNVRPS (SEQ ID NO: 194) | |
| CDRL3 | QSYDSDNQRVV (SEQ ID NO: 195) | |
| SR-AB47 | | |
| CDRH1 | FTFRSYVMH (SEQ ID NO: 196) | |
| CDRH2 | VISHEGSGKYYADSVKG (SEQ ID NO: 197) | |
| CDRH3 | ARPRIAARRGGFGS (SEQ ID NO: 198) | |

TABLE 5-continued

Complementary determining regions of the heavy chain (CDRHs) and the light chain (CDRLs) of SR-AB2, SR-AB10, SR-AB13, SR-AB22, SR-AB23, SR-AB31, SR-AB34, SR-AB37, and SR-AB38 to SR-AB64 as determined using the Kabat numbering scheme.

| Antibody | |
|---|---|
| CDRL1 | TRSSGNIDYNYVQ (SEQ ID NO: 199) |
| CDRL2 | EDNVRPS (SEQ ID NO: 200) |
| CDRL3 | QSYDYDNQAVV (SEQ ID NO: 201) |
| SR-AB48 | |
| CDRH1 | FTFRSYVMH (SEQ ID NO: 202) |
| CDRH2 | VISHEGSGKYYADSVKG (SEQ ID NO: 203) |
| CDRH3 | ARPRIAARRGGFGS (SEQ ID NO: 204) |
| CDRL1 | TRSSGNIDYNYVQ (SEQ ID NO: 205) |
| CDRL2 | EDNVRPS (SEQ ID NO: 206) |
| CDRL3 | QSYDYDTQGVV (SEQ ID NO: 207) |
| SR-AB49 | |
| CDRH1 | FTFRSYVMH (SEQ ID NO: 208) |
| CDRH2 | VISHEGSGKYYADSVKG (SEQ ID NO: 209) |
| CDRH3 | ARPRIAARRGGFGS (SEQ ID NO: 210) |
| CDRL1 | TRSSGNIDYNYVQ (SEQ ID NO: 211) |
| CDRL2 | EDNVRPS (SEQ ID NO: 212) |
| CDRL3 | QGYDWDTQGVV (SEQ ID NO: 213) |
| SR-AB50 | |
| CDRH1 | FTFRSYVMH (SEQ ID NO: 214) |
| CDRH2 | VISHEGSGKYYADSVKG (SEQ ID NO: 215) |
| CDRH3 | ARPRIAARRGGFGT (SEQ ID NO: 216) |
| CDRL1 | TRSSGNIDYNYVQ (SEQ ID NO: 217) |
| CDRL2 | EDNVRPS (SEQ ID NO: 218) |
| CDRL3 | QSYDSDNQRVV (SEQ ID NO: 219) |

TABLE 5-continued

Complementary determining regions of the heavy chain (CDRHs) and the light chain (CDRLs) of SR-AB2, SR-AB10, SR-AB13, SR-AB22, SR-AB23, SR-AB31, SR-AB34, SR-AB37, and SR-AB38 to SR-AB64 as determined using the Kabat numbering scheme.

| Antibody | |
|---|---|
| SR-AB51 | |
| CDRH1 | FTFRSYVMH (SEQ ID NO: 220) |
| CDRH2 | VISHEGSGKYYADSVKG (SEQ ID NO: 221) |
| CDRH3 | ARPRIAARRGGFGT (SEQ ID NO: 222) |
| CDRL1 | TRSSGNIDYNYVQ (SEQ ID NO: 223) |
| CDRL2 | EDNVRPS (SEQ ID NO: 224) |
| CDRL3 | QSYDYDNQAVV (SEQ ID NO: 225) |
| SR-AB52 | |
| CDRH1 | FTFRSYVMH (SEQ ID NO: 226) |
| CDRH2 | VISHEGSGKYYADSVKG (SEQ ID NO: 227) |
| CDRH3 | ARPRIAARRGGFGT (SEQ ID NO: 228) |
| CDRL1 | TRSSGNIDYNYVQ (SEQ ID NO: 229) |
| CDRL2 | EDNVRPS (SEQ ID NO: 230) |
| CDRL3 | QSYDYDTQGVV (SEQ ID NO: 231) |
| SR-AB53 | |
| CDRH1 | FTFRSYVMH (SEQ ID NO: 232) |
| CDRH2 | VISHEGSGKYYADSVKG (SEQ ID NO: 233) |
| CDRH3 | ARPRIAARRGGFGT (SEQ ID NO: 234) |
| CDRL1 | TRSSGNIDYNYVQ (SEQ ID NO: 235) |
| CDRL2 | EDNVRPS (SEQ ID NO: 236) |
| CDRL3 | QGYDWDTQGVV (SEQ ID NO: 237) |
| SR-AB54 | |
| CDRH1 | FTFRSYVMH (SEQ ID NO: 238) |
| CDRH2 | VISHEGSGKYYADSVKG (SEQ ID NO: 239) |

TABLE 5-continued

Complementary determining regions of the heavy chain (CDRHs) and the light chain (CDRLs) of SR-AB2, SR-AB10, SR-AB13, SR-AB22, SR-AB23, SR-AB31, SR-AB34, SR-AB37, and SR-AB38 to SR-AB64 as determined using the Kabat numbering scheme.

| Antibody | | |
|---|---|---|
| CDRH3 | ALPRIAARRGGFGS | (SEQ ID NO: 240) |
| CDRL1 | TRSSGNIDYNYVQ | (SEQ ID NO: 241) |
| CDRL2 | EDNVRPS | (SEQ ID NO: 242) |
| CDRL3 | QSYDSDNQRVV | (SEQ ID NO: 243) |
| | SR-AB55 | |
| CDRH1 | FTFRSYVMH | (SEQ ID NO: 244) |
| CDRH2 | VISHEGSGKYYADSVKG | (SEQ ID NO: 245) |
| CDRH3 | ALPRIAARRGGFGS | (SEQ ID NO: 246) |
| CDRL1 | TRSSGNIDYNYVQ | (SEQ ID NO: 247) |
| CDRL2 | EDNVRPS | (SEQ ID NO: 248) |
| CDRL3 | QSYDYDNQAVV | (SEQ ID NO: 249) |
| | SR-AB56 | |
| CDRH1 | FTFRSYVMH | (SEQ ID NO: 250) |
| CDRH2 | VISHEGSGKYYADSVKG | (SEQ ID NO: 251) |
| CDRH3 | ALPRIAARRGGFGS | (SEQ ID NO: 252) |
| CDRL1 | TRSSGNIDYNYVQ | (SEQ ID NO: 253) |
| CDRL2 | EDNVRPS | (SEQ ID NO: 254) |
| CDRL3 | QSYDYDTQGVV | (SEQ ID NO: 255) |
| | SR-AB57 | |
| CDRH1 | FTFRSYVMH | (SEQ ID NO: 256) |
| CDRH2 | VISHEGSGKYYADSVKG | (SEQ ID NO: 257) |
| CDRH3 | ALPRIAARRGGFGS | (SEQ ID NO: 258) |
| CDRL1 | TRSSGNIDYNYVQ | (SEQ ID NO: 259) |
| CDRL2 | EDNVRPS | (SEQ ID NO: 260) |
| CDRL3 | QGYDWDTQGVV | (SEQ ID NO: 261) |
| | SR-AB58 | |
| CDRH1 | FTFRSYVMH | (SEQ ID NO: 262) |
| CDRH2 | VISHEGSGKYYADSVKG | (SEQ ID NO: 263) |
| CDRH3 | ALPRIAARRGGFGT | (SEQ ID NO: 264) |
| CDRL1 | TRSSGNIDYNYVQ | (SEQ ID NO: 265) |
| CDRL2 | EDNVRPS | (SEQ ID NO: 266) |
| CDRL3 | QSYDSDNQRVV | (SEQ ID NO: 267) |
| | SR-AB59 | |
| CDRH1 | FTFRSYVMH | (SEQ ID NO: 268) |
| CDRH2 | VISHEGSGKYYADSVKG | (SEQ ID NO: 269) |
| CDRH3 | ALPRIAARRGGFGT | (SEQ ID NO: 270) |
| CDRL1 | TRSSGNIDYNYVQ | (SEQ ID NO: 271) |
| CDRL2 | EDNVRPS | (SEQ ID NO: 272) |
| CDRL3 | QSYDYDNQAVV | (SEQ ID NO: 273) |
| | SR-AB60 | |
| CDRH1 | FTFRSYVMH | (SEQ ID NO: 274) |
| CDRH2 | VISHEGSGKYYADSVKG | (SEQ ID NO: 275) |
| CDRH3 | ALPRIAARRGGFGT | (SEQ ID NO: 276) |
| CDRL1 | TRSSGNIDYNYVQ | (SEQ ID NO: 277) |
| CDRL2 | EDNVRPS | (SEQ ID NO: 278) |
| CDRL3 | QSYDYDTQGVV | (SEQ ID NO: 279) |
| | SR-AB61 | |
| CDRH1 | FTFRSYVMH | (SEQ ID NO: 280) |
| CDRH2 | VISHEGSGKYYADSVKG | (SEQ ID NO: 281) |

TABLE 5-continued

Complementary determining regions of the heavy chain (CDRHs) and the light chain (CDRLs) of SR-AB2, SR-AB10, SR-AB13, SR-AB22, SR-AB23, SR-AB31, SR-AB34, SR-AB37, and SR-AB38 to SR-AB64 as determined using the Kabat numbering scheme.

| Antibody | | |
|---|---|---|
| CDRH3 | ALPRIAARRGGFGT | (SEQ ID NO: 282) |
| CDRL1 | TRSSGNIDYNYVQ | (SEQ ID NO: 283) |
| CDRL2 | EDNVRPS | (SEQ ID NO: 284) |
| CDRL3 | QGYDWDTQGVV | (SEQ ID NO: 285) |
| SR-AB62 | | |
| CDRH1 | GSIRSSSYYWG | (SEQ ID NO: 286) |
| CDRH2 | SISYSATTYY | (SEQ ID NO: 287) |
| CDRH3 | ASDPSYDSAAGMDV | (SEQ ID NO: 288) |
| CDRL1 | RASKVISSYLN | (SEQ ID NO: 289) |
| CDRL2 | YASSLQS | (SEQ ID NO: 290) |
| CDRL3 | QQSNDWPFT | (SEQ ID NO: 291) |
| SR-AB63 | | |
| CDRH1 | GSIRSSSYYWG | (SEQ ID NO: 292) |
| CDRH2 | SISYSATTYY | (SEQ ID NO: 293) |
| CDRH3 | AGDPSYDSIAGMQV | (SEQ ID NO: 294) |
| CDRL1 | RASQSISSYLN | (SEQ ID NO: 295) |
| CDRL2 | AASNLQS | (SEQ ID NO: 296) |
| CDRL3 | QQSFDWPLT | (SEQ ID NO: 297) |
| SR-AB64 | | |
| CDRH1 | GSIRSSSYYWG | (SEQ ID NO: 298) |
| CDRH2 | SISYSATTYY | (SEQ ID NO: 299) |
| CDRH3 | AGDPSYDSIAGMQV | (SEQ ID NO: 300) |
| CDRL1 | RASQSISYYLN | (SEQ ID NO: 301) |
| CDRL2 | SASSRQS | (SEQ ID NO: 302) |
| CDRL3 | QQGFDFPLT | (SEQ ID NO: 303) |

In some embodiments, antibodies of the present invention that selectively bind to a LTBP1-TGFβ3 complex and/or a LTBP3-TGFβ complex include any antibody, or antigen-binding portion thereof, comprising a CDRH1, CDRH2, CDRH3, CDRL1, CDRL2, or CDRL3, or combinations thereof, as provided in Table 5. In some embodiments, antibodies that selectively bind to a LTBP1-TGFβ3 complex and/or a LTBP3-TGFβ complex include CDRH1, CDRH2, CDRH3, CDRL1, CDRL2, and CDRL3 as provided in Table 5.

The present invention also provides a nucleic acid sequence that encodes a molecule comprising CDRH1, CDRH2, CDRH3, CDRL1, CDRL2, or CDRL3, or combinations thereof, as provided in Table 5.

Antibody heavy and light chain CDR3 domains may play a particularly important role in the binding specificity/affinity of an antibody for an antigen. Accordingly, in some embodiments, the antibodies, or antigen-binding portions thereof, that selectively bind to a LTBP1-TGFβ complex and/or a LTBP3-TGFβ complex, or the nucleic acid molecules that encode these antibodies, or antigen-binding portions thereof, can include at least the heavy and/or light chain CDR3 of the antibody shown in Table 5.

Aspects of the invention relate to a monoclonal antibody, or antigen-binding portion thereof, that binds selectively to a LTBP1-TGFβ complex and/or a LTBP3-TGFβ complex, and that comprises six complementarity determining regions (CDRs): CDRH1, CDRH2, CDRH3, CDRL1, CDRL2, and CDRL3. The antibody, or antigen-binding portion thereof may have the CDRH1, CDRH2, CDRH3, CDRL1, CDRL2, and CDRL3 of one of the antibodies (e.g., Ab42) shown in Table 5.

In some embodiments, CDRH1 comprises a sequence as set forth in SEQ ID NO: 1. In some embodiments, CDRH2 comprises a sequence as set forth in SEQ ID NO: 2. In some embodiments, CDRH3 comprises a sequence as set forth in SEQ ID NO: 3. In some embodiments, CDRL1 comprises a sequence as set forth in SEQ ID NO: 4. In some embodiments, CDRL2 comprises a sequence as set forth in SEQ ID NO: 5. In some embodiments, CDRL3 comprises a sequence as set forth in SEQ ID NO: 6.

In one aspect, the invention provides an isolated antibody, or an antigen-binding fragment thereof, that specifically binds a human LTBP1-proTGFβ complex and/or a human LTBP3-proTGFβ complex and does not bind a human GARP-proTGFβ1 complex; wherein the antibody or the antigen-binding fragment thereof does not bind mature TGFβ1, mature TGFβ2 or mature TGFβ3; wherein the antibody or the antigen-binding fragment thereof is a fully human or humanized antibody or antigen-binding fragment thereof, wherein the antibody or the antigen-binding fragment thereof comprises at least three CDRs selected from the following, optionally comprising up to one or more amino acid changes for each of the CDRs: CDR-H1: SEQ ID NO:1; CDR-H2: SEQ ID NO:2; CDR-H3: SEQ ID NO:3; CDR-L1: SEQ ID NO:4; CDR-L2: SEQ ID NO:5; and, CDR-L3: SEQ ID NO:6. In some embodiments, the one or more amino acid changes comprises up to 1, 2, 3, 4, 5, or 6 amino acid changes for each of the CDRs.

In some embodiments (e.g., as for antibody SR-AB2, shown in Table 5), the antibody, or antigen-binding portion thereof, that selectively binds to a LTBP1-TGFβ complex and/or a LTBP3-TGFβ3 complex comprises: a CDRH1 comprising an amino acid sequence as set forth in SEQ ID NO: 1, a CDRH2 comprising an amino acid sequence as set forth in SEQ ID NO: 2, a CDRH3 comprising an amino acid sequence as set forth in SEQ ID NO: 3, a CDRL1 comprising an amino acid sequence as set forth in SEQ ID NO: 4, a CDRL2 comprising an amino acid sequence as set forth in SEQ ID NO: 5, and a CDRL3 comprising an amino acid sequence as set forth in SEQ ID NO: 6.

In some embodiments, the antibody, or antigen-binding portion thereof, comprises a heavy chain variable region comprising a complementarity determining region 3 (CDR3) having the amino acid sequence of SEQ ID NO: 3 and a light chain variable region comprising a CDR3 having the amino acid sequence of SEQ ID NO: 6. In some embodiments, the antibody, or antigen-binding portion thereof, comprises a heavy chain variable region comprising a complementarity determining region 2 (CDR2) having the amino acid sequence of SEQ ID NO: 2 and a light chain variable region comprising a CDR2 having the amino acid sequence of SEQ ID NO: 5. In some embodiments, the antibody, or antigen-binding portion thereof, comprises a heavy chain variable region comprising a complementarity determining region 1 (CDR1) having the amino acid sequence of SEQ ID NO: 1 and a light chain variable region comprising a CDR1 having the amino acid sequence of SEQ ID NO: 4.

The amino acid sequences of the heavy chain variable region (HCVR) and the light chain variable region (LCVR) of the antibody set forth in Table 5 (e.g., SR-AB2) are provided in Table 6.

In some embodiments, CDRH1 comprises a sequence as set forth in SEQ ID NO: 94. In some embodiments, CDRH2 comprises a sequence as set forth in SEQ ID NO: 95. In some embodiments, CDRH3 comprises a sequence as set forth in SEQ ID NO: 96. In some embodiments, CDRL1 comprises a sequence as set forth in SEQ ID NO: 97. In some embodiments, CDRL2 comprises a sequence as set forth in SEQ ID NO: 98. In some embodiments, CDRL3 comprises a sequence as set forth in SEQ ID NO: 99.

In one aspect, the invention provides an isolated antibody, or an antigen-binding fragment thereof, that specifically binds a human LTBP1-proTGFβ complex and/or a human LTBP3-proTGFβ complex and does not bind a human GARP-proTGFβ1 complex; wherein the antibody or the antigen-binding fragment thereof does not bind mature TGFβ1, mature TGFβ2 or mature TGFβ3; wherein the antibody or the antigen-binding fragment thereof is a fully human or humanized antibody or antigen-binding fragment thereof, wherein the antibody or the antigen-binding fragment thereof comprises at least three CDRs selected from the following, optionally comprising one or more amino acid changes for each of the CDRs: CDR-H1: SEQ ID NO:94; CDR-H2: SEQ ID NO:95; CDR-H3: SEQ ID NO:96; CDR-L1: SEQ ID NO:97; CDR-L2: SEQ ID NO:98; and, CDR-L3: SEQ ID NO:99. In some embodiments, the one or more amino acid changes comprises up to 1, 2, 3, 4, 5, or 6 amino acid changes for each of the CDRs.

In some embodiments (e.g., as for antibody SR-AB10, shown in Table 5), the antibody, or antigen-binding portion thereof, that selectively binds to a LTBP1-TGFβ complex and/or a LTBP3-TGFβ3 complex comprises: a CDRH1 comprising an amino acid sequence as set forth in SEQ ID NO: 94, a CDRH2 comprising an amino acid sequence as set forth in SEQ ID NO: 95, a CDRH3 comprising an amino acid sequence as set forth in SEQ ID NO: 96, a CDRL1 comprising an amino acid sequence as set forth in SEQ ID NO: 97, a CDRL2 comprising an amino acid sequence as set forth in SEQ ID NO: 98, and a CDRL3 comprising an amino acid sequence as set forth in SEQ ID NO: 99.

In some embodiments, the antibody, or antigen-binding portion thereof, comprises a heavy chain variable region comprising a complementarity determining region 3 (CDR3) having the amino acid sequence of SEQ ID NO: 96 and a light chain variable region comprising a CDR3 having the amino acid sequence of SEQ ID NO: 99. In some embodiments, the antibody, or antigen-binding portion thereof, comprises a heavy chain variable region comprising a complementarity determining region 2 (CDR2) having the amino acid sequence of SEQ ID NO: 95 and a light chain variable region comprising a CDR2 having the amino acid sequence of SEQ ID NO: 98. In some embodiments, the antibody, or antigen-binding portion thereof, comprises a heavy chain variable region comprising a complementarity determining region 1 (CDR1) having the amino acid sequence of SEQ ID NO: 94 and a light chain variable region comprising a CDR1 having the amino acid sequence of SEQ ID NO: 97.

The amino acid sequences of the heavy chain variable region (HCVR) and the light chain variable region (LCVR) of the antibody set forth in Table 5 (e.g., SR-AB10) are provided in Table 6.

In some embodiments, CDRH1 comprises a sequence as set forth in SEQ ID NO: 100. In some embodiments, CDRH2 comprises a sequence as set forth in SEQ ID NO: 101. In some embodiments, CDRH3 comprises a sequence as set forth in SEQ ID NO: 102. In some embodiments, CDRL1 comprises a sequence as set forth in SEQ ID NO: 103. In some embodiments, CDRL2 comprises a sequence as set forth in SEQ ID NO: 104. In some embodiments, CDRL3 comprises a sequence as set forth in SEQ ID NO: 105.

In one aspect, the invention provides an isolated antibody, or an antigen-binding fragment thereof, that specifically binds a human LTBP1-proTGFβ complex and/or a human LTBP3-proTGFβ complex and does not bind a human GARP-proTGFβ1 complex; wherein the antibody or the antigen-binding fragment thereof does not bind mature TGFβ1, mature TGFβ2 or mature TGFβ3; wherein the antibody or the antigen-binding fragment thereof is a fully human or humanized antibody or antigen-binding fragment thereof, wherein the antibody or the antigen-binding fragment thereof comprises at least three CDRs selected from the following, optionally comprising one or more amino acid changes for each of the CDRs: CDR-H1: SEQ ID NO:100; CDR-H2: SEQ ID NO:101; CDR-H3: SEQ ID NO:102; CDR-L1: SEQ ID NO:103; CDR-L2: SEQ ID NO:104; and, CDR-L3: SEQ ID NO:105. In some embodiments, the one or more amino acid changes comprises up to 1, 2, 3, 4, 5, or 6 amino acid changes for each of the CDRs.

In some embodiments (e.g., as for antibody SR-AB13, shown in Table 5), the antibody, or antigen-binding portion thereof, that selectively binds to a LTBP1-TGFβ complex and/or a LTBP3-TGFβ complex comprises: a CDRH1 comprising an amino acid sequence as set forth in SEQ ID NO: 100, a CDRH2 comprising an amino acid sequence as set forth in SEQ ID NO: 101, a CDRH3 comprising an amino acid sequence as set forth in SEQ ID NO: 102, a CDRL1 comprising an amino acid sequence as set forth in SEQ ID NO: 103, a CDRL2 comprising an amino acid sequence as set forth in SEQ ID NO: 104, and a CDRL3 comprising an amino acid sequence as set forth in SEQ ID NO: 105.

In some embodiments, the antibody, or antigen-binding portion thereof, comprises a heavy chain variable region comprising a complementarity determining region 3 (CDR3) having the amino acid sequence of SEQ ID NO: 102 and a light chain variable region comprising a CDR3 having the amino acid sequence of SEQ ID NO: 105. In some embodiments, the antibody, or antigen-binding portion thereof, comprises a heavy chain variable region comprising a complementarity determining region 2 (CDR2) having the amino acid sequence of SEQ ID NO: 101 and a light chain variable region comprising a CDR2 having the amino acid sequence of SEQ ID NO: 104. In some embodiments, the antibody, or antigen-binding portion thereof, comprises a heavy chain variable region comprising a complementarity determining region 1 (CDR1) having the amino acid sequence of SEQ ID NO: 100 and a light chain variable region comprising a CDR1 having the amino acid sequence of SEQ ID NO: 103.

The amino acid sequences of the heavy chain variable region (HCVR) and the light chain variable region (LCVR) of the antibody set forth in Table 5 (e.g., SR-AB13) are provided in Table 6.

In some embodiments, CDRH1 comprises a sequence as set forth in SEQ ID NO: 124. In some embodiments, CDRH2 comprises a sequence as set forth in SEQ ID NO: 125. In some embodiments, CDRH3 comprises a sequence as set forth in SEQ ID NO: 126. In some embodiments, CDRL1 comprises a sequence as set forth in SEQ ID NO: 127. In some embodiments, CDRL2 comprises a sequence as set forth in SEQ ID NO: 128. In some embodiments, CDRL3 comprises a sequence as set forth in SEQ ID NO: 129.

In one aspect, the invention provides an isolated antibody, or an antigen-binding fragment thereof, that specifically binds a human LTBP1-proTGFβ complex and/or a human LTBP3-proTGFβ complex; wherein the antibody or the antigen-binding fragment thereof does not bind mature TGFβ1, mature TGFβ2 or mature TGFβ3; wherein the antibody or the antigen-binding fragment thereof is a fully human or humanized antibody or antigen-binding fragment thereof, wherein the antibody or the antigen-binding fragment thereof comprises at least three (optionally all six) CDRs selected from the following, optionally comprising up to one or more amino acid changes for each of the CDRs: CDR-H1: SEQ ID NO:124; CDR-H2: SEQ ID NO:125; CDR-H3: SEQ ID NO:126; CDR-L1: SEQ ID NO:127; CDR-L2: SEQ ID NO:128; and, CDR-L3: SEQ ID NO:129. In some embodiments, the one or more amino acid changes comprises up to 1, 2, 3, 4, 5, or 6 amino acid changes for each of the CDRs.

In some embodiments (e.g., as for antibody SR-AB31, shown in Table 5), the antibody, or antigen-binding portion thereof, that selectively binds to a LTBP1-TGFβ complex and/or a LTBP3-TGFβ complex comprises: a CDRH1 comprising an amino acid sequence as set forth in SEQ ID NO: 124, a CDRH2 comprising an amino acid sequence as set forth in SEQ ID NO: 125, a CDRH3 comprising an amino acid sequence as set forth in SEQ ID NO: 126, a CDRL1 comprising an amino acid sequence as set forth in SEQ ID NO: 127, a CDRL2 comprising an amino acid sequence as set forth in SEQ ID NO: 128, and a CDRL3 comprising an amino acid sequence as set forth in SEQ ID NO: 129.

In some embodiments, the antibody, or antigen-binding portion thereof, comprises a heavy chain variable region comprising a complementarity determining region 3 (CDR3) having the amino acid sequence of SEQ ID NO: 126 and a light chain variable region comprising a CDR3 having the amino acid sequence of SEQ ID NO: 129. In some embodiments, the antibody, or antigen-binding portion thereof, comprises a heavy chain variable region comprising a complementarity determining region 2 (CDR2) having the amino acid sequence of SEQ ID NO: 125 and a light chain variable region comprising a CDR2 having the amino acid sequence of SEQ ID NO: 128. In some embodiments, the antibody, or antigen-binding portion thereof, comprises a heavy chain variable region comprising a complementarity determining region 1 (CDR1) having the amino acid sequence of SEQ ID NO: 124 and a light chain variable region comprising a CDR1 having the amino acid sequence of SEQ ID NO: 127.

The amino acid sequences of the HCVR and the LCVR of the antibody set forth in Table 5 (e.g., SR-AB31) are provided in Table 6.

In some embodiments, CDRH1 comprises a sequence as set forth in SEQ ID NO: 166. In some embodiments, CDRH2 comprises a sequence as set forth in SEQ ID NO: 167. In some embodiments, CDRH3 comprises a sequence as set forth in SEQ ID NO: 168. In some embodiments, CDRL1 comprises a sequence as set forth in SEQ ID NO: 169. In some embodiments, CDRL2 comprises a sequence as set forth in SEQ ID NO: 170. In some embodiments, CDRL3 comprises a sequence as set forth in SEQ ID NO: 171.

In one aspect, the invention provides an isolated antibody, or an antigen-binding fragment thereof, that specifically binds a human LTBP1-proTGFβ complex and/or a human LTBP3-proTGFβ complex; wherein the antibody or the antigen-binding fragment thereof does not bind mature TGFβ1, mature TGFβ2 or mature TGFβ3; wherein the antibody or the antigen-binding fragment thereof is a fully human or humanized antibody or antigen-binding fragment thereof, wherein the antibody or the antigen-binding fragment thereof comprises at least three (optionally all six) CDRs selected from the following, optionally comprising up to one or more amino acid changes for each of the CDRs: CDR-H1: SEQ ID NO:166; CDR-H2: SEQ ID NO:167; CDR-H3: SEQ ID NO:168; CDR-L1: SEQ ID NO:169; CDR-L2: SEQ ID NO:170; and, CDR-L3: SEQ ID NO:171. In some embodiments, the one or more amino acid changes comprises up to 1, 2, 3, 4, 5, or 6 amino acid changes for each of the CDRs.

In some embodiments (e.g., as for antibody SR-AB42, shown in Table 5), the antibody, or antigen-binding portion thereof, that selectively binds to a LTBP1-TGFβ complex and/or a LTBP3-TGFβ complex comprises: a CDRH1 comprising an amino acid sequence as set forth in SEQ ID NO: 166, a CDRH2 comprising an amino acid sequence as set forth in SEQ ID NO: 167, a CDRH3 comprising an amino acid sequence as set forth in SEQ ID NO: 168, a CDRL1 comprising an amino acid sequence as set forth in SEQ ID NO: 169, a CDRL2 comprising an amino acid sequence as set forth in SEQ ID NO: 170, and a CDRL3 comprising an amino acid sequence as set forth in SEQ ID NO: 171.

In some embodiments, the antibody, or antigen-binding portion thereof, comprises a heavy chain variable region comprising a complementarity determining region 3 (CDR3) having the amino acid sequence of SEQ ID NO: 168 and a light chain variable region comprising a CDR3 having the amino acid sequence of SEQ ID NO: 171. In some embodiments, the antibody, or antigen-binding portion thereof, comprises a heavy chain variable region comprising a complementarity determining region 2 (CDR2) having the amino acid sequence of SEQ ID NO: 167 and a light chain variable region comprising a CDR2 having the amino acid sequence of SEQ ID NO: 170. In some embodiments, the antibody, or antigen-binding portion thereof, comprises a heavy chain variable region comprising a complementarity determining region 1 (CDR1) having the amino acid sequence of SEQ ID NO: 166 and a light chain variable region comprising a CDR1 having the amino acid sequence of SEQ ID NO: 169.

The amino acid sequences of the HCVR and the LCVR of the antibody set forth in Table 5 (e.g., SR-AB42) are provided in Table 6.

In some embodiments, CDRH1 comprises a sequence as set forth in SEQ ID NO: 292. In some embodiments, CDRH2 comprises a sequence as set forth in SEQ ID NO: 293. In some embodiments, CDRH3 comprises a sequence as set forth in SEQ ID NO: 294. In some embodiments, CDRL1 comprises a sequence as set forth in SEQ ID NO: 295. In some embodiments, CDRL2 comprises a sequence as set forth in SEQ ID NO: 296. In some embodiments, CDRL3 comprises a sequence as set forth in SEQ ID NO: 297.

In one aspect, the invention provides an isolated antibody, or an antigen-binding fragment thereof, that specifically binds a human LTBP1-proTGFβ complex and/or a human LTBP3-proTGFβ complex; wherein the antibody or the antigen-binding fragment thereof does not bind mature TGFβ1, mature TGFβ2 or mature TGFβ3; wherein the antibody or the antigen-binding fragment thereof is a fully human or humanized antibody or antigen-binding fragment thereof, wherein the antibody or the antigen-binding fragment thereof comprises at least three (optionally all six) CDRs selected from the following, optionally comprising up to one or more amino acid changes for each of the CDRs: CDR-H1: SEQ ID NO:292; CDR-H2: SEQ ID NO:293; CDR-H3: SEQ ID NO:294; CDR-L1: SEQ ID NO:295; CDR-L2: SEQ ID NO:296; and, CDR-L3: SEQ ID NO:297. In some embodiments, the one or more amino acid changes comprises up to 1, 2, 3, 4, 5, or 6 amino acid changes for each of the CDRs.

In some embodiments (e.g., as for antibody SR-AB63, shown in Table 5), the antibody, or antigen-binding portion thereof, that selectively binds to a LTBP1-TGFβ complex and/or a LTBP3-TGFβ complex comprises: a CDRH1 comprising an amino acid sequence as set forth in SEQ ID NO: 292, a CDRH2 comprising an amino acid sequence as set forth in SEQ ID NO: 293, a CDRH3 comprising an amino acid sequence as set forth in SEQ ID NO: 294, a CDRL1 comprising an amino acid sequence as set forth in SEQ ID NO: 295, a CDRL2 comprising an amino acid sequence as set forth in SEQ ID NO: 296, and a CDRL3 comprising an amino acid sequence as set forth in SEQ ID NO: 297.

In some embodiments, the antibody, or antigen-binding portion thereof, comprises a heavy chain variable region comprising a complementarity determining region 3 (CDR3) having the amino acid sequence of SEQ ID NO: 294 and a light chain variable region comprising a CDR3 having the amino acid sequence of SEQ ID NO: 297. In some embodiments, the antibody, or antigen-binding portion thereof, comprises a heavy chain variable region comprising a complementarity determining region 2 (CDR2) having the amino acid sequence of SEQ ID NO: 293 and a light chain variable region comprising a CDR2 having the amino acid sequence of SEQ ID NO: 296. In some embodiments, the antibody, or antigen-binding portion thereof, comprises a heavy chain variable region comprising a complementarity determining region 1 (CDR1) having the amino acid sequence of SEQ ID NO: 292 and a light chain variable region comprising a CDR1 having the amino acid sequence of SEQ ID NO: 295.

The amino acid sequences of the HCVR and the LCVR of the antibody set forth in Table 5 (e.g., SR-AB63) are provided in Table 6.

Ten additional antibodies (Ab3-Ab12) were developed that specifically bind to a LTBP1-TGFβ3 complex and/or a LTBP3-TGFβ complex, and inhibit release of mature TGFβ presented in the context of LTBP1/3. Table 6 also provides the HCVR and LCVR amino acid sequences of these additional LTBP context-specific antibodies, in addition to the HCVR and LCVR amino acid sequences of the antibodies referred to in Table 5.

TABLE 6

Heavy Chain Variable Region Sequence and Light Chain Variable Region Sequence of Antibodies that Specifically Bind a LTBP1/3-TGFβ1 Complex

| Antibody | HCVR Sequence | LCVR Sequence |
|---|---|---|
| SR-AB2 | QVQLVQSGAEVKKPGASVKVSCKA SGYTFTSYGISWVRQAPGQGLEWM GWISAYNGNTNYAQKLQGRVTMTT DTSTSTAYMELRSLRSDDTAVYYCA RAPLGNFDSWGQGTMVTVSS (SEQ ID NO: 7) | NFMLTQPHSVSESPGKTVTISCTRSS GSIASNYVQWYQQRPGSSPTTVIYE DNQRPSGVPDRFSGSIDSSSNSASLTI SGLKTEDEADYYCQSYDSSNHPVVF GGGTKLTVL (SEQ ID NO: 8) |
| SR-AB3 | QMQLVQSGAEVKKPGASVKVSCKA SGYTFTSYGISWVRQAPGQGLEWM GWISAYNGNTNYAQKLQGRVTMTT NTSTSTAYMELRSLRSDDTAVYYCA RDDYYYYGMDVWGQGTLVTVSS (SEQ ID NO: 74) | QSGLTQPASVSGSPGQSVTISCTGTS SDVGGYNYASWYQQHPGKAPKLMI YDVSKRPSGVPDRFSGSKSGNTASL TISGLQAEDEADYYCSSYTSSSTYVF GTGTKLTVL (SEQ ID NO: 75) |
| SR-AB4 | QVQLQQWGAGLLKPSETLSLTCAV YGGSFSGYYWSWIRQPPGKGLEWI GEIIHSGSTNYNPSLKSRVTISVDTSK NQFSLKLSSVTAADTAVYYCARGV GLGRFDPWGQGTLVTVSS (SEQ ID NO: 76) | QSELTQSPSASGTPGQRVTISCSGSN SNIGTNTVNWYQQFPGTAPKLLIYY NDQRPSGVSDRFSGSRSGTSASLAIN GLQSEDEADYYCATWDDSLSGVVF GGGTKLTVL (SEQ ID NO: 77) |
| SR-AB5 | QVQLQQWGAGLLKPSETLSLTCAV YGGSFSGYYWSWIRQPPGKGLEWI GEINHSGSTNYNPSLKSRVTISVDTS KNQFSLKLSSVTAADTAVYYCARG VGLGRFDPWGQGTLVTVSS (SEQ ID NO: 78) | QSELTQSPSASGTPGQRVTISCSGSN SNIGTNTVNWYQQFPGTAPKLLIYY NDQRPSGVSDRFSGSRSGTSASLAIN GLQSEDEADYYCATWDDSLSGVVF GGGTKLTVL (SEQ ID NO: 79) |

TABLE 6-continued

Heavy Chain Variable Region Sequence and Light Chain Variable Region Sequence of
Antibodies that Specifically Bind a LTBP1/3-TGFβ1 Complex

| Antibody | HCVR Sequence | LCVR Sequence |
| --- | --- | --- |
| SR-AB6 | QVQLQQSGPGLVRPSQTLSLTCAISG DSVSSNGAAWNWIRQSPSRGLEWL GRTYYRSKWYNDYAVSVKSRITINP DTSKNQFSLKLTSVTPEDTAVYYCA RGEDWGYAFDIWGQGTLVTVSS (SEQ ID NO: 80) | NFMLTQPHSVSESPGKTVTISCTRSS GSIASNYVQWYQQRPGSAPTTVIYD DKQRPSGIPDRFSGSIDSSSNSASLTI SGLKTEDEADYYCQSYDSSNVVFG GGTKVTVL (SEQ ID NO: 81) |
| SR-AB7 | QVQLVQSGAEVKKPGASVKVSCKA SGYTFTSYGISWVRQAPGQGLEWM GWISAYDGNTNYAQKLQGRVTMTT DTSTSTAYMELSSLRSDDTAVYYCA RNPYYYYMDVWGQGTTVTVSS (SEQ ID NO: 82) | QSELTQAPSVSVAPGQTARITCGGN NIGGRSKSVHWYQHKLGQAPVLIV YDNTDRPSGISERFSGSSSVNAATLT ITTAEAGDEGDYYCQVWDVSTDHV VFGGGTKVTVL (SEQ ID NO: 83) |
| SR-AB8 | QVQLVESGAEVKKPGASVKVSCKA SGYTFTGYYMHWVRQAPGQGLEW MGWINPNGGGTNYAQKFQGRVTM TRDTSISTAYMELSRLRSDDTAVYY CANRRRGSAFDIWGQGTLVTVSS (SEQ ID NO: 84) | NFMLTQPHSVSESPGKTVTISCTGSS GSIASNYVQWYQQRPGSSPTTVIYE DNQRPSGVPDRFSGSIDSSSNSASLTI SGLKTEDEADYYCQSYDDNYHVIF GGGTKLTVL (SEQ ID NO: 85) |
| SR-AB9 | QVQLVESGGALVQPGGSLRLSCAAS GFTFSSYAMHWVRQAPGKGLEWV AVISYDGSNKYYADSVKGRFTISRD NSKNTLYLQMNSLRAEDTAVYYCA KETGYGFGLFWGQGTMVTVSS (SEQ ID NO: 86) | NFMLTQPHSVSESPGRTLTIPCFRSS GNIGDSYVHWYQQRPGSAPTTVIYR DSQRPSGVPDRFSGSIDFSSNSASLTI SGLKTEDEAAYYCQSYDRSNQWVF GGGTKLTVL (SEQ ID NO: 87) |
| SR-AB10 | QLQLQESGGGVVQPGRSLRLSCAAS GFTFNNYPIHWVRQAPGKGLEWVA VMSYDGINKYYADSVKGRFTISRDN SKNTLYLQMNSLRAEDTAVYYCAR PRIAARRGGFDYWGQGTLVTVSS (SEQ ID NO: 88) | NFMLTQPHSVSESPGKTVTISCTRSS GNIDNNYVQWYQQRPGSSPTTVIYE DNQRPSGVPDRFSGSIDSSSNSASLTI SGLKTEDEADYYCQSYDSDNQGVV FGGGTKLTVL (SEQ ID NO: 89) |
| SR-AB11 | QVQLVQSGAEVKKPGASVKVSCKA SGYTFTSYGISWVRQAPGQGLEWM GWISAYNGNTDYAQKLQGRVTMTT DTSTSTAYMELRGLRSDDTAVYYC ARAPLGNFDSWGQGTLVTVSS (SEQ ID NO: 90) | NFMLTQPHSVSESPGKTVTISCTRSS GSIASNYVQWYQQRPGSAPTTVIYE DNQRPSGVPDRFSGSIDSSSNSASLTI SGLKTEDEADYYCQSYDSSNHVVF GGGTKVTVL (SEQ ID NO: 91) |
| SR-AB12 | EVQLLESGGGVVQPGRSLRLSCAAS GFTFPNYAMSWVRQAPGKGLEWVS AISGSGGSTYYADSVKGRFTISRDNS KNTLYLQMNSLRAEDTAVYYCAKD LEGGYYWDYYYYGMDVWGQGTL VTVSS (SEQ ID NO: 92) | NFMLTQPHSVSESPGKTVTISCTRSS GSIASNYVQWYQQRPGSSPTTVIYE DNQRPSGVPDRFSGSIDSSSNSASLTI SGLKTEDEADYYCQSYDSSIVVFGG GTQLTVL (SEQ ID NO: 93) |
| SR-AB13 | QLQLQESGPGLVKPSETLSLTCTVSG GSISSSSYYWGWIRQPPGKGLEWIG SISYSGSTYYNPSLKSRVTISVDTSK NQFSLKLSSVTAADTAVYYCARDPS YDSIAGMDVWGQGTTVTVSS (SEQ ID NO: 106) | DIQLTQSPSSLSASVGDRVTITCRAS QSISSYLNWYQQKPGKAPKLLIYAA SNLQSGVPSRFSGSGSGTDFTLTISSL QPEDFATYYCQQSFDFPFTFGGGTK VEIK (SEQ ID NO: 107) |
| SR-AB22 | QVQLVESGGGVVQPGRSLRLSCAAS GFTFRSYVMHWVRQAPGKGLEWV AVISHEGSLKYYADSVKGRFTISRD NSKNTLYLQMNSLRAEDTAVYYCA VPRIAARRGGFGYWGQGTLVTVSS (SEQ ID NO: 114) | NFMLTQPHSVSESPGKTVTISCTRSS GNIDNNYVQWYQQRPGSSPTTVIYE DNQRPSGVPDRFSGSIDSSSNSASLTI SGLKTEDEADYYCQSYDSDNQGVV FGGGTKLTVL (SEQ ID NO: 115) |
| SR-AB23 | QVQLVESGGGVVQPGRSLRLSCAAS GFTFRSYVMHWVRQAPGKGLEWV AVISHEGSLKYYADSVKGRFTISRD NSKNTLYLQMNSLRAEDTAVYYCA RPRIAARRGGFGYWGQGTLVTVSS (SEQ ID NO: 122) | NFMLTQPHSVSESPGKTVTISCTRSS GNIDNNYVQWYQQRPGSSPTTVIYE DNQRPSGVPDRFSGSIDSSSNSASLTI SGLKTEDEADYYCQSYDSDNQGVV FGGGTKLTVL (SEQ ID NO: 123) |

TABLE 6-continued

Heavy Chain Variable Region Sequence and Light Chain Variable Region Sequence of Antibodies that Specifically Bind a LTBP1/3-TGFβ1 Complex

| Antibody | HCVR Sequence | LCVR Sequence |
| --- | --- | --- |
| SR-AB31 | QVQLVESGGGVVQPGRSLRLSCAAS GFTFRSYVMHWVRQAPGKGLEWV AVISHEGSLKYYADSVKGRFTISRD NSKNTLYLQMNSLRAEDTAVYYCA VPRIAARRGGFGYWGQGTLVTVSS (SEQ ID NO: 304) | NFMLTQPHSVSESPGKTVTISCTRSS GNIDNNYVQWYQQRPGSSPTTVIYE DNQRPSGVPDRFSGSIDSSSNSASLTI SGLKTEDEADYYCQSYDFNNQGVV FGGGTKLTVL (SEQ ID NO: 305) |
| SR-AB34 | QVQLVESGGGVVQPGRSLRLSCAAS GFTFRSYVMHWVRQAPGKGLEWV AVISHEGSLKYYADSVKGRFTISRD NSKNTLYLQMNSLRAEDTAVYYCA VPRIAARRGGFGYWGQGTLVTVSS (SEQ ID NO: 306) | NFMLTQPHSVSESPGKTVTISCTRSS GNIDNNYVQWYQQRPGSSPTTVIYE DNQRPSGVPDRFSGSIDSSSNSASLTI SGLKTEDEADYYCQSYDYDAQGVV FGGGTKLTVL (SEQ ID NO: 307) |
| SR-AB37 | QVQLVESGGGVVQPGRSLRLSCAAS GFTFRSYVMHWVRQAPGKGLEWV AVISHEGSLKYYADSVKGRFTISRD NSKNTLYLQMNSLRAEDTAVYYCA VPRIAARRGGFGYWGQGTLVTVSS (SEQ ID NO: 308) | NFMLTQPHSVSESPGKTVTISCTRSS GLIDDNYVQWYQQRPGSSPTTVIYE DNQRPSGVPDRFSGSIDSSSNSASLTI SGLKTEDEADYYCQSYDSDLQRVV FGGGTKLTVL (SEQ ID NO: 309) |
| SR-AB38 | QVQLVESGGGVVQPGRSLRLSCAAS GFTFRSYVMHWVRQAPGKGLEWV AVISHEGSLKYYADSVKGRFTISRD NSKNTLYLQMNSLRAEDTAVYYCA VPRIAARRGGFGYWGQGTLVTVSS (SEQ ID NO: 310) | NFMLTQPHSVSESPGKTVTISCTRSS GSIDNNYVQWYQQRPGSSPTTVIYE DFIRPSGVPDRFSGSIDSSSNSASLTIS GLKTEDEADYYCQSYDDDLQGVVF GGGTKLTVL (SEQ ID NO: 311) |
| SR-AB39 | QVQLVESGGGVVQPGRSLRLSCAAS GFTFRSYVMHWVRQAPGKGLEWV AVISHEGSLKYYADSVKGRFTISRD NSKNTLYLQMNSLRAEDTAVYYCA VPRIAARRGGFGYWGQGTLVTVSS (SEQ ID NO: 312) | NFMLTQPHSVSESPGKTVTISCTRSS GLIDDNYVQWYQQRPGSSPTTVIYE DAQRPSGVPDRFSGSIDSSSNSASLTI SGLKTEDEADYYCQSYDHDEQGVV FGGGTKLTVL (SEQ ID NO: 313) |
| SR-AB40 | QVQLVESGGGVVQPGRSLRLSCAAS GFTFRSYVMHWVRQAPGKGLEWV AVISHEGSLKYYADSVKGRFTISRD NSKNTLYLQMNSLRAEDTAVYYCA RPRIAARRGGFGYWGQGTLVTVSS (SEQ ID NO: 314) | NFMLTQPHSVSESPGKTVTISCTRSS GNIDNNYVQWYQQRPGSSPTTVIYE DNQRPSGVPDRFSGSIDSSSNSASLTI SGLKTEDEADYYCQSYDYSNQGVV FGGGTKLTVL (SEQ ID NO: 315) |
| SR-AB41 | QVQLVESGGGVVQPGRSLRLSCAAS GFTFRSYVMHWVRQAPGKGLEWV AVISHEGSLKYYADSVKGRFTISRD NSKNTLYLQMNSLRAEDTAVYYCA RPRIAARRGGFGYWGQGTLVTVSS (SEQ ID NO: 316) | NFMLTQPHSVSESPGKTVTISCTRSS GNIDNNYVQWYQQRPGSSPTTVIYE DNQRPSGVPDRFSGSIDSSSNSASLTI SGLKTEDEADYYCQSYDYDNQAVV FGGGTKLTVL (SEQ ID NO: 317) |
| SR-AB42 | QVQLVESGGGVVQPGRSLRLSCAAS GFTFRSYVMHWVRQAPGKGLEWV AVISHEGSLKYYADSVKGRFTISRD NSKNTLYLQMNSLRAEDTAVYYCA RPRIAARRGGFGYWGQGTLVTVSS (SEQ ID NO: 318) | NFMLTQPHSVSESPGKTVTISCTRSS GNIDNNYVQWYQQRPGSSPTTVIYE DNQRPSGVPDRFSGSIDSSSNSASLTI SGLKTEDEADYYCQSYDYDTQGVV FGGGTKLTVL (SEQ ID NO: 319) |
| SR-AB43 | QVQLVESGGGVVQPGRSLRLSCAAS GFTFRSYVMHWVRQAPGKGLEWV AVISHEGSLKYYADSVKGRFTISRD NSKNTLYLQMNSLRAEDTAVYYCA RPRIAARRGGFGYWGQGTLVTVSS (SEQ ID NO: 320) | NFMLTQPHSVSESPGKTVTISCTRSS GNIDYNYVQWYQQRPGSSPTTVIYE DNVRPSGVPDRFSGSIDSSSNSASLTI SGLKTEDEADYYCQSYDSDNQRVV FGGGTKLTVL (SEQ ID NO: 321) |
| SR-AB44 | QVQLVESGGGVVQPGRSLRLSCAAS GFTFRSYVMHWVRQAPGKGLEWV AVISHEGSLKYYADSVKGRFTISRD NSKNTLYLQMNSLRAEDTAVYYCA RPRIAARRGGFGYWGQGTLVTVSS (SEQ ID NO: 322) | NFMLTQPHSVSESPGKTVTISCTRSH GNIDDNYVQWYQQRPGSSPTTVIYE DNVRPSGVPDRFSGSIDSSSNSASLTI SGLKTEDEADYYCQSYDSDNQLVV FGGGTKLTVL (SEQ ID NO: 323) |

TABLE 6-continued

Heavy Chain Variable Region Sequence and Light Chain Variable Region Sequence of Antibodies that Specifically Bind a LTBP1/3-TGFβ1 Complex

| Antibody | HCVR Sequence | LCVR Sequence |
|---|---|---|
| SR-AB45 | QVQLVESGGGVVQPGRSLRLSCAAS GFTFRSYVMHWVRQAPGKGLEWV AVISHEGSLKYYADSVKGRFTISRD NSKNTLYLQMNSLRAEDTAVYYCA RPRIAARRGGFGYWGQGTLVTVSS (SEQ ID NO: 324) | NFMLTQPHSVSESPGKTVTISCTRSS GAIDDNYVQWYQQRPGSSPTTVIYE DFQRPSGVPDRFSGSIDSSSNSASLTI SGLKTEDEADYYCQSYDDDLQGVV FGGGTKLTVL (SEQ ID NO: 325) |
| SR-AB46 | QVQLVESGGGVVQPGRSLRLSCAAS GFTFRSYVMHWVRQAPGKGLEWV AVISHEGSGKYYADSVKGRFTISRD NSKNTLYLQMNSLRAEDTAVYYCA RPRIAARRGGFGSWGQGTLVTVSS (SEQ ID NO: 326) | NFMLTQPHSVSESPGKTVTISCTRSS GNIDYNYVQWYQQRPGSSPTTVIYE DNVRPSGVPDRFSGSIDSSSNSASLTI SGLKTEDEADYYCQSYDSDNQRVV FGGGTKLTVL (SEQ ID NO: 327) |
| SR-AB47 | QVQLVESGGGVVQPGRSLRLSCAAS GFTFRSYVMHWVRQAPGKGLEWV AVISHEGSGKYYADSVKGRFTISRD NSKNTLYLQMNSLRAEDTAVYYCA RPRIAARRGGFGSWGQGTLVTVSS (SEQ ID NO: 328) | NFMLTQPHSVSESPGKTVTISCTRSS GNIDYNYVQWYQQRPGSSPTTVIYE DNVRPSGVPDRFSGSIDSSSNSASLTI SGLKTEDEADYYCQSYDYDNQAVV FGGGTKLTVL (SEQ ID NO: 329) |
| SR-AB48 | QVQLVESGGGVVQPGRSLRLSCAAS GFTFRSYVMHWVRQAPGKGLEWV AVISHEGSGKYYADSVKGRFTISRD NSKNTLYLQMNSLRAEDTAVYYCA RPRIAARRGGFGSWGQGTLVTVSS (SEQ ID NO: 330) | NFMLTQPHSVSESPGKTVTISCTRSS GNIDYNYVQWYQQRPGSSPTTVIYE DNVRPSGVPDRFSGSIDSSSNSASLTI SGLKTEDEADYYCQSYDYDTQGVV FGGGTKLTVL (SEQ ID NO: 331) |
| SR-AB49 | QVQLVESGGGVVQPGRSLRLSCAAS GFTFRSYVMHWVRQAPGKGLEWV AVISHEGSGKYYADSVKGRFTISRD NSKNTLYLQMNSLRAEDTAVYYCA RPRIAARRGGFGSWGQGTLVTVSS (SEQ ID NO: 332) | NFMLTQPHSVSESPGKTVTISCTRSS GNIDYNYVQWYQQRPGSSPTTVIYE DNVRPSGVPDRFSGSIDSSSNSASLTI SGLKTEDEADYYCQGYDWDTQGV VFGGGTKLTVL (SEQ ID NO: 333) |
| SR-AB50 | QVQLVESGGGVVQPGRSLRLSCAAS GFTFRSYVMHWVRQAPGKGLEWV AVISHEGSGKYYADSVKGRFTISRD NSKNTLYLQMNSLRAEDTAVYYCA RPRIAARRGGFGTWGQGTLVTVSS (SEQ ID NO: 334) | NFMLTQPHSVSESPGKTVTISCTRSS GNIDYNYVQWYQQRPGSSPTTVIYE DNVRPSGVPDRFSGSIDSSSNSASLTI SGLKTEDEADYYCQSYDSDNQRVV FGGGTKLTVL (SEQ ID NO: 335) |
| SR-AB51 | QVQLVESGGGVVQPGRSLRLSCAAS GFTFRSYVMHWVRQAPGKGLEWV AVISHEGSGKYYADSVKGRFTISRD NSKNTLYLQMNSLRAEDTAVYYCA RPRIAARRGGFGTWGQGTLVTVSS (SEQ ID NO: 336) | NFMLTQPHSVSESPGKTVTISCTRSS GNIDYNYVQWYQQRPGSSPTTVIYE DNVRPSGVPDRFSGSIDSSSNSASLTI SGLKTEDEADYYCQSYDYDNQAVV FGGGTKLTVL (SEQ ID NO: 337) |
| SR-AB52 | QVQLVESGGGVVQPGRSLRLSCAAS GFTFRSYVMHWVRQAPGKGLEWV AVISHEGSGKYYADSVKGRFTISRD NSKNTLYLQMNSLRAEDTAVYYCA RPRIAARRGGFGTWGQGTLVTVSS (SEQ ID NO: 338) | NFMLTQPHSVSESPGKTVTISCTRSS GNIDYNYVQWYQQRPGSSPTTVIYE DNVRPSGVPDRFSGSIDSSSNSASLTI SGLKTEDEADYYCQSYDYDTQGVV FGGGTKLTVL (SEQ ID NO: 339) |
| SR-AB53 | QVQLVESGGGVVQPGRSLRLSCAAS GFTFRSYVMHWVRQAPGKGLEWV AVISHEGSGKYYADSVKGRFTISRD NSKNTLYLQMNSLRAEDTAVYYCA RPRIAARRGGFGTWGQGTLVTVSS (SEQ ID NO: 340) | NFMLTQPHSVSESPGKTVTISCTRSS GNIDYNYVQWYQQRPGSSPTTVIYE DNVRPSGVPDRFSGSIDSSSNSASLTI SGLKTEDEADYYCQGYDWDTQGV VFGGGTKLTVL (SEQ ID NO: 341) |
| SR-AB54 | QVQLVESGGGVVQPGRSLRLSCAAS GFTFRSYVMHWVRQAPGKGLEWV AVISHEGSGKYYADSVKGRFTISRD NSKNTLYLQMNSLRAEDTAVYYCA LPRIAARRGGFGSWGQGTLVTVSS (SEQ ID NO: 342) | NFMLTQPHSVSESPGKTVTISCTRSS GNIDYNYVQWYQQRPGSSPTTVIYE DNVRPSGVPDRFSGSIDSSSNSASLTI SGLKTEDEADYYCQSYDSDNQRVV FGGGTKLTVL (SEQ ID NO: 343) |

TABLE 6-continued

Heavy Chain Variable Region Sequence and Light Chain Variable Region Sequence of Antibodies that Specifically Bind a LTBP1/3-TGFβ1 Complex

| Antibody | HCVR Sequence | LCVR Sequence |
|---|---|---|
| SR-AB55 | QVQLVESGGGVVQPGRSLRLSCAAS GFTFRSYVMHWVRQAPGKGLEWV AVISHEGSGKYYADSVKGRFTISRD NSKNTLYLQMNSLRAEDTAVYYCA LPRIAARRGGFGSWGQGTLVTVSS (SEQ ID NO: 344) | NFMLTQPHSVSESPGKTVTISCTRSS GNIDYNYVQWYQQRPGSSPTTVIYE DNVRPSGVPDRFSGSIDSSSNSASLTI SGLKTEDEADYYCQSYDYDNQAVV FGGGTKLTVL (SEQ ID NO: 345) |
| SR-AB56 | QVQLVESGGGVVQPGRSLRLSCAAS GFTFRSYVMHWVRQAPGKGLEWV AVISHEGSGKYYADSVKGRFTISRD NSKNTLYLQMNSLRAEDTAVYYCA LPRIAARRGGFGSWGQGTLVTVSS (SEQ ID NO: 346) | NFMLTQPHSVSESPGKTVTISCTRSS GNIDYNYVQWYQQRPGSSPTTVIYE DNVRPSGVPDRFSGSIDSSSNSASLTI SGLKTEDEADYYCQSYDYDTQGVV FGGGTKLTVL (SEQ ID NO: 347) |
| SR-AB57 | QVQLVESGGGVVQPGRSLRLSCAAS GFTFRSYVMHWVRQAPGKGLEWV AVISHEGSGKYYADSVKGRFTISRD NSKNTLYLQMNSLRAEDTAVYYCA LPRIAARRGGFGSWGQGTLVTVSS (SEQ ID NO: 348) | NFMLTQPHSVSESPGKTVTISCTRSS GNIDYNYVQWYQQRPGSSPTTVIYE DNVRPSGVPDRFSGSIDSSSNSASLTI SGLKTEDEADYYCQGYDWDTQGV VFGGGTKLTVL (SEQ ID NO: 349) |
| SR-AB58 | QVQLVESGGGVVQPGRSLRLSCAAS GFTFRSYVMHWVRQAPGKGLEWV AVISHEGSGKYYADSVKGRFTISRD NSKNTLYLQMNSLRAEDTAVYYCA LPRIAARRGGFGTWGQGTLVTVSS (SEQ ID NO: 350) | NFMLTQPHSVSESPGKTVTISCTRSS GNIDYNYVQWYQQRPGSSPTTVIYE DNVRPSGVPDRFSGSIDSSSNSASLTI SGLKTEDEADYYCQSYDSDNQRVV FGGGTKLTVL (SEQ ID NO: 351) |
| SR-AB59 | QVQLVESGGGVVQPGRSLRLSCAAS GFTFRSYVMHWVRQAPGKGLEWV AVISHEGSGKYYADSVKGRFTISRD NSKNTLYLQMNSLRAEDTAVYYCA LPRIAARRGGFGTWGQGTLVTVSS (SEQ ID NO: 352) | NFMLTQPHSVSESPGKTVTISCTRSS GNIDYNYVQWYQQRPGSSPTTVIYE DNVRPSGVPDRFSGSIDSSSNSASLTI SGLKTEDEADYYCQSYDYDNQAVV FGGGTKLTVL (SEQ ID NO: 353) |
| SR-AB60 | QVQLVESGGGVVQPGRSLRLSCAAS GFTFRSYVMHWVRQAPGKGLEWV AVISHEGSGKYYADSVKGRFTISRD NSKNTLYLQMNSLRAEDTAVYYCA LPRIAARRGGFGTWGQGTLVTVSS (SEQ ID NO: 354) | NFMLTQPHSVSESPGKTVTISCTRSS GNIDYNYVQWYQQRPGSSPTTVIYE DNVRPSGVPDRFSGSIDSSSNSASLTI SGLKTEDEADYYCQSYDYDTQGVV FGGGTKLTVL (SEQ ID NO: 355) |
| SR-AB61 | QVQLVESGGGVVQPGRSLRLSCAAS GFTFRSYVMHWVRQAPGKGLEWV AVISHEGSGKYYADSVKGRFTISRD NSKNTLYLQMNSLRAEDTAVYYCA LPRIAARRGGFGTWGQGTLVTVSS (SEQ ID NO: 356) | NFMLTQPHSVSESPGKTVTISCTRSS GNIDYNYVQWYQQRPGSSPTTVIYE DNVRPSGVPDRFSGSIDSSSNSASLTI SGLKTEDEADYYCQGYDWDTQGV VFGGGTKLTVL (SEQ ID NO: 357) |
| SR-AB62 | QLQLQESGPGLAKPSETLSLTCTVSG GSIRSSSYYWGWIRQPPGKGLEWIG SISYSATTYYNPSLKSRVTISVDTSK NQFSLKLSSVTAADTAVYYCASDPS YDSAAGMDVWGQGTTVTVSS (SEQ ID NO: 358) | DIQMTQSPSSLSASVGDRVTITCRAS KVISSLNWYQQKGKAPKLLIYYA SSLQSGVPSRFSGSGSGTDFTLTISSL QPEDFATYYCQQSNDWPFTFGGGT KVEIK (SEQ ID NO: 359) |
| SR-AB63 | QLQLQESGPGLVKPSETLSLTCTVSG GSIRSSSYYWGWIRQPPGKGLEWIG SISYSATTYYNPSLKSRVTISVDTSK NQFSLKLSSVTAADTAVYYCAGDPS YDSIAGMQVWGQGTTVTVSS (SEQ ID NO: 360) | DIQLTQSPSSLSASVGDRVTITCRAS QSISSYLNWYQQKPGKAPKLLIYAA SNLQSGVPSRFSGSGSGTDFTLTISSL QPEDFATYYCQQSFDWPLTFGGGT KVEIK (SEQ ID NO: 361) |
| SR-AB64 | QLQLQESGPGLVKPSETLSLTCTVSG GSIRSSSYYWGWIRQPPGKGLEWIG SISYSATTYYNPSLKSRVTISVDTSK NQFSLKLSSVTAADTAVYYCAGDPS YDSIAGMQVWGQGTTVTVSS (SEQ ID NO: 362) | DIQMTQSPSSLSASVGDRVTITCRAS QSISYYLNWYQQKPGKAPKLLIYSA SSRQSGVPSRFSGSGSGTDFTLTISSL QPEDFATYYCQQGFDFPLTFGGGTK VEIK (SEQ ID NO: 363) |

Aspects of the invention relate to a monoclonal antibody, or antigen-binding portion thereof, that binds selectively to a LTBP1-TGFβ complex and/or a LTBP3-TGFβ complex, and that comprises a heavy chain variable region sequence and a light chain variable region sequence.

In one aspect, the invention provides an isolated antibody or an antigen-binding fragment thereof, that specifically binds a human LTBP1-proTGFβ complex and/or a human LTBP3-proTGFβ complex and does not bind a human GARP-proTGFβ1 complex; wherein the antibody or the antigen-binding fragment thereof does not bind mature TGFβ1, mature TGFβ2 or mature TGFβ3; wherein the antibody or the antigen-binding fragment thereof is a fully human or humanized antibody or an antigen-binding fragment thereof; wherein the antibody or the antigen-binding fragment thereof comprises a variable heavy chain having an amino acid sequence that is at least 90%, 91%, 92%, 93%, 94%, 95%, 96%, 97%, 98% or 99% identical to any one of the variable region amino acid sequences set forth in Table 6.

In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 7, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, or SEQ ID NO: 106. In one embodiment, the antibody, or antigen-binding fragment thereof, comprises a light chain variable region having an amino acid sequence that is at least 90%, 91%, 92%, 93%, 94%, 95%, 96%, 97%, 98% or 99% identical to SEQ ID NO: 8, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, or SEQ ID NO: 107.

In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 7 and/or a light chain variable region having an amino acid sequence that is at least 90%, 91%, 92%, 93%, 94%, 95%, 96%, 97%, 98% or 99% identical to SEQ ID NO: 8. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 7 or a light chain variable region having an amino acid sequence that is at least 90%, 91%, 92%, 93%, 94%, 95%, 96%, 97%, 98% or 99% identical to SEQ ID NO: 8. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 7 and a light chain variable region having an amino acid sequence that is at least 90%, 91%, 92%, 93%, 94%, 95%, 96%, 97%, 98% or 99% identical to SEQ ID NO: 8.

In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 74 and/or a light chain variable region having an amino acid sequence that is at least 90%, 91%, 92%, 93%, 94%, 95%, 96%, 97%, 98% or 99% identical to SEQ ID NO: 75. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 74 or a light chain variable region having an amino acid sequence that is at least 90%, 91%, 92%, 93%, 94%, 95%, 96%, 97%, 98% or 99% identical to SEQ ID NO: 75. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 74 and a light chain variable region having an amino acid sequence that is at least 90%, 91%, 92%, 93%, 94%, 95%, 96%, 97%, 98% or 99% identical to SEQ ID NO: 75.

In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 76 and/or a light chain variable region having an amino acid sequence that is at least 90%, 91%, 92%, 93%, 94%, 95%, 96%, 97%, 98% or 99% identical to SEQ ID NO: 77. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 76 or a light chain variable region having an amino acid sequence that is at least 90%, 91%, 92%, 93%, 94%, 95%, 96%, 97%, 98% or 99% identical to SEQ ID NO: 77. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 76 and a light chain variable region having an amino acid sequence that is at least 90%, 91%, 92%, 93%, 94%, 95%, 96%, 97%, 98% or 99% identical to SEQ ID NO: 77.

In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 78 and/or a light chain variable region having an amino acid sequence that is at least 90%, 91%, 92%, 93%, 94%, 95%, 96%, 97%, 98% or 99% identical to SEQ ID NO: 79. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 78 or a light chain variable region having an amino acid sequence that is at least 90%, 91%, 92%, 93%, 94%, 95%, 96%, 97%, 98% or 99% identical to SEQ ID NO: 79. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 78 and a light chain variable region having an amino acid sequence that is at least 90%, 91%, 92%, 93%, 94%, 95%, 96%, 97%, 98% or 99% identical to SEQ ID NO: 79.

In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 80 and/or a light chain variable region having an amino acid sequence that is at least 90%, 91%, 92%, 93%, 94%, 95%, 96%, 97%, 98% or 99% identical to SEQ ID NO: 81. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 80 or a light chain variable region having an amino acid sequence that is at least 90%, 91%, 92%, 93%, 94%, 95%, 96%, 97%, 98% or 99% identical to SEQ ID NO: 81. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 80 and a light chain variable region having an amino acid sequence that is at least 90%, 91%, 92%, 93%, 94%, 95%, 96%, 97%, 98% or 99% identical to SEQ ID NO: 81.

In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 82 and/or a light chain variable region having an amino acid sequence that is at least 90%, 91%, 92%, 93%, 94%, 95%, 96%, 97%, 98% or 99% identical to SEQ ID NO: 83. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 82 or a light chain variable region having an amino acid sequence that is at least 90%, 91%, 92%, 93%, 94%, 95%, 96%, 97%, 98% or 99% identical to SEQ ID NO: 83. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 82 and a light chain variable region having an amino acid sequence that is at least 90%, 91%, 92%, 93%, 94%, 95%, 96%, 97%, 98% or 99% identical to SEQ ID NO: 83.

In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 84 and/or a light chain variable region having an amino acid sequence that is at least 90%, 91%, 92%, 93%, 94%, 95%, 96%, 97%, 98% or 99% identical to SEQ ID NO: 85. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 84 or a light chain variable region having an amino acid sequence that is at least 90%, 91%, 92%, 93%, 94%, 95%, 96%, 97%, 98% or 99% identical to SEQ ID NO: 85. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 84 and a light chain variable region having an amino acid sequence that is at least 90%, 91%, 92%, 93%, 94%, 95%, 96%, 97%, 98% or 99% identical to SEQ ID NO: 85.

In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 86 and/or a light chain variable region having an amino acid sequence that is at least 90%, 91%, 92%, 93%, 94%, 95%, 96%, 97%, 98% or 99% identical to SEQ ID NO: 87. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 86 or a light chain variable region having an amino acid sequence that is at least 90%, 91%, 92%, 93%, 94%, 95%, 96%, 97%, 98% or 99% identical to SEQ ID NO: 87. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 86 and a light chain variable region having an amino acid sequence that is at least 90%, 91%, 92%, 93%, 94%, 95%, 96%, 97%, 98% or 99% identical to SEQ ID NO: 87.

In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 88 and/or a light chain variable region having an amino acid sequence that is at least 90%, 91%, 92%, 93%, 94%, 95%, 96%, 97%, 98% or 99% identical to SEQ ID NO: 89. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 88 or a light chain variable region having an amino acid sequence that is at least 90%, 91%, 92%, 93%, 94%, 95%, 96%, 97%, 98% or 99% identical to SEQ ID NO: 89. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 88 and a light chain variable region having an amino acid sequence that is at least 90%, 91%, 92%, 93%, 94%, 95%, 96%, 97%, 98% or 99% identical to SEQ ID NO: 89.

In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 90 and/or a light chain variable region having an amino acid sequence that is at least 90%, 91%, 92%, 93%, 94%, 95%, 96%, 97%, 98% or 99% identical to SEQ ID NO: 91. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 90 or a light chain variable region having an amino acid sequence that is at least 90%, 91%, 92%, 93%, 94%, 95%, 96%, 97%, 98% or 99% identical to SEQ ID NO: 91. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 90 and a light chain variable region having an amino acid sequence that is at least 90%, 91%, 92%, 93%, 94%, 95%, 96%, 97%, 98% or 99% identical to SEQ ID NO: 91.

In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 92 and/or a light chain variable region having an amino acid sequence that is at least 90%, 91%, 92%, 93%, 94%, 95%, 96%, 97%, 98% or 99% identical to SEQ ID NO: 93. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 92 or a light chain variable region having an amino acid sequence that is at least 90%, 91%, 92%, 93%, 94%, 95%, 96%, 97%, 98% or 99% identical to SEQ ID NO: 93. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 92 and a light chain variable region having an amino acid sequence that is at least 90%, 91%, 92%, 93%, 94%, 95%, 96%, 97%, 98% or 99% identical to SEQ ID NO: 93.

In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 106 and/or a light chain variable region having an amino acid sequence that is at least 90%, 91%, 92%, 93%, 94%, 95%, 96%, 97%, 98% or 99% identical to SEQ ID NO: 107. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 106 or a light chain variable region having an amino acid sequence that is at least 90%, 91%, 92%, 93%, 94%, 95%, 96%, 97%, 98% or 99% identical to SEQ ID NO: 107. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 106 and a light chain variable region having an amino acid sequence that is at least 90%, 91%, 92%, 93%, 94%, 95%, 96%, 97%, 98% or 99% identical to SEQ ID NO: 107.

In one aspect, the invention provides an isolated antibody or an antigen-binding fragment thereof, that specifically binds a human LTBP1-proTGFβ complex and/or a human LTBP3-proTGFβ complex. The antibody may selectively bind a human LTBP1-proTGFβ complex and/or a human LTBP3-proTGFβ complex. The antibody or the antigen-binding fragment thereof may not bind mature TGFβ1, mature TGFβ2 or mature TGFβ3. The antibody or the antigen-binding fragment thereof may be a fully human or humanized antibody or an antigen-binding fragment thereof. The antibody or the antigen-binding fragment thereof may comprises a variable heavy chain having an amino acid sequence that is at least 90%, 91%, 92%, 93%, 94%, 95%, 96%, 97%, 98% or 99% identical to any one of the variable region amino acid sequences set forth in Table 6. In some embodiments, the level of identity is at least 95% (optionally at least 98%).

Accordingly, in one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 318 and/or a light chain variable region having an amino acid sequence that is at least 90%, 91%, 92%, 93%, 94%, 95%, 96%, 97%, 98% or 99% identical to SEQ ID NO: 319. The antibody, or antigen-binding fragment thereof, may comprise a heavy chain variable region having an amino acid sequence that is at least 90%, 91%, 92%, 93%, 94%, 95%, 96%, 97%, 98% or 99% identical to SEQ ID NO: 318 or a light chain variable region having an amino acid sequence that is at least 90%, 91%, 92%, 93%, 94%, 95%, 96%, 97%, 98% or 99% identical to SEQ ID NO: 319. The antibody, or antigen-binding fragment thereof, may comprise a heavy chain variable region having an amino acid sequence that is at least 90%, 91%, 92%, 93%, 94%, 95%, 96%, 97%, 98% or 99% identical to SEQ ID NO: 318 and a light chain variable region having an amino acid sequence that is at least 90%, 91%, 92%, 93%, 94%, 95%, 96%, 97%, 98% or 99% identical to SEQ ID NO: 319.

In another embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 360 and/or a light chain variable region having an amino acid sequence that is at least 90%, 91%, 92%, 93%, 94%, 95%, 96%, 97%, 98% or 99% identical to SEQ ID NO: 361. The antibody, or antigen-binding fragment thereof, may comprise a heavy chain variable region having an amino acid sequence that is at least 90%, 91%, 92%, 93%, 94%, 95%, 96%, 97%, 98% or 99% identical to SEQ ID NO: 360 or a light chain variable region having an amino acid sequence that is at least 90%, 91%, 92%, 93%, 94%, 95%, 96%, 97%, 98% or 99% identical to SEQ ID NO: 361. The antibody, or antigen-binding fragment thereof, may comprise a heavy chain variable region having an amino acid sequence that is at least 90%, 91%, 92%, 93%, 94%, 95%, 96%, 97%, 98% or 99% identical to SEQ ID NO: 360 and a light chain variable region having an amino acid sequence that is at least 90%, 91%, 92%, 93%, 94%, 95%, 96%, 97%, 98% or 99% identical to SEQ ID NO: 361.

In some embodiments, the heavy chain variable region and/or the light chain variable region sequences do not vary within any of the CDR sequences provided herein. For example, in some embodiments, the degree of sequence variation (e.g., 80%, 81%, 82%, 83%, 84%, 85%, 86%, 87%, 88%, 89%, 90%, 91%, 92%, 93%, 94%, 95%, 96%, 97%, 98%, or 99%) may occur within a heavy chain variable and/or a light chain variable amino acid sequence excluding any of the CDR sequences provided herein. In some embodiments, the antibody, or antigen-binding portion thereof, comprises a heavy chain variable domain comprising an amino acid sequence set forth in SEQ ID NO: 7 and a light chain variable domain comprising an amino acid sequence set forth in SEQ ID NO: 8. In some embodiments, the antibody, or antigen-binding fragment thereof, comprising a heavy chain variable region having an amino acid sequence that is at least 90% identical to SEQ ID NO: 318 and/or a light chain variable region having an amino acid sequence that is at least 90% identical to SEQ ID NO: 319 does not vary within any of the CDR sequences of Ab42 provided herein. In some embodiments, the antibody, or antigen-binding fragment thereof, comprising a heavy chain variable region having an amino acid sequence that is at least 90% identical to SEQ ID NO: 360 and/or a light chain variable region having an amino acid sequence that is at least 90% identical to SEQ ID NO: 361 does not vary within any of the CDR sequences of Ab63 provided herein.

In some embodiments, the antibody, or antigen-binding portion thereof, comprises a heavy chain variable domain comprising an amino acid sequence set forth in Table 6, and/or a light chain variable domain comprising an amino acid sequence set forth in Table 6. For example, in some embodiments, the antibody, or antigen-binding portion thereof, comprises a heavy chain variable domain comprising an amino acid sequence set forth in SEQ ID NO: 6 and/or a light chain variable domain comprising an amino acid sequence set forth in SEQ ID NO: 7. In some embodiments, the antibody, or antigen-binding portion thereof, comprises a heavy chain variable domain comprising an amino acid sequence set forth in SEQ ID NO: 6 or a light chain variable domain comprising an amino acid sequence set forth in SEQ ID NO: 7. In some embodiments, the antibody, or antigen-binding portion thereof, comprises a heavy chain variable domain comprising an amino acid sequence set forth in SEQ ID NO: 6 and a light chain variable domain comprising an amino acid sequence set forth in SEQ ID NO: 7.

In some embodiments, the antibody, or antigen-binding portion thereof, comprises a heavy chain variable domain comprising an amino acid sequence set forth in SEQ ID NO: 74 and/or a light chain variable domain comprising an amino acid sequence set forth in SEQ ID NO: 75. In some embodiments, the antibody, or antigen-binding portion thereof, comprises a heavy chain variable domain comprising an amino acid sequence set forth in SEQ ID NO: 74 or a light chain variable domain comprising an amino acid sequence set forth in SEQ ID NO: 75. In some embodiments, the antibody, or antigen-binding portion thereof, comprises a heavy chain variable domain comprising an amino acid sequence set forth in SEQ ID NO: 74 and a light chain variable domain comprising an amino acid sequence set forth in SEQ ID NO: 75.

In some embodiments, the antibody, or antigen-binding portion thereof, comprises a heavy chain variable domain comprising an amino acid sequence set forth in SEQ ID NO: 76 and/or a light chain variable domain comprising an amino acid sequence set forth in SEQ ID NO: 77. In some embodiments, the antibody, or antigen-binding portion thereof, comprises a heavy chain variable domain comprising an amino acid sequence set forth in SEQ ID NO: 76 or a light chain variable domain comprising an amino acid sequence set forth in SEQ ID NO: 77. In some embodiments, the antibody, or antigen-binding portion thereof, comprises a heavy chain variable domain comprising an amino acid sequence set forth in SEQ ID NO: 76 and a light chain variable domain comprising an amino acid sequence set forth in SEQ ID NO: 77.

In some embodiments, the antibody, or antigen-binding portion thereof, comprises a heavy chain variable domain comprising an amino acid sequence set forth in SEQ ID NO: 78 and/or a light chain variable domain comprising an amino acid sequence set forth in SEQ ID NO: 79. In some embodiments, the antibody, or antigen-binding portion thereof, comprises a heavy chain variable domain comprising an amino acid sequence set forth in SEQ ID NO: 78 or a light chain variable domain comprising an amino acid sequence set forth in SEQ ID NO: 79. In some embodiments, the antibody, or antigen-binding portion thereof, comprises a heavy chain variable domain comprising an amino acid sequence set forth in SEQ ID NO: 78 and a light chain variable domain comprising an amino acid sequence set forth in SEQ ID NO: 79.

In some embodiments, the antibody, or antigen-binding portion thereof, comprises a heavy chain variable domain comprising an amino acid sequence set forth in SEQ ID NO: 80 and/or a light chain variable domain comprising an amino acid sequence set forth in SEQ ID NO: 81. In some embodiments, the antibody, or antigen-binding portion thereof, comprises a heavy chain variable domain comprising an amino acid sequence set forth in SEQ ID NO: 80 or a light chain variable domain comprising an amino acid sequence set forth in SEQ ID NO: 81. In some embodiments, the antibody, or antigen-binding portion thereof, comprises a heavy chain variable domain comprising an amino acid sequence set forth in SEQ ID NO: 80 and a light chain variable domain comprising an amino acid sequence set forth in SEQ ID NO: 81.

In some embodiments, the antibody, or antigen-binding portion thereof, comprises a heavy chain variable domain comprising an amino acid sequence set forth in SEQ ID NO: 82 and/or a light chain variable domain comprising an amino acid sequence set forth in SEQ ID NO: 83. In some embodiments, the antibody, or antigen-binding portion thereof, comprises a heavy chain variable domain comprising an amino acid sequence set forth in SEQ ID NO: 82 or a light chain variable domain comprising an amino acid sequence set forth in SEQ ID NO: 83. In some embodiments, the antibody, or antigen-binding portion thereof, comprises a heavy chain variable domain comprising an amino acid sequence set forth in SEQ ID NO: 82 and a light chain variable domain comprising an amino acid sequence set forth in SEQ ID NO: 83.

In some embodiments, the antibody, or antigen-binding portion thereof, comprises a heavy chain variable domain comprising an amino acid sequence set forth in SEQ ID NO: 84 and/or a light chain variable domain comprising an amino acid sequence set forth in SEQ ID NO: 85. In some embodiments, the antibody, or antigen-binding portion thereof, comprises a heavy chain variable domain comprising an amino acid sequence set forth in SEQ ID NO: 84 or a light chain variable domain comprising an amino acid sequence set forth in SEQ ID NO: 85. In some embodiments, the antibody, or antigen-binding portion thereof, comprises a heavy chain variable domain comprising an amino acid sequence set forth in SEQ ID NO: 84 and a light chain variable domain comprising an amino acid sequence set forth in SEQ ID NO: 85.

In some embodiments, the antibody, or antigen-binding portion thereof, comprises a heavy chain variable domain comprising an amino acid sequence set forth in SEQ ID NO: 86 and/or a light chain variable domain comprising an amino acid sequence set forth in SEQ ID NO: 87. In some embodiments, the antibody, or antigen-binding portion thereof, comprises a heavy chain variable domain comprising an amino acid sequence set forth in SEQ ID NO: 86 or a light chain variable domain comprising an amino acid sequence set forth in SEQ ID NO: 87. In some embodiments, the antibody, or antigen-binding portion thereof, comprises a heavy chain variable domain comprising an amino acid sequence set forth in SEQ ID NO: 86 and a light chain variable domain comprising an amino acid sequence set forth in SEQ ID NO: 87.

In some embodiments, the antibody, or antigen-binding portion thereof, comprises a heavy chain variable domain comprising an amino acid sequence set forth in SEQ ID NO: 88 and/or a light chain variable domain comprising an amino acid sequence set forth in SEQ ID NO: 89. In some embodiments, the antibody, or antigen-binding portion thereof, comprises a heavy chain variable domain comprising an amino acid sequence set forth in SEQ ID NO: 88 or a light chain variable domain comprising an amino acid sequence set forth in SEQ ID NO: 89. In some embodiments, the antibody, or antigen-binding portion thereof, comprises a heavy chain variable domain comprising an amino acid sequence set forth in SEQ ID NO: 88 and a light chain variable domain comprising an amino acid sequence set forth in SEQ ID NO: 89.

In some embodiments, the antibody, or antigen-binding portion thereof, comprises a heavy chain variable domain comprising an amino acid sequence set forth in SEQ ID NO: 90 and/or a light chain variable domain comprising an amino acid sequence set forth in SEQ ID NO: 91. In some embodiments, the antibody, or antigen-binding portion thereof, comprises a heavy chain variable domain comprising an amino acid sequence set forth in SEQ ID NO: 90 or a light chain variable domain comprising an amino acid sequence set forth in SEQ ID NO: 91. In some embodiments, the antibody, or antigen-binding portion thereof, comprises a heavy chain variable domain comprising an amino acid sequence set forth in SEQ ID NO: 90 and a light chain variable domain comprising an amino acid sequence set forth in SEQ ID NO: 91.

In some embodiments, the antibody, or antigen-binding portion thereof, comprises a heavy chain variable domain comprising an amino acid sequence set forth in SEQ ID NO: 92 and/or a light chain variable domain comprising an amino acid sequence set forth in SEQ ID NO: 93. In some embodiments, the antibody, or antigen-binding portion thereof, comprises a heavy chain variable domain comprising an amino acid sequence set forth in SEQ ID NO: 92 or a light chain variable domain comprising an amino acid sequence set forth in SEQ ID NO: 93. In some embodiments, the antibody, or antigen-binding portion thereof, comprises a heavy chain variable domain comprising an amino acid sequence set forth in SEQ ID NO: 92 and a light chain variable domain comprising an amino acid sequence set forth in SEQ ID NO: 93.

In some embodiments, the antibody, or antigen-binding portion thereof, comprises a heavy chain variable domain comprising an amino acid sequence set forth in SEQ ID NO: 106 and/or a light chain variable domain comprising an amino acid sequence set forth in SEQ ID NO: 107. In some embodiments, the antibody, or antigen-binding portion thereof, comprises a heavy chain variable domain comprising an amino acid sequence set forth in SEQ ID NO: 106 or a light chain variable domain comprising an amino acid sequence set forth in SEQ ID NO: 107. In some embodiments, the antibody, or antigen-binding portion thereof, comprises a heavy chain variable domain comprising an amino acid sequence set forth in SEQ ID NO: 106 and a light chain variable domain comprising an amino acid sequence set forth in SEQ ID NO: 107.

In some embodiments, the antibody, or antigen-binding portion thereof, comprises a heavy chain variable domain comprising an amino acid sequence set forth in SEQ ID NO: 318 and/or a light chain variable domain comprising an amino acid sequence set forth in SEQ ID NO: 319. In some embodiments, the antibody, or antigen-binding portion thereof, comprises a heavy chain variable domain comprising an amino acid sequence set forth in SEQ ID NO: 318 or a light chain variable domain comprising an amino acid sequence set forth in SEQ ID NO: 319. In some embodiments, the antibody, or antigen-binding portion thereof, comprises a heavy chain variable domain comprising an amino acid sequence set forth in SEQ ID NO: 318 and a light chain variable domain comprising an amino acid sequence set forth in SEQ ID NO: 319.

In some embodiments, the antibody, or antigen-binding portion thereof, comprises a heavy chain variable domain comprising an amino acid sequence set forth in SEQ ID NO: 360 and/or a light chain variable domain comprising an amino acid sequence set forth in SEQ ID NO: 361. In some embodiments, the antibody, or antigen-binding portion thereof, comprises a heavy chain variable domain comprising an amino acid sequence set forth in SEQ ID NO: 360 or a light chain variable domain comprising an amino acid sequence set forth in SEQ ID NO: 361. In some embodiments, the antibody, or antigen-binding portion thereof, comprises a heavy chain variable domain comprising an amino acid sequence set forth in SEQ ID NO: 360 and a light chain variable domain comprising an amino acid sequence set forth in SEQ ID NO: 361.

The amino acid sequences of the heavy chain variable region (HCVR) and the light chain variable region (LCVR) of the antibody SR-AB2 set forth in Table 5 are provided below.

```
SR-AB2 - Heavy chain variable region amino acid
sequence
                                       (SEQ ID NO: 7)
QVQLVQSGAEVKKPGASVKVSCKASGYTFTSYGISWVRQAPGQGLEWMGW

ISAYNGNTNYAQKLQGRVTMTTDTSTSTAYMELRSLRSDDTAVYYCARAP

LGNFDSWGQGTMVTVSS

SR-AB2 - Light chain variable region amino acid
sequence
                                       (SEQ ID NO: 8)
NFMLTQPHSVSESPGKTVTISCTRSSGSIASNYVQWYQQRPGSSPTTVIY

EDNQRPSGVPDRFSGSIDSSSNSASLTISGLKTEDEADYYCQSYDSSNHP

VVFGGGTKLTVL
```

The amino acid sequences of the heavy chain variable region (HCVR) and the light chain variable region (LCVR) of the antibody SR-AB10 set forth in Table 5 are provided below.

```
SR-AB10 - Heavy chain variable region amino acid
sequence
                                      (SEQ ID NO: 88)
QLQLQESGGGVVQPGRSLRLSCAASGFTFNNYPIHWVRQAPGKGLEWVAV

MSYDGINKYYADSVKGRFTISRDNSKNTLYLQMNSLRAEDTAVYYCARPR

IAARRGGFDYWGQGTLVTVSS

SR-AB10 - Light chain variable region amino acid
sequence
                                      (SEQ ID NO: 89)
NFMLTQPHSVSESPGKTVTISCTRSSGNIDNNYVQWYQQRPGSSPTTVIY

EDNQRPSGVPDRFSGSIDSSSNSASLTISGLKTEDEADYYCQSYDSDNQG

VVFGGGTKLTVL
```

The amino acid sequences of the heavy chain variable region (HCVR) and the light chain variable region (LCVR) of the antibody SR-AB13 set forth in Table 5 are provided below.

```
SR-AB13 - Heavy chain variable region amino acid
sequence
                                     (SEQ ID NO: 106)
QLQLQESGPGLVKPSETLSLTCTVSGGSISSSSYYWGWIRQPPGKGLEWI

GSISYSGSTYYNPSLKSRVTISVDTSKNQFSLKLSSVTAADTAVYYCARD

PSYDSIAGMDVWGQGTTVTVSS

SR-AB13 - Light chain variable region amino acid
sequence
                                     (SEQ ID NO: 107)
DIQLTQSPSSLSASVGDRVTITCRASQSISSYLNWYQQKPGKAPKLLIYA

ASNLQSGVPSRFSGSGSGTDFTLTISSLQPEDFATYYCQQSFDFPFTFGG

GTKVEIK
```

The amino acid sequences of the heavy chain variable region (HCVR) and the light chain variable region (LCVR) of the antibody SR-AB42 set forth in Table 5 are provided below.

SR-AB42 - Heavy chain variable region amino acid
sequence
(SEQ ID NO: 318)
QVQLVESGGGVVQPGRSLRLSCAASGFTFRSYVMHWVRQAPGKGLEWVAV

ISHEGSLKYYADSVKGRFTISRDNSKNTLYLQMNSLRAEDTAVYYCARPR

IAARRGGFGYWGQGTLVTVSS

63 - Light chain variable region amino acid
sequence
(SEQ ID NO: 319)
NFMLTQPHSVSESPGKTVTISCTRSSGNIDNNYVQWYQQRPGSSPTTVIY

EDNQRPSGVPDRFSGSIDSSSNSASLTISGLKTEDEADYYCQSYDYDTQG

VVFGGGTKLTVL

The amino acid sequences of the heavy chain variable region (HCVR) and the light chain variable region (LCVR) of the antibody SR-AB63 set forth in Table 5 are provided below.

SR-AB63 - Heavy chain variable region amino acid
sequence
(SEQ ID NO: 360)
QLQLQESGPGLVKPSETLSLTCTVSGGSIRSSSYYWGWIRQPPGKGLEWI

GSISYSATTYYNPSLKSRVTISVDTSKNQFSLKLSSVTAADTAVYYCAGD

PSYDSIAGMQVWGQGTTVTVSS

SR-AB63 - Light chain variable region amino acid
sequence
(SEQ ID NO: 361)
DIQLTQSPSSLSASVGDRVTITCRASQSISSYLNWYQQKPGKAPKLLIYA

ASNLQSGVPSRFSGSGSGTDFTLTISSLQPEDFATYYCQQSFDWPLTFGG

GTKVEIK

In some embodiments, antibodies, or antigen-binding portions thereof, of the invention that selectively bind to a LTBP1-TGFβ complex and/or a LTBP3-TGFβ complex have one or more CDR sequences substantially similar to CDRH1, CDRH2, CDRH3, CDRL1, CDRL2, and/or CDRL3. For example, the antibodies may include one or more CDR sequences as shown in Table 5 (SEQ ID NOs: 1-6, SEQ ID NOs: 94-99 or SEQ ID NOs: 100-105) containing up to 6, 5, 4, 3, 2, or 1 amino acid residue variations as compared to the corresponding CDR region in any one of SEQ ID NOs: 1-6, SEQ ID NOs: 94-99 or SEQ ID NOs: 100-105.

In one embodiment, the antibody, or antigen-binding fragment thereof, comprises at least three CDRs selected from the following, optionally comprising up to 6 amino acid changes, for example 1, 2, 3, 4, 5, or 6 amino acid changes, for each of the CDRs CDR-H1: SEQ ID NO: 1; CDR-H2: SEQ ID NO: 2; CDR-H3: SEQ ID NO: 3; CDR-L1: SEQ ID NO: 4; CDR-L2: SEQ ID NO: 5; and, CDR-L3: SEQ ID NO: 6. In one embodiment, the antibody, or antigen-binding fragment thereof, comprises at least three CDRs selected from the following, optionally comprising up to 6 amino acid changes, for example 1, 2, 3, 4, 5, or 6 amino acid changes, for each of the CDRs CDR-H1: SEQ ID NO: 94; CDR-H2: SEQ ID NO: 95; CDR-H3: SEQ ID NO: 96; CDR-L1: SEQ ID NO: 97; CDR-L2: SEQ ID NO: 98; and, CDR-L3: SEQ ID NO: 99. In one embodiment, the antibody, or antigen-binding fragment thereof, comprises at least three CDRs selected from the following, optionally comprising up to 6 amino acid changes, for example 1, 2, 3, 4, 5, or 6 amino acid changes, for each of the CDRs CDR-H1: SEQ ID NO: 100; CDR-H2: SEQ ID NO: 101; CDR-H3: SEQ ID NO: 102; CDR-L1: SEQ ID NO: 103; CDR-L2: SEQ ID NO: 104; and, CDR-L3: SEQ ID NO: 105. In one embodiment, the antibody, or antigen-binding fragment thereof, comprises at least three CDRs selected from the following, optionally comprising up to 6 amino acid changes, for example 1, 2, 3, 4, 5, or 6 amino acid changes, for each of the CDRs CDR-H1: SEQ ID NO: 166; CDR-H2: SEQ ID NO: 167; CDR-H3: SEQ ID NO: 168; CDR-L1: SEQ ID NO: 169; CDR-L2: SEQ ID NO: 170; and, CDR-L3: SEQ ID NO: 171. In one embodiment, the antibody, or antigen-binding fragment thereof, comprises at least three CDRs selected from the following, optionally comprising up to 6 amino acid changes, for example 1, 2, 3, 4, 5, or 6 amino acid changes, for each of the CDRs CDR-H1: SEQ ID NO: 292; CDR-H2: SEQ ID NO: 293; CDR-H3: SEQ ID NO: 294; CDR-L1: SEQ ID NO: 295; CDR-L2: SEQ ID NO: 296; and, CDR-L3: SEQ ID NO: 297.

In one aspect, the invention provides an antibody, or antigen-binding fragment thereof, comprising a heavy chain variable region comprising CDR-H1: SEQ ID NO: 1; CDR-H2: SEQ ID NO: 2; and CDR-H3: SEQ ID NO: 3; and a light chain variable region comprising CDR-L1: SEQ ID NO: 4; CDR-L2: SEQ ID NO: 5; and CDR-L3: SEQ ID NO: 6, optionally comprising one or more amino acid changes, for example 1, 2, 3, 4, 5, or 6 amino acid changes, for each of the CDRs.

In one aspect, the invention provides an antibody, or antigen-binding fragment thereof, comprising a heavy chain variable region comprising CDR-H1: SEQ ID NO: 94; CDR-H2: SEQ ID NO: 95; and CDR-H3: SEQ ID NO: 96; and a light chain variable region comprising CDR-L1: SEQ ID NO: 97; CDR-L2: SEQ ID NO: 98; and CDR-L3: SEQ ID NO: 99, optionally comprising one or more amino acid changes, for example 1, 2, 3, 4, 5, or 6 amino acid changes, for each of the CDRs.

In one aspect, the invention provides an antibody, or antigen-binding fragment thereof, comprising a heavy chain variable region comprising CDR-H1: SEQ ID NO: 100; CDR-H2: SEQ ID NO: 101; and CDR-H3: SEQ ID NO: 102; and a light chain variable region comprising CDR-L1: SEQ ID NO: 103; CDR-L2: SEQ ID NO: 104; and CDR-L3: SEQ ID NO: 105, optionally comprising one or more amino acid changes, for example 1, 2, 3, 4, 5, or 6 amino acid changes, for each of the CDRs.

In one aspect, the invention provides an antibody, or antigen-binding fragment thereof, comprising a heavy chain variable region comprising CDR-H1: SEQ ID NO: 166; CDR-H2: SEQ ID NO: 167; and CDR-H3: SEQ ID NO: 168; and a light chain variable region comprising CDR-L1: SEQ ID NO: 169; CDR-L2: SEQ ID NO: 170; and CDR-L3: SEQ ID NO: 171, optionally comprising one or more amino acid changes, for example 1, 2, 3, 4, 5, or 6 amino acid changes, for each of the CDRs. For instance, if there are changes within the CDRs, there may be up to 1 change per CDR. There may be no more than 2 changes across all 6 CDRs.

In one aspect, the invention provides an antibody, or antigen-binding fragment thereof, comprising a heavy chain variable region comprising CDR-H1: SEQ ID NO: 292; CDR-H2: SEQ ID NO: 293; and CDR-H3: SEQ ID NO: 294; and a light chain variable region comprising CDR-L1: SEQ ID NO: 295; CDR-L2: SEQ ID NO: 296; and CDR-L3: SEQ ID NO: 297, optionally comprising one or more amino acid changes, for example 1, 2, 3, 4, 5, or 6 amino acid changes (e.g., up to 2), for each of the CDRs. For instance, if there are changes within the CDRs, there may be up to 1 change per CDR. There may be no more than 2 changes across all 6 CDRs.

In one aspect, the invention provides an antibody, or antigen-binding fragment thereof comprising a heavy chain variable region comprising a CDR-H1, CDR-H2, CDR-H3, CDR-L1, CDR-L2, and/or CDR-L3 having particular amino acid changes. As used herein, the phrase "amino acid changes" or "changes in amino acid residues" includes amino acid substitutions, additions, and/or deletions. In some embodiments, there are one or more changes to the amino acid residues with any one of the CDRs and/or variable regions described herein. For example, in some embodiments, the one or more amino acid changes comprises one amino acid change. In some embodiments, the one or more amino acid changes comprises up to two amino acid changes. In some embodiments, the one or more amino acid changes comprises up to three amino acid changes. In some embodiments, the one or more amino acid changes comprises up to four amino acid changes. In some embodiments, the one or more amino acid changes comprises up to five amino acid changes. In some embodiments, the one or more amino acid changes comprises up to six amino acid changes. In some embodiments, the one or more amino acid changes comprises up to seven amino acid changes.

For example, in some embodiments, the antibody, or antigen-binding fragment thereof, comprises a CDR-H1: SEQ ID NO:1, with the proviso that the threonine residue at position 4 of SEQ ID NO:1 may be substituted with a histidine, lysine, phenylalanine, or glycine. In some embodiments, the antibody, or antigen-binding fragment thereof, comprises a CDR-H1: SEQ ID NO:1, with the proviso that the serine residue at position 5 of SEQ ID NO:1 may be substituted with a leucine. In some embodiments, the antibody, or antigen-binding fragment thereof, comprises a CDR-H1: SEQ ID NO:1, with the proviso that the serine residue at position 9 of SEQ ID NO:1 may be substituted with an alanine.

In some embodiments, the antibody, or antigen-binding fragment thereof, comprises a CDR-H1: SEQ ID NO:1, with the proviso that (i) the threonine residue at position 4 of SEQ ID NO:1 may be substituted with a histidine, lysine, phenylalanine, or glycine; (ii) the serine residue at position 5 of SEQ ID NO:1 may be substituted with a leucine; and/or, (iii) the serine residue at position 9 of SEQ ID NO:1 may be substituted with an alanine.

In some embodiments, the antibody, or antigen-binding fragment thereof, comprises a CDR-H2: SEQ ID NO:2, with the proviso that the serine residue at position 3 of SEQ ID NO:2 may be substituted with an aspartate or asparagine. In some embodiments, the antibody, or antigen-binding fragment thereof, comprises a CDR-H2: SEQ ID NO:2, with the proviso that the tyrosine residue at position 5 of SEQ ID NO:2 may be substituted with a histidine. In some embodiments, the antibody, or antigen-binding fragment thereof, comprises a CDR-H2: SEQ ID NO:2, with the proviso that the asparagine residue at position 6 of SEQ ID NO:2 may be substituted with a serine. In some embodiments, the antibody, or antigen-binding fragment thereof, comprises a CDR-H2: SEQ ID NO:2, with the proviso that the asparagine residue at position 8 of SEQ ID NO:2 may be substituted with a phenylalanine, leucine, alanine, tyrosine, aspartate, or serine. In some embodiments, the antibody, or antigen-binding fragment thereof, comprises a CDR-H2: SEQ ID NO:2, with the proviso that the asparagine residue at position 10 of SEQ ID NO:2 may be substituted with an aspartate or alanine.

In some embodiments, the antibody, or antigen-binding fragment thereof, comprises a CDR-H2: SEQ ID NO:2, with the proviso that (i) the serine residue at position 3 of SEQ ID NO:2 may be substituted with an aspartate or asparagine; (ii) the tyrosine residue at position 5 of SEQ ID NO:2 may be substituted with a histidine; (iii) the asparagine residue at position 6 of SEQ ID NO:2 may be substituted with a serine; (iv) the asparagine residue at position 8 of SEQ ID NO:2 may be substituted with a phenylalanine, leucine, alanine, tyrosine, aspartate, or serine; and/or, (v) the asparagine residue at position 10 of SEQ ID NO:2 may be substituted with a aspartate or alanine.

In some embodiments, the antibody, or antigen-binding fragment thereof, comprises three heavy chain CDRs and three light chain CDRs, wherein the heavy chain CDRs comprise:
  a) CDR-H1: SEQ ID NO:1, with the proviso that:
    i. the threonine residue at position 4 of SEQ ID NO:1 may be substituted with a histidine, lysine, phenylalanine, or glycine;
    ii. the serine residue at position 5 of SEQ ID NO:1 may be substituted with a leucine; and/or,
    iii. the serine residue at position 9 of SEQ ID NO:1 may be substituted with an alanine;
  b) CDR-H2: SEQ ID NO:2, with the proviso that:
    i. the serine residue at position 3 of SEQ ID NO:2 may be substituted with an aspartate or asparagine;
    ii. the tyrosine residue at position 5 of SEQ ID NO:2 may be substituted with a histidine;
    iii. the asparagine residue at position 6 of SEQ ID NO:2 may be substituted with a serine;
    iv. the asparagine residue at position 8 of SEQ ID NO:2 may be substituted with a phenylalanine, leucine, alanine, tyrosine, aspartate, or serine; and/or,
    v. the asparagine residue at position 10 of SEQ ID NO:2 may be substituted with a aspartate or alanine;
  c) CDR-H3: SEQ ID NO:3, optionally comprising one or more amino acid changes.

In some embodiments, the antibody, or antigen-binding fragment thereof, further comprises a CDR-L1 as set forth in SEQ ID NO:4, optionally comprising one or more amino acid changes. In some embodiments, the antibody, or antigen-binding fragment thereof, further comprises a CDR-L2 as set forth in SEQ ID NO:5, optionally comprising one or more amino acid changes. In some embodiments, the antibody, or antigen-binding fragment thereof, further comprises a CDR-L3 as set forth in SEQ ID NO:6, optionally comprising one or more amino acid changes.

In some embodiments, the antibody, or antigen-binding fragment thereof, comprises at least three of the following six CDRs:
  a) CDR-H1: SEQ ID NO:1, with the proviso that:
    i. the threonine residue at position 4 of SEQ ID NO:1 may be substituted with a histidine, lysine, phenylalanine, or glycine;
    ii. the serine residue at position 5 of SEQ ID NO:1 may be substituted with an leucine; and/or,
    iii. the serine residue at position 9 of SEQ ID NO:1 may be substituted with an alanine;
  b) CDR-H2: SEQ ID NO:2, with the proviso that:
    i. the serine residue at position 3 of SEQ ID NO:2 may be substituted with an aspartate or asparagine;
    ii. the tyrosine residue at position 5 of SEQ ID NO:2 may be substituted with a histidine;
    iii. the asparagine residue at position 6 of SEQ ID NO:2 may be substituted with a serine;

iv. the asparagine residue at position 8 of SEQ ID NO:2 may be substituted with a phenylalanine, leucine, alanine, tyrosine, aspartate, or serine; and/or,
v. the asparagine residue at position 10 of SEQ ID NO:2 may be substituted with a aspartate or alanine;
c) CDR-H3: SEQ ID NO:3, optionally comprising one or more amino acid changes;
d) CDR-L1: SEQ ID NO:4, optionally comprising one or more amino acid changes;
e) CDR-L2: SEQ ID NO:5, optionally comprising one or more amino acid changes; and,
f) CDR-L3: SEQ ID NO:6, optionally comprising one or more amino acid changes.

In some embodiments, the antibody, or antigen-binding fragment thereof, specifically binds a human LTBP1-proTGFβ1 complex and/or a human LTBP3-proTGFβ1 complex, and does not bind a human GARP-proTGFβ1 complex. In some embodiments, the antibody, or antigen-binding fragment thereof, does not bind a human GARP-proTGFβ1 complex. In some embodiments, the antibody, or antigen-binding fragment thereof, does not bind mature TGFβ1, mature TGFβ2 or mature TGFβ3.

In a particular embodiment, the invention provides an isolated antibody that specifically binds a human LTBP1-proTGFβ1 complex and/or a human LTBP3-proTGFβ1 complex, and does not bind a human GARP-proTGFβ1 complex or a human LRRC33-proTGFβ1 complex; wherein the antibody does not bind mature TGFβ1, mature TGFβ2 or mature TGFβ33; wherein the antibody is a fully human or humanized antibody or a fragment thereof, and wherein the antibody comprises at least three of the following six CDRs:
a) CDR-H1: SEQ ID NO:1, with the proviso that:
  i. the threonine residue at position 4 of SEQ ID NO:1 may be substituted with a histidine, lysine, phenylalanine, or glycine;
  ii. the serine residue at position 5 of SEQ ID NO:1 may be substituted with an leucine; and/or,
  iii. the serine residue at position 9 of SEQ ID NO:1 may be substituted with an alanine;
b) CDR-H2: SEQ ID NO:2, with the proviso that:
  i. the serine residue at position 3 of SEQ ID NO:2 may be substituted with an aspartate or asparagine;
  ii. the tyrosine residue at position 5 of SEQ ID NO:2 may be substituted with a histidine;
  iii. the asparagine residue at position 6 of SEQ ID NO:2 may be substituted with a serine;
  iv. the asparagine residue at position 8 of SEQ ID NO:2 may be substituted with a phenylalanine, leucine, alanine, tyrosine, aspartate, or serine; and/or,
  v. the asparagine residue at position 10 of SEQ ID NO:2 may be substituted with a aspartate or alanine;
c) CDR-H3: SEQ ID NO:3, optionally comprising one or more amino acid changes;
d) CDR-L1: SEQ ID NO:4, optionally comprising one or more amino acid changes;
e) CDR-L2: SEQ ID NO:5, optionally comprising one or more amino acid changes; and,
f) CDR-L3: SEQ ID NO:6, optionally comprising one or more amino acid changes.

In some embodiments, such antibody binds a human LTBP1-proTGFβ1 complex with a $K_D$ of <100 nM as measured in a suitable in vitro binding assay such as Bio-Layer Interferometry (BLI); and/or, such antibody binds a human LTBP3-proTGFβ1 complex with a $K_D$ of <100 nM as measured in a suitable in vitro binding assay such as Bio-Layer Interferometry (BLI). In some embodiments, such antibody binds a human LTBP1-proTGFβ1 complex with a $K_D$ of <50 nM as measured in a suitable in vitro binding assay such as Bio-Layer Interferometry (BLI); and/or, such antibody binds a human LTBP3-proTGFβ1 complex with a $K_D$ of <50 nM as measured in a suitable in vitro binding assay such as Bio-Layer Interferometry (BLI). In some embodiments, such antibody binds a human LTBP1-proTGFβ1 complex with a $K_D$ of <25 nM as measured in a suitable in vitro binding assay such as Bio-Layer Interferometry (BLI); and/or, such antibody binds a human LTBP3-proTGFβ1 complex with a $K_D$ of <25 nM as measured in a suitable in vitro binding assay such as Bio-Layer Interferometry (BLI). In some embodiments, such antibody binds a human LTBP1-proTGFβ1 complex with a $K_D$ of <10 nM as measured in a suitable in vitro binding assay such as Bio-Layer Interferometry (BLI); and/or, such antibody binds a human LTBP3-proTGFβ1 complex with a $K_D$ of <10 nM as measured in a suitable in vitro binding assay such as Bio-Layer Interferometry (BLI).

In another embodiment, such antibody is cross-reactive with mouse LTBP1-proTGFβ1. In some embodiments, such antibody is also cross-reactive with mouse LTBP3-proTGFβ1. In some embodiments, such antibody binds a mouse LTBP1-proTGFβ1 complex with a $K_D$ of <100 nM as measured in a suitable in vitro binding assay such as Bio-Layer Interferometry (BLI); and/or, the antibody binds a mouse LTBP3-proTGFβ1 complex with a $K_D$ of <100 nM as measured in a suitable in vitro binding assay such as Bio-Layer Interferometry (BLI). In some embodiments, such antibody binds a mouse LTBP1-proTGFβ1 complex with a $K_D$ of <50 nM as measured in a suitable in vitro binding assay such as Bio-Layer Interferometry (BLI); and/or, the antibody binds a mouse LTBP3-proTGFβ1 complex with a $K_D$ of <50 nM as measured in a suitable in vitro binding assay such as Bio-Layer Interferometry (BLI). In some embodiments, such antibody binds a mouse LTBP1-proTGFβ1 complex with a $K_D$ of <25 nM as measured in a suitable in vitro binding assay such as Bio-Layer Interferometry (BLI); and/or, the antibody binds a mouse LTBP3-proTGFβ1 complex with a $K_D$ of <25 nM as measured in a suitable in vitro binding assay such as Bio-Layer Interferometry (BLI). In some embodiments, such antibody binds a mouse LTBP1-proTGFβ1 complex with a $K_D$ of <10 nM as measured in a suitable in vitro binding assay such as Bio-Layer Interferometry (BLI); and/or, the antibody binds a mouse LTBP3-proTGFβ1 complex with a $K_D$ of <10 nM as measured in a suitable in vitro binding assay such as Bio-Layer Interferometry (BLI).

In another embodiment, such antibody does not bind to human GARP-proTGFβ1. In preferred embodiments, such context-selective antibody is isoform-specific in that it selectively binds and inhibits the activation of TGFβ1 associated with LTBP1/3 and does not bind to human GARP-proTGFβ1.

In another aspect, the antibody, or antigen-binding fragment thereof, comprises a CDR-H1: SEQ ID NO:94, with the proviso that the threonine residue at position 2 of SEQ ID NO:94 may be substituted with an alanine. In some embodiments, the antibody, or antigen-binding fragment thereof, comprises a CDR-H1: SEQ ID NO:94, with the proviso that the asparagine residue at position 4 of SEQ ID NO:94 may be substituted with an alanine, tyrosine, aspartate, serine, arginine, or histidine. In some embodiments, the antibody, or antigen-binding fragment thereof, comprises a CDR-H1: SEQ ID NO:94, with the proviso that the asparagine residue at position 5 of SEQ ID NO:94 may be substituted with a glutamine, serine, glycine, lysine, glutamate, arginine, or histidine. In some embodiments, the antibody, or antigen-binding fragment thereof, comprises a CDR-H1: SEQ ID NO:94, with the proviso that the tyrosine residue at position 6 of SEQ ID NO:94 may be substituted with a arginine. In some embodiments, the antibody, or antigen-binding fragment thereof, comprises a CDR-H1: SEQ ID NO:94, with the proviso that the proline residue at position 7 of SEQ ID NO:94 may be substituted with a glycine, alanine, leucine, serine, asparagine, valine, aspartate, or glutamine. In some embodiments, the antibody, or antigen-binding fragment thereof, comprises a CDR-H1: SEQ ID NO:94, with the proviso that the isoleucine residue at position 8 of SEQ ID NO:94 may be substituted with a methionine or leucine. In some embodiments, the antibody, or antigen-binding fragment thereof, comprises a CDR-H1: SEQ ID NO:94, with the proviso that the histidine residue at position 9 of SEQ ID NO:94 may be substituted with a phenylalanine, tyrosine, asparagine, or serine. SEQ ID NO: 94 comprising these substitutions is disclosed as SEQ ID NO: 399.

In some embodiments, the antibody, or antigen-binding fragment thereof, comprises a CDR-H1: SEQ ID NO:94, with the proviso that (i) the threonine residue at position 2 of SEQ ID NO:94 may be substituted with an alanine; (ii) the asparagine residue at position 4 of SEQ ID NO:94 may be substituted with an alanine, tyrosine, aspartate, serine, arginine, or histidine; (iii) the asparagine residue at position 5 of SEQ ID NO:94 may be substituted with a glutamine, serine, glycine, lysine, glutamate, arginine, or histidine; (iv) the tyrosine residue at position 6 of SEQ ID NO:94 may be substituted with a arginine; (v) the proline residue at position 7 of SEQ ID NO:94 may be substituted with a glycine, alanine, leucine, serine, asparagine, valine, aspartate, or glutamine; (vi) the isoleucine residue at position 8 of SEQ ID NO:94 may be substituted with a methionine or leucine; and/or, (vii) the histidine residue at position 9 of SEQ ID NO:94 may be substituted with a phenylalanine, tyrosine, asparagine, or serine. SEQ ID NO: 94 comprising these substitutions is disclosed as SEQ ID NO: 399.

In some embodiments, the antibody, or antigen-binding fragment thereof, comprises three heavy chain CDRs and three light chain CDRs, wherein the heavy chain CDRs comprise:
 a) CDR-H1: SEQ ID NO:94 (SEQ ID NO: 94 comprising these substitutions is disclosed as SEQ ID NO: 399), with the proviso that:
  i. the threonine residue at position 2 of SEQ ID NO:94 may be substituted with an alanine;
  ii. the asparagine residue at position 4 of SEQ ID NO:94 may be substituted with an alanine, tyrosine, aspartate, serine, arginine, or histidine;
  iii. the asparagine residue at position 5 of SEQ ID NO:94 may be substituted with a glutamine, serine, glycine, lysine, glutamate, arginine, or histidine;
  iv. the tyrosine residue at position 6 of SEQ ID NO:94 may be substituted with a arginine;
  v. the proline residue at position 7 of SEQ ID NO:94 may be substituted with a glycine, alanine, leucine, serine, asparagine, valine, aspartate, or glutamine;
  vi. the isoleucine residue at position 8 of SEQ ID NO:94 may be substituted with a methionine or leucine; and/or,
  vii. the histidine residue at position 9 of SEQ ID NO:94 may be substituted with a phenylalanine, tyrosine, asparagine, or serine;
 b) CDR-H2: SEQ ID NO:95, optionally comprising one or more amino acid changes; and
 c) CDR-H3: SEQ ID NO:96, optionally comprising one or more amino acid changes.

In some embodiments, the antibody, or antigen-binding fragment thereof, further comprises a CDR-L1 as set forth in SEQ ID NO:97, optionally comprising one or more amino acid changes. In some embodiments, the antibody, or antigen-binding fragment thereof, further comprises a CDR-L2 as set forth in SEQ ID NO:98, optionally comprising one or more amino acid changes. In some embodiments, the antibody, or antigen-binding fragment thereof, further comprises a CDR-L3 as set forth in SEQ ID NO:99, optionally comprising one or more amino acid changes.

In some embodiments, the antibody, or antigen-binding fragment thereof, comprises at least three of the following six CDRs:
 a) CDR-H1: SEQ ID NO:94 (SEQ ID NO: 94 comprising these substitutions is disclosed as SEQ ID NO: 399), with the proviso that:
  i. the threonine residue at position 2 of SEQ ID NO:94 may be substituted with an alanine;
  ii. the asparagine residue at position 4 of SEQ ID NO:94 may be substituted with an alanine, tyrosine, aspartate, serine, arginine, or histidine;
  iii. the asparagine residue at position 5 of SEQ ID NO:94 may be substituted with a glutamine, serine, glycine, lysine, glutamate, arginine, or histidine;
  iv. the tyrosine residue at position 6 of SEQ ID NO:94 may be substituted with a arginine;
  v. the proline residue at position 7 of SEQ ID NO:94 may be substituted with a glycine, alanine, leucine, serine, asparagine, valine, aspartate, or glutamine;
  vi. the isoleucine residue at position 8 of SEQ ID NO:94 may be substituted with a methionine or leucine; and/or,
  vii. the histidine residue at position 9 of SEQ ID NO:94 may be substituted with a phenylalanine, tyrosine, asparagine, or serine;
 b) CDR-H2: SEQ ID NO:95, optionally comprising one or more amino acid changes;
 c) CDR-H3: SEQ ID NO:96, optionally comprising one or more amino acid changes;
 d) CDR-L1: SEQ ID NO:97, optionally comprising one or more amino acid changes;
 e) CDR-L2: SEQ ID NO:98, optionally comprising one or more amino acid changes; and,
 f) CDR-L3: SEQ ID NO:99, optionally comprising one or more amino acid changes.

In some embodiments, the antibody, or antigen-binding fragment thereof, specifically binds a human LTBP1-proTGFβ1 complex and/or a human LTBP3-proTGFβ1 complex, and does not bind a human GARP-proTGFβ1 complex. In some embodiments, the antibody, or antigen-binding fragment thereof, does not bind a human GARP-proTGFβ1 complex. In some embodiments, the antibody, or antigen-binding fragment thereof, does not bind mature TGFβ1, mature TGFβ2 or mature TGFβ3.

In a particular embodiment, the antibody, or antigen-binding fragment thereof, specifically binds a human LTBP1-proTGFβ1 complex and/or a human LTBP3-proTGFβ1 complex, and does not bind a human GARP-proTGFβ1 complex; wherein the antibody does not bind mature TGFβ1, mature TGFβ2 or mature TGFβ33; wherein the antibody is a fully human or humanized antibody or a fragment thereof, and wherein the antibody comprises at least three of the following six CDRs:

a) CDR-H1: SEQ ID NO:94 (SEQ ID NO: 94 comprising these substitutions is disclosed as SEQ ID NO: 399), with the proviso that:
   i. the threonine residue at position 2 of SEQ ID NO:94 may be substituted with an alanine;
   ii. the asparagine residue at position 4 of SEQ ID NO:94 may be substituted with an alanine, tyrosine, aspartate, serine, arginine, or histidine;
   iii. the asparagine residue at position 5 of SEQ ID NO:94 may be substituted with a glutamine, serine, glycine, lysine, glutamate, arginine, or histidine;
   iv. the tyrosine residue at position 6 of SEQ ID NO:94 may be substituted with a arginine;
   v. the proline residue at position 7 of SEQ ID NO:94 may be substituted with a glycine, alanine, leucine, serine, asparagine, valine, aspartate, or glutamine;
   vi. the isoleucine residue at position 8 of SEQ ID NO:94 may be substituted with a methionine or leucine; and/or,
   vii. the histidine residue at position 9 of SEQ ID NO:94 may be substituted with a phenylalanine, tyrosine, asparagine, or serine;
b) CDR-H2: SEQ ID NO:95, optionally comprising one or more amino acid changes;
c) CDR-H3: SEQ ID NO:96, optionally comprising one or more amino acid changes;
d) CDR-L1: SEQ ID NO:97, optionally comprising one or more amino acid changes;
e) CDR-L2: SEQ ID NO:98, optionally comprising one or more amino acid changes; and,
f) CDR-L3: SEQ ID NO:99, optionally comprising one or more amino acid changes.

In some embodiments, such antibody binds a human LTBP1-proTGFβ1 complex with a $K_D$ of <100 nM as measured in a suitable in vitro binding assay such as Bio-Layer Interferometry (BLI); and/or, such antibody binds a human LTBP3-proTGFβ1 complex with a $K_D$ of <100 nM as measured in a suitable in vitro binding assay such as Bio-Layer Interferometry (BLI). In some embodiments, such antibody binds a human LTBP1-proTGFβ1 complex with a $K_D$ of <50 nM as measured in a suitable in vitro binding assay such as Bio-Layer Interferometry (BLI); and/or, such antibody binds a human LTBP3-proTGFβ1 complex with a $K_D$ of <50 nM as measured in a suitable in vitro binding assay such as Bio-Layer Interferometry (BLI). In some embodiments, such antibody binds a human LTBP1-proTGFβ1 complex with a $K_D$ of <25 nM as measured in a suitable in vitro binding assay such as Bio-Layer Interferometry (BLI); and/or, such antibody binds a human LTBP3-proTGFβ1 complex with a $K_D$ of <25 nM as measured in a suitable in vitro binding assay such as Bio-Layer Interferometry (BLI). In some embodiments, such antibody binds a human LTBP1-proTGFβ1 complex with a $K_D$ of <10 nM as measured in a suitable in vitro binding assay such as Bio-Layer Interferometry (BLI); and/or, such antibody binds a human LTBP3-proTGFβ1 complex with a $K_D$ of <10 nM as measured in a suitable in vitro binding assay such as Bio-Layer Interferometry (BLI).

In another embodiment, such antibody is cross-reactive with mouse LTBP1-proTGFβ1. In some embodiments, such antibody is also cross-reactive with mouse LTBP3-proTGFβ1. In some embodiments, such antibody binds a mouse LTBP1-proTGFβ1 complex with a $K_D$ of <100 nM as measured in a suitable in vitro binding assay such as Bio-Layer Interferometry (BLI); and/or, the antibody binds a mouse LTBP3-proTGFβ1 complex with a $K_D$ of <100 nM as measured in a suitable in vitro binding assay such as Bio-Layer Interferometry (BLI). In some embodiments, such antibody binds a mouse LTBP1-proTGFβ1 complex with a $K_D$ of <50 nM as measured in a suitable in vitro binding assay such as Bio-Layer Interferometry (BLI); and/or, the antibody binds a mouse LTBP3-proTGFβ1 complex with a $K_D$ of <50 nM as measured in a suitable in vitro binding assay such as Bio-Layer Interferometry (BLI). In some embodiments, such antibody binds a mouse LTBP1-proTGFβ1 complex with a $K_D$ of <25 nM as measured in a suitable in vitro binding assay such as Bio-Layer Interferometry (BLI); and/or, the antibody binds a mouse LTBP3-proTGFβ1 complex with a $K_D$ of <25 nM as measured in a suitable in vitro binding assay such as Bio-Layer Interferometry (BLI). In some embodiments, such antibody binds a mouse LTBP1-proTGFβ1 complex with a $K_D$ of <10 nM as measured in a suitable in vitro binding assay such as Bio-Layer Interferometry (BLI); and/or, the antibody binds a mouse LTBP3-proTGFβ1 complex with a $K_D$ of <10 nM as measured in a suitable in vitro binding assay such as Bio-Layer Interferometry (BLI).

In another embodiment, such antibody does not bind to human GARP-proTGFβ1. In preferred embodiments, such context-selective antibody is also isoform-specific in that it selectively binds and inhibits the activation of TGFβ1 associated with LTBP1/3.

In another aspect, the antibody, or antigen-binding fragment thereof, comprises a CDR-H1 comprising the amino acid sequence FTF($X_1$)($X_2$)YVMH, wherein, optionally: $X_1$ is S or R; and $X_2$ is G or S (SEQ ID NO: 392). In some embodiments, $X_1$ is S. In some embodiments, $X_1$ is R. In some embodiments, $X_2$ is G. In some embodiments, $X_2$ is S.

In some embodiments, the antibody, or antigen-binding fragment thereof, comprises a CDR-H2 comprising the amino acid sequence ($X_1$)ISHEG($X_2$)($X_3$)KYYADSVKG, wherein, optionally: $X_1$ is V or S; $X_2$ is S or G; and $X_3$ is F or L (SEQ ID NO: 393). In some embodiments, $X_1$ is a V. In some embodiment, $X_1$ is a S. In some embodiments, $X_2$ is S. In some embodiments, $X_2$ is G. In some embodiments, $X_3$ is F. In some embodiments, $X_3$ is L.

In some embodiments, the antibody, or antigen-binding fragment thereof, comprises a CDR-H3 comprising the amino acid sequence ($X_1$)($X_2$)P($X_3$)($X_4$)($X_5$)($X_6$)RRGG($X_7$)($X_8$)($X_9$), wherein, optionally: $X_1$ is A or V; $X_2$ is R, V, G or K; $X_3$ is R, H or L; $X_4$ is I, V or G; $X_5$ is A, S, or L; $X_6$ is A or V; $X_7$ is F or Y; $X_8$ is D, G, R, or S; and, $X_9$ is Y, G, R, L, V, A or K (SEQ ID NO: 394). In some embodiments, $X_1$ is A. In some embodiments, $X_1$ is V. In some embodiments, $X_2$ is R. In some embodiments, $X_2$ is V. In some embodiments, $X_2$ is G. In some embodiments, $X_2$ is K. In some embodiments, $X_3$ is R. In some embodiments, $X_3$ is H. In some embodiments, $X_3$ is L. In some embodiments, $X_4$ is I. In some embodiments, $X_4$ is V. In some embodiments, $X_4$ is G. In some embodiments, $X_5$ is A. In some embodiments, $X_5$ is S. In some embodiments, $X_5$ is L. In some embodiments, $X_6$ is A. In some embodiments, $X_6$ is V. In some embodiments, $X_7$ is F. In some embodiments, $X_7$ is Y. In some embodiments, $X_8$ is D. In some embodiments, $X_8$ is G. In some embodiments, $X_8$ is R. In some embodiments, $X_8$ is S. In some embodiments, $X_9$ is Y. In some embodiments, $X_9$ is G. In some embodiments, $X_9$ is R. In some embodiments, $X_9$ is L. In some embodiments, $X_9$ is V. In some embodiments, $X_9$ is A. In some embodiments, $X_9$ is K.

In some embodiments, the antibody, or antigen-binding fragment thereof, comprises three heavy chain CDRs and three light chain CDRs, wherein the heavy chain CDRs comprise:

a) CDR-H1 comprising the amino acid sequence FTF($X_1$)($X_2$)YVMH, wherein, optionally: $X_1$ is S or R; and $X_2$ is G or S (SEQ ID NO: 392);
b) CDR-H2 comprising the amino acid sequence ($X_1$)ISHEG($X_2$)($X_3$)KYYADSVKG, wherein, optionally: $X_1$ is V or S; $X_2$ is S or G; and $X_3$ is F or L (SEQ ID NO: 393); and
c) CDR-H3 comprising the amino acid sequence ($X_1$)($X_2$)P($X_3$)($X_4$)($X_5$)($X_6$)RRGG($X_7$) ($X_8$)($X_9$), wherein, optionally: $X_1$ is A or V; $X_2$ is R, V, G or K; $X_3$ is R, H or L; $X_4$ is I, V or G; $X_5$ is A, S, or L; $X_6$ is A or V; $X_7$ is F or Y; $X_8$ is D, G, R, or S; and, $X_9$ is Y, G, R, L, V, A or K (SEQ ID NO: 394).

In some embodiments, the antibody, or antigen-binding fragment thereof, further comprises a CDR-L1 as set forth in SEQ ID NO:97, optionally comprising one or more amino acid changes. In some embodiments, the antibody, or antigen-binding fragment thereof, further comprises a CDR-L2 as set forth in SEQ ID NO:98, optionally comprising one or more amino acid changes. In some embodiments, the antibody, or antigen-binding fragment thereof, further comprises a CDR-L3 as set forth in SEQ ID NO:99, optionally comprising one or more amino acid changes.

In some embodiments, the antibody, or antigen-binding fragment, comprises at least three of the following six CDRs:
a) CDR-H1 comprising the amino acid sequence FTF($X_1$)($X_2$)YVMH, wherein, optionally: $X_1$ is S or R; and $X_2$ is G or S (SEQ ID NO: 392);
b) CDR-H2 comprising the amino acid sequence ($X_1$)ISHEG($X_2$)($X_3$)KYYADSVKG, wherein, optionally: $X_1$ is V or S; $X_2$ is S or G; and $X_3$ is F or L (SEQ ID NO: 393);
c) CDR-H3 comprising the amino acid sequence ($X_1$)($X_2$)P($X_3$)($X_4$)($X_5$)($X_6$)RRGG($X_7$) ($X_8$)($X_9$), wherein, optionally: $X_1$ is A or V; $X_2$ is R, V, G or K; $X_3$ is R, H or L; $X_4$ is I, V or G; $X_5$ is A, S, or L; $X_6$ is A or V; $X_7$ is F or Y; $X_8$ is D, G, R, or S; and, $X_9$ is Y, G, R, L, V, A or K (SEQ ID NO: 394);
d) CDR-L1 as set forth in SEQ ID NO:97, optionally comprising one or more amino acid changes;
e) CDR-L2 as set forth in SEQ ID NO:98, optionally comprising one or more amino acid changes; and
f) CDR-L3 as set forth in SEQ ID NO:99, optionally comprising one or more amino acid changes.

In some embodiments, the antibody, or antigen-binding fragment thereof, specifically binds a human LTBP1-proTGFβ1 complex and/or a human LTBP3-proTGFβ1 complex, and does not bind a human GARP-proTGFβ1 complex. In some embodiments, the antibody, or antigen-binding fragment thereof, does not bind a human GARP-proTGFβ1 complex. In some embodiments, the antibody, or antigen-binding fragment thereof, does not bind mature TGFβ1, mature TGFβ2 or mature TGFβ3.

In a particular embodiment, the antibody, or antigen-binding fragment, specifically binds a human LTBP1-proTGFβ1 complex and/or a human LTBP3-proTGFβ1 complex, and does not bind a human GARP-proTGFβ1 complex; wherein the antibody does not bind mature TGFβ1, mature TGFβ2 or mature TGFβ33; wherein the antibody is a fully human or humanized antibody or a fragment thereof, wherein the antibody comprises at least three of the following six CDRs:
a) CDR-H1 comprising the amino acid sequence FTF($X_1$)($X_2$)YVMH, wherein, optionally: $X_1$ is S or R; and $X_2$ is G or S (SEQ ID NO: 392);
b) CDR-H2 comprising the amino acid sequence ($X_1$)ISHEG($X_2$)($X_3$)KYYADSVKG, wherein, optionally: $X_1$ is V or S; $X_2$ is S or G; and $X_3$ is F or L (SEQ ID NO: 393);
c) CDR-H3 comprising the amino acid sequence ($X_1$)($X_2$)P($X_3$)($X_4$)($X_5$)($X_6$)RRGG($X_7$) ($X_8$)($X_9$), wherein, optionally: $X_1$ is A or V; $X_2$ is R, V, G or K; $X_3$ is R, H or L; $X_4$ is I, V or G; $X_5$ is A, S, or L; $X_6$ is A or V; $X_7$ is F or Y; $X_8$ is D, G, R, or S; and, $X_9$ is Y, G, R, L, V, A or K (SEQ ID NO: 394);
d) CDR-L1 as set forth in SEQ ID NO:97, optionally comprising one or more amino acid changes;
e) CDR-L2 as set forth in SEQ ID NO:98, optionally comprising one or more amino acid changes; and
f) CDR-L3 as set forth in SEQ ID NO:99, optionally comprising one or more amino acid changes.

In some embodiments, such antibody binds a human LTBP1-proTGFβ1 complex with a $K_D$ of <100 nM as measured in a suitable in vitro binding assay such as Bio-Layer Interferometry (BLI); and/or, such antibody binds a human LTBP3-proTGFβ1 complex with a $K_D$ of <100 nM as measured in a suitable in vitro binding assay such as Bio-Layer Interferometry (BLI). In some embodiments, such antibody binds a human LTBP1-proTGFβ1 complex with a $K_D$ of <50 nM as measured in a suitable in vitro binding assay such as Bio-Layer Interferometry (BLI); and/or, such antibody binds a human LTBP3-proTGFβ1 complex with a $K_D$ of <50 nM as measured in a suitable in vitro binding assay such as Bio-Layer Interferometry (BLI). In some embodiments, such antibody binds a human LTBP1-proTGFβ1 complex with a $K_D$ of <25 nM as measured in a suitable in vitro binding assay such as Bio-Layer Interferometry (BLI); and/or, such antibody binds a human LTBP3-proTGFβ1 complex with a $K_D$ of <25 nM as measured in a suitable in vitro binding assay such as Bio-Layer Interferometry (BLI). In some embodiments, such antibody binds a human LTBP1-proTGFβ1 complex with a $K_D$ of <10 nM as measured in a suitable in vitro binding assay such as Bio-Layer Interferometry (BLI); and/or, such antibody binds a human LTBP3-proTGFβ1 complex with a $K_D$ of <10 nM as measured in a suitable in vitro binding assay such as Bio-Layer Interferometry (BLI).

In another embodiment, such antibody is cross-reactive with mouse LTBP1-proTGFβ1. In some embodiments, such antibody is also cross-reactive with mouse LTBP3-proTGFβ1. In some embodiments, such antibody binds a mouse LTBP1-proTGFβ1 complex with a $K_D$ of <100 nM as measured in a suitable in vitro binding assay such as Bio-Layer Interferometry (BLI); and/or, the antibody binds a mouse LTBP3-proTGFβ1 complex with a $K_D$ of <100 nM as measured in a suitable in vitro binding assay such as Bio-Layer Interferometry (BLI). In some embodiments, such antibody binds a mouse LTBP1-proTGFβ1 complex with a $K_D$ of <50 nM as measured in a suitable in vitro binding assay such as Bio-Layer Interferometry (BLI); and/or, the antibody binds a mouse LTBP3-proTGFβ1 complex with a $K_D$ of <50 nM as measured in a suitable in vitro binding assay such as Bio-Layer Interferometry (BLI). In some embodiments, such antibody binds a mouse LTBP1-proTGFβ1 complex with a $K_D$ of <25 nM as measured in a suitable in vitro binding assay such as Bio-Layer Interferometry (BLI); and/or, the antibody binds a mouse LTBP3-proTGFβ1 complex with a $K_D$ of <25 nM as measured in a suitable in vitro binding assay such as Bio-Layer Interferometry (BLI). In some embodiments, such antibody binds a mouse LTBP1-proTGFβ1 complex with a $K_D$ of <10 nM as measured in a suitable in vitro binding assay such as Bio-Layer Interferometry (BLI); and/or, the antibody binds a mouse LTBP3-proTGFβ1 complex with a $K_D$ of <10 nM as measured in a suitable in vitro binding assay such as Bio-Layer Interferometry (BLI).

In another embodiment, such antibody does not bind to human GARP-proTGFβ1. In preferred embodiments, such context-selective antibody is also isoform-specific in that it selectively binds and inhibits the activation of TGFβ1 associated with LTBP1/3.

In another aspect, the antibody, or antigen-binding fragment thereof, comprises a CDR-H1 comprising the amino acid sequence FTF($X_1$)($X_2$)YVMH, wherein, optionally: $X_1$ is S or R; and $X_2$ is G or S (SEQ ID NO: 392). In some embodiments, $X_1$ is S. In some embodiments, $X_1$ is R. In some embodiments, $X_2$ is G. In some embodiments, $X_2$ is S.

In some embodiments, the antibody, or antigen-binding fragment thereof, comprises a CDR-H2 comprising the amino acid sequence ($X_1$)ISHEGS($X_2$)KYYADSVKG, wherein, optionally: $X_1$ is V or S; and, $X_2$ is F or L (SEQ ID NO: 382). In some embodiments, $X_1$ is a V. In some embodiment, $X_1$ is a S. In some embodiments, $X_3$ is F. In some embodiments, $X_3$ is L.

In some embodiments, the antibody, or antigen-binding fragment thereof, comprises a CDR-H3 comprising the amino acid sequence A($X_1$)PRI($X_2$)ARRGGFGY, wherein, optionally: $X_1$ is R or V; $X_2$ is A or L (SEQ ID NO: 383). In some embodiments, $X_1$ is R. In some embodiments, $X_1$ is V. In some embodiments, $X_2$ is A. In some embodiments, $X_2$ is L.

In some embodiments, the antibody, or antigen-binding fragment thereof, comprises three heavy chain CDRs and three light chain CDRs, wherein the heavy chain CDRs comprise:
  a) CDR-H1 comprising the amino acid sequence FTF($X_1$)($X_2$)YVMH, wherein, optionally: $X_1$ is S or R; and $X_2$ is G or S (SEQ ID NO: 392);
  b) CDR-H2 comprising the amino acid sequence ($X_1$)ISHEGS($X_2$)KYYADSVKG, wherein, optionally: $X_1$ is V or S; and, $X_2$ is F or L (SEQ ID NO: 382); and
  c) CDR-H3 comprising the amino acid sequence A($X_1$)PRI($X_2$)ARRGGFGY, wherein, optionally: $X_1$ is R or V; $X_2$ is A or L (SEQ ID NO: 383).

In some embodiments, the antibody, or antigen-binding fragment thereof, further comprises a CDR-L1 as set forth in SEQ ID NO:97, optionally comprising one or more amino acid changes. In some embodiment, the antibody, or antigen-binding fragment thereof, further comprises a CDR-L2 as set forth in SEQ ID NO:98, optionally comprising one or more amino acid changes. In some embodiments, the antibody, or antigen-binding fragment thereof, further comprises a CDR-L3 as set forth in SEQ ID NO:99, optionally comprising one or more amino acid changes.

In some embodiments, the antibody, or antigen-binding fragment, comprises at least three of the following six CDRs:
  a) CDR-H1 comprising the amino acid sequence FTF($X_1$)($X_2$)YVMH, wherein, optionally: $X_1$ is S or R; and $X_2$ is G or S (SEQ ID NO: 392);
  b) CDR-H2 comprising the amino acid sequence ($X_1$)ISHEGS($X_2$)KYYADSVKG, wherein, optionally: $X_1$ is V or S; and, $X_2$ is F or L (SEQ ID NO: 382);
  c) CDR- comprising the amino acid sequence A($X_1$)PRI($X_2$)ARRGGFGY, wherein, optionally: $X_1$ is R or V; $X_2$ is A or L (SEQ ID NO: 383);
  d) CDR-L1 as set forth in SEQ ID NO:97, optionally comprising one or more amino acid changes;
  e) CDR-L2 as set forth in SEQ ID NO:98, optionally comprising one or more amino acid changes; and
  f) CDR-L3 as set forth in SEQ ID NO:99, optionally comprising one or more amino acid changes.

In some embodiments, the antibody, or antigen-binding fragment thereof, specifically binds a human LTBP1-proTGFβ1 complex and/or a human LTBP3-proTGFβ1 complex, and does not bind a human GARP-proTGFβ1 complex. In some embodiments, the antibody, or antigen-binding fragment thereof, does not bind a human GARP-proTGFβ1 complex. In some embodiments, the antibody, or antigen-binding fragment thereof, does not bind mature TGFβ1, mature TGFβ2 or mature TGFβ3.

In a particular embodiment, the antibody, or antigen-binding fragment thereof, specifically binds a human LTBP1-proTGFβ1 complex and/or a human LTBP3-proTGFβ1 complex, and does not bind a human GARP-proTGFβ1 complex; wherein the antibody does not bind mature TGFβ1, mature TGFβ2 or mature TGFβ33; wherein the antibody is a fully human or humanized antibody or a fragment thereof, wherein the antibody comprises at least three of the following six CDRs:
  a) CDR-H1 comprising the amino acid sequence FTF($X_1$)($X_2$)YVMH, wherein, optionally: $X_1$ is S or R; and $X_2$ is G or S (SEQ ID NO: 392);
  b) CDR-H2 comprising the amino acid sequence ($X_1$)ISHEGS($X_2$)KYYADSVKG, wherein: $X_1$ is V or S; and, $X_2$ is F or L (SEQ ID NO: 382);
  c) CDR-H3 comprising the amino acid sequence A($X_1$)PRI($X_2$)ARRGGFGY, wherein, optionally: $X_1$ is R or V; $X_2$ is A or L (SEQ ID NO: 383);
  d) CDR-L1 as set forth in SEQ ID NO:97, optionally comprising one or more amino acid changes;
  e) CDR-L2 as set forth in SEQ ID NO:98, optionally comprising one or more amino acid changes; and
  f) CDR-L3 as set forth in SEQ ID NO:99, optionally comprising one or more amino acid changes.

In some embodiments, such antibody binds a human LTBP1-proTGFβ1 complex with a $K_D$ of <100 nM as measured in a suitable in vitro binding assay such as Bio-Layer Interferometry (BLI); and/or, such antibody binds a human LTBP3-proTGFβ1 complex with a $K_D$ of <100 nM as measured in a suitable in vitro binding assay such as Bio-Layer Interferometry (BLI). In some embodiments, such antibody binds a human LTBP1-proTGFβ1 complex with a $K_D$ of <50 nM as measured in a suitable in vitro binding assay such as Bio-Layer Interferometry (BLI); and/or, such antibody binds a human LTBP3-proTGFβ1 complex with a $K_D$ of <50 nM as measured in a suitable in vitro binding assay such as Bio-Layer Interferometry (BLI). In some embodiments, such antibody binds a human LTBP1-proTGFβ1 complex with a $K_D$ of <25 nM as measured in a suitable in vitro binding assay such as Bio-Layer Interferometry (BLI); and/or, such antibody binds a human LTBP3-proTGFβ1 complex with a $K_D$ of <25 nM as measured in a suitable in vitro binding assay such as Bio-Layer Interferometry (BLI). In some embodiments, such antibody binds a human LTBP1-proTGFβ1 complex with a $K_D$ of <10 nM as measured in a suitable in vitro binding assay such as Bio-Layer Interferometry (BLI); and/or, such antibody binds a human LTBP3-proTGFβ1 complex with a $K_D$ of <10 nM as measured in a suitable in vitro binding assay such as Bio-Layer Interferometry (BLI).

In another embodiment, such antibody is cross-reactive with mouse LTBP1-proTGFβ1. In some embodiments, such antibody is also cross-reactive with mouse LTBP3-proTGFβ1. In some embodiments, such antibody binds a mouse LTBP1-proTGFβ1 complex with a K_D of <100 nM as measured in a suitable in vitro binding assay such as Bio-Layer Interferometry (BLI); and/or, the antibody binds a mouse LTBP3-proTGFβ1 complex with a K_D of <100 nM as measured in a suitable in vitro binding assay such as Bio-Layer Interferometry (BLI). In some embodiments, such antibody binds a mouse LTBP1-proTGFβ1 complex with a K_D of <50 nM as measured in a suitable in vitro binding assay such as Bio-Layer Interferometry (BLI); and/or, the antibody binds a mouse LTBP3-proTGFβ1 complex with a K_D of <50 nM as measured in a suitable in vitro binding assay such as Bio-Layer Interferometry (BLI). In some embodiments, such antibody binds a mouse LTBP1-proTGFβ1 complex with a K_D of <25 nM as measured in a suitable in vitro binding assay such as Bio-Layer Interferometry (BLI); and/or, the antibody binds a mouse LTBP3-proTGFβ1 complex with a K_D of <25 nM as measured in a suitable in vitro binding assay such as Bio-Layer Interferometry (BLI). In some embodiments, such antibody binds a mouse LTBP1-proTGFβ1 complex with a K_D of <10 nM as measured in a suitable in vitro binding assay such as Bio-Layer Interferometry (BLI); and/or, the antibody binds a mouse LTBP3-proTGFβ1 complex with a K_D of <10 nM as measured in a suitable in vitro binding assay such as Bio-Layer Interferometry (BLI).

In another embodiment, such antibody does not bind to human GARP-proTGFβ1. In preferred embodiments, such context-selective antibody is also isoform-specific in that it selectively binds and inhibits the activation of TGFβ1 associated with LTBP1/3.

In another aspect, the antibody, or antigen-binding fragment thereof, comprises a CDR-H1: SEQ ID NO:100, with the proviso that the serine residue at position 4 of SEQ ID NO:100 may be substituted with a histidine. In some embodiments, the antibody, or antigen-binding fragment thereof, comprises a CDR-H1: SEQ ID NO:100, with the proviso that the serine residue at position 7 of SEQ ID NO:100 may be substituted with an alanine or glycine. In some embodiments, the antibody, or antigen-binding fragment thereof, comprises a CDR-H1: SEQ ID NO:100, with the proviso that the glycine residue at position 11 of SEQ ID NO:100 may be substituted with a threonine, serine, histidine, leucine, isoleucine, asparagine, valine, or alanine. SEQ ID NO: 100 comprising these substitutions is disclosed as SEQ ID NO: 400.

In some embodiments, the antibody, or antigen-binding fragment thereof, comprises a CDR-H1: SEQ ID NO:100, with the proviso that (i) the serine residue at position 4 of SEQ ID NO:100 may be substituted with a histidine; (ii) the serine residue at position 7 of SEQ ID NO:100 may be substituted with an alanine or glycine; and/or, (iii) the glycine residue at position 11 of SEQ ID NO:100 may be substituted with a threonine, serine, histidine, leucine, isoleucine, asparagine, valine, or alanine. SEQ ID NO: 100 comprising these substitutions is disclosed as SEQ ID NO: 400.

In some embodiments, the antibody, or antigen-binding fragment thereof, comprises a CDR-H1: SEQ ID NO:101, with the proviso that the serine residue at position 3 of SEQ ID NO:101 may be substituted with an alanine. In some embodiments, the antibody, or antigen-binding fragment thereof, comprises a CDR-H1: SEQ ID NO:101, with the proviso that the glycine residue at position 6 of SEQ ID NO:101 may be substituted with an alanine or serine. In some embodiments, the antibody, or antigen-binding fragment thereof, comprises a CDR-H1: SEQ ID NO:101, with the proviso that the serine residue at position 7 of SEQ ID NO:101 may be substituted with a threonine. SEQ ID NO: 101 comprising these substitutions is disclosed as SEQ ID NO: 401.

In some embodiments, the antibody, or antigen-binding fragment thereof, comprises a CDR-H1: SEQ ID NO:101, with the proviso that (i) the serine residue at position 3 of SEQ ID NO:101 may be substituted with an alanine; (ii) the glycine residue at position 6 of SEQ ID NO:101 may be substituted with an alanine or serine; and/or, (iii) the serine residue at position 7 of SEQ ID NO:101 may be substituted with a threonine. SEQ ID NO: 101 comprising these substitutions is disclosed as SEQ ID NO: 401.

In some embodiments, the antibody, or antigen-binding fragment thereof, comprises three heavy chain CDRs and three light chain CDRs, wherein the heavy chain CDRs comprise:
  a) CDR-H1: SEQ ID NO:100 (SEQ ID NO: 100 comprising these substitutions is disclosed as SEQ ID NO: 400), with the proviso that:
    i. the serine residue at position 4 of SEQ ID NO:100 may be substituted with a histidine;
    ii. the serine residue at position 7 of SEQ ID NO:100 may be substituted with an alanine or glycine; and/or,
    iii. the glycine residue at position 11 of SEQ ID NO:100 may be substituted with a threonine, serine, histidine, leucine, isoleucine, asparagine, valine, or alanine;
  b) CDR-H2: SEQ ID NO:101 (SEQ ID NO: 101 comprising these substitutions is disclosed as SEQ ID NO: 401), with the proviso that:
    i. the serine residue at position 3 of SEQ ID NO:101 may be substituted with an alanine;
    ii. the glycine residue at position 6 of SEQ ID NO:101 may be substituted with an alanine or serine; and/or,
    iii. the serine residue at position 7 of SEQ ID NO:101 may be substituted with a threonine; and
  c) CDR-H3: SEQ ID NO:102, optionally comprising up to three, four, five or six amino acid changes.

In some embodiments, the antibody, or antigen-binding fragment thereof, further comprises a CDR-L1 as set forth in SEQ ID NO:103, optionally comprising one or more amino acid changes. In some embodiments, the antibody, or antigen-binding fragment thereof, further comprises a CDR-L2 as set forth in SEQ ID NO:104, optionally comprising one or more amino acid changes. In some embodiments, the antibody, or antigen-binding fragment thereof, further comprises a CDR-L3 as set forth in SEQ ID NO:105, optionally comprising one or more amino acid changes.

In some embodiments, the antibody, or antigen-binding fragment thereof, comprises at least three of the following six CDRs:
  a) CDR-H1: SEQ ID NO:100 (SEQ ID NO: 100 comprising these substitutions is disclosed as SEQ ID NO: 400), with the proviso that:
    i. the serine residue at position 4 of SEQ ID NO:100 may be substituted with a histidine;
    ii. the serine residue at position 7 of SEQ ID NO:100 may be substituted with an alanine or glycine; and/or,
    iii. the glycine residue at position 11 of SEQ ID NO:100 may be substituted with a threonine, serine, histidine, leucine, isoleucine, asparagine, valine, or alanine;
  b) CDR-H2: SEQ ID NO:101 (SEQ ID NO: 101 comprising these substitutions is disclosed as SEQ ID NO: 401), with the proviso that:

i. the serine residue at position 3 of SEQ ID NO:101 may be substituted with an alanine;
ii. the glycine residue at position 6 of SEQ ID NO:101 may be substituted with an alanine or serine; and/or,
iii. the serine residue at position 7 of SEQ ID NO:101 may be substituted with a threonine; and
c) CDR-H3: SEQ ID NO:102, optionally comprising one or more amino acid changes.
d) CDR-L1: SEQ ID NO:103, optionally comprising one or more amino acid changes;
e) CDR-L2: SEQ ID NO:104, optionally comprising one or more amino acid changes; and,
f) CDR-L3: SEQ ID NO:105, optionally comprising one or more amino acid changes.

In some embodiments, the antibody, or antigen-binding fragment, specifically binds a human LTBP1-proTGFβ1 complex and/or a human LTBP3-proTGFβ1 complex, and does not bind a human GARP-proTGFβ1 complex. In some embodiments, the antibody, or antigen-binding fragment thereof, does not bind a human GARP-proTGFβ1 complex. In some embodiments, the antibody, or antigen-binding fragment thereof, does not bind mature TGFβ1, mature TGFβ2 or mature TGFβ3.

In a particular embodiment, the antibody, or antigen-binding fragment, specifically binds a human LTBP1-proTGFβ1 complex and/or a human LTBP3-proTGFβ1 complex, and does not bind a human GARP-proTGFβ1 complex; wherein the antibody does not bind mature TGFβ1, mature TGFβ2 or mature TGFβ33; wherein the antibody is a fully human or humanized antibody or a fragment thereof, wherein the antibody comprises at least three of the following six CDRs:
a) CDR-H1: SEQ ID NO:100 (SEQ ID NO: 100 comprising these substitutions is disclosed as SEQ ID NO: 400), with the proviso that:
i. the serine residue at position 4 of SEQ ID NO:100 may be substituted with a histidine;
ii. the serine residue at position 7 of SEQ ID NO:100 may be substituted with an alanine or glycine; and/or,
iii. the glycine residue at position 11 of SEQ ID NO:100 may be substituted with a threonine, serine, histidine, leucine, isoleucine, asparagine, valine, or alanine;
b) CDR-H2: SEQ ID NO:101 (SEQ ID NO: 101 comprising these substitutions is disclosed as SEQ ID NO: 401), with the proviso that:
i. the serine residue at position 3 of SEQ ID NO:101 may be substituted with an alanine;
ii. the glycine residue at position 6 of SEQ ID NO:101 may be substituted with an alanine or serine; and/or,
iii. the serine residue at position 7 of SEQ ID NO:101 may be substituted with a threonine;
c) CDR-H3: SEQ ID NO:102, optionally comprising one or more amino acid changes;
d) CDR-L1: SEQ ID NO:103, optionally comprising one or more amino acid changes;
e) CDR-L2: SEQ ID NO:104, optionally comprising one or more amino acid changes; and,
f) CDR-L3: SEQ ID NO:105, optionally comprising one or more amino acid changes.

In some embodiments, such antibody binds a human LTBP1-proTGFβ1 complex with a KD of <100 nM as measured in a suitable in vitro binding assay such as Bio-Layer Interferometry (BLI); and/or, such antibody binds a human LTBP3-proTGFβ1 complex with a KD of <100 nM as measured in a suitable in vitro binding assay such as Bio-Layer Interferometry (BLI). In some embodiments, such antibody binds a human LTBP1-proTGFβ1 complex with a KD of <50 nM as measured in a suitable in vitro binding assay such as Bio-Layer Interferometry (BLI); and/or, such antibody binds a human LTBP3-proTGFβ1 complex with a KD of <50 nM as measured in a suitable in vitro binding assay such as Bio-Layer Interferometry (BLI). In some embodiments, such antibody binds a human LTBP1-proTGFβ1 complex with a KD of <25 nM as measured in a suitable in vitro binding assay such as Bio-Layer Interferometry (BLI); and/or, such antibody binds a human LTBP3-proTGFβ1 complex with a KD of <25 nM as measured in a suitable in vitro binding assay such as Bio-Layer Interferometry (BLI). In some embodiments, such antibody binds a human LTBP1-proTGFβ1 complex with a KD of <10 nM as measured in a suitable in vitro binding assay such as Bio-Layer Interferometry (BLI); and/or, such antibody binds a human LTBP3-proTGFβ1 complex with a KD of <10 nM as measured in a suitable in vitro binding assay such as Bio-Layer Interferometry (BLI).

In another embodiment, such antibody is cross-reactive with mouse LTBP1-proTGFβ1. In some embodiments, such antibody is also cross-reactive with mouse LTBP3-proTGFβ1. In some embodiments, such antibody binds a mouse LTBP1-proTGFβ1 complex with a KD of <100 nM as measured in a suitable in vitro binding assay such as Bio-Layer Interferometry (BLI); and/or, the antibody binds a mouse LTBP3-proTGFβ1 complex with a KD of <100 nM as measured in a suitable in vitro binding assay such as Bio-Layer Interferometry (BLI). In some embodiments, such antibody binds a mouse LTBP1-proTGFβ1 complex with a KD of <50 nM as measured in a suitable in vitro binding assay such as Bio-Layer Interferometry (BLI); and/or, the antibody binds a mouse LTBP3-proTGFβ1 complex with a KD of <50 nM as measured in a suitable in vitro binding assay such as Bio-Layer Interferometry (BLI). In some embodiments, such antibody binds a mouse LTBP1-proTGFβ1 complex with a KD of <25 nM as measured in a suitable in vitro binding assay such as Bio-Layer Interferometry (BLI); and/or, the antibody binds a mouse LTBP3-proTGFβ1 complex with a KD of <25 nM as measured in a suitable in vitro binding assay such as Bio-Layer Interferometry (BLI). In some embodiments, such antibody binds a mouse LTBP1-proTGFβ1 complex with a KD of <10 nM as measured in a suitable in vitro binding assay such as Bio-Layer Interferometry (BLI); and/or, the antibody binds a mouse LTBP3-proTGFβ1 complex with a KD of <10 nM as measured in a suitable in vitro binding assay such as Bio-Layer Interferometry (BLI).

In another embodiment, such antibody does not bind to human GARP-proTGFβ1. In preferred embodiments, such context-selective antibody is also isoform-specific in that it selectively binds and inhibits the activation of TGFβ1 associated with LTBP1/3.

In another aspect, the antibody, or antigen-binding fragment thereof, comprises a CDR-H1 comprising the amino acid sequence $G(X_1)I(X_2)S(X_3)SYYW(X_4)$, wherein, optionally: $X_1$ is S or P; $X_2$ is S, H or R; $X_3$ is S or G; and, $X_4$ is G, I, N or V (SEQ ID NO: 395). In some embodiments, $X_1$ is a S. In some embodiments, $X_1$ is P. In some embodiments, $X_2$ is S. In some embodiments, $X_2$ is H. In some embodiments, $X_2$ is R. In some embodiments, $X_3$ is S. In some embodiments, $X_3$ is G. In some embodiments, $X_4$ is G. In some embodiments, $X_4$ is I. In some embodiments, $X_4$ is N. In some embodiments, $X_4$ is V.

In some embodiments, the antibody, or antigen-binding fragment thereof, comprises a CDR-H2 comprising the amino acid sequence SISYSA($X_1$)TYYNPSLKS, wherein, optionally, $X_1$ is S or T (SEQ ID NO: 396). In some embodiments, $X_1$ is a S. In some embodiment, $X_1$ is a T.

In some embodiments, the antibody, or antigen-binding fragment thereof, comprises a CDR-H3 comprising the amino acid sequence ($X_1$)($X_2$)D($X_3$)($X_4$)Y($X_5$)($X_6$)($X_7$)($X_8$)G($X_9$)($X_{10}$)($X_{11}$), wherein, optionally: $X_1$ is A or V; $X_2$ is R, S or G, $X_3$ is P, Y, R, V, I, H, T or E; $X_4$ is S, D, E or N; $X_5$ is D, A or T; $X_6$ is S, G, T or A; $X_7$ is I, A, R, Q, or V; $X_8$ is A, E, K, G or T; $X_9$ is M or I; $X_{10}$ is D, L, Q, V, N or G; and, $X_{11}$ is V, R, N, E or K (SEQ ID NO: 397). In some embodiments, $X_1$ is A. In some embodiments, $X_1$ is V. In some embodiments, $X_2$ is R. In some embodiments, $X_2$ is S. In some embodiments, $X_2$ is G. In some embodiments, $X_3$ is P. In some embodiments, $X_3$ is Y. In some embodiments, $X_3$ is R. In some embodiments, $X_3$ is V. In some embodiments, $X_3$ is I. In some embodiments, $X_3$ is H. In some embodiments, $X_3$ is T. In some embodiments, $X_3$ is E. In some embodiments, $X_4$ is S. In some embodiments, $X_4$ is D. In some embodiments, $X_4$ is E. In some embodiments, $X_4$ is N. In some embodiments, $X_5$ is D. In some embodiments, $X_5$ is A. In some embodiments, $X_5$ is T. In some embodiments, $X_6$ is S. In some embodiments, $X_6$ is G. In some embodiments, $X_6$ is T. In some embodiments, $X_6$ is A. In some embodiments, $X_7$ is I. In some embodiments, $X_7$ is A. In some embodiments, $X_7$ is R. In some embodiments, $X_7$ is Q. In some embodiments, $X_7$ is V. In some embodiments, $X_8$ is A. In some embodiments, $X_8$ is E. In some embodiments, $X_8$ is K. In some embodiments, $X_8$ is G. In some embodiments, $X_8$ is T. In some embodiments, $X_9$ is M. In some embodiments, $X_9$ is I. In some embodiments, $X_{10}$ is D. In some embodiments, $X_{10}$ is L. In some embodiments, $X_{10}$ is Q. In some embodiments, $X_{10}$ is V. In some embodiments, $X_{10}$ is N. In some embodiments, $X_{10}$ is G. In some embodiments, $X_{11}$ is V. In some embodiments, $X_{11}$ is R. In some embodiments, $X_{11}$ is N. In some embodiments, $X_{11}$ is E. In some embodiments, $X_{11}$ is K.

In some embodiments, the antibody, or antigen-binding fragment thereof, comprises three heavy chain CDRs and three light chain CDRs, wherein the heavy chain CDRs comprise:
- a) CDR-H1 comprising the amino acid sequence G($X_1$)I($X_2$)S($X_3$)SYYW($X_4$), wherein, optionally: $X_1$ is S or P; $X_2$ is S, H or R; $X_3$ is S or G; and, $X_4$ is G, I, N or V (SEQ ID NO: 395);
- b) CDR-H2 comprising the amino acid sequence SISYSA($X_1$)TYYNPSLKS, wherein, optionally, $X_1$ is S or T (SEQ ID NO: 396); and
- c) CDR-H3 comprising the amino acid sequence ($X_1$)($X_2$)D($X_3$)($X_4$)Y($X_5$)($X_6$)($X_7$)($X_8$)G($X_9$)($X_{10}$)($X_{11}$), wherein, optionally: $X_1$ is A or V; $X_2$ is R, S or G, $X_3$ is P, Y, R, V, I, H, T or E; $X_4$ is S, D, E or N; $X_5$ is D, A or T; $X_6$ is S, G, T or A; $X_7$ is I, A, R, Q, or V; $X_8$ is A, E, K, G or T; $X_9$ is M or I; $X_{10}$ is D, L, Q, V, N or G; and, $X_{11}$ is V, R, N, E or K (SEQ ID NO: 397).

In some embodiments, the antibody, or antigen-binding fragment thereof, further comprises a CDR-L1 as set forth in SEQ ID NO:103, optionally comprising one or more amino acid changes. In some embodiment, the antibody, or antigen-binding fragment thereof, further comprises a CDR-L2 as set forth in SEQ ID NO:104, optionally comprising one or more amino acid changes. In some embodiments, the antibody, or antigen-binding fragment thereof, further comprises a CDR-L3 as set forth in SEQ ID NO:105, optionally comprising one or more amino acid changes.

In some embodiments, the antibody, or antigen-binding fragment, comprises at least three of the following six CDRs:
- a) CDR-H1 comprising the amino acid sequence G($X_1$)I($X_2$)S($X_3$)SYYW($X_4$), wherein, optionally: $X_1$ is S or P; $X_2$ is S, H or R; $X_3$ is S or G; and, $X_4$ is G, I, N or V (SEQ ID NO: 395);
- b) CDR-H2 comprising the amino acid sequence SISYSA($X_1$)TYYNPSLKS, wherein, optionally, $X_1$ is S or T (SEQ ID NO: 396);
- c) CDR-H3 comprising the amino acid sequence ($X_1$)($X_2$)D($X_3$)($X_4$)Y($X_5$)($X_6$)($X_7$)($X_8$)G($X_9$)($X_{10}$)($X_{11}$), wherein, optionally: $X_1$ is A or V; $X_2$ is R, S or G, $X_3$ is P, Y, R, V, I, H, T or E; $X_4$ is S, D, E or N; $X_5$ is D, A or T; $X_6$ is S, G, T or A; $X_7$ is I, A, R, Q, or V; $X_8$ is A, E, K, G or T; $X_9$ is M or I; $X_{10}$ is D, L, Q, V, N or G; and, $X_{11}$ is V, R, N, E or K (SEQ ID NO: 397);
- d) CDR-L1: SEQ ID NO:103, optionally comprising one or more amino acid changes;
- e) CDR-L2: SEQ ID NO: 104, optionally comprising one or more amino acid changes; and
- f) CDR-L3: SEQ ID NO: 105, optionally comprising one or more amino acid changes.

In some embodiments, the antibody, or antigen-binding fragment thereof, specifically binds a human LTBP1-proTGFβ1 complex and/or a human LTBP3-proTGFβ1 complex, and does not bind a human GARP-proTGFβ1 complex. In some embodiments, the antibody, or antigen-binding fragment thereof, does not bind a human GARP-proTGFβ1 complex. In some embodiments, the antibody, or antigen-binding fragment thereof, does not bind mature TGFβ1, mature TGFβ2 or mature TGFβ3.

In a particular embodiment, the antibody, or antigen-binding fragment, specifically binds a human LTBP1-proTGFβ1 complex and/or a human LTBP3-proTGFβ1 complex, and does not bind a human GARP-proTGFβ1 complex; wherein the antibody does not bind mature TGFβ1, mature TGFβ2 or mature TGFβ33; wherein the antibody is a fully human or humanized antibody or a fragment thereof, wherein the antibody comprises at least three of the following six CDRs:
- a) CDR-H1 comprising the amino acid sequence G($X_1$)I($X_2$)S($X_3$)SYYW($X_4$), wherein, optionally: $X_1$ is S or P; $X_2$ is S, H or R; $X_3$ is S or G; and, $X_4$ is G, I, N or V (SEQ ID NO: 395);
- b) CDR-H2 comprising the amino acid sequence SISYSA($X_1$)TYYNPSLKS, wherein, optionally, $X_1$ is S or T (SEQ ID NO: 396);
- c) CDR-H3 comprising the amino acid sequence ($X_1$)($X_2$)D($X_3$)($X_4$)Y($X_5$)($X_6$)($X_7$)($X_8$)G($X_9$) ($X_{10}$) ($X_{11}$), wherein, optionally: $X_1$ is A or V; $X_2$ is R, S or G, $X_3$ is P, Y, R, V, I, H, T or E; $X_4$ is S, D, E or N; $X_5$ is D, A or T; $X_6$ is S, G, T or A; $X_7$ is I, A, R, Q, or V; $X_8$ is A, E, K, G or T; $X_9$ is M or I; $X_{10}$ is D, L, Q, V, N or G; and, $X_{11}$ is V, R, N, E or K (SEQ ID NO: 397);
- d) CDR-L1 as set forth in SEQ ID NO:103, optionally comprising one or more amino acid changes;
- e) CDR-L2 as set forth in SEQ ID NO: 104, optionally comprising one or more amino acid changes; and
- f) CDR-L3 as set forth in SEQ ID NO: 105, optionally comprising one or more amino acid changes.

In some embodiments, such antibody binds a human LTBP1-proTGFβ1 complex with a KD of <100 nM as measured in a suitable in vitro binding assay such as Bio-Layer Interferometry (BLI); and/or, such antibody binds a human LTBP3-proTGFβ1 complex with a KD of <100 nM as measured in a suitable in vitro binding assay such as Bio-Layer Interferometry (BLI). In some embodiments, such antibody binds a human LTBP1-proTGFβ1 complex with a KD of <50 nM as measured in a suitable in vitro binding assay such as Bio-Layer Interferometry (BLI); and/or, such antibody binds a human LTBP3-proTGFβ1 complex with a KD of <50 nM as measured in a suitable in vitro binding assay such as Bio-Layer Interferometry (BLI). In some embodiments, such antibody binds a human LTBP1-proTGFβ1 complex with a KD of <25 nM as measured in a suitable in vitro binding assay such as Bio-Layer Interferometry (BLI); and/or, such antibody binds a human LTBP3-proTGFβ1 complex with a KD of <25 nM as measured in a suitable in vitro binding assay such as Bio-Layer Interferometry (BLI). In some embodiments, such antibody binds a human LTBP1-proTGFβ1 complex with a KD of <10 nM as measured in a suitable in vitro binding assay such as Bio-Layer Interferometry (BLI); and/or, such antibody binds a human LTBP3-proTGFβ1 complex with a KD of <10 nM as measured in a suitable in vitro binding assay such as Bio-Layer Interferometry (BLI).

In another embodiment, such antibody is cross-reactive with mouse LTBP1-proTGFβ1. In some embodiments, such antibody is also cross-reactive with mouse LTBP3-proTGFβ1. In some embodiments, such antibody binds a mouse LTBP1-proTGFβ1 complex with a KD of <100 nM as measured in a suitable in vitro binding assay such as Bio-Layer Interferometry (BLI); and/or, the antibody binds a mouse LTBP3-proTGFβ1 complex with a KD of <100 nM as measured in a suitable in vitro binding assay such as Bio-Layer Interferometry (BLI). In some embodiments, such antibody binds a mouse LTBP1-proTGFβ1 complex with a KD of <50 nM as measured in a suitable in vitro binding assay such as Bio-Layer Interferometry (BLI); and/or, the antibody binds a mouse LTBP3-proTGFβ1 complex with a KD of <50 nM as measured in a suitable in vitro binding assay such as Bio-Layer Interferometry (BLI). In some embodiments, such antibody binds a mouse LTBP1-proTGFβ1 complex with a KD of <25 nM as measured in a suitable in vitro binding assay such as Bio-Layer Interferometry (BLI); and/or, the antibody binds a mouse LTBP3-proTGFβ1 complex with a KD of <25 nM as measured in a suitable in vitro binding assay such as Bio-Layer Interferometry (BLI). In some embodiments, such antibody binds a mouse LTBP1-proTGFβ1 complex with a KD of <10 nM as measured in a suitable in vitro binding assay such as Bio-Layer Interferometry (BLI); and/or, the antibody binds a mouse LTBP3-proTGFβ1 complex with a KD of <10 nM as measured in a suitable in vitro binding assay such as Bio-Layer Interferometry (BLI).

In another embodiment, such antibody does not bind to human GARP-proTGFβ1. In preferred embodiments, such context-selective antibody is also isoform-specific in that it selectively binds and inhibits the activation of TGFβ1 associated with LTBP1/3.

In another aspect, the antibody, or antigen-binding fragment thereof, comprises a CDR-H1 comprising the amino acid $G(X_1)I(X_2)SSSYYW(X_3)$, wherein, optionally: $X_1$ is S or P; $X_2$ is H or R; and, $X_3$ is G, I or N (SEQ ID NO: 384). In some embodiments, $X_1$ is a S. In some embodiments, $X_1$ is a P. In some embodiments, $X_2$ is a H. In some embodiments, $X_2$ is an R. In some embodiments, $X_3$ is a G. In some embodiments, $X_3$ is an I. In some embodiments, $X_3$ is an N.

In some embodiments, the antibody, or antigen-binding fragment thereof, comprises a CDR-H2 comprising the amino acid sequence $SISYSA(X_1)TYYNPSLKS$, wherein, optionally, $X_1$ is S or T (SEQ ID NO: 396). In some embodiments, $X_1$ is a S. In some embodiment, $X_1$ is a T.

In some embodiments, the antibody, or antigen-binding fragment thereof, comprises a CDR-H3 comprising the amino acid sequence $A(X_1)D(X_2)SYD(X_3)(X_4)AGM(X_5)(X_6)$, wherein, optionally: $X_1$ is R, S or G, $X_2$ is P or V; $X_3$ is S or A; $X_4$ is A, R, I or V; $X_5$ D, Q, or G; and, $X_6$ is V or R (SEQ ID NO: 385). In some embodiments, $X_1$ is R. In some embodiments, $X_1$ is S. In some embodiments, $X_1$ is G. In some embodiments, $X_2$ is P. In some embodiments, $X_2$ is V. In some embodiments, $X_3$ is S. In some embodiments, $X_3$ is A. In some embodiments, $X_4$ is A. In some embodiments, $X_4$ is R. In some embodiments, $X_4$ is I. In some embodiments, $X_4$ is V. In some embodiments, $X_5$ is D. In some embodiments, $X_5$ is Q. In some embodiments, $X_5$ is G. In some embodiments, $X_6$ is V. In some embodiments, $X_6$ is R.

In some embodiments, the antibody, or antigen-binding fragment thereof, comprises three heavy chain CDRs and three light chain CDRs, wherein the heavy chain CDRs comprise:

a) CDR-H1 comprising the amino acid sequence $G(X_1)I(X_2)SSSYYW(X_3)$, wherein, optionally: $X_1$ is S or P; $X_2$ is H or R; and, $X_3$ is G, I or N (SEQ ID NO: 384);
    b) CDR-H2 comprising the amino acid sequence $SISYSA(X_1)TYYNPSLKS$, wherein, optionally, $X_1$ is S or T (SEQ ID NO: 396); and
    c) CDR-H3 comprising the amino acid sequence $A(X_1)D(X_2)SYD(X_3)(X_4)AGM(X_5)(X_6)$, wherein, optionally: $X_1$ is R, S or G, $X_2$ is P or V; $X_3$ is S or A; $X_4$ is A, R, I or V; $X_5$ D, Q, or G; and, $X_6$ is V or R (SEQ ID NO: 385).

In some embodiments, the antibody, or antigen-binding fragment thereof, further comprises a CDR-L1 as set forth in SEQ ID NO:103, optionally comprising one or more amino acid changes. In some embodiment, the antibody, or antigen-binding fragment thereof, further comprises a CDR-L2 as set forth in SEQ ID NO:104, optionally comprising one or more amino acid changes. In some embodiments, the antibody, or antigen-binding fragment thereof, further comprises a CDR-L3 as set forth in SEQ ID NO:105, optionally comprising one or more amino acid changes.

In some embodiments, the antibody, or antigen-binding fragment, comprises at least three of the following six CDRs:

a) CDR-H1 comprising the amino acid sequence $G(X_1)I(X_2)SSSYYW(X_3)$, wherein, optionally: $X_1$ is S or P; $X_2$ is H or R; and, $X_3$ is G, I or N (SEQ ID NO: 384);
    b) CDR-H2 comprising the amino acid sequence $SISYSA(X_1)TYYNPSLKS$, wherein, optionally, $X_1$ is S or T (SEQ ID NO: 396);
    c) CDR-H3 comprising the amino acid sequence $A(X_1)D(X_2)SYD(X_3)(X_4)AGM(X_5)(X_6)$, wherein, optionally: $X_1$ is R, S or G, $X_2$ is P or V; $X_3$ is S or A; $X_4$ is A, R, I or V; $X_5$ D, Q, or G; and, $X_6$ is V or R (SEQ ID NO: 385);
    d) CDR-L1: SEQ ID NO:103, optionally comprising one or more amino acid changes;
    e) CDR-L2: SEQ ID NO: 104, optionally comprising one or more amino acid changes; and
    f) CDR-L3: SEQ ID NO: 105, optionally comprising one or more amino acid changes.

In some embodiments, the antibody, or antigen-binding fragment thereof, specifically binds a human LTBP1-proTGFβ1 complex and/or a human LTBP3-proTGFβ1 complex, and does not bind a human GARP-proTGFβ1 complex. In some embodiments, the antibody, or antigen-binding fragment thereof, does not bind a human GARPproTGFβ1 complex. In some embodiments, the antibody, or antigen-binding fragment thereof, does not bind mature TGFβ1, mature TGFβ2 or mature TGFβ3.

In a particular embodiment, the antibody, or antigen-binding fragment thereof, specifically binds a human LTBP1-proTGFβ1 complex and/or a human LTBP3-proTGFβ1 complex, and does not bind a human GARP-proTGFβ1 complex; wherein the antibody does not bind mature TGFβ1, mature TGFβ2 or mature TGFβ33; wherein the antibody is a fully human or humanized antibody or a fragment thereof, wherein the antibody comprises at least three of the following six CDRs:

a) CDR-H1 comprising the amino acid sequence G($X_1$)I($X_2$)SSSYYW($X_3$), wherein, optionally: $X_1$ is S or P; $X_2$ is H or R; and, $X_3$ is G, I or N (SEQ ID NO: 384);

b) CDR-H2 comprising the amino acid sequence SISYSA($X_1$)TYYNPSLKS, wherein, optionally, $X_1$ is S or T (SEQ ID NO: 396);

c) CDR-H3 comprising the amino acid sequence A($X_1$)D($X_2$)SYD($X_3$)($X_4$)AGM($X_5$)($X_6$), wherein, optionally: $X_1$ is R, S or G, $X_2$ is P or V; $X_3$ is S or A; $X_4$ is A, R, I or V; $X_5$ D, Q, or G; and, $X_6$ is V or R (SEQ ID NO: 385);

d) CDR-L1: SEQ ID NO:103, optionally comprising one or more amino acid changes;

e) CDR-L2: SEQ ID NO: 104, optionally comprising one or more amino acid changes; and f) CDR-L3: SEQ ID NO: 105, optionally comprising one or more amino acid changes.

In some embodiments, such antibody binds a human LTBP1-proTGFβ1 complex with a KD of <100 nM as measured in a suitable in vitro binding assay such as Bio-Layer Interferometry (BLI); and/or, such antibody binds a human LTBP3-proTGFβ1 complex with a KD of <100 nM as measured in a suitable in vitro binding assay such as Bio-Layer Interferometry (BLI). In some embodiments, such antibody binds a human LTBP1-proTGFβ1 complex with a KD of <50 nM as measured in a suitable in vitro binding assay such as Bio-Layer Interferometry (BLI); and/or, such antibody binds a human LTBP3-proTGFβ1 complex with a KD of <50 nM as measured in a suitable in vitro binding assay such as Bio-Layer Interferometry (BLI). In some embodiments, such antibody binds a human LTBP1-proTGFβ1 complex with a KD of <25 nM as measured in a suitable in vitro binding assay such as Bio-Layer Interferometry (BLI); and/or, such antibody binds a human LTBP3-proTGFβ1 complex with a KD of <25 nM as measured in a suitable in vitro binding assay such as Bio-Layer Interferometry (BLI). In some embodiments, such antibody binds a human LTBP1-proTGFβ1 complex with a KD of <10 nM as measured in a suitable in vitro binding assay such as Bio-Layer Interferometry (BLI); and/or, such antibody binds a human LTBP3-proTGFβ1 complex with a KD of <10 nM as measured in a suitable in vitro binding assay such as Bio-Layer Interferometry (BLI).

In another embodiment, such antibody is cross-reactive with mouse LTBP1-proTGFβ1. In some embodiments, such antibody is also cross-reactive with mouse LTBP3-proTGFβ1. In some embodiments, such antibody binds a mouse LTBP1-proTGFβ1 complex with a KD of <100 nM as measured in a suitable in vitro binding assay such as Bio-Layer Interferometry (BLI); and/or, the antibody binds a mouse LTBP3-proTGFβ1 complex with a KD of <100 nM as measured in a suitable in vitro binding assay such as Bio-Layer Interferometry (BLI). In some embodiments, such antibody binds a mouse LTBP1-proTGFβ1 complex with a KD of <50 nM as measured in a suitable in vitro binding assay such as Bio-Layer Interferometry (BLI); and/or, the antibody binds a mouse LTBP3-proTGFβ1 complex with a KD of <50 nM as measured in a suitable in vitro binding assay such as Bio-Layer Interferometry (BLI). In some embodiments, such antibody binds a mouse LTBP1-proTGFβ1 complex with a KD of <25 nM as measured in a suitable in vitro binding assay such as Bio-Layer Interferometry (BLI); and/or, the antibody binds a mouse LTBP3-proTGFβ1 complex with a KD of <25 nM as measured in a suitable in vitro binding assay such as Bio-Layer Interferometry (BLI). In some embodiments, such antibody binds a mouse LTBP1-proTGFβ1 complex with a KD of <10 nM as measured in a suitable in vitro binding assay such as Bio-Layer Interferometry (BLI); and/or, the antibody binds a mouse LTBP3-proTGFβ1 complex with a KD of <10 nM as measured in a suitable in vitro binding assay such as Bio-Layer Interferometry (BLI).

In another embodiment, such antibody does not bind to human GARP-proTGFβ1. In preferred embodiments, such context-selective antibody is also isoform-specific in that it selectively binds and inhibits the activation of TGFβ1 associated with LTBP1/3.

Also provided herein are antibodies, or antigen-binding fragments thereof, which binds a human LTBP1-proTGFβ1 complex and/or a human LTBP3-TGFβ1 complex with yet higher affinities and further advantageous combinations of binding properties.

Accordingly, in one aspect, the antibody, or antigen-binding fragment thereof, comprises the following six CDRs:

a) CDR-H1 comprising the amino acid sequence FTFRSYVMH (SEQ ID NO: 166);

b) CDR-H2 comprising the amino acid sequence VISHEGS($X_1$)KYYADSVKG, wherein: $X_1$ is L or G (SEQ ID NO: 366); and c) CDR-H3 comprising the amino acid sequence A($X_1$)PRIAARRGGFG($X_2$), wherein: $X_1$ is V, R or L; and $X_2$ is Y, S or T (SEQ ID NO: 367);

d) CDR-L1 comprising the amino acid sequence TRS($X_1$)G($X_2$)ID($X_3$)NYVQ, wherein, $X_1$ is S or H; $X_2$ is N, L, S or A; and $X_3$ is N, D or Y (SEQ ID NO: 368);

e) CDR-L2 comprising the amino acid sequence ED($X_1$)($X_2$)RPS, wherein: $X_1$ is N, F or A; and $X_2$ is Q, I or V (SEQ ID NO: 369); and f) CDR-L3 comprising the amino acid sequence Q($X_1$)YD($X_2$)($X_3$)($X_4$)Q($X_5$)VV, wherein: $X_1$ is S or G; $X_2$ is 5, F, Y, D, H or W; $X_3$ is N, D or S; $X_4$ is N, A, L, E or T; and $X_5$ is G, R, A or L (SEQ ID NO: 370).

In some embodiments, within CDR-H3: $X_1$ is R or L. Within CDR-L3: $X_2$ may be Y. Within CDR-L3: $X_3$ may be D; and $X_4$ may be T. In some preferred embodiments, within CDR-H3: $X_1$ is R or L (optionally R), within CDR-L3: $X_2$ is Y; and within CDR-L3: $X_3$ is D; and $X_4$ is T.

In alternative embodiments, within CDR-H3: $X_1$ is R or L (optionally R), within CDR-L3: $X_2$ is Y and within CDR-L3: $X_3$ is D; $X_4$ is N; and $X_5$ is A.

In some embodiments within CDR-L1: $X_1$ is S or H; $X_2$ is N or A; and $X_3$ is N, D or Y; within CDR-L2: $X_1$ is N or F; and $X_2$ is Q or V; and within CDR-L3: $X_1$ is S or G; $X_2$ is 5, Y, D or W; $X_3$ is D or S; $X_4$ is N, L or T; and $X_5$ is G, R, A or L. In some embodiments, within CDR-L1: $X_1$ is S; $X_2$ is N; and $X_3$ is N or Y; within CDR-L2: $X_1$ is N; and $X_2$ is Q or V; and within CDR-L3: $X_1$ is S or G; $X_2$ is 5, Y or W; $X_3$ is D; $X_4$ is N or T; and $X_5$ is G, R or A. In some embodiments, within CDR-L3: $X_1$ is S; $X_2$ is S or Y; $X_3$ is D; $X_4$ is N or T; and $X_5$ is G, R or A. In some embodiments, within CDR-L3: $X_1$ is S; $X_2$ is Y; $X_3$ is D; $X_4$ is N or T; and X₅ is G or A. In some preferred embodiments, within CDR-L3: X₁ is S; X₂ is Y; X₃ is D; X₄ is T; and X₅ is G.

In particularly preferred embodiments, the antibody or antigen-binding fragment has the CDRs of Ab42, e.g.: CDR-H1 comprising the amino acid sequence FTFRSYVMH (SEQ ID NO: 166); CDR-H2 comprising the amino acid sequence VISHEGSLKYYADSVKG (SEQ ID NO: 167); CDR-H3 comprising the amino acid sequence ARPRIAARRGGFGY (SEQ ID NO: 168); CDR-L1 comprising the amino acid sequence TRSSGNIDNNYVQ (SEQ ID NO: 169); CDR-L2 comprising the amino acid sequence EDNQRPS (SEQ ID NO: 170); and CDR-L3 comprising the amino acid sequence QSYDYDTQGVV (SEQ ID NO: 171).

In some embodiments, the antibody or antigen-binding fragment comprises a heavy chain variable region having an amino acid sequence that is at least 90% identical to SEQ ID NO: 318; and a light chain variable region having an amino acid sequence that is at least 90% identical to SEQ ID NO: 319.

In some embodiments, the antibody, or antigen-binding fragment, binds a human LTBP1-proTGFβ1 complex and/or a human LTBP3-TGFβ1 complex with a $K_D$ of <5 nM as measured by suitable in vitro binding assay, such as BLI. For example, the antibody, or antigen-binding fragment, may bind a human LTBP1-proTGFβ1 complex and a human LTBP3-TGFβ1 complex with a $K_D$ of <5 nM as measured by suitable in vitro binding assay, such as BLI. In some embodiments, the antibody, or antigen-binding fragment, binds the human LTBP1- and/or LTBP3-proTGFβ1 complex with a $K_D$ of <1 nM as measured by suitable in vitro binding assay, such as BLI.

In some embodiments, the antibody, or antigen-binding fragment thereof does not show detectable binding to a human GARP-proTGFβ1 complex, as measured by BLI, under the same assay conditions as used to measure binding to human LTBP1-proTGFβ1 complex and/or human LTBP3-TGFβ1. For example, the antibody, or antigen-binding fragment may not show detectable binding to a human GARP-proTGFβ1 complex, as measured by BLI, under the same assay conditions as used to measure binding to human LTBP1-proTGFβ1 complex and human LTBP3-TGFβ1 complex.

In some embodiments, the antibody, or antigen-binding fragment thereof, binds a human LTBP1-proTGFβ1 complex and/or a human LTBP3-TGFβ1 complex with a $K_D$ that is at least 50 times lower (e.g., at least 75 times lower, at least 100 times lower) than the $K_D$ when binding to a human GARP-proTGFβ1 complex under the same assay conditions. For example, the antibody, or antigen-binding fragment thereof, may bind a human LTBP1-proTGFβ1 complex and a human LTBP3-TGFβ1 complex with a $K_D$ that is at least 50 times lower (e.g., at least 75 times lower, at least 100 times lower) than the $K_D$ when binding to a human GARP-proTGFβ1 complex under the same assay conditions. In some embodiments, $K_D$ is as determined by BLI or SPR. In some embodiments, $K_D$ is as determined by SPR.

In some embodiments, the antibody, or antigen-binding fragment thereof does not show detectable binding to an LRRC33-proTGFβ1 latent complex, as measured by BLI, under the same assay conditions as used to measure binding to human LTBP1-proTGFβ1 complex and/or human LTBP3-TGFβ1. For example, the antibody, or antigen-binding fragment thereof may not show detectable binding to an LRRC33-proTGFβ1 latent complex, as measured by BLI, under the same assay conditions as used to measure binding to human LTBP1-proTGFβ1 complex and human LTBP3-TGFβ1.

In some embodiments, the antibody, or antigen-binding fragment thereof, binds a human LTBP1-proTGFβ1 complex and/or a human LTBP3-TGFβ1 complex with a $K_D$ that is at least 50 times lower (e.g., at least 75 times lower, at least 100 times lower) than the $K_D$ when binding to a human LRRC33-proTGFβ1 complex under the same assay conditions. For example, the antibody, or antigen-binding fragment thereof, may bind a human LTBP1-proTGFβ1 complex and a human LTBP3-TGFβ1 complex with a $K_D$ that is at least 50 times lower (e.g., at least 75 times lower, at least 100 times lower) than the $K_D$ when binding to a human LRRC33-proTGFβ1 complex under the same assay conditions. In some embodiments, $K_D$ is as determined by BLI or SPR. In some embodiments, $K_D$ is as determined by SPR.

In some embodiments, the antibody, or antigen-binding fragment thereof, is cross-reactive with mouse LTBP1-proTGFβ1. In some embodiments, the antibody, or antigen-binding fragment thereof, is cross-reactive with mouse LTBP3-proTGFβ1. In some embodiments, the antibody, or antigen-binding fragment thereof, binds a mouse LTBP1-proTGFβ1 complex with a $K_D$ of <10 nM as measured by BLI. In some embodiments, the antibody, or antigen-binding fragment thereof, binds a mouse LTBP3-proTGFβ1 complex with a $K_D$ of <10 nM as measured by BLI.

In further embodiments, the antibody which selectively binds a human LTBP1-TGFβ1 complex and/or a human LTBP3-TGFβ1 complex may not show meaningful binding (e.g., may not show a response of more than 0.1 units (nm)) on exposure to a human GARP-proTGFβ1 complex in a BLI assay (e.g., Octet) when the human GARP-proTGFβ1 complex is at a concentration of 200 nM.

In another aspect, the antibody, or antigen-binding fragment thereof, comprises the following six CDRs:
a) CDR-H1 comprising the amino acid sequence G(X₁)I(X₂)S(X₃)SYYW(X₄), wherein, optionally: X₁ is S; X₂ is S, H or R; X₃ is S or G; and, X₄ is G, I, N or V (SEQ ID NO: 386);
b) CDR-H2 comprising the amino acid sequence SISYS(X₁)(X₂)TYY, wherein, optionally: X₁ is G or A; and X₂ is S or T (SEQ ID NO: 398);
c) CDR-H3 comprising the amino acid sequence A(X₁)DPSYDS(X₂)AGM(X₃)V, wherein, optionally: X₁ is R, S or G; X₂ is A or I; and X₃ is D or Q (SEQ ID NO: 387);
d) CDR-L1 comprising the amino acid sequence RAS(X₁)(X₂)IS(X₃)YLN, wherein, optionally: X₁ is K or Q; X₂ is V or S; and X₃ is S or Y (SEQ ID NO: 389);
e) CDR-L2 comprising the amino acid sequence (X₁)AS(X₂)(X₃)QS, wherein, optionally: X₁ is Y, A or S; X₂ is S or N; and X₃ is L or R (SEQ ID NO: 390);
f) CDR-L3 comprising the amino acid sequence QQ(X₁)(X₂)D(X₃)P(X₄)T, wherein, optionally: X₁ is S or G; X₂ is F or N; X₃ is W or F; and X₄ is F or L (SEQ ID NO: 391).

In some embodiments: within CDR-H1: X₁ is S; X₂ is S or R; X₃ is 5; and, X₄ is G; within CDR-H2: X₁ is G or A; and X₂ is S or T; within CDR-H3: X₁ is R, S or G; X₂ is A or I; and X₃ is D or Q; within CDR-L1: X₁ is K or Q; X₂ is V or S; and X₃ is S or Y; within CDR-L2: X₁ is Y, A or S; X₂ is S or N; and X₃ is L or R; and within CDR-L3: X₁ is S or G; X₂ is F or N; X₃ is W or F; and X₄ is F or L.

In some embodiments: CDR-H1 comprises the amino acid sequence GSIRSSSYYWG (SEQ ID NO: 292); CDR-H2 comprises the amino acid sequence SISYSATTYY (SEQ ID NO: 293); within CDR-H3: X₁ is S or G; X₂ is A or I; and X₃ is D or Q; within CDR-L1: X₁ is K or Q; X₂ is V or S; and X₃ is S or Y; within CDR-L2: X₁ is Y, A or S; X₂ is S or N; and X₃ is L or R; and within CDR-L3: X₁ is S or G; X₂ is F or N; X₃ is W or F; and X₄ is F or L.

In some embodiments: CDR-H1 comprises the amino acid sequence GSIRSSSYYWG (SEQ ID NO: 292); CDR-H2 comprises the amino acid sequence SISYSATTYY (SEQ ID NO: 293); CDR-H3 comprises the amino acid sequence AGDPSYDSIAGMQV (SEQ ID NO: 294); CDR-L1 comprises the amino acid sequence RASQSISSYLN (SEQ ID NO: 295); CDR-L2 comprises the amino acid sequence AASNLQS (SEQ ID NO: 296); and CDR-L3 comprises the amino acid sequence QQSFDWPLT (SEQ ID NO: 297).

In some embodiments, the antibody or antigen-binding fragment comprises a heavy chain variable region having an amino acid sequence that is at least 90% identical to SEQ ID NO: 360; and a light chain variable region having an amino acid sequence that is at least 90% identical to SEQ ID NO: 361.

In some embodiments, the antibody, or antigen-binding fragment, binds a human LTBP1-proTGFβ1 complex and/or a human LTBP3-TGFβ1 complex with a $K_D$ of <5 nM as measured by suitable in vitro binding assay, such as BLI. For example, the antibody, or antigen-binding fragment, may bind a human LTBP1-proTGFβ1 complex and a human LTBP3-TGFβ1 complex with a $K_D$ of <5 nM as measured by suitable in vitro binding assay, such as BLI. In some embodiments, the antibody, or antigen-binding fragment, binds the human LTBP1- and/or LTBP3-proTGFβ1 complex with a $K_D$ of <1 nM as measured by suitable in vitro binding assay, such as BLI.

In some embodiments, the antibody, or antigen-binding fragment thereof does not show detectable binding to a human GARP-proTGFβ1 complex, as measured by BLI, under the same assay conditions as used to measure binding to human LTBP1-proTGFβ1 complex and/or human LTBP3-TGFβ1. For example, the antibody, or antigen-binding fragment may not show detectable binding to a human GARP-proTGFβ1 complex, as measured by BLI, under the same assay conditions as used to measure binding to human LTBP1-proTGFβ1 complex and human LTBP3-TGFβ1 complex.

In some embodiments, the antibody, or antigen-binding fragment thereof, binds a human LTBP1-proTGFβ1 complex and/or a human LTBP3-TGFβ1 complex with a $K_D$ that is at least 50 times lower (e.g., at least 75 times lower, at least 100 times lower) than the $K_D$ when binding to a human GARP-proTGFβ1 complex under the same assay conditions. For example, the antibody, or antigen-binding fragment thereof, may bind a human LTBP1-proTGFβ1 complex and a human LTBP3-TGFβ1 complex with a $K_D$ that is at least 50 times lower (e.g., at least 75 times lower, at least 100 times lower) than the $K_D$ when binding to a human GARP-proTGFβ1 complex under the same assay conditions. In some embodiments, $K_D$ is as determined by BLI or SPR. In some embodiments, $K_D$ is as determined by SPR.

In some embodiments, the antibody, or antigen-binding fragment thereof does not show detectable binding to an LRRC33-proTGFβ1 latent complex, as measured by BLI, under the same assay conditions as used to measure binding to human LTBP1-proTGFβ1 complex and/or human LTBP3-TGFβ1. For example, the antibody, or antigen-binding fragment thereof may not show detectable binding to an LRRC33-proTGFβ1 latent complex, as measured by BLI, under the same assay conditions as used to measure binding to human LTBP1-proTGFβ1 complex and human LTBP3-TGFβ1.

In some embodiments, the antibody, or antigen-binding fragment thereof, binds a human LTBP1-proTGFβ1 complex and/or a human LTBP3-TGFβ1 complex with a $K_D$ that is at least 50 times lower (e.g., at least 75 times lower, at least 100 times lower) than the $K_D$ when binding to a human LRRC33-proTGFβ1 complex under the same assay conditions. For example, the antibody, or antigen-binding fragment thereof, may bind a human LTBP1-proTGFβ1 complex and a human LTBP3-TGFβ1 complex with a $K_D$ that is at least 50 times lower (e.g., at least 75 times lower, at least 100 times lower) than the $K_D$ when binding to a human LRRC33-proTGFβ1 complex under the same assay conditions. In some embodiments, $K_D$ is as determined by BLI or SPR. In some embodiments, $K_D$ is as determined by SPR.

In some embodiments, the antibody, or antigen-binding fragment thereof, is cross-reactive with mouse LTBP1-proTGFβ1. In some embodiments, the antibody, or antigen-binding fragment thereof, is cross-reactive with mouse LTBP3-proTGFβ1. In some embodiments, the antibody, or antigen-binding fragment thereof, binds a mouse LTBP1-proTGFβ1 complex with a $K_D$ of <10 nM as measured by BLI. In some embodiments, the antibody, or antigen-binding fragment thereof, binds a mouse LTBP3-proTGFβ1 complex with a $K_D$ of <10 nM as measured by BLI.

In further embodiments, the antibody which selectively binds a human LTBP1-TGFβ1 complex and/or a human LTBP3-TGFβ1 complex may not show meaningful binding (e.g., may not show a response of more than 0.1 units (nm)) on exposure to a human GARP-proTGFβ1 complex in a BLI assay (e.g., Octet) when the human GARP-proTGFβ1 complex is at a concentration of 200 nM.

In some embodiments, the "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word length=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In any of the antibodies or antigen-binding fragments described herein, one or more conservative mutations can be introduced into the CDRs or framework sequences at positions where the residues are not likely to be involved in an antibody-antigen interaction. In some embodiments, such conservative mutation(s) can be introduced into the CDRs or framework sequences at position(s) where the residues are not likely to be involved in interacting with a LTBP1-TGFβ complex and/or a LTBP3-TGFβ complex, as determined based on the crystal structure. In some embodiments, the likely interface (e.g., residues involved in an antigen-antibody interaction) may be deduced from known structural information on another antigens sharing structural similarities.

As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g., Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In some embodiments, the antibodies provided herein comprise mutations that confer desirable properties to the antibodies. For example, to avoid potential complications due to Fab-arm exchange, which is known to occur with native IgG4 mAbs, the antibodies provided herein may comprise a stabilizing 'Adair' mutation (Angal et al., "A single amino acid substitution abolishes the heterogeneity of chimeric mouse/human (IgG4) antibody," Mol Immunol 30, 105-108; 1993), where serine 228 (EU numbering; residue 241 Kabat numbering) is converted to proline resulting in an IgG1-like (CPPCP (SEQ ID NO: 45)) hinge sequence. Accordingly, any of the antibodies may include a stabilizing 'Adair' mutation or the amino acid sequence CPPCP (SEQ ID NO: 45). In one embodiment, an antibody described herein comprises a heavy chain immunoglobulin constant domain of a human IgG$_4$ having a backbone substitution of Ser to Pro, that produces an IgG$_1$-like hinge and permits formation of inter-chain disulfide bonds.

Antibodies of this disclosure that selectively bind to a LTBP1-TGFβ complex and/or a LTBP3-TGFβ complex may optionally comprise antibody constant regions or parts thereof. For example, a V$_L$ domain may be attached at its C-terminal end to a light chain constant domain such as C$_κ$ or C$_λ$. Similarly, a V$_H$ domain or portion thereof may be attached to all or part of a heavy chain such as IgA, IgD, IgE, IgG, and IgM, and any isotype subclass. Antibodies may include suitable constant regions (see, for example, Kabat et al., Sequences of Proteins of Immunological Interest, No. 91-3242, National Institutes of Health Publications, Bethesda, Md. (1991)). Therefore, antibodies within the scope of this may disclosure include V$_H$ and V$_L$ domains, or antigen-binding portions thereof, combined with any suitable constant region. In exemplary embodiments, the antibodies, or antigen-binding portions thereof, comprise a heavy chain immunoglobulin constant domain containing all or a portion of a human IgG$_1$ or a human IgG$_4$ constant domain. In some embodiments, the antibody, or antigen-binding portion thereof, comprises a light chain immunoglobulin constant domain containing all or a portion of a human Ig lambda constant domain or a human Ig kappa constant domain.

In some embodiments, antibodies that selectively bind to a LTBP1-TGFβ complex and/or a LTBP3-TGFβ complex may or may not include the framework region of the antibodies of SEQ ID NOs: 7 and 8. In some embodiments, antibodies that selectively bind to a LTBP1-TGFβ complex and/or a LTBP3-TGFβ complex are murine antibodies and include murine framework region sequences. In other embodiments, the antibodies are chimeric antibodies, or antigen-binding fragments thereof. In another embodiment, the antibodies are humanized antibodies, or antigen-binding fragments thereof. In another embodiment, the antibodies are fully human antibodies, or antigen-binding fragments thereof. In one embodiment, the antibody comprises a framework region comprising a human germline amino acid sequence.

The antibodies, and antigen-binding fragments thereof, described herein can have any configuration suitable for binding antigen. For example, in one embodiment, the antibody, or antigen-binding portion thereof, comprises four polypeptide chains, including two heavy chain variable regions and two light chain variable regions. In another embodiment, the antibody, or antigen-binding portion thereof, comprises one heavy chain variable region and one light chain variable region. In exemplary embodiments, the antibody, or antigen-binding portion thereof, is a Fab fragment, a F(ab')2 fragment, a scFab fragment, an scFv, or a diabody.

In one embodiment, the antibody, or antigen-binding portion thereof, comprises a heavy chain immunoglobulin constant domain of a human IgG$_1$ constant domain or a human IgG$_4$ constant domain. In an exemplary embodiment, the heavy chain immunoglobulin constant domain is a human IgG$_4$ constant domain. In one embodiment, the antibody, or antigen-binding portion thereof, binds a conformational epitope. In one embodiment, the antibody, or antigen-binding portion thereof, binds a combinatorial epitope.

In one embodiment, the antibody, or antigen-binding portion thereof, comprises a heavy chain immunoglobulin constant domain of a human IgG$_4$ constant domain having a backbone substitution of Ser to Pro that produces an IgG$_1$-like hinge and permits formation of inter-chain disulfide bonds. In one embodiment, the antibody, or antigen-binding portion thereof, further comprises a light chain immunoglobulin constant domain comprising a human Ig lambda constant domain, or a human Ig kappa constant domain.

In one embodiment, the antibody is an IgG having four polypeptide chains which are two heavy chains and two light chains. In exemplary embodiments, the antibody can be a humanized antibody, a human antibody, or a chimeric antibody. In one embodiment, the antibody comprises a framework having a human germline amino acid sequence.

In one embodiment, the invention provides an antibody, or antigen-binding portion thereof, that competes for binding with an antibody, or antigen-binding portion thereof, described herein. In one embodiment, the invention provides an antibody, or antigen-binding portion thereof, that binds to the same epitope as an antibody, or antigen-binding portion thereof, described herein. In one embodiment, the antibody, or antigen-binding fragment thereof, does not compete with antibody SR-Ab1 for binding to a human LTBP1-proTGFβ1 complex.

Binding Kinetics of Novel Antibodies

The novel antibodies and antigen-binding fragments thereof (e.g., Fabs) disclosed herein are characterized by enhanced binding properties. The antibodies and the fragments are capable of selectively binding to a LTBP1-TGFβ1 complex and/or a LTBP3-TGFβ1 complex (also known as large latent complexes (LLCs). Recombinantly produced, purified protein complexes may be used as antigens (e.g., antigen complexes) to screen, evaluate or confirm the ability of an antibody to bind the antigen complexes in suitable in vitro binding assays. Such assays are well known in the art and include but are not limited to: BLI-based assays (such as Octet®) and SPR-based assays (such as Biacore).

Previously, antibodies and fragments that exhibited high affinities (e.g., sub-nanomolar K$_D$) to the LLCs were identified. Here, advantageously, antibodies and fragments with particularly slow dissociation rates were specifically selected, aimed to achieve particularly durable inhibitory effects.

Accordingly, selection of suitable TGFβ inhibitors for carrying out the methods and therapeutic use in accordance with the present disclosure may include carrying out in vitro binding assays to measure binding kinetics. In preferred embodiments, the antibody or the antigen-binding fragment binds hLTBP1-pro TGFβ1 and/or hLTBP3-proTGFβ1 with high affinity and low dissociation rate $k_{OFF}$, as described herein. Preferably, the antibody or the fragment further binds the murine LLC counterparts, namely, mLTBP1-proTGFβ1 and/or mLTBP3-proTGFβ1, with equivalent affinities as the human LLCs. In vitro binding kinetics may be readily determined by measuring interactions of test antibodies (such as antigen-binding fragments) and suitable antigen, such as LLCs and small latent complexes (SLCs). Suitable methods for in vitro binding assays to determine the parameters of binding kinetics include BLI-based assays such as Octet, and surface plasmon resonance-based assays, such as Biacore systems. An example of an Octet-based in vitro binding assay is provided in Example 9/Table 9. Several antibodies were shown in this experiment to have "OFF" rates ($k_{OFF}$) that are $<5\times10^{-4}$ (1/s). These results are in stark contrast to the results shown for Ab10, for which binding to hLTBP1-pro TGFβ1 and/or hLTBP3-proTGFβ1 could not even be detected by the same Octet assay (Table 8). An example of SPR-based in vitro binding assay is provided in Example 9. Fab fragments of Ab42, Ab63 and Ab43, which are activation inhibitors of TGFβ1, were used in this experiment. As illustrated in this example, these antibodies have sub-nanomolar $K_D$ and "OFF" rates that are $<5\times10^{-4}$ (1/s). Thus, for example, Ab42 is able to remain bound to the antigen for a much longer duration of time (e.g., greater t½) than an antibody with much higher "OFF" rate, which "falls off" (e.g., dissociates from) the antigen relatively quickly. Thus, the difference in the dissociation kinetics predominantly attributes to the notable difference in their overall affinities ($K_D$), which may result in enhanced potency. Therefore, characterization of binding kinetics provides useful information as to potential durability of effects and resulting in vivo potency.

Accordingly, the invention includes a method of selecting a TGFβ activation inhibitor for therapeutic use, wherein the method comprises selection of an antibody or antigen-binding fragment thereof that has a dissociation rate of $<5\times10^{-4}$ ((1/s) as measured by SPR. In some embodiments, the antibody or the fragment binds antigen with an affinity of less than 1 nM (i.e., sub-nanomolar), e.g., less than 500 pM, 400 pM, 300 pM, 200 pM, 100 pM, or 50 pM.

The selection method may include determining or measuring dissociation half-time (also referred to as half binding time or t') of test antibody by suitable means, such as BLI-based assays and SPR-based assays. Monovalent or multivalent (e.g., divalent) test antibodies may be used. For example, Fab fragments are suitable monovalent antibodies that can be used to determine dissociation half time. Similarly, full length immunoglobulins (e.g., IgGs) may be used to determine dissociation half time. In some embodiments, the method comprises selection of an antibody or antigen-binding fragment thereof that has t' of 45 minutes or longer to human LTBP1-proTGFβ1 and/or human LTBP3-proTGFβ1. Preferably, the antibody or the fragment has t' of 45 minutes or longer to each of human LTBP1-proTGFβ1 and human LTBP3-proTGFβ1. More preferably, the antibody or the fragment further has t' of 45 minutes or longer to murine LTBP1-proTGFβ1 and/or murine LTBP3-proTGFβ1. Most preferably, the antibody or the fragment has t' of 45 minutes or longer to each of murine LTBP1-proTGFβ1 and murine LTBP3-proTGFβ1. The method may further include selection of an antibody or an antigen-binding fragment that has t½ of 5 minutes or less to human GARP-proTGFβ1. Any of these antibodies with advantageous dissociation half time should preferably have a KD of less than 1 nM as measured by BLI (e.g., Octet) or SPR (e.g., Biacore). Preferably, SPR assays are used to determine dissociation half-time (t½).

Polypeptides

Some aspects of the disclosure relate to isolated polypeptides. For example, in one embodiment, the invention provides an isolated polypeptide comprising CDRH1, CDRH2, CDRH3, CDRL1, CDRL2, or CDRL3, or combinations thereof, as provided in Table 5. In an exemplary embodiment, the isolated polypeptide can contain CDRH1, CDRH2, and CDRH3 as provided in Table 5. In other embodiments, the isolated polypeptide can contain CDRL1, CDRL2, and CDRL3 as provided in Table 5. In some embodiments, the polypeptide can contain up to 6, 5, 4, 3, 2, or 1 amino acid residue variations as compared to the corresponding CDR region in any one of CDRH1, CDRH2, CDRH3, CDRL1, CDRL2, or CDRL3, or combinations thereof, as provided in Table 5. In one embodiment, the invention provides an isolated polypeptide comprising SEQ ID NO: 7. In another embodiment, the invention provides an isolated polypeptide comprising SEQ ID NO: 8. In another embodiment, the invention provides an isolated polypeptide comprising SEQ ID NO:7 and SEQ ID NO:8. In this embodiment, SEQ ID NO:7 and SEQ ID NO:8 can optionally be connected by a linker peptide. In some embodiments, the polypeptide is a heavy chain variable domain. In some embodiments, the polypeptide is at least 75% (e.g., 80%, 81%, 82%, 83%, 84%, 85%, 86%, 87%, 88%, 89%, 90%, 91%, 92%, 93%, 94%, 95%, 96%, 97%, 98%, or 99%) identical to SEQ ID NO: 7. In some embodiments, the polypeptide is a light chain variable domain. In some embodiments, the polypeptide is at least 75% (e.g., 80%, 81%, 82%, 83%, 84%, 85%, 86%, 87%, 88%, 89%, 90%, 91%, 92%, 93%, 94%, 95%, 96%, 97%, 98%, or 99%) identical to SEQ ID NO: 8.

In another embodiment, the invention provides an isolated polypeptide comprising a heavy chain variable region sequence set forth in Table 6. In one embodiment, the invention provides an isolated polypeptide comprising SEQ ID NO: 7, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, or SEQ ID NO: 106. In one embodiment, the invention provides an isolated polypeptide comprising SEQ ID NO: 8, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, or SEQ ID NO: 107. In one embodiment, the invention provides an isolated polypeptide comprising SEQ ID NO: 318. In one embodiment, the invention provides an isolated polypeptide comprising SEQ ID NO: 319. In one embodiment, the invention provides an isolated polypeptide comprising SEQ ID NO: 360. In one embodiment, the invention provides an isolated polypeptide comprising SEQ ID NO: 361.

In another embodiment, the invention provides an isolated polypeptide comprising a light chain variable region set forth in Table 6. In another embodiment, the invention provides an isolated polypeptide comprising a heavy chain variable region sequence set forth in Table 6 (e.g., SEQ ID NO: 7, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, or SEQ ID NO: 106) and a light chain variable region sequence set forth in Table 6 (e.g., SEQ ID NO: 8, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, or SEQ ID NO: 107). In this embodiment, the heavy chain and light chain sequences (e.g., SEQ ID NO:7 and SEQ ID NO:8) can optionally be connected by a linker peptide. In some embodiments, the polypeptide is a heavy chain variable domain. In some embodiments, the polypeptide is at least 75% (e.g., 80%, 81%, 82%, 83%, 84%, 85%, 86%, 87%, 88%, 89%, 90%, 91%, 92%, 93%, 94%, 95%, 96%, 97%, 98%, or 99%) identical to SEQ ID NO: 7, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, or SEQ ID NO: 106. In some embodiments, the polypeptide is a light chain variable domain. In some embodiments, the polypeptide is at least 75% (e.g., 80%, 81%, 82%, 83%, 84%, 85%, 86%, 87%, 88%, 89%, 90%, 91%, 92%, 93%, 94%, 95%, 96%, 97%, 98%, or 99%) identical to SEQ ID NO: 8, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, or SEQ ID NO: 107.

In another embodiment, the invention provides an isolated polypeptide comprising a heavy chain variable region sequence set forth in SEQ ID NO: 318 and a light chain variable region sequence set forth in SEQ ID NO: 319. In another embodiment, the invention provides an isolated polypeptide comprising a heavy chain variable region sequence set forth in SEQ ID NO: 360 and a light chain variable region sequence set forth in SEQ ID NO: 361. In this embodiment, the heavy chain and light chain sequences (e.g., SEQ ID NO: 318 and SEQ ID NO: 319) can be connected by a linker peptide. In some embodiments, the polypeptide is a heavy chain variable domain. In some embodiments, the polypeptide is at least 85% (e.g., 90%, 91%, 92%, 93%, 94%, 95%, 96%, 97%, 98%, or 99%) identical to SEQ ID NO: 318 or SEQ ID NO: 360. In some embodiments, the polypeptide is a light chain variable domain. In some embodiments, the polypeptide is at least 85% (e.g., 90%, 91%, 92%, 93%, 94%, 95%, 96%, 97%, 98%, or 99%) identical to SEQ ID NO: 319 or SEQ ID NO: 361.

Nucleic Acids

In some embodiments, antibodies, antigen-binding portions thereof, and/or compositions of the present disclosure may be encoded by nucleic acid molecules. Such nucleic acid molecules include, without limitation, DNA molecules, RNA molecules, polynucleotides, oligonucleotides, mRNA molecules, vectors, plasmids and the like. In some embodiments, the present disclosure may comprise cells programmed or generated to express nucleic acid molecules encoding compounds and/or compositions of the present disclosure.

In some embodiments, the invention provides a nucleic acid molecule that encodes the foregoing antibodies, or an antigen-binding portion thereof. For example, in one embodiment, the invention provides a nucleic acid molecule that encodes a polypeptide comprising CDRH1, CDRH2, CDRH3, CDRL1, CDRL2, or CDRL3, or combinations thereof, as provided in Table 5. The nucleic acid molecule can, in some embodiments, encode a polypeptide comprising CDRH1, CDRH2, and CDRH3 as provided in Table 5. In some embodiments, the nucleic acid molecule can encode a polypeptide comprising CDRL1, CDRL2, and CDRL3 as provided in Table 5. In some embodiments, the nucleic acid molecule encodes a polypeptide that can contain up to 6, 5, 4, 3, 2, or 1 amino acid residue variations as compared to the corresponding CDR region in any one of CDRH1, CDRH2, CDRH3, CDRL1, CDRL2, or CDRL3, or combinations thereof, as provided in Table 5. In an exemplary embodiment, the nucleic acid molecule encodes a polypeptide comprising a heavy chain variable domain having at least 70%, 75%, 80%, 85%, 90%, 95%, 96%, 97%, 98%, or 99% identity to the amino acid sequence set forth in SEQ ID NO: 7, and/or a light chain variable domain having at least 70%, 75%, 80%, 85%, 90%, 95%, 96%, 97%, 98%, or 99% identity to the amino acid sequence set forth in SEQ ID NO: 8. In one embodiment, the nucleic acid molecule encodes a polypeptide comprising a heavy chain variable domain having at least 70%, 75%, 80%, 85%, 90%, 95%, 96%, 97%, 98%, or 99% identity to a heavy chain variable region sequence set forth in Table 6, and/or a light chain variable domain having at least 70%, 75%, 80%, 85%, 90%, 95%, 96%, 97%, 98%, or 99% identity to a light chain variable region sequence set forth in Table 6. In an exemplary embodiment, the nucleic acid molecule encodes a polypeptide comprising a heavy chain variable domain having at least 70%, 75%, 80%, 85%, 90%, 95%, 96%, 97%, 98%, or 99% identity to the amino acid sequence set forth in SEQ ID NO: 7, and/or a light chain variable domain having at least 70%, 75%, 80%, 85%, 90%, 95%, 96%, 97%, 98%, or 99% identity to the amino acid sequence set forth in SEQ ID NO: 8. In some embodiments, the nucleic acid molecule encodes an antibody, or antigen-binding portion thereof, comprising a heavy chain variable domain amino acid sequence set forth in SEQ ID NO: 7, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, or SEQ ID NO: 106, and a light chain variable domain amino acid sequence set forth in SEQ ID NO: 8, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, or SEQ ID NO: 107. In some embodiments, the nucleic acid molecule encodes an antibody, or antigen-binding portion thereof, comprising a heavy chain variable domain amino acid sequence set forth in SEQ ID NO: 7, and a light chain variable domain amino acid sequence set forth in SEQ ID NO: 8.

In another embodiment, the invention provides nucleic acid molecule that encodes the foregoing antibodies, or an antigen-binding portion thereof. In an exemplary embodiment, the nucleic acid molecule encodes a polypeptide comprising a heavy chain variable domain having at least 85%, 90%, 95%, 96%, 97%, 98%, or 99% identity to the amino acid sequence set forth in SEQ ID NO: 318, and/or a light chain variable domain having at least 85%, 90%, 95%, 96%, 97%, 98%, or 99% identity to the amino acid sequence set forth in SEQ ID NO: 319. In another embodiment, the nucleic acid molecule encodes a polypeptide comprising a heavy chain variable domain having at least 85%, 90%, 95%, 96%, 97%, 98%, or 99% identity to the amino acid sequence set forth in SEQ ID NO: 360, and/or a light chain variable domain having at least 85%, 90%, 95%, 96%, 97%, 98%, or 99% identity to the amino acid sequence set forth in SEQ ID NO: 361.

In another embodiment, the invention provides a nucleic acid molecule that encodes a polypeptide comprising a heavy chain variable region sequence set forth in SEQ ID NO: 318 and a light chain variable region sequence set forth in SEQ ID NO: 319. In another embodiment, the invention provides a nucleic acid molecule that encodes an isolated polypeptide comprising a heavy chain variable region sequence set forth in SEQ ID NO: 360 and a light chain variable region sequence set forth in SEQ ID NO: 361. In this embodiment, the heavy chain and light chain sequences (e.g., SEQ ID NO: 318 and SEQ ID NO: 319) can be connected by a linker peptide. In some embodiments, the nucleic acid molecule encodes a polypeptide which is a heavy chain variable domain. In some embodiments, the nucleic acid molecule encodes a polypeptide which is at least 85% (e.g., 90%, 91%, 92%, 93%, 94%, 95%, 96%, 97%, 98%, or 99%) identical to SEQ ID NO: 318 or SEQ ID NO: 360. In some embodiments, the nucleic acid molecule encodes a polypeptide which is a light chain variable domain. In some embodiments, the nucleic acid molecule encodes a polypeptide which is at least 85% (e.g., 90%, 91%, 92%, 93%, 94%, 95%, 96%, 97%, 98%, or 99%) identical to SEQ ID NO: 319 or SEQ ID NO: 361. In some embodiments, the nucleic acid molecule encodes an antibody, or antigen-binding portion thereof, comprising a heavy chain variable domain amino acid sequence set forth in SEQ ID NO: 318, and a light chain variable domain amino acid sequence set forth in SEQ ID NO: 319. In some embodiments, the nucleic acid molecule encodes an antibody, or antigen-binding portion thereof, comprising a heavy chain variable domain amino acid sequence set forth in SEQ ID NO: 360, and a light chain variable domain amino acid sequence set forth in SEQ ID NO: 361.

In some cases, nucleic acids of the disclosure include codon-optimized nucleic acids. Methods of generating codon-optimized nucleic acids are known in the art and may include, but are not limited to those described in U.S. Pat. Nos. 5,786,464 and 6,114,148, the contents of each of which are herein incorporated by reference in their entirety. Also provided herein are expression vectors comprising any of the aforementioned nucleus acid(s).

Production of Antibodies that Bind a LTBP1/3-TGFβ1 Complex

The art is familiar with various techniques and methods that may be used for obtaining antibodies, or antigen-binding fragments thereof, of the disclosure. For example, antibodies can be produced using recombinant DNA methods, hybridoma techniques, phage or yeast display technologies, transgenic animals (e.g., a XenoMouse®) or some combination thereof.

Immunization and Hybridomas

In some methods described herein, the specified antigen (e.g., an LTBP1-TGFβ1 complex and/or an LTBP3-TGFβ1 complex) can be used to immunize a non-human animal ("host"), e.g., a rodent, e.g., a mouse, hamster, or rat. In one embodiment, the non-human animal is a mouse. In another embodiment, the host may be a camelid.

After immunization, which may include single or multiple steps of antigen exposures (e.g., injections), splenocytes are harvested from the animal and the associated B cells are fused with immortalized myeloma cells to form hybridomas for antibody production. Hybridomas may be generated in accordance with known methods (see e.g., Kohler and Milstein (1975) Nature, 256: 495-499). Hybridomas formed in this manner are then screened using standard methods, such as enzyme-linked immunosorbent assay (ELISA), Bio-Layer Interferometry (BLI) technology (e.g., OCTET) and surface plasmon resonance (e.g., BIACORE) analysis, to identify one or more hybridomas that produce an antibody that specifically binds to a specified antigen. Any form of the specified antigen may be used as the immunogen, e.g., recombinant antigen, naturally occurring forms, any variants or fragments thereof, as well as antigenic peptide thereof (e.g., any of the epitopes described herein as a linear epitope or within a scaffold as a conformational epitope).

Screening Library/Libraries

In some embodiments, the method or process of making or identifying antibodies includes a step of screening protein expression libraries that express antibodies or fragments thereof (e.g., scFv), e.g., phage, yeast, or ribosome display libraries. For example, a library of human combinatorial antibodies or scFv fragments can synthesized on phages or yeast, the library is then screened with the antigen of interest or an antibody-binding portion thereof, and the phage or yeast that binds the antigen is isolated, from which one may obtain the antibodies or immunoreactive fragments (Vaughan et a/., 1996, PMID: 9630891; Sheets et a/., 1998, PMID: 9600934; Boder et a/., 1997, PMID: 9181578; Pepper et a/., 2008, PMID: 18336206).

Phage display is further described, for example, in Ladner et al., U.S. Pat. No. 5,223,409; Smith (1985) Science 228: 1315-1317; Clackson et al. (1991) Nature, 352: 624-628; Marks et al. (1991) J. Mol. Biol., 222: 581-597; WO 92/18619; WO 91/17271; WO 92/20791; WO 92/15679; WO 93/01288; WO 92/01047; WO 92/09690; and WO 90/02809. Yeast display is further described, for example, in U.S. Pat. Nos. 7,700,302 and 8,877,688. In particular methods, the yeast display library expresses full-length antibodies (e.g., Adimab, LLC).

Kits for generating phage or yeast display libraries are commercially available. There also are other methods and reagents that can be used in generating and screening antibody display libraries (see U.S. Pat. No. 5,223,409; WO 92/18619, WO 91/17271, WO 92/20791, WO 92/15679, WO 93/01288, WO 92/01047, WO 92/09690; and Barbas et a/., 1991, PMID: 1896445). Such techniques advantageously allow for the screening of large numbers of candidate antibodies.

No matter how obtained, antibody producing cells (e.g., yeast colonies, hybridomas, etc.) may be selected, cloned and further screened for desirable characteristics including, for example, robust growth, high antibody production and desirable antibody characteristics such as high affinity for the antigen of interest. Methods of selecting, cloning and expanding colonies and/or hybridomas are well known to those of ordinary skill in the art. Once the desired antibodies are identified, the relevant genetic material may be isolated, manipulated, and expressed using common, art-recognized molecular biology and biochemical techniques.

Humanization

The antibodies or fragments of the present invention are preferably fully human antibodies or humanized antibodies. Thus, whatever the source, it will be appreciated that the method may comprise humanizing one or more antibodies or fragments thereof, wherein the human antibody sequences may be fabricated using art-known molecular engineering techniques and introduced into expression systems and host cells as described herein. Such non-natural recombinantly produced human antibodies (and subject compositions) are entirely compatible with the teachings of this disclosure and are expressly held to be within the scope of the instant invention. In certain select aspects, the LTBP1-TGFβ1 complex-binding and/or a LTBP3-TGFβ1 complex-binding antibodies of the invention will comprise a recombinantly produced human antibody.

Affinity Maturation

In some embodiments, antibodies produced by the methods described-above may be of moderate affinity (Ka of about $10^6$ to $10^7 M-1$). Accordingly, antibodies or fragments thereof may be subjected to a process of affinity maturation as part of optimization, if desired. The term "affinity maturation" shall have the meaning readily understood by the skilled artisan. Briefly, it refers to further modifying the amino acid sequence of candidate antibodies or fragments (often referred to as "parent") to achieve improved binding profiles to the specific antigen. Typically, a parental antibody and an affinity-matured counterpart (sometimes referred to as "progeny" or "offspring") retain the same epitope. Suitable in vitro binding assays may be carried out to screen for improved binders at appropriate step(s) during the affinity maturation process. Optionally, in some embodiments, functional assays (e.g., cell-based potency assays) may also be performed to confirm desired functionality.

Affinity maturation typically involves sequence diversification and/or mutagenesis, whilst the exact means of introducing or generating mutations is not limiting. In some embodiments, mutagenesis comprises introducing one or more changes (e.g., substitutions or deletions) in amino acid residues of one or more CDRs. Accordingly, in some embodiments the VR or CDR sequences described herein may comprise up to one, two, three, four, five, or six amino acid changes. In some embodiments, the VR or CDR sequences described herein may comprise up to one, two, three, four, five, or six amino acid substitutions. In some embodiments, the VR or CDR sequences described herein may comprise up to one, two, three, or four deletions. Additionally or alternatively, mutagenesis may comprise so-called oligo-walking of variable regions or CDRs.

For example, affinity maturation of antibodies can be accomplished by a number of methods including random mutagenesis (Gram H., et al. Proc. Natl. Acad. Sci. U.S.A. (1992) 89, 3576-3580, and Hawkins R. E., et al. J. Mol. Biol. (1992) 226, 889-896), random mutagenesis of CDR sequences, e.g., CDR walking (Yang W. P., et al., J. Mol. Biol. (1995) 254, 392-403), directed mutagenesis of residues (Ho M., et al., J. Biol. Chem. (2005) 280, 607-617 and Ho M., et al., Proc. Natl. Acad. Sci. U.S.A. (2006) 103, 9637-9642), and approaches that reproduce somatic hypermutation (SHM) in vitro (Bowers P. M., et al., Proc. Natl. Acad. Sci. U.S.A. (2011) 108, 20455-20460).

In one embodiment, antibodies may be affinity matured by conducting mutagenesis on the variable heavy or variable light chain regions. In another embodiment, antibodies may be affinity matured by conducting mutagenesis on any one of the variable heavy chain CDRs or variable light chain CDRs. In another embodiment, antibodies may be affinity matured by conducting mutagenesis on the variable heavy chain CDR3 (e.g., CDR-H3 mutagenesis). In another embodiment, antibodies may be affinity matured by conducting mutagenesis on the variable heavy chain CDR2 (e.g., CDR-H2 mutagenesis). In another embodiment, antibodies may be affinity matured by conducting mutagenesis on the variable heavy chain CDR1 (e.g., CDR-H1 mutagenesis). In another embodiment, antibodies may be affinity matured by conducting mutagenesis on the variable light chain CDR3 (e.g., CDR-L3 mutagenesis). In another embodiment, antibodies may be affinity matured by conducting mutagenesis on the variable light chain CDR2 (e.g., CDR-L2 mutagenesis). In another embodiment, antibodies may be affinity matured by conducting mutagenesis on the variable light chain CDR1 (e.g., CDR-L1 mutagenesis).

In some embodiments, an antibody may be affinity matured and/or optimized by separately conducting mutagenesis on some or all of the three light chain CDRs (i.e., CDR-L1, CDR-L2, and CDR-L3) to generate up to three different libraries of antibodies, each having unique mutations in one of the three CDRs. The new antibodies can then be screened for improved properties (e.g., antigen-binding). Then, if further affinity improvements are desired, unique CDRs from each of the libraries can be mixed and matched to generate a new library of antibodies and screened for improved properties (e.g., antigen-binding). In some embodiments, affinity maturation involves screening an antibody library comprising variants of one or more CDRs ("repertoire"), which may be combined with at least one CDR of a parent antibody. This process is sometimes called CDR shuffling or CDR diversification. In some embodiments, a variable heavy chain CDR3 (e.g., CDR-H3) may be used to screen a library that contains variable heavy chain CDR1 and CDR2 repertoires of variants (a.k.a., CDR-H1/H2 diversification). In some embodiments, variable light chain CDR3 (e.g., CDR-L3) may be used to screen a library that contains variable light chain CDR1 and CDR2 repertoires of variants (a.k.a., CDR-L1/L2 diversification).

In some embodiments, affinity maturation involves screening an antibody library comprising light chain variants ("repertoire"), which may be combined with a heavy chain of a parent antibody (light-chain shuffling). For example, in some embodiments, selected heavy chains are introduced into an antibody library comprising light chain variants thereby producing a new library of antibodies that can be screened for improved affinity. In some embodiments, repertoires of naturally occurring variable region variants may be obtained from unimmunized donors. Examples of heavy or light-chain shuffling are described in the following documents: Marks et al., (1992) Nature Biotech 10: 779-78; Schier et al., (1996) J. Mol. Biol. 255, 28-43; Park et al., (2000) BBRC. 275. 553-557; and Chames et al., (2002) J. Immunol 1110-1118. In some embodiments, the light chain library comprises lambda light chains variants. In some embodiments, the light chain library comprises kappa light chains variants. In some embodiments, the light chain library comprises both lambda and kappa light chains variants.

It should be appreciated that the various methods for affinity maturation may be combined in any order. For example, in one embodiment, a select antibody may undergo heavy chain CDR-H1/H2 diversification, followed by CDR-H3 mutagenesis. In another embodiment, a select antibody may undergo heavy chain CDR-H1/H2 diversification, followed by CDR-H3 mutagenesis, followed by light chain shuffling. In another embodiment, a select antibody may undergo heavy chain CDR-H1/H2 diversification, followed by light chain shuffling, followed by CDR-H3 mutagenesis. In another embodiment, a select antibody may undergo light chain shuffling, followed by heavy chain CDR-H1/H2 diversification, followed by CDR-H3 mutagenesis. In another embodiment, a select antibody may undergo light chain shuffling, followed by heavy chain CDR-H1/H2 diversification, followed by CDR-H3 mutagenesis, followed by CDR-L3 mutagenesis.

In some embodiment, a select antibody may undergo light chain shuffling, followed by heavy chain CDR-H1/H2 diversification, followed by CDR-H3 mutagenesis, followed by CDR-L1, CDR-L2, and/or CDRL3 mutagenesis. In some embodiments, a select antibody may undergo heavy chain CDR-H1/H2 diversification, followed by CDR-H3 mutagenesis, followed by CDR-L1, CDR-L2, and/or CDRL3 mutagenesis. In some embodiments, light chain CDR mutagenesis is separately conducted on some or all of the three light chain CDRs (CDR-L1, CDR-L2, and CDRL3) to produce up to three libraries of antibodies. In some embodiments, the light chain CDRs from each of the libraries are mixed and matched to generate a new library of antibodies having unique combinations of light chain CDR mutations.

In any of the methods for affinity maturation described above, the resulting new antibodies may be selected for binding to the target antigen (e.g., a LTBP1-TGFβ1 complex and/or a LTBP3-TGFβ1 complex) using known techniques (e.g., FACS). Binding specificity and affinity using FACS may be tested by varying antigen concentration and/or competition for unlabeled (cold) antigen. Binding affinity can be further assessed using other techniques known in the art, such as ELISA, BLI (e.g., OCTET), and SPR (e.g., BIACORE).

In addition to the affinity maturation process discussed above, further optimization may be performed to achieve desired product profiles. Thus, antibodies may be further subjected to a step of optimization and selected based on certain physicochemical properties that are advantageous. For therapeutic antibodies (biologics), physicochemical criteria for developability that may be evaluated include, but are not limited to: solubility, stability, immunogenicity, lack of self-association or aggregation, Fc functionality, internalization profiles, pH-sensitivity, glycosylation and manufacturability such as cell viability and/or gene expression. In some embodiments, the process of optimization involves mutagenesis of one or more amino acid sequences within the constant regions.

In one aspect, the invention provides a method for making a composition comprising an antibody, or antigen-binding fragment thereof, that specifically binds a human LTBP1-proTGFβ1 complex and/or a human LTBP3-proTGFβ1 complex, and does not bind a human GARP-proTGFβ1 complex; wherein the antibody, or antigen-binding fragment thereof, inhibits TGFβ1 but does not inhibit TGFβ2 or TGFβ3, the method comprising steps of i) providing at least one antigen comprising LTBP1-proTGFβ1 and/or LTBP3-proTGFβ31, ii) selecting a first pool of antibodies, or antigen-binding fragments thereof, that specifically bind the at least one antigen of step (i) so as to provide specific binders of LTBP1-proTGFβ1 and/or LTBP3-proTGFβ31; iii) selecting a second pool of antibodies, or antigen-binding fragments thereof, that inhibit activation of TGFβ1, so as to generate specific inhibitors of TGFβ1 activation; iv) formulating an antibody, or antigen-binding fragment thereof, that is present in the first pool of antibodies and the second pool of antibodies into a pharmaceutical composition, thereby making the composition comprising the antibody, or antigen-binding fragment thereof.

In one embodiment, the method further comprises a step of removing from the first pool of antibodies, or antigen-binding fragments thereof, any antibodies, or antigen-binding fragments thereof, that bind GARP-proTGFβ1, LRRC33-proTGFβ1, mature TGFβ1, GARP-proTGFβ2, LRRC33-proTGFβ2, mature TGFβ2, GARP-proTGFβ3, LRRC33-proTGFβ3, mature TGFβ3, or any combinations thereof. In one embodiment, the method further comprises a step of determining or confirming isoform-specificity of the antibodies, or antigen-binding fragments thereof, selected in steps (ii) and/or (iii). In one embodiment, the method further comprises a step of selecting for antibodies, or antigen-binding fragments thereof, that are cross-reactive to human and rodent antigens. In one embodiment, the method further comprises a step of generating a fully human or humanized antibody, or antigen-binding fragment thereof, of the antibody, or antigen-binding fragment thereof, that is present in the first pool of antibodies and the second pool of antibodies.

In one embodiment, the method further comprises a step of subjecting the antibody, or antigen-binding fragment thereof, that is present in the first pool of antibodies and/or the second pool of antibodies to affinity maturation and/or optimization, so as to provide an affinity matured and/or optimized antibody or fragment thereof. In one embodiment, the affinity maturation and/or optimization comprises a step of subjecting the antibody, or antigen-binding fragment thereof, to light chain shuffling as described herein. In one embodiment, the affinity maturation and/or optimization comprises the step of subjecting the antibody, or antigen-binding fragment thereof, to CDR H1/H2 diversification as described herein. In one embodiment, the affinity maturation and/or optimization comprises the step of subjecting the antibody, or antigen-binding fragment thereof, to CDR-H3 mutagenesis as described herein. In one embodiment, the affinity maturation and/or optimization comprises the step of subjecting antibody, or antigen-binding fragment thereof, to light chain CDR mutagenesis as described herein. In one embodiment, the affinity maturation and/or optimization comprises the step of subjecting the antibody, or antigen-binding fragment thereof, to light chain CDR L1/L2 diversification as described herein.

Further optimization steps may be carried out to provide physicochemical properties that are advantageous for therapeutic compositions. Such steps may include, but are not limited to, mutagenesis or engineering to provide improved solubility, lack of self-aggregation, stability, pH sensitivity, Fc function, and so on.

In one embodiment, the method further comprises a step of determining affinity of the antibodies, or antigen-binding fragments thereof, to human LTBP1-proTGFβ1 and/or human LTBP3-proTGFβ1. In some embodiments, the method further comprises a step of removing from the first and/or second pools of antibodies, or antigen-binding fragments thereof, any antibodies, or antigen-binding fragments thereof, that bind to human LTBP1-proTGFβ1 and/or human LTBP3-proTGFβ1 with a $K_D$ of >100 nM, as measured in a suitable in vitro binding assay such as Bio-Layer Interferometry (BLI). In some embodiments, the method further comprises a step of removing from the first and/or second pools of antibodies, or antigen-binding fragments thereof, any antibodies, or antigen-binding fragments thereof, that bind to human LTBP1-proTGFβ1 and/or human LTBP3-proTGFβ1 with a $K_D$ of >50 nM, as measured in a suitable in vitro binding assay such as Bio-Layer Interferometry (BLI). In some embodiments, the method further comprises a step of removing from the first and/or second pools of antibodies, or antigen-binding fragments thereof, any antibodies, or antigen-binding fragments thereof, that bind to human LTBP1-proTGFβ1 and/or human LTBP3-proTGFβ1 with a $K_D$ of >25 nM, as measured in a suitable in vitro binding assay such as Bio-Layer Interferometry (BLI). In some embodiments, the method further comprises a step of removing from the first and/or second pools of antibodies, or antigen-binding fragments thereof, any antibodies, or antigen-binding fragments thereof, that bind to human LTBP1-proTGFβ1 and/or human LTBP3-proTGFβ1 with a $K_D$ of >10 nM, as measured in a suitable in vitro binding assay such as Bio-Layer Interferometry (BLI).

In one embodiment, the method further comprises a step of determining affinity of the antibodies, or antigen-binding fragments thereof, from the first and/or second pools of antibodies to mouse LTBP1-proTGFβ1 and/or mouse LTBP3-proTGFβ1. In some embodiments, the method further comprises a step of removing from the first and/or second pools of antibodies, or antigen-binding fragments thereof, any antibodies, or antigen-binding fragments thereof, that bind to mouse LTBP1-proTGFβ1 and/or mouse LTBP3-proTGFβ1 with a $K_D$ of >100 nM, as measured in a suitable in vitro binding assay such as Bio-Layer Interferometry (BLI). In some embodiments, the method further comprises a step of removing from the first and/or second pools of antibodies, or antigen-binding fragments thereof, any antibodies, or antigen-binding fragments thereof, that bind to mouse LTBP1-proTGFβ1 and/or mouse LTBP3-proTGFβ1 with a $K_D$ of >50 nM, as measured in a suitable in vitro binding assay such as Bio-Layer Interferometry (BLI). In some embodiments, the method further comprises a step of removing from the first and/or second pools of antibodies, or antigen-binding fragments thereof, any antibodies, or antigen-binding fragments thereof, that bind to mouse LTBP1-proTGFβ1 and/or mouse LTBP3-proTGFβ1 with a $K_D$ of >25 nM, as measured in a suitable in vitro binding assay such as Bio-Layer Interferometry (BLI). In some embodiments, the method further comprises a step of removing from the first and/or second pools of antibodies, or antigen-binding fragments thereof, any antibodies, or antigen-binding fragments thereof, that bind to mouse LTBP1-proTGFβ1 and/or mouse LTBP3-proTGFβ1 with a $K_D$ of >10 nM, as measured in a suitable in vitro binding assay such as Bio-Layer Interferometry (BLI).

In one embodiment, the method further comprises a step of removing from the first and/or second pool of antibodies, or antigen-binding fragments thereof, any antibodies, or antigen-binding fragments thereof, that do not bind mouse LTBP1-proTGFβ1 and/or mouse LTBP3-proTGFβ1.

In one embodiment, the method further comprises a step of determining the $IC_{50}$ of the antibodies, or antigen-binding fragments thereof, from the first and/or second pools of antibodies, or antigen-binding fragments thereof, as measured by a suitable functional in vitro cell-based assay such as a caga assay, as described herein. In some embodiments, the method comprises the step of removing antibodies, or antigen-binding fragments thereof, from the first and/or second pools of antibodies, or antigen-binding fragments thereof, that have an $IC_{50}$ of greater than 50 nM as measured by a caga assay as described herein. In some embodiments, the method comprises the step of removing antibodies, or antigen-binding fragments thereof, from the first and/or second pools of antibodies, or antigen-binding fragments thereof, that have an $IC_{50}$ of greater than 25 nM as measured by a caga assay as described herein. In some embodiments, the method comprises the step of removing antibodies, or antigen-binding fragments thereof, from the first and/or second pools of antibodies, or antigen-binding fragments thereof, that have an $IC_{50}$ of greater than 10 nM as measured by a caga assay as described herein. In some embodiments, the method comprises the step of removing antibodies, or antigen-binding fragments thereof, from the first and/or second pools of antibodies, or antigen-binding fragments thereof, that have an $IC_{50}$ of greater than 5 nM as measured by a caga assay as described herein.

In some embodiments, the method comprises the step of removing antibodies, or antigen-binding fragments thereof, from the first and/or second pools of antibodies, or antigen-binding fragments thereof, that have an $IC_{50}$ of greater than 100 nM as measured by an endogenous LTBP caga assay as described herein. In some embodiments, the method comprises the step of removing antibodies, or antigen-binding fragments thereof, from the first and/or second pools of antibodies, or antigen-binding fragments thereof, that have an $IC_{50}$ of greater than 50 nM as measured by an endogenous LTBP caga assay as described herein. In some embodiments, the method comprises the step of removing antibodies, or antigen-binding fragments thereof, from the first and/or second pools of antibodies, or antigen-binding fragments thereof, that have an $IC_{50}$ of greater than 25 nM as measured by an endogenous LTBP caga assay as described herein. In some embodiments, the method comprises the step of removing antibodies, or antigen-binding fragments thereof, from the first and/or second pools of antibodies, or antigen-binding fragments thereof, that have an $IC_{50}$ of greater than 10 nM as measured by an endogenous LTBP caga assay as described herein. In some embodiments, the method comprises the step of removing antibodies, or antigen-binding fragments thereof, from the first and/or second pools of antibodies, or antigen-binding fragments thereof, that have an $IC_{50}$ of greater than 5 nM as measured by an endogenous LTBP caga assay as described herein.

In some embodiments, the method comprises the step of removing antibodies, or antigen-binding fragments thereof, from the first and/or second pools of antibodies, or antigen-binding fragments thereof, that have an $IC_{50}$ of greater than 100 nM as measured by a human LTBP overexpression caga assay as described herein. In some embodiments, the method comprises the step of removing antibodies, or antigen-binding fragments thereof, from the first and/or second pools of antibodies, or antigen-binding fragments thereof, that have an $IC_{50}$ of greater than 50 nM as measured by a human LTBP overexpression caga assay as described herein. In some embodiments, the method comprises the step of removing antibodies, or antigen-binding fragments thereof, from first and/or second pools of antibodies, or antigen-binding fragments thereof, that have an $IC_{50}$ of greater than 25 nM as measured by a human LTBP overexpression caga assay as described herein. In some embodiments, the method comprises the step of removing antibodies, or antigen-binding fragments thereof, from the first and/or second pools of antibodies, or antigen-binding fragments thereof, that have an $IC_{50}$ of greater than 10 nM as measured by a human LTBP overexpression caga assay as described herein. In some embodiments, the method comprises the step of removing antibodies, or antigen-binding fragments thereof, from the first and/or second pools of antibodies, or antigen-binding fragments thereof, that have an $IC_{50}$ of greater than 5 nM as measured by a human LTBP overexpression caga assay as described herein.

In some embodiments, the method comprises the step of removing antibodies, or antigen-binding fragments thereof, from the first and/or second pools of antibodies, or antigen-binding fragments thereof, that have an $IC_{50}$ of greater than 100 nM as measured by a murine LTBP overexpression caga assay as described herein. In some embodiments, the method comprises the step of removing antibodies, or antigen-binding fragments thereof, from the first and/or second pools of antibodies, or antigen-binding fragments thereof, that have an $IC_{50}$ of greater than 50 nM as measured by a murine LTBP overexpression caga assay as described herein. In some embodiments, the method comprises the step of removing antibodies, or antigen-binding fragments thereof, from first and/or second pools of antibodies, or antigen-binding fragments thereof, that have an $IC_{50}$ of greater than 25 nM as measured by a murine LTBP overexpression caga assay as described herein. In some embodiments, the method comprises the step of removing antibodies, or antigen-binding fragments thereof, from first and/or second pools of antibodies, or antigen-binding fragments thereof, that have an $IC_{50}$ of greater than 10 nM as measured by a murine LTBP overexpression caga assay as described herein. In some embodiments, the method comprises the step of removing antibodies, or antigen-binding fragments thereof from first and/or second pools of antibodies, or antigen-binding fragments thereof, that have an $IC_{50}$ of greater than 5 nM as measured by a murine LTBP overexpression caga assay as described herein.

In another embodiment, a monoclonal antibody is obtained from the non-human animal, and then modified, e.g., made chimeric, using suitable recombinant DNA techniques. A variety of approaches for making chimeric antibodies have been described. See e.g., Morrison et al., Proc. Natl. Acad. Sci. U.S.A. 81:6851, 1985; Takeda et al., Nature 314:452, 1985, Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B.

For additional antibody production techniques, see, e.g., Antibodies: A Laboratory Manual, eds. Harlow et al., Cold Spring Harbor Laboratory, 1988. The present disclosure is not necessarily limited to any particular source, method of production, or other special characteristics of an antibody.

Some aspects of the present disclosure relate to host cells transformed with a polynucleotide or vector. Host cells may be a prokaryotic or eukaryotic cell. The polynucleotide or vector which is present in the host cell may either be integrated into the genome of the host cell or it may be maintained extrachromosomally. The host cell can be any prokaryotic or eukaryotic cell, such as a bacterial, insect, fungal, plant, animal or human cell. In some embodiments, fungal cells are, for example, those of the genus Saccharomyces, in particular those of the species S. cerevisiae. The term "prokaryotic" includes all bacteria which can be transformed or transfected with a DNA or RNA molecules for the expression of an antibody or the corresponding immunoglobulin chains. Prokaryotic hosts may include gram negative as well as gram positive bacteria such as, for example, *E. coli, S. typhimurium, Serratia marcescens* and *Bacillus subtilis*. The term "eukaryotic" includes yeast, higher plants, insects and vertebrate cells, e.g., mammalian cells, such as NSO and CHO cells. Depending upon the host employed in a recombinant production procedure, the antibodies or immunoglobulin chains encoded by the polynucleotide may be glycosylated or may be non-glycosylated. Antibodies or the corresponding immunoglobulin chains may also include an initial methionine amino acid residue.

In some embodiments, once a vector has been incorporated into an appropriate host, the host may be maintained under conditions suitable for high level expression of the nucleotide sequences, and, as desired, the collection and purification of the immunoglobulin light chains, heavy chains, light/heavy chain dimers or intact antibodies, antigen-binding fragments or other immunoglobulin forms may follow; see, Beychok, Cells of Immunoglobulin Synthesis, Academic Press, N.Y., (1979). Thus, polynucleotides or vectors are introduced into the cells which in turn produce the antibody or antigen-binding fragments. Furthermore, transgenic animals, preferably mammals, comprising the aforementioned host cells may be used for the large scale production of the antibody or antibody fragments.

The transformed host cells can be grown in fermenters and cultured using any suitable techniques to achieve optimal cell growth. Once expressed, the whole antibodies, their dimers, individual light and heavy chains, other immunoglobulin forms, or antigen-binding fragments, can be purified according to standard procedures of the art, including ammonium sulfate precipitation, affinity columns, column chromatography, gel electrophoresis and the like; see, Scopes, "Protein Purification", Springer Verlag, N.Y. (1982). The antibody or antigen-binding fragments can then be isolated from the growth medium, cellular lysates, or cellular membrane fractions. The isolation and purification of the, e.g., microbially expressed antibodies or antigen-binding fragments may be by any conventional means such as, for example, preparative chromatographic separations and immunological separations such as those involving the use of monoclonal or polyclonal antibodies directed, e.g., against the constant region of the antibody.

Aspects of the disclosure relate to a hybridoma, which provides an indefinitely prolonged source of monoclonal antibodies. As an alternative to obtaining immunoglobulins directly from the culture of hybridomas, immortalized hybridoma cells can be used as a source of rearranged heavy chain and light chain loci for subsequent expression and/or genetic manipulation. Rearranged antibody genes can be reverse transcribed from appropriate mRNAs to produce cDNA. In some embodiments, heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Any appropriate method may be used for cloning of antibody variable regions and generation of recombinant antibodies.

In some embodiments, an appropriate nucleic acid that encodes variable regions of a heavy and/or light chain is obtained and inserted into an expression vectors which can be transfected into standard recombinant host cells. A variety of such host cells may be used. In some embodiments, mammalian host cells may be advantageous for efficient processing and production. Typical mammalian cell lines useful for this purpose include CHO cells, 293 cells, or NSO cells. The production of the antibody or antigen-binding fragment may be undertaken by culturing a modified recombinant host under culture conditions appropriate for the growth of the host cells and the expression of the coding sequences. The antibodies or antigen-binding fragments may be recovered by isolating them from the culture. The expression systems may be designed to include signal peptides so that the resulting antibodies are secreted into the medium; however, intracellular production is also possible.

The disclosure also includes a polynucleotide encoding at least a variable region of an immunoglobulin chain of the antibodies described herein. In some embodiments, the variable region encoded by the polynucleotide comprises at least one complementarity determining region (CDR) of the VH and/or VL of the variable region of the antibody produced by any one of the above described hybridomas.

Polynucleotides encoding antibody or antigen-binding fragments may be, e.g., DNA, cDNA, RNA or synthetically produced DNA or RNA or a recombinantly produced chimeric nucleic acid molecule comprising any of those polynucleotides either alone or in combination. In some embodiments, a polynucleotide is part of a vector. Such vectors may comprise further genes such as marker genes which allow for the β the vector in a suitable host cell and under suitable conditions.

In some embodiments, a polynucleotide is operatively linked to expression control sequences allowing expression in prokaryotic or eukaryotic cells. Expression of the polynucleotide comprises transcription of the polynucleotide into a translatable mRNA. Regulatory elements ensuring expression in eukaryotic cells, preferably mammalian cells, are well known to those skilled in the art. They may include regulatory sequences that facilitate initiation of transcription and optionally poly-A signals that facilitate termination of transcription and stabilization of the transcript. Additional regulatory elements may include transcriptional as well as translational enhancers, and/or naturally associated or heterologous promoter regions. Possible regulatory elements permitting expression in prokaryotic host cells include, e.g., the PL, Lac, Trp or Tac promoter in *E. coli*, and examples of regulatory elements permitting expression in eukaryotic host cells are the AOX1 or GAL$_1$ promoter in yeast or the CMV-promoter, SV40-promoter, RSV-promoter (Rous sarcoma virus), CMV-enhancer, SV40-enhancer or a globin intron in mammalian and other animal cells.

Beside elements which are responsible for the initiation of transcription such regulatory elements may also include transcription termination signals, such as the SV40-poly-A site or the tk-poly-A site, downstream of the polynucleotide. Furthermore, depending on the expression system employed, leader sequences capable of directing the polypeptide to a cellular compartment or secreting it into the medium may be added to the coding sequence of the polynucleotide and have been described previously. The leader sequence(s) is (are) assembled in appropriate phase with translation, initiation and termination sequences, and preferably, a leader sequence capable of directing secretion of translated protein, or a portion thereof, into, for example, the extracellular medium. Optionally, a heterologous polynucleotide sequence can be used that encode a fusion protein including a C- or N-terminal identification peptide imparting desired characteristics, e.g., stabilization or simplified purification of expressed recombinant product.

In some embodiments, polynucleotides encoding at least the variable domain of the light and/or heavy chain may encode the variable domains of both immunoglobulin chains or only one. Likewise, polynucleotides may be under the control of the same promoter or may be separately controlled for expression. Furthermore, some aspects relate to vectors, particularly plasmids, cosmids, viruses and bacteriophages used conventionally in genetic engineering that comprise a polynucleotide encoding a variable domain of an immunoglobulin chain of an antibody or antigen-binding fragment; optionally in combination with a polynucleotide that encodes the variable domain of the other immunoglobulin chain of the antibody.

In some embodiments, expression control sequences are provided as eukaryotic promoter systems in vectors capable of transforming or transfecting eukaryotic host cells, but control sequences for prokaryotic hosts may also be used. Expression vectors derived from viruses such as retroviruses, vaccinia virus, adeno-associated virus, herpes viruses, or bovine papilloma virus, may be used for delivery of the polynucleotides or vector into targeted cell population (e.g., to engineer a cell to express an antibody or antigen-binding fragment). A variety of appropriate methods can be used to construct recombinant viral vectors. In some embodiments, polynucleotides and vectors can be reconstituted into liposomes for delivery to target cells. The vectors containing the polynucleotides (e.g., the heavy and/or light variable domain (s) of the immunoglobulin chains encoding sequences and expression control sequences) can be transferred into the host cell by suitable methods, which vary depending on the type of cellular host.

Modifications

Antibodies, or antigen-binding portions thereof, of the disclosure may be modified with a detectable label or detectable moiety, including, but not limited to, an enzyme, prosthetic group, fluorescent material, luminescent material, bioluminescent material, radioactive material, positron emitting metal, nonradioactive paramagnetic metal ion, and affinity label for detection and/or isolation of a LTBP1-TGFβ1 complex or a LTBP3-TGFβ1 complex. The detectable substance or moiety may be coupled or conjugated either directly to the polypeptides of the disclosure or indirectly, through an intermediate (such as, for example, a linker (e.g., a cleavable linker)) using suitable techniques. Non-limiting examples of suitable enzymes include horseradish peroxidase, alkaline phosphatase, β-galactosidase, glucose oxidase, or acetylcholinesterase; non-limiting examples of suitable prosthetic group complexes include streptavidin/biotin and avidin/biotin; non-limiting examples of suitable fluorescent materials include biotin, umbelliferone, fluorescein, fluorescein isothiocyanate, rhodamine, dichlorotriazinylamine fluorescein, dansyl chloride, or phycoerythrin; an example of a luminescent material includes luminol; non-limiting examples of bioluminescent materials include luciferase, luciferin, and aequorin; and examples of suitable radioactive material include a radioactive metal ion, e.g., alpha-emitters or other radioisotopes such as, for example, iodine ($^{131}$I, $^{125}$I, $^{123}$I, $^{121}$I) carbon ($^{14}$C), sulfur ($^{35}$S), tritium ($^{3}$H), indium ($^{115}$mIn, $^{113}$mIn, $^{112}$In, $^{111}$In), and technetium ($^{99}$Tc, $^{99}$mTc), thallium ($^{201}$Ti), gallium ($^{68}$Ga, $^{67}$Ga), palladium ($^{103}$Pd) molybdenum ($^{99}$Mo), xenon ($^{133}$Xe), fluorine ($^{18}$F), $^{153}$Sm, Lu, $^{159}$Gd, $^{149}$Pm, $^{140}$La, $^{175}$Yb, 166Ho, $^{90}$Y, $^{47}$Sc, $^{86}$R, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, and tin ($^{113}$Sn, $^{117}$Sn). The detectable substance may be coupled or conjugated either directly to the antibodies of the disclosure that bind selectively to a LTBP1-TGFβ1 complex and/or a LTBP3-TGFβ1 complex, or indirectly, through an intermediate (such as, for example, a linker) using suitable techniques. Any of the antibodies provided herein that are conjugated to a detectable substance may be used for any suitable diagnostic assays, such as those described herein.

In addition, antibodies, or antigen-binding portions thereof, of the disclosure may also be modified with a drug to form, e.g., an antibody-drug conjugate. The drug may be coupled or conjugated either directly to the polypeptides of the disclosure, or indirectly, through an intermediate (such as, for example, a linker (e.g., a cleavable linker)) using suitable techniques.

Targeting Agents

In some embodiments methods of the present disclosure comprise the use of one or more targeting agents to target an antibody, or antigen-binding portion thereof, as disclosed herein, to a particular site in a subject for purposes of enriching or localizing such agent(s) to a niche of interest. In some embodiments, such targeting may achieve modulating mature TGFβ release from a LTBP1-TGFβ1 complex and/or a LTBP3-TGFβ1 complex. For example, LTBP1-TGFβ1 and LTBP3-TGFβ1 complexes are typically localized to extracellular matrix. Thus, in some embodiments, antibodies disclosed herein can be conjugated to extracellular matrix targeting agents for purposes of localizing the antibodies to sites where LTBP1-TGFβ1 and LTBP3-TGFβ1 complexes reside. In such embodiments, selective targeting of antibodies leads to selective modulation of LTBP1-TGFβ1 and/or LTBP3-TGFβ1 complexes. In some embodiments, selective targeting of antibodies leads to selective inhibition of LTBP1-TGFβ1 and/or LTBP3-TGFβ1 complexes (e.g., for purposes of treating fibrosis). In some embodiments, extracellular matrix targeting agents include heparin binding agents, matrix metalloproteinase binding agents, lysyl oxidase binding domains, fibrillin-binding agents, hyaluronic acid binding agents, and others.

In some embodiments, bispecific antibodies may be used having a first portion that selectively binds a LTBP1/3-TGFβ1 complex and a second portion that selectively binds a component of a target site, e.g., a component of the ECM (e.g., fibrillin).

In some embodiments, such a target agent may be coupled to another agent or therapeutics to carry or localize the complex to a niche of interest.

Safety/Toxicity Considerations
Histopathology, Toxicology

As mentioned above, known pan-inhibitors that antagonize all TGFβ isoforms, namely, TGFβ1, TGFβ2 and TGFβ3, have been documented to cause various toxicities across multiple mammalian species. Most notable known toxicities include cardiovascular toxicities (such as valvulopathy) and epithelial hyperplasia, skin lesions, inflammation and bleeding. More specifically, some of the observed toxicities associated with pan-TGFβ inhibitors (e.g., small molecule antagonists of the TGFβR and non-selective neutralizing antibodies) reported in the literature include the following.

Cardiovascular toxicities associated with TGFβ inhibition include, hyperplasia in aortic valve, right AV valve, and left AV valve; inflammation in aortic valve, left AV valve, and ascending aorta; hemorrhage in ascending aorta, aortic valve and left AV valve; connective tissue degeneration in ascending aorta (see for example, Strauber et al. (2014) "Nonclinical safety evaluation of a Transforming Growth Factor β receptor I kinase inhibitor in Fischer 344 rats and beagle dogs" J. Clin. Pract 4(3): 1000196).

In addition, neutralizing antibodies that bind all three TGFβ isoforms have been associated with certain epithelial toxicities, which are summarized in the table below.

| Epithelial and other toxicities across species for 1D11 and GC1008 | | | |
|---|---|---|---|
| | Mice | Cyno | Human |
| Toxicities | Hyperplasia and inflammation of tongue, gingiva, and esophagus. Findings not reversible (12 wk recovery) | Hyperplasia of gingiva, nasal epithelium, and bladder Anemia lead to cessation of treatment Changes were reversible (except bladder) | Gingival bleeding Epistaxis Headache Fatigue Various skin disorders, including keratoacanthomas (KA), hyperkeratosis, cutaneous SCC, and basal cell carcinoma |
| Drug/ | 1D11 | GC1008 | GC1008 |
| Dose/ Duration | Dosing: 50 mg/kg(3×/week) Duration: 9-12 weeks | Dosing: 10 and 50 mg/kg Duration: 6 months | Dose: 0.1, 0.3, 1, 3, 10, 15 mg/kg Duration: 4 monthly doses |
| Exposure | Serum conc. = 1-2 mg/mL (over 4-12 weeks) | Not disclosed | Half-life: 21.7 d DN Cmax~(350 ng/mL)mg |

*Vitsky et. Al. Am. J Pathology vol. 174, 2009; and Lonning et. al. Current Pharmaceutical Biotech, 2011

Applicant of the present disclosure previously demonstrated the improved safety profiles of monoclonal antibodies that selectively block the activation step of TGFβ1 by targeting latent proTGFβ1 complex (see, for example, WO 2017/156500 and WO 2018/129329). In rat toxicology studies described therein, there were no observable test article-related toxicities when the animals were dosed with the inhibitors up to 100 mg/kg per week for 4 weeks.

Building upon the earlier recognition by the applicant of the present disclosure (see PCT/US2017/021972) that lack of isoform-specificity of conventional TGFβ antagonists may underlie the source of toxicities associated with TGFβ inhibition, the present inventors sought to further achieve context-selective TGFβ1 inhibition for treating various diseases that manifest TGFβ1 dysregulation, particularly fibrotic conditions, with enhanced safety/tolerability. The work presented herein therefore further provided, among high-affinity inhibitors, a subset of antibodies with particularly low dissociation rates ($k_{OFF}$) in order to improve durability.

Thus, in some embodiments, the novel antibody according to the present disclosure has the maximally tolerated dose (MTD) of >100 mg/kg when dosed weekly for at least 4 weeks (e.g., 4, 6, 8, 10, 12 weeks). In some embodiments, the novel antibody according to the present disclosure has the no observed adverse effect level (NOAEL) of up to 100 mg/kg when dosed weekly for at least 4 weeks in rats. In some embodiments, the antibody has a NOAEL of at least 100 mg/kg/week when dosed for 4 weeks or 12 weeks in mice. Suitable animal models to be used for conducting safety/toxicology studies for TGFβ inhibitors and TGFβ1 inhibitors include, but are not limited to: rats, dogs, cynos, and mice. In preferred embodiments, the minimum effective amount of the antibody based on a suitable preclinical efficacy study is below the NOAEL. More preferably, the minimum effective amount of the antibody is about one-third or less of the NOAEL. In particularly preferred embodiments, the minimum effective amount of the antibody is about one-sixth or less of the NOAEL. In some embodiments, the minimum effective amount of the antibody is about one-tenth or less of the NOAEL.

In some embodiments, the invention encompasses an isoform-selective antibody capable of inhibiting TGFβ1 signaling, which, when administered to a subject, does not cause cardiovascular or known epithelial toxicities at a dose effective to treat a TGFβ1-related indication. In some embodiments, the antibody has a minimum effective amount of about 3-10 mg/kg administered weekly, biweekly or monthly. Preferably, the antibody causes no to minimum toxicities at a dose that is at least six-times the minimum effective amount (e.g., a six-fold therapeutic window). More preferably, the antibody causes no to minimum toxicities at a dose that is at least ten-times the minimum effective amount (e.g., a ten-fold therapeutic window). Even more preferably, the antibody causes no to minimum toxicities at a dose that is at least fifteen-times the minimum effective amount (e.g., a fifteen-fold therapeutic window).

Thus, selection of an antibody or an antigen-binding fragment thereof for therapeutic use may include: selecting an antibody or antigen-binding fragment that meets the criteria of one or more of TGFβ inhibitors (such as monoclonal antibodies and antigen-binding fragments selected for example for having slow dissociation rates, e.g., $k_{OFF}$ of <5×10 (1/s)); carrying out an in vivo efficacy study in a suitable preclinical model to determine an effective amount of the antibody or the fragment; carrying out an in vivo safety/toxicology study in a suitable model to determine an amount of the antibody that is safe or toxic (e.g., MTD, NOAEL, or any art-recognized parameters for evaluating safety/toxicity); and, selecting the antibody or the fragment that provides at least a three-fold therapeutic window (preferably 6-fold, more preferably a 10-fold therapeutic window, even more preferably a 15-fold therapeutic window). The selected antibody or the fragment may be used in the manufacture of a pharmaceutical composition comprising the antibody or the fragment. Such pharmaceutical composition may be used in the treatment of a TGFβ1 indication in a subject as described herein. For example, the TGFβ1 indication may be a fibrotic disorder. Preferably, a TGFβ3 inhibitor to be selected for therapeutic use or large-scale manufacture, does not produce observable adverse effects in the treated animals after at least 4 week, e.g., 8 weeks, and 12 weeks, of sustained exposure. In some embodiments, certain toxicities observed in histopathological analyses are considered non-adverse.

Immune Safety Assessment

Cytokines play an important role in normal immune responses, but when the immune system is triggered to become hyperactive, the positive feedback loop of cytokine production can lead to a "cytokine storm" or hypercytokinemia, a situation in which excessive cytokine production causes an immune response that can damage organs, especially the lungs and kidneys, and even lead to death. Such condition is characterized by markedly elevated proinflammatory cytokines in the serum. Historically, a Phase 1 Trial of the anti-CD28 monoclonal antibody TGN1412 in healthy volunteers led to a life-threatening "cytokine storm" response resulted from an unexpected systemic and rapid induction of proinflammatory cytokines (Suntharalingam G et al. N Engl J Med. 2006 Sep. 7; 355(10):1018-28). This incident prompted heightened awareness of the potential danger associated with pharmacologic stimulation of T cells.

Whilst TGFβ-directed therapies do not target a specific T cell receptor or its ligand, it is contemplated that it is prudent to carry out immune safety assessment, including, for example, in vitro cytokine release assays, in vivo cytokine measurements from plasma samples of non-human primate treated with a TGFβ3 inhibitor, and platelet assays using human platelets.

In some embodiments, selection of a TGFβ3 inhibitor for therapeutic use and/or large-scale production thereof includes an assessment of the ability for the TGFβ3 inhibitor to trigger cytokine release from cytokine-producing cells. In such an assessment, one or more of the cytokines (e.g., inflammatory cytokines) IL-2, TNFα, IFNγ, IL-1β, CCL2 (MCP-1), and IL-6 may be assayed. In some embodiments, the cytokine-producing cells may include peripheral blood mononuclear cell (PBMC) constituents from heathy donors. Cytokine response after exposure to the TGFβ3 inhibitor (such as an antibody disclosed) herein may be compared to release after exposure to a control, e.g., an IgG isotype negative control, or any other suitable control depending on the TGFβ3 inhibitor being tested. Cytokine activation may be assessed in plate-bound (e.g., immobilized) and/or soluble assay formats. Levels of IFNγ, IL-2, IL-1β, TNFα, IL-6, and CCL2 (MCP-1) should not exceed 10-fold, e.g., 8-, 6-, 4-, or 2-fold the activation in the negative control. In some embodiments, a positive control may also be used to confirm cytokine activation in the sample, e.g., in the PBMCs. In some embodiments, these in vitro cytokine release results may be further confirmed in vivo, e.g., in an animal model such as a monkey toxicology study, e.g., a 4-week GLP or non-GLP repeat-dose monkey study.

In some embodiments, selection of an antibody or an antigen-binding fragment thereof for therapeutic use may include: identifying an antibody or antigen-binding fragment that meets the criteria of one or more of those described herein; carrying out an in vivo efficacy study in a suitable preclinical model to determine an effective amount of the antibody or the fragment; carrying out an in vivo safety/toxicology study in a suitable model to determine an amount of the antibody that is safe or toxic (e.g., MTD, NOAEL, or any art-recognized parameters for evaluating safety/toxicity); and, selecting the antibody or the fragment that provides at least a three-fold therapeutic window (preferably 6-fold, more preferably a 10-fold therapeutic window, even more preferably a 15-fold therapeutic window). In certain embodiments, the in vivo efficacy study is carried out in two or more suitable preclinical models that recapitulate human conditions. In some embodiments, such preclinical models comprise TGFβ1-positive fibrosis. In some embodiments, the preclinical models are selected from liver fibrosis model, kidney fibrosis model, lung fibrosis model, heart (cardiac) fibrosis model, skin fibrosis model.

Identification of an antibody or antigen-binding fragment thereof for therapeutic use may further include carrying out an immune safety assay, which may include, but is not limited to, measuring cytokine release and/or determining the impact of the antibody or antigen-binding fragment on platelet binding, activation, and/or aggregation. In certain embodiments, cytokine release may be measured in vitro using PBMCs or in vivo using a preclinical model such as non-human primates. In certain embodiments, the antibody or antigen-binding fragment thereof does not induce a greater than 10-fold release in IL-6, IFNγ, and/or TNFα levels as compared to levels in an IgG control sample in the immune safety assessment. In certain embodiments, assessment of platelet binding, activation, and aggregation may be carried out in vitro using PBMCs. In some embodiments, the antibody or antigen-binding fragment thereof does not induce a more than 10% increase in platelet binding, activation, and/or aggregation as compared to buffer or isotype control in the immune safety assessment.

The selected antibody or the fragment may be used in the manufacture of a pharmaceutical composition comprising the antibody or the fragment. Such pharmaceutical composition may be used in the treatment of a TGFβ indication in a subject as described herein. For example, the TGFβ indication may be a fibrotic disorder, such as organ fibrosis, e.g., liver fibrosis. Thus, the invention includes a method for manufacturing a pharmaceutical composition comprising a TGFβ inhibitor, wherein the method includes the step of selecting a TGFβ inhibitor which is tested for immune safety as assessed by immune safety assessment comprising a cytokine release assay and optionally further comprising a platelet assay. The TGFβ inhibitor selected by the method does not trigger unacceptable levels of cytokine release, as compared to control (such as IgG control). Similarly, the TGFβ inhibitor selected by the method does not cause unacceptable levels of platelet aggregation, platelet activation and/or platelet binding. Such TGFβ inhibitor is then manufactured at large-scale, for example 250 L or greater, e.g., 1000L, 2000L, 3000L, 4000L or greater, for commercial production of the pharmaceutical composition comprising the TGFβ inhibitor.

Pharmaceutical Compositions

The invention further provides pharmaceutical compositions used as a medicament suitable for administration in human and non-human subjects. One or more antibodies that selectively binds an LTBP1-TGFβ1 complex and/or an LTBP3-TGFβ1 complex can be formulated or admixed with a pharmaceutically acceptable carrier (excipient), including, for example, a buffer, to form a pharmaceutical composition. Such formulations may be used for the treatment of a disease or disorder that involves TGFβ signaling or dysregulation thereof. In some embodiments, such disease or disorder associated with TGFβ signaling involves one or more contexts, i.e., the TGFβ is associated with a particular type or types of presenting molecules. In some embodiments, such context occurs in a cell type-specific and/or tissue-specific manner. In some embodiments, for example, such context-dependent action of TGFβ signaling is mediated in part via GARP, LRRC33, LTBP1 and/or LTBP3.

In some embodiments, the antibody of the present invention binds selectively to a single context of TGFβ, such that the antibody binds TGFβ in a complex with LTBP presenting molecules, e.g., LTBP1 and/or LTBP3. Thus, such pharmaceutical compositions may be administered to patients for alleviating a TGFβ-related indication (e.g., fibrosis) associated with TGFβ1 activation/release from LTBP1 and/or LTBP3.

A pharmaceutically "acceptable" carrier (excipient) means that the carrier is compatible with the active ingredient of the composition (and preferably, capable of stabilizing the active ingredient) and not deleterious to the subject to be treated. Examples of pharmaceutically acceptable excipients (carriers), including buffers, would be apparent to the skilled artisan and have been described previously. See, e.g., Remington: The Science and Practice of Pharmacy 20th Ed. (2000) Lippincott Williams and Wilkins, Ed. K. E. Hoover. In one example, a pharmaceutical composition described herein contains more than one antibody that selectively binds a LTBP1-TGFβ1 complex and/or a LTBP3-TGFβ1 complex, where the antibodies recognize different epitopes/residues of the LTBP1-TGFβ1 complex and/or LTBP3-TGFβ1 complex.

The pharmaceutical compositions to be used in the present methods can comprise pharmaceutically acceptable carriers, excipients, or stabilizers in the form of lyophilized formulations or aqueous solutions (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/ or non-ionic surfactants such as TWEEN™, PLURONICS™ or polyethylene glycol (PEG). Pharmaceutically acceptable excipients are further described herein.

The invention also includes pharmaceutical compositions that comprise an antibody or fragment thereof according to the present invention, and a pharmaceutically acceptable excipient.

Thus, the antibody or a molecule comprising an antigen-binding fragment of such antibody can be formulated into a pharmaceutical composition suitable for human administration.

The pharmaceutical formulation may include one or more excipients. In some embodiments, excipient(s) may be selected from the list provided in the following: https://www.accessdata.fda.gov/scripts/cderhig/index.Cfm?event=browseByLetter.page&Letter=A The pharmaceutical composition is typically formulated to a final concentration of the active biologic (e,g., monoclonal antibody, engineered binding molecule comprising an antigen-binding fragment, etc.) to be between about 2 mg/mL and about 200 mg/mL. For example, the final concentration (wt/vol) of the formulations may range between about 2-200, 2-180, 2-160, 2-150, 2-120, 2-100, 2-80, 2-70, 2-60, 2-50, 2-40, 5-200, 5-180, 5-160, 5-150, 5-120, 5-100, 5-80, 5-70, 5-60, 5-50, 5-40, 10-200, 10-180, 10-160, 10-150, 10-120, 10-100, 10-80, 10-70, 10-60, 10-50, 10-40, 20-200, 20-180, 20-160, 20-150, 20-120, 20-100, 20-80, 20-70, 20-60, 20-50, 20-40, 30-200, 30-180, 30-160, 30-150, 30-120, 30-100, 30-80, 30-70, 30-60, 30-50, 30-40, 40-200, 40-180, 40-160, 40-150, 40-120, 40-100, 40-80, 40-70, 40-60, 40-50, 50-200, 50-180, 50-160, 50-150, 50-120, 50-100, 50-80, 50-70, 50-60, 60-200, 60-180, 60-160, 60-150, 60-120, 60-100, 60-80, 60-70, 70-200, 70-180, 70-160, 70-150, 70-120, 70-100, 70-80 mg/mL. In some embodiments, the final concentration of the biologic in the formulation is about 10, 15, 20, 25, 30, 35, 40, 45, 50, 55, 60, 65, 70, 75, 80, 85, 90, 95, 100, 110, 120, 130, 140, 150, 160, 170, 180, 190, or 200 mg/mL.

According to some embodiments, the TGFβ inhibitor is administered in an amount of about 3000 mg, 2400 mg, 1600 mg, 800 mg, 240 mg, 80 mg, or less.

The pharmaceutical compositions of the present invention are preferably formulated with suitable buffers. Suitable buffers include but are not limited to: phosphate buffer, citric buffer, and histidine buffer.

The final pH of the formulation is typically between pH 5.0 and 8.0. For example, the pH of the pharmaceutical composition may be about 5.0, 5.2, 5.5, 6.0, 6.2, 6.5, 6.8, 7.0, 7.2, 7.4, 7.5, 7.6, or 7.8.

The pharmaceutical composition of the present disclosure may comprise a surfactant, such as nonionic detergent, approved for the use in pharmaceutical formulations. Such surfactants include, for example, polysorbates, such as Polysorbate 20 (Tween-20), Polysorbate 80 (Tween-80) and NP-40.

The pharmaceutical composition of the present disclosure may comprise a stabilizer. For liquid-protein preparations, stability can be enhanced by selection of pH-buffering salts, and often amino acids can also be used. It is often interactions at the liquid/air interface or liquid/solid interface (with the packaging) that lead to aggregation following adsorption and unfolding of the protein. Suitable stabilizers include but are not limited to: sucrose, maltose, sorbitol, as well as certain amino acids such as histidine, glycine, methionine and arginine.

The pharmaceutical composition of the present disclosure may contain one or any combinations of the following excipients: Sodium Phosphate, Arginine, Sucrose, Sodium Chloride, Tromethamine, Mannitol, Benzyl Alcohol, Histidine, Sucrose, Polysorbate 80, Sodium Citrate, Glycine, Polysorbate 20, Trehalose, Poloxamer 188, Methionine, Trehalose, rhHyaluronidase, Sodium Succinate, Potassium Phosphate, Disodium Edetate, Sodium Chloride, Potassium Chloride, Maltose, Histidine Acetate, Sorbitol, Pentetic Acid, Human Serum Albumin, Pentetic Acid.

In some embodiments, the pharmaceutical composition of the present disclosure may contain a preservative.

The pharmaceutical composition of the present disclosure is typically presented as a liquid or a lyophilized form. Typically, the products can be presented in vial (e.g., glass vial). Products available in syringes, pens, or autoinjectors may be presented as pre-filled liquids in these container/closure systems.

In some examples, the pharmaceutical composition described herein comprises liposomes containing an antibody that selectively binds a LTBP1-TGFβ1 complex and/or a LTBP3-TGFβ1 complex, which can be prepared by any suitable method, such as described in Epstein et al., Proc. Natl. Acad. Sci. USA 82:3688 (1985); Hwang et al. Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

In some embodiments, liposomes with targeting properties are selected to preferentially deliver or localize the pharmaceutical composition to certain tissues or cell types. For example, certain nanoparticle-based carriers with bone marrow-targeting properties may be employed, e.g., lipid-based nanoparticles or liposomes. See, for example, Sou (2012) "Advanced drug carriers targeting bone marrow", ResearchGate publication 232725109.

The antibodies that selectively bind a LTBP1-TGFβ1 complex and/or a LTBP3-TGFβ1 complex may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Exemplary techniques have been described previously, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(-)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

Suitable surface-active agents include, in particular, non-ionic agents, such as polyoxyethylenesorbitans (e.g., TWEEEN™ 20, 40, 60, 80 or 85) and other sorbitans (e.g., SPAN™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as INTRALIPID™, LIPSYN™, INFONUTROL™, LIPOFUNDIN™ and LIPIPHYSAN™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%.

The emulsion compositions can be those prepared by mixing an antibody that selectively binds a LTBP1-TGFβ1 complex and/or a LTBP3-TGFβ1 complex with Intralipid™ or the components thereof (soybean oil, egg phospholipids, glycerol and water).

Use of Inhibitors that Selectively Bind a LTBP1/3-TGFβ1 Complex

The inhibitors, e.g., antibodies and antigen-binding portions thereof, described herein that selectively bind a LTBP1/3-TGFβ1 complex can be used in a wide variety of applications in which modulation of TGFβ1 activity associated with LTBP1 or LTBP3 is desired.

In one embodiment, the invention provides a method of inhibiting TGFβ1 activation by exposing a LTBP1-TGFβ1 complex and/or a LTBP3-TGFβ1 complex to an inhibitor, e.g., antibody, or antigen-binding portion thereof, which selectively binds a LTBP1/3-TGFβ1 complex. The foregoing method can be performed in vitro, e.g., to inhibit TGFβ1 activation in cultured cells. The foregoing method can also be performed in vivo, e.g., in a subject in need of TGFβ1 inhibition, or in an animal model in which the effect of TGFβ1 inhibition is to be assessed.

Any inhibitor, e.g., antibody, or antigen-binding portion thereof, described herein which selectively binds a LTBP1-TGFβ1 complex and/or a LTBP3-TGFβ1 complex, and any pharmaceutical composition comprising such antibody, is suitable for use in the methods of the invention. For example, in one embodiment, the inhibitor, e.g., antibody, or antigen-binding portion thereof, selectively binds to a LTBP1-TGFβ1 complex and a LTBP3-TGFβ1 complex, but does not bind to one or more targets selected from LTBP1 alone, mature TGFβ1 alone, a GARP-TGFβ1 complex, a LRRC33-TGFβ1 complex, and combinations thereof. Exemplary inhibitor, e.g., antibodies, can inhibit the release of mature TGFβ1 from a LTBP1-proTGFβ1 complex and/or a LTBP3-proTGFβ1 complex, without inhibiting the release of mature TGFβ1 from a GARP-proTGFβ1 complex and/or a LRRC33-proTGFβ1 complex.

The antibody, or antigen-binding portion thereof, can, in some embodiments, bind a LTBP1-proTGFβ1 complex and/or a LTBP3-proTGFβ1 complex with a dissociation constant ($K_D$) of about $10^{-8}$ M or less. In some embodiments, the antibody, or antigen-binding portion thereof has a $K_D$ value of about $10^{-9}$ M or less. In some embodiments, the antibody, or antigen-binding portion thereof has a $K_D$ value of about $10^{-10}$ M or less (e.g., about $10^{-11}$ M or less). In some embodiments, the antibody, or antigen-binding portion thereof has a $K_D$ value of <10 nM, <5 nM<1 nM) towards a LTBP1-proTGFβ1 complex and/or a LTBP3-proTGFβ1 complex as measured in a suitable in vitro binding assay such as BLI (e.g., Octet). In one embodiment, the antibody, or antigen-binding portion thereof, comprises at least one (e.g., one, two, or three) heavy chain CDRs shown in Table 5, and/or at least one (e.g., one, two, three) light chain CDRs shown in Table 5. In an exemplary embodiment, the antibody, or antigen-binding portion thereof, comprises a heavy chain variable region comprising SEQ ID NO:7, and/or a light chain variable region comprising SEQ ID NO:8. Antibodies and antigen-binding portions thereof which bind the same epitope as the foregoing antibodies, and/or which compete for binding with the foregoing antibodies to LTBP1/3-proTGFβ1, are also useful in the methods described herein. Additional features of the antibodies, or antigen-binding portions thereof, that are suitable for practicing the methods of the invention are described herein.

In one embodiment, contacting a LTBP1-TGFβ1 complex and/or a LTBP3-TGFβ1 complex with the inhibitor, e.g., antibody, or antigen-binding portion thereof, inhibits the release of mature TGFβ1 from the LTBP1-TGFβ1 complex and/or the LTBP3-TGFβ1 complex. In one embodiment, said contacting does not inhibit the release of mature TGFβ1 from presenting molecules other than LTBP1 and LTBP3. For example, exposing a GARP-TGFβ1 complex or a LRRC33-TGFβ1 complex to a context-specific inhibitor, e.g., antibody, that selectively binds LTBP1/3-TGFβ1 but does not bind TGFβ1 in the context of GARP or LRRC33 will not inhibit the release of mature TGFβ1 from the GARP-TGFβ1 complex or the LRRC33-TGFβ1 complex.

LTBP1 and LTBP3 are generally deposited in the extracellular matrix. Accordingly, in one embodiment, complexes comprising LTBP1-TGFβ1 and/or LTBP3-TGFβ1 are associated with the extracellular matrix, e.g., bound to the extracellular matrix. In some embodiments, the LTBP1/3-TGFβ1 complexes are bound to extracellular matrix comprising fibrillin, and/or a protein containing an RGD motif.

The invention also provides a method of reducing TGFβ1 activation in a subject, by administering to the subject an inhibitor, e.g., antibody, or antigen-binding portion thereof, which selectively binds a LTBP1/3-TGFβ1 complex, as described herein. Any antibody, or antigen-binding portion thereof, described herein which selectively binds a LTBP1-TGFβ1 complex and/or a LTBP3-TGFβ1 complex, and any pharmaceutical composition comprising such antibody, is suitable for use in the methods of the invention.

Exemplary LTBP1/3 inhibitors, e.g., antibodies, bind a LTBP1/3-TGFβ1 complex, and inhibit TGFβ1 activation in a context-specific manner, by inhibiting release of TGFβ1 presented by LTBP1 and LTBP3, without inhibiting release of TGFβ1 presented by GARP and/or LRRC33. Such antibodies are useful for blocking a particular subset of TGFβ1 activity in vivo. In one embodiment, the context-specific antibodies provided herein can be used to inhibit TGFβ1 localized to the extracellular matrix. In another embodiment, the context-specific antibodies can inhibit TGFβ1 without modulating TGFβ1-associated immune activity or immune response, which is primarily mediated by TGFβ1 presented by GARP and LRRC33. In another embodiment, the context-specific antibodies can be used to inhibit TGFβ1 activity associated with the extracellular matrix (e.g., LTBP1-associated TGFβ1 activity and LTBP3-associated TGFβ1 activity) without modulating TGFβ1 activity associated with hematopoietic cells, e.g., hematopoietic cells that express GARP and/or LRRC33.

Clinical Applications

Applicant previously described so-called "context-independent" inhibitors of TGFβ1 (see, for example: PCT/US2017/021972 and PCT/US2018/012601) which may be useful for treating various diseases and disorders involving TGFβ1 dysregulation, including, but are not limited to, cancer and fibrosis. Unlike traditional TGFβ1 antagonists, these context-independent TGFβ1 inhibitors are capable of selectively targeting the TGFβ1 isoform. Within the multi-faceted biological functions driven by the TGFβ1 isoform, however, the context-independent inhibitors do not discriminate tissue-specific (thus context-specific) proTGFβ1 complexes, such that such inhibitors are capable of binding and thereby inhibiting release or activation of mature growth factor from any of the presenting molecule-proTGFβ1 complexes.

Based at least in part on the recognition that it may be advantageous to provide even greater selectivity in targeting only a subset of TGFβ activities, context-selective inhibitors of the present disclosure have been generated. It is contemplated that by further narrowing particular biological contexts in which to inhibit TGFβ function, greater safety may be achieved in a subset of disease conditions or patient populations. Specifically, the inventors of the present invention have recognized that in certain conditions, systemic perturbation of immune regulation may be particularly undesirable. Because TGFβ plays an important role in mediating immune response and maintaining immune homeostasis, broad inhibition of TGFβ activities effectuated in a context-independent manner may lead to unwanted side effects without justifiable benefits. In these circumstances, it is envisaged that it is advantageous to specifically target and inhibit matrix-associated TGFβ function using a context-selective inhibitor, such as those encompassed herein, which does not inhibit the immune components of TGFβ1 function.

Accordingly, the context-specific antibodies can be used to inhibit LTBP1/3-associated TGFβ activity in applications in which TGFβ activation in the context of LTBP1 or LTBP3 is desirable, and in which TGFβ activation in the context of GARP and/or or LRRC33 is detrimental.

The disease may involve dysregulation or impairment of ECM components or function and comprises increased collagen deposition. In some embodiments, the dysregulation or impairment of ECM components or function may further comprise increased stiffness and/or ECM reorganization. In some embodiments, the dysregulation or impairment of ECM components or function includes increased myofibroblast cells within the disease site. In some embodiments, the dysregulation of the ECM includes increased stiffness of the matrix, which is implicated in the pathogenesis and/or disease progression of a variety of fibrotic conditions and tumors. In some embodiments, the dysregulation of the ECM involves fibronectin and/or fibrillin.

Rationale for the Development of Matrix-Targeted TGFβ Inhibitors that do not Inhibit GARP-Associated TGFβ

The invention includes context-specific inhibitors of LTBP1-associated and/or LTBP3-associated TGFβ. Such inhibitors therefore are capable of specifically targeting the ECM-associated latent TGFβ complexes (e.g., LTBP1-proTGFβ1 and/or LTBP3-proTGFβ1) thereby inhibiting the release of mature TGFβ growth factor from the latent complex at disease environments, e.g., fibrotic tissues. Such inhibitors show no significant binding activities towards a GARP-proTGFβ1 complex, thereby minimizing unwanted systemic immune modulations. Such antibodies may be advantageous for use in the treatment of conditions with ECM dysregulation, such as abnormal remodeling and/or stiffness of the ECM.

The context-selective antibodies provided herein may be used in the treatment of a condition where it is undesirable to stimulate the subject's immune response and/or in situations where the subject is expected to benefit from a long-term TGFβ inhibition therapy to manage a chronic condition, such as many types of fibrosis.

At least three bases for supporting potential benefits of a TGFβ inhibitor that does not target the GARP-proTGFβ1 complex expressed on regulatory T cells are discussed below.

First, GARP-expressing T regulatory cells are a component of the immune system that suppress or dampen immune responses of other cells. This notion may be referred to as "tolerance." This is an important "self-check" built into the immune system to prevent excessive reactions that in some situations can result in life-threatening conditions, such as sepsis, cytokine release syndrome and cytokine storm. TGFβ inhibition therapies that exert Treg-inhibitory effects may, therefore, pose certain risk when the normal Treg function is impaired, particularly for a prolonged duration of time, e.g., therapeutic regimen involving treatment of six months or longer, and chronic treatment that is administered for an indefinite period of time. For this reason, patients in need of TGFβ inhibition therapies, particularly to avoid the risk of eliciting autoimmunity, may benefit from TGFβ1 inhibitors that do not directly perturb the normal Treg function. For example, patient populations in need of a long-term TGFβ inhibition therapy may include those with genetic or congenital conditions, such as DMD, CF and others. In addition, patient populations that suffer from conditions that include inflammation may benefit from a context-specific inhibitor that does not perturb the GARP/Treg function so as to minimize the risk of exacerbating the existing inflammatory conditions.

Second, increasing evidence points to a link between disproportionate Th17/Treg ratios and pathologies involving inflammation and/or fibrosis. It is generally accepted that the differentiation of the two cell types, Th17 and Treg, is negatively regulated with an inverse relationship. TGFβ1 appears to be a master gatekeeper of this process, such that, TGFβ1 exposure promotes naïve T cells to differentiate into Foxp3+Tregs, whereas TGFβ1 in combination with IL-6, promotes naïve T cells to differentiate into RORγt+Th17 cells instead. In addition, once differentiated, these cell populations negatively regulate each other.

Lines of evidence suggest that an imbalance in Th17/Treg ratios correlates with the pathogenesis and/or progression of fibrotic conditions involving chronic inflammation, or severity thereof.

For example, Shoukry et al. reported that Th17 cytokines drive liver fibrosis by regulating TGFβ signaling. The authors examined ex vivo the frequency of Th17 and Treg populations in liver biopsy samples and found that increased Th17/Treg ratio correlated with advanced fibrosis, as compared to moderate fibrosis or healthy tissue samples. Consistent with the observation, a strong bias towards Th17 cytokines, IL-22 in particular, was also detected in fibrotic livers. These data suggest that increased Th17/Treg ratios lead to an imbalance in pro-fibrotic Th17 cytokines, which correlate with severity of liver fibrosis.

Similar inverse correlations of Th17 and Treg populations are observed in other diseases.

For example, increased muscle expression of IL-17 has been reported in patients with Duchenne muscular dystrophy (DMD), which is a condition that manifests chronic inflammation. De Pasquale et al. (Neurology 78(17): 1309-14) found that DMD muscle biopsy samples contained higher levels of IL-17 (a Th17 marker) and lower levels of Foxp3 (a Treg marker) mRNA compared to control. Elevations in other proinflammatory cytokines, such as TNF-α and MCP-1, were also observed and were found to be associated with worse clinical outcome of patients. The authors concluded that the data point to a possible pathogenic role of IL-17.

Similarly, Jamshidian et al. (J Neuroimmunol 2013, 262 (1-2): 106-12) reported biased Treg/Th17 balance away from regulatory toward inflammatory phenotype in patients with relapsed multiple sclerosis and its correlation with severity of clinical symptoms.

A role of regulatory T cells is also implicated in the pathogenesis of cystic fibrosis (CF). In particular, CF lungs affected by the disease are associated with exaggerated Th17 and Th2 cell responses, indicative of a classic inflammatory phenotype, but also with a deficiency in numbers or function (i.e., impairment) of Treg cells (McGuire (2015) Am J Respir Crit Care Med 191(8): 866-8).

Furthermore, Zhuang et al. (Scientific Reports (2017) 7: 40141) found imbalance of Th17/Treg cells in patients with acute anteir uveitis (anterior segment intraocular inflammation with the positive of human class I major histocompatibility complex), in which both a marked increase in Th17 cells and a marked decrease in Treg cells were seen.

Taken together, the inventors of the present disclosure recognized that what appears to be a common feature in these various diseases associated with elevated Th17/Treg rations is that the patient suffers from a fibrotic condition accompanied by an inflammatory component.

Thus, it is envisaged in the present disclosure that TGFβ inhibition therapy that spares the Treg/GARP-arm of the TGFβ function may be particularly advantageous for an effective treatment of diseases characterized by an elevated level of Th17/Treg ratios. In this way, the context-selective inhibitors of TGFβ according to the invention are aimed to avoid more systemic effects of TGFβ inhibition that may interfere with Treg function, which may lead to exacerbation of existing fibrotic/inflammatory conditions in patients. Thus, the matrix-targeted TGFβ inhibitors described herein are used in a method for treating a patient who has or at risk of developing a fibrotic disorder that comprises inflammation. In some embodiments, the patient has an elevated Th17-to-Treg cell ratio. In some embodiments, the elevated Th17/Treg ratio may be predominantly caused by an increased number of Th17 cells, while in other embodiments, the elevated Th17/Treg ratio may be predominantly caused by a decreased number of Treg cells in the patient (or a biological sample collected from the patient). Yet in further embodiments, the elevated Th17/Treg ratio may be caused by a combination of an increased number of Th17 cells and a decreased number of Treg cells. In some embodiments, elevated levels of IL-17 and/or IL-22 detected in patients (or measured in samples collected from the patients) are also indicative of fibrotic conditions accompanied by chronic inflammation. Such patients may be therefore selected as candidates for receiving a context-selective TGFβ1 inhibitor therapy disclosed herein.

The third line of reasoning for keeping the GARP-TGFβ1 axis intact in a TGFβ inhibition therapy relates to the benefit of maintaining normal Treg function. As mentioned, GARP is expressed on the cell surface of Tregs and are thought to play a role in TGFβ-mediated immunomodulation. Because Tregs are indispensable for immune homeostasis and the prevention of autoimmunity, unnecessary perturbation of which may put certain patient populations at higher risk of, for example, infections (reviewed, for example, by: Richert-Spuhler and Lund (2015) Prog Mol Biol Transl Sci.

The third line of reasoning for keeping the GARP-TGFβ1 axis intact in a TGFβ inhibition therapy is that regulatory T cells function as a "break" to modulate or dampen over-reactive immune response. The discovery of Foxp3 as the master regulator of Treg cell development and function was critical for the understanding of Treg cell biology. Inactivating mutations in Foxp3 result in the spontaneous development of severe autoimmunity with a scurfy phenotype in mice and IPEX syndrome ('immune dysregulation, polyendocrinopathy, enteropathy, X-linked') in humans (see Dominguez-Villear and Haler, Nature Immunology 19, 665-

673, 2018). Thus, it raises the possibility that TGFb1 therapy that elicits inhibitory effects of the Treg/GARP arm of TGFb function, especially in a prolonged treatment, may cause or exacerbate autoimmune response.

Increasing evidence suggests that Tregs not only act to dampen over exuberant effector immune responses, they also have the ability to potentiate appropriate immune responses to pathogens, by participating in pathogen clearance and protection of the host from collateral damage. Such diverse function of Treg cells is particularly apparent in delicate tissues such as the lung, which is constantly exposed to an external environment from which a variety of pathogens and other foreign components (e.g., viral pathogens, bacterial pathogens, fungal pathogens, and allergens) may gain access to host cells.

For example, influenza virus infection elicits a strong proinflammatory cytokine response with abundance immune cell infiltration. In acute and/or severe infections, such response can cause serious sequelae in susceptible individuals. Tregs provide a mechanism for dampening viral infection-associated pathology by controlling the magnitude of immune response in the host. Indeed, pathogen-exposed Tregs retain protective effects in adoptive transfer. Moreover, such adoptive transfer of primed Tregs have been shown to ameliorate influenza virus-associated morbidity and to prolong survival in severe immunocompromised animal models.

Accordingly, the invention provides use of an ECM-targeted, context-selective TGFβ inhibitor (e.g., LTBP1-selective or LTBP1/3-selective inhibitors of TGFβ1 activation inhibitors) for the treatment of a disease that involves matrix-associated TGFβ dysregulation in a subject. The subject is suffering from or at risk of an infection. The infection can be viral infections (e.g., influenza virus, respiratory syncytial virus or RSV, human immunodeficiency virus or HIV, MARS, SARS, herpes simplex virus or HSV, hepatitis A virus or HAV, hepatitis B virus or HBV, hepatitis C virus or HCV, CMV, Dengue virus, lymphocytic choriomeningitis virus, and West Nile virus), bacterial infections (meningitis, *Mycobacterium tuberculosis*, *Listeria monocytogenes*, *Citrobacter rodentium*, *Salmonella*, and *E. coli*), and/or fungal infections (e.g., *Candida*, *Pneumocytis*, *Aspergillus*, *Cryptococcus*, and *Coccidioides*).

Typically, high-risk or at-risk populations (individuals that are considered particularly susceptible to severe infections or infection-triggered responses) include pediatric populations (infants, young children, e.g., human individuals under the age of 7); elderly populations (those who are 65 years or older); those with compromised immune system due to medical condition, health status, life styles such as smoking, and/or medications with immunosuppressive effects, etc.

For example, certain medications cause weakened immunity, such as chemotherapy, therapies that target hematopoietic cells such as CD33 therapy, steroids, immunosuppressants, and statins.

In some embodiments, high-risk or at-risk populations are those with existing medical conditions, such as those with chronic infections such as HIV, those with bone marrow transplantation, pre-diabetic individuals, diabetic individuals, those with autoimmune disorders such as RA, asthma and allergy.

Thus, matrix-targeted, context-selective TGFβ inhibitors encompassed herein may be particularly advantageous for treating patients who require a long-term or chronic TGFβ therapy since in these scenarios it is beneficial to avoid impairment of immune homeostasis and the normal immune function that provides the ability to respond effectively to possible infections caused by a variety of pathogens such as those listed above.

Accordingly, antibodies that selectively bind LTBP-TGFβ (e.g., LTBP1-TGFβ1 and LTBP3-TGFβ31), and that do not inhibit TGFβ in the context of the immune-associated TGFβ presenters GARP and LRRC33, are therapeutic candidates for the treatment of fibrotic indications such as organ fibrosis, and are aimed to avoid TGFβ-related global immune activation. In one embodiment, the context-specific antibodies can be used to inhibit LTBP1/3-associated TGFβ activity in applications in which TGFβ-mediated immune suppression is beneficial, e.g., in a subject who has received a transplant, who is a candidate for receiving a transplant, or who is expected to receive a transplant. In some embodiments, the subject has an advanced stage fibrosis and/or a bone marrow disease. In some embodiments, the subject has or is at risk of developing an autoimmune disorder.

The foregoing methods can be used to treat a subject having a condition for which inhibition or reduction in LTBP-associated TGFβ activity is beneficial. For example, the subject may have or be at risk for developing a disorder in which extracellular matrix-associated TGFβ activity has been implicated.

Integrin-mediated activation of latent TGFβ in the extracellular matrix is a key contributor to fibrosis. Without wishing to be bound by theory, it is presently understood that integrins, including αVβ6 and αVβ8, can trigger the release of TGFβ from presenting molecules including LTBP1 and LTBP3. Inhibiting release or activation of TGFβ in this context can reduce or eliminate fibrosis, and/or symptoms associated therewith.

As described, LTBP1 and LTBP3 are produced and are deposited extracellularly as components of the ECM, where they can "present" a proTGFβ complex (latent, inactive precursor of TGFβ1) within the ECM. Upon stimulation, the LTBP1/3-proTGFβ complex releases the TGFβ growth factor (the active, mature form of growth factor) which in turn is thought to be involved in the regulation of the local tissue microenvironment, such as ECM maintenance/remodeling and the process of fibrosis, possibly by responding to various cytokines, chemokines and growth factors, and by interacting with other ECM components, such as fibronectin, Fibrillin, collagen, elastin, and matrix metallopeptidases (MMPs).

In the normal wound healing process that occurs in response to an injury, for example, TGFβ is thought to facilitate granular tissue formation, angiogenesis, and collagen synthesis and production. TGFβ signaling is also implicated in abnormal tissue fibrogenesis (i.e., fibrosis), which results in formation of excess fibrous connective tissue in an organ or tissue in a reparative or reactive process characterized by the pathological accumulation of extracellular matrix (ECM) components, such as collagens. In these and other situations, the TGFβ axis may affect further aspects (in addition to fibrotic aspect), such as inflammation, recruitment and phenotypic switch of various cell types, which may be mediated by its interaction with one or more of the other presenting molecules, such as GARP/LRRC32 and LRRC33. In certain instances, it is advantageous to preferentially inhibit the LTBP1/3-context of TGFβ activation, without significantly inhibiting one or more of the other contexts of TGFβ1 activation, in situations where ECM-associated TGFβ that drives fibrosis is to be selectively inhibited.

Accordingly, in one embodiment, the invention provides a method of reducing TGFβ activation in a subject having, or at risk of developing, a fibrotic disorder by administering to the subject an antibody, or antigen-binding portion thereof, which selectively binds a LTBP1/3-TGFβ complex, as described herein. In another embodiment, the invention provides a method of treating a fibrotic disorder by administering to the subject an antibody, or antigen-binding portion thereof, which selectively binds a LTBP1/3-TGFβ complex, as described herein.

In one embodiment, the fibrotic disorder is an organ fibrosis, wherein optionally, the organ fibrosis is an advanced organ fibrosis. In a further embodiment, the organ fibrosis is selected from the group consisting of kidney fibrosis, liver fibrosis, lung fibrosis, cardiac fibrosis, pancreatic fibrosis, skin fibrosis, scleroderma, muscle fibrosis, uterine fibrosis and endometriosis. In another further embodiment, the fibrotic disorder comprising chronic inflammation is a muscular dystrophy, multiple sclerosis (MS), or Cystic Fibrosis (CF). In a further embodiment, the muscular dystrophy is Duchenne muscular dystrophy (DMD). In another further embodiment, the MS comprises perivascular fibrosis. In a further embodiment, the lung fibrosis is idiopathic pulmonary fibrosis (IPF). In another further embodiment, the subject has chronic kidney disease (CKD). In another embodiment, the subject has nonalcoholic steatohepatitis (NASH).

In exemplary embodiments, the fibrotic disorder is fibrosis, Alport syndrome, fibroids, desmoplasia, amyotrophic lateral sclerosis (ALS), or Duchenne muscular dystrophy (DMD).

In one embodiment, the subject has desmoplasia.

In one embodiment, the subject has organ fibrosis, for example, kidney fibrosis (e.g., fibrosis associated with chronic kidney disease (CKD)), liver fibrosis (e.g., fibrosis associated with nonalcoholic steatohepatitis (NASH)), lung fibrosis (e.g., idiopathic pulmonary fibrosis (IPF)), cardiac fibrosis, and/or skin fibrosis (e.g., scleroderma). In some embodiments, the subject can have advanced organ fibrosis. For example, the subject may be in need of an organ transplant. In one embodiment, the subject may be in need of an organ transplant, and the compounds and compositions described herein are administered to prevent allograft fibrosis from developing in the subject following receipt of the transplant.

A recent study examined whether inhibiting integrin αVβ6 could prevent TGFβ-mediated allograft fibrosis after kidney transplantation (Lo et al., Am. J. Transplant. (2013), 13:3085-3093). Surprisingly, animals treated with an inhibitory anti-αVβ6 antibody experienced a significant decrease in rejection-free survival compared to placebo animals. The authors conclude that this result cautions against TGFβ inhibition in kidney transplantation, because the immunosuppressive properties of TGFβ help prevent allograft rejection. The inhibitors, e.g., antibodies, and antigen-binding portions thereof, described herein advantageously inhibit activation of TGFβ presented by LTBP1 or LTBP3 in the extracellular matrix, but do not inhibit activation of TGFβ presented by GARP or LRRC33 on immune cells. Accordingly, the context-specific LTBP1/3-TGFβ inhibitors, e.g., antibodies, described herein can prevent or reduce allograft fibrosis, without eliminating the immunosuppressive properties of TGFβ that are useful for preventing allograft rejection. Accordingly, in one aspect, the invention provides a method for treating a fibrotic disorder in a subject, comprising administering to the subject a therapeutically effective amount of an inhibitor of TGFβ signaling, wherein the inhibitor is a selective inhibitor of ECM-associated TGFβ; and, wherein the subject benefits from suppressed immunity.

In one embodiment, the subject has a fibrotic condition and would benefit from an allograft transplant, or has received an allograft transplant.

Additional fibrotic conditions for which antibodies and/or compositions of the present disclosure may be used therapeutically include, but are not limited to, lung indications (e.g., idiopathic pulmonary fibrosis (IPF), chronic obstructive pulmonary disorder (COPD), allergic asthma, cystic fibrosis (CF), acute lung injury, eosinophilic esophagitis, pulmonary arterial hypertension and chemical gas-injury), kidney indications (e.g., diabetic glomerulosclerosis, focal segmental glomeruloclerosis (FSGS), chronic kidney disease, fibrosis associated with kidney transplantation and chronic rejection, IgA nephropathy, and hemolytic uremic syndrome), liver fibrosis (e.g., non-alcoholic steatohepatitis (NASH), chronic viral hepatitis, parasitemia, inborn errors of metabolism, toxin-mediated fibrosis, such as alcohol fibrosis, non-alcoholic steatohepatitis-hepatocellular carcinoma (NASH-HCC), primary biliary cirrhosis, and sclerosing cholangitis), cardiovascular fibrosis (e.g., cardiomyopathy, hypertrophic cardiomyopathy, atherosclerosis and restenosis,) systemic sclerosis, skin fibrosis (e.g., skin fibrosis in systemic sclerosis, diffuse cutaneous systemic sclerosis, scleroderma, pathological skin scarring, keloid, post-surgical scarring, scar revision surgery, radiation-induced scarring and chronic wounds), eye-related conditions such as subretinal fibrosis, uveitis syndrome, uveitis associated with idiopathic retroperitoneal fibrosis, extraocular muscle fibrosis, eye diseases associated with the major histocompatibility complex (MHC class I) or histocompatibility antigens, subretinal fibrosis in macular degeneration (e.g., age-related macular degeneration) and cancers or secondary fibrosis (e.g., myelofibrosis, head and neck cancer, M7 acute megakaryoblastic leukemia and mucositis). Other diseases, disorders or conditions related to fibrosis that may be treated using compounds and/or compositions of the present disclosure, include, but are not limited to Marfan's syndrome, stiff skin syndrome, scleroderma, rheumatoid arthritis, bone marrow fibrosis, Crohn's disease, ulcerative colitis, systemic lupus erythematosus, muscular dystrophy, (such as DMD), Dupuytren's contracture, Camurati-Engelmann disease, neural scarring, dementia, proliferative vitreoretinopathy, corneal injury, complications after glaucoma drainage surgery, and multiple sclerosis (MS). Many such fibrotic indications are also associated with inflammation of the affected tissue(s), indicating involvement of an immune component. Such inflammation may be accompanied by aberrant immune cell populations, such as increased numbers of Th17 cells, reduced numbers of Treg cells, and/or both. In each case, the affected patient may exhibit increased Th17/Treg cell ratios. In some embodiments, diseases to be treated with an antibody according to the present disclosure include metabolic disorders, such as metabolic liver disorders. Non-limiting examples of metabolic disorders include NASH, NAFLD, type 2 diabetes and obesity. In some embodiments, the disease to be treated with an antibody according to the present disclosure is aortic stenosis.

In another aspect, the invention provides a method of selecting an isoform-specific TGFβ1 inhibitor for the treatment of a fibrotic disorder in a subject, comprising: (a) determining whether the subject manifests clinical presentations including fibrosis and one or more of the following: (i) inflammation; (ii) immune suppression; (iii) proliferative dysregulation; (iv) need for an allograft transplant; (v) at risk of severe infection; (vi) in need of a long-term TGFβ1 inhibition therapy; and (vii) manifestation of an autoimmune conditions(s); and (b) selecting an isoform-specific, context-dependent TGFβ1 inhibitor or an isoform-specific, context-independent TGFβ1 inhibitor for treatment of the fibrotic disorder based on the clinical presentations determined in step (a).

In another aspect, the invention provides a method of treating a subject having a fibrotic disorder, comprising (a) selecting a treatment regimen comprising an isoform-specific TGFβ1 inhibitor for the subject, said selection comprising (i) determining whether the fibrotic disorder manifests clinical presentations including fibrosis and one or more of the following: inflammation, immune suppression, proliferative dysregulation, and need for an allograft transplant; and (ii) selecting a treatment regimen comprising an isoform-specific, context-dependent TGFβ1 inhibitor or an isoform-specific, context-independent TGFβ1 inhibitor, based on the clinical presentations determined in step (i); and (b) administering the selected treatment regimen to the subject.

In one embodiment of the foregoing aspects, the fibrotic disorder manifests clinical presentations comprising fibrosis, inflammation, immune suppression, and proliferative dysregulation. In an exemplary embodiment, the fibrotic disorder is myelofibrosis, and the selected isoform-specific TGFβ1 inhibitor is an isoform-specific, context-independent TGFβ1 inhibitor.

In another embodiment, the fibrotic disorder manifests clinical presentations comprising fibrosis, inflammation, and need for an allograft transplant. In one embodiment, the fibrotic disorder manifests clinical presentations comprising fibrosis and inflammation. In another embodiment, the fibrotic disorder is a degenerative disease.

In one embodiment, the fibrotic disorder manifests clinical presentations comprising immune suppression and proliferative dysregulation. In an exemplary embodiment, the fibrotic disorder is associated with a solid tumor, and the selected isoform-specific TGFβ1 inhibitor is an isoform-specific LTBP1/3-specific inhibitor and/or a GARP-selective inhibitor. In one embodiment, the solid tumor is a malignant tumor. In another embodiment, the tumor is a benign tumor. In one embodiment, the subject has desmoplasia, for example, pancreatic desmoplasia. In another embodiment, the subject has fibroids.

In another aspect, the invention provides a method of treating a subject having a fibrotic disorder with an isoform-specific, LTBP1/3-specific TGFβ1 inhibitor, comprising determining whether the fibrotic disorder manifests clinical presentations including fibrosis and the need for an allograft transplant; and administering an effective amount of an isoform-specific, LTBP1/3-specific TGFβ1 inhibitor to the subject if the fibrotic disorder manifests fibrosis and the need for an allograft transplant.

In another aspect, the invention provides a method of treating a subject having a fibrotic disorder with an isoform-specific, context-independent TGFβ1 inhibitor, comprising determining whether the fibrotic disorder manifests clinical presentations including fibrosis, immune suppression and/or proliferative dysregulation; and administering an effective amount of an isoform-specific, context-independent TGFβ1 inhibitor to the subject if the fibrotic disorder manifests fibrosis in conjunction with immune suppression and/or proliferative dysregulation.

The inhibitors, e.g., antibodies, described herein can be administered to a subject in an amount effective to treat or reduce symptoms of fibrosis. The effective amount of such an inhibitor is an amount effective to achieve both therapeutic efficacy and clinical safety in the subject. In one embodiment, an effective amount is an amount effective to reduce TGFβ1 activity in the extracellular matrix. In another embodiment, an effective amount is an amount effective to reduce fibrosis in a subject. In another embodiment, the effective amount does not inhibit TGFβ1-mediated immune suppression. In some embodiments, such an inhibitor, e.g., antibody, is a context-specific inhibitor that can block activation of TGFβ1 that is mediated by an LTBP-containing, ECM-associated TGFβ1. In some embodiments, the LTBP is LTBP1 and/or LTBP3. Assays useful for determining the efficacy of the inhibitors, e.g., antibodies, and/or compositions of the present disclosure for the alteration of fibrosis include, but are not limited to, histological assays for counting fibroblasts and basic immunohistochemical analyses known in the art.

Diseases Involving Proteases:

Activation of TGFβ from its latent complex may be triggered by integrin in a force-dependent manner, and/or by proteases. Evidence suggests that certain classes of proteases may be involved in the process, including but are not limited to Ser/Thr proteases such as thrombin, Kallikreins, chemotrypsin, elastases, plasmin, as well as zinc metalloproteases of ADAM family such as ADAM 10 and ADAM 17, as well as MMP family, such as MMP-2, MMP-9 and MMP-13. MMP-2 degrades the most abundant component of the basement membrane, Collagen IV, raising the possibility that it may play a role in ECM-associated TGFβ1 regulation. MMP-9 has been implicated to play a central role in tumor progression, angiogenesis, stromal remodeling and metastasis. Thus, protease-dependent activation of TGFβ1 in the ECM may be important for treating cancer.

Kallikreins (KLKs) are trypsin- or chymotrypsin-like serine proteases that include plasma Kallikreins and tissue Kallikreins. The ECM plays a role in tissue homeostasis acting as a structural and signaling scaffold and barrier to suppress malignant outgrowth. KLKs may play a role in degrading ECM proteins and other components which may facilitate tumor expansion and invasion. For example, KLK1 is highly upregulated in certain breast cancers and can activate pro-MMP-2 and pro-MMP-9. KLK2 activates latent TGFβ1, rendering prostate cancer adjacent to fibroblasts permissive to cancer growth. KLK3 has been widely studied as a diagnostic marker for prostate cancer (PSA). KLK3 may directly activate TGFβ1 by processing plasminogen into plasmin, which proteolytically cleaves LAP. KLK6 may be a potential marker for Alzheimer's disease.

Known activators of TGFβ1, such as plasmin, TSP-1 and αVβ6 integrin, all interact directly with LAP. It is postulated that proteolytic cleavage of LAP may destabilize the LAP-TGFβ interaction, thereby releasing active TGFβ1. It has been suggested that the region containing 54-LSKLRL-59 (SEQ ID NO: 388) is important for maintaining TGFβ1 latency. Thus, agents (e.g., antibodies) that stabilize the interaction, or block the proteolytic cleavage of LAP may prevent TGFβ activation.

Many of these proteases associated with pathological conditions (e.g., cancer) function through distinct mechanisms of action. Thus, targeted inhibition of particular proteases, or combinations of proteases, may provide therapeutic benefits for the treatment of conditions involving the protease-TGFβ axis. Accordingly, it is contemplated that inhibitors (e.g., TGFβ1 antibodies) that selectively inhibit protease-induced activation of TGFβ1 may be advantageous in the treatment of such diseases (e.g., cancer). Similarly, selective inhibition of TGFβ1 activation by one protease over another protease may also be preferred, depending on the condition being treated.

Plasmin is a serine protease produced as a precursor form called Plasminogen. Upon release, Plasmin enters circulation and therefore is detected in serum. Elevated levels of Plasmin appear to correlate with cancer progression, possibly through mechanisms involving disruption of the extracellular matrix (e.g., basement membrane and stromal barriers) which facilitates tumor cell motility, invasion, and metastasis. Plasmin may also affect adhesion, proliferation, apoptosis, cancer nutrition, oxygen supply, formation of blood vessels, and activation of VEGF (Didiasova et al., *Int. J. Mol. Sci*, 2014, 15, 21229-21252). In addition, Plasmin may promote the migration of macrophages into the tumor microenvironment (Philips et al., *Cancer Res.* 2011 Nov. 1; 71(21):6676-83 and Choong et al., *Clin. Orthop. Relat. Res.* 2003, 415S, S46-S58). Indeed, tumor-associated macrophages (TAMs) are well characterized drivers of tumorigenesis through their ability to promote tumor growth, invasion, metastasis, and angiogenesis.

Plasmin activities have been primarily tied to the disruption of the ECM. However, there is mounting evidence that Plasmin also regulate downstream MMP and TGF beta activation. Specifically, Plasmin has been suggested to cause activation of TGF beta through proteolytic cleavage of the Latency Associated Peptide (LAP), which is derived from the N-terminal region of the TGF beta gene product (Horiguchi et al., *J Biochem.* 2012 October; 152(4):321-9), resulting in the release of active growth factor. Since TGFβ1 may promote cancer progression, this raises the possibility that plasmin-induced activation of TGFb may at least in part mediate this process.

TGFβ1 has also been shown to regulate expression of uPA, which is a critical player in the conversion of Plasminogen into Plasmin (Santibanez, Juan F., *ISRN Dermatology*, 2013: 597927). uPA has independently been shown to promote cancer progression (e.g., adhesion, proliferation, and migration) by binding to its cell surface receptor (uPAR) and promoting conversion of Plasminogen into Plasmin. Moreover, studies have shown that expression of uPA and/or plasminogen activator inhibitor-1 (PAI-1) are predictors of poor prognosis in colorectal cancer (D. Q. Seetoo, et al., *Journal of Surgical Oncology*, vol. 82, no. 3, pp. 184-193, 2003), breast cancer (N. Harbeck et al., *Clinical Breast Cancer*, vol. 5, no. 5, pp. 348-352, 2004), and skin cancer (Santibanez, Juan F., *ISRN Dermatology*, 2013: 597927). Thus, without wishing to be bound by a particular theory, the interplay between Plasmin, TGFβ1, and uPA may create a positive feedback loop towards promoting cancer progression. Accordingly, inhibitors that selectively inhibit Plasmin-dependent TGFβ1 activation may be particularly suitable for the treatment of cancers reliant on the Plasmin/TGFβ1 signaling axis.

In one aspect of the invention, the isoform-specific inhibitors of TGFβ1 described herein include inhibitors that can inhibit protease-dependent activation of TGFβ1. In some embodiments, the inhibitors can inhibit protease-dependent TGFβ1 activation in an integrin-independent manner. In some embodiments, such inhibitors can inhibit TGFβ1 activation irrespective of the mode of activation, e.g., inhibit both integrin-dependent activation and protease-dependent activation of TGFβ1. In some embodiments, the protease is selected from the group consisting of: serine proteases, such as Kallikreins, Chemotrypsin, Trypsin, Elastases, Plasmin, as well as zinc metalloproteases (MMP family) such as MMP-2, MMP-9 and MMP-13.

In some embodiments, the inhibitors can inhibit Plasmin-induced activation of TGFβ1. In some embodiments, the inhibitors can inhibit Plasmin- and integrin-induced TGFβ1 activation. In some embodiments, the inhibitors are monoclonal antibodies that specifically bind TGFβ1. In some embodiments, the antibody is a monoclonal antibody that specifically binds proTGFβ1. In some embodiments, the antibody binds latent proTGFβ1 thereby inhibiting release of mature growth factor from the latent complex. In some embodiments, the high-affinity, LTBP-complex specific inhibitor of TGFβ1 activation suitable for use in the method of inhibiting Plasmin-dependent activation of TGFβ1. In some embodiments, the LTBP-complex specific inhibitor of TGFβ1 activation is selected from Ab31, Ab34, Ab37, Ab38, Ab39, Ab40, Ab41, Ab42, Ab43, Ab44, Ab45, Ab62, Ab63, and Ab64 (optionally Ab42 or Ab63) (i.e., an antibody or antigen-binding fragment having the heavy and light chain variable regions of the corresponding Ab, as provided herein) a variant/derivative or antigen-binding fragment thereof thereof, or an engineered molecule comprising an antigen-binding fragment thereof. In some preferred embodiments, the LTBP-complex specific inhibitor of TGFβ1 activation is Ab42, a variant/derivative or antigen-binding fragment thereof, or an engineered molecule comprising an antigen-binding fragment thereof. In preferred embodiments, the LTBP-complex specific inhibitor of TGFβ1 activation is Ab42 or an antigen-binding fragment thereof.

In some embodiments, the inhibitor (e.g., TGFβ1 antibody) inhibits cancer cell migration. In some embodiments, the inhibitor inhibits macrophage migration. In some embodiments, the inhibitor inhibits accumulation of TAMs.

In another aspect, provided herein is a method for treating cancer in a subject in need thereof, the method comprising administering to the subject an effective amount of an TGFβ1 inhibitor (e.g., TGFβ1 antibody), wherein the inhibitor inhibits protease-induced activation of TGFβ1 (e.g., Plasmin), thereby treating cancer in the subject.

In another aspect, provided herein is a method of reducing tumor growth in a subject in need thereof, the method comprising administering to the subject an effective amount of an TGFβ1 inhibitor (e.g., TGFβ1 antibody), wherein the inhibitor inhibits protease-induced activation of TGFβ1 (e.g., Plasmin), thereby reducing tumor growth in the subject.

Disease Involving ECM Dysregulation

The extracellular matrix is a cell-secreted network that surrounds cells and is primarily composed of proteoglycans and fibrous proteins, the most abundant of which is collagen. The novel antibodies disclosed herein may be used in the treatment of diseases associated with extracellular matrix dysregulation. The diseases associated with extracellular matrix dysregulation are typically myofibroblast-driven pathologies and include cancer, fibrosis, and cardiovascular disease (reviewed, for example, in: Lampi and Reinhart-King (2018) "Targeting extracellular matrix stiffness to attenuate disease: From molecular mechanisms to clinical trials" Sci Tarnsl Med 10(422): eaao0475). Progression of fibrotic conditions involves increased levels of matrix components deposited into the ECM and/or maintenance/remodeling of the ECM. TGFβ1 at least in part contributes to this process. This is supported, for example, by the observation that increased deposition of ECM components such as collagens can alter the mechanophysical properties of the ECM (e.g., the stiffness of the matrix/substrate) and this phenomenon is associated with TGFβ1 signaling. The inhibitors of TGFβ1, such as those described herein may be used to block this process to counter disease progression involving ECM alterations, such as fibrosis. The LTBP-arm of such inhibitors can directly block ECM-associated pro/ latent TGFβ3 complexes which are presented by LTBP1 and/or LTBP3, thereby preventing activation/release of the growth factor from the complex in the disease niche. In some embodiments, the isoform-specific TGFβ1 inhibitors such as those described herein may normalize ECM stiffness to treat a disease that involves integrin-dependent signaling. In some embodiments, the integrin comprises an aII chain, β1 chain, or both.

Thus, the antibody may be administered to a subject diagnosed with a disease with extracellular matrix dysregulation in an amount effective to treat the disease. Therapeutically effective amount of the antibody may be an amount sufficient to reduce expression of one or more markers of myofibroblasts, such as α-SMA. The amount may be an amount sufficient to reduce the stiffness of the extracellular matrix of an affected tissue (e.g., fibrotic tissues). The amount may be an amount sufficient to reduce TGFβ1 downstream effectors, such as phosphorylation of SMAD2 and/or SMAD3. In some embodiments, the isoform-selective activation inhibitor of TGFβ1 is selected from Ab31, Ab34, Ab37, Ab38, Ab39, Ab40, Ab41, Ab42, Ab43, Ab44, Ab45, Ab62, Ab63, and Ab64 (optionally Ab42 or Ab63) a variant/derivative or antigen-binding fragment thereof thereof, or an engineered molecule comprising an antigen-binding fragment thereof. In some preferred embodiments, the isoform-selective activation inhibitor of TGFβ1 is Ab42, a variant/derivative or antigen-binding fragment thereof, or an engineered molecule comprising an antigen-binding fragment thereof. In preferred embodiments, the TGFβ1-selective inhibitor is Ab42 or an antigen-binding fragment thereof.

Diseases Involving Epithelial-to-Mesenchymal Transition (EMT):

EMT (epithelial mesenchymal transition) is the process by which epithelial cells with tight junctions switch to mesenchymal properties (phenotypes) such as loose cell-cell contacts. The process is observed in a number of normal biological processes as well as pathological situations, including embryogenesis, wound healing, cancer metastasis and fibrosis (reviewed in, for example, Shiga et al. (2015) "Cancer-Associated Fibroblasts: Their Characteristics and Their Roles in Tumor Growth." Cancers, 7: 2443-2458). Generally, it is believed that EMT signals are induced mainly by TGFβ. Many types of cancer, for example, appear to involve transdifferentiation of cells towards mesenchymal phenotype (such as CAFs) which correlate with poorer prognosis. Thus, LTBP-specific inhibitors of TGFβ1, such as those described herein, may be used to treat a disease that is initiated or driven by EMT. Indeed, data exemplified herein (e.g., FIGS. 12 and 13) show that such inhibitors have the ability to suppress expression of CAF markers in vivo, such as α-SMA, Col1 (Type I collagen), and FN (fibronectin).

Diseases Involving Matrix Stiffening and Remodeling

Progression of fibrotic conditions involves increased levels of matrix components deposited into the ECM and/or maintenance/remodeling of the ECM. TGFβ1 at least in part contributes to this process. This is supported, for example, by the observation that increased deposition of ECM components such as collagens can alter the mechanophysical properties of the ECM (e.g., the stiffness of the matrix/substrate) and this phenomenon is associated with TGFβ1 signaling. To confirm this notion, the present inventors have evaluated the role of matrix stiffness in affecting integrin-dependent activation of TGFβ in primary fibroblasts transfected with proTGFβ and LTBP1, and grown on silicon-based substrates with defined stiffness (e.g., 5 kPa, 15 kPa or 100 kPa). Matrices with greater stiffness enhance TGFβ1 activation, and this can be suppressed by antibodies, and antigen-binding portions thereof, which are capable of binding and thereby inhibiting TGFβ1 activation associated with LTBP1/3. These observations suggest that TGFβ1 influences ECM properties (such as stiffness), which in turn can further induce TGFβ1 activation, reflective of disease progression. Thus, antibodies, and antigen-binding portions thereof, that selectively bind complexes of LTBP1-TGFβ1 and/or LTBP3-TGFβ1, such as those described herein may be used to block this process to counter disease progression involving ECM alterations, such as fibrosis, tumor growth, invasion, metastasis and desmoplasia. Such inhibitors can directly block ECM-associated pro/latent TGFβ complexes which are presented by LTBP1 and/or LTBP3, thereby preventing activation/release of the growth factor from the complex in the disease niche.

Fibrosis:

In response to tissue injury or chronic insult due to physical damage/trauma, toxic substances, and/or infection, a natural reparative process begins which involves several cell types including fibroblasts, several different types of immune cells, and resident epithelial and endothelial cells. However, if left unchecked, this process can lead to excessive accumulation of extracellular matrix (ECM) and fibrosis, which in turn can lead to progressive loss of tissue function and organ failure (Caja et al., *Int. J. Mol. Sci.* 2018, 19, 1294).

Fibrosis can occur in several different organs, including lung, kidney, liver, heart, and skin. Independent of the organ, the fibrotic response is characterized by inflammation, altered epithelial-mesenchymal interactions, and proliferation of fibroblasts. One of the hallmarks of fibrosis is the differentiation of fibroblasts into myofibroblasts, which greatly contribute to the dysregulation of the ECM. However, myofibroblasts have also been proposed to come from other cellular sources (e.g., endothelial cells, epithelial cells, and mesenchymal stem cells (Kim, K K et al, Cold Spring Harb. Perspect. Biol., 2017; Okabe, H. Histol. Histophathol., 2016, 31, 141-148; and Li, C et al, Nat Commun., 2016, 7, 11455). Moreover, immune cells play an important role in the process by secreting cytokines and chemokines which promote differentiation of myofibroblasts, stimulate ECM deposition, and recruit additional immune cells to the damaged tissue (Caj a et al., *Int. J. Mol. Sci.* 2018, 19, 1294).

Similar to fibrotic tissue, activation of cancer-associated fibroblasts can occur in the tumor milieu, which produces excessive amounts of ECM. The ECM provides a scaffold for the infiltration of other cells (e.g., pro-tumorigenic immune cells) and a substrate for cell migration. In other cases, excessive ECM may act as a barrier against anti-tumorigenic immune cells.

TGFβ is recognized as the central orchestrator of the fibrotic response. TGFβ can promote myofibroblast differentiation, recruit immune cells, and affect epithelial and endothelial cell differentiation. Particularly, TGFβ upregulates the production of ECM and basement membrane proteins, such as fibronectin, collagen, laminin, osteopontin, tenascin, elastin, decorin. TGFβ-induced myofibroblast differentiation can lead to additional deposition of ECM proteins, secretion of matric metalloproteinase (MMPs), and myofibroblast proliferation (Fabregat et al, FEBS J. 2016, 283, 2219-2232; Meng et al, Nat. Rev. Nephrol. 2016, 12, 325-338; and Kulkarni et al., Am. J. Respir. Cell Mol. Biol., 2016, 54, 751-760). Additionally, TGFβ mediates phenotypic changes affecting contractile proteins and collagen I in vascular smooth muscle cells (VSCM), and can activate myofibroblasts and other stromal cells to enhance the synthesis of collagen cross-linking proteins, such as lysyl oxidase (LOX) family of matrix-remodeling enzymes (Busnadiego et al., Mol. Cell. Biol. 2013, 33, 2388-2401). Moreover, TGFβ has been shown to regulate both EMT and EndMT, which contributes to the differentiation of pro-fibrotic cell types, such as myofibroblasts and CAFs. Moreover, TGFβ has been shown to induce epithelial apoptosis, which can promote lung and liver fibrosis among other tissues (Barbas-Filho et al., J. Clin. Pathol. 2001, 54, 132-138; and Wang et al., Dev. Dyn. 2017, 247, 492-508).

Whether innate or recruited, macrophages are thought to play an important role in responding to tissue damage and repair. However, upon certain signals they can become pro-fibrotic. TGFβ, among other cytokines, has also been shown to activate M2 macrophages, which are pro-inflammatory. Upon activation, these macrophages secrete their own cytokines, including TGFβ, ECM components, angiogenic factors, and chemotactic factors. M2 macrophages have been shown to be essential for TGFβ-driven lung fibrosis (Murray et al., Int. J. Biochem. Cell Biol. 2011, 43, 154-162).

In light of increasing evidence pointing to the importance of M2-type macrophages for diseases progression in many types of fibrosis, a question remained as to whether context-selective inhibition of LTBP1/3-associated TGFβ1 alone (that is, without addressing the macrophage-associated, LRRC33-arm of TGFβ1 activity) might be sufficient to produce a potent anti-fibrotic effect in vivo. Surprisingly, however, data presented herein suggest that selectively targeting the matrix-associated TGFβ1 (e.g., LTBP1/3-proTGFβ31) appears to be just as effective—if not better—in achieving anti-fibrotic effects in multiple preclinical models, as targeting all four known LLCs (e.g., LTBP1/3-proTGFβ1, GARP-proTGFβ1 and LRRC33-proTGFβ1) with the use of a so-called context-independent inhibitor of TGFβ1 (see, for example, FIGS. 19 and 20) and do so without triggering T cell stimulation mediated via GARP-proTGFβ1 inhibition. Moreover, previously disclosed LTBP1/3 complex-selective antibodies lacked robust species cross-reactivity that would be advantageous for both preclinical (e.g., rodent) and clinical (e.g., human) use. It was not clear whether the rare epitopes being sought which would confer both isoform-selectivity and context-selectivity would also enable favorable species cross-reactivity profiles. Advantageously, novel antibodies disclosed herein possess all of these criteria.

According to the invention, isoform-specific TGFβ1 such as those described herein are used in the treatment of fibrosis (e.g., fibrotic indications, fibrotic conditions) in a subject. Suitable inhibitors to carry out the present invention include antibodies and/or compositions according to the present disclosure which may be useful for altering or ameliorating fibrosis. More specifically, such antibodies and/or compositions are selective antagonists of TGFβ1 that are capable of targeting TGFβ1 presented by various types of presenting molecules. TGFβ1 is recognized as the central orchestrator of the fibrotic response. Antibodies targeting TGFβ decrease fibrosis in numerous preclinical models. Such antibodies and/or antibody-based compounds include LY2382770 (Eli Lilly, Indianapolis, IN). Also included are those described in U.S. Pat. Nos. 6,492,497, 7,151,169, 7,723,486 and U.S. Appl. Publ. No. 2011/0008364, the contents of each of which are herein incorporated by reference in their entirety. Prior art TGFβ antagonists include, for example, agents that target and block integrin-dependent activation of TGFβ.

However, evidence suggests that such prior art agents may not mediate isoform-specific inhibition and may cause unwanted effects by inadvertently blocking normal function of TGFβ2 and/or TGFβ3. Indeed, data presented herein support this notion. Normal (undiseased) lung tissues contain relatively low but measurable levels of TGFβ2 and TGFβ3, but notably less TGFβ1. In comparison, in certain disease conditions such as fibrosis, TGFβ1 becomes preferentially upregulated relative to the other isoforms. Preferably, TGFβ antagonists for use in the treatment of such conditions exert their inhibitory activities only towards the disease-induced or disease-associated isoform, while preserving the function of the other isoforms that are normally expressed to mediate tonic signaling in the tissue. Prior art inhibitors (LY2109761, a small molecule TGFβ receptor antagonist, and a monoclonal antibody that targets αVβ6 integrin) both are shown to inhibit TGFβ downstream tonic signaling in non-diseased rat BAL, raising the possibility that these inhibitors may cause unwanted side effects. Alternatively or additionally, agents that target and block integrin-dependent activation of TGFβ may be capable of blocking only a subset of integrins responsible for disease-associated TGFβ1 activation, among numerous integrin types that are expressed by various cell types and play a role in the pathogenesis. Furthermore, even where such antagonists may selectively block integrin-mediated activation of the TGFβ1 isoform, it may be ineffective in blocking TGFβ1 activation triggered by other modes, such as protease-dependent activation. Accordingly, the isoform-specific inhibitors of TGFβ1 such as those described herein are aimed to prevent the activation step of TGFβ1 regardless of the particular mode of activation, while maintaining isoform selectivity.

It is further contemplated that isoform-specific TGFβ1 inhibitors that preferentially inhibit matrix-associated over cell-associated antigen complexes (i.e., display context-bias) may offer a therapeutic advantage in certain clinical situations (e.g., the LTBP-specific inhibitors described herein). For example, TGFβ1 context-independent inhibitors (which target all four antigen complexes), may increase immune activation through the targeting of cell-associated TGFβ1 (e.g., GARP-TGFβ1 which is expressed on regulatory T cells) Immune activation may be disadvantageous for certain patients, e.g., patients with autoimmune disease or who are at risk of sepsis. Accordingly, context-bias antibodies may be useful for treating diseases associate with matrix-associated TGFβ1 complexes (e.g., fibrosis), while minimizing immune activation.

Previously, it was contemplated that isoform-specific TGFβ3 inhibitors might offer an added therapeutic benefit in particular disease states. For example, certain fibrotic diseases to be treated with a TGFβ1 inhibitor may also be TGFβ3-positive (i.e., TGFβ31+/TGFβ3+fibrotic tissue) characterized in that the disease tissue (e.g., fibrotic tissue) expresses both the isoforms. Accordingly, the invention includes the use of isoform-selective TGFβ1 inhibitor in conjunction with an isoform-selective TGFβ3 inhibitor in the treatment of such conditions.

Fibrotic indications for which antibodies and/or compositions of the present disclosure may be used therapeutically include, but are not limited to lung indications (e.g., idiopathic pulmonary fibrosis (IPF), chronic obstructive pulmonary disorder (COPD), allergic asthma, acute lung injury, eosinophilic esophagitis, pulmonary arterial hypertension and chemical gas-injury), kidney indications (e.g., diabetic glomerulosclerosis, focal segmental glomeruloclerosis (FSGS), chronic kidney disease (CKD), fibrosis associated with kidney transplantation and chronic rejection, IgA nephropathy, and hemolytic uremic syndrome), liver fibrosis (e.g., non-alcoholic steatohepatitis (NASH), chronic viral hepatitis, parasitemia, inborn errors of metabolism, toxin-mediated fibrosis, such as alcohol fibrosis, non-alcoholic steatohepatitis-hepatocellular carcinoma (NASH-HCC), primary biliary cirrhosis, and sclerosing cholangitis), cardiovascular fibrosis (e.g., cardiomyopathy, hypertrophic cardiomyopathy, atherosclerosis and restenosis,) systemic sclerosis, skin fibrosis (e.g., skin fibrosis in systemic sclerosis, diffuse cutaneous systemic sclerosis, scleroderma, pathological skin scarring, keloid, post-surgical scarring, scar revision surgery, radiation-induced scarring and chronic wounds), eye-related conditions such as subretinal fibrosis, uveitis syndrome, uveitis associated with idiopathic retroperitoneal fibrosis, extraocular muscle fibrosis, eye diseases associated with the major histocompatibility complex (MHC class I) or histocompatibility antigens, subretinal fibrosis in macular degeneration (e.g., age-related macular degeneration), and cancers or secondary fibrosis (e.g., myelofibrosis, head and neck cancer, M7 acute megakaryoblastic leukemia and mucositis). Other diseases, disorders or conditions related to fibrosis (including degenerative disorders) that may be treated using compounds and/or compositions of the present disclosure, include, but are not limited to adenomyosis, endometriosis, Marfan's syndrome, stiff skin syndrome, scleroderma, rheumatoid arthritis, bone marrow fibrosis, Crohn's disease, ulcerative colitis, systemic lupus erythematosus, muscular dystrophy (such as DMD), Parkinson's disease, ALS, Dupuytren's contracture, Camurati-Engelmann disease, neural scarring, dementia, proliferative vitreoretinopathy, corneal injury, complications after glaucoma drainage surgery, and multiple sclerosis (MS). Many such fibrotic indications are also associated with inflammation of the affected tissue(s), indicating involvement of an immune component. Such inflammation may be accompanied by aberrant immune cell populations, such as increased numbers of Th17 cells, reduced numbers of Treg cells, and/or both. In each case, the affected patient may exhibit increased Th17/Treg cell ratios.

In some embodiments, fibrotic indications that may be treated with the compositions and/or methods described herein include organ fibrosis, such as fibrosis of the lung (e.g., IPF), fibrosis of the kidney (e.g., fibrosis associated with CKD), fibrosis of the liver, fibrosis of the heart or cardiac tissues, fibrosis of the skin (e.g., scleroderma), fibrosis of the uterus (e.g., endometrium, myometrium), and fibrosis of the bone marrow. In some embodiments, such therapy may reduce or delay the need for organ transplantation in patients. In some embodiments, such therapy may prolong the survival of the patients.

To treat IPF, patients who may benefit from the treatment include those with familial IPF and those with sporadic IPF. Administration of a therapeutically effective amount of an isoform-specific inhibitor of TGFβ1 may reduce myofibroblast accumulation in the lung tissues, reduce collagen deposits, reduce IPF symptoms, improve or maintain lung function, and prolong survival. In some embodiments, the inhibitor blocks activation of ECM-associated TGFβ1 (e.g., pro/latent TGFβ1 presented by LTBP1/3) within the fibrotic environment of IPF.

Nonalcoholic fatty liver disease (NAFLD) includes a spectrum of histological changes that begin with simple fatty infiltration of the liver, also known as simple or isolated steatosis or nonalcoholic fatty liver (NAFL), which may gradually, sometimes over decades, progress to the development of chronic inflammation (steatohepatitis or NASH), fibrosis, and ultimately cirrhosis. Only a subgroup of patients with NAFL will progress to NASH and subsequent cirrhosis. Currently, there are no clear criteria to identify this group of patients. NAFLD is the most common cause of chronic liver disease in North America. Currently, there are no approved drugs for the treatment of NASH. Given the high prevalence of NASH, the associated morbidity, the growing burden of end-stage liver disease, and limited availability of livers for organ transplantation, identifications of therapies that will slow the progress of, halt, or reverse NASH and NAFLD will address an unmet medical need.

There is a consensus that TGFβ is a central player in liver fibrosis (reviewed in, for example, Dewidar et al., Cells 2019, 8, 1419, the contents of which are incorporated herein by reference). The isoform-specific TGFβ1 inhibitors such as those provided herein (i.e., isoform-specific inhibitors of TGFβ1 that are selective for LTBP1/3-TGFβ1 complexes, or "matrix-targeted" inhibitors) may be used to treat fibrotic conditions of the liver, such as nonalcoholic fatty liver (NAFL) and fibrosis associated with fatty liver (e.g., NASH). The fatty liver may or may not be inflamed. Inflammation of the liver due to fatty liver (i.e., steatohepatitis) may develop into scarring (fibrosis), which then often progresses to cirrhosis (scarring that distorts the structure of the liver and impairs its function). The inhibitor may therefore be used to treat such conditions. In some embodiments, the inhibitor blocks activation of ECM-associated TGFβ1 (e.g., pro/latent TGFβ1 presented by LTBP1/3) within the fibrotic environment of the liver. Administration of the inhibitor in a subject with such conditions may reduce one or more symptoms, prevent or retard progression of the disease, reduce or stabilize fat accumulations in the liver, reduce disease-associated biomarkers (such as serum collagen fragments), reduce liver scarring, reduce liver stiffness, and/or otherwise produce clinically meaningful outcome in a patient population treated with the inhibitor, as compared to a control population not treated with the inhibitor. In some embodiments, an effective amount of the inhibitor may achieve both reduced liver fat and reduced fibrosis (e.g., scarring) in NASH patients. In some embodiment, an effective amount of the inhibitor may achieve improvement in fibrosis by at least one stage with no worsening steatohepatitis in NASH patients. In some embodiments, an effective amount of the inhibitor may reduce the rate of occurrence of liver failure and/or liver cancer in NASH patients. In some embodiments, an effective amount of the inhibitor may normalize, as compared to control, the levels of multiple inflammatory or fibrotic serum biomarkers as assessed following the start of the therapy, at, for example, 12-36 weeks. In some embodiments in NASH patients, the isoform-specific TGFβ1 inhibitors may be administered in patients who receive one or more additional therapies, including, but are not limited to myostatin inhibitors, which may generally enhance metabolic regulation in patients with clinical manifestation of metabolic syndrome, including NASH.

In some embodiments, in NASH or NAFLD patients, the isoform-specific, matrix-targeted, TGFβ1 inhibitors may be administered in patients who receive an Acetyl CoA Carboxylase inhibitor (ACCi) (e.g., firsocostat (aka GS-0976) or PF-05221304). Other therapeutics which may be useful in combination with the improved isoform-specific TGFβ1 inhibitors described herein, include, but are not limited to: GLP-1 receptor agonists or analgues (e.g., semaglutide), farnesoid X receptor (FXR) agonists (e.g., GS-9674; aka Cilofexor), ASK1 inhibitors (e.g., selonsertib); obeticholic acid, PPAR agonists (e.g., GFT505; aka elafibranor); nitazoxanide, ketohexokinase (KHK) inhibitors (e.g., PF-06835919); myostatin inhibitors and/or Diacylglycerol 0-Acyltransferase 2 (DGAT2) inhibitors (e.g., PF-06865571). In some embodiments, any one or more of the above-mentioned therapeutics can be used in combination with an isoform specific TGFβ1 inhibitor of the present disclosure, for example, an isoform-specific TGFβ1 inhibitor in combination with a FXR agonist, an ACC inhibitor, and/or a GLP-1 analogue. In some embodiments, TGFβ inhibitors may be used in combination with a myostatin inhibitor in the treatment of a metabolic liver disease in a subject, such as NASH and NAFLD, and liver fibrosis associated therewith. The subject may also suffer from type 2 diabetes and/or obesity. The TGFβ inhibitors used are preferably TGFβ31-selective inhibitors, more preferably context-selective TGFβ1-selective inhibitors that target LTBP1/2-associated TGFβ1, such as those disclosed herein. The myostatin inhibitor is preferably a myostatin-selective inhibitor, such as SRK-015 (e.g., see WO2017/218592A1) and trevogrumab, or any variant thereof, or an antibody according to WO 2016/098357.

In some embodiments, treatment with the isoform specific TGFβ1 inhibitors alone or in combination with one or more additional therapeutics reduces hepatic fat as measured by MRI-PDFF. In some embodiments, the reduction of hepatic fat is at least ≥20%, e.g., ≥20%, ≥25%, ≥30%, ≥35%, ≥40%, ≥45%, or ≥50%. In some embodiments, treatment with the isoform specific TGFβ1 inhibitors alone or in combination with one or more additional therapeutics reduces serum ALT and/or GGT by at least 20%, e.g., ≥20%, ≥25%, ≥30%, ≥35%, ≥40%, ≥45%, or ≥50%. In some embodiments, treatment with the isoform specific TGFβ1 inhibitors alone or in combination with one or more additional therapeutics reduces bile acid synthesis.

In some embodiments, either as monotherapy or in conjunction with one or more additional therapy (e.g., combination therapy), the TGFβ1 inhibitors of the present disclosure may be effective to treat NASH. "Effective treatment" may refer to improvements in hepatic steatosis, liver stiffness, liver biochemistry and serum fibrosis markers. In some embodiments, a 12-week treatment may result in significant decline of at least 30 percent in hepatic fat measured by magnetic resonance imaging-proton density fat fraction (MRI-PDFF) from baseline to 12 weeks in at least 50% percent of patients. Improvements in liver biochemistry tests including serum ALT of median relative reduction of at least 25% and GGT of at least 25% along with markers of reduced bile acid synthesis, may be achieved at 12 weeks.

In some embodiments, the NASH patients may have advanced liver fibrosis (stage F3/F4). In some embodiments, such patients have stage F3 advanced liver fibrosis. In some embodiments, such patients have stage F4 liver fibrosis characterized by cirrhosis. In some embodiments, the NASH patients develop or at risk of developing hepatocellular carcinoma and/or esophageal varices.

Fibrosis staging in non-alcoholic fatty liver disease according to the classification derived by the Nonalcoholic Steatohepatitis Clinical Research Network Pathology Committee is provided below:

| Stages of fibrosis | |
| --- | --- |
| Fibrotic manifestation | Fibrosis Stage |
| Perisinusoidal or periportal fibrosis | 1 |
| Mild perisinusoidal fibrosis (zone 3) | 1A |
| Moderate perisinusoidal fibrosis (zone 3) | 1B |
| Portal/periportal fibrosis | 1C |
| Perisinusoidal and portal/periportal fibrosis | 2 |
| Bridging fibrosis | 3 |
| Cirrhosis | 4 |

Therapeutic benefits may by also evaluated by burden of disease and patient-reported outcomes. NASH also has an impact on quality of life for those living with the condition, measured through patient-reported outcomes (PROs). PROs may be assessed using tools such as the Chronic Liver Disease Questionnaire (CLDQ-NASH) prior to treatment (e.g., baseline), particularly those related to physical health-related scores, Treatment with a TGFβ1 inhibitor (such as LTBP1/3 complex-selective inhibitors described herein) either alone (e.g., monotherapy) or in combination with another therapy, may be effective to improve the PROs as compared to the baseline, or as compared to those of population norms. In some embodiments, diabetes mellitus may be associated with impairment in PROs including physical functioning, bodily pain, general health and vitality. Treatment with a TGFβ1 inhibitor (such as LTBP1/3 complex-selective inhibitors described herein) either alone (e.g., monotherapy) or in combination with another therapy, may be effective to improve physical health-related scores (such as PROs) among subjects with diabetes (e.g., type 2 diabetes) and/or obesity.

Published studies in the literature suggest that regulatory T cells (Tregs) may play a role in the progression of liver disease into later-stage fibrosis with greater severity. For example, Zhang et al. reported that persistence of liver cirrhosis is maintained by intrahepatic regulatory T cells that inhibit the process of fibrosis resolution (Transl Res. 2016; 169: 67-79.e1-2). Kobayashi et al. suggested that Tregs are involved in the progression of liver fibrosis into hepatocellular carcinoma (HCC), a process referred to as hepatocarcinogenesis (Clin Cancer Res. 2007; 13(3): 902-911).

Accordingly, it is contemplated that careful selection of suitable TGFβ inhibitor tailored to the disease type and stage of the disease progression should be considered to maximize therapeutic benefit to a particular patient or patient population.

In some embodiments, a TGFβ1-selective, context-selective inhibitor that targets matrix-associated TGFβ1 (e.g., LTBP1-proTGFβ1 and/or LTBP3-proTGFβ31), such as those disclosed herein, is selected for use in the treatment of an early-stage liver disease such as nonalchoholic fatty liver ("NAFL") and noncirrhotic liver fibrosis associated with NASH. The noncirrhotic liver fibrosis includes liver fibrosis of stages 1-3. The TGFβ1-selective, context-selective inhibitor is administered to the subject in an amount effective to treat the disease, e.g., slow the progress of, halt, or reverse NAFL and noncirrhotic NASH. Preferably, the effective amount is sufficient to prevent progression to cirrhosis and cirrhosis complications, reduce the need for liver transplantation, and/or improve survival. In some embodiments, efficacy may be shown by, for example, reduction of inflammatory changes, improvement in fibrosis, or both. In some embodiments, the subject has a metabolic condition, such as obesity, type 2 diabetes. The subject with noncirrhotic NASH may include those with a NASH activity score (NAS) greater than or equal to 4 with at least 1 point each in inflammation and ballooning along with a NASH Clinical Research Network (CRN) fibrosis score greater than stage 1 fibrosis but less than stage 4 fibrosis. In some embodiments, the treatment achieves resolution of steatohepatitis on overall histopathological reading and no worsening of liver fibrosis on NASH CRN fibrosis score. Resolution of steatohepatitis is defined as absent fatty liver disease or isolated or simple steatosis without steatohepatitis and a NAS score of 0-1 for inflammation, 0 for ballooning, and any value for steatosis; or, improvement in liver fibrosis greater than or equal to one stage (NASH CRN fibrosis score) and no worsening of steatohepatitis (defined as no increase in NAS for ballooning, inflammation or steatosis); or, both resolution of steatohepatitis and improvement in fibrosis as defined above.

In some embodiments, a TGFβ1-selective, context-selective inhibitor that targets matrix-associated TGFβ1 (e.g., LTBP1-proTGFβ1 and/or LTBP3-proTGFβ31), such as those disclosed herein, is selected for use in the treatment of NASH with compensated cirrhosis. NASH-associated compensated cirrhosis is characterized by significant scar formation that is evident by histopathology, with hepatocytes clustered in nodules surrounded by dense extracellular matrix. The TGFβ1-selective, context-selective inhibitor is administered to the subject in an amount effective to halt or slow progression of fibrosis, prevent clinical decompensation, reduce the need for liver transplantation, and/or improve survival.

NASH with decompensated cirrhosis may be characterized by one or more of the following criteria: portal hypertension (evidence of portal hypertension may include low platelet counts, esophageal varices, ascites, history of hepatic encephalopathy, splenomegaly); elevated bilirubin; or elevated international normalized ratio or prolonged prothrombin time. Thus, patients having NASH with compensated cirrhosis may be those not meeting one or more of the aforementioned decompensated cirrhosis criteria.

In some embodiments, a TGFβ1-selective, context-selective inhibitor that targets matrix-associated TGFβ1 (e.g., LTBP1-proTGFβ1 and/or LTBP3-proTGFβ31), such as those disclosed herein, is selected for use in the treatment of NASH with decompensated cirrhosis or HCC associated with liver fibrosis. In some embodiments, upon progression of the disease into a late-stage or end-stage liver disease characterized by manifestation of cirrhosis or HCC, the TGFβ1-selective, context-selective inhibitor is replaced with a TGFβ1-selective, context-independent inhibitor capable of targeting both matrix-associated and immune cell-associated TGFβ1, e.g., LTBP1-proTGFβ1, LTBP3-proTGFβ1, GARP-proTGFβ1 and LRRC33-proTGFβ1 (see, for example, WO 2020/014473) in an amount effective to treat liver cirrhosis or HCC. In some embodiments, the TGFβ1-selective, context-selective inhibitor and/or the TGFβ1-selective, context-independent inhibitor may be used as monotherapy or in conjunction with one or more additional therapy.

In some embodiments, an effective amount of the inhibitor may normalize, as compared to control, the levels of multiple inflammatory or fibrotic serum biomarkers as assessed following the start of the therapy, at, for example, 12-36 weeks. In some embodiments, inflammatory or fibrotic biomarkers may be used to assess severity of NAFLD (by measure levels of hepatic steatosis), select patients for treatment, and/or monitor disease progression or treatment response. For example, blood biomarkers and panels may include, but are not limited to:

i) the Fatty liver index (BMI, waist circumference, serum triglycerides, and gamma-glutamyltransferase (GGT);
ii) the Hepatic steatosis index (serum aspartate aminotransferase (AST):alanine aminotransferase (ALT) ratio, BMI, gender, and presence of diabetes mellitus);
i) the NAFLD liver fat score (serum ALT, HDL cholesterol, triglicerides, haemoglobin $A_{1c}$ and leukocyte count);
ii) the SteatoTest (BioPredictive) (serum levels of total bilirubin, GGT, α2-macroglobin, haptoglobin, ALT, apolipoprotein AI, total cholesterol, triglycerides, glucose (adjusted for age and gender) and BMI); and
iii) the NAFLD ridge score (serum levels of ALT, HDL cholesterol, triglycerides, haemoglobin $A_{1c}$, leukocyte count, and comorbidity data (and the presence of hypertension)).

In some embodiments, imaging biomarkers can be used to assess levels of hepatic steatosis. For example, imaging biomarkers may include but are not limited to: ultrasonography, controlled attenuation parameter (CAP), MRI-estimated proton density fat fraction (MRI-PDFF), and magnetic resonance spectroscopy (MRS).

Liver biopsies are the current standard for diagnosis NASH, however, variability among pathologists limits the effectiveness of such diagnostic method. Accordingly, use of the Fatty Liver Inhibition of Progression (FLIP) algorithm (comprising histological steatosis, activity and fibrosis scores) may be used to improve the consistency of NASH diagnosis by biopsy. Moreover, many noninvasive biomarkers may also be useful for diagnosing and monitoring disease. Accordingly, in some embodiments, inflammatory or fibrotic biomarkers may be used to assess severity of NASH, select patients for treatment, and/or monitor disease progression or treatment response. Blood biomarkers may include:

i) apoptosis markers, such as CK18 fragments, total cytokeratin and sFAS;
ii) inflammatory markers, such as CRP, TNF, IL-8, and CXCL10;
iii) lipid oxidation products, such as 11-HETE, 9-HODE, 13-HODE, 12-oxo-ODE, LA-13-HODE (oxNASH-score), and 11,12-diHETrE;
iv) lysosomal enzymes, such as cathepsin D; and
v) combination panels, such as NASHTest (BioPredictive) and NASH Diagnostics Panel (comprising, presence of diabetes mellitus, sex, BMI, and serum levels of triglyceride, CK18 fragments, and total CK18).

In some embodiments, biomarkers and related panels may be useful in diagnosis levels of fibrosis and/or cirrhosis, select patients for treatment, and/or monitor disease progression or treatment response. For example, noninvasive tests of liver fibrosis and cirrhosis include, but are not limited to: AST:ALT ratio, AST:platelet ratio index, fibrosis-4 index (age, AST, ALT, and platelet count), NAFLD fibrosis score (age, BMI, impaired fasting glucose and/or diabetes, AST ALT, platelet count, and albumin), BARD score (AST, ALT, BMI, and diabetes).

Specific fibrosis markers and panels may also be useful, and include, but are not limited to: hyaluronic acid; PIIPNP; Pro-C3; TIMP1; Laminin; enhanced liver fibrosis (ELF) panel (PIINP, hyaluronic acid, TIMP1); FibroTest (GGT, total bilirubin, atm, apolipoprotein AI, and haptoglobin); and FibroMeter NAFLD (body weight, prothrombin index, ALT, AST, ferritin, and fasting glucose). Imaging biomarkers for liver fibrosis may include, but are not limited to: FibroScan (TE), point shear wave elastography (pSWE) (aka acoustic radiation force impulse (ARFI)), 2D-3D SWE, magnetic resonance elastography (MRE), and multiparameteric MRI.

Any RGFb-related disease with an inflammatory or auto inflammatory element may benefit from the novel inhibitors of the present disclosure which spare the regulatory T cell function. Particularly in liver diseases, e.g., metabolic liver conditions, it may be advantageous to select a TGFb inhibitor that selectivity target the matrix-associated TGFb1 signaling.

In one embodiment, the methods and compositions for use as described herein are useful for treating a subject having primary biliary cholangitis (PBC). In one embodiment, the subject having PBC has been nonresponsive to UDCA (ursodeoxycholic acid) treatment. In one embodiment, the subject has Barcelona, Paris-I, Toronto, Rotterdam, or Paris-II insufficient response to UCDA. In one embodiment, the subject having PBC has ALP≥2×ULN (upper limit of normal), and bilirubin >1×ULN despite an at least 1 year therapy with UDCA at the standard recommended dose (10-15 mg/kg b.w./day).

In another embodiment, the methods and compositions for use as described herein are useful for treating a subject having primary sclerosing cholangitis (PSC). In one embodiment, the subject having PSC has an elevated ALP, an abnormal cholangiography, endoscopic retrograde cholangiopancreatography, or percutaneous transhepatic cholangiography. In one embodiment, the subject having PSC has a model for end-stage liver disease (MELD) score of at least 14.

In another embodiment, the methods and compositions for use as described herein are useful for treating a subject having NASH. In one embodiment, a subject has fibrosis stage 2 NASH, fibrosis stage 3 NASH, or fibrosis stage 4 NASH. In one embodiment, a subject has a NAS (NAFLD activity score) of at least 4, or of at least 5. In one embodiment, a subject with NASH has a NAS>4 and fibrosis stage 2 or stage 3. In one embodiment, a subject with NASH has a NAS>5 and fibrosis stage 2 or stage 3. In one embodiment, a subject with NASH has a model for end-stage liver disease (MELD) score of at least 14.

The isoform-specific TGFβ1 inhibitors such as those provided herein may be used to treat fibrotic conditions of the kidney, e.g., diseases characterized by extracellular matrix accumulation (IgA nephropathy, focal and segmental glomerulosclerosis, crescentic glomerulonephritis, lupus nephritis and diabetic nephropathy) in which significantly increased expression of TGFβ in glomeruli and the tubulointerstitium has been observed. While glomerular and tubulointerstitial deposition of two matrix components induced by TGFβ, fibronectin EDA+ and PAI-1, was significantly elevated in all diseases with matrix accumulation, correlation analysis has revealed a close relationship primarily with the TGFβ1 isoform. Accordingly, the isoform-specific TGFβ1 inhibitors are useful as therapeutic for a spectrum of human glomerular disorders, in which TGFβ is associated with pathological accumulation of extracellular matrix.

In some embodiments, the fibrotic condition of the kidney is associated with chronic kidney disease (CKD). CKD is caused primarily by high blood pressure or diabetes and claims more than one million lives each year. CKD patients require lifetime medical care that ranges from strict diets and medications to dialysis and transplants. In some embodiments, the TGFβ1 inhibitor therapy described herein may reduce or delay the need for dialysis and/or transplantation. In some embodiments, such therapy may reduce the need (e.g., dosage, frequency) for other treatments. In some embodiments, the isoform-specific TGFβ1 inhibitors may be administered in patients who receive one or more additional therapies, including, but are not limited to myostatin inhibitors, which may generally enhance metabolic regulation in patients with CKD.

Fibrotic conditions that may be treated with the TGFβ1 inhibitor of the present disclosure include conditions involving fibrosis and/or chronic inflammation. Such conditions may be neuromuscular disorders, including but are not limited to Duchenne muscular dystrophy (DMD), and other genetic disorders such as multiple sclerosis (MS) and cystic fibrosis (CF). Through the inhibition of both the ECM- and immune cell-associated TGFβ1 arms, the TGFβ1 inhibitor such as those described herein is thought to suppress fibrotic progression and restore M1/M2 macrophage polarization.

The organ fibrosis which may be treated with the methods provided herein includes cardiac (e.g., cardiovascular) fibrosis. In some embodiments, the cardiac fibrosis is associated with heart failure, e.g., chronic heart failure (CHF). In some embodiments, the heart failure may be associated with myocardial diseases and/or metabolic diseases. In some embodiments, the isoform-specific, TGFβ1 inhibitors may be administered in patients who receive one or more additional therapies, including, but are not limited to myostatin inhibitors in patients with cardiac dysfunction that involves heart fibrosis and metabolic disorder.

In some embodiments, fibrotic conditions that may be treated with the compositions and/or methods described herein include desmoplasia. Desmoplasia may occur around a neoplasm, causing dense fibrosis around the tumor (e.g., desmoplastic stroma), or scar tissue within the abdomen after abdominal surgery. In some embodiments, desmoplasia is associated with malignant tumor. Due to its dense formation surrounding the malignancy, conventional anti-cancer therapeutics (e.g., chemotherapy) may not effectively penetrate to reach cancerous cells for clinical effects. Isoform-specific, inhibitors of TGFβ1 such as those described herein may be used to disrupt the desmoplasia, such that the fibrotic formation can be loosened to aid effects of anti-cancer therapy. In some embodiments, the isoform-specific inhibitors of TGFβ1 can be used as monotherapy (more below).

In some embodiments, a patient has a fibrotic solid tumor (e.g., desmoplasia) and is or has been excluded from a surgical candidate pool, such that the fibrotic solid tumor is considered to be non-resectable or non-operable (e.g., risk of surgical intervention outweighs potential benefit thereof). Such patient may be a candidate for receiving a TGFβ1 inhibition therapy of the present disclosure. The TGFβ1 inhibition therapy of the present invention administered to such patients may render the tumor become resectable or operable so that the patient may become a candidate for surgical resection.

To treat patients with fibrotic conditions, TGFβ1 isoform-specific inhibitors are administered to a subject in an amount effective to treat the fibrosis. The effective amount of such an antibody is an amount effective to achieve both therapeutic efficacy and clinical safety in the subject. In some embodiments, the inhibitor is an antibody that can block activation of an LTBP-mediated TGFβ1 localized (e.g., tethered) in the ECM. In some embodiments, the LTBP is LTBP1 and/or LTBP3. In some embodiments, a LTBP-specific inhibitor of TGFβ1 can be combined with an inhibitor of LRRC33-proTGFβ.

Assays useful in determining the efficacy of the antibodies and/or compositions of the present disclosure for the alteration of fibrosis include, but are not limited to, histological assays for counting fibroblasts and basic immunohistochemical analyses known in the art.

In some embodiments, circulating LAP fragment(s) may be used as a serum marker of fibrogenesis. See for example, U.S. Pat. No. 8,198,412, the contents of which are incorporated herein by reference.

There are many animal models that have been developed to study fibrosis. For example, certain high fat diets in mice has been shown to mimic both the histopathology and pathogenesis of human NAFLD. Moreover, some genetic models also display features of human metabolic syndrome and NAFLD, such as db/db and ob/ob mouse models. There are also animal models for the study of NASH, which mainly consist of various diet-induced models, including, but not limited to, methionine and choline-deficient diet (MCD), high-cholesterol diet (HCD), choline-deficient high fat diet (CDHFD), choline-deficient L-amino acid-deficient diet, choline-deficient L-amino acid-deficient diet+carbon tetrachloride, high-fat diet +streptozotocin, high fat +high cholesterol diet (HFHC), high-fructose diet (HFD), and high-fructose high fat diet (HFHF). Genetic mouse models for the study of NASH include, but are not limited to foz/foz mice, Hepatocyte-specific PTEN-deficient mice, Db/db mice+diethylnitrosamine (DEN), and db/db mice+MCD. The details of all of these models, including the pluses and minus of each, are outlined in Jennie Ka Ching Lau et al., J Pathol 2017; 241: 36-44; the contents of which are incorporated herein by reference.

Other models useful for testing the efficacy of TGFβ inhibitors in fibrosis include the carbon tetrachloride (CCL$_4$)-induced liver fibrosis model and adenine-induced kidney fibrosis model. Another model useful for testing the efficacy of isoform-specific TGFβ inhibitors in liver fibrosis include the bile duct ligation (BDL) model (see, e.g., Tag et al., J Vis Exp. 2015; (96): 52438). A useful genetic model of kidney fibrosis includes Alport model (discussed elsewhere herein).

In any of such preclinical models, efficacy in fibrosis (e.g., pro-fibrotic or anti-fibrotic effects in vivo) may be assessed by any suitable methods, such as: percent of picosirius red (PSR)-positive area in tissue sections; contents (quantification) of hydroxyproline in tissue; and immunohistochemical detection and quantification of collA staining on tissue sections. In some embodiments, histopathological appraisal may be carried out, in which fibrosis scoring system can be employed. Pharmachological effects of test articles (e.g., TGFβ inhibitors) may be examined by suitable pharmacodynamics (PD) measures, such as measuring downstream signal transduction events. In case of the TGFβ pathway, for example, suitable PD measure includes relative phosphorylation of SMAD2/3.

Muscle Conditions Associated with Fibrosis

Accumulating evidence indicates that TGFβ plays an important role in muscle homeostasis, repair, and regeneration. Agents, such as monoclonal antibodies described herein, that selectively modulate LTBP-associated TGFβ signaling may be effective for treating damaged muscle fibers, such as in chronic/genetic muscular dystrophies, congenital fibrosis of ocular/extraocular muscles, and acute muscle injuries, without the toxicities associated with more broadly-acting TGFβ inhibitors.

Accordingly, the present invention provides methods for treating damaged muscle fibers using an agent that preferentially modulates a subset, but not all, of TGFβ effects in vivo. Such agents can selectively modulate TGFβ1 signaling ("isoform-specific modulation") in a particular context, i.e., when presented by LTBP1 or LTBP3.

In skeletal muscle, TGFβ plays a variety of roles including inhibition of proliferation and differentiation, induction of atrophy, and development of fibrosis. TGFβ reduces satellite cell proliferation and prevents differentiation (via inhibition of MyoD and myogenin) (Allen, R. E. and L. K. J Cell Physiol, 1987. 133(3): p. 567-72; Brennan, T. J., et al., Proc Natl Acad Sci USA, 1991. 88(9): p. 3822-6; Massague, J., et al., Proc Natl Acad Sci USA, 1986. 83(21): p. 8206-10; Olson, E. N., et al., J Cell Biol, 1986. 103(5): p. 1799-805). The isoform of TGFβ (i.e., TGFβ31, 2, or 3) is not specified in these early papers, but is presumed to be TGFβ1. TGFβ also contributes to muscle fibrosis; direct injection of recombinant TGFβ1 results in skeletal muscle fibrosis, and pan-TGFβ inhibition decreases fibrosis in acute and chronically injured muscle (Li, Y., et al., Am J Pathol, 2004. 164(3): p. 1007-19; Mendias, C. L., et al., Muscle Nerve, 2012. 45(1): p. 55-9; Nelson, C. A., et al., Am J Pathol, 2011. 178(6): p. 2611-21). TGFβ1 is expressed by myofibers, macrophages, regulatory T cells, fibroblasts, and fibrocytes within the skeletal muscle (Li, Y., et al., Am J Pathol, 2004. 164(3): p. 1007-19; Lemos, D. R., et al., Nat Med, 2015. 21(7): p. 786-94; Villalta, S. A., et al., Sci Transl Med, 2014. 6(258): p. 258ra142; Wang, X., et al., J Immunol, 2016. 197(12): p. 4750-4761); and expression is increased upon injury and in disease (Li, Y., et al., Am J Pathol, 2004. 164(3): p. 1007-19; Nelson, C. A., et al., Am J Pathol, 2011. 178(6): p. 2611-21; Bernasconi, P., et al., J Clin Invest, 1995. 96(2): p. 1137-44; Ishitobi, M., et al., Neuroreport, 2000. 11(18): p. 4033-5). TGFβ2 and TGFβ3 are also upregulated (at the mRNA level) in mdx muscle (a mouse model of Duchenne muscular dystrophy), although to a lesser extent than TGFβ1 (Nelson, C. A., et al., Am J Pathol, 2011. 178(6): p. 2611-21; Zhou, L., et al., Neuromuscul Disord, 2006. 16(1): p. 32-8). Pessina, et al., recently used lineage tracing experiments to show that cells of multiple origins within dystrophic muscle adopt a fibrogenic fate via a TGFβ-dependent pathway (Pessina, P., et al., Stem Cell Reports, 2015. 4(6): p. 1046-60).

TGFβ1 has been implicated in human muscular dystrophies. Duchenne muscular dystrophy (DMD) is a severe, progressive, and ultimately fatal disease caused by the absence of dystrophin (Bushby, K., et al., Lancet Neurol, 2010. 9(1): p. 77-93). Lack of dystrophin results in increased susceptibility to contraction-induced injury, leading to continual muscle degeneration (Petrof, B. J., et al., Proc Natl Acad Sci USA, 1993. 90(8): p. 3710-4; Dellorusso, C., et al., J Muscle Res Cell Motil, 2001. 22(5): p. 467-75; Pratt, S. J., et al., Cell Mol Life Sci, 2015. 72(1): p. 153-64). Repeated rounds of repair contribute to chronic inflammation, fibrosis, exhaustion of the satellite cell pool, eventual loss of mobility and death (Bushby, K., et al., Lancet Neurol, 2010. 9(1): p. 77-93; McDonald, C. M., et al., Muscle Nerve, 2013. 48(3): p. 343-56). Expression of TGFβ1 is significantly increased in patients with DMD and correlates with the extent of fibrosis observed in these patients (Bernasconi, P., et al., J Clin Invest, 1995. 96(2): p. 1137-44; Chen, Y. W., et al., Neurology, 2005. 65(6): p. 826-34). Excessive ECM deposition has detrimental effects on the contractile properties of the muscle and can limit access to nutrition as the myofibers are isolated from their blood supply (Klingler, W., et al., Acta Myol, 2012. 31(3): p. 184-95). Recently, additional data has further implicated TGFβ1 in muscular dystrophies. Variants in LTBP4 have been found to modify disease severity in mouse and human. In mouse, a variant of LTBP4 is protective in mice lacking dystrophin or γ-sarcoglycan (Coley, W. D., et al., Hum Mol Genet, 2016. 25(1): p. 130-45; Heydemann, A., et al., J Clin Invest, 2009. 119(12):

p. 3703-12). In humans, two groups independently identified a variant of LTBP4 as protective in DMD, delaying loss of ambulation by several years (Flanigan, K. M., et al., Ann Neurol, 2013. 73(4): p. 481-8; van den Bergen, J. C., et al., J Neurol Neurosurg Psychiatry, 2015. 86(10): p. 1060-5).

Although the nature of the genetic variants in mouse and human differs, in both species the protective variant results in decreased TGFβ signaling (Heydemann, A., et al., J Clin Invest, 2009. 119(12): p. 3703-12); Ceco, E., et al., Sci Transl Med, 2014. 6(259): p. 259ra144). Many of the functions of TGFβ1 in skeletal muscle biology have been inferred from experiments in which purified active growth factor is injected into animals or added to cells in culture (Massague, J., et al., Proc Natl Acad Sci USA, 1986. 83(21): p. 8206-10; Li, Y., et al., Am J Pathol, 2004. 164(3): p. 1007-19; Mendias, C. L., et al., Muscle Nerve, 2012. 45(1): p. 55-9). Given the importance of cellular context for specific functions of TGFβ1 (see, for example, Hinck et al., Cold Spring Harb. Perspect. Biol, 2016. 8(12)) it is possible that some of the effects observed in these experiments do not reflect the endogenous role(s) of the cytokine in vivo. For example, treatment of human dermal fibroblasts with recombinant TGFβ1, myostatin, or GDF11 results in nearly identical changes in gene expression in these cells, although in vivo the roles of these proteins are quite different (Tanner, J. W., Khalil, A., Hill, J., Franti, M., MacDonnell, S. M., Growth Differentiation Factor 11 Potentiates Myofibroblast Activation, in Fibrosis: From Basic Mechanisms to Targeted therapies. 2016: Keystone, CO).

Multiple investigators have used inhibitors of TGFβ to clarify the role of the growth factor in vivo. Treatment of mdx mice with the pan-TGFβ neutralizing antibody 1D11 clearly results in reduced fibrosis (by histology and hydroxyproline content), reduced muscle damage (reduced serum creatine kinase and greater myofiber density), and improved muscle function (by plethysmography, force generation of isolated EDL muscles, and increased forelimb grip strength) (Nelson, C. A., et al., Am J Pathol, 2011. 178(6): p. 2611-21; Andreetta, F., et al., J Neuroimmunol, 2006. 175(1-2): p. 77-86; Gumucio, J. P., et al., J Appl Physiol (1985), 2013. 115(4): p. 539-45). In addition, myofiber-specific expression of a dominant negative TGFβ type II receptor protects against muscle damage after cardiotoxin injury and in 6-sarcoglycan−/− mice (Accornero, F., et al., Hum Mol Genet, 2014. 23(25): p. 6903-15). The proteoglycan decorin, which is abundant in skeletal muscle and inhibits TGFβ activity, decreases muscle fibrosis in mdx mice and following laceration injury (Li, Y., et al., Mol Ther, 2007. 15(9): p. 1616-22; Gosselin, L. E., et al., Muscle Nerve, 2004. 30(5): p. 645-53). Other molecules with TGFβ inhibitory activity, such as suramin (an anti-neoplastic agent) and losartan (an angiotensin receptor blocker) have been effective in improving muscle pathology and reducing fibrosis in mouse models of injury, Marfan's syndrome, and muscular dystrophy (Spurney, C. F., et al., J Cardiovasc Pharmacol Ther, 2011. 16(1): p. 87-95; Taniguti, A. P., et al., Muscle Nerve, 2011. 43(1): p. 82-7; Bedair, H. S., et al., Am J Sports Med, 2008. 36(8): p. 1548-54; Cohn, R. D., et al., Nat Med, 2007. 13(2): p. 204-10). While all of the therapeutic agents described above do inhibit TGFβ1 or its signaling, none of them is specific for the TGFβ1 isoform. For example, 1D11 binds to and inhibits the TGFβ1, 2, and 3 isoforms (Dasch, J. R., et al., J Immunol, 1989. 142(5): p. 1536-41). Suramin inhibits the ability of multiple growth factors to bind to their receptors, including PDGF, FGF, and EGF, in addition to TGFβ1 (Hosang, M., J Cell Biochem, 1985. 29(3): p. 265-73; Olivier, S., et al., Eur J Cancer, 1990. 26(8): p. 867-71; Scher, H. I. and W. D. Heston, Cancer Treat Res, 1992. 59: p. 131-51). Decorin also inhibits myostatin activity, both by direct binding and through upregulation of follistatin, a myostatin inhibitor (Miura, T., et al., Biochem Biophys Res Commun, 2006. 340(2): p. 675-80; Brandan, E., C. Cabello-Verrugio, and C. Vial, Matrix Biol, 2008. 27(8): p. 700-8; Zhu, J., et al., J Biol Chem, 2007. 282(35): p. 25852-63). Losartan affects additional signaling pathways through its effects on the renin-angiotensin-aldosterone system, including the IGF-1/AKT/mTOR pathway (Burks, T. N., et al., Sci Transl Med, 2011. 3(82): p. 82ra37; Sabharwal, R. and M. W. Chapleau, Exp Physiol, 2014. 99(4): p. 627-31; McIntyre, M., et al., Pharmacol Ther, 1997. 74(2): p. 181-94). Therefore, all of these therapies inhibit additional molecules which may contribute to their therapeutic effects, as well as toxicities.

Apart from chronic inflammation, the hallmark of DMD is excessive, and progressive, fibrosis. In advanced disease the fibrosis is so severe that it can actually isolate individual muscle fibers from their blood supply. It also alters the contractile properties of the muscle. In human patients, there is a strong correlation between the extent of TGFβ1 upregulation and fibrosis, and a strong link between the extent of fibrosis and negative mobility outcomes. Therefore, in some embodiments, LTBP-proTGFβ1 inhibitors may be administered to dystrophic patients for the prevention and/or reduction of fibrosis to selectively target the ECM-associated TGFβ1 effects in the disease. In some embodiments, various isoform- and/or context-selective agents described herein can be employed to achieve inhibition of TGFβ1 signaling to prevent fibrosis and promote myogenesis, but without having unwanted effects on the immune system (e.g., through GARP or LRRC33).

Administration

To practice the method disclosed herein, an effective amount of the pharmaceutical composition described above can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. When used in the treatment of fibrosis and/or metabolic conditions, preferably the TGFβ inhibitor is administered subcutaneously. Commercially available nebulizers for liquid formulations, including jet nebulizers and ultrasonic nebulizers are useful for administration. Liquid formulations can be directly nebulized and lyophilized powder can be nebulized after reconstitution. Alternatively, inhibitors, e.g., antibodies, or antigen-binding portions thereof, that selectively bind a LTBP1-TGFβ complex and/or a LTBP3-TGFβ complex can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having a TGFβ-related indication, such as those noted above. A subject having a TGFβ-related indication can be identified by routine medical examination, e.g., laboratory tests, organ functional tests, CT scans, or ultrasounds. A subject suspected of having any of such indication might show one or more symptoms of the indication. A subject at risk for the indication can be a subject having one or more of the risk factors for that indication.

As used herein, the terms "effective amount" and "effective dose" refer to any amount or dose of a compound or composition that is sufficient to fulfill its intended purpose (s), i.e., a desired biological or medicinal response in a tissue or subject at an acceptable benefit/risk ratio. For example, in certain embodiments of the present invention, the intended purpose may be to inhibit TGFβ-1 activation in vivo, to achieve clinically meaningful outcome associated with the TGFβ-1 inhibition. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of a TGFβ-related indication. Alternatively, sustained continuous release formulations of an antibody that selectively binds a LTBP1-TGFβ1 complex and/or a LTBP3-TGFβ1 complex may be appropriate. Various formulations and devices for achieving sustained release would be apparent to the skilled artisan and are within the scope of this disclosure.

In one example, dosages for an inhibitor, e.g., antibody, that selectively binds a LTBP1-TGFβ1 complex and/or a LTBP3-TGFβ1 complex as described herein may be determined empirically in individuals who have been given one or more administration(s) of the inhibitor. Individuals are given incremental dosages of the inhibitor. To assess efficacy, an indicator of the TGFβ-related indication can be followed. For example, methods for measuring for myofiber damage, myofiber repair, inflammation levels in muscle, and/or fibrosis levels in muscle are well known to one of ordinary skill in the art.

The present invention encompasses the recognition that agents capable of modulating the activation step of TGFβ s in an isoform-specific manner, and a context-specific manner, may provide improved safety profiles when used as a medicament. Accordingly, the invention includes inhibitors, e.g., antibodies and antigen-binding fragments thereof, that selectively bind and inhibit activation of TGFβ1, but not TGFβ2 or TGFβ3, thereby conferring specific inhibition of the TGFβ1 signaling in vivo while minimizing unwanted side effects from affecting TGFβ2 and/or TGFβ3 signaling. Likewise, the invention includes inhibitors, e.g., antibodies and antigen-binding fragments thereof, that selectively inhibit activation of TGFβ1 presented by LTBP1 and/or LTBP3, but not TGFβ1 presented by GARP or LRRC33, thereby conferring specific inhibition of LTBP1/3-associated TGFβ1 signaling in vivo while minimizing unwanted side effects caused by modulation of GARP-associated TGFβ1 and/or LRRC33-associated TGFβ1.

In some embodiments, the inhibitors, e.g., antibodies, or antigen-binding portions thereof, as described herein, are not toxic when administered to a subject. In some embodiments, the inhibitors, e.g., antibodies, or antigen-binding portions thereof, as described herein, exhibit reduced toxicity when administered to a subject as compared to an antibody that binds to both TGFβ1 and TGFβ2. In some embodiments, the inhibitors, e.g., antibodies, or antigen-binding portions thereof, as described herein, exhibit reduced toxicity when administered to a subject as compared to an inhibitor that binds to both TGFβ1 and TGFβ3. In some embodiments, the inhibitors, e.g., antibodies, or antigen-binding portions thereof, as described herein, exhibit reduced toxicity when administered to a subject as compared to an inhibitor that binds to TGFβ1, TGFβ2 and TGFβ3.

Generally for administration of any of the inhibitors, e.g., antibodies, described herein, an initial candidate dosage can be about 0.5-30 mg/kg per dose, e.g., about 0.5 mg/kg, about 1 mg/kg, about 2 mg/kg, about 5 mg/kg, about 10 mg/kg, about 15 mg/kg, about 20 mg/kg, about 30 mg/kg per dose. Typically, the composition comprising an antibody or a fragment thereof encompassed by the present disclosure is administered to a human patient at the dosage at suitable intervals, such as once or twice weekly, every 1-8 weeks, etc. In some embodiments, frequency of administration may be adjusted to, for example, twice a week, once a week, every two weeks, every three weeks, every four weeks, every six weeks, every eight weeks, etc. For the purpose of the present disclosure, a typical daily dosage might range from about any of 1 mg/kg to 20 mg/kg or more, depending on the factors mentioned above. For repeated administrations over several days or longer, depending on the condition, the treatment is sustained until a desired suppression of symptoms occurs or until sufficient therapeutic levels are achieved to alleviate a TGFβ-related indication, or a symptom thereof.

In one embodiment, the antibody, or antigen-binding fragment thereof, is administered to the subject at a dosage of between 0.1 and 30 mg/kg, between 0.5 and 30 mg/kg, between 1 and 30 mg/kg, between 5 and 30 mg/kg, between 10 and 30 mg/kg, between 15 and 30 mg/kg, between 20 and 30 mg/kg, between 25 and 30 mg/kg, between 0.1 and 25 mg/kg, between 0.5 and 25 mg/kg, between 1 and 25 mg/kg, between 5 and 25 mg/kg, between 10 and 25 mg/kg, between 15 and 25 mg/kg, between 20 and 25 mg/kg, between 0.1 and 20 mg/kg, between 0.5 and 20 mg/kg, between 1 and 20 mg/kg, between 5.0 and 20 mg/kg, between 10 and 20 mg/kg, between 15 and 20 mg/kg, between 0.1 and 15 mg/kg, between 0.5 and 15 mg/kg, between 1 and 15 mg/kg, between 5 and 15 mg/kg, between 10 and 15 mg/kg, between 5.0 and 20 mg/kg, between 10 and 20 mg/kg, between 15 and 20 mg/kg, between 0.1 and 10 mg/kg, between 0.5 and 10 mg/kg, between 1 and 10 mg/kg, between 5 and 10 mg/kg, optionally, wherein the subject is administered the antibody, or antigen-binding portion thereof, twice a week, once a week, once every 2 weeks, once every 3 weeks, once a month, or every other month.

An exemplary dosing regimen comprises administering an initial dose of about 2 mg/kg, followed by one or more maintenance doses. For example, an initial dose may be between about 2 and 30 mg/kg, for instance, once a week or twice a week. Thereafter, maintenance dose(s) may follow, for example, between about 0.1 and 20 mg/kg, for instance, once a week, every other week, once a month, etc. However, other dosage regimens may be useful, depending on the pattern of pharmacokinetic decay that the practitioner wishes to achieve. Pharmacokinetics experiments have shown that the serum concentration of an inhibitor, e.g., antibody, disclosed herein (e.g., SR-AB2) remains stable for at least 7 days after administration to a preclinical animal model (e.g., a mouse model). Without wishing to be bound by any particular theory, this stability post-administration may be advantageous since the antibody may be administered less frequently while maintaining a clinically effective serum concentration in the subject to whom the antibody is administered (e.g., a human subject). In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

According to some embodiments, serum concentrations of the LTBP context-selective TGFβ1 inhibitor that are therapeutically effective to treat a TGFβ1-related indication in accordance with the present disclosure may be at least about 10 μg/mL, e.g., between about 10 μg/mL and 1.0 mg/mL. In some embodiments, effective amounts of the antibody as measured by serum concentrations are about 20-400 μg/mL. In some embodiments, effective amounts of the antibody as measured by serum concentrations are about 100-800 μg/mL. In some embodiments, effective amounts of the inhibitor as measured by serum concentrations are at least about 20 μg/mL, e.g., at least about 50 μg/mL, 100 μg/mL, 150 μg/mL or 200 μg/mL. In preferred embodiments, in non-human primates, there are no observed toxicities (for example: no cardiotoxicities, hyperplasia and inflammation, dental and gingival findings) associated with such inhibitor after maintaining serum concentration levels of about 2,000-3,000 μg/mL for at least 4 weeks, e.g., at least 4 weeks, preferably at least 8 weeks, more preferably at least 12 weeks. Therefore, about 10-100 fold therapeutic window may be achieved.

In some embodiments, for an adult patient of normal weight, doses ranging from about 0.3 to 5.00 mg/kg may be administered. The particular dosage regimen, e.g., dose, timing and repetition, will depend on the particular individual and that individual's medical history, as well as the properties of the individual agents (such as the half-life of the agent, and other relevant considerations).

For the purpose of the present disclosure, the appropriate dosage of an inhibitor, e.g., antibody or antigen-binding fragment thereof, that selectively binds a LTBP1-TGFβ complex and/or a LTBP3-TGFβ complex will depend on the specific antibody (or compositions thereof) employed, the type and severity of the indication, whether the antibody is administered for preventive or therapeutic purposes, previous therapy, the patient's clinical history and response to the inhibitor, and the discretion of the attending physician. In some embodiments, a clinician will administer an inhibitor, e.g., antibody, that selectively binds a LTBP1-TGFβ1 complex and/or a LTBP3-TGFβ1 complex, until a dosage is reached that achieves the desired result. Administration of an inhibitor, e.g., antibody, that selectively binds a LTBP1-TGFβ1 complex and/or a LTBP3-TGFβ1 complex can be continuous or intermittent, depending, for example, upon the recipient's physiological condition, whether the purpose of the administration is therapeutic or prophylactic, and other factors known to skilled practitioners. The administration of an inhibitor, e.g., antibody, that selectively binds a LTBP1-TGFβ1 complex and/or a LTBP3-TGFβ1 complex may be essentially continuous over a preselected period of time or may be in a series of spaced dose, e.g., either before, during, or after developing a TGFβ-related indication.

Based on the observation that inhibiting TGFβ3 can increase collagen deposition or accumulation in fibrosis, add-on therapy comprising a TGFβ1-selective inhibitor (such as the novel antibodies disclosed herein) may be considered for patients who are treated with a TGFβ inhibitor with TGFβ3-inhibiting activity, e.g., inhibitors of TGFβ1/2/3, TGFβ1/3 and TGFβ3. Examples of TGFβ inhibitors with TGFβ3-inhibiting activity include but are not limited to: low molecular weight antagonists of TGFβ receptors, e.g., ALK5 antagonists, such as Galunisertib (LY2157299 monohydrate); monoclonal antibodies (such as neutralizing antibodies) that inhibit all three isoforms ("pan-inhibitor" antibodies) (see, for example, WO 2018/134681); monoclonal antibodies that preferentially inhibit two of the three isoforms (e.g., TGFβ1/3 (for example WO 2006/116002); and engineered molecules (e.g., fusion proteins) such as ligand traps (for example, WO 2018/029367; WO 2018/129331 and WO 2018/158727). In some embodiments, the ligand trap comprises the structure in accordance with the disclosure of WO/2018/15872. In some embodiments, the ligand trap comprises the structure in accordance with the disclosure of WO 2018/029367; WO 2018/129331. In some embodiments, the ligand trap is a construct known as M7824. In some embodiments, the ligand trap is a construct known as AVID200. In some embodiments, the neutralizing pan-TGFβ antibody is GC1008 or a derivative thereof. In some embodiments, such antibody comprises the sequence in accordance with the disclosure of WO/2018/134681.

In some embodiments, the antibody is a neutralizing antibody that specifically binds both TGFβ1 and TGFβ3. In some embodiments such antibody preferentially binds TGFβ1 over TGFβ3. For example, the antibody comprises the sequence in accordance with the disclosure of WO/2006/116002. In some embodiments, the antibody is 21D1.

The add-on therapy is aimed to counter or overcome the pro-fibrotic effect of TGFβ3 inhibition in patients who have received or are receiving a TGFβ inhibitor with TGFβ3 inhibitory activities. In some embodiments, the patient has a fibrotic disorder or is at risk of developing a fibrotic disorder. For example, the patient may suffer from a metabolic condition that is associated with higher risk of developing liver fibrosis. The metabolic conditions linked to such risk include obesity, type 2 diabetes and NASH. Accordingly, the invention includes a TGFβ1-selective inhibitor for use in an add-on therapy of a subject treated with a TGFβ3 inhibitor, in an amount sufficient to reduce pro-fibrotic effects of the TGFβ3 inhibitor. In some embodiments, the subject has fibrosis. In some embodiments, the subject has myelofibrosis. In some embodiments, the subject has advanced cancer, e.g., metastatic or locally advanced tumor. In some embodiments, the TGFβ1-selective inhibitor is selected from Ab31, Ab34, Ab37, Ab38, Ab39, Ab40, Ab41, Ab42, Ab43, Ab44, Ab45, Ab62, Ab63, and Ab64 (optionally Ab42 or Ab63) a variant/derivative or antigen-binding fragment thereof thereof, or an engineered molecule comprising an antigen-binding fragment thereof. In some embodiments, the TGFβ1-selective inhibitor is Ab42, a variant/derivative or antigen-binding fragment thereof, or an engineered molecule comprising an antigen-binding fragment thereof. In preferred embodiments, the TGFβ1-selective inhibitor is Ab42 or an antigen-binding fragment thereof.

Without being bound by theory, in some embodiments, sparing of TGFβ inhibitors with anti-TGFβ3 activities may be especially useful for treating patients who are diagnosed with a type of cancer known to be highly metastatic, myelofibrotic, and/or those having or are at risk of developing a fibrotic condition. Accordingly, the disclosure herein includes a TGFβ inhibitor for use in the treatment of cancer wherein the inhibitor does not inhibit TGFβ3 and wherein the patient has a metastatic cancer or myelofibrosis, or the patient has or is at risk of developing a fibrotic condition, wherein optionally the fibrotic condition is non-alcoholic steatohepatitis (NASH).

As used herein, the term "treating" refers to the application or administration of a composition including one or more active agents to a subject, who has a TGFβ-related indication, a symptom of the indication, or a predisposition toward the indication, with the purpose to cure, heal, alleviate, relieve, alter, remedy, ameliorate, improve, or affect the indication, the symptom of the indication, or the predisposition toward the indication.

Alleviating a TGFβ-related indication with an inhibitor, e.g., antibody, that selectively binds a LTBP1-TGFβ1 complex and/or a LTBP3-TGFβ1 complex includes delaying the development or progression of the indication, or reducing indication's severity. Alleviating the indication does not necessarily require curative results. As used therein, "delaying" the development of an indication associated with a TGFβ-related indication means to defer, hinder, slow, retard, stabilize, and/or postpone progression of the indication. This delay can be of varying lengths of time, depending on the history of the indication and/or individuals being treated. A method that "delays" or alleviates the development of an indication, or delays the onset of the indication, is a method that reduces probability of developing one or more symptoms of the indication in a given time frame and/or reduces extent of the symptoms in a given time frame, when compared to not using the method. Such comparisons are typically based on clinical studies, using a number of subjects sufficient to give a statistically significant result.

Selection of a TGFβ Inhibitor for Treating a Fibrotic Disorder

Inhibitors of TGFβ include isoform-non-selective inhibitors and isoform-selective inhibitors, with the former being the majority of known TGFβ inhibitors/antagonists. Among the isoform-non-selective inhibitors are pan-inhibitors (TGFβ1/2/3 inhibitors), TGFβ1/2 inhibitors and TGFβ1/3 inhibitors. Isoform-selective inhibitors include neutralizing antibodies that selectively bind one isoform and activation inhibitors that target latent proTGFβ complexes in an isoform-selective manner. The class of activation inhibitors include context-independent and context-selecitve inhibitors. For example, isoform-specific, context-independent TGFβ1 inhibitors have also been described, which bind pro/latent TGFβ1 presented by LTBP1/3, GARP, or LRRC33, and inhibit the release of mature TGFβ1 from the presenting molecule complex (see, e.g., WO 2017/156500, WO 2020/014473 and WO 2020/014460). The entire contents of each of the foregoing applications are incorporated herein by reference. Context-specific antibodies that selectively bind a GARP-TGFβ1 complex and inhibit activation of TGFβ1 presented in the context of GARP have recently been described in WO 2018/013939.

The present invention includes specific inhibitors of ECM-associated TGFβ1 activation, e.g., antibodies, and antigen-binding portions thereof, that selectively bind a LTBP1/3-TGFβ1 complex, and which inhibit activation of TGFβ1 presented in the context of LTBP1 or LTBP3. The present disclosure further provides guidance as to both selection of a suitable TGFβ inhibitor among those listed above, tailored to certain patient populations and related therapeutic regimen.

Figure 22:
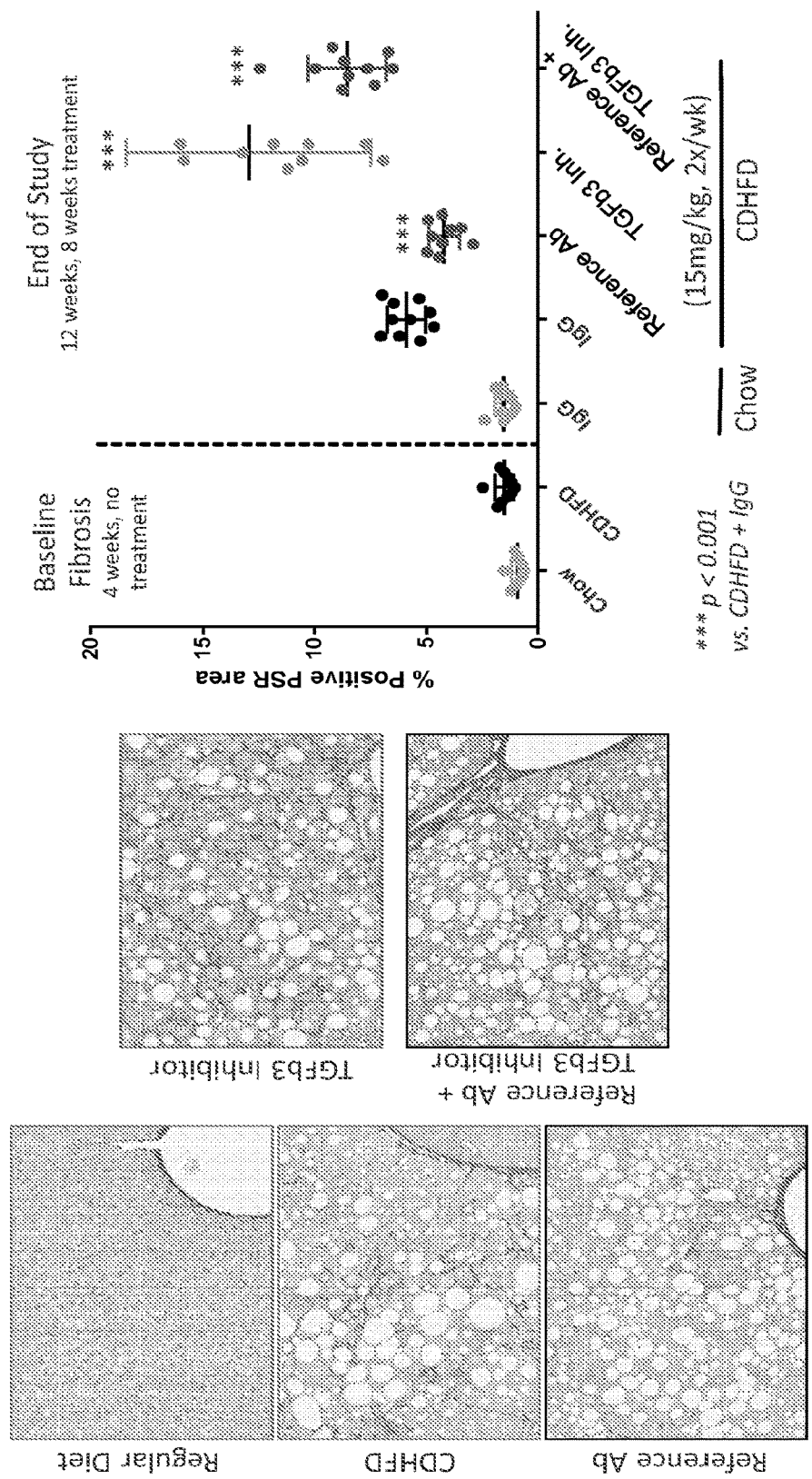
FIG. 22 provides 5 representative PSR-stained images from controls, CDHFD mice treated with Reference Ab, a TGFβ3 inhibitor, or both (left). A graph showing picosirius red area (%) in liver sections of CDHFD mice treated with Reference Ab, a TGFβ3 inhibitor, or both, as compared to control, is also provided (right).

The surprising observations demonstrated herein (see Example 17; FIG. 22) that showing that TGFβ3 inhibition may in fact aggravate ECM dysregulation are informative in a decision making process of selecting the right TGFβ inhibitor. For example, for use in the treatment of a fibrotic condition, it may be advantageous to select a TGFβ inhibitor that lacks inhibitory activities towards TGFβ3. The observed exacerbation of fibrosis (e.g., profibrotic effects) in response to TGFβ3 inhibition raises the possibility that role of TGFβ3 expands beyond homeostasis. Even more importantly, this may be relevant not only to fibrotic conditions but also in other disease contexts. Ample evidence suggests that dysregulation of the ECM is found in a number of disease conditions, including fibrosis and cancer. Indeed, many of the key profibrotic genes are also recognized among markers of various cancers. These markers include, for example, col1A1, col3A1, PAI-1, CCL2, ACTA2, FN-1, CTGF and TGFB1. Therefore, the finding that blockade of TGFβ3 appears harmful in fibrosis (e.g., having a profibrotic effect) may be applicable to a broader scope of conditions associated with ECM dysregulation.

The present invention encompasses insights into selecting "the right TGFβ inhibitor" for "the right patient" to treat a disease condition with certain criteria and/or clinical features. In one aspect, the present invention provides use of preferred TGFβ1 inhibitors suitable for a particular patient population with fibrotic conditions. Accordingly, the invention includes use of an LTBP1/LTBP3-proTGFβ1 inhibitor in the treatment of a fibrotic condition in a subject, wherein the subject benefits from immunosuppression. This is based on the notion that at least a subset of TGFβ1 activities involves immune regulation which is mediated by GARP-associated and/or LRRC33-associated TGFβ1. Thus, the invention includes the recognition that use of TGFβ1 inhibitors that also affect the immune aspect of TGFβ1 effects may be detrimental for treating patients with fibrotic conditions where immunostimulation may cause exacerbation of the disease. The invention therefore aims at least in part to provide means of selectively inhibiting TGFβ1 effects within the ECM context (e.g., LTBP-associated) while sparing TGFβ1 effects associated with non-ECM contexts (e.g., immune cells, leukocytes, etc. expressing GARP or LRRC33 on cell surface), so as to prevent unwanted immunostimulation. This approach may be particularly advantageous in early-stage fibrosis, such as noncirrhotic liver fibrosis.

In some embodiments, patient populations who benefit from both: i) inhibition of TGFβ1 signaling, and, ii) immunosuppression, include those who suffer from a severe or late stage organ fibrosis and who are to receive an allograft organ transplant. The severe or late stage organ fibrosis may be associated with IPF, CKD, and/or NASH. Such patients may have already received other therapies for treating the fibrotic disease, yet which may have failed to sufficiently treat or manage the condition. Attending physicians may determine that remaining treatment options may include allograft transplantation. Such patients may be placed in a wait list for an available organ for transplantation. Such patients may be treated with an immunosuppressant. A selective inhibitor of LTBP1/LTBP3-presented TGFβ1 activation, which does not inhibit GARP-presented TGFβ1 activation, can be used to treat such patients, without raising risk of triggering immunostimulation mediated by effector T cells. Similarly, following the transplantation, such patients may continue to receive the selective inhibitor of LTBP1/LTBP3-presented TGFβ1 activation to avoid risk of an organ rejection.

In some embodiments, patient populations who benefit from both: i) inhibition of TGFβ1 signaling, and, ii) immunosuppression, include those who suffer from a fibrotic disorder and who have an inflammatory or autoimmune condition.

In some embodiments, the patient or patient population has or is at risk of developing one or more autoimmune disorders, such as: Achalasia; Addison's disease; Adult Still's disease; Agammaglobulinemia; Alopecia areata; Amyloidosis; Ankylosing spondylitis; Anti-GBM/Anti-TBM nephritis; Antiphospholipid syndrome; Autoimmune angioedema; Autoimmune dysautonomia; Autoimmune encephalomyelitis; Autoimmune hepatitis; Autoimmune inner ear disease (AIED); Autoimmune myocarditis; Autoimmune oophoritis; Autoimmune orchitis; Autoimmune pancreatitis; Autoimmune retinopathy; Autoimmune urticaria; Axonal & neuronal neuropathy (AMAN); Baló disease; Behcet's disease; Benign mucosal pemphigoid; Bullous pemphigoid; Castleman disease (CD); Celiac disease; Chagas disease; Chronic inflammatory demyelinating polyneuropathy (CIDP); Chronic recurrent multifocal osteomyelitis (CRMO); Churg-Strauss Syndrome (CSS) or Eosinophilic Granulomatosis (EGPA); Cicatricial pemphigoid; Cogan's syndrome; Cold agglutinin disease; Congenital heart block; Coxsackie myocarditis; CREST syndrome; Crohn's disease; Dermatitis herpetiformis; Dermatomyositis; Devic's disease (neuromyelitis optica); Discoid lupus; Dressler's syndrome; Endometriosis; Eosinophilic esophagitis (EoE); Eosinophilic fasciitis; Erythema nodosum; Essential mixed cryoglobulinemia; Evans syndrome; Fibromyalgia; Fibrosing alveolitis; Giant cell arteritis (temporal arteritis); Giant cell myocarditis; Glomerulonephritis; Goodpasture's syndrome; Granulomatosis with Polyangiitis; Graves' disease; Guillain-Barre syndrome; Hashimoto's thyroiditis; Hemolytic anemia; Henoch-Schonlein purpura (HSP); Herpes gestationis or pemphigoid gestationis (PG); Hidradenitis Suppurativa (HS) (Acne Inversa); Hypogammalglobulinemia; IgA Nephropathy; IgG4-related sclerosing disease; Immune thrombocytopenic purpura (ITP); Inclusion body myositis (IBM); Interstitial cystitis (IC); Juvenile arthritis; Juvenile diabetes (Type 1 diabetes); Juvenile myositis (JM); Kawasaki disease; Lambert-Eaton syndrome; Leukocytoclastic vasculitis; Lichen planus; Lichen sclerosus; Ligneous conjunctivitis; Linear IgA disease (LAD); Lupus; Lyme disease chronic; Meniere's disease; Microscopic polyangiitis (MPA); Mixed connective tissue disease (MCTD); Mooren's ulcer; Mucha-Habermann disease; Multifocal Motor Neuropathy (MMN) or MMNCB; Multiple sclerosis; Myasthenia gravis; Myositis; Narcolepsy; Neonatal Lupus; Neuromyelitis optica; Neutropenia; Ocular cicatricial pemphigoid; Optic neuritis; Palindromic rheumatism (PR); PANDAS; Paraneoplastic cerebellar degeneration (PCD); Paroxysmal nocturnal hemoglobinuria (PNH); Parry Romberg syndrome; Pars planitis (peripheral uveitis); Parsonage-Turner syndrome; Pemphigus; Peripheral neuropathy; Perivenous encephalomyelitis; Pernicious anemia (PA); POEMS syndrome; Polyarteritis nodosa; Polyglandular syndromes type I, II, III; Polymyalgia rheumatica; Polymyositis; Postmyocardial infarction syndrome; Postpericardiotomy syndrome; Primary biliary cirrhosis; Primary sclerosing cholangitis; Progesterone dermatitis; Psoriasis; Psoriatic arthritis; Pure red cell aplasia (PRCA); Pyoderma gangrenosum; Raynaud's phenomenon; Reactive Arthritis; Reflex sympathetic dystrophy; Relapsing polychondritis; Restless legs syndrome (RLS); Retroperitoneal fibrosis; Rheumatic fever; Rheumatoid arthritis; Sarcoidosis; Schmidt syndrome; Scleritis; Scleroderma; Sjögren's syndrome; Sperm & testicular autoimmunity; Stiff person syndrome (SPS); Subacute bacterial endocarditis (SBE); Susac's syndrome; Sympathetic ophthalmia (SO); Takayasu's arteritis; Temporal arteritis/Giant cell; arteritis Thrombocytopenic purpura (TTP); Tolosa-Hunt syndrome (THS); Transverse myelitis; Type 1 diabetes; Ulcerative colitis (UC); Undifferentiated connective tissue disease (UCTD); Uveitis; Vasculitis; Vitiligo; Vogt-Koyanagi-Harada Disease.

In some embodiments, the inflammatory or autoimmune condition is associated with the fibrosis. Non-limiting examples of inflammatory or autoimmune conditions associated with fibrosis include muscular dystrophy, such as DMD.

In other embodiments, where patient populations who benefit from both: i) inhibition of TGFβ1 signaling, and, ii) immunosuppression, include those who suffer from a fibrotic disease and who have an inflammatory or autoimmune condition that is not directly associated with the fibrosis, but rather a discrete disorder.

Such inflammatory or autoimmune conditions, whether or not directly associated with the underlining fibrotic disease or separate condition(s), may be caused by or associated with imbalance of regulatory T cells (Treg) in human autoimmune diseases. For example, such disorders that are linked to Treg dysregulation include, but are not limited to: Juvenile idiopathic arthritis; Rheumatoid arthritis (RA); Spondyloarthritis; Psoriatic arthritis; HCV mixed cryoglobulinaemia; cryoglobulinaemia; Multiple sclerosis; Autoimmune liver disease; Systemic lupus erythematodes; Immune-mediated diabetes; Myasthenia gravis; Primary Sjögren syndrome; Kawasaki disease; and, Inflammatory bowel disease (IBD).

Thus, LTBP1/3-sepective inhibitors of TGFβ1 signaling, such as those described herein, can be used to treat patients who suffer from a fibrotic condition and inflammatory or autoimmune condition such as one or more of the disorders listed above. The LTBP1/3-sepective inhibitors of TGFβ1 signaling used accordingly can treat or alleviate TGFβ1-dependent fibrosis in the ECM, while sparing immune-associated TGFβ1 signaling.

Accordingly, related methods of the invention include methods for selecting an appropriate TGFβ1 inhibitor for treating a fibrotic disorder, based on the clinical manifestations of the fibrotic disorder in a subject. In one embodiment, the invention provides a method of selecting an isoform-specific TGFβ1 inhibitor for treatment of a fibrotic disorder in a subject. The method comprises (a) determining whether the fibrotic disorder manifests clinical presentations including fibrosis and one or more of inflammation, immune suppression, proliferative dysregulation, and need for an allograft transplant, and (b) selecting an isoform-specific, context-dependent TGFβ1 inhibitor or an isoform-specific, context-independent TGFβ1 inhibitor for treatment of the fibrotic disorder based on the clinical presentations determined in step (a). In another embodiment, the invention provides a method of treating a subject having a fibrotic disorder, comprising selecting a treatment regimen including an isoform-specific TGFβ1 inhibitor for the subject, and administering the selected treatment regimen to the subject, wherein the selection comprises (a) determining whether the fibrotic disorder manifests clinical presentations including fibrosis and one or more of the following: inflammation, immune suppression, proliferative dysregulation, and need for an allograft transplant; and (b) selecting a treatment regimen comprising an isoform-specific, context-dependent TGFβ1 inhibitor or an isoform-specific, context-independent TGFβ1 inhibitor, based on the clinical presentations determined in step (a).

Subjects afflicted with fibrotic disorders can display a wide range of symptoms, in addition to fibrosis. The specific combination of clinical manifestations in a subject can guide the selection of an appropriate TGFβ1-inhibitory treatment regimen. For example, a context-independent, isoform-specific TGFβ1 inhibitor can be used to treat the subject if the subject's clinical manifestations indicate a need for inhibition of TGFβ1, without modulating the activity of TGFβ2 or TGFβ3. A treatment regimen including a LTBP context-specific inhibitor can be used to treat the subject if the subject's clinical manifestations indicate that inhibition of TGFβ1 in the extracellular matrix would be beneficial. A LTBP context-specific inhibitor is also advantageous if the subject's clinical manifestations indicate that stimulation of immune effector cells is undesirable. A GARP context-specific inhibitor can be used to treat the subject if the subject's clinical manifestations indicate that blocking the activation/release of TGFβ1 on regulatory T cells (Treg cells) would be beneficial, e.g., to prevent Treg cells from suppressing effector T cell activity. A LRRC33 context-specific inhibitor can be used to treat the subject if the subject's clinical manifestations indicate that blocking the activation/release of TGFβ1 on myeloid cells, monocytes, macrophages, dendritic cells and/or microglia would be beneficial, e.g., to reverse or reduce immune suppression in the subject.

By way of example, a subject having a fibrotic disorder may display clinical manifestations including fibrosis, inflammation, immune suppression, and proliferative dysregulation. Fibrotic disorders which commonly present with the foregoing combination of symptoms include, e.g., myelofibrosis. In this embodiment, an isoform-specific, context-independent TGFβ1 inhibitor can be selected for treating the subject.

A subject having a fibrotic disorder may display clinical manifestations including fibrosis, inflammation, and need for an allograft transplant. Fibrotic disorders which commonly present with the foregoing combination of symptoms include, e.g., organ fibrosis, such as kidney fibrosis (e.g., fibrosis associated with chronic kidney disease), liver fibrosis (e.g., fibrosis associated with nonalcoholic steatohepatitis (NASH)), or lung fibrosis (e.g., fibrosis associated with idiopathic pulmonary fibrosis (IPF)). In this embodiment, a context-specific LTBP1/3-specific inhibitor is selected for treating the subject.

In another example, a subject having a fibrotic disorder may display clinical manifestations including fibrosis and inflammation. Fibrotic disorders which commonly present with the foregoing combination of symptoms include, e.g., scleroderma. In this embodiment, a context-specific LTBP1/3-specific inhibitor is selected for treating the subject. Additional fibrotic disorders which commonly present with the foregoing combination of symptoms include, e.g., degenerative diseases, such as muscular dystrophy, e.g., Duchenne muscular dystrophy (DMD). In this embodiment, a context-specific LTBP1/3-specific inhibitor is selected for treating the subject.

A subject having a fibrotic disorder may display clinical manifestations including immune suppression and proliferative dysregulation. Fibrotic disorders which commonly present with the foregoing combination of symptoms include, e.g., solid tumors. In some embodiments, the solid tumor is a malignant tumor. In other embodiments, the solid tumor is a benign tumor. In an exemplary embodiment, the subject has desmoplasia (e.g., pancreatic desmoplasia). In some embodiments, patients may have a solid tumor that has been assessed as "inoperable" or not suitable for surgical resection. Thus, in some embodiments, patients are not candidates for surgical resection of the tumor. However, TGFβ1 inhibition therapy comprising a context-selective TGFβ1 inhibitor of the present invention may reverse such non-candidate patients to be more suited for receiving a surgery. In some embodiments, subjects having a solid tumor are poorly responsive to cancer therapy (e.g., the tumor is resistant to the cancer therapy), such as chemotherapy, radiation therapy, CAR-T therapy and checkpoint inhibitor therapy. TGFβ1 inhibition therapy comprising a context-selective TGFβ1 inhibitor of the present invention may at least in part reverse the resistance to render the patient more responsive to the cancer therapy. In some embodiments, a combination therapy comprising both the context-selective TGFβ1 inhibition therapy and the cancer therapy may synergistically treat the cancer. In some embodiments, the context-selective TGFβ1 inhibition therapy administered in conjunction with the cancer therapy may reduce the required dosage of the cancer therapy to produce equivalent or improved clinical effects.

In another exemplary embodiment, the subject has fibroids. In the foregoing embodiments, in which the fibrotic disorder displays clinical manifestations including immune suppression and proliferative dysregulation, a context-specific LTBP1/3-specific inhibitor and/or a context-specific GARP-specific inhibitor are selected for treating the subject.

In another aspect, the invention provides a method of treating a subject having a fibrotic disorder with an isoform-specific, LTBP1/3 context-specific TGFβ1 inhibitor, by selecting a subject having a fibrotic disorder manifesting clinical presentations including fibrosis and the need for an allograft transplant, and administering an effective amount of an isoform-specific, LTBP1/3-specific TGFβ1 inhibitor to the subject. In one embodiment, the method comprises determining whether the fibrotic disorder manifests clinical presentations including fibrosis and the need for an allograft transplant. The LTBP1/3-specific TGFβ1 inhibitor is administered to the subject if the subject exhibits symptoms including fibrosis and the need for an allograft transplant.

In another aspect, the invention provides a method of treating a subject having a fibrotic disorder with an isoform-specific, context-independent TGFβ1 inhibitor, by selecting a subject having a fibrotic disorder manifesting clinical presentations including fibrosis, immune suppression, and/or proliferative dysregulation, and administering an effective amount of an isoform-specific, context-independent TGFβ1 inhibitor to the subject. In one embodiment, the method comprises determining whether the fibrotic disorder manifests clinical presentations including fibrosis, immune suppression, and/or proliferative dysregulation. The isoform-specific, context-independent TGFβ1 inhibitor is administered to the subject if the subject inhibits symptoms including fibrosis, immune suppression, and/or proliferative dysregulation.

Clinical manifestations including inflammation, immune suppression, proliferative dysregulation, and/or the need for an allograft transplant can be determined in a subject having a fibrotic disorder using methods and practices known in the art. Such methods include, for example, physical examination and standard diagnostic tests. In one embodiment, inflammation can be assessed by determining if a subject displays an elevated level of inflammatory biomarkers in plasma, blood, or serum. Such inflammatory biomarkers include, for example, C-reactive protein, interleukin 1 (IL-1), interleukin 6 (IL-6), tumor necrosis factor α (TNF-α), or combinations thereof. Blood tests including erythrocyte sedimentation rate (ESR) and plasma viscosity (PV) can also indicate the presence of inflammation in a subject with a fibrotic disorder. In another embodiment, immune suppression can be assessed by determining the number and composition of a subject's blood cells, e.g., T cells, B cells, NK cells, monocytes, macrophages, etc Immune suppression can also be assessed by determining if the subject is taking or has a history of taking immunosuppressant medications, or determining if the subject has a condition associated with immune suppression (e.g., hematological malignancies, HIV/AIDS, etc.). In another embodiment, proliferative dysregulation can be assessed using standard tests including blood tests, biopsy, and/or imaging procedures such as CT scan, ultrasound, and MRI. Other standard tests for diagnosing cancer (e.g., biomarker tests, etc.) can also be used to assess proliferative dysregulation. The need for an allograft transplant can be determined by a clinician using standard procedures. In one embodiment, the loss or partial loss of organ function, or an increased likelihood of loss of organ function, indicates the need for a transplant.

As mentioned, the present invention provides selective targeting of the ECM-associated TGFβ1 complexes enabled by the use of antibodies that are capable of specifically binding LTBP-presented TGFβ1 precursors. While some antibodies of the present invention are capable of binding and inhibiting both LTBP1- and LTBP3-associated proTGFβ1 complexes, others show even greater selectivity in that they only bind either LTBP1-proTGFβ1 or LTBP3-proTGFβ1.

The invention therefore encompasses the recognition that certain patient populations may benefit from TGFβ1 inhibition therapy comprising a context-selective inhibitor that is specific to LTBP1/3-proTGFβ1, over TGFβ inhibitors that also affect the immune components of TGFβ signaling namely, TGFβ associated with GARP. Accordingly, it is contemplated herein that to treat a TGFβ-related condition in a subject who has or is at risk of developing an autoimmune condition, a TGFβ inhibitor that selectively inhibits matrix-associated TGFβ (such as LTBP1/3 context-selective inhibitors of TGFβ1 disclosed herein) may provide therapeutic benefits while minimizing risk of overstimulating the immune system. Such subject may suffer from or may be at risk of developing an autoimmune disorder, such as: Achalasia; Addison's disease; Adult Still's disease; Agammaglobulinemia; Alopecia areata; Amyloidosis; Ankylosing spondylitis; Anti-GBM/Anti-TBM nephritis; Antiphospholipid syndrome; Autoimmune angioedema; Autoimmune dysautonomia; Autoimmune encephalomyelitis; Autoimmune hepatitis; Autoimmune inner ear disease (AIED); Autoimmune myocarditis; Autoimmune oophoritis; Autoimmune orchitis; Autoimmune pancreatitis; Autoimmune retinopathy; Autoimmune urticaria; Axonal & neuronal neuropathy (AMAN); Baló disease; Behcet's disease; Benign mucosal pemphigoid; Bullous pemphigoid; Castleman disease (CD); Celiac disease; Chagas disease; Chronic inflammatory demyelinating polyneuropathy (CIDP); Chronic recurrent multifocal osteomyelitis (CRMO); Churg-Strauss Syndrome (CSS) or Eosinophilic Granulomatosis (EGPA); Cicatricial pemphigoid; Cogan's syndrome; Cold agglutinin disease; Congenital heart block; Coxsackie myocarditis; CREST syndrome; Crohn's disease; Dermatitis herpetiformis; Dermatomyositis; Devic's disease (neuromyelitis optica); Discoid lupus; Dressler's syndrome; Endometriosis; Eosinophilic esophagitis (EoE); Eosinophilic fasciitis; Erythema nodosum; Essential mixed cryoglobulinemia; Evans syndrome; Fibromyalgia; Fibrosing alveolitis; Giant cell arteritis (temporal arteritis); Giant cell myocarditis; Glomerulonephritis; Goodpasture's syndrome; Granulomatosis with Polyangiitis; Graves' disease; Guillain-Barre syndrome; Hashimoto's thyroiditis; Hemolytic anemia; Henoch-Schonlein purpura (HSP); Herpes gestationis or pemphigoid gestationis (PG); Hidradenitis Suppurativa (HS) (Acne Inversa); Hypogammalglobulinemia; IgA Nephropathy; IgG4-related sclerosing disease; Immune thrombocytopenic purpura (ITP); Inclusion body myositis (IBM); Interstitial cystitis (IC); Juvenile arthritis; Juvenile diabetes (Type 1 diabetes); Juvenile myositis (JM); Kawasaki disease; Lambert-Eaton syndrome; Leukocytoclastic vasculitis; Lichen planus; Lichen sclerosus; Ligneous conjunctivitis; Linear IgA disease (LAD); Lupus; Lyme disease chronic; Meniere's disease; Microscopic polyangiitis (MPA); Mixed connective tissue disease (MCTD); Mooren's ulcer; Mucha-Habermann disease; Multifocal Motor Neuropathy (MMN) or MMNCB; Multiple sclerosis; Myasthenia gravis; Myositis; Narcolepsy; Neonatal Lupus; Neuromyelitis optica; Neutropenia; Ocular cicatricial pemphigoid; Optic neuritis; Palindromic rheumatism (PR); PANDAS; Paraneoplastic cerebellar degeneration (PCD); Paroxysmal nocturnal hemoglobinuria (PNH); Parry Romberg syndrome; Pars planitis (peripheral uveitis); Parsonage-Turner syndrome; Pemphigus; Peripheral neuropathy; Perivenous encephalomyelitis; Pernicious anemia (PA); POEMS syndrome; Polyarteritis nodosa; Polyglandular syndromes type I, II, III; Polymyalgia rheumatica; Polymyositis; Postmyocardial infarction syndrome; Postpericardiotomy syndrome; Primary biliary cirrhosis; Primary sclerosing cholangitis; Progesterone dermatitis; Psoriasis; Psoriatic arthritis; Pure red cell aplasia (PRCA); Pyoderma gangrenosum; Raynaud's phenomenon; Reactive Arthritis; Reflex sympathetic dystrophy; Relapsing polychondritis; Restless legs syndrome (RLS); Retroperitoneal fibrosis; Rheumatic fever; Rheumatoid arthritis; Sarcoidosis; Schmidt syndrome; Scleritis; Scleroderma; Sjögren's syndrome; Sperm & testicular autoimmunity; Stiff person syndrome (SPS); Subacute bacterial endocarditis (SBE); Susac's syndrome; Sympathetic ophthalmia (SO); Takayasu's arteritis; Temporal arteritis/Giant cell; arteritis Thrombocytopenic purpura (TTP); Tolosa-Hunt syndrome (THS); Transverse myelitis; Type 1 diabetes; Ulcerative colitis (UC); Undifferentiated connective tissue disease (UCTD); Uveitis; Vasculitis; Vitiligo; Vogt-Koyanagi-Harada Disease.

LTBP1 and LTBP3 are both components of the ECM, where they can display or "present" a latent TGFβ precursor complex. Some observations from expression studies raise the possibility that deletion, ablation or functional inhibition of LTBP3 may cause certain toxicities. LTBP3−/− mice (as well as some human mutations) have short stature, as well as bone and dental anomalies. These phenotypes are likely associated with disruptions in development, however, but it is possible that LTBP3 plays a role in homeostasis of these tissues in adults (expression in adult bone is reported). Based on these observations, in certain clinical situations (where the disease manifests in a tissue known to express LTBP3 and associated with toxicities) or in certain patient populations, such as pediatric patients who are still in active development, it may be advisable to avoid potential toxicities of LTBP3-related inhibition. Loss of LTBP1 function does appear to be sufficient to protect against at least some forms of fibrosis, as LTBP1−/− KO mice are protected against liver fibrosis (induced by bile duct ligation). Taken together, these data raise the possibility that LTBP1-specific TGFβ1 inhibition could have a superior safety profile as compared to LTBP1/3-TGFβ1 inhibitors in certain situations.

Accordingly, selection of patients or patient populations suitable or likely to benefit from the LTBP1/3-selective inhibitors of the present invention may involve evaluating or confirming expression profiles of LTBP1, LTBP2, LTBP3, LTBP4, GARP, LRRC33, pro- or mature TGFβ1, pro- or mature TGFβ2, pro- or mature TGFβ3, or any combinations thereof. Expression profiles may be obtained by measuring the presence/absence or levels of mRNA and/or proteins in suitable assays from biological samples collected from the subject (e.g., patients). In some embodiments, a sluble circulating fragment(s) of LAP may be used as surrogate marker for the expression of the particular TGFβ3 isoform. In some embodiments, TGFβ1 LAP fragments may be used as a marker of fibrogenesis. See for example, U.S. Pat. No. 8,198,412, the contents of which are incorporated herein by reference.

Genetic Markers of Disease:

It has been observed that abnormal activation of the TGFβ1 signal transduction pathway in various disease conditions is associated with altered gene expression of a number of markers. These gene expression markers (e.g., as measured by mRNA) include, but are not limited to: Serpine 1 (encoding PAI-1), MCP-1 (also known as CCL2), Col1a1, Col3a1, FN1, TGFβ1, CTGF, ACTA2 (encoding α-SMA), SNAI1 (drives EMT in fibrosis and metastasis by down-regulating E-cadherin (Cdh1), MMP2 (matrix metalloprotease associated with EMT), MMP9 (matrix metalloprotease associated with EMT), TIMP1 (matrix metalloprotease associated with EMT), FOXP3 (marker of Treg induction), CDH1 (E cadherin (marker of epithelial cells) which is downregulated by TGFβ3), and, CDH2 (N cadherin (marker of mesenchymal cells) which is upregulated by TGFβ3). Interestingly, many of these genes are implicated to play a role in a diverse set of disease conditions, including various types of organ fibrosis, as well as in many cancers, which include myelofibrosis. Indeed, pathophysiological link between fibrotic conditions and abnormal cell proliferation, tumorigenesis and metastasis has been suggested. See for example, Cox and Erler (2014) Clinical Cancer Research 20(14): 3637-43 "Molecular pathways: connecting fibrosis and solid tumor metastasis"; Shiga et al. (2015) Cancers 7:2443-2458 "Cancer-associated fibroblasts: their characteristics and their roles in tumor growth"; Wynn and Barron (2010) Semin. Liver Dis. 30(3): 245-257 "Macrophages: master regulators of inflammation and fibrosis", contents of which are incorporated herein by reference. Without wishing to be bound by a particular theory, the inventors of the present disclosure contemplate that the TGFβ1 signaling pathway may in fact be a key link between these broad pathologies.

The ability of chemotactic cytokines (or chemokines) to mediate leukocyte recruitment (e.g., monocytes/macrophages) to injured or disease tissues has crucial consequences in disease progression. Members of the C-C chemokine family, such as monocyte chemoattractant protein 1 (MCP-1), also known as CCL2, macrophage inflammatory protein 1-alpha (MIP-1a), also known as CCL3, and MIP-1l3, also known as CCL4, have been implicated in this process.

For example, MCP-1/CCL2 is thought to play a role in both fibrosis and cancer. MCP-1/CCL2 is characterized as a profibrotic chemokine and is a monocyte chemoattractant, and evidence suggests that it may be involved in both initiation and progression of cancer. In fibrosis, MCP-1/CCL2 has been shown to play an important role in the inflammatory phase of fibrosis. For example, neutralization of MCP-1 resulted in a dramatic decrease in glomerular crescent formation and deposition of type I collagen. Similarly, passive immunotherapy with either anti-MCP-1 or anti-MIP-1 alpha antibodies is shown to significantly reduce mononuclear phagocyte accumulation in bleomycin-challenged mice, suggesting that MIP-1 alpha and MCP-1 contribute to the recruitment of leukocytes during the pulmonary inflammatory response (Smith, Biol Signals. 1996 July-August; 5(4):223-31, "Chemotactic cytokines mediate leukocyte recruitment in fibrotic lung disease"). Elevated levels of MIP-1alpha in patients with cystic fibrosis and multiple myeloma have been reported (see, for example: Mrugacz et al., J Interferon Cytokine Res. 2007 June; 27(6):491-5), supporting the notion that MIP-1α is associated with localized or systemic inflammatory responses.

Lines of evidence point the involvement of C-C chemokines in tumor progression. For example, tumor-derived MCP-1/CCL2 can promote "pro-cancer" phenotypes in macrophages. For example, in lung cancer, MCP-1/CCL2 has been shown to be produced by stromal cells and promote metastasis. In human pancreatic cancer, tumors secrete CCL2, and immunosuppressive CCR2-positive macrophages infiltrate these tumors. Patients with tumors that exhibit high CCL2 expression/low CD8 T-cell infiltrate have significantly decreased survival. Without wishing to be bound by particular theory, it is contemplated that monocytes that are recruited to an injured or diseased tissue environment may subsequently become polarized in response to local cues (such as in response to tumor-derived cytokines), thereby further contributing to disease progression. These M2-like macrophages are likely to contribute to immune evasion by suppressing effector cells, such as CD4+ and CD8+ T cells. In some embodiments, this process is in part mediated by LRRC33-TGFβ1 expressed by activated macrophages. In some embodiments, the process is in part mediated by GARP-TGFβ1 expressed by Tregs.

Similarly, involvement of PAI-1/Serpine1 has been implicated in a variety of cancers, angiogenesis, inflammation, neurodegenerative diseases (e.g., Alzheimer's Disease). Elevated expression of PAI-1 in tumor and/or serum is correlated with poor prognosis (e.g., shorter survival, increased metastasis) in various cancers, such as breast cancer and bladder cancer (e.g., transitional cell carcinoma) as well as myelofibrosis. In the context of fibrotic conditions, PAI-1 has been recognized as an important downstream effector of TGFβ1-induced fibrosis, and increased PAI-1 expression has been observed in various forms of tissue fibrosis, including lung fibrosis (such as Idiopathic Pulmonary Fibrosis (IPF)), kidney fibrosis, liver fibrosis and scleroderma. In some embodiments, the process is in part mediated by ECM-associated TGFβ1, e.g., via LTBP1 and/or LTBP3.

Accordingly, in some embodiments, in vivo effects of the TGFβ1 inhibitor therapy may be assessed by measuring changes in gene markers. Suitable markers include TGFβ (e.g., TGFβ31, TGFβ2, and TGFβ3). Suitable markers may also include one or more presenting molecules for TGFβ1 (e.g., TGFβ31, TGFβ2, and TGFβ3), such as LTBP1, LTBP3, GARP (or LRRC32) and LRRC33. In some embodiments, suitable markers include mesenchymal transition genes (e.g., AXL, ROR2, WNT5A, LOXL2, TWIST2, TAGLN, and/or FAP), immunosuppressive genes (e.g., IL10, VEGFA, VEGFC), monocyte and macrophage chemotactic genes (e.g., CCL2, CCL3, CCL4, CCL7, CCL8 and CCL13), and/or various fibrotic markers discussed herein. Preferred markers are plasma markers.

In some embodiments, an LTBP complex inhibitor of TGFβ1 is used in the treatment of a disease associated with overexpression of one or more of the following: PAI-1 (encoded by Serpine1), MMP2, MMP9, MCP-1 (also known as CCL2), Col1a1, Col3a1, FN1, TGFβ1, CTGF, α-SMA, ITGA11, and ACTA2, wherein the treatment comprises administration of the inhibitor to a subject suffering from the disease in an amount effective to treat the disease. In some embodiments, the inhibitor is used to treat a disease associated with overexpression of PAI-1, MCP-1/CCL2, CTGF, and/or α-SMA. In some embodiments, the disease is myelofibrosis. In some embodiments, the disease is cancer, for example, cancer comprising a solid tumor. In some embodiments, the disease is organ fibrosis, e.g., fibrosis of the liver, the kidney, the lung, the muscle, the skin and/or the cardiac or cardiovascular tissue. In some embodiments, the disease is Alport Syndrom. In some embodiments, the inhibitor reduces expression of one or more of the following: PAI-1 (encoded by Serpine1), MMP2, MMP9, MCP-1 (also known as CCL2), Col1a1, Col3a1, FN1, TGFβ1, CTGF, α-SMA, ITGA11, and ACTA2.

Another biomarker which may be used to assess the in vivo effects of the TGFβ1 inhibitor therapy is blood urea nitrogen (BUN). Urea is naturally formed in the body as a by-product of protein breakdown. The urea travels from you liver to your kidneys where it is filtered/removed from the blood. Accordingly, BUN levels may increase in situations when a patient's kidneys are not functioning properly. For example, patients having kidney fibrosis may display increased BUN. Accordingly, in some embodiments, BUN is measured to assess the in vivo effects of the LTBP-specific inhibitors of TGFβ1 as described herein. In other embodiments, an LTBP-specific inhibitor of TGFβ1 is used in the treatment of a disease associated with increased BUN (e.g., kidney fibrosis and/or acute or chronic kidney disease, damage, or failure). In a particular embodiment, the disease associated with increased BUN is Alport Syndrome.

Accordingly, the present disclosure includes a method of selecting a candidate patient or patient population likely to respond to a TGFβ1 inhibition therapy. Such method may comprise a step of testing a biological sample collected from the patient (or patient population), such as biopsy samples, for the expression of one or more of the markers discussed herein. Similarly, such genetic marker(s) may be used for purposes of monitoring the patient's responsiveness to a therapy. Monitoring may include testing two or more biological samples collected from the patient, for example, before and after administration of a therapy, and during the course of a therapeutic regimen over time, to evaluate changes in gene expression levels of one or more of the markers, indicative of therapeutic response or effectiveness.

In some embodiments, a method of selecting a candidate patient or patient population likely to respond to a TGFβ1 inhibition therapy may comprise a step of identifying a patient or patient population previously tested for the genetic marker(s), such as those described herein, which showed aberrant expression thereof. In some embodiments, the aberrant marker expression includes elevated levels of at least one of the following: TGFβ1 (and/or TGFB1), LRRC33, GARP, LTBP1, LTBP3, CCL2, CCL3, PAI-1/Serpine1, MMP2, MMP9, Col1a1, Col3a1, FN1, CTGF, α-SMA, ITGA11, and ACTA2. In some embodiments, the patient or patient population (e.g., biological samples collected therefrom) shows elevated TGFβ1 activation, phospho-Smad2/3, or combination thereof. In some embodiments, the patient or patient population shows elevated BUN.

Combination Therapies

The disclosure further encompasses pharmaceutical compositions and related methods used as combination therapies for treating subjects who may benefit from TGFβ1 inhibition in vivo. In any of these embodiments, such subjects may receive combination therapies that include a first composition comprising at least one TGFβ1 inhibitor, e.g., antibody or antigen-binding portion thereof, described herein, in conjunction with a second composition comprising at least one additional therapeutic intended to treat the same or overlapping disease or clinical condition. The first and second compositions may both act on the same cellular target, or discrete cellular targets. In some embodiments, the first and second compositions may treat or alleviate the same or overlapping set of symptoms or aspects of a disease or clinical condition. In some embodiments, the first and second compositions may treat or alleviate a separate set of symptoms or aspects of a disease or clinical condition. To give but one example, the first composition may treat a disease or condition associated with TGFβ1 signaling, while the second composition may treat inflammation or fibrosis associated with the same disease, etc. Such combination therapies may be administered in conjunction with each other. The phrase "in conjunction with," in the context of combination therapies, means that therapeutic effects of a first therapy overlaps temporarily and/or spatially with therapeutic effects of a second therapy in the subject receiving the combination therapy. Thus, the combination therapies may be formulated as a single formulation for concurrent administration, or as separate formulations, for sequential administration of the therapies.

In preferred embodiments, combination therapies produce synergistic effects in the treatment of a disease. The term "synergistic" refers to effects that are greater than additive effects (e.g., greater efficacy) of each monotherapy in aggregate.

In some embodiments, combination therapies comprising a pharmaceutical composition described herein produce efficacy that is overall equivalent to that produced by another therapy (such as monotherapy of a second agent) but are associated with fewer unwanted adverse effect or less severe toxicity associated with the second agent, as compared to the monotherapy of the second agent. In some embodiments, such combination therapies allow lower dosage of the second agent but maintain overall efficacy. Such combination therapies may be particularly suitable for patient populations where a long-term treatment is warranted and/or involving pediatric patients.

Accordingly, the invention provides pharmaceutical compositions and methods for use in combination therapies for the reduction of TGFβ1 protein activation and the treatment or prevention of diseases or conditions associated with TGFβ1 signaling, as described herein. Accordingly, the methods or the pharmaceutical compositions further comprise a second therapy. In some embodiments, the second therapy may be useful in treating or preventing diseases or conditions associated with TGFβ1 signaling. The second therapy may diminish or treat at least one symptom(s) associated with the targeted disease. The first and second therapies may exert their biological effects by similar or unrelated mechanisms of action; or either one or both of the first and second therapies may exert their biological effects by a multiplicity of mechanisms of action.

It should be understood that the pharmaceutical compositions described herein may have the first and second therapies in the same pharmaceutically acceptable carrier or in a different pharmaceutically acceptable carrier for each described embodiment. It further should be understood that the first and second therapies may be administered simultaneously or sequentially within described embodiments.

In one embodiment, the inhibitors, e.g., antibodies, described herein that selectively binds a LTBP1-TGFβ1 complex and/or a LTBP3-TGFβ1 complex can be administered with another agent that inhibits TGFβ1 activity. For example, the second agent can be another context-specific TGFβ1 inhibitor. In one embodiment, the combination therapy comprises (i) an inhibitor, e.g., antibody or antigen-binding portion thereof, that selectively binds a LTBP1-TGFβ1 complex and/or a LTBP3-TGFβ1 complex, and (ii) an inhibitor, e.g., antibody or antigen-binding portion thereof, that selectively binds a GARP-TGFβ1 complex. In another embodiment, the combination therapy comprises (i) an inhibitor, e.g., antibody or antigen-binding portion thereof, that selectively binds a LTBP1-TGFβ1 complex and/or a LTBP3-TGFβ1 complex, and (ii) an inhibitor, e.g., antibody or antigen-binding portion thereof, that selectively binds a LRRC33-TGFβ1 complex. Context-specific antibodies that selectively bind LRRC33-TGFβ1 are described, for example, in U.S. 62/503,785, and context-specific antibodies that selectively bind GARP-TGFβ1 are described, above. The entire contents of the foregoing applications are incorporated by reference herein. In one embodiment, the combination therapy comprises (i) an inhibitor, e.g., antibody or antigen-binding portion thereof, that selectively binds a LTBP1-TGFβ1 complex and/or a LTBP3-TGFβ1 complex, and (ii) an context-independent inhibitor, e.g., antibody or antigen-binding portion thereof, that selectively binds pro/latent TGFβ1 in a complex with a presenting molecule (e.g., LTBP1/3, GARP, and/or LRRC33). Context-independent inhibitors of TGFβ1 are described, for example, in WO 2017/156500, the entire contents of which are incorporated herein by reference.

The one or more anti-TGFβ1 inhibitors, e.g., antibodies, or antigen-binding portions thereof, of the invention may be used in combination with one or more additional therapeutic agents. Examples of the additional therapeutic agents which can be used with an anti-TGFβ antibody of the invention include, but are not limited to, a myostatin inhibitor, a VEGF agonist, an IGF1 agonist, an FXR agonist, a CCR2 inhibitor, a CCR5 inhibitor, a dual CCR2/CCR5 inhibitor, a lysyl oxidase-like-2 inhibitor, an ASK1 inhibitor, an Acetyl-CoA Carboxylase (ACC) inhibitor, a p38 kinase inhibitor, Pirfenidone, Nintedanib, selonsertib, cilofexor, firsocostat, Pirfenidone, obeticholic acid, elafibranor, an anti-CD147 antibody, an anti-GP73 antibody, a Galactin-1 inhibitor, selonsertib, a caspase inhibitor (Emricasan, IDN-6556, PF-03491390), a GDF11 inhibitor, a GDF8/myostatin inhibitor, and the like. The GDF8/myostatin inhibitor is preferably a myostatin-selective inhibitor (e.g., an antibody or antigen-biding fragment). The myostatin-selective inhibitor may bind latent myostatin. Non-limiting examples of myostatin-selective inhibitors include SRK-015 (e.g., see WO2017/218592A1) and trevogrumab, or any variant thereof, or an antibody according to WO 2016/098357.

In some embodiments, the additional agent is a checkpoint inhibitor. In some embodiments, the additional agent is selected from the group consisting of a PD-1 antagonist, a PDL1 antagonist, a PD-L1 or PDL2 fusion protein, a CTLA4 antagonist, a GITR agonist, an anti-ICOS antibody, an anti-ICOSL antibody, an anti-B7H3 antibody, an anti-B7H4 antibody, an anti-TIM3 antibody, an anti-LAG3 antibody, an anti-OX40 antibody, an anti-CD27 antibody, an anti-CD70 antibody, an anti-CD47 antibody, an anti-41BB antibody, an anti-PD-1 antibody, an oncolytic virus, and a PARP inhibitor. In some embodiments, the additional therapy is radiation. In some embodiments, the additional agent is a chemotherapeutic agent. In some embodiments, the chemotherapeutic agent is Taxol. In some embodiments, the additional agent is an anti-inflammatory agent. In some embodiments, the additional agent inhibits the process of monocyte/macrophage recruitment and/or tissue infiltration. In some embodiments, the additional agent is an inhibitor of hepatic stellate cell activation. In some embodiments, the additional agent is a chemokine receptor antagonist, e.g., CCR2 antagonists and CCR5 antagonists. In some embodiments, such chemokine receptor antagonist is a dual specific antagonist, such as a CCR2/CCR5 antagonist. In some embodiments, the additional agent to be administered as combination therapy is or comprises a member of the TGFβ superfamily of growth factors or regulators thereof. In some embodiments, such agent is selected from modulators (e.g., inhibitors and activators) of GDF8/myostatin and GDF11. In some embodiments, such agent is an inhibitor of GDF8/myostatin signaling. In some embodiments, such agent is a monoclonal antibody that binds a pro/latent myostatin complex and blocks activation of myostatin. In some embodiments, the monoclonal antibody that binds a pro/latent myostatin complex and blocks activation of myostatin does not bind free, mature myostatin.

Combination therapy that includes a TGFβ inhibitor (such as TGFβ1-selective inhibitors disclosed herein), in conjunction with one or more additional therapies, may be considered for treating a variety of liver diseases. Non-limiting examples of liver diseases include: non-alcoholic fatty liver disease (NAFLD), e.g., non-alcoholic fatty liver (NAFL) and non-alcoholic steatohepatitis (NASH), which may include: noncirrhotic NASH with liver fibrosis, liver cirrhosis, NASH with compensated cirrhosis, NASH with decompensated cirrhosis, liver inflammation with fibrosis, liver inflammation without fibrosis; stage 2 and 3 liver fibrosis, stage 4 fibrosis (NASH cirrhosis or cirrhotic NASH with fibrosis), primary biliary cholangitis (PBC) (formerly known as primary biliary cirrhosis), and primary sclerosing cholangitis (PSC).

One or more of the following therapies may be used in conjunction with the TGFβ inhibitor (such as TGFβ1-selective inhibitors disclosed herein) for the treatment of a liver disease such as those listed above: Pioglitazone (PPARγ agonist); Elafibranor (PPARα/β agonist); Saroglitazar (PPARα/γ agonist); Obeticholic acid (FXR agonist); Liraglutide (GLP-1 receptor agonist); Aramchol (SCD inhibitor); Volixibat (SHP-626) (ASBT inhibitor); BMS-986036 (FGF-21 analogue); NGM-282 (FGF-19 analogue); Tesamorelin (GHRH analogue); NDI-010976 (ACC inhibitor); GS-9674 (FXR agonist); Dur-928 (Sulfated oxysterol); AZD4076 (miR-103/107 antagonist); Rosuvastatin (HMG-CoA reductase inhibitor); INT-767 (FXR/TGR5 agonist); Sevelamer (Bile acid sequestrant); Vitamin E (Antioxidant); Pentoxifylline (PDE inhibitor); Cenicriviroc (CCR2/CCR5 antagonist); Emricasan (Caspase inhibitors); GS-4997 (ASK1 inhibitor); Amlexanox (IKKε/TBK1 inhibitor); PXS-4728A (VAP-1 inhibitor); Orlistat (Intestinal lipase inhibitor); IMM-124e (IgG-rich bovine colostrum); Solithromycin (Antibiotic); Faecal microbial transplant (Modulation of gut microbiome); Simtuzumab (LOXL2 antibody);

GR-MD-02 (Galectin-3 inhibitor); Trevogrumab (myostatin inhibitor); Garetosmab (activin A inhibitor); and SRK-015 (myostatin inhibitor).

Such combination therapies may advantageously utilize lower dosages of the administered therapeutic agents, thus avoiding possible toxicities or complications associated with the various monotherapies.

Assays for Detecting a LTBP1-TGFβ1 Complex and/or a LTBP3-TGFβ1 Complex

In some embodiments, methods and compositions provided herein relate to a method for detecting a LTBP1-TGFβ1 complex and/or a LTBP3-TGFβ1 complex in a sample obtained from a subject. As used herein, a "subject" refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, poultry, a cat, or a dog. In some embodiments, the subject is a vertebrate, an amphibian, a reptile, a fish, an insect, a fly, or a nematode. In some embodiments, the subject is a research animal. In some embodiments, the subject is genetically engineered, e.g., a genetically engineered non-human subject. The subject may be of either sex and at any stage of development. In some embodiments, the subject is a patient or a healthy volunteer.

In some embodiments, a method for detecting a LTBP1-TGFβ1 complex and/or a LTBP3-TGFβ1 complex in a sample obtained from a subject involves (a) contacting the sample with an antibody that selectively binds a LTBP1-TGFβ1 complex and/or a LTBP3-TGFβ1 complex under conditions suitable for binding of the antibody to the antigen, if the antigen is present in the sample, thereby forming binding complexes; and (b) determining the level of the antibody bound to the antigen (e.g., determining the level of the binding complexes).

In one embodiment, a screening assay that utilizes biotinylated latent TGFβ1 complexes immobilized onto a surface is utilized, which allows for the activation of latent TGFβ by integrins, e.g., by providing a tether. Other, non-integrin activators could also be tested in that system. A readout can be measured through reporter cells or other TGFβ-dependent cellular responses.

Cell-Based Assays for Measuring TGFβ Activation

Activation of TGFβ (and inhibition thereof by a TGFβ test inhibitor, such as an antibody) may be measured by any suitable method known in the art. For example, integrin-mediated activation of TGFβ can be utilized in a cell-based assay, such as the "CAGA12" luciferase assay, described in more detail herein. Such an assay system may comprise the following components: i) a source of TGFβ (recombinant, endogenous or transfected); ii) a source of integrin (recombinant, endogenous, or transfected); and iii) a reporter system that responds to TGFβ activation, such as cells expressing TGFβ receptors capable of responding to TGFβ and translating the signal into a readable output (e.g., luciferase activity in CAGA12 cells or other reporter cell lines). In some embodiments, the reporter cell line comprises a reporter gene (e.g., a luciferase gene) under the control of a TGFβ-responsive promoter (e.g., a PAI-1 promoter). In some embodiments, certain promoter elements that confer sensitivity may be incorporated into the reporter system. In some embodiments, such promoter element is the CAGA12 element. Reporter cell lines that may be used in the assay have been described, for example, in Abe et al. (1994) Anal Biochem. 216(2): 276-84, incorporated herein by reference. In some embodiments, each of the aforementioned assay components are provided from the same source (e.g., the same cell). In some embodiments, two of the aforementioned assay components are provided from the same source, and a third assay component is provided from a different source. In some embodiments, all three assay components are provided from different sources. For example, in some embodiments, the integrin and the latent TGFβ complex (proTGFβ and a presenting molecule) are provided for the assay from the same source (e.g., the same transfected cell line). In some embodiments, the integrin and the TGF are provided for the assay from separate sources (e.g., two different cell lines, a combination of purified integrin and a transfected cell). When cells are used as the source of one or more of the assay components, such components of the assay may be endogenous to the cell, stably expressed in the cell, transiently transfected, or any combination thereof.

A skilled artisan could readily adapt such assays to various suitable configurations. For instance, a variety of sources of TGFβ3 may be considered. In some embodiments, the source of TGFβ3 is a cell that expresses and deposits TGFβ3 (e.g., a primary cell, a propagated cell, an immortalized cell or cell line, etc.). In some embodiments, the source of TGFβ3 is purified and/or recombinant TGFβ3 immobilized in the assay system using suitable means. In some embodiments, TGFβ3 immobilized in the assay system is presented within an extracellular matrix (ECM) composition on the assay plate, with or without de-cellularization, which mimics fibroblast-originated TGFβ3. In some embodiments, TGFβ3 is presented on the cell surface of a cell used in the assay. Additionally, a presenting molecule of choice may be included in the assay system to provide suitable latent-TGFβ complex. One of ordinary skill in the art can readily determine which presenting molecule(s) may be present or expressed in certain cells or cell types. Using such assay systems, relative changes in TGFβ3 activation in the presence or absence of a test agent (such as an antibody) may be readily measured to evaluate the effects of the test agent on TGFβ3 activation in vitro.

Such cell-based assays may be modified or tailored in a number of ways depending on the TGFβ3 isoform being studied, the type of latent complex (e.g., presenting molecule), and the like. In some embodiments, a cell known to express integrin capable of activating TGFβ3 may be used as the source of integrin in the assay. Such cells include SW480/136 cells (e.g., clone 1E7). In some embodiments, integrin-expressing cells may be co-transfected with a plasmid encoding a presenting molecule of interest (such as GARP, LRRC33, LTBP (e.g., LTBP1 or LTBP3), etc.) and a plasmid encoding a pro-form of the TGFβ3 isoform of interest (such as proTGFβ31). After transfection, the cells are incubated for sufficient time to allow for the expression of the transfected genes (e.g., about 24 hours), cells are washed, and incubated with serial dilutions of a test agent (e.g., an antibody). In some embodiments, tissue culture wells or plates may be coated with a substance that provides a favorable substrate upon which cells may adhere, grow, and/or deposit ECM components. This may facilitate ECM architecture, organization or adhesion of the cells thereto. For example, charged substances such as poly-lysine may be used to pre-coad the tissue culture substrate. Additionally or alternatively, one or more components of ECM, such as laminins, fibronectins, etc., may be used as substrate for coating. In some embodiments, the cells are seeded on ECM protein-coated wells/plates prior to transfection. In some embodiments, the cells are seeded on ECM coated wells/ plates after transfection. In some embodiments, the wells/plates are coated with fibronectin. In some embodiments, the wells/plates are coated with human fibronectin.

After transfection (and optionally seeding on ECM coated well/plates), a reporter cell line (e.g., CAGA12 cells) is added to the assay system, followed by appropriate incubation time to allow TGFβ signaling. After an incubation period (e.g., about 18-20 hours) following the addition of the test agent, signal/read-out (e.g., luciferase activity) is detected using suitable means (e.g., for luciferase-expressing reporter cell lines, the Bright-Glo reagent (Promega) can be used). In some embodiments, Luciferase fluorescence may be detected using a BioTek (Synergy H1) plate reader, with autogain settings.

Kits for Use in Alleviating Diseases/Disorders Associated with LTBP1/3-TGFβ

The present disclosure also provides kits for use in alleviating diseases/disorders associated with a TGFβ-related indication. Such kits can include one or more containers comprising an inhibitor, e.g., antibody, or antigen-binding portion thereof, that selectively binds to a LTBP1-TGFβ1 complex and/or a LTBP3-TGFβ1 complex, e.g., any of those described herein.

In some embodiments, the kit can comprise instructions for use in accordance with any of the methods described herein. The included instructions can comprise a description of administration of the inhibitor, e.g., antibody, or antigen-binding portion thereof, that selectively binds a LTBP1-TGFβ1 complex and/or a LTBP3-TGFβ1 complex to treat, delay the onset, or alleviate a target disease as those described herein. The kit may further comprise a description of selecting an individual suitable for treatment based on identifying whether that individual has the target disease. In still other embodiments, the instructions comprise a description of administering an antibody, or antigen-binding portion thereof, to an individual at risk of the target disease.

The instructions relating to the use of inhibitors, e.g., antibodies, or antigen-binding portions thereof, that selectively bind a LTBP1-TGFβ1 complex and/or a LTBP3-TGFβ1 complex generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert (e.g., a paper sheet included in the kit), but machine-readable instructions (e.g., instructions carried on a magnetic or optical storage disk) are also acceptable. The label or package insert can indicate that the composition is used for treating, delaying the onset and/or alleviating a disease or disorder associated with a TGFβ-related indication. Instructions may be provided for practicing any of the methods described herein.

The kits of this disclosure can be provided in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an inhibitor, e.g., antibody, or antigen-binding portion thereof, that selectively binds a LTBP1-TGFβ1 complex and/or a LTBP3-TGFβ1 complex, as described herein.

Kits may optionally provide additional components such as buffers and interpretive information. Normally, the kit comprises a container and a label or package insert(s) on or associated with the container. In some embodiments, the disclosure provides articles of manufacture comprising contents of the kits described above.

Diagnostics, Patient Selection, Monitoring

Therapeutic methods that include TGFβ1 inhibition therapy may comprise diagnosis of a TGFβ1 indication and/or selection of patients likely to respond to such therapy. Additionally, patients who receive the TGFβ1 inhibitor may be monitored for therapeutic effects of the treatment, which typically involves measuring one or more suitable parameters which are indicative of the condition and which can be measured (e.g., assayed) before and after the treatment and evaluating treatment-related changes in the parameters. For example, such parameters may include levels of biomarkers present in biological samples collected from the patients. Biomarkers may be RNA-based, protein-based, cell-based and/or tissue-based. For example, genes that are overexpressed in certain disease conditions may serve as the biomarkers to diagnose and/or monitor the disease or response to the therapy. Cell-surface proteins of disease-associated cell populations may serve as biomarkers. Such methods may include the direct measurements of disease parameters indicative of the extent of the particular disease. Any suitable sampling methods may be employed, such as serum/blood samples, biopsies, and imaging.

While biopsies have traditionally been the standard for diagnosing and monitoring various diseases, such as fibrosis (e.g., organ fibrosis) and proliferative disorders (e.g., cancer), less invasive alternatives may be preferred. For example, many non-invasive in vivo imaging techniques may be used to diagnose, monitor, and select patients for treatment. Thus, the invention includes the use of in vivo imaging techniques to diagnose and/or monitor disease in a patient or subject. In some embodiments, the patient or subject is receiving an isoform-specific TGFβ1 inhibitor as described herein. In some embodiments, the patient or subject is receiving an isoform-specific TGFβ1 inhibitor as described herein. In other embodiments, an in vivo imaging technique may be used to select patients for treatment with an isoform-specific TGFβ1 inhibitor. In some embodiments, such techniques may be used to determine if or how patients respond to a therapy, e.g., TGFβ1 inhibition therapy.

Exemplary in vivo imaging techniques used for the methods include, but are not limited to X-ray radiography, magnetic resonance imaging (MRI), medical ultrasonography or ultrasound, endoscopy, elastography, tactile imaging, thermography, medical photography. Other imaging techniques include nuclear medicine functional imaging, e.g., positron emission tomography (PET) and Single-photon emission computed tomography (SPECT). Methods for conducting these techniques and analyzing the results are known in the art.

Non-invasive imaging techniques commonly used to diagnose and monitor cancer include, but are not limited to: magnetic resonance imaging (MRI), computed tomography (CT), ultrasound, positron emission tomography (PET), single-photon emission computed tomography (SPECT), fluorescence reflectance imaging (FRI), and fluorescence mediated tomography (FMT). Hybrid imaging platforms may also be used to diagnose and monitor cancer. For example, hybrid techniques include, but are not limited to: PET-CT, FMT-CT, FMT-MRI, and PET-MRI. Dynamic contrast enhanced MRI (DCE-MRI) is another imaging technique commonly used to detect breast cancers. Methods for conducting these techniques and analyzing the results are known in the art.

Non-invasive imaging techniques commonly used to diagnosis and monitor fibrosis include, but are not limited to: ultrasound (e.g., conventional or contrast-enhanced ultrasound), ultrasound elastography (e.g., transient elastography, point shear wave elastography and 2D-shear wave elastography), CT scan (e.g., conventional CT or CT perfusion imaging), magnetic resonance imaging (MRI) (e.g., conventional MRI, Magnetic resonance elastography, diffusion weighted magnetic resonance imaging, gadoxetic acid disodium, and magnetic resonance perfusion imaging).

In some embodiments, non-invasive imaging techniques are used to assess levels of liver fibrosis or hepatic steatosis. For example, imaging techniques particularly useful to assess liver fibrosis may include but are not limited to: FibroScan (transient elastography; TE), point shear wave elastography (pSWE; a.k.a. acoustic radiation force impulse (ARFI)), 2D-3D SWE, magnetic resonance elastography (MRE), and multiparameteric MRI. Imaging techniques particularly useful to assess hepatic steatosis may include but are not limited to: ultrasonography, controlled attenuation parameter (CAP) elastography, MRI-estimated proton density fat fraction (MRI-PDFF), and magnetic resonance spectroscopy (MRS). In some embodiments, the in vivo imaging technique is used to assess liver stiffness. In some embodiments, the in vivo imaging technique is used to detect and assess intrahepatic triglyceride levels. In some embodiments, in vivo imaging technique is used to assess liver surface nodularity (LSN; a.k.a. "liver score"), liver stiffness, and/or liver segmental volume ratio (LSVR), which are all beneficial in the staging of hepatic fibrosis and sub-staging cirrhosis. Methods for conducting these techniques and analyzing the results are known in the art.

More recently, non-invasive imaging methods are being developed which will allow the detection of cells of interest (e.g., cytotoxic T cells, macrophages, and cancer cells) in vivo. See for example, www.imaginab.com/technology/; Tavare et al. (2014) PNAS, 111(3): 1108-1113; Tavare et al. (2015) J Nucl Med 56(8): 1258-1264; Rashidian et al. (2017) J Exp Med 214(8): 2243-2255; Beckford Vera et al. (2018) PLoS ONE 13(3): e0193832; and Tavare et al. (2015) Cancer Res 76(1): 73-82, each of which is incorporated herein by reference. So-called "T-cell tracking" is aimed to detect and localize anti-tumor effector T-cells in vivo. This may provide useful insights into understanding the immunosuppressive phenotype of solid tumors. Tumors that are well-infiltrated with cytotoxic T cells ("inflamed" or "hot" tumors) are likely to respond to cancer therapies such as checkpoint blockade therapy (CBT). On the other hand, tumors with immunosuppressive phenotypes tend to have poor T-cell infiltration even when there is an anti-tumor immune response. These so-called "immune excluded" tumors likely fail to respond to cancer therapies such as CBT. T-cell tracking techniques may reveal these different phenotypes and provide information to guide in therapeutic approach that would likely benefit the patients. For example, patients with an "immune excluded" tumor are likely benefit from a TGFβ1 inhibitor therapy to help reverse the immunosuppressive phenotype. It is contemplated that similar techniques may be used to diagnose and monitor other diseases, for example, fibrosis. Typically, antibodies or antibody-like molecules engineered with a detection moiety (e.g., radiolabel, fluorescence, etc.) can be infused into a patient, which then will distribute and localize to sites of the particular marker (for instance CD8+ and M2 macrophages).

Non-invasive in vivo imaging techniques may be applied in a variety of suitable methods for purposes of diagnosing patients; selecting or identifying patients who are likely to benefit from TGFβ1 inhibitor therapy; and/or, monitoring patients for therapeutic response upon treatment. Any cells with a known cell-surface marker may be detected/localized by virtue of employing an antibody or similar molecules that specifically bind to the cell marker. Typically, cells to be detected by the use of such techniques are immune cells, such as cytotoxic T lymphocytes, regulatory T cells, MDSCs, disease-associated macrophages, (M2 macrophages such as TAMs and FAMs), NK cells, dendritic cells, and neutrophils.

Non-limiting examples of suitable immune cell markers include monocyte markers, macrophage markers (e.g., M1 and/or M2 macrophage markers), CTL markers, suppressive immune cell markers, MDSC markers (e.g., markers for G- and/or M-MDSCs), including but are not limited to: CD8, CD3, CD4, CD11b, CD163, CD206, CD68, CD14, CD15, CD66, CD34, CD25, and CD47.

In some embodiments, the in vivo imaging technique measures hepatic steatosis, hepatic triglycerides, immune cells (e.g., as described below), and/or myofibroblasts. In some embodiments, the treatment reduces triglycerides, steatosis, liver surface nodules, inflammation, and/or macrophages, in the diseased tissue. In some embodiments, the selected patient has an intrahepatic triglyceride content of ≥5.5% of liver volume, optionally wherein the intrahepatic triglyceride content is >10% of liver volume. In some embodiments, the treatment reduces intrahepatic triglyceride content to ≤5.5% of liver volume. In some embodiments, the treatment reduces MDSCs in the diseased tissue. In some embodiments, the treatment reduces macrophages in the diseased tissue. In some embodiments, the effective amount is from 0.1 mg/kg to 30 mg/kg, optionally 3 mg/kg to 30 mg/kg. In some embodiments, the method further comprises monitoring the subject for a therapeutic response as described herein (e.g., reduced triglycerides, reduced steatosis, reduced liver surface nodules, reduced inflammation, reduced macrophages, and/or reduced liver score).

Process of Screening; Manufacture

The invention encompasses screening methods, production methods and manufacture processes of antibodies or fragments thereof which bind to and dissociates at slow rates from a hLTBP1-proTGFβ1 complex and/or a hLTBP3-proTGFβ1 complex, and pharmaceutical compositions and related kits comprising the same.

Methods for making a pharmaceutical composition comprising the antibody (or an engineered construct comprising an antigen-binding fragment thereof) require identification and selection of such antibodies with desirable attributes. Here, the invention includes the recognition that antibodies with low $k_{OFF}$ values may provide the durability that reflects the mechanism of action of these activation inhibitors, which do not rely on the ability to rapidly compete binding with endogenous receptors, but rather, exert inhibitory effects by latching onto inactive latent forms of TGFβ1 within the tissue. The ability to stay bound to the latent antigen complex (corresponding to low dissociation rates) may achieve durable potency in vivo.

Accordingly, the invention provides a method for manufacturing a pharmaceutical composition comprising a TGFβ1-selective activation inhibitor, wherein the method comprises the steps of: selecting an antibody or antigen-binding fragment thereof that specifically binds a human LLC with a low dissociation rate (e.g., ≤5×10$^{-4}$ (1/s)), and producing the antibody at large-scale.

The selection of inhibitors with favorable off rates (low dissociation) may be determined with monovalent antibodies (e.g., Fab fragments) or full-length antibodies (e.g., IgGs).

In some embodiments, the step of producing comprises a mammalian cell culture having a volume of 250 L or greater, e.g., 1000 L, 2000 L, 3000 L, 4000 L. The method may further comprise the step of purifying the antibody from the cell culture, and optionally formulating the purified antibody into a pharmaceutical composition. In some embodiments, the method further comprises the step of testing the selected antibody in a suitable preclinical model for efficacy and safety and confirming that the antibody is efficacious at a NOAEL. The safety assessment may include in vivo toxicology study comprising histopathology and immune-directed safety assessment including, for example, in vitro cytokine release assays and platelet assays.

In order to achieve durable inhibitory effects, antibodies with dissociation rates (e.g., monovalent dissociation rates) of no greater than 10.0E-4 (s$^{-1}$) (e.g., 5.0E-4 or less, 1.0E-4 or less, 5.0E-5 or less) may be selected for therapeutic use and/or large-scale manufacture in accordance with the present disclosure.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present disclosure.

The present invention is further illustrated by the following examples, which are not intended to be limiting in any way. The entire contents of all references, patents and published patent applications cited throughout this application, as well as the Figures, are hereby incorporated herein by reference.

EXAMPLES

Transforming growth factor beta 1 (TGFβ31) is expressed as a pro-protein that is proteolytically cleaved into a C-terminal growth factor and an N-terminal prodomain After cleavage, the prodomain remains noncovalently associated with the growth factor, preventing receptor binding. This latent TGFβ1 forms a large latent complex (LLC) through disulfide bonds that link the prodomain to presenting molecules, and these large latent complexes are then deposited into the extracellular matrix (ECM) or brought to the cell surface. These presenting molecules provide an anchor for specific αVβ integrins to exert traction force on latent TGFβ1. Four TGFβ1 presenting proteins have been identified: Latent TGFβ Binding Protein-1 (LTBP1) and LTBP3 are deposited in the extracellular matrix, while Glycoprotein-A Repetitions Predominant (GARP/LRRC32) and Leucine-Rich Repeat-Containing Protein 33 (LRRC33) present latent TGFβ1 on the surface of immune cells. TGFβ1 is involved in tissue homeostasis processes and regulation of immune responses, and dysregulation of its activation is a key driver of organ fibrosis, cancer, and autoimmunity.

As compared to the TGFβ growth factors and the receptors, which are expressed broadly, the four presenting molecule-proTGFβ complexes, namely, LTBP1-proTGFβ, LTBP3-proTGFβ, GARP-proTGFβ and LRRC33-proTGFβ, show more restricted or selective (e.g., tissue-specific) expression patterns, giving rise to functional compartmentalization of TGFβ activities by virtue of association. The presenting molecule-proTGFβ complexes therefore provide discrete "contexts" of TGFβ signaling within the tissue in which the presenting molecules are expressed. These contexts may be divided into two broad categories: i) TGFβ signaling associated with the ECM (e.g., matrix-associated TGFβ function); and ii) TGFβ signaling associated with cells (particularly certain immune cell function). The LTBP1-proTGFβ and LTBP3-proTGFβ complexes fall under the first category, while GARP-proTGFβ and LRRC33-proTGFβ complexes fall under the second category.

Non-selective targeting of TGFβ activity for therapeutic purposes has been challenging due to dose-limiting toxicities reported for pan-TGFβ pathway inhibitors, as well as immune system activation through chronic TGFβ suppression. In an effort to address this therapeutic need for both isoform- and context-selectivity for TGFβ1 targeting, provided herein are inhibitors of TGFβ that are capable of selectively inhibiting the activation of TGFβ that is associated with the ECM. In some embodiments, the inhibitors are also selective for a particular TGFβ isoform (e.g., proTGFβ1, proTGFβ2, and/or proTGFβ33). The isoform-specific monoclonal antibodies bind the latent TGFβ1 pro-domain, with no detectable binding to latent TGFβ2 or TGFβ3, and inhibit integrin-mediated activation of latent TGFβ1 in vitro with context-selectivity. In order to facilitate antibody discovery and characterization efforts, context-dependent cell-based assays of TGFβ1 activation were developed.

Example 1

Development of Context-Specific Inhibitors that Bind a LTBP1/3-TGFβ1 Complex SR-AB1 was used as a control. SR-AB1 binds latent TGFβ1 independent of the presenting molecule (see FIG. 2A).

Antibodies that are selective for TGFβ1-containing large latent complexes were developed. SR-AB2 was selected for further analysis using the functional assays described in the below examples. The heavy and light chain variable regions of SR-AB2 were sequenced (FIG. 8); complementarity determining regions are underlined. It was demonstrated that SR-AB2 binds LTBP-presented latent TGFβ1 complexes but does not bind GARP-TGFβ1 or proTGFβ1 alone (FIG. 2B). However, as described below, the functional effect of such selective binding was unknown and could not be determined using currently known techniques without the further development of novel functional assays.

Example 2

Functional Assays to Detect Inhibition of Activated Recombinant Latent TGFβ1

In order to identify isoform-specific inhibitors that bind the latent TGFβ1 prodomain with no detectable binding to latent TGFβ2 or TGFβ3 and that inhibit integrin-mediated activation of latent TGFβ1 in vitro with context-dependency, new functional assays were required. Prior to the instant invention, assays were not available which could detect isoform-specific TGFβ1 antibodies that bound only to LTBPs. Specifically, previous assay formats could not differentiate between the activation of proTGFβ1 presented by endogenous presenting molecules and the activation of proTGFβ1 presented by exogenous LTBPs. By directly transfecting integrin-expressing cells, the novel assays disclosed herein establish a window between endogenous presenter-proTGFβ1 activity and exogenous LTBP-proTGFβ1 activity. As LTBP-proTGFβ1 complexes are embedded in the extracellular matrix, the assay plate coating is also an important component of the assay. The use of high binding plates, coated with the ECM protein Fibronectin, made the LTBP assays more robust. In other words, prior to the instant disclosure, there was no assay window between proTGFβ1 transfection and co-transfection of LTBP1/3+proTGFβ1. Prior to the instant invention, the only available assay format was a triple co-culture system: transfectants (latent TGFβ presenting cells) +integrin expressing cells (activator) +CAGA cells (reporter). By combining the first two cell populations, and directly transfecting the integrin expressing cells with TGFβ and presenting molecules, a window for LTBP-proTGFβ1 activation was established herein.

The issue of 'bulk transfection' (i.e., transfection in a separate well/plate/dish prior to seeding in the assay well) vs 'direct transfection' (i.e., transfection in the assay well) protocol and whether an assay window is seen for LTBP complexes seems to be cell dependent in some situations. Thus, the discovery and characterization of LTBP1/3-TGFβ1 inhibitors, e.g., antibodies and antigen-binding portions thereof, would not have been possible without the development of context-dependent cell-based assays of TGFβ1 activation described herein (see also FIGS. 3A and 3B).

Specifically, to determine if the antibodies developed in Example 1 were functional, cell-based assays of αVβ integrin activation of TGFβ1 large latent complex (LLC) were developed, which are specific for each known presenting molecule: LTBP1, LTBP3, GARP and LRRC33. Through the process of assay development and optimization, it was determined that fibronectin is a critical ECM protein for the integrin-dependent in vitro activation of LTBP presented TGFβ1 LLCs. The context-independent and LTBP complex-specific TGFβ1 LLC antibodies were also validated as inhibitors of integrin-dependent activation using the below assays. Thus, the antibodies developed in Example 1 can be divided into 2 classes: antibodies which bind all TGFβ1 containing complexes (isoform-specific and context independent), and antibodies which only bind LTBP presented TGFβ1 LLC. As described in more detail herein, the development of an LTBP complex-specific class of inhibitor, which was not capable of being identified prior to the assays developed and described herein, enables a therapeutic approach for treating fibrotic indications, and could allow for chronic dosing while avoiding immune system activation due to TGFβ1 inhibition of immune suppressive cells.

Assay I. Activation of Latent TGF/β1 using SW4801/β Cells

For the assay depicted in FIG. 3A, the following protocol was developed. This assay is optimal for extracellular matrix (LTBP presented) activation by integrin cells.

Materials:
- MvLul-CAGA12 cells (Clone 4A4)
- SW480/β6 cells (Clone 1E7) (αV subunit is endogenously expressed at high levels; β6 subunit is stably overexpressed)
- Costar white walled TC treated 96 well assay plate #3903
- Greiner Bio-One High Binding white μclear 96 well assay plate #655094
- Human Fibronectin (Corning #354008)
- P200 multichannel pipet
- P20, P200, and P1000 pipets with sterile filter tips for each
- Sterile microfuge tubes and rack
- Sterile reagent reservoirs
- 0.4% trypan blue
- 2 mL, 5 mL, 10 mL, and 25 mL sterile pipets
- Tissue culture treated 100 mm or 150 mm plates
- 70% Ethanol
- Opti-MEM reduced serum media (Life Tech #31985-070)
- Lipofectamine 3000 (Life Tech #L3000015)
- Bright-Glo luciferase assay reagent (Promega #E2620)
- 0.25% Trypsin +0.53 mM EDTA
- proTGFb1 expression plasmid, human (SR005)
- LTBP1S expression plasmid, human (SR044)
- LTBP3 expression plasmid, human (SR117)
- LRRC32 (GARP) expression plasmid, human (SR116)
- LRRC33 expression plasmid, human (SR386)

Equipment:
- BioTek Synergy H1 plate reader
- TC hood
- Bench top centrifuge
- $CO_2$ incubator 37° C. 5% $CO_2$
- 37° C. water/bead bath
- Platform shaker
- Microscope
- Hemocytometer/countess Definitions:
- CAGA12 4A4 cells: Derivative of MvLul cells (Mink Lung Epithelial Cells), stably transfected with CAGA12 synthetic promoter, driving luciferase gene expression
- DMEM-0.1% BSA: Assay media; base media is DMEM (Gibco Cat #11995-065), media also contains BSA diluted to 0.1% w/v, penicillin/streptinomycin, and 4 mM glutamine
- D10: DMEM 10% FBS, P/S, 4 mM glutamine, 1% NEAA, 1× GlutaMAX (Gibco Cat#35050061)
- SW480/β6 Media: D10+1000 μg/mL G-418
- CAGA12 (4A4) media: D10+0.75 μg/mL puromycin Procedure:

On Day 0, cells were seeded for transfection. SW480/β6 (clone 1E7) cells were detached with trypsin and pelleted (spin 5 min @ 200×g). Cell pellet was resuspended in D10 media and viable cells per ml were counted. Cells were seeded at 5.0e6 cells/12ml/100 mm TC dish. For CAGA12 cells, cells were passaged at a density of 1.0 million per T75 flask, to be used for the assay on Day 3. Cultures were incubated at 37° C. and 5% $CO_2$.

On Day 1, integrin-expressing cells were transfected. Manufacturer's protocol for transfection with Lipofectamine 3000 reagent was followed. Briefly, the following were diluted into OptiMEM I, for 125 μl per well: 7.5 μg DNA (presenting molecule) +7.5 μg DNA (proTGFβ31), 30 μl P3000, and up to 125 μl with OptiMEM I. The well was mixed by pipetting DNA together, then OptiMEM was added. P3000 was added, and everything was mixed well by pipetting. A master mix of Lipofectamine3000 was made, to be added to DNA mixes: for the LTBP1 assay: 15 μl Lipofectamine3000, up to 125 μl in OptiMEM I, per well; for the LTBP3 assay: 45 μl Lipofectamine3000, up to 125 μl in OptiMEM I, per well. Diluted Lipofectamine3000 was added to DNA, mixed well by pipetting, and incubated at room temp for 15 min. After the incubation, the solution was mixed a few times by pipetting, and then 250 μl of DNA:Lipofectamine3000 (2×125 μl) per dish was added dropwise. Each dish was gently swirled to mix and the dish was returned to the tissue culture incubator for ~24 hrs.

On Days 1-2, the assay plates were coated with human fibronectin. Specifically, lyophilized fibronectin was diluted to 1 mg/ml in ultra-pure distilled water (sterile). 1 mg/ml stock solution was diluted to 19.2 μg/ml in PBS (sterile). 50 μl/well was then added to the assay plate (high binding) and incubated O/N in tissue culture incubator (37° C. and 5% $CO_2$). Final concentration was 3.0 μg/cm².

On Day 2, transfected cells were plated for assay and inhibitor addition. First, the fibronectin coating was washed by adding 200 μl well PBS to the fibronectin solution already in the assay plate. Removed wash manually with multichannel pipette. Wash was repeated for two washes total. The plate was allowed to dry at room temperature with lid off prior to cell addition. The cells were then plated by detaching with trypsin and pelleted (spin 5 min @ 200×g.). The pellet was resuspended in assay media and viable cells were counted per ml. For the LTBP1 assay cells were diluted to 0.10e6 cells/ml and seeded 50 μl per well (5,000 cells per well). For the LTBP3 assay, cells were diluted to 0.05 e6 cells/ml and seeded 50 μl per well (2,500 cells per well). To prepare functional antibody dilutions, antibodies were pre-diluted to a consistent working concentration in vehicle. Stock antibodies were serially diluted in vehicle (PBS is optimal, avoid sodium citrate buffer). Each point of serial dilution was diluted into assay media for a 4× final concentration of antibody. 25 μl of 4× antibody was added per well and cultures were incubated at 37° C. and 5% $CO_2$ for ~24 hours.

On Day 3, the TGFβ3 reporter cells were added. CAGA12 (clone 4A4) cells for the assay were detached with trypsin and pelleted (spin 5 min @ 200×g.). The pellet was resuspended in assay media and viable cells per ml were counted. Cells were diluted to $0.4e^6$ cells/ml and seeded 50 μl per well (20,000 cells per well). Cells were returned to incubator.

On Day 4, the assay was read (16-20 hours after antibody and/or reporter cell addition). Bright-Glo reagent and test plate were allowed to come to room temperature before reading. Read settings on BioTek Synergy H1 were set using TMLC_std protocol—this method has an auto-gain setting. Selected positive control wells for autoscale (high). 100 μL of Bright-Glo reagent was added per well. Incubated for 2 min with shaking, at room temperature, protected plate from light. The plate was read on BioTek Synergy H1.

In some embodiments, TGFβ3 activity associated with endogenous presenting molecules (e.g., LTBP1/3) may be assessed by only transfecting proTGFβ1 (i.e., without co-transfecting LTBP1/3). In some embodiments, the presenting molecule and proTGFβ3 DNA may be directly transfected into SW480/136 cells seeded in an assay well (i.e., "direct transfection"), rather than transfecting the cells in a separate well/dish/plate as essentially described above (i.e., "bulk transfection"). See also Assay II below for direct transfection protocol. In some embodiments, SW480/136 cells may be seeded in assay wells without fibronectin as essentially described in Assay II below.

Results:

Data generated from this assay reflected TGFβ3 activity in cell supernatants (FIG. 3A). Specifically, SW480/136 cells were bulk transfected with LTBP1/3 and proTGFβ1, and seeded on fibronectin as described above. Raw data units were relative light units (RLU). FIG. 3A demonstrates that transfection of LTBP1-proTGFβ1 and/or LTBP3-proTGFβ1, but not proTGFβ1 alone, induces a TGFβ3 activation signal.

Figure 4B:
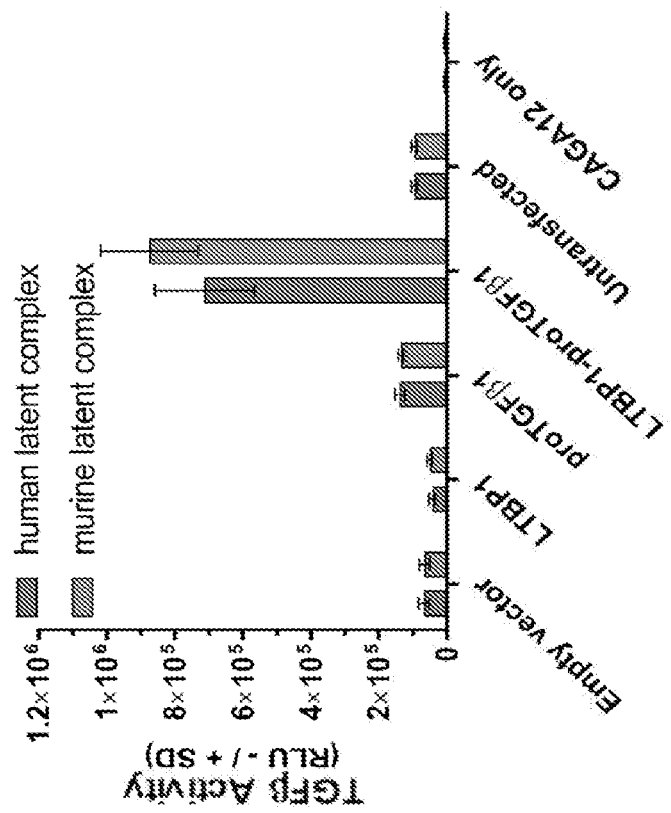

The assay was further optimized as described in FIG. 4. Specifically, the relative contribution of presenting molecule and/or proTGFβ1 to latent TGFβ1 activation was determined. In this assay, SW480/β6 cells were bulk transfected with the indicated DNA molecules and seeded on pre-coated assay wells with fibronectin as essentially described above. As shown in FIG. 4A, a significant increase in latent TGFβ1 activation upon co-transfection of presenting molecule and proTGFβ1 was observed. FIG. 4B depicts the optimization of co-transfection by changing the ratio of plasmid DNAs for presenting molecule and proTGFβ1. Equivalent amounts of each plasmid were found to be optimal for co-transfection.

FIG. 5 demonstrates that fibronectin promotes integrin activation of LTBP-presented latent TGFβ1. In this assay, SW480/β36 cells were bulk transfected with the indicated DNA molecules and seeded on pre-coated assay well with varying concentrations of fibronectin purified from human plasma. Fibronectin increased activation of latent TGFβ presented by LTBP1 and LTBP3.

Assay II. Activation of Latent TGFβ1 using LN229 cells

For the assay depicted in FIG. 3B, the following protocol was developed. This assay, or "direct-transfection" protocol, is optimal for cell-surface presented TGFβ1 (GARP or LRRC33 presenter) activation by integrin cells. LN229 cells express integrin αVβ8 (as opposed to the SW480b6 cell line, which was engineered to express αVβ6).

These two cell lines enable testing of antibodies on latent TGFβ1 activated by either of the two best validated TGFβ-activating integrins.

Materials:
- MvLu1-CAGA12 cells (Clone 4A4)
- LN229 cell line (high levels of endogenous αVβ8 integrin)
- Costar white walled TC treated 96 well assay plate #3903
- Greiner Bio-One High Binding white μclear 96 well assay plate #655094
- Human Fibronectin (Corning #354008)
- P200 multichannel pipet
- P20, P200, and P1000 pipets with sterile filter tips for each
- Sterile microfuge tubes and rack
- Sterile reagent reservoirs
- 0.4% trypan blue
- 2 mL, 5 mL, 10 mL, and 25 mL sterile pipets
- Tissue culture treated 100 mm or 150 mm plates
- 70% Ethanol
- Opti-MEM reduced serum media (Life Tech #31985-070)
- Lipofectamine 3000 (Life Tech #L3000015)
- Bright-Glo luciferase assay reagent (Promega #E2620)
- 0.25% Trypsin +0.53 mM EDTA proTGFb1 expression plasmid, human (SR005)
LTBP1S expression plasmid, human (SR044)
LTBP3 expression plasmid, human (SR117)
LRRC32 (GARP) expression plasmid, human (SR116)
LRRC33 expression plasmid, human (SR386)

Equipment:
  BioTek Synergy H1 plate reader
  TC hood
  Bench top centrifuge
  $CO_2$ incubator 37° C. 5% CO2
  37° C. water/bead bath
  Platform shaker
  Microscope
  Hemocytometer/countess Definitions:
  CAGA12 4A4 cells: Derivative of MvLul cells (Mink Lung Epithelial Cells), stably transfected with CAGA12 synthetic promoter, driving luciferase gene expression
  DMEM-0.1% BSA: Assay media; base media is DMEM (Gibco Cat #11995-065), media also contains BSA diluted to 0.1% w/v, penicillin/streptinomycin, and 4 mM glutamine
  D10: DMEM 10% FBS, P/S, 4 mM glutamine, 1% NEAA, 1× GlutaMAX (Gibco Cat#35050061)
  CAGA12 (4A4) media: D10+0.75ug/mL puromycin Procedure:
On Day 0, integrin expressing cells were seeded for transfection. Cells were detached with trypsin and pelleted (spin 5 min @ 200×g). Cell pellet was resuspended in D10 media and count viable cells per ml. Cells were diluted to $0.1e^6$ cells/ml and seeded 100 µl per well (10,000 cells per well) in an assay plate. For CAGA12 cells, passaged at a density of 1.5 million per T75 flask, to be used for the assay on Day 2. Cultures were incubated at 37° C. and 5% $CO_2$.

On Day 1, cells were transfected. The manufacturer's protocol was followed for transfection with Lipofectamine 3000 reagent. Briefly, the following was diluted into OptiMEM I, for 5 µl per well: 0.1 µg DNA (presenting molecule) +0.1 µg DNA (proTGFβ31), 0.4 µl P3000, and up to 5 µl with OptiMEM I. The well was mixed by pipetting DNA together, then add OptiMEM. Add P3000 and mix everything well by pipetting. A master mix was made with Lipofectamine3000, to be added to DNA mixes: 0.2 µl Lipofectamine3000, up to 5 µl in OptiMEM I, per well. Diluted Lipofectamine3000 was added to DNA, mixed well by pipetting, and incubated at room temp for 15 min. After the incubation, the solution was mixed a few times by pipetting, and then 10 µl per well of DNA:Lipofectamine3000 (2×5 µl) was added. The cell plate was returned to the tissue culture incubator for ~24 hrs.

On Day 2, the antibody and TGFβ3 reporter cells were added. In order to prepare functional antibody dilutions, stock antibody in vehicle (PBS is optimal) was serially diluted. Then each point was diluted into assay media for 2× final concentration of antibody. After preparing antibodies, the cell plate was washed twice with assay media, by aspirating (vacuum aspirator) followed by the addition of 100 µl per well assay media. After second wash, the assay media was replaced with 50 µl per well of 2× antibody. The cell plate was returned to the incubator for ~15-20 min.

In order to prepare the CAGA12 (clone 4A4) cells for the assay, the cells were detached with trypsin and pelleted (spin 5 min @ 200×g.). The pellet was resuspended in assay media and viable cells per ml were counted. Cells were diluted to $0.3e^6$ cells/ml and seeded 50 µl per well (15,000 cells per well). Cells were returned to incubator.

On Day 3, the assay was read about 16-20 hours after the antibody and/or reporter cell addition. Bright-Glo reagent and test plate were allowed to come to room temperature before reading. The read settings on BioTek Synergy H1 were set to use TMLC_std protocol—this method has an auto-gain setting. Positive control wells were set for autoscale (high). 100 µL of Bright-Glo reagent was added per well. Incubated for 2 min with shaking, at room temperature, protected plate from light. The plate was read on BioTek Synergy H1.

In some embodiments, TGFβ3 activity associated with endogenous presenting molecules (e.g., LTBP1/3) may be assessed by only transfecting proTGFβ1 (i.e., without co-transfecting LTBP1/3). In some embodiments, the presenting molecule and proTGFβ3 DNA may be bulk transfected into LN229 cells in a separate well/dish/plate (i.e., "bulk transfection") as essentially described above in Assay I, rather than directly transfecting the cells (i.e., "direct transfection"). In some embodiments, LN229 cells may be seeded in assay wells with fibronectin (see Assay I for fibronectin pre-coating protocol).

Data generated from this assay reflects TGFβ1 activity in cell supernatants (FIG. 3B). Specifically, LN229 cells were seeded in assay wells without fibronectin and transfected with the indicated DNA molecules by "direct transfection". Raw data units are relative light units (RLU). Samples with high RLU values contained high amounts of free TGFβ3, samples with low RLU values contained low levels of TGFβ3.

Example 3

SR-AB1 Is A Context-Independent Inhibitor of TGF/3 LLC Activation by Integrin

FIG. 6 is a graph demonstrating that SR-AB1 is a context-independent inhibitor of TGFβ1 large latent complex (LLC) by integrin. In this assay, SW480/136 cells were seeded in assay wells without fibronectin and directly transfected with GARP-proTGFβ1 or LRRC33-proTGFβ1, respectively, as essentially described in the above protocols in Example 2. To assess activation of TGFβ1 by LTBP1, LN229 cells were seeded in assay wells pre-coated with fibronectin and directly transfected with LTBP1-proTGFβ1, as essentially described in the above protocols in Example 2. SR-AB1 was shown to inhibit integrin activation of TGFβ independent of the presenting molecule.

Example 4

SR-AB2 Is A Complex-Specific Inhibitor of LTBP-proTGFβ1

SR-AB2 was selected for further analysis and testing for specificity for binding to different TGFβ presenting molecules. Initially, an ELISA assay was conducted to test complex-specificity as follows.

Materials:
  Solid white 96-well plates from the NeutrAvidin Coating of 96-Well Plates SOP
  Biotinylated antigen
  Maine Biotechnology Services Anti-His antibody MAB230P
  Jackson ImmunoResearch Laboratories Peroxidase Affinipure Goat a-human FCγ
  Fragment Specific. Catalogue number 109-035-008.

Jackson ImmunoResearch Laboratories Affinipure Goat α-mouse FCγ Fragment Specific.
Catalogue number 115-035-008
QuantaBlu ELISA Substrate (Pierce Biotech catalog number 15162)

Equipment:
Multi-channel pipette
P200 tips
Tabletop ultracentrifuge
1.5 mL centrifuge tubes
0.5 mL centrifuge tubes
P1000
P1000 tips
P200
P10
P10 tips
15 mL Falcon tubes
50 mL Falcon tubes
Biotek ELx 405 Select CW plate washer
Multidrop
Biotek Synergy H1 plate reader Definitions:
Wash buffer: TBS (Tris-Buffered Saline; 50 mM Tris-Cl, 150 mM NaCl, pH 7.6) with 0.05% Tween-20. For manual (hand) wash add 0.1% BSA as BSA is sticky and should not be used with the automated plate washer system.
Sample Buffer: TBS (Tris-Buffered Saline; 50 mM Tris-Cl, 150 mM NaCl, pH 7.6) with 0.05% Tween-20 and 0.1% BSA.
ELISA 3× protocol: Wash protocol on the Biotek ELx 405 Select CW plate washer. Washes with 2004, of wash buffer. Repeats the wash two additional times. Specifications: 3 cycles. No shaking. Dispenses 200 μL per well. Dispense flow rate setting 7 (range 1-10). Dispense height 15.24 mm Horizontal×dispense position 0 mm Horizontal y dispense position 0 mm Aspirate height 3.048 mm horizontal×aspirate position 1.372 mm horizontal aspirate y position 0.452 mm Aspiration rate 3.4 mm/second. Aspiration delay 0 milliseconds. Crosswire aspiration on final wash. Crosswire height 3.048 mm Crosswire horizontal×position: −1.829 mm Crosswire horizontal y position: −0.457 mm Procedure:
Remove a pre-coated and pre-blocked 96-well plate from 4° C. Dump out the 1×PBS pH 7.4 1% BSA with 0.1% Tween-20 from the plate and forcefully hit the plate on a Styrofoam pad lined with paper towels. If a 96-well plate is not already prepared, prepare one with the NeutrAvidin Coating of 96-Well Plates protocol. Specifically, for one NeutrAvidin coated plate, remove 5 μL from the top of the 1 mg/mL NeutrAvidin stock solution and dilute it into 10 mL of 1× carbonate buffer pH 9.4. Mix by inverting the falcon tube. Using a multi-channel pipette, place 100 μL in each well of the Corning high binding 96-well assay plate and incubate the 96-well plate overnight at 4° C. Wash the 96-well plate with 200 μL of wash buffer per well and repeat this step two additional times. The plate should be washed for a total of three times. Block the plate with 200 μL per well of 1% BSA in PBS pH 7.4 and incubate the plate for 1 hour at 37° C. or overnight at 4° C.

Dilute biotinylated antigen in sample buffer. Optimal capture concentration should first be determined by titration for each individual protein. Add 50 μl per well and incubate at room temperature for 1 hour.

Wash plates using the plate washer with wash buffer using the ELISA 3× protocol.

Dilute antibody in sample buffer. Screening of antibodies is performed at 1 μg/mL. Prepare α-His coating control antibody (Maine Biotechnology Services catalogue number: MAB230P) at 1 μg/mL in sample buffer. Place 50 μL of diluted antibody on designated wells and incubate at room temperature for 1 hour.

Wash plates using the plate washer with wash buffer using the ELISA 3× protocol.

Dilute human secondary antibody (Jackson ImmunoResearch Laboratories Peroxidase Affinipure Goat α-human FCγ Fragment Specific. Catalogue number 109-035-008) 1:10,000 in sample buffer. For α-his wells, dilute mouse secondary antibody (Jackson ImmunoResearch Laboratories Affinipure Goat α-mouse FCγ Fragment Specific. Catalogue number 115-035-008) 1:10,000 in sample buffer.

Place 50 μL of diluted antibody on designated wells. Incubate at room temperature for 1 hour. Wash plates using the plate washer with wash buffer using the ELISA 3× protocol.

Prepare SuperSignal ELISA Femto Substrate (Pierce Biotech catalog number 15162) working solution according to manufacturer's protocol. 10 mL will be needed for one plate. Place 100 μL QuantBlu Substrate working solution per well. Incubate for 10 minutes at room temperature.

Measure relative fluorescent units (RFU's) on a plate reader with an excitation of 325 nm and emission of 420 nm.

Figure 7A:
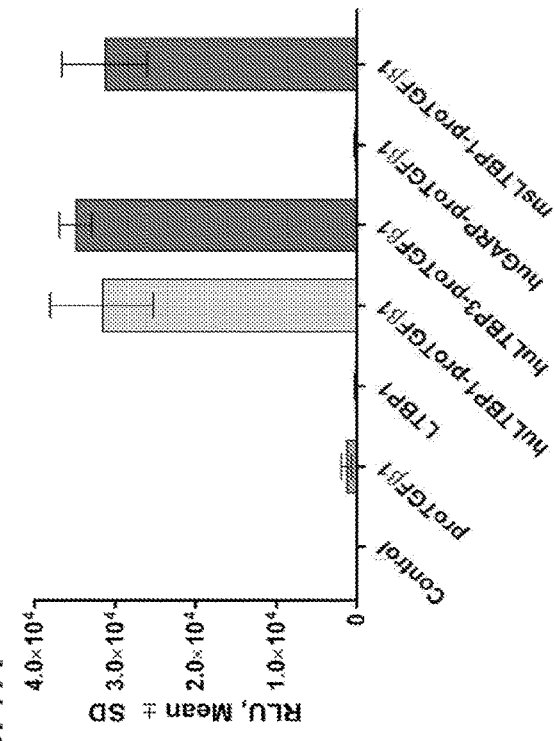
FIGS. 7A, 7B, and 7C present data confirming LTBP-selective inhibition of TGFβ1 large latent complex (LLC).

Results:
FIG. 7A demonstrates that SR-AB2 only binds LTBP-proTGFβ1 complex; it does not bind proTGFβ1 or LTBP1 alone by ELISA. FIG. 7A demonstrates that SR-AB2 does not bind GARP-proTGFβ1 by ELISA.

Figure 7C:
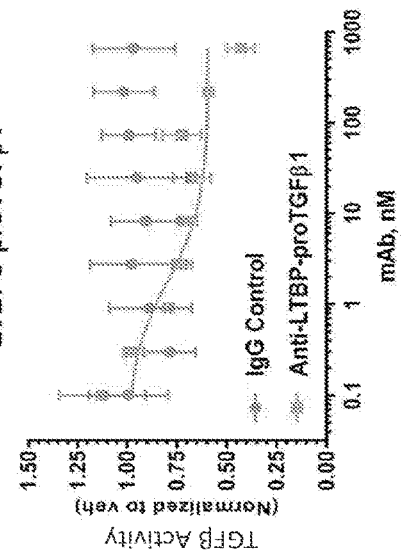
Figure 7B:
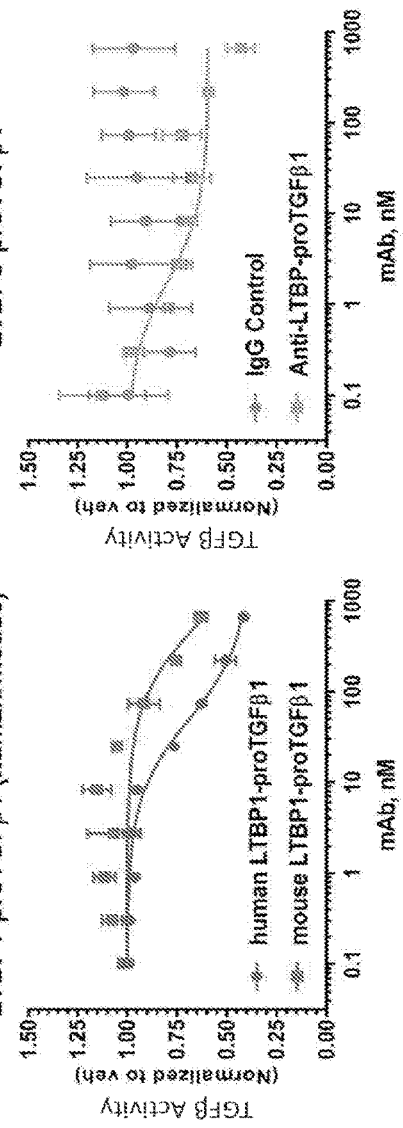

Additionally, the ability of SR-AB2 to inhibit LTBP1/3-proTGFβ1 in a cell-based assay was also conducted. As essentially described above in Example 2, LN229 cells were seeded on fibronectin pre-coated assay wells and directly transfected with the indicated DNA molecules. FIG. 7B depicts that SR-AB2 inhibits integrin activation of LTBP1-proTGFβ1 (human and mouse complexes). FIG. 7C depicts that SR-AB2 inhibits integrin activation of LTBP3-proTGFβ1.

It was demonstrated that SR-AB2 specifically binds to proTGFβ1:LTBP1 & 3 complexes, and not GARP-TGFβ1 or GARP-Lap complexes by ELISA as essentially described above (see FIG. 9).

As discussed above, LTBP1 and LTBP3 are deposited in the extracellular matrix, while GARP/LRRC32 and LRRC33 present latent TGFβ1 on the surface of immune cells. It was demonstrated that SR-AB2 inhibits LTBP-proTGFβ1 signaling, but does not affect GARP-proTGFβ1 (FIG. 10A and FIG. 10B). FIG. 10A demonstrates that SR-AB2 inhibits LTBP-proTGFβ presented by endogenous LTBP1/3. This assay was performed in LN229 cells, which were seeded on fibronectin pre-coated wells and directly transfected with proTGFβ1. FIG. 10B demonstrates that SR-AB2 does not inhibit GARP-proTGFβ. SR-AB1 binds latent TGFβ1 independent of the presenting molecule. This assay was performed in LN229 cells, were seeded in assay wells without fibronectin and directly transfected with GARP-proTGFβ1.

Inhibition of LTBP-proTGFβ1 by SR-AB2 was also shown in αVβ6 Integrin-dependent activation of LTBP1-presented TGFβ1 in cell-based assays (human and mouse, data not shown). SR-AB2 showed no inhibitory effects on overexpressed LRRC33-proTGFβ1.

Example 5

Octet Binning of LTBP1-proTGF A1 Antibodies 500 nM of human LTBP1-proTGFb1 complex was pre-incubated with 1 μM of each test antibody. After an overnight incubation, the LTBP1-proTGFβ1+first antibody was tested for binding to a second antibody which was immobilized to an Anti-Human IgG Fc Capture (AHC) sensor tip at 67 nM. The sensor tip was blocked with a negative control antibody (HuNeg) before seeing the LTBP1-proTGFβ1+first antibody.

Binding of the complex to a specific second antibody was normalized to the uninhibited interaction, that is the complex in the presence of a negative control antibody (HuNeg) that does not bind to the TGFβ complex. Normalized responses less than 70% or less than 0.7 of the uninhibited interaction were considered antibodies that cross block. A response greater than 1 indicated that both antibodies were bound simultaneously. The results are shown in Table 7, below.

TABLE 7

|  | SR-AB13 | SR-AB10 | SR-AB2 | SR-AB1 | Second Antibody |
|---|---|---|---|---|---|
| SR-AB13 | 0.47 | 1.38 | 1.29 | 1.08 | |
| SR-AB10 | 1.27 | 0.51 | 1.53 | 0.82 | |
| SR-AB2 | 1.31 | 1.54 | 0.47 | 1.11 | |
| SR-AB1 | 1.43 | 0.76 | 1.38 | 0.69 | |
| HuNeg First Antibody | 1 | 1 | 1 | 1 | |

As shown in Table 7, antibodies SR-AB13, SR-AB10, SR-AB2 and SR-AB1 do not cross block each other, and therefore each antibody occupies a distinct epitope on the surface of human LTBP1-proTGFβ1.

Example 6

In Vitro Binding Profile and Affinity Data

Suitable methods for in vitro binding assays to determine the parameters of binding kinetics include Bio-layer Interferometry (BLI)-based assays such as Octet, and surface plasmon resonance (SPR)-based assays, such as Biacore systems (see, for example: http://www.biophysics.bioc.cam.ac.uk/wp-content/uploads/2011/02/Biacore_assay_handbook.pdf).

The affinity of SR-AB10, SR-AB2 and SR-AB13 was measured by Octet assay. The protocol used to measure the affinity of the antibodies to the complexes provided herein is summarized below.

Materials:
  96 well black polypropylene plates
  AHC Octet tips (anti-human IgG Fc capture tips) (ForteBio)
  10× kinetics buffer (ForteBio) (diluted to 1× in PBS)
  reiner Bio-One 96-Well Half Area Microplates (VWR cat #82050-044)

Procedure:
  Notes: The volume within each well during an Octet experiment is 100 uL. A shake speed of 1000 rpm is used for all assay steps.

Pre-Wet Tips:
  Biosensors must be pre-wet in 1×kinetics buffer (1×KB) for at least 10 minutes before starting an experiment. This can be done inside the Octet or on the bench.

Loading:
  Tips are baselined in 1×KB for 1 minute before loading.
  AHC tips are loaded with antibody at a concentration of 1 μg/mL (~7 nM) for 3 minutes. A limit is set so that loading will stop when any one sensor reaches a response of 1 nanometer.
  Tips are baselined in buffer for 1 minute after loading. The antibody should not dissociate from the tips during this time.

Antigen Association:
  TGFβ1 in complex with various presentation molecules was associated to the immobilized antibodies at a single concentration of 100 nM in 1×KB.

Antibody Dissociation:
  Dissociation in 1×KB was performed for 3 minutes.
  Data Analysis using ForteBio Data analysis software 8.2:
  Processing: align Y axis to last 5 seconds of baseline, perform inter-step correction with align to dissociation, and perform Savitzky-Golay filtering.
  Analysis: 1:1 fitting model is utilized. Fitting is local and full. (Local indicates each antibody is evaluated separately and full indicates that both association and dissociation are considered) Fit the curves and then save the report/export the data.

Results:
  FIG. 11 presents the binding profile and affinity data for LTBP complex-specific antibodies SR-AB10, SR-AB2, and SR-AB13. Notably, SR-AB13 binds both human LTBP1 and human LTBP3 complexed with proTGFβ1, while SR-AB2 and SR-AB10 are specific to human LTBP1 complexed with TGFβ1.

Example 7

Improved Potency of Optimized LTBP-Complex-Specific Antibodies

LTBP complex-specific antibodies SR-AB10 and SR-AB13 were selected for an initial round of affinity maturation/optimization (i.e., H1/H2 CDR shuffling/diversification as described herein) and particular progeny antibodies (SR-AB14 and SR-AB15) were assessed for their ability to inhibit TGFβ activity using LN229 cells. For the assays depicted in FIGS. 12A and 12B, the following protocol was used, which is a modified version of Assay II in Example 2.

Materials:
  MvLu1-CAGA12 cells (Clone 4A4)
  LN229 cell line (high levels of endogenous αVβ8 integrin)
  Costar white walled TC treated 96 well assay plate #3903
  Greiner Bio-One High Binding white μclear 96 well assay plate #655094
  Human Fibronectin (Corning #354008)
  P200 multichannel pipet
  P20, P200, and P1000 pipets with sterile filter tips for each
  Sterile microfuge tubes and rack
  Sterile reagent reservoirs
  0.4% trypan blue
  2 mL, 5 mL, 10 mL, and 25 mL sterile pipets
  Tissue culture treated 100 mm or 150 mm plates
  70% Ethanol
  Opti-MEM reduced serum media (Life Tech #31985-070)
  Lipofectamine 3000 (Life Tech #L3000015)

Bright-Glo luciferase assay reagent (Promega #E2620)
0.25% Trypsin +0.53 mM EDTA
proTGFb1 expression plasmid, human
LTBP1S expression plasmid, human Equipment:
   PerkinElmer EnVision plate reader
   TC hood
   Bench top centrifuge
   $CO_2$ incubator 37° C. 5% CO2
   37° C. water/bead bath
   Platform shaker
Microscope
   Hemocytometer/countess
Definitions:
   CAGA12 4A4 cells: Derivative of MvLul cells (Mink Lung Epithelial Cells), stably transfected with CAGA12 synthetic promoter, driving luciferase gene expression
   DMEM-0.1% BSA: Assay media; base media is DMEM (Gibco Cat #11995-065), media also contains BSA diluted to 0.1% w/v, penicillin/streptinomycin, and 4 mM glutamine
   D10: DMEM 10% FBS, P/S, 4 mM glutamine, 1% NEAA, 1× GlutaMAX (Gibco Cat#35050061)
   CAGA12 (4A4) media: D10+0.75ug/mL puromycin
Procedure:
   Always work in sterile biosafety cabinet, and sterile technique should be used at all times.
   Prepare all media, sterilize all materials, and move materials into biosafety cabinet before starting.
   Growth medium should be warmed to 37° C.
   Use the reverse pipetting technique for almost all steps during this assay.
   Assays that rely on LTBP presentation of proTGFβ1 require pre-coating of assay plates with fibronectin, for 4 hrs—overnight prior to seeding cells for transfection.

On day −1, assay plates were coated with Fibronectin. A 1 mg/ml stock solution of fibronectin was prepared in ultrapure water (sterile). Stock solution was diluted in PBS to 19.2 µg/ml working solution and 50 µl was added to each well (3 µg/cm$^2$). Plates were incubated at 37° C. and 5% $CO_2$ overnight.

On day 0, prior to cell seeding, assay plates were coated with Fibronectin (LTBP over expression assay only). A 1 mg/ml stock solution of fibronectin was prepared in ultrapure water (sterile). Stock solution was diluted in PBS to 19.2 µg/ml working solution and 50 µl was added to each well (3 µg/cm$^2$). Plates were incubated at 37° C. and 5% $CO_2$ for 4 hours. Following coating, assay plates were washed manually with multichannel pipette for 2 washes of 200 µl/well PBS. After final wash, plates were allowed to dry in the hood with lid off. LN229 cells were then detached with trypsin and pelleted (spun for 5 min at 200×g). The cell pellet was resuspended in D10 media and viable cells per ml counted. Cells were diluted to 0.125e$^6$ cells/ml and seeded 100 µl per well (12,500 cells per well) in an assay plate. For CAGA12 cells to be used for assay on Day 2, cells passaged at a density of 1.5 million per T75 flask. Cultures were incubated at 37° C. and 5% $CO_2$.

On Day 1, LN229 cells were transfected. The manufacturer's protocol was followed for transfection with Lipofectamine 3000 reagent. Briefly, the following was diluted into OptiMEM I, for 5 µl per well: 0.1 µg DNA (proTGFβ31), optionally 0.1 µg LTBP1 DNA, 0.4 µl P3000, and up to 5 µl with OptiMEM I. For FIG. 12A, 0.1 µg proTGFβ1 (human) DNA was transfected alone, without LTBP DNA, to measure activation in the presence of endogenous presenting molecules. For FIG. 12B, 0.1 µg LTBP1 (human) DNA was co-transfected with the proTGFβ1 (human) DNA to measure activation in the presence of overexpressed LTBP1.

A master mix of Lipofectamine3000 was made by diluting 0.41 Lipofectamine3000 in OptiMEM I, up to 5 µl in OptiMEM I, per well. Diluted Lipofectamine3000 was added to the DNA mixture, mixed well by pipetting, and incubated at room temperature for 15 min. After the incubation, 10 µl of DNA:Lipofectamine3000 (2×5 µl) mixture was added to each well. Plates were returned to the tissue culture incubator for ~24 hrs.

On day 2 the indicated antibodies and TGFβ reporter cells (CAGA12) were added to the wells. Antibodies were serially diluted into PBS, then further diluted into assay media until 2× final concentration. Plates were washed twice with assay media by aspirating (vacuum aspirator) followed by addition of 100 µl per well assay media. After second wash, assay media was replaced with 50 per well of 2× antibody. Cell plate was returned to the incubator for ~15-20 min. CAGA12 (clone 4A4) cells were detached with trypsin and pelleted (spun 5 min at 200×g.). Pellet was resuspended in assay media and viable cells counted. Viable cells were diluted to 0.3e$^6$ cells/ml and seeded 50 µl per well (15,000 cells per well). Cells were returned to the incubator.

On Day 3, the assay was read about 16-20 hours after the antibody and/or reporter cell addition. Bright-Glo reagent and test plate were allowed to come to room temperature before reading. The read settings on BioTek Synergy H1 were set to use TMLC_std protocol—this method has an auto-gain setting. Positive control wells were set for autoscale (high). 100 µL of Bright-Glo reagent was added per well. Incubated for 2 min with shaking, at room temperature, protected plate from light. The luminescence was then detected on a plate reader.

Results:

Data generated from this assay reflected TGFβ activity in cell supernatants. FIG. 12A is a graph showing improved potency of SR-AB14 (optimized SR-AB10) as measured by TGFβ activity. Notably, SR-AB14 activity is similar to the context-independent antibody SR-AB 1. This assay was performed without overexpressing LTBP1 and thus measures activation of TGFβ in the presence of endogenous presenting molecules. FIG. 12B is a graph showing improved potency of SR-AB15 (optimized SR-AB13) as measured by TGFβ activity. This assay was performed in the presence of overexpressed human LTBP1-pro TGFβ1. Notably, SR-AB14 activity is similar to the context-independent antibody SR-AB 1.

The assays depicted in FIGS. 12A and 12B were both performed in LN229 cells, which express low LTBP1 mRNA, high LTBP3 mRNA, undetectable GARP, and undetectable LRRC33.

Example 8

Improved Affinity of Optimized LTBP-proTGF 1-Specific Antibodies after CDR-H3 Mutagenesis LTBP complex-specific antibodies from the first round of affinity maturation/optimization (SR-AB14, SR-AB16, SR-AB17, SR-AB18, SR-AB19) were selected for a second round of affinity maturation/optimization (i.e., CDR-H3 mutagenesis as described herein) and particular progeny antibodies (SR-AB20, SR-AB21, SR-AB22, SR-AB23, SR-AB24, SR-AB25, SR-AB26, SR-AB27, SR-AB28, and SR-AB29) were assessed for their ability to bind various proTGFβ1 constructs. Binding affinities of the optimized antibodies were measured by Octet against human LTBP1-proTGFβ1, human LTBP3-proTGFb1, mouse LTBP1-proTGFβ1, mouse LTBP3-proTGFb1, and GARP-proTGFβ1 complexes, essentially as described in Example 6. In brief, test antibodies were immobilized to the surface of anti-human Fc capture biosensors (AHC) (ForteBio®) and binding was then tested against the various TGFβ1 complexes at a single concentration of 100 nM to assess binding affinities. The antigens were allowed to associate for 3 minutes followed by a 5-minute dissociation. Kinetics buffer (ForteBio®) was used throughout the experiment, and $K_D$ was determined using a 1:1 fitting model for each antibody antigen pair.

Table 8 presents the binding profile and affinity data for the indicated LTBP complex-specific antibodies (IgGβ1-agly) determined by Octet. Notably, optimized antibodies SR-AB20, SR-AB21, SR-AB22, SR-AB23, SR-AB24, SR-AB25, SR-AB26, SR-AB27, SR-AB28, and SR-AB29 display single digit nM affinity for both human LTBP1 and human LTBP3 complexed with proTGFβ1. Additionally, none of the antibodies bound human GARP complexed with proTGFβ1 indicating that the antibodies are specific for LTBP complexes.

TABLE 8

| Ref | Lineage | ForteBio IgG $K_D$ Hu LTBP1-proTGFβ1 (M) Avid | ForteBio IgG $K_D$ Hu LTBP3-proTGFβ1 (M) Avid | ForteBio IgG $K_D$ Mo LTBP1-proTGFβ1 (M) Avid | ForteBio IgG $K_D$ Hu LTBP1-proTGFβ1 (M) Avid | ForteBio IgG $K_D$ Hu GARP-proTGFβ1 (M) Avid |
|---|---|---|---|---|---|---|
| SR-AB10 |  | P.F. | N.B. | 1.42E−08 | 2.30E−08 | N.B. |
| SR-AB16 | SR-AB 10 | 3.44E−08 | 1.69E−08 | 3.29E−08 | 2.12E−08 | N.B. |
| SR-AB14 | SR-AB 10 | 2.44E−08 | 1.46E−08 | 2.04E−08 | 1.23E−08 | N.B. |
| SR-AB20 | SR-AB16 | 3.93E−09 | 2.08E−09 | 6.46E−09 | 2.23E−09 | N.B. |
| SR-AB21 | SR-AB16 | 6.78E−09 | 1.08E−09 | 1.06E−08 | 3.29E−08 | N.B. |
| SR-AB22 | SR-AB14 | 1.88E−09 | P.F. | 2.43E−09 | 1.56E−09 | P.F. |
| SR-AB23 | SR-AB14 | 5.98E−09 | 1.26E−09 | 8.38E−09 | 7.93E−09 | N.B. |
| SR-AB13 |  | 3.92E−08 | 3.59E−08 | 5.95E−08 | N.B. | N.B. |
| SR-AB17 | SR-AB13 | 6.16E−09 | 5.28E−09 | 8.83E−09 | 5.36E−08 | N.B. |
| SR-AB18 | SR-AB13 | 9.27E−09 | 1.17E−08 | 1.45E−08 | 8.66E−08 | N.B. |
| SR-AB19 | SR-AB13 | 1.10E−08 | 1.64E−08 | 1.59E−08 | 8.40E−08 | N.B. |
| SR-AB24 | SR-AB17 | 1.74E−09 | 1.27E−09 | 2.07E−09 | 7.85E−08 | N.B. |
| SR-AB25 | SR-AB17 | 2.37E−09 | 1.05E−09 | 2.92E−09 | 3.88E−08 | N.B. |
| SR-AB26 | SR-AB17 | 2.73E−09 | 2.13E−09 | 3.73E−09 | 1.38E−08 | N.B. |
| SR-AB27 | SR-AB18 | 2.70E−09 | 2.33E−09 | 3.89E−09 | 5.11E−07 | N.B. |
| SR-AB28 | SR-AB18 | 2.84E−09 | 2.70E−09 | 4.52E−09 | 1.25E−08 | N.B. |
| SR-AB29 | SR-AB19 | 4.23E−09 | 4.08E−09 | 7.22E−09 | 7.91E−08 | N.B. |

P.F. = Poor Fit
N.B. = Non-binder under conditions of this assay

Example 9

Improved Affinity of Optimized LTBP-Complex-specific Antibodies after Light Chain Optimization Cycle 3

LTBP complex-specific antibodies from the second round of affinity maturation/optimization were selected for a third round of affinity maturation/optimization (i.e., light chain optimization as described herein) and particular progeny antibodies, were assessed for their ability to bind various proTGFβ1 constructs.

Cycle 3 antibodies were generated by performing mutagenesis throughout the light chain CDR3 and performing a shuffle of premade sequences for the light chain CDR1 and CDR2. Antibodies of interest were identified through yeast display utilizing both positive and negative selections followed by sequencing.

Binding affinities of the optimized antibodies were measured by Octet against human LTBP1-proTGFβ1, human LTBP3-proTGFβ1, mouse LTBP1-proTGFβ1, mouse LTBP3-proTGFβ1, and GARP-proTGFβ1 complexes, essentially as described in Example 6. In brief, test antibodies were immobilized to the surface of anti-human Fc capture biosensors (AHC) (ForteBio®) and binding was then tested against the various TGFβ1 complexes at a single concentration of 100 nM to assess binding affinities. The antigens were allowed to associate for 3 minutes followed by a 5-minute dissociation. Kinetics buffer (ForteBio®) was used throughout the experiment, and KD was determined using a 1:1 fitting model for each antibody antigen pair.

Table 9 presents the binding profile and affinity data for the indicated LTBP complex-specific antibodies (IgG1-agly) identified from the light chain optimization cycle 3, determined by Octet. Notably, several optimized antibodies display single digit nM affinity for both human LTBP1 and human LTBP3 complexed proTGFβ1. Additionally, as shown in Table 10, several antibodies did not bind human GARP complexed with proTGFβ1, under the same assay conditions, indicating that the antibodies are specific for LTBP complexes.

FIG. 15 shows the 200 nM values, where the 0.1 nm cutoff is used to determine what is and what is not meaningful binding. As shown in FIG. 15, for some antibodies, binding to GARP-proTGFβ1 is meaningful only at very high concentrations (200 nM), and some antibodies show no binding to GARP-proTGFβ1 even at that high concentration.

Surface Plasmon Resonance (SPR)-Based Assays

A Biacore 8K system was employed to determine the monovalent binding affinity and the kinetic parameters for antigen binding of test antibodies. Association and disso-

TABLE 9

Binding Profile and Affinity Data for Cycle 3 Optimized Antibodies (N.B. = non-binder under conditions of this assay)

| Ref | Optimization Lineage | ForteBio IgG $K_D$ Hu LTBP1-proTGFβ1 (M) Avid | Hu LTBP1-proTGFβ1 Kon (1/Ms) | Hu LTBP1-proTGFβ1 Koff (1/s) | Fortebio IgG $K_D$ Hu LTBP3-proTGFβ1 (M) Avid | Hu LTBP3-proTGFβ1 Kon (1/Ms) | Hu LTBP3-proTGFβ1 Koff (1/s) | ForteBio IgG $K_D$ Mo LTBP1-proTGFβ1 (M) Avid | ForteBio IgG $K_D$ Mo LTBP3-proTGFβ1 (M) Avid | ForteBio IgG $K_D$ Hu GARP-proTGFβ1 (M) Avid |
|---|---|---|---|---|---|---|---|---|---|---|
| SR-AB30 | SR-AB22 | 2.17E−10 | 2.77E+05 | 6.00E−05 | 1.56E−10 | 3.85E+05 | 6.00E−05 | 4.38E−10 | 4.21E−10 | 1.09E−08 |
| SR-AB31 | SR-AB22 | 4.12E−10 | 2.40E+05 | 9.89E−05 | 2.21E−10 | 3.08E+05 | 6.81E−05 | 6.82E−10 | 5.89E−10 | 1.12E−08 |
| SR-AB32 | SR-AB22 | 3.22E−10 | 2.83E+05 | 9.14E−05 | 1.49E−10 | 4.02E+05 | 6.00E−05 | 4.85E−10 | 4.18E−10 | 1.09E−08 |
| SR-AB33 | SR-AB22 | 5.61E−10 | 3.02E+05 | 1.69E−04 | 2.72E−10 | 4.45E+05 | 1.21E−04 | 8.67E−10 | 4.78E−10 | 1.61E−08 |
| SR-AB34 | SR-AB22 | 2.31E−10 | 2.59E+05 | 6.00E−05 | 1.79E−10 | 3.72E+05 | 6.68E−05 | 4.17E−10 | 4.50E−10 | 7.35E−08 |
| SR-AB35 | SR-AB22 | 3.15E−10 | 3.42E+05 | 1.08E−04 | 1.41E−10 | 4.85E+05 | 6.85E−05 | 3.89E−10 | 3.98E−10 | 6.66E−09 |
| SR-AB36 | SR-AB22 | 2.54E−10 | 2.89E+05 | 7.34E−05 | 1.46E−10 | 4.10E+05 | 6.00E−05 | 3.35E−10 | 4.29E−10 | 9.55E−09 |
| SR-AB37 | SR-AB22 | 3.28E−10 | 3.60E+05 | 1.18E−04 | 1.39E−10 | 5.45E+05 | 7.58E−05 | 3.84E−10 | 3.25E−10 | 3.61E−08 |
| SR-AB38 | SR-AB22 | 3.57E−10 | 3.27E+05 | 1.17E−04 | 1.45E−10 | 5.02E+05 | 7.26E−05 | 3.91E−10 | 3.31E−10 | 8.42E−09 |
| SR-AB39 | SR-AB22 | 2.05E−10 | 2.92E+05 | 6.00E−05 | 1.36E−10 | 4.41E+05 | 6.00E−05 | 2.32E−10 | 3.42E−10 | 3.89E−07 |
| SR-AB40 | SR-AB23 | 4.01E−10 | 1.50E+05 | 6.00E−05 | 3.33E−10 | 1.82E+05 | 6.07E−05 | 1.08E−09 | 1.16E−09 | N.B. |
| SR-AB41 | SR-AB23 | 2.96E−10 | 2.03E+05 | 6.00E−05 | 2.35E−10 | 2.55E+05 | 6.00E−05 | 4.04E−10 | 7.17E−10 | 7.64E−07 |
| SR-AB42 | SR-AB23 | 3.89E−10 | 1.54E+05 | 6.00E−05 | 2.59E−10 | 2.32E+05 | 6.00E−05 | 3.59E−10 | 1.05E−09 | N.B. |
| SR-AB43 | SR-AB23 | 6.49E−10 | 2.44E+05 | 1.59E−04 | 1.78E−10 | 3.37E+05 | 6.00E−05 | 7.31E−10 | 8.91E−10 | N.B. |
| SR-AB44 | SR-AB23 | 2.14E−10 | 2.80E+05 | 6.00E−05 | 1.46E−10 | 4.10E+05 | 6.00E−05 | 2.10E−10 | 4.07E−10 | 2.12E−07 |
| SR-AB45 | SR-AB23 | 1.93E−10 | 3.10E+05 | 6.00E−05 | 1.22E−10 | 4.91E+05 | 6.00E−05 | 1.93E−10 | 2.69E−10 | 1.95E−07 |
| SR-AB62 | SR-AB24 | 4.86E−10 | 1.40E+05 | 6.82E−05 | 3.68E−10 | 2.03E+05 | 7.47E−05 | 6.09E−10 | 3.37E−09 | N.B. |
| SR-AB63 | SR-AB26 | 6.11E−10 | 1.18E+05 | 7.24E−05 | 4.94E−10 | 1.59E+05 | 7.84E−05 | 1.09E−09 | 2.00E−09 | N.B. |
| SR-AB64 | SR-AB26 | 4.67E−10 | | | 4.71E−10 | 1.95E+05 | 9.18E−05 | 1.03E−09 | 2.85E−09 | N.B. |
| Human IgG1 isotype control | N.A. | N.B. | | | N.B. | | | N.B. | N.B. | N.B. |

TABLE 10

| Ref | VHCDR3 Lineage | ForteBio IgG $K_D$ Hu GARP-proTGFβ1 in solution (M) Avid |
|---|---|---|
| SR-AB30 | SR-AB10 | 1.09E−08 |
| SR-AB31 | SR-AB10 | 1.12E−08 |
| SR-AB32 | SR-AB10 | 1.09E−08 |
| SR-AB33 | SR-AB10 | 1.61E−08 |
| SR-AB34 | SR-AB10 | 7.35E−08 |
| SR-AB35 | SR-AB10 | 6.66E−09 |
| SR-AB36 | SR-AB10 | 9.55E−09 |
| SR-AB37 | SR-AB10 | 3.61E−08 |
| SR-AB38 | SR-AB10 | 8.42E−09 |
| SR-AB39 | SR-AB10 | 3.89E−07 |
| SR-AB40 | SR-AB10 | N.B. |
| SR-AB41 | SR-AB10 | 7.63909E−07 |
| SR-AB42 | SR-AB10 | N.B. |
| SR-AB43 | SR-AB10 | N.B. |
| SR-AB44 | SR-AB10 | 2.1153E−07 |
| SR-AB45 | SR-AB10 | 1.95124E−07 |
| SR-AB62 | SR-AB13 | N.B. |
| SR-AB63 | SR-AB13 | N.B. |
| SR-AB64 | SR-AB13 | N.B. |
| Human IgG1 isotype control | N.A. | N.B. |

N.B. = non-binder under conditions of this assay

FIG. 15 shows that affinity matured antibodies show specific binding to the LTBP-proTGFβ1 complex. This experiment was performed at 200, 100, 50, and 25 nM human GARP proTGFb1 and human LTBP1 proTGFb1.

ciation kinetics of Fab fragments SR-AB42-HuFab, SR-AB63-HuFab and SR-AB43-HuFab to antigen complexes were measured, and resulting ka, kd and KD are provided below. Briefly, the binding kinetics were evaluated by surface plasmon resonance using Biacore 8K (GE Healthcare). Biotinylated capture antigens were immobilized to the chip (10 nM, ~200 RU loading). A Biotin CAPture sensor chip was used to capture the biotinylated antigens. Fabs at 10, 5, 2.5, 1.25, and 0.6 nM concentrations were injected over the captured antigens. 0 nM was used as a reference. Affinities of LTBP antibodies to GARP and LRRC33 were confirmed using higher concentration of Fabs (100, 50, 25, 12.5, 6.25 nM). 0 nM was used as a reference. Multi-cycle kinetics was employed where each analyte concentration was injected in a separate cycle and the sensor chip surface was regenerated after each cycle. All the assays were carried out in freshly prepared 1× HBS-EP+buffer (10 mM HEPES, 150 mM NaCl, 3 mM EDTA, 0.05% Tween20, pH 7.4). Data were fit globally to a 1:1 binding model to obtain the kinetic parameters. The sensorgram for 0 nM analyte concentration was used as reference.

Results are shown in Tables 11-15 below. FIG. 23 and FIG. 24, respectively, show that SR-AB63 and SR-AB42 human Fabs show context-selective binding of novel antibodies for huLTBP1 proTGFβ1 and huLTBP3 proTGFβ1.

TABLE 11

| | huLTBP1 proTGFβ1 | | |
|---|---|---|---|
| | ka (1/Ms) | kd (1/s) | KD (M) |
| SR-AB42-HuFab* | 5.43E+05 | 1.05E-04 | 1.94E-10 |
| SR-AB63-HuFab** | 3.71E+05 | 3.82E-08 | 1.03E-13 |
| SR-AB43-HuFab | 1.03E+06 | 2.84E-04 | 2.76E-10 |
| SR-AB46-HuFab | 2.47E+06 | 1.10E-04 | 4.44E-11 |
| SR-AB47-HuFab | 1.84E+06 | 1.36E-04 | 7.40E-11 |
| SR-AB48-HuFab | 1.76E+06 | 1.04E-04 | 5.93E-11 |
| SR-AB49-HuFab | 8.09E+05 | 1.38E-04 | 1.70E-10 |
| SR-AB50-HuFab | 3.31E+06 | 1.82E-04 | 5.50E-11 |
| SR-AB51-HuFab | 2.55E+06 | 1.50E-04 | 5.89E-11 |
| SR-AB52-HuFab | 2.50E+06 | 9.91E-05 | 3.96E-11 |
| SR-AB53-HuFab | 1.82E+06 | 1.28E-04 | 7.07E-11 |
| SR-AB54-HuFab | 1.80E+06 | 8.83E-05 | 4.91E-11 |
| SR-AB55-HuFab | 8.62E+05 | 1.13E-04 | 1.31E-10 |
| SR-AB56-HuFab | 2.58E+06 | 1.26E-04 | 4.89E-11 |
| SR-AB57-HuFab | 1.35E+06 | 1.81E-04 | 1.33E-10 |
| SR-AB58-HuFab | 3.11E+06 | 1.62E-04 | 5.21E-11 |
| SR-AB59-HuFab | 2.55E+06 | 1.30E-04 | 5.09E-11 |
| SR-AB60-HuFab | 2.35E+06 | 1.20E-04 | 5.10E-11 |
| SR-AB61-HuFab | 1.17E+06 | 1.55E-04 | 1.32E-10 |

*Average of five replicate experiments
**Average of four replicate experiments

TABLE 12

| | huLTBP3 proTGFb1 | | |
|---|---|---|---|
| | ka (1/Ms) | kd (1/s) | KD (M) |
| SR-AB42-HuFab | 4.05E+05 | 1.42E-04 | 3.50E-10 |
| SR-AB63-HuFab | 3.94E+05 | 4.99E-05 | 1.27E-10 |

TABLE 13

| | huGARP proTGFb1 | | |
|---|---|---|---|
| | ka (1/Ms) | kd (1/s) | KD (M) |
| SR-AB42-HuFab | 1.55E+05 | 6.04E-03 | 3.89E-08 |
| SR-AB63-HuFab | 2.66E+03 | 9.30E-04 | 3.49E-07 |

TABLE 14

| | huLRRC33 proTGFb1 | | |
|---|---|---|---|
| | ka (1/Ms) | kd (1/s) | KD (M) |
| SR-AB42-HuFab | 8.09E+04 | 3.53E-03 | 4.36E-08 |
| SR-AB63-HuFab | 5.00E+03 | 1.08E-03 | 2.16E-07 |

TABLE 15

| | Murine LTBP3 proTGFb1 | | |
|---|---|---|---|
| | ka (1/Ms) | kd (1/s) | KD (M) |
| SR-AB42-HuFab* | 1.23E+08 | 3.97E-01 | 2.66E-09 |
| SR-AB43-HuFab* | 1.82E+09 | 6.37E+00 | 4.43E-09 |

*Average of two replicate experiments

Example 10

Improved Potency of Optimized LTBP Complex-Specific Antibodies after CDR-H3 Mutagenesis LTBP complex-specific antibodies from the first round of affinity maturation/optimization (i.e., SR-AB14, SR-AB16, SR-AB17, SR-AB18, SR-AB19) were selected for a second round of affinity maturation/optimization (i.e., CDR-H3 mutagenesis as described herein) and particular progeny antibodies (SR-AB20, SR-AB21, SR-AB22, SR-AB23, SR-AB24, SR-AB25, SR-AB26, SR-AB27, SR-AB28, and SR-AB29) were assessed for their ability to inhibit TGFβ activity using LN229 cells. For the assays depicted in FIGS. 13A, 13B, 14A, and 14B the following protocol was used, which is a modified version of Assay II in Example 2.

Materials:
- MvLul-CAGA12 cells (Clone 4A4)
- LN229 cell line (high levels of endogenous αVβ8 integrin)
- Costar white walled TC treated 96 well assay plate #3903
- Greiner Bio-One High Binding white uclear 96 well assay plate #655094
- Human Fibronectin (Corning #354008)
- P200 multichannel pipet
- P20, P200, and P1000 pipets with sterile filter tips for each
- Sterile microfuge tubes and rack
- Sterile reagent reservoirs
- 0.4% trypan blue
- 2 mL, 5 mL, 10 mL, and 25 mL sterile pipets
- Tissue culture treated 100 mm or 150 mm plates
- 70% Ethanol
- Opti-MEM reduced serum media (Life Tech #31985-070)
- Lipofectamine 3000 (Life Tech #L3000015)
- Bright-Glo luciferase assay reagent (Promega #E2620)
- 0.25% Tryspin +0.53 mM EDTA
- proTGFb1 expression plasmid, human
- proTGFb1 expression plasmid, mouse
- LTBP1S expression plasmid, mouse Equipment:
- PerkinElmer EnVision plate reader
- TC hood
- Bench top centrifuge
- $CO_2$ incubator 37C 5% CO2
- 37C water/bead bath
- Platform shaker
- Microscope
- Hemocytometer/countess Definitions:
- CAGA12 4A4 cells: Derivative of MvLul cells (Mink Lung Epithelial Cells), stably transfected with CAGA12 synthetic promoter, driving luciferase gene expression
- DMEM-0.1% BSA: Assay media; base media is DMEM (Gibco Cat #11995-065), media also contains BSA diluted to 0.1% w/v, penicillin/streptinomycin, and 4 mM glutamine
- D10: DMEM 10% FBS, P/S, 4 mM glutamine, 1% NEAA, 1× GlutaMAX (Gibco Cat#35050061)
- CAGA12 (4A4) media: D10+0.75ug/mL puromycin Procedure:
Always work in sterile biosafety cabinet, and sterile technique should be used at all times. Prepare all media, sterilize all materials, and move materials into biosafety cabinet before starting. Growth medium should be warmed to 37° C.

Use the reverse pipetting technique for almost all steps during this assay.

On day 0, prior to cell seeding, assay plates were coated with Fibronectin (LTBP over expression assay only). A 1 mg/ml stock solution of fibronectin was prepared in ultra-pure water (sterile). Stock solution was diluted in PBS to 19.2ug/ml working solution and 50 µl was added to each well (3 ug/cm$^2$). Plates were incubated at 37° C. and 5% $CO_2$ for 4 hours. Following coating, assay plates were washed manually with multichannel pipette for 2 washes of 200 µl/well PBS. After final wash, plates were allowed to dry in the hood with lid off. LN229 cells were then detached with trypsin and pelleted (spun for 5 min at 200×g). The cell pellet was resuspended in D10 media and viable cells per ml counted. Cells were diluted to 0.125e$^6$ cells/ml and seeded 100 µl per well (12,500 cells per well) in an assay plate. For CAGA12 cells to be used for assay on Day 2, cells passaged at a density of 1.5 million per T75 flask. Cultures were incubated at 37° C. and 5% $CO_2$.

On Day 1, LN229 cells were transfected. The manufacturer's protocol was followed for transfection with Lipofectamine 3000 reagent. Briefly, the following was diluted into OptiMEM I, for 5 µl per well: 0.1 µg proTGFβ1 DNA combined with 0.1 µg presentation molecule DNA, and 0.4 µl P3000, up to 5 µl with OptiMEM I. For FIG. 13A and FIG. 14A, 0.1 µg human proTGFβ1 DNA was transfected with 0.1ug empty vector, without LTBP DNA, to measure activation in the presence of endogenous presenting molecules. For FIG. 13B and FIG. 14B, 0.1 µg mouse LTBP1 DNA was co-transfected with the mouse proTGFβ1 DNA to measure activation in the presence of overexpressed LTBP1.

A master mix of Lipofectamine3000 was made by diluting 0.41 Lipofectamine3000 in OptiMEM I, up to 5 µl in OptiMEM I, per well. Diluted Lipofectamine3000 was added to the DNA mixture, mixed well by pipetting, and incubated at room temperature for 15 min. After the incubation, 10 µl of DNA:Lipofectamine3000 (2×5 µl) mixture was added to each well. Plates were returned to the tissue culture incubator for ~24 hrs.

On day 2 the indicated antibodies and TGFβ reporter cells (CAGA12) were added to the wells. Antibodies were serially diluted into PBS, then further diluted into assay media until 2× final concentration. Plates were washed twice with assay media by aspirating (vacuum aspirator) followed by addition of 100 µl per well assay media. After second wash, assay media was replaced with 50 µl per well of 2× antibody. Cell plate was returned to the incubator for ~15-20 min. CAGA12 (clone 4A4) cells were detached with trypsin and pelleted (spun 5 min at 200×g.). Pellet was resuspended in assay media and viable cells counted. Viable cells were diluted to 0.3e$^6$ cells/ml and seeded 50 µl per well (15,000 cells per well). Cells were returned to the incubator.

On Day 3, the assay was read about 16-20 hours after the antibody and/or reporter cell addition. Bright-Glo reagent and test plate were allowed to come to room temperature before reading. 100 µL of Bright-Glo reagent was added per well. Incubated for 2 min with shaking, at room temperature, protected plate from light. The luminescence was then detected on a plate reader.

Figure 13A:
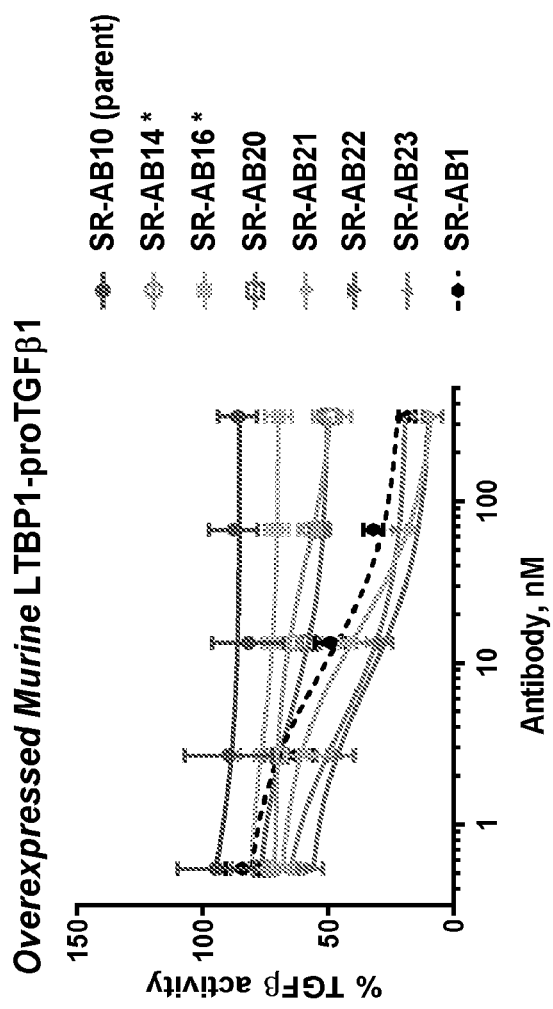
FIGS. 13A and 13B are graphs showing improved potency of optimized LTBP complex-specific antibodies after CDR-H3 mutagenesis (i.e., SR-AB20, SR-AB21, SR-AB22, and SR-AB23), as measured by cell-based TGFβ reporter assays.
Figure 13B:
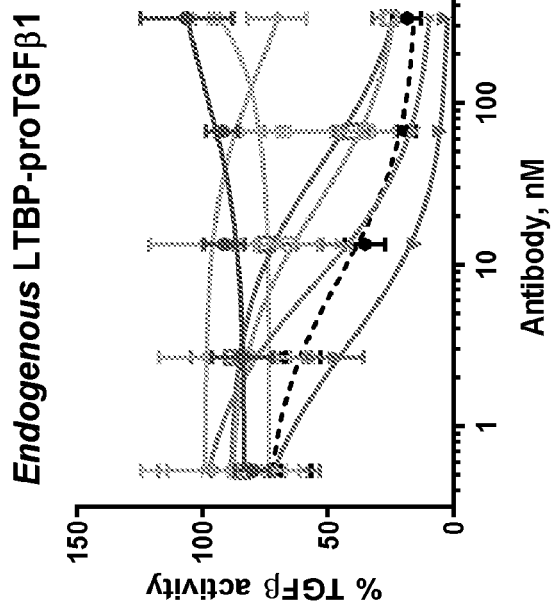

Results:

Data generated from this assay reflected TGFβ activity in cell supernatants. FIGS. 13A and 13B are graphs showing improved potency of antibodies SR-AB20, SR-AB21, SR-AB22, and SR-AB23 (SR-AB10 family antibodies) as measured by TGFβ activity. The FIG. 13A assay was performed without overexpressing LTBP1 and thus measures activation of TGFβ in the presence of endogenous presenting molecules. The FIG. 13B assay was performed with overexpressed murine LTBP1-proTGFβ1. Notably, antibodies SR-AB22 and SR-AB23 show activity that is similar to (or greater than) the context-independent antibody SR-AB1 in both assays.

FIG. 14A and FIG. 14B are graphs showing improved potency of antibodies SR-AB24, SR-AB25, SR-AB26, SR-AB27, SR-AB28, and SR-AB29 (SR-AB13 family antibodies) as measured by TGFβ activity. The FIG. 14A assay was performed without overexpressing LTBP1 and thus measures activation of TGFβ in the presence of endogenous presenting molecules. The FIG. 14B assay was performed with overexpressed murine LTBP1-proTGFβ1. Notably, the optimized antibodies show activity that is greater than the context-independent antibody SR-AB1 in the LTBP1-proTGFβ1 overexpression cell assay (FIG. 14B).

The assays depicted in FIG. 13A, FIG. 13B, FIG. 14A, and FIG. 14B were all performed in LN229 cells, which express low LTBP1 mRNA, high LTBP3 mRNA, undetectable GARP, and undetectable LRRC33.

Example 11

Improved Potency of Optimized LTBP Complex-Specific Antibodies after Light Chain Mutagenesis LTBP complex-specific antibodies from the third and fourth rounds of affinity maturation/optimization were assessed for their ability to inhibit TGFβ activity using LN229 cells. The assays were carried out using the protocol described in Example 10.

To calculate inhibitory potency (IC50) values, raw luminescence values were normalized against wells treated with PBS only (vehicle). Normalized values were plotted using PRISM® software, and values were calculated using 3-point non-linear regression. The Tables below show IC50 values (nM) for isoform-specific antibodies in two different assay formats: an endogenous human LTBP (hLTBP) assay and mouse LTBP assay (mLTBP). IC50 values were determined in the two assay formats for 4 different antibody lineages: SR-AB22, SR-AB23, SR-AB24 and SR-AB26, shown in Tables 16-19.

TABLE 16

| SR-AB22 lineage | | | |
|---|---|---|---|
| Endogenous hLTBP assay | | | mLTBP1 assay |
| Ref Ab | 0.7682 | SR-AB36 (cycle 3) | 0.3 |
| SR-AB34 (cycle 3) | 0.9088 | SR-AB30 (cycle 3) | 0.4038 |
| SR-AB39 (cycle 3) | 1.015 | SR-AB34 (cycle 3) | 0.4231 |
| SR-AB36 (cycle 3) | 1.153 | SR-AB35 (cycle 3) | 0.4298 |
| SR-AB31 (cycle 3) | 1.261 | SR-AB31 (cycle 3) | 0.4313 |
| SR-AB35 (cycle 3) | 1.343 | SR-AB33 (cycle 3) | 0.4491 |
| SR-AB30 (cycle 3) | 1.344 | SR-AB32 (cycle 3) | 0.4744 |
| SR-AB31 (cycle 3) | 1.563 | SR-AB39 (cycle 3) | 0.4786 |
| SR-AB37 (cycle 3) | 1.93 | SR-AB37 (cycle 3) | 0.5426 |
| SR-AB32 (cycle 3) | 2.223 | SR-AB22 (cycle 2) | 1.394 |
| SR-AB10 (parent) | 3.64 | Ref Ab | 1.571 |
| SR-AB1 | 4.446 | SR-AB1 | 6.381 |
| SR-AB22 (cycle 2) | 4.618 | SR-AB14 (cycle1) | 12.59 |
| SR-AB14 (cycle1) | 51.65 | SR-AB10 (parent) | 118.9 |

TABLE 17

SR-AB23 lineage

| | Endogenous hLTBP | | mLTBP1 |
|---|---|---|---|
| Ref Ab | 0.7682 | SR-AB45 (cycle 3) | 0.2638 |
| SR-AB42 (cycle 3) | 1.434 | SR-AB42 (cycle 3) | 0.2708 |
| SR-AB44 (cycle 3) | 1.515 | SR-AB44 (cycle 3) | 0.3001 |
| SR-AB41 (cycle 3) | 1.542 | SR-AB43 (cycle 3) | 0.3189 |
| SR-AB43 (cycle 3) | 1.756 | SR-AB40 (cycle 3) | 0.333 |
| SR-AB40 (cycle 3) | 2.105 | SR-AB41 (cycle 3) | 0.4086 |
| SR-AB45 (cycle 3) | 2.247 | SR-AB23 (cycle 2) | 0.9458 |
| SR-AB10 (parent) | 3.64 | Ref Ab | 1.571 |
| SR-AB1 | 4.446 | SR-AB1 | 6.381 |
| SR-AB23 (cycle 2) | 6.043 | SR-AB14 (cycle1) | 12.59 |
| SR-AB14 (cycle1) | 51.65 | SR-AB10 (parent) | 118.9 |

TABLE 18

SR-AB24 lineage

| | Endogenous hLTBP | | mLTBP1 |
|---|---|---|---|
| Ref Ab | 0.7682 | SR-AB62 (cycle 3) | 0.3861 |
| SR-AB1 | 4.446 | SR-AB24 (cycle 2) | 1.313 |
| SR-AB13 (parent) | 4.825 | Ref Ab | 1.571 |
| SR-AB62 (cycle 3) | 8.683 | SR-AB17 (cycle 1) | 4.038 |
| SR-AB24 (cycle 2) | 9.599 | SR-AB1 | 6.381 |
| SR-AB17 (cycle 1) | 24.14 | SR-AB13 (parent) | 25.44 |

TABLE 19

SR-AB26 lineage

| | Endogenous hLTBP | | mLTBP1 |
|---|---|---|---|
| SR-AB1 | 0.7682 | SR-AB63 (cycle 3) | 0.2075 |
| SR-AB63 (cycle 3) | 1.777 | SR-AB64 (cycle 3) | 0.2683 |
| SR-AB64 (cycle 3) | 3.12 | SR-AB26 (cycle 2) | 1.172 |
| SR-AB1 | 4.446 | Ref Ab | 1.571 |
| SR-AB13 (parent) | 4.825 | SR-AB17 (cycle 1) | 4.038 |
| SR-AB26 (cycle 2) | 8.742 | SR-AB1 | 6.381 |
| SR-AB17 (cycle 1) | 24.14 | SR-AB13 (parent) | 25.44 |

Data generated from this assay reflected TGFβ activity in cell supernatants. As shown in FIG. 16, the functional activity (potency) of LTBP complex specific antibodies improved in each cycle of affinity maturation. As shown in FIG. 16, improvement from each cycle of affinity maturation resulted in activity exceeding the context-independent reference antibody (Ref Ab), a potent context-independent inhibitor of latent TGFβ1. The assays described above were all performed in LN229 cells transiently transfected with murine LTBP1 and murine proTGFβ1.

For the results shown in Table 20, the assay was carried out using the protocol described in Example 10, but in this assay Fabs were utilized.

TABLE 20

| Antibody | IC50, nM |
|---|---|
| RefAb (hIgG4) | 0.7676 |
| RefAb (Fab) | 3.607 |
| SR-AB47 Fab | 0.1861 |
| SR-AB59 Fab | 0.1947 |
| SR-Ab56 Fab | 0.4393 |
| SR-AB52 Fab | 0.4589 |
| SR-AB61 Fab | 0.4699 |

TABLE 20-continued

| Antibody | IC50, nM |
|---|---|
| SR-AB41 Fab | 0.4861 |
| SR-AB46 Fab | 0.4946 |
| SR-AB48 Fab | 0.5233 |
| SR-AB51 Fab | 0.5354 |
| SR-AB55 Fab | 0.5363 |
| SR-AB42 Fab | 0.6675 |
| SR-AB60 Fab | 0.742 |
| SR-AB57 Fab | 0.7754 |
| SR-AB49 Fab | 1.024 |
| SR-AB43 Fab | 1.077 |
| SR-AB53 Fab | 1.181 |
| SR-AB58 Fab | 4.856 |
| SR-AB54 Fab | 5.87 |
| SR-AB23 Fab | 8.533 |
| SR-AB50 Fab | 10.97 |

Example 12

Developability

Figure 17:
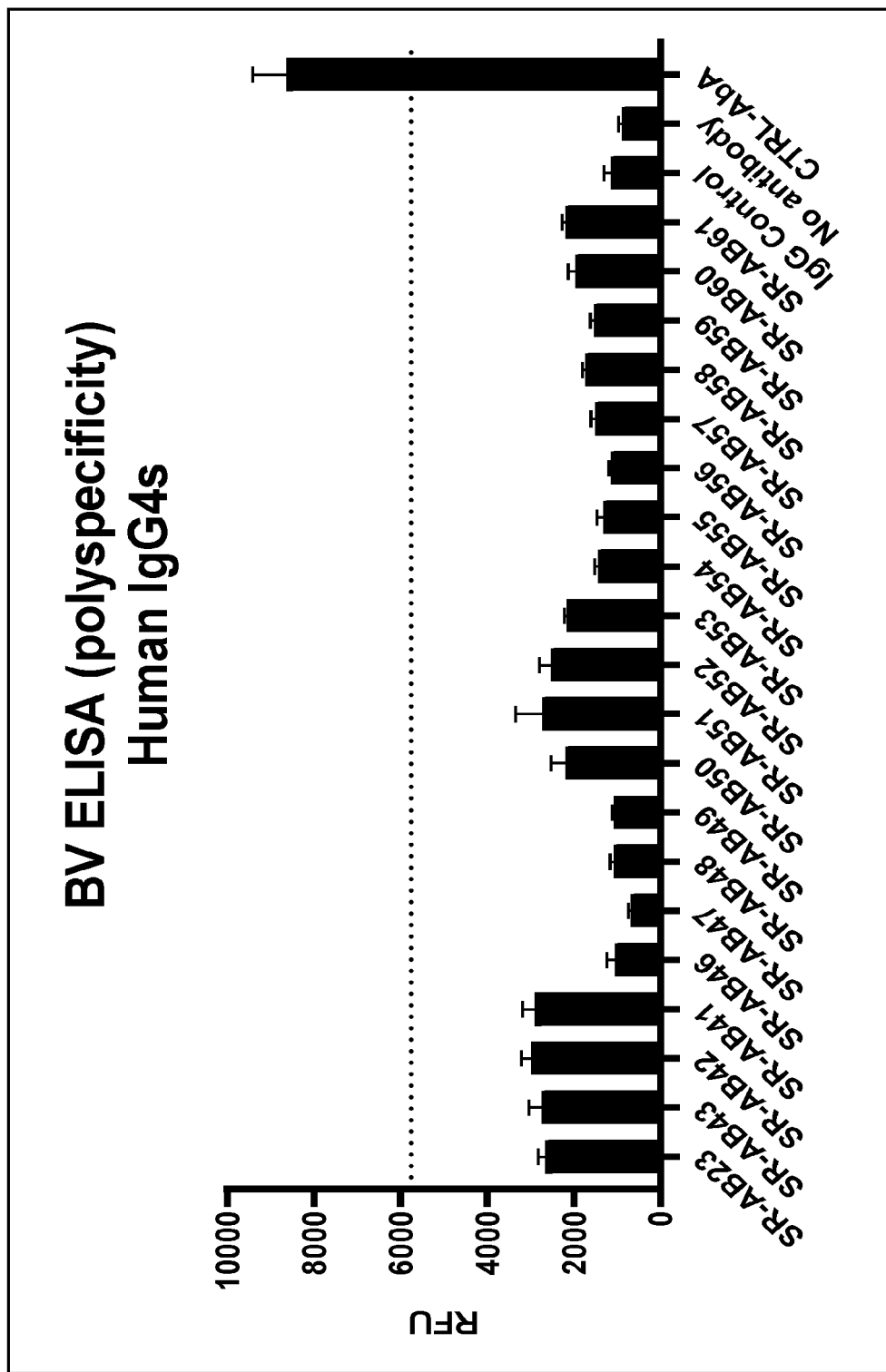
FIG. 17 depicts the results of an enzyme-linked immunosorbent assay (ELISA) showing antibody binding to baculovirus (BV) particles, which tests antibody polyspecificity.
Figure 18:
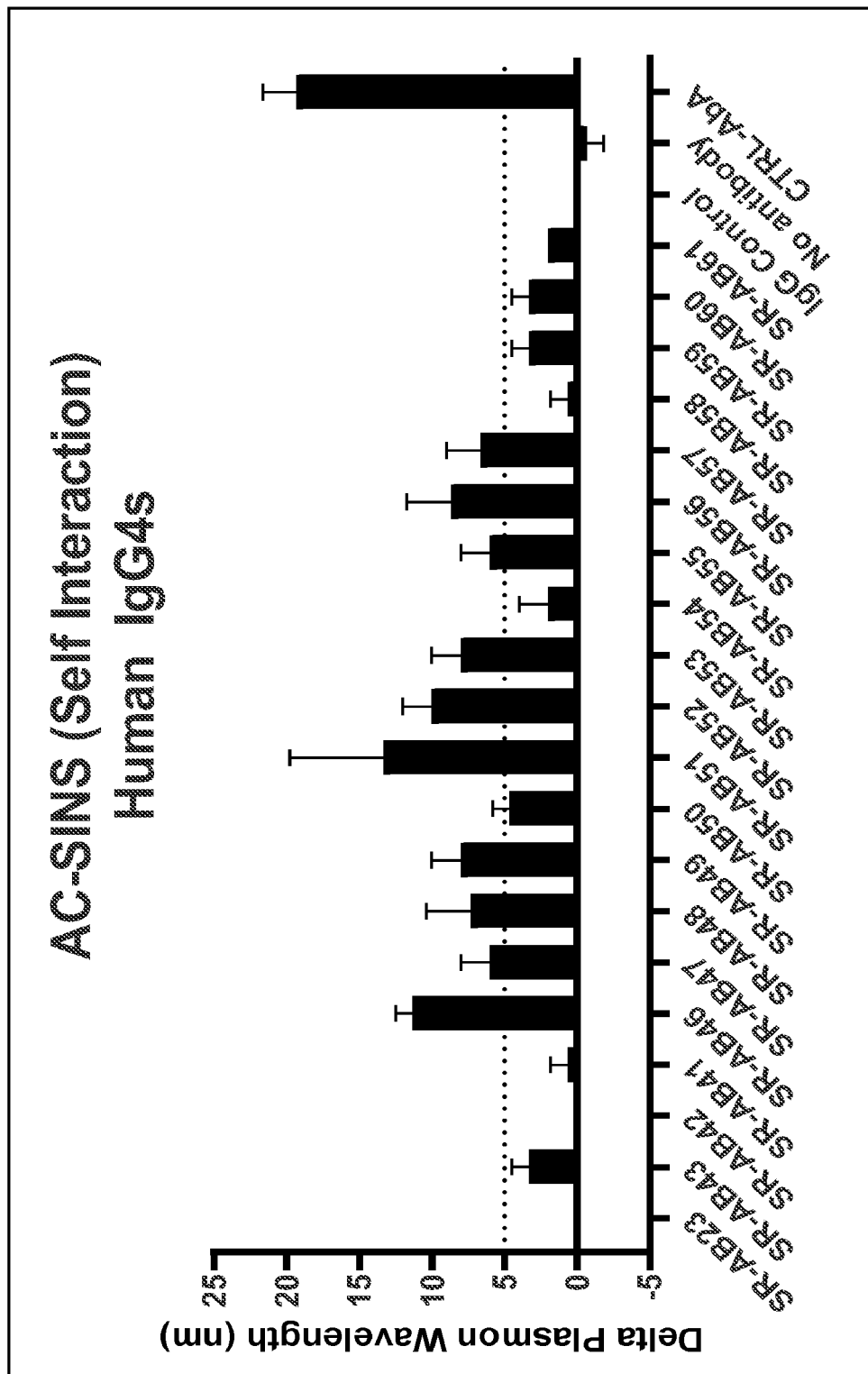
FIG. 18 depicts the results of affinity-capture Self-interaction Nanoparticle Spectroscopy (AC-SINS) assay, which tests antibody self-interaction. Increased plasmon wavelength indicates self-interaction.

Antibodies that exhibit favorable biophysical properties have an increased success rate in development. LTBP complex-specific antibodies from the third and fourth rounds of affinity maturation/optimization were assessed for aggregation propensity and polyspecificity. FIG. 17 shows the results of an enzyme-linked immunosorbent assay (ELISA) showing SR-AB binding to baculovirus (BV) particles. FIG. 18 shows the results of affinity-capture Self-interaction Nanoparticle Spectroscopy (AC-SINS) Assay. This assay tests how likely an antibody is to interact with itself. It uses gold nanoparticles that are coated with anti-Fc antibodies. When a dilute solution of antibodies is added, they rapidly become immobilized on the Fc-coated gold beads. If these antibodies subsequently interact with one another, it leads to shorter interatomic distances and an increase in the plasmon wavelength that can be detected by spectroscopy.

These results show that the candidate antibodies demonstrate favorable developability properties, as evidenced by a plasmon shift less than 5 nM in the AC-SINS assay and a BV ELISA signal less than 5 fold of the negative control.

Example 13

Inhibition of TGFβ Signaling by LTBP Complex-Specific Antibodies in Choline-Deficient High Fat Diet (CDHFD) Model of Mouse NASH The Choline deficient high fat diet (CDHFD) is an established diet-induced model of Non-Alcoholic steatohepatitis (NASH). In this model, male C57BL/6J mice are fed a choline deficient, 0.1% Methionine, high fat diet for 12 weeks. Three to six weeks after the start of the CDHFD, activation of pro-fibrotic processes can be detected through increased expression of a-smooth muscle actin (α-SMA) protein, a marker for activation of hepatic stellate cells, and elevated tissue hydroxyproline content reflecting increased collagen synthesis and deposition (Matsumoto et. al, Int J Exp Pathol. 2013 April; 94(2):93-103).

LTBP complex-specific antibodies were tested for their ability to inhibit and/or reduce the extent of liver fibrosis in mice in the CDHFD model as follows. An outline of the study is shown below in Table 21.

TABLE 21

| Group | Diet | Lineage | Ab (mIgG1) | Dose (mg/kg) | Frequency | Takedown | N |
|---|---|---|---|---|---|---|---|
| 1 | Regular Chow | | NA | NA | NA | 4 weeks | 5 |
| 2 | CDAA/HFD | | NA | NA | NA | 4 weeks | 8 |
| 3 | Regular Chow | | HuNeg | 15 | 2× weekly | 12 weeks | 5 |
| 4 | CDAA/HFD | | HuNeg | 15 | 2× weekly | 12 weeks | 10 |
| 3 | CDAA/HFD | | Ref Ab | 15 | 2× weekly | 12 weeks | 10 |
| 4 | CDAA/HFD | SR-AB23 | SR-AB42 | 15 | 2× weekly | 12 weeks | 10 |
| 5 | CDAA/HFD | SR-AB22 | SR-AB31 | 15 | 2× weekly | 12 weeks | 10 |

Animals in the test cohorts were on the CDHFD for the duration of the study. A separate cohort of mice (Group 1) were administered a regular chow diet as a study control. Antibodies SR-AB42 and SR-AB31 were administered to mice by intraperitoneal (i.p.) injection beginning at 4 weeks post start of the CDHFD Animals were dosed at antibody test concentrations 15 mg/kg twice a week (i.e., 30 mg/kg/week) for a test duration of 8 weeks (i.e., weeks 4 through 12). A mouse IgG1 isotype antibody was used as a negative control at 15 mg/kg twice weekly (i.e., 30 mg/kg/week). Ref Ab was used as a reference antibody due to it being a potent context-independent inhibitor of TGFβ1. Following 8 weeks of dosing, animals were sacrificed and livers were collected for analysis. Endpoint readout was hydroxyproline content.

Hydroxyproline Content in CDHFD Liver Fibrosis Model

Hydroxyproline, produced by hydroxylation of the amino acid proline, is a signature amino acid for major component of fibrillar collagens, and comprises approximately 13.5% of the protein. Hydroxyproline acts as an important diagnostic indicator of the severity of fibrosis. Animals fed a CDHFD show an increase in hydroxyproline (HYP) in liver tissue. As shown in FIG. 19, treatment with SR-AB42 and SR-AB31 inhibited the increase in HYP (μg/mg tissue) in liver tissue in animals on CDHFD.

Example 14

Inhibition of TGFβ Signaling by LTBP Complex-Specific Antibodies in a Genetic Model of Alport Syndrome The murine Col4a3-/- model is an established genetic model of autosomal recessive Alport syndrome. Alport mice lack a functional collagen 4A3 gene (Col4A3-/-) and therefore cannot form normal type IV collagen trimers, which require a3, a4, and a5 chains. Col4a3-/- mice develop fibrosis in the kidney consistent with renal fibrosis in human patients, including interstitial fibrosis and tubular atrophy, and Col4a3-/- mice develop end-stage renal disease (ESRD) between 8 and 30 weeks of age, depending on the genetic background of the mouse. The structural and functional manifestation of renal pathology in Col4a3-/- mice, combined with the progression to ESRD make Col4a3-/- mice an ideal model to understand kidney fibrosis. Previous reports point to the importance of the TGFβ signaling pathway in this process, and treatment with either an inhibitor of αVβ6 integrin, a known activator of TGFβ1 and TGFβ3, or with a TGFβ ligand trap has been reported to prevent renal fibrosis and inflammation in Alport mice (Hahm et al. (2007) The American Journal of Pathology, 170(1): 110-125).

LTBP complex-specific antibodies were tested for their ability to inhibit and/or reduce the renal fibroses in Alport mice as follows. An outline of the study is shown below in Table 22.

TABLE 22

| Group | Genotype | Ab (hIgG4) | Dose (mg/kg) | Frequency | N |
|---|---|---|---|---|---|
| 1 | Het | HuNeg | 30 | 1 | 6 |
| 2 | KO | HuNeg | 30 | 1 | 10 |
| 3 | KO | Ref Ab | 30 | 1 | 10 |
| 4 | KO | SR-AB42 | 30 | 1 | 10 |
| 5 | KO | SR-AB63 | 30 | 1 | 10 |

F1 offspring from Col4a3+/- males on a 129/Sv genetic background crossed to Col4a3+/- females on a C57BL/6 genetic background were employed for the study. These mice typically exhibit proteinuria by 4-5 weeks old and typically progress to ESRD by 13-15 weeks old, providing a good therapeutic window for testing efficacy of treatment. 11 week old Col4a3-/- mice were dosed with 30 mg/kg SR-AB42 and SR-AB63 intraperitoneally (i.p.) 48 hours prior to animal sacrifice and kidney collection. Ref Ab was used as a reference antibody due to it being a potent context-independent inhibitor of TGFβ1 activation. pSMAD Analysis in Alport Kidney Model It is well documented that TGFβ receptor activation leads to a downstream signaling cascade of intracellular events, including phosphorylation of Smad2/3. Therefore, the ability of SR-AB42 and SR-AB63 treatment to inhibit TGFβ signaling was assessed in kidney lysate samples by measuring relative phosphorylation levels of Smad2/3 as assayed by ELISA (Cell Signaling Technologies) according to the manufacturer's instructions. FIG. 20A is a graph showing relative ratios of phosphorylated versus total (phosphorylated and unphosphorylated) Smad2/3 (pSMAD2/3:tSMAD2/3) in an Alport mouse model. FIG. 20B is a graph showing the amount of phosphorylated SMAD2/3 (pSMAD2/3) as determined by ELISA and FIG. 20C is a graph showing the amount of total SMAD2/2 (tSMAD2/3) protein as determined by ELISA. As shown by FIG. 20B and FIG. 20C, reduction of pSMAD is contributing to the change in ratio shown in FIG. 20A. A single dose of SR-AB42 or SR-AB63 was sufficient to significantly inhibit pSmad2/3 signaling in whole kidney lysates, demonstrating efficient target engagement by SR-AB42 and SR-AB63 and that LTBP complex-specific inhibition in the Alport model reduces pSmad levels.

Example 15

Determination of proTGβ1 C4S Binding

A modified proTGFβ1 complex (proTGFβ1 C4S) in which the cysteine residue at position 4 of the pro-domain has been substituted with a serine residue (described in WO 2014/182676) was used to assess antibody binding to C4S antigen by Octet. Cycle 2 antibodies were immobilized and tested against 3 antigens. As shown in the Tables below, robust antibody binding to LTBP-1 proTGFβ1 antigen (Table 23) and proTGFβ1C4S antigen was observed (Table 24), while binding to LRRC33 proTGFβ1 antigen was not observed (Table 25).

TABLE 23

Binding to human LTBP-1 proTGFb1

| Sample ID | Loading Sample ID | Response (nm) |
|---|---|---|
| human LTBP-1 proTGFb1 | SR-AB14 | 0.3197 |
| human LTBP-1 proTGFb1 | SR-AB20 | 0.4132 |
| human LTBP-1 proTGFb1 | SR-AB21 | 0.3196 |
| human LTBP-1 proTGFb1 | SR-AB22 | 0.4317 |
| human LTBP-1 proTGFb1 | SR-AB23 | 0.3449 |
| human LTBP-1 proTGFb1 | SR-AB17 | 0.3036 |
| human LTBP-1 proTGFb1 | SR-AB24 | 0.3796 |
| human LTBP-1 proTGFb1 | SR-AB25 | 0.3085 |
| human LTBP-1 proTGFb1 | SR-AB26 | 0.2953 |
| human LTBP-1 proTGFb1 | SR-AB27 | 0.3717 |
| human LTBP-1 proTGFb1 | SR-AB28 | 0.4046 |
| human LTBP-1 proTGFb1 | SR-AB29 | 0.3242 |
| human LTBP-1 proTGFb1 | HuNeg | −0.0007 |
| human LTBP-1 proTGFb1 | SR-AB16 | 0.2594 |
| human LTBP-1 proTGFb1 | SR-AB1 | 0.4311 |

TABLE 24

Binding to human TGFb1 C4S

| Sample ID | Loading Sample ID | Response (nm) |
|---|---|---|
| human TGFb1 C4S | SR-AB14 | 0.2002 |
| human TGFb1 C4S | SR-AB20 | 0.2891 |
| human TGFb1 C4S | SR-AB21 | 0.1812 |
| human TGFb1 C4S | SR-AB22 | 0.2937 |
| human TGFb1 C4S | SR-AB23 | 0.2263 |
| human TGFb1 C4S | SR-AB17 | 0.2835 |
| human TGFb1 C4S | SR-AB24 | 0.3846 |
| human TGFb1 C4S | SR-AB25 | 0.329 |
| human TGFb1 C4S | SR-AB26 | 0.3764 |
| human TGFb1 C4S | SR-AB27 | 0.3814 |
| human TGFb1 C4S | SR-AB28 | 0.3605 |
| human TGFb1 C4S | SR-AB29 | 0.3334 |
| human TGFb1 C4S | HuNeg | 0.001 |
| human TGFb1 C4S | SR-AB16 | 0.1454 |
| human TGFb1 C4S | SR-AB1 | 0.3604 |

TABLE 25

Binding to human LRRC33 proTGFb1

| Sample ID | Loading Sample ID | Response (nm) |
|---|---|---|
| human LRRC33 proTGFb1 | SR-AB14 | 0.03 |
| human LRRC33 proTGFb1 | SR-AB20 | 0.0894 |
| human LRRC33 proTGFb1 | SR-AB21 | 0.0141 |
| human LRRC33 proTGFb1 | SR-AB22 | 0.1329 |
| human LRRC33 proTGFb1 | SR-AB23 | 0.0233 |
| human LRRC33 proTGFb1 | SR-AB17 | 0.0043 |
| human LRRC33 proTGFb1 | SR-AB24 | 0.0394 |
| human LRRC33 proTGFb1 | SR-AB25 | 0.024 |
| human LRRC33 proTGFb1 | SR-AB26 | 0.0208 |
| human LRRC33 proTGFb1 | SR-AB27 | 0.0317 |
| human LRRC33 proTGFb1 | SR-AB28 | 0.037 |
| human LRRC33 proTGFb1 | SR-AB29 | 0.0288 |
| human LRRC33 proTGFb1 | HuNeg | 0.0023 |
| human LRRC33 proTGFb1 | SR-AB16 | 0.0161 |
| human LRRC33 proTGFb1 | SR-AB1 | 0.4006 |

Example 16

Cycle 3 Lead Antibodies Show No Inhibition in TGF/β3 Assay

FIG. 21 is a graph showing that the lead cycle 3 antibodies show no inhibition in the LTBP-TGFβ33 assay. The TGFβ3 assay is performed similarly to the assay in Example 10, but proTGFβ3 is transfected instead of proTGFβ1. No LTBP construct is transfected as this assay relies on the endogenous presentation molecules in the LN229 cell line Example 17

Pro Fibrotic Effects of TGF/13-Selective Activation Inhibitor in Liver Fibrosis Model Liver expresses both TGFβ1 and TGFβ3. To investigate whether inhibition of both isoforms in the CDHFD model would further mitigate fibrosis of the liver, CDHFD mice were treated with a potent TGFβ1-selective activation inhibitor (which inhibits activation of TGFβ1 in the context of human LTBP1 and LTBP3 complexes) and a TGFβ3-selective activation inhibitor, either alone or in combination. In mice treated with TGFβ3 inhibitor, exacerbation of the disease was observed, as evidenced by PSR analysis and additional histopathology analyses (FIG. 22). At 12 weeks, e.g., end of the study, animals that received the TGFβ1-selective activation inhibitor showed significantly less fibrosis as compared to IgG-treated animals (negative control). By contrast, animals treated with TGFβ3-selective inhibitor showed significantly more fibrosis with approximately 12% PSR positive area Animals that received a combination of both TGFβ3-selective inhibitor and TGFβ1-selective inhibitor showed an intermediate level of fibrosis, indicating that antifibrotic effects of the TGFβ1-selective activation inhibitor is being mitigated by TGFβ3 inhibition.

Example 18

Improved Affinity of Optimized LTBP-Complex-specific Antibodies after Light Chain Optimization Cycle 4

LTBP complex-specific antibodies from the third round of affinity maturation/optimization were selected for a fourth round of affinity maturation/optimization (i.e., light chain optimization as described herein) and particular progeny antibodies, were assessed for their ability to bind various proTGFβ1 constructs.

Materials:
  96 well plates—Greinerbio-one REF 650101
  Microplate Foils-GE Healthcare—CAT #28-9758-16
  Biotin CAPture Kit GE Healthcare product number 28920233
  Biacore running buffer—supplied as a 20× solution, diluted in Milli-Q water, TEKnova CAT #H8022

Method:
  These experiments were performed using the Biacore 8K using the method "multi-cycle kinetics/affinity using Biotin CAPture kit."
  Data collection rate was set to 10 Hz and the Biotin CAPture step was performed for 300 seconds with a flow rate of 2 μL/minute. The Biotin CAPture reagent was used after a 1:5 dilution in 1×Biacore running buffer. Biotinylated ligands (the various complexes of TGFβ31) were utilized at a concentration of 10 nM and were immobilized to the sensor chip for 180 seconds with a flow rate of 10 μL/minute. The analytes, which are each of the Fabs, were tested at 10, 5, 2.5, 1.25, and 0.625 nM with a 0 nM control included. Analyte contact time was 120 seconds and the dissociation time was 900 seconds. The regeneration cycle utilized was 120 seconds with a flow rate of 10 μL/minute.

The evaluation method used was "multi-cycle affinity using capture" and a 1:1 binding model was used. For every Fab tested against a given biotinylated antigen, the Rmax was set to equal the Rmax of an affinity-matured version of Reference Ab with significantly slower binding off-rate and therefore higher affinity binding to that same antigen in the same experiment. Global fits were utilized for every KD determination. The KD values are shown in Table 26 below.

TABLE 26

|  | HuLTBP1-ProTGFb1 | HuLTBP3-ProTGFb1 | HuGARP-ProTGFb1 | HuLRRC33-ProTGFb1 |
|---|---|---|---|---|
| SR-AB42-HuFab | 0.381 | 0.57 | 144.614 | 134.249 |
| SR-AB47-HuFab | 0.217 | 0.33 | 6.496 | 6.663 |
| SR-AB49-HuFab | 0.319 | 0.58 | 6.551 | 7.704 |
| Ref Ab-HuFab | 0.077 | 0.11 | 0.202 | 0.154 |

|  | MuLTBP1-ProTGFb1 | MuLTBP3-ProTGFb1 | MuGARP-ProTGFb1 | MuLRRC33-ProTGFb1 |
|---|---|---|---|---|
| SR-AB42-HuFab | 0.611 | 0.68 | 29.102 | 109.989 |
| SR-AB47-HuFab | 0.198 | 0.40 | 1.950 | 9.164 |
| SR-AB49HuFab | 0.379 | 0.65 | 2.820 | 6.945 |
| Ref Ab-HuFab | 0.078 | 0.09 | 0.264 | 0.107 |

Table 27 shows the monovalent half-binding-times (T½). The monovalent half-binding-time (T½) value was at least 45 minutes for each of hLTBP1-proTGFβ1 and hLTBP3-proTGFβ1 complexes. The monovalent T½ value was less than 5 minutes for each of hGARP-proTGFβ1 and hLRRC33-proTGFβ1 complexes, as measured by SPR.

TABLE 27

Monovalent Half-Binding Times (T 1/2)

| LTBP-SR-AB42 HuFab | KD (nM) | $T_{1/2}$ Binding |
|---|---|---|
| Hu LTBP1-ProTGFβ1 | 0.38 | 1.7 hours |
| Hu LTBP3-ProTGFβ1 | 0.57 | 1.7 hours |
| Hu GARP-ProTGFβ1 | 144 | 1.9 min |
| Hu LRRC33-ProTGFβ1 | 134 | 4.3 min |
| Mu LTBP1-ProTGFβ1 | 0.6 | 1.1 hours |
| Mu LTBP3-ProTGFβ1 | 0.68 | 1.2 hours |
| Mu GARP-ProTGFβ1 | 29 | 5.1 min |
| Mu LRRC33-ProTGFβ1 | 110 | 7.4 min |

Embodiments

The present invention encompasses various embodiments. Non-limiting examples are listed below:

1. An antibody, or antigen-binding fragment thereof, comprising at least three of the following six CDRs:
   a) CDR-H1: SEQ ID NO:94 (SEQ ID NO: 94 comprising these substitutions is disclosed as SEQ ID NO: 399), with the proviso that, optionally:
      i. the threonine residue at position 2 of SEQ ID NO:94 may be substituted with an alanine;
      ii. the asparagine residue at position 4 of SEQ ID NO:94 may be substituted with an alanine, tyrosine, aspartate, serine, arginine, or histidine;
      iii. the asparagine residue at position 5 of SEQ ID NO:94 may be substituted with a glutamine, serine, glycine, lysine, glutamate, arginine, or histidine;
      iv. the tyrosine residue at position 6 of SEQ ID NO:94 may be substituted with a arginine;
      v. the proline residue at position 7 of SEQ ID NO:94 may be substituted with a glycine, alanine, leucine, serine, asparagine, valine, aspartate, or glutamine;
      vi. the isoleucine residue at position 8 of SEQ ID NO:94 may be substituted with a methionine or leucine; and/or,
      vii. the histidine residue at position 9 of SEQ ID NO:94 may be substituted with a phenylalanine, tyrosine, asparagine, or serine;
   b) CDR-H2: SEQ ID NO:95, optionally comprising one or more amino acid changes;
   c) CDR-H3: SEQ ID NO:96, optionally comprising one or more amino acid changes;
   d) CDR-L1: SEQ ID NO:97, optionally comprising one or more amino acid changes;
   e) CDR-L2: SEQ ID NO:98, optionally comprising one or more amino acid changes; and,
   f) CDR-L3: SEQ ID NO:99, optionally comprising one or more amino acid changes.

2. The antibody, or antigen-binding fragment thereof, according to embodiment 1, comprising at least three of the following six CDRs:
   a) CDR-H1 comprising the amino acid sequence FTF($X_1$)($X_2$)YVMH, wherein, optionally: $X_1$ is S or R; and $X_2$ is G or S (SEQ ID NO: 392);
   b) CDR-H2 comprising the amino acid sequence ($X_1$)ISHEG($X_2$)($X_3$)KYYADSVKG, wherein, optionally: $X_1$ is V or S; $X_2$ is S or G; and $X_3$ is F or L (SEQ ID NO: 393); and
   c) CDR-H3 comprising the amino acid sequence ($X_1$)($X_2$)P($X_3$)($X_4$)($X_5$)($X_6$)RRGG($X_7$) ($X_8$)($X_9$), wherein, optionally: $X_1$ is A or V; $X_2$ is R, V, G or K; $X_3$ is R, H or L; $X_4$ is I, V or G; $X_5$ is A, S, or L; $X_6$ is A or V; $X_7$ is F or Y; $X_8$ is D, G, R, or S; and, $X_9$ is Y, G, R, L, V, A or K (SEQ ID NO: 394).
   d) CDR-L1 as set forth in SEQ ID NO:97, optionally comprising one or more amino acid changes;
   e) CDR-L2 as set forth in SEQ ID NO:98, optionally comprising one or more amino acid changes; and
   f) CDR-L3 as set forth in SEQ ID NO:99, optionally comprising one or more amino acid changes.

3. The antibody, or antigen-binding fragment thereof, according to embodiment 2, wherein:
   a) within CDR-H2; $X_2$ is S; and
   b) within CDR-H3; $X_1$ is A; $X_2$ is R or V; $X_3$ is R; $X_4$ is I; $X_5$ is A or L; $X_6$ is A; $X_7$ is F; $X_8$ is G; and $X_9$ and Y.

3.1 The antibody, or antigen-binding fragment thereof, according to embodiment 3, wherein one or more of the CDR-L1, CDR-L2, and CDR-L3 is/are affinity matured and/or optimized by CDR diversification and/or mutagenesis.

4. The antibody, or antigen-binding fragment thereof, according to any one of the preceding embodiments, wherein the antibody, or antigen-binding fragment thereof, comprises a heavy chain variable region having an amino acid sequence that is at least 90% identical to SEQ ID NO: SEQ ID NO: 88; and/or, wherein the antibody comprises a variable light chain variable region having an amino acid sequence that is at least 90% identical to SEQ ID NO: 89.
5. The antibody, or antigen-binding fragment thereof, according to any one of the preceding embodiments, comprising:
a heavy chain variable region having an amino acid sequence that is at least 90% identical to SEQ ID NO: 88; and
a light chain variable region having an amino acid sequence that is at least 90% identical to SEQ ID NO: 89.
6. An antibody, or antigen-binding fragment thereof, comprising at least three of the following six CDRs:
  a) CDR-H1: SEQ ID NO:100 (SEQ ID NO: 100 comprising these substitutions is disclosed as SEQ ID NO: 400), with the proviso that, optionally:
    i. the serine residue at position 4 of SEQ ID NO:100 may be substituted with a histidine;
    ii. the serine residue at position 7 of SEQ ID NO:100 may be substituted with an alanine or glycine; and/or,
    iii. the glycine residue at position 11 of SEQ ID NO:100 may be substituted with a threonine, serine, histidine, leucine, isoleucine, asparagine, valine, or alanine;
  b) CDR-H2: SEQ ID NO:101 (SEQ ID NO: 101 comprising these substitutions is disclosed as SEQ ID NO: 401), with the proviso that, optionally:
    i. the serine residue at position 3 of SEQ ID NO:101 may be substituted with an alanine;
    ii. the glycine residue at position 6 of SEQ ID NO:101 may be substituted with an alanine or serine; and/or,
    iii. the serine residue at position 7 of SEQ ID NO:101 may be substituted with a threonine;
  c) CDR-H3: SEQ ID NO:102, optionally comprising one or more amino acid changes;
  d) CDR-L1: SEQ ID NO:103, optionally comprising one or more amino acid changes;
  e) CDR-L2: SEQ ID NO:104, optionally comprising one or more amino acid changes; and,
  f) CDR-L3: SEQ ID NO:105, optionally comprising one or more amino acid changes.
7. The antibody, or antigen-binding fragment thereof, according to embodiment 6, comprising at least three of the following six CDRs:
  g) CDR-H1 comprising the amino acid sequence G($X_1$)I($X_2$)S($X_3$)SYYW($X_4$), wherein, optionally: $X_1$ is S or P; $X_2$ is S, H or R; $X_3$ is S or G; and, $X_4$ is G, I, N or V (SEQ ID NO: 395);
  h) CDR-H2 comprising the amino acid sequence SISYSA($X_1$)TYYNPSLKS, wherein, optionally: $X_1$ is S or T (SEQ ID NO: 396);
  i) CDR-H3 comprising the amino acid sequence ($X_1$)($X_2$)D($X_3$)($X_4$)Y($X_5$)($X_6$)($X_7$)($X_8$)G($X_9$) ($X_{10}$)($X_{11}$), wherein, optionally: $X_1$ is A or V; $X_2$ is R, S or G, $X_3$ is P, Y, R, V, I, H, T or E; $X_4$ is S, D, E or N; $X_5$ is D, A or T; $X_6$ is S, G, T or A; $X_7$ is I, A, R, Q, or V; $X_8$ is A, E, K, G or T; $X_9$ is M or I; $X_{10}$ is D, L, Q, V, N or G; and, $X_{11}$ is V, R, N, E or K (SEQ ID NO: 397);
  j) CDR-L1: SEQ ID NO:103, optionally comprising one or more amino acid changes;
  k) CDR-L2: SEQ ID NO: 104, optionally comprising one or more amino acid changes; and
  l) CDR-L3: SEQ ID NO: 105, optionally comprising one or more amino acid changes.
8. The antibody, or antigen-binding fragment thereof, according to embodiment 7, wherein:
  g) within CDR-H1: $X_2$ is H or R; $X_3$ is S; and, $X_4$ is G, I or N; and
  h) within CDR-H3: $X_1$ is A; $X_3$ is P or V; $X_4$ is S; $X_5$ is D; $X_6$ is S or A; $X_7$ is A, R, I or V; $X_8$ is A; $X_9$ is M; $X_{10}$ is D, Q, or G; and, $X_{11}$ is V or R.
8.1 The antibody, or antigen-binding fragment thereof, according to embodiment 8, wherein one or more of the CDR-L1, CDR-L2, and CDR-L3 is/are affinity matured and/or optimized by CDR diversification and/or mutagenesis.
9. The antibody, or antigen-binding fragment thereof, according to any one of embodiments 6-8.1, comprising at least three CDRs selected from the following, optionally comprising one or more amino acid changes for each of the CDRs:
  CDR-H1: SEQ ID NO:100;
  CDR-H2: SEQ ID NO:101;
  CDR-H3: SEQ ID NO:102;
  CDR-L1: SEQ ID NO:103;
  CDR-L2: SEQ ID NO:104; and,
  CDR-L3: SEQ ID NO:105.
10. The antibody, or antigen-binding fragment thereof, according to one of embodiments 6-9, comprising a variable heavy chain region and a variable light chain region, wherein:
  i) the variable heavy chain region comprises an amino acid sequence that is at least 90% identical to SEQ ID NO: SEQ ID NO: 106; and/or,
  ii) the variable light chain variable region comprises an amino acid sequence that is at least 90% identical to SEQ ID NO: 107.
11. The antibody, or antigen-binding fragment thereof, according to one of embodiments 6-9, wherein the antibody or antigen-binding portion thereof, comprises:
  i) a variable heavy chain region having an amino acid sequence that is at least 90% identical to SEQ ID NO: 106; and,
  ii) a light chain variable region having an amino acid sequence that is at least 90% identical to SEQ ID NO: 107.
12. The antibody, or antigen-binding fragment thereof, according to any one of the preceding embodiments, comprising all six CDRs.
12.1 The antibody, or antigen-binding fragment thereof, according to any one of the preceding embodiments, wherein the one or more amino acid changes comprises one amino acid change.
12.2 The antibody, or antigen-binding fragment thereof, according to any one of the preceding embodiments, wherein the one or more amino acid changes comprises up to two amino acid changes.
12.3 The antibody, or antigen-binding fragment thereof, according to any one of the preceding embodiments, wherein the one or more amino acid changes comprises up to three amino acid changes.
12.4 The antibody, or antigen-binding fragment thereof, according to any one of the preceding embodiments, wherein the one or more amino acid changes comprises up to four amino acid changes.
12.5 The antibody, or antigen-binding fragment thereof, according to any one of the preceding embodiments, wherein the one or more amino acid changes comprises up to five amino acid changes.

12.6 The antibody, or antigen-binding fragment thereof, according to any one of the preceding embodiments, wherein the one or more amino acid changes comprises up to six amino acid changes.

12.7 The antibody, or antigen-binding fragment thereof, according to any one of the preceding embodiments, wherein the one or more amino acid changes comprises up to seven amino acid changes.

12.8 The antibody, or antigen-binding fragment thereof, according to any one of the preceding embodiments, wherein any one of the CDRs comprise no amino acid changes.

13. The antibody, or antigen-binding fragment thereof, according to any one of the preceding embodiments, wherein the antibody, or antigen-binding fragment thereof, specifically binds a human LTBP1-proTGFβ complex.

14. The antibody, or antigen-binding fragment thereof, according to any one of the preceding embodiments, wherein the antibody, or antigen-binding fragment thereof, specifically binds a human LTBP3-proTGFβ complex.

15. The antibody, or antigen-binding fragment thereof, according to any one of the preceding embodiments, wherein the antibody, or antigen-binding fragment thereof, does not bind a human GARP-proTGFβ complex.

16. The antibody, or antigen-binding fragment thereof, according to any one of the preceding embodiments, wherein the antibody, or antigen-binding fragment thereof, specifically binds a human LTBP1-proTGFβ complex and/or a human LTBP3-proTGFβ complex, and does not bind a human GARP-proTGFβ complex.

17. The antibody, or antigen-binding fragment thereof, according to any one of the preceding embodiments, wherein the antibody, or antigen-binding fragment thereof does not bind mature TGFβ1, mature TGFβ2 or mature TGFβ3.

18. The antibody, or antigen-binding fragment thereof, according to any one of the preceding embodiments, wherein the antibody, or antigen-binding fragment thereof, is a fully human or humanized antibody.

19. The antibody, or antigen-binding fragment thereof, according to any one of the preceding embodiments, wherein the antibody, or antigen-binding fragment thereof, is an isolated antibody, or antigen-binding fragment thereof.

20. The antibody, or antigen-binding fragment thereof, according to any one of the preceding embodiments, wherein the antibody, or antigen-binding fragment thereof, does not compete with any one of the antibodies SR-Ab1, SR-Ab2 or SR-Ab13 for binding to a human LTBP1-proTGFβ1 complex.

21. The antibody, or antigen-binding fragment thereof, according to any one of the preceding embodiments, wherein the antibody, or antigen-binding fragment thereof, does not compete with any one of the antibodies SR-Ab1, SR-Ab2 or SR-Ab10 for binding to a human LTBP1-proTGFβ1 complex.

22. The antibody, or antigen-binding fragment thereof, according to any one of the preceding embodiments, wherein the antibody is an IgG4 or IgG1 subtype.

23. The antibody, or antigen-binding fragment thereof, according to any one of the preceding embodiments, wherein the antibody is specific for human LTBP1-TGFβ1 complex.

24. The antibody, or antigen-binding fragment thereof, according to any one of the preceding embodiments, wherein the antibody is specific for human LTBP3-TGFβ1 complex.

25. The antibody, or antigen-binding fragment thereof, according to any one of the preceding embodiments, wherein the antibody is specific for human LTBP1-TGFβ1 complex and human LTBP3-TGFβ1 complex.

26. The antibody, or antigen-binding fragment thereof, according to any one of the preceding embodiments, wherein the antibody does not bind a human GARP-TGFβ1 complex or GARP-TGFβ3 complex.

27. The antibody, or antigen-binding fragment thereof, according to any one of the preceding embodiments, wherein the antibody, or antigen-binding fragment thereof, binds a human LTBP1-proTGFβ1 complex with a $K_D$ of <50 nM as measured by Bio-Layer Interferometry (BLI).

28. The antibody, or antigen-binding fragment thereof, according to any one of the preceding embodiments, wherein the antibody, or antigen-binding fragment thereof, binds a human LTBP3-proTGFβ1 complex with a $K_D$ of <50 nM as measured by Bio-Layer Interferometry (BLI).

29. The antibody, or antigen-binding fragment thereof, according to any one of the preceding embodiments, wherein the antibody, or antigen-binding fragment thereof, binds a human LTBP1-proTGFβ1 complex with a $K_D$ of <10 nM as measured by Bio-Layer Interferometry (BLI).

30. The antibody, or antigen-binding fragment thereof, according to any one of the preceding embodiments, wherein the antibody, or antigen-binding fragment thereof, binds a human LTBP3-proTGFβ1 complex with a $K_D$ of <10 nM as measured by Bio-Layer Interferometry (BLI).

31. The antibody, or antigen-binding fragment thereof, according to any one of embodiments 27-30, wherein the antibody, or antigen-binding fragment thereof, is cross-reactive with mouse LTBP1-proTGFβ1.

32. The antibody, or antigen-binding fragment thereof, according to any one of embodiments 27-30, wherein the antibody, or antigen-binding fragment thereof, is cross-reactive with mouse LTBP3-proTGFβ1.

33. The antibody, or antigen-binding fragment thereof, according to any one of embodiments 27-30, wherein the antibody, or antigen-binding fragment thereof, is cross-reactive with both mouse LTBP1-proTGFβ1 and mouse LTBP3-proTGFβ1.

34. The antibody, or antigen-binding fragment thereof, according to any one of the preceding embodiments, wherein the antibody, or antigen-binding fragment thereof, binds a mouse LTBP1-proTGFβ1 complex with a $K_D$ of <50 nM as measured by Bio-Layer Interferometry (BLI).

35. The antibody, or antigen-binding fragment thereof, according to any one of the preceding embodiments, wherein the antibody, or antigen-binding fragment thereof, binds a mouse LTBP3-proTGFβ1 complex with a $K_D$ of <50 nM as measured by Bio-Layer Interferometry (BLI).

36. The antibody, or antigen-binding fragment thereof, according to any one of the preceding embodiments, wherein the antibody, or antigen-binding fragment thereof, binds a mouse LTBP1-proTGFβ1 complex with a $K_D$ of <10 nM as measured by Bio-Layer Interferometry (BLI).

37. The antibody, or antigen-binding fragment thereof, according to any one of the preceding embodiments, wherein the antibody, or antigen-binding fragment thereof, binds a mouse LTBP3-proTGFβ1 complex with a $K_D$ of <10 nM as measured by Bio-Layer Interferometry (BLI).

38. The antibody, or antigen-binding fragment thereof, according to any one of the preceding embodiments, wherein the antibody, or antigen-binding fragment thereof, is isoform-specific in that it selectively binds and inhibits the activation of TGFβ1 associated with LTBP1/3.

39. The antibody, or antigen-binding fragment thereof, according to embodiment 38, wherein the antibody, or antigen-binding fragment thereof, does not bind GARP- TGFβ31.

40. An antibody, or antigen-binding fragment thereof, comprising the following six CDRs:
    a) CDR-H1 comprising the amino acid sequence FTFRSYVMH (SEQ ID NO: 166);
    b) CDR-H2 comprising the amino acid sequence VISHEGS($X_1$)KYYADSVKG, wherein: $X_1$ is L or G (SEQ ID NO: 366); and
    c) CDR-H3 comprising the amino acid sequence A($X_1$)PRIAARRGGFG($X_2$), wherein: $X_1$ is V, R or L; and $X_2$ is Y, S or T (SEQ ID NO: 367);
    d) CDR-L1 comprising the amino acid sequence TRS($X_1$)G($X_2$)ID($X_3$)NYVQ, wherein, $X_1$ is S or H; $X_2$ is N, L, S or A; and $X_3$ is N, D or Y (SEQ ID NO: 368);
    e) CDR-L2 comprising the amino acid sequence ED($X_1$)($X_2$)RPS, wherein: $X_1$ is N, F or A; and $X_2$ is Q, I or V (SEQ ID NO: 369); and
    f) CDR-L3 comprising the amino acid sequence Q($X_1$)YD($X_2$)($X_3$)($X_4$)Q($X_5$)VV, wherein: $X_1$ is S or G; $X_2$ is S, F, Y, D, H or W; $X_3$ is N, D or S; $X_4$ is N, A, L, E or T; and $X_5$ is G, R, A or L (SEQ ID NO: 370).

41. The antibody, or antigen-binding fragment thereof, according to embodiment 40, wherein:
    within CDR-H3: $X_1$ is R or L.

42. The antibody, or antigen-binding fragment thereof, according to embodiment 41, wherein:
    within CDR-L3: $X_2$ is Y.

43. The antibody, or antigen-binding fragment thereof, according to embodiment 42, wherein:
    within CDR-L3: $X_3$ is D; and $X_4$ is T.

44. The antibody, or antigen-binding fragment thereof, according to embodiment 42, wherein:
    within CDR-L3: $X_3$ is D; $X_4$ is N; and $X_5$ is A.

45. The antibody, or antigen-binding fragment thereof, according embodiment 41, wherein:
    within CDR-L1: $X_1$ is S or H; $X_2$ is N or A; and $X_3$ is N, D or Y;
    within CDR-L2: $X_1$ is N or F; and $X_2$ is Q or V; and
    within CDR-L3: $X_1$ is S or G; $X_2$ is S, Y, D or W; $X_3$ is D or S; $X_4$ is N, L or T; and $X_5$ is G, R, A or L.

46. The antibody, or antigen-binding fragment thereof, according to embodiment 45, wherein:
    within CDR-L1: $X_1$ is S; $X_2$ is N; and $X_3$ is N or Y;
    within CDR-L2: $X_1$ is N; and $X_2$ is Q or V; and
    within CDR-L3: $X_1$ is S or G; $X_2$ is S, Y or W; $X_3$ is D; $X_4$ is N or T; and $X_5$ is G, R or A.

47. The antibody, or antigen-binding fragment thereof, according to embodiment 46, wherein:
    within CDR-L3: $X_1$ is S; $X_2$ is S or Y; $X_3$ is D; $X_4$ is N or T; and $X_5$ is G, R or A.

48. The antibody, or antigen-binding fragment thereof, according to embodiment 47, wherein:
    within CDR-L3: $X_1$ is S; $X_2$ is Y; $X_3$ is D; $X_4$ is N or T; and $X_5$ is G or A.

49. The antibody, or antigen-binding fragment thereof, according to embodiment 48, wherein:
    within CDR-L3: $X_1$ is S; $X_2$ is Y; $X_3$ is D; $X_4$ is T; and $X_5$ is G.

50. The antibody, or antigen-binding fragment thereof, according to any one of embodiments 45-49, wherein:
    a) CDR-H1 comprises the amino acid sequence of SEQ ID NO: 166;
    b) CDR-H2 comprises the amino acid sequence of SEQ ID NO: 167;
    c) CDR-H3 comprises the amino acid sequence of SEQ ID NO: 168;
    d) CDR-L1 comprises the amino acid sequence of SEQ ID NO: 169;
    e) CDR-L2 comprises the amino acid sequence of SEQ ID NO: 170; and
    f) CDR-L3 comprises the amino acid sequence of SEQ ID NO: 171.

51. The antibody, or antigen-binding fragment thereof, according to any one of embodiments 40-50, which comprises:
    a heavy chain variable region having an amino acid sequence that is at least 90% identical to SEQ ID NO: 318; and
    a light chain variable region having an amino acid sequence that is at least 90% identical to SEQ ID NO: 319.

52. The antibody, or antigen-binding fragment thereof, according to any one of embodiments 40-51, which competes or cross-competes with an antibody having a heavy chain variable region sequence as set forth in SEQ ID NO: 318 and light chain variable region sequence as set forth in SEQ ID NO: 319.

53. An antibody, or antigen-binding fragment thereof, which selectively binds to human LTBP1-TGFβ1 complex and human LTBP3-TGFβ1 complex and competes or cross-competes with an antibody having a heavy chain variable region sequence as set forth in SEQ ID NO: 318 and light chain variable region sequence as set forth in SEQ ID NO: 319.

54. An antibody, or antigen-binding fragment thereof, comprising the following six CDRs:
    g) CDR-H1 comprising the amino acid sequence G($X_1$)I($X_2$)S($X_3$)SYYW($X_4$), wherein, optionally: $X_1$ is S; $X_2$ is S, H or R; $X_3$ is S or G; and, $X_4$ is G, I, N or V (SEQ ID NO: 386);
    h) CDR-H2 comprising the amino acid sequence SISYS($X_1$)($X_2$)TYY, wherein, optionally: $X_1$ is G or A; and $X_2$ is S or T (SEQ ID NO: 398);
    i) CDR-H3 comprising the amino acid sequence A($X_1$)DPSYDS($X_2$)AGM($X_3$)V, wherein, optionally: $X_1$ is R, S or G; $X_2$ is A or I; and $X_3$ is D or Q (SEQ ID NO: 387);
    j) CDR-L1 comprising the amino acid sequence RAS($X_1$)($X_2$)IS($X_3$)YLN, wherein, optionally: $X_1$ is K or Q; $X_2$ is V or S; and $X_3$ is S or Y (SEQ ID NO: 389);
    k) CDR-L2 comprising the amino acid sequence ($X_1$)AS($X_2$)($X_3$)QS, wherein, optionally: $X_1$ is Y, A or S; $X_2$ is S or N; and $X_3$ is L or R (SEQ ID NO: 390);
    l) CDR-L3 comprising the amino acid sequence QQ($X_1$)($X_2$)D($X_3$)P($X_4$)T, wherein, optionally: $X_1$ is S or G; $X_2$ is F or N; $X_3$ is W or F; and $X_4$ is F or L (SEQ ID NO: 391).

55. The antibody, or antigen-binding fragment thereof, according to embodiment 54, wherein:
   a) within CDR-H1: $X_1$ is S; $X_2$ is S or R; $X_3$ is S; and, $X_4$ is G;
   b) within CDR-H2: $X_1$ is G or A; and $X_2$ is S or T;
   c) within CDR-H3: $X_1$ is R, S or G; $X_2$ is A or I; and $X_3$ is D or Q;
   d) within CDR-L1: $X_1$ is K or Q; $X_2$ is V or S; and $X_3$ is S or Y;
   e) within CDR-L2: $X_1$ is Y, A or S; $X_2$ is S or N; and $X_3$ is L or R; and
   f) within CDR-L3: $X_1$ is S or G; $X_2$ is F or N; $X_3$ is W or F; and $X_4$ is F or L.
56. The antibody, or antigen-binding fragment thereof, according to embodiment 55, wherein:
   a) CDR-H1 comprises the amino acid sequence GSIRSSSYYWG (SEQ ID NO: 292);
   b) CDR-H2 comprises the amino acid sequence SISYSATTYY (SEQ ID NO: 293);
   c) within CDR-H3: $X_1$ is S or G; $X_2$ is A or I; and $X_3$ is D or Q;
   d) within CDR-L1: $X_1$ is K or Q; $X_2$ is V or S; and $X_3$ is S or Y;
   e) within CDR-L2: $X_1$ is Y, A or S; $X_2$ is S or N; and $X_3$ is L or R; and
   f) within CDR-L3: $X_1$ is S or G; $X_2$ is F or N; $X_3$ is W or F; and $X_4$ is F or L.
57. The antibody, or antigen-binding fragment thereof, according to embodiment 56, wherein:
   g) CDR-H1 comprises the amino acid sequence of SEQ ID NO: 292;
   h) CDR-H2 comprises the amino acid sequence of SEQ ID NO: 293;
   i) CDR-H3 comprises the amino acid sequence of SEQ ID NO: 294;
   j) CDR-L1 comprises the amino acid sequence of SEQ ID NO: 295;
   k) CDR-L2 comprises the amino acid sequence of SEQ ID NO: 296; and
   l) CDR-L3 comprises the amino acid sequence of SEQ ID NO: 297.
58. The antibody, or antigen-binding fragment thereof, according to any one of embodiments 54-57, which is an antibody according to any one of claims 1-5.
59. The antibody, or antigen-binding fragment thereof, according to any one of embodiments 54-58, which comprises:
   a heavy chain variable region having an amino acid sequence that is at least 90% identical to SEQ ID NO: 360; and
   a light chain variable region having an amino acid sequence that is at least 90% identical to SEQ ID NO: 361.
60. The antibody, or antigen-binding fragment thereof, according to any one of embodiments 54-59, which competes or cross-competes with an antibody having a heavy chain variable region sequence as set forth in SEQ ID NO: 360 and light chain variable region sequence as set forth in SEQ ID NO: 361.
61. An antibody, or antigen-binding fragment thereof, which selectively binds to human LTBP1-TGFβ1 complex and human LTBP3-TGFβ1 complex and competes or cross-competes with an antibody having a heavy chain variable region sequence as set forth in SEQ ID NO: 360 and light chain variable region sequence as set forth in SEQ ID NO: 361.
62. The antibody, or antigen-binding fragment thereof, according to any one of embodiments 40-61, which does not show detectable binding to a human GARP-proTGFβ1 complex, as measured by BLI, under the same assay conditions as used to measure binding to human LTBP1-proTGFβ1 complex and human LTBP3-TGFβ1 complex.
63. The antibody, or antigen-binding fragment thereof, according to any one of embodiments 40-62, which binds a human LTBP1-proTGFβ1 complex and/or a human LTBP3-TGFβ1 complex with a $K_D$ that is at least 50 times lower than the $K_D$ when binding to a human GARP-proTGFβ1 complex under the same assay conditions.
64. The antibody, or antigen-binding fragment thereof, according to any one of embodiments 40-63, which does not show detectable binding to an LRRC33-proTGFβ1 complex, as measured by BLI, under the same assay conditions as used to measure binding to human LTBP1-proTGFβ1 complex and human LTBP3-TGFβ1 complex.
65. The antibody, or antigen-binding fragment thereof, according to any one of embodiments 40-64, wherein the antibody, or antigen-binding fragment thereof has a monovalent half-binding-time t½) of at least 45 minutes for each of hLTBP1-proTGFβ1 and hLTBP3-proTGFβ1 complexes, as measured by SPR.
66. The antibody, or antigen-binding fragment thereof, according to embodiment 65 which has a monovalent t½ of less than 5 minutes for each of hGARP-proTGFβ1 and hLRRC33-proTGFβ1 complexes, as measured by SPR.
67. The antibody, or antigen-binding fragment thereof, according to any one of the preceding embodiments, which binds a human LTBP1-proTGFβ1 complex and a human LTBP3-TGFβ1 complex with a $K_D$ of <5 nM as measured by Bio-Layer Interferometry (BLI), optionally <1 nM.
68. The antibody, or antigen-binding fragment thereof, according to any one of the preceding embodiments, which is cross-reactive with mouse LTBP1-proTGFβ1.
69. The antibody, or antigen-binding fragment thereof, according to any one of the preceding embodiments, which is cross-reactive with mouse LTBP3-proTGFβ1.
70. The antibody, or antigen-binding fragment thereof, according to any one of the preceding embodiments, wherein the antibody, or antigen-binding fragment thereof, binds a mouse LTBP1-proTGFβ1 complex with a $K_D$ of <10 nM as measured by Bio-Layer Interferometry (BLI).
71. The antibody, or antigen-binding fragment thereof, according to any one of the preceding embodiments, wherein the antibody, or antigen-binding fragment thereof, binds a mouse LTBP3-proTGFβ1 complex with a $K_D$ of <10 nM as measured by Bio-Layer Interferometry (BLI).
72. The antibody, or antigen-binding fragment thereof, according to any one of the preceding embodiments, wherein the antibody, or antigen-binding fragment thereof cross-reacts with human and murine LTBP1-proTGFβ1 and LTBP3-proTGFβ1 complexes, each with a $K_D$ of <5 nM, optionally <1 nM.
73. The antibody, or antigen-binding fragment thereof, according to any one of the preceding embodiments, wherein the antibody is an IgG4 or IgG1 subtype.
74. The antibody, or antigen-binding fragment thereof, according to embodiment 73, wherein the antibody is a human IgG4 subtype, wherein optionally the antibody comprises a backbone substitution of Ser to Pro that produces an IgG1-like hinge.

75. A pharmaceutical composition comprising the antibody, or antigen-binding fragment thereof, according to any one of the preceding embodiments and a pharmaceutically acceptable excipient.

76. The pharmaceutical composition according to embodiment 75, which is prepared for intravenous administration or subcutaneous administration.

77. A composition comprising a multi-dose vial containing the pharmaceutical composition of embodiments 75 or 76.

78. A composition comprising a single-dose syringe containing the pharmaceutical composition of embodiments 75 or 76, optionally wherein the syringe is a disposable syringe.

79. The composition according to any one of embodiments 75 or 78 for use in a method for the treatment of a fibrotic condition in a human subject, wherein the treatment comprises administration of the composition to the subject in an amount effective to treat the fibrotic disorder.

80. The composition for use according to embodiment 79, wherein the fibrotic disorder is an organ fibrosis.

81. The composition for use according to embodiment 80, wherein the organ fibrosis is an advanced organ fibrosis.

82. The composition for use according to embodiments 80 or 81, wherein the organ fibrosis is selected from the group consisting of: kidney fibrosis, liver fibrosis, lung fibrosis, cardiac fibrosis, pancreatic fibrosis, skin fibrosis, scleroderma, muscle fibrosis, uterine fibrosis and endometriosis.

83. The composition for use according to embodiment 82, wherein:
  a) the fibrotic disorder comprises chronic inflammation;
  b) the subject benefits from immune suppression;
  c) the subject has or is at risk of developing an autoimmune disease;
  d) the subject is a candidate for an allograft transplant; and/or,
  e) the subject has received an allograft transplant.

84. The composition for use according to embodiment 79, wherein the fibrotic disorder comprising chronic inflammation is a muscular dystrophy, multiple sclerosis (MS), or Cystic Fibrosis (CF).

85. The composition for use according to embodiment 84, wherein the muscular dystrophy is Duchenne muscular dystrophy (DMD).

86. The composition for use according to embodiment 84, wherein the MS comprises perivascular fibrosis.

87. The composition for use according to embodiment 82, wherein the lung fibrosis is idiopathic pulmonary fibrosis (IPF).

88. The composition for use according to embodiment 82, wherein the subject has chronic kidney disease (CKD).

89. The composition for use according to embodiment 82, wherein the subject has liver fibrosis associated with nonalcoholic steatohepatitis (NASH) ornonalcoholic fatty liver disease (NAFLD).

90. The composition for use according to embodiment 89, wherein the subject has cirrhosis or hepatocellular carcinoma associated with NASH.

91. The composition for use according to embodiment 90, wherein the subject suffers from a metabolic condition (e.g., obesity, type 2 diabetes).

92. The composition for use according to any one of embodiments 89-91, wherein the the subject is further treated with a myostatin inhibitor, wherein optionally the myostatin inhibitor is a myostatin-selective inhibitor, wherein further optionally the myostatin-selective inhibitor is SRK-015, trevogrumab, or any variant thereof, or an antibody according to WO 2016/098357.

93. The composition for use according to any one of embodiments 79-92, wherein the antibody is administered to the subject at a dosage of between 0.1 and 30 mg/kg.

94. The composition for use according to embodiment 93, wherein the antibody is administered twice a week, once a week, once every 2 weeks, once every 3 weeks, once every 4 weeks, once a month, once every 6 weeks, or every other month.

95. The composition for use according to embodiment 93, wherein a therapeutic regimen comprises an initial phase of a therapy and a subsequent phase of the therapy, wherein the subject receives a loading dose during the initial phase followed by a maintenance dose during the subsequent phase.

96. The composition for use according to embodiment 95, wherein the loading dose is between 2-30 mg/kg, and the maintenance dose is between 0.1-20 mg/kg.

97. The composition for use according to embodiment 95 or 96, wherein the loading dose is administered to the subject twice a week, once a week, once every 2 weeks or every 3 weeks.

98. The composition for use according to any one of embodiments 95-97, wherein the maintenance dose is administered to the subject once every 2-12 weeks.

99. The composition for use according to any one of embodiments 95-97, wherein the maintenance dose is administered to the subject on an as-needed basis.

100. The composition for use according to any one of embodiments 79-99, wherein the method further comprises testing or confirming expression of TGFβ1, LTBP1 or LTBP3 in a biological sample collected from the subject.

101. A method for making a composition according to any one of embodiments 75-78, comprising an antibody, or antigen-binding fragment thereof, that specifically binds a human LTBP1-proTGFβ complex and/or a human LTBP3-proTGFβ complex, and does not bind a human GARP-proTGFβ complex; wherein the antibody or fragment inhibits TGFβ1 but does not inhibit TGFβ2 or TGFβ3, the method comprising steps of:
  i) providing at least one antigen comprising LTBP1-proTGFβ1 and/or LTBP3-proTGFβ31,
  ii) selecting a first pool of antibodies or fragments that specifically bind the at least one antigen of step (i) so as to provide specific binders of LTBP1-proTGFβ1 and/or LTBP3-proTGFβ31;
  iii) selecting a second pool of antibodies or fragments that inhibit activation of TGFβ1, so as to generate specific inhibitors of TGFβ1 activation; and
  iv) formulating an antibody or fragment that is present in the first pool of antibodies and the second pool of antibodies into a pharmaceutical composition, thereby making the composition comprising the antibody or fragment.

102. The method of embodiment 101, wherein the method further comprises a step of:

removing from the first pool of antibodies, or fragments, any antibodies or fragments that bind GARP-proTGFβ1, LRRC33-proTGFβ1, mature TGFβ1, GARP-proTGFβ2, LRRC33-proTGFβ2, mature TGFβ2, GARP-proTGFβ3, LRRC33-proTGFβ3, mature TGFβ3, or any combinations thereof.
103. The method of embodiment 101 or 102, wherein the method further comprises a step of:
determining or confirming isoform-specificity of the antibodies or fragments selected in steps (ii) and/or (iii).
104. The method according to any one of embodiments 101-103, wherein the method further comprises a step of:
selecting antibodies or fragments that are cross-reactive to human and rodent antigens.
105. The method according to any one of embodiments 101-104, wherein the method further comprises a step of:
generating a fully human or humanized antibody or fragment, of the antibody or fragment that is presented in the first pool of antibodies and the second pool of antibodies.
106. The method according to any one of embodiments 101-105, wherein the method further comprises a step of:
subjecting the antibody or fragment that is present in the first pool of antibodies and the second pool of antibodies to affinity maturation and/or optimization, so as to provide an affinity matured and/or optimized antibody or fragment.
107. The method according to any one of embodiments 101-106, wherein the affinity maturation and/or optimization comprises a step of subjecting the antibody, or antigen-binding fragment thereof, to light chain shuffling.
108. The method according to any one of embodiments 101-107, wherein the affinity maturation and/or optimization comprises the step of subjecting the antibody, or antigen-binding fragment thereof, to CDR H1/H2 diversification.
109. The method according to any one of embodiments 101-108, wherein the affinity maturation and/or optimization comprises the step of subjecting the antibody, or antigen-binding fragment thereof, to CDR-H3 mutagenesis.
110. The method according to any one of embodiments 101-109, wherein the affinity maturation and/or optimization comprises the step of subjecting antibody, or antigen-binding fragment thereof, to light chain CDR mutagenesis.
111. The method according to any one of embodiments 101-110, wherein the affinity maturation and/or optimization comprises the step of subjecting the antibody, or antigen-binding fragment thereof, to light chain CDR L1/L2 diversification.
112. The method according to any one of embodiments 101-111, wherein the method further comprises a step of determining affinity of the antibodies, or antigen-binding fragments thereof, to human LTBP1-proTGFβ1 and/or human LTBP3-proTGFβ1.
113. The method according to embodiments 101-112, wherein the method further comprises a step of removing from the first and/or second pools of antibodies, or antigen-binding fragments thereof, any antibodies, or antigen-binding fragments thereof, that bind to human LTBP1-proTGFβ1 and/or human LTBP3-proTGFβ1 with a $K_D$ of >100 nM, as measured by Bio-Layer Interferometry (BLI).
114. The method according to embodiment 101-113, wherein the method further comprises a step of removing from the first and/or second pools of antibodies, or antigen-binding fragments thereof, any antibodies, or antigen-binding fragments thereof, that bind to human LTBP1-proTGFβ1 and/or human LTBP3-proTGFβ1 with a $K_D$ of >50 nM, as measured by Bio-Layer Interferometry (BLI).
115. The method according to embodiment 101-114, wherein the method further comprises a step of removing from the first and/or second pools of antibodies, or antigen-binding fragments thereof, any antibodies, or antigen-binding fragments thereof, that bind to human LTBP1-proTGFβ1 and/or human LTBP3-proTGFβ1 with a $K_D$ of >25 nM, as measured by Bio-Layer Interferometry (BLI).
116. The method according to embodiment 101-115, wherein the method further comprises a step of removing from the first and/or second pools of antibodies, or antigen-binding fragments thereof, any antibodies, or antigen-binding fragments thereof, that bind to human LTBP1-proTGFβ1 and/or human LTBP3-proTGFβ1 with a $K_D$ of >10 nM, as measured by Bio-Layer Interferometry (BLI).
117. The method according to any one of embodiments 101-116, wherein the method further comprises a step of determining affinity of the antibodies, or antigen-binding fragments thereof, from the first and/or second pools of antibodies to mouse LTBP1-proTGFβ1 and/or mouse LTBP3-proTGFβ31.
118. The method according to embodiment 117, wherein the method further comprises a step of removing from the first and/or second pools of antibodies, or antigen-binding fragments thereof, any antibodies, or antigen-binding fragments thereof, that bind to mouse LTBP1-proTGFβ1 and/or mouse LTBP3-proTGFβ1 with a $K_D$ of >100 nM, as measured by Bio-Layer Interferometry (BLI).
119. The method according to embodiment 117, wherein the method further comprises a step of removing from the first and/or second pools of antibodies, or antigen-binding fragments thereof, any antibodies, or antigen-binding fragments thereof, that bind to mouse LTBP1-proTGFβ1 and/or mouse LTBP3-proTGFβ1 with a $K_D$ of >50 nM, as measured by Bio-Layer Interferometry (BLI).
120. The method according to embodiment 117, wherein the method further comprises a step of removing from the first and/or second pools of antibodies, or antigen-binding fragments thereof, any antibodies, or antigen-binding fragments thereof, that bind to mouse LTBP1-proTGFβ1 and/or mouse LTBP3-proTGFβ1 with a $K_D$ of >25 nM, as measured by Bio-Layer Interferometry (BLI).
121. The method according to embodiment 117, wherein the method further comprises a step of removing from the first and/or second pools of antibodies, or antigen-binding fragments thereof, any antibodies, or antigen-binding fragments thereof, that bind to mouse LTBP1-proTGFβ1 and/or mouse LTBP3-proTGFβ1 with a $K_D$ of >10 nM, as measured by Bio-Layer Interferometry (BLI).
122. The method according to any one of embodiments 101-121, wherein the method further comprises a step of removing from the first and/or second pool of antibodies, or antigen-binding fragments thereof, any antibodies, or antigen-binding fragments thereof, that do not bind mouse LTBP1-proTGFβ1 and/or mouse LTBP3-proTGFβ1.

123. The method according to any one of embodiments 101-122, wherein the method further comprises a step of determining the $IC_{50}$ of the antibodies, or antigen-binding fragments thereof, from the first and/or second pools of antibodies, or antigen-binding fragments thereof, as measured by a suitable functional in vitro cell-based assay.

124. The method according to embodiments 123, wherein the suitable functional in vitro cell-based assay is a caga assay.

125. The method according to embodiments 123 or 124, wherein the method comprises the step of removing antibodies, or antigen-binding fragments thereof, from the first and/or second pools of antibodies, or antigen-binding fragments thereof, that have an $IC_{50}$ of >100 nM.

126. The method according to embodiments 123 or 124, wherein the method comprises the step of removing antibodies, or antigen-binding fragments thereof, from the first and/or second pools of antibodies, or antigen-binding fragments thereof, that have an $IC_{50}$ of >50 nM.

127. The method according to embodiments 123 or 124, wherein the method comprises the step of removing antibodies, or antigen-binding fragments thereof, from the first and/or second pools of antibodies, or antigen-binding fragments thereof, that have an $IC_{50}$ of >25 nM.

128. The method according to embodiments 123 or 124, wherein the method comprises the step of removing antibodies, or antigen-binding fragments thereof, from the first and/or second pools of antibodies, or antigen-binding fragments thereof, that have an $IC_{50}$ of >10 nM.

129. The method according to embodiments 123 or 124, wherein the method comprises the step of removing antibodies, or antigen-binding fragments thereof, from the first and/or second pools of antibodies, or antigen-binding fragments thereof, that have an $IC_{50}$ of >5 nM.

130. The method according to any one of embodiments 124-129, wherein the caga assay is an endogenous LTBP caga assay.

131. The method according to any one of embodiments 124-129, wherein the caga assay is a human LTBP overexpression caga assay.

132. The method according to any one of embodiments 124-129, wherein the caga assay is a murine LTBP overexpression caga assay.

133. A method for manufacturing a pharmaceutical composition comprising an antibody, or antigen-binding fragment thereof, that selectively binds a human LTBP1-proTGFβ complex and/or a human LTBP3-proTGFβ complex, the method comprising the steps of:
selecting an antibody or antigen-binding fragment thereof that preferentially inhibits matrix-associated TGFβ1 over immune cell-associated TGFβ1;
producing the antibody in a cell culture comprising cells expressing the antibody, wherein the cell culture has a volume of 250 L or greater,
optionally further comprising the step of purifying the antibody from the cell culture; and
further optionally comprising the step of formulating the purised antibody into a pharmaceutical composition.

134. The method according to 133, wherein the pharmaceutical composition is formulated for subcutaneous administration.

135. The method according to 133, wherein the selection step further comprises selecting an antibody or antigen-binding fragment that has t½ of 45 minutes or longer for each of human LTBP1-proTGFβ and human LTBP3-proTGFβ complexes and optionally t½ of 5 minutes or less for human GARP-proTGFβ complex, as measured by SPR.

136. A method for making an antibody, or an antigen-binding fragment thereof, the method comprising steps of:
i) providing an antibody or a fragment that comprises at least three heavy chain CDR sequences of (CDR-H1) SEQ ID NO:94, (CDR-H2) SEQ ID NO:95, and (CDR-H3) SEQ ID NO:96; and
ii) subjecting the antibody or fragment of step (i) to affinity maturation and/or optimization, so as to provide an affinity matured and/or optimized antibody or fragment.

137. The method according to embodiment 136, wherein the antibody, or antigen-binding fragment thereof, further comprises light chain CDR sequences of (CDR-L1) SEQ ID NO:97, (CDR-L2) SEQ ID NO:98, and (CDR-L3) SEQ ID NO:99.

138. The method according to embodiments 136 or 137, wherein the antibody or fragment comprises a variable heavy chain region having an amino acid sequence as set forth in SEQ ID NO: 88.

139. The method according to any one of embodiments 136-138, wherein the antibody or fragment comprises a variable light chain region having an amino acid sequence as set forth in SEQ ID NO: 89.

140. A method for making an antibody, or an antigen-binding fragment thereof, the method comprising steps of:
i) providing an antibody or a fragment that comprises at least three CDR sequences of (CDR-H1) SEQ ID NO:100, (CDR-H2) SEQ ID NO:101, and (CDR-H3) SEQ ID NO:102; and
ii) subjecting the antibody or fragment of step (i) to affinity maturation and/or optimization, so as to provide an affinity matured and/or optimized antibody or fragment.

141. The method of embodiment 140, wherein the antibody, or antigen-binding fragment thereof, further comprises light chain CDR sequences of (CDR-L1) SEQ ID NO:103, (CDR-L2) SEQ ID NO:104, and (CDR-L3) SEQ ID NO:105.

142. The method according to embodiments 140 or 141, wherein the antibody or fragment comprises a variable heavy chain region having an amino acid sequence as set forth in SEQ ID NO: 106.

143. The method according to any one of embodiments 140-142, wherein the antibody or fragment comprises a variable light chain region having an amino acid sequence as set forth in SEQ ID NO: 107.

144. A method for making an antibody, or an antigen-binding fragment thereof, the method comprising steps of:
i) providing an antibody or a fragment that comprises at least three heavy chain CDR sequences of (CDR- H1) SEQ ID NO:108, (CDR-H2) SEQ ID NO:109, and (CDR-H3) SEQ ID NO:110 and
  ii) subjecting the antibody or fragment of step (i) to affinity maturation and/or optimization, so as to provide an affinity matured and/or optimized antibody or fragment.
145. The method according to embodiment 144, wherein the antibody, or antigen-binding fragment thereof, further comprises light chain CDR sequences of (CDR-L1) SEQ ID NO:111, (CDR-L2) SEQ ID NO:112, and (CDR-L3) SEQ ID NO:113.
146. The method according to embodiments 144 or 145, wherein the antibody or fragment comprises a variable heavy chain region having an amino acid sequence as set forth in SEQ ID NO: 114.
147. The method according to any one of embodiments 144-146, wherein the antibody or fragment comprises a variable light chain region having an amino acid sequence as set forth in SEQ ID NO: 115.
148. A method for making an antibody, or an antigen-binding fragment thereof, the method comprising steps of:
  i) providing an antibody or a fragment that comprises at least three heavy chain CDR sequences of (CDR-H1) SEQ ID NO:116, (CDR-H2) SEQ ID NO:117, and (CDR-H3) SEQ ID NO:118 and
  ii) subjecting the antibody or fragment of step (i) to affinity maturation and/or optimization, so as to provide an affinity matured and/or optimized antibody or fragment.
149. The method according to embodiment 148, wherein the antibody, or antigen-binding fragment thereof, further comprises light chain CDR sequences of (CDR-L1) SEQ ID NO:119, (CDR-L2) SEQ ID NO:120, and (CDR-L3) SEQ ID NO:121.
150. The method according to embodiments 148 or 149, wherein the antibody or fragment comprises a variable heavy chain region having an amino acid sequence as set forth in SEQ ID NO: 122.
151. The method according to any one of embodiments 148-150, wherein the antibody or fragment comprises a variable light chain region having an amino acid sequence as set forth in SEQ ID NO: 123.
152. The method according to any one of embodiments 136-151, wherein step (ii) comprises light-chain shuffling.
153. The method according to any one of embodiments 136-152, wherein step (ii) comprises CDR-H1/H2 diversification.
154. The method according to any one of embodiments 136-153, wherein step (ii) comprises CDR-L1/L2 diversification.
155. The method according to any one of embodiments 136-154, wherein step (ii) comprises mutagenesis within any one of the CDRs, variable regions, and/or constant regions.
156. The method according to embodiment 155, wherein the mutagenesis is within a CDR.
157. The method according to any one of embodiments 155 and 156, wherein the mutagenesis is within a CDR-H3.
158. The method according to any one of embodiments 155-157, wherein the mutagenesis is within a CDR-L1.
159. The method according to any one of embodiments 155-158, wherein the mutagenesis is within a CDR-L2.
160. The method according to any one of embodiments 155-159, wherein the mutagenesis is within a CDR-L3.
161. The method according to embodiment 155, wherein the mutagenesis is within a variable region.
162. The method according to embodiment 155, wherein the mutagenesis is within a constant region.
163. The method of any one of embodiments 136-162, wherein the method further comprises a step of:
  selecting affinity matured and/or optimized antibodies, or antigen-binding fragments thereof, that do not bind GARP-proTGFβ1, LRRC33-proTGFβ1, mature TGFβ1, GARP-proTGFβ2, LRRC33-proTGFβ2, mature TGFβ2, GARP-proTGFβ3, LRRC33-proTGFβ3, mature TGFβ3, or any combinations thereof.
164. The method of any one of embodiments 136-163, wherein the method further comprises a step of:
  determining or confirming isoform-specificity of the affinity matured and/or optimized antibodies or fragments.
165. The method according to any one of embodiments 136-164, wherein the method further comprises a step of:
  selecting antibodies or fragments that are cross-reactive to human and rodent antigens.
166. The method according to any one of embodiments 136-165, wherein the method further comprises a step of:
  generating a fully human or humanized antibody or fragment, of the affinity matured and/or optimized antibody or fragment.
167. The method according to any one of embodiments 136-166, wherein the method further comprises a step of:
  determining affinity of the affinity matured and/or optimized antibodies, or fragments, to human LTBP1-proTGFβ1 and/or human LTBP3-proTGFβ1.
168. The method according to embodiments 136-167, wherein the method further comprises a step of: selecting affinity matured and/or optimized antibodies, or fragments, that bind to human LTBP1-proTGFβ1 and/or human LTBP3-proTGFβ1 with a $K_D$ of <100 nM, as measured by Bio-Layer Interferometry (BLI).
169. The method according to embodiment 136-168, wherein the method further comprises a step of: selecting affinity matured and/or optimized antibodies, or fragments, that bind to human LTBP1-proTGFβ1 and/or human LTBP3-proTGFβ1 with a $K_D$ of <50 nM, as measured by Bio-Layer Interferometry (BLI).
170. The method according to embodiment 136-169, wherein the method further comprises a step of: selecting affinity matured and/or optimized antibodies, or fragments, that bind to human LTBP1-proTGFβ1 and/or human LTBP3-proTGFβ1 with a $K_D$ of <25 nM, as measured by Bio-Layer Interferometry (BLI).
171. The method according to embodiment 136-170, wherein the method further comprises a step of: selecting affinity matured and/or optimized antibodies, or fragments, that bind to human LTBP1-proTGFβ1 and/or human LTBP3-proTGFβ1 with a $K_D$ of <10 nM, as measured by Bio-Layer Interferometry (BLI).
172. The method according to any one of embodiments 136-171, wherein the method further comprises a step of:
  determining affinity of the affinity matured and/or optimized antibodies or fragments, to mouse LTBP1-proTGFβ1 and/or mouse LTBP3-proTGFβ1.
173. The method according to embodiment 136-172, wherein the method further comprises a step of: selecting affinity matured and/or optimized antibodies, or fragments, that bind to mouse LTBP1-proTGFβ1 and/or mouse LTBP3-proTGFβ1 with a K$_D$ of <100 nM, as measured by Bio-Layer Interferometry (BLI).
174. The method according to embodiment 136-173, wherein the method further comprises a step of: selecting affinity matured and/or optimized antibodies, or fragments, that bind to mouse LTBP1-proTGFβ1 and/or mouse LTBP3-proTGFβ1 with a K$_D$ of <50 nM, as measured by Bio-Layer Interferometry (BLI).
175. The method according to embodiment 136-174, wherein the method further comprises a step of: selecting affinity matured and/or optimized antibodies, or fragments, that bind to mouse LTBP1-proTGFβ1 and/or mouse LTBP3-proTGFβ1 with a K$_D$ of <25 nM, as measured by Bio-Layer Interferometry (BLI).
176. The method according to embodiment 136-175, wherein the method further comprises a step of: selecting affinity matured and/or optimized antibodies, or fragments, that bind to mouse LTBP1-proTGFβ1 and/or mouse LTBP3-proTGFβ1 with a K$_D$ of <10 nM, as measured by Bio-Layer Interferometry (BLI).
177. The method according to any one of embodiments 136-176, wherein the method further comprises a step of:
  selecting affinity matured and/or optimized antibodies, or fragments, that do not bind mouse LTBP1-proTGFβ1 and/or mouse LTBP3-proTGFβ1.
178. The method according to any one of embodiments 136-177, wherein the method further comprises a step of:
  determining the IC$_{50}$ of the affinity matured and/or optimized antibodies, or fragments, as measured by a suitable functional in vitro cell-based assay.
179. The method according to embodiments 178, wherein the suitable functional in vitro cell-based assay is a caga assay.
180. The method according to any one of embodiments 136-179, wherein the method comprises the step of:
  selecting affinity matured and/or optimized antibodies, or fragments, that have an IC$_{50}$ of <100 nM.
181. The method according to any one of embodiments 136-179, wherein the method comprises the step of: selecting affinity matured and/or optimized antibodies, or fragments, that have an IC$_{50}$ of <50 nM.
182. The method according to embodiments 136-179, wherein the method comprises the step of:
  selecting affinity matured and/or optimized antibodies, or fragments, that have an IC$_{50}$ of <25 nM.
183. The method according to embodiments 136-179, wherein the method comprises the step of:
  selecting affinity matured and/or optimized antibodies, or fragments, that have an IC$_{50}$ of <10 nM.
184. The method according to embodiments 136-179, wherein the method comprises the step of:
  selecting affinity matured and/or optimized antibodies, or fragments, that have an IC$_{50}$ of <5 nM.
185. The method according to any one of embodiments 179-184, wherein the caga assay is an endogenous LTBP caga assay.
186. The method according to any one of embodiments 179-184, wherein the caga assay is a human LTBP overexpression caga assay.
187. The method according to any one of embodiments 179-184, wherein the caga assay is a murine LTBP overexpression caga assay.
188. The antibody or the fragment, use thereof, or related methods thereof, according to any one of the preceding embodiments,
  a) which comprises the following variable heavy and/or variable light chain sequences, or a variant thereof:
    i) the variable heavy chain sequences
QVQLVESGGGVVQPGRSLRLS-CAASGFTFRSYVMHWVRQAPGKGLEWVAV-ISHEGSLKYY ADSVKGRFTISRDNSKNT-LYLQMNSLRAEDTAVYYCAVPRIAARRGGFG-YWGQGTLVTVSS (SEQ ID NO: 114) or
QVQLVESGGGVVQPGRSLRLS-CAASGFTFRSYVMHWVRQAPGKGLEWVAV-ISHEGSLKYY AD SVKGRFTISRDNSKNT-LYLQMNSLRAEDTAVYYCARPRIAARRGGFGY-WGQGTLVTVS S (SEQ ID NO: 318), wherein optionally the variant is at least 85% identical, 90% identical, or 95% identical to the corresponding variable heavy chain sequence.
    ii) the variable light chain sequences

```
                                            (SEQ ID NO: 89)
NFMLTQPHSVSESPGKTVTISCTRSSGNIDNNYVQWYQQRPGSSPTTVIY

EDNQRPSGVPDRFSGSIDSSSNSASLTISGLKTEDEADYYCQSYDSDNQG

VVFGGGTKLTVL
or
                                            (SEQ ID NO: 89)
NFMLTQPHSVSESPGKTVTISCTRSSGNIDNNYVQWYQQRPGSSPTTVIY

EDNQRPSGVPDRFSGSIDSSSNSASLTISGLKTEDEADYYCQSYDSDNQG

VVFGGGTKLTVL,
``` wherein optionally the variant is at least 85% identical, 90% identical, or 95% identical to the corresponding variable light chain sequence;
  b) which has the following variable heavy chain CDR sequences, or variant thereof:
    i) CDR-H1 of FTFRSYVMH (SEQ ID NO: 166) optionally comprising one or more amino acid changes;
    ii) CDR-H2 of VISHEGSLKYYADSVKG (SEQ ID NO: 167) optionally comprising one or more amino acid changes; and/or;
    iii) CDR-H3 of AVPRIAARRGGFGY (SEQ ID NO: 110) or ARPRIAARRGGFGY (SEQ ID NO: 168) optionally comprising one or more amino acid changes; and/or;
  c) which has the following variable light chain CDR sequences, or variant thereof:
    i) CDR1-L1 of TRSSGNIDNNYVQ (SEQ ID NO: 169) optionally comprising one or more amino acid changes;
    ii) CDR-L2 of EDNQRPS (SEQ ID NO: 170) optionally comprising one or more amino acid changes; and/or;
    iii) CDR-L3 of QSYDSDNQGVV (SEQ ID NO: 113) optionally comprising one or more amino acid changes.
A1. An isolated antibody that specifically binds a human LTBP1-proTGFβ complex and/or a human LTBP3-proTGFβ complex, and does not bind a human GARP-proTGFβ complex;
  wherein the antibody does not bind mature TGFβ1, mature TGFβ2 or mature TGFβ3;
  wherein the antibody is a fully human or humanized antibody, or antigen-binding fragment thereof, wherein the antibody comprises at least three CDRs selected from the following, optionally comprising up to 3 amino acid changes for each of the CDRs:
CDR-H1: SEQ ID NO:100;
CDR-H2: SEQ ID NO:101;
CDR-H3: SEQ ID NO:102;
CDR-L1: SEQ ID NO:103;
CDR-L2: SEQ ID NO:104; and,
CDR-L3: SEQ ID NO:105.

A1.1. An isolated antibody that specifically binds a human LTBP1-proTGFβ complex and/or a human LTBP3-proTGFβ complex, and does not bind a human GARP-proTGFβ complex;
wherein the antibody does not bind mature TGFβ1, mature TGFβ2 or mature TGFβ3;
wherein the antibody is a fully human or humanized antibody, or antigen-binding fragment thereof,
wherein the antibody comprises at least three of the following six CDRs:
a) CDR-H1: SEQ ID NO:100 (SEQ ID NO: 100 comprising these substitutions is disclosed as SEQ ID NO: 400), with the proviso that:
  i. the serine residue at position 4 of SEQ ID NO:100 may be substituted with a histidine;
  ii. the serine residue at position 7 of SEQ ID NO:100 may be substituted with an alanine or glycine; and/or,
  iii. the glycine residue at position 11 of SEQ ID NO:100 may be substituted with a threonine, serine, histidine, leucine, isoleucine, asparagine, valine, or alanine;
b) CDR-H2: SEQ ID NO:101 (SEQ ID NO: 101 comprising these substitutions is disclosed as SEQ ID NO: 401), with the proviso that:
  i. the serine residue at position 3 of SEQ ID NO:101 may be substituted with an alanine;
  ii. the glycine residue at position 6 of SEQ ID NO:101 may be substituted with an alanine or serine; and/or,
  iii. the serine residue at position 7 of SEQ ID NO:101 may be substituted with a threonine;
c) CDR-H3: SEQ ID NO:102, optionally comprising up to three amino acid changes;
d) CDR-L1: SEQ ID NO:103, optionally comprising up to three amino acid changes;
e) CDR-L2: SEQ ID NO:104, optionally comprising up to three amino acid changes; and,
f) CDR-L3: SEQ ID NO:105, optionally comprising up to three amino acid changes.

A2. An isolated antibody that specifically binds a human LTBP1-proTGFβ complex and/or a human LTBP3-proTGFβ complex, and does not bind a human GARP-proTGFβ complex;
wherein the antibody does not bind mature TGFβ1, mature TGFβ2 or mature TGFβ3;
wherein the antibody is a fully human or humanized antibody, or antigen-binding fragment thereof;
wherein the antibody comprises a heavy chain variable region having an amino acid sequence that is at least 90% identical to SEQ ID NO: SEQ ID NO: 106; and/or,
wherein the antibody comprises a variable light chain variable region having an amino acid sequence that is at least 90% identical to SEQ ID NO: 107.

A3. The antibody according to embodiment A2, wherein the antibody comprises:
a heavy chain variable region having an amino acid sequence that is at least 90% identical to SEQ ID NO: 106; and
a light chain variable region having an amino acid sequence that is at least 90% identical to SEQ ID NO: 107.

A3.1 An isolated antibody that specifically binds a human LTBP1-proTGFβ complex and/or a human LTBP3-proTGFβ complex, and does not bind a human GARP-proTGFβ complex;
wherein the antibody does not bind mature TGFβ1, mature TGFβ2 or mature TGFβ33;
wherein the antibody is a fully human or humanized antibody, or antigen-binding fragment thereof,
wherein the antibody comprises at least three of the following six CDRs:
a) CDR-H1: SEQ ID NO:94 (SEQ ID NO: 94 comprising these substitutions is disclosed as SEQ ID NO: 399), with the proviso that:
  i. the threonine residue at position 2 of SEQ ID NO:94 may be substituted with an alanine;
  ii. the asparagine residue at position 4 of SEQ ID NO:94 may be substituted with an alanine, tyrosine, aspartate, serine, arginine, or histidine;
  iii. the asparagine residue at position 5 of SEQ ID NO:94 may be substituted with a glutamine, serine, glycine, lysine, glutamate, arginine, or histidine;
  iv. the tyrosine residue at position 6 of SEQ ID NO:94 may be substituted with a arginine;
  v. the proline residue at position 7 of SEQ ID NO:94 may be substituted with a glycine, alanine, leucine, serine, asparagine, valine, aspartate, or glutamine;
  vi. the isoleucine residue at position 8 of SEQ ID NO:94 may be substituted with a methionine or leucine; and/or,
  vii. the histidine residue at position 9 of SEQ ID NO:94 may be substituted with a phenylalanine, tyrosine, asparagine, or serine;
b) CDR-H2: SEQ ID NO:95, optionally comprising up to six amino acid changes;
c) CDR-H3: SEQ ID NO:96, optionally comprising up to three amino acid changes;
d) CDR-L1: SEQ ID NO:97, optionally comprising up to three amino acid changes;
e) CDR-L2: SEQ ID NO:98, optionally comprising up to three amino acid changes; and,
f) CDR-L3: SEQ ID NO:99, optionally comprising up to three amino acid changes.

A3.2. An isolated antibody that specifically binds a human LTBP1-proTGFβ complex and/or a human LTBP3-proTGFβ complex, and does not bind a human GARP-proTGFβ complex;
wherein the antibody does not bind mature TGFβ1, mature TGFβ2 or mature TGFβ3;
wherein the antibody is a fully human or humanized antibody, or antigen-binding fragment thereof;
wherein the antibody comprises a heavy chain variable region having an amino acid sequence that is at least 90% identical to SEQ ID NO: SEQ ID NO: 88; and/or, wherein the antibody comprises a variable light chain variable region having an amino acid sequence that is at least 90% identical to SEQ ID NO: 89.

A3.3. The antibody according to embodiment A3.2, wherein the antibody comprises:

a heavy chain variable region having an amino acid sequence that is at least 90% identical to SEQ ID NO: 88; and a light chain variable region having an amino acid sequence that is at least 90% identical to SEQ ID NO: 89.

A3.4. An isolated antibody that specifically binds a human LTBP1-proTGFβ complex and/or a human LTBP3-proTGFβ complex, and does not bind a human GARP-proTGFβ complex;

wherein the antibody does not bind mature TGFβ1, mature TGFβ2 or mature TGFβ3;

wherein the antibody is a fully human or humanized antibody, or antigen-binding fragment thereof, wherein the antibody comprises at least three of the following six CDRs:

a) CDR-H1: SEQ ID NO:1, with the proviso that:
  i. the threonine residue at position 4 of SEQ ID NO:1 may be substituted with a histidine, lysine, phenylalanine, or glycine;
  ii. the serine residue at position 5 of SEQ ID NO:1 may be substituted with an leucine; and/or,
  iii. the serine residue at position 9 of SEQ ID NO:1 may be substituted with an alanine;

b) CDR-H2: SEQ ID NO:2, with the proviso that:
  i. the serine residue at position 3 of SEQ ID NO:2 may be substituted with an aspartate or asparagine;
  ii. the tyrosine residue at position 5 of SEQ ID NO:2 may be substituted with a histidine;
  iii. the asparagine residue at position 6 of SEQ ID NO:2 may be substituted with a serine;
  iv. the asparagine residue at position 8 of SEQ ID NO:2 may be substituted with a phenylalanine, leucine, alanine, tyrosine, aspartate, or serine; and/or,
  v. the asparagine residue at position 10 of SEQ ID NO:2 may be substituted with a aspartate or alanine;

c) CDR-H3: SEQ ID NO:3, optionally comprising up to three amino acid changes;
d) CDR-L1: SEQ ID NO:4, optionally comprising up to three amino acid changes;
e) CDR-L2: SEQ ID NO:5, optionally comprising up to three amino acid changes; and,
f) CDR-L3: SEQ ID NO:6, optionally comprising up to three amino acid changes.

A3.5. An isolated antibody that specifically binds a human LTBP1-proTGFβ complex and/or a human LTBP3-proTGFβ complex, and does not bind a human GARP-proTGFβ complex;

wherein the antibody does not bind mature TGFβ1, mature TGFβ2 or mature TGFβ3;

wherein the antibody is a fully human or humanized antibody, or antigen-binding fragment thereof;

wherein the antibody comprises a heavy chain variable region having an amino acid sequence that is at least 90% identical to SEQ ID NO: SEQ ID NO: 7; and/or, wherein the antibody comprises a variable light chain variable region having an amino acid sequence that is at least 90% identical to SEQ ID NO: 8.

A3.6. The antibody according to embodiment A3.5, wherein the antibody comprises:

a heavy chain variable region having an amino acid sequence that is at least 90% identical to SEQ ID NO: 7; and a light chain variable region having an amino acid sequence that is at least 90% identical to SEQ ID NO: 8.

A4. The antibody according to any one of embodiments A1-A3.6, wherein the antibody does not compete with any one of the antibodies SR-Ab1, SR-Ab2 or SR-Ab10 for binding to a human LTBP1-proTGFβ1 complex.

A5. The antibody according to any one of embodiments A1-A4, wherein the antibody is an IgG4 or IgG1 subtype.

A5.1 The antibody according to any one of embodiments A1-A5, wherein the antibody is specific for human LTBP1-TGFβ1 complex.

A5.2 The antibody according to any one of embodiments A1-A5.1, wherein the antibody is specific for human LTBP3-TGFβ1 complex.

A5.3 The antibody according to any one of embodiments A1-A5.2, wherein the antibody is specific for human LTBP1-TGFβ1 complex and human LTBP3-TGFβ1 complex.

A5.4 The antibody according to any one of embodiments A1-A5.3, wherein the antibody does not bind a human GARP-TGFβ1 complex or GARP-TGFβ3 complex.

A6. A pharmaceutical composition comprising the antibody of any one of embodiments A1-A5.4 and a pharmaceutically acceptable excipient.

A7. The pharmaceutical composition according to embodiment A6, which is prepared for intravenous administration or subcutaneous administration.

A8. A composition comprising a multi-dose vial containing the pharmaceutical composition of embodiment A6 or A7.

A9. A composition comprising a single-dose syringe containing the pharmaceutical composition of embodiment A6 or A7, optionally wherein the syringe is a disposable syringe.

A10. The composition of any one of embodiments A6-A9 for use in a method for the treatment of a fibrotic condition in a human subject, wherein the treatment comprises administration of the composition to the subject in an amount effective to treat the fibrotic disorder.

A11. The composition for use according to embodiment A10, wherein the fibrotic disorder is an organ fibrosis.

A12. The composition for use according to embodiment A11, wherein the organ fibrosis is an advanced organ fibrosis.

A13. The composition for use according to embodiment A10 or A11, wherein the organ fibrosis is selected from the group consisting of: kidney fibrosis, liver fibrosis, lung fibrosis, cardiac fibrosis, pancreatic fibrosis, skin fibrosis, scleroderma, muscle fibrosis, uterine fibrosis and endometriosis.

A14. The composition for use according to embodiment A10, wherein:
a) the fibrotic disorder comprises chronic inflammation;
b) the subject benefits from immune suppression;
c) the subject has or is at risk of developing an autoimmune disease;
d) the subject is a candidate for an allograft transplant; and/or,
e) the subject has received an allograft transplant.

A15. The composition for use according to embodiment A10, wherein the fibrotic disorder comprising chronic inflammation is a muscular dystrophy, multiple sclerosis (MS), or Cystic Fibrosis (CF).

A16. The composition for use according to embodiment A15, wherein the muscular dystrophy is Duchenne muscular dystrophy (DMD).

A17. The composition for use according to embodiment A15, wherein the MS comprises perivascular fibrosis.

A18. The composition for use according to embodiment A13, wherein the lung fibrosis is idiopathic pulmonary fibrosis (IPF).

A19. The composition for use according to embodiment A13, wherein the subject has chronic kidney disease (CKD).

A20. The composition for use according to embodiment A13, wherein the subject has nonalcoholic steatohepatitis (NASH).

A21. The composition for use according to any one of embodiments A10-A20, wherein the antibody is administered to the subject at a dosage of between 0.1 and 30 mg/kg.

A22. The composition for use according to embodiment A21, wherein the antibody is administered twice a week, once a week, once every 2 weeks, once every 3 weeks, once a month, or every other month.

A23. The composition for use according to embodiment A21, wherein a therapeutic regimen comprises an initial phase of a therapy and a subsequent phase of the therapy,
wherein the subject receives a loading dose during the initial phase followed by a maintenance dose during the subsequent phase.

A24. The composition for use according to embodiment A21, wherein the loading dose is between 2-30 mg/kg, and the maintenance dose is between 0.1-20 mg/kg.

A25. The composition for use according to embodiment A21, wherein the loading dose is administered to the subject twice a week or once a week.

A26. The composition for use according to embodiment A21, wherein the maintenance dose is administered to the subject once every 2-8 weeks.

A27. The composition for use according to any one of embodiments A10-A26, wherein the method further comprises testing or confirming expression of TGFβ1, LTBP1 or LTBP3 in a biological sample collected from the subject.

A28. A method for making a composition of any one of embodiments A6-A9, comprising an antibody, or antigen-binding fragment thereof, that specifically binds a human LTBP1-proTGFβ complex and/or a human LTBP3-proTGFβ complex, and does not bind a human GARP-proTGFβ complex; wherein the antibody or fragment inhibits TGFβ1 but does not inhibit TGFβ2 or TGFβ3, the method comprising steps of:
  i) providing at least one antigen comprising LTBP1-proTGFβ1 and/or LTBP3-proTGFβ31,
  ii) selecting a first pool of antibodies or fragments that specifically bind the at least one antigen of step (i) so as to provide specific binders of LTBP1-proTGFβ1 and/or LTBP3-proTGFβ31;
  iii) selecting a second pool of antibodies or fragments that inhibit activation of TGFβ1, so as to generate specific inhibitors of TGFβ1 activation; and
  iv) formulating an antibody or fragment that is present in the first pool of antibodies and the second pool of antibodies into a pharmaceutical composition, thereby making the composition comprising the antibody or fragment.

A29. The method of embodiment A28, wherein the method further comprises a step of:
  removing from the first pool of antibodies, or fragments, any antibodies or fragments that bind GARP-proTGFβ1, LRRC33-proTGFβ1, mature TGFβ1, GARP-proTGFβ2, LRRC33-proTGFβ2, mature TGFβ2, GARP-proTGFβ3, LRRC33-proTGFβ3, mature TGFβ3, or any combinations thereof.

A30. The method of embodiment A28 or A29, wherein the method further comprises a step of:
  determining or confirming isoform-specificity of the antibodies or fragments selected in steps (ii) and/or (iii).

A31. The method of any one of embodiments A28-A30, wherein the method further comprises a step of:
  selecting antibodies or fragments that are cross-reactive to human and rodent antigens.

A32. The method of any one of embodiments A28-A31, wherein the method further comprises a step of:
  generating a fully human or humanized antibody or fragment, of the antibody or fragment that is presented in the first pool of antibodies and the second pool of antibodies.

A33. The method of any one of embodiments A28-A32, wherein the method further comprises a step of:
  subjecting the antibody or fragment that is present in the first pool of antibodies and the second pool of antibodies to affinity maturation and/or optimization, so as to provide an affinity matured and/or optimized antibody or fragment.

A34. A method for making an antibody, or an antigen-binding fragment thereof, the method comprising steps of:
  i) providing an antibody or a fragment that comprises at least three CDR sequences of (CDR-H1) SEQ ID NO:1, (CDR-H2) SEQ ID NO:2, and (CDR-H3) SEQ ID NO:3; and
  ii) subjecting the antibody or fragment of step (i) to affinity maturation and/or optimization, so as to provide an affinity matured and/or optimized antibody or fragment.

A35. A method for making an antibody, or an antigen-binding fragment thereof, the method comprising steps of:
  i) providing an antibody or a fragment that comprises at least three CDR sequences of (CDR-H1) SEQ ID NO:94, (CDR-H2) SEQ ID NO:95, and (CDR-H3) SEQ ID NO:96; and
  ii) subjecting the antibody or fragment of step (i) to affinity maturation and/or optimization, so as to provide an affinity matured and/or optimized antibody or fragment.

A36. A method for making an antibody, or an antigen-binding fragment thereof, the method comprising steps of:
  i) providing an antibody or a fragment that comprises at least three CDR sequences of (CDR-H1) SEQ ID NO:100, (CDR-H2) SEQ ID NO:101, and (CDR-H3) SEQ ID NO:102; and
  ii) subjecting the antibody or fragment of step (i) to affinity maturation and/or optimization, so as to provide an affinity matured and/or optimized antibody or fragment.

A37. A method for making an antibody, or an antigen-binding fragment thereof, the method comprising steps of:
  i) providing an antibody or a fragment that comprises a heavy chain variable region having an amino acid sequence set forth in SEQ ID NO: 7; and ii) subjecting the antibody or fragment of step (i) to affinity maturation and/or optimization, so as to provide an affinity matured and/or optimized antibody, or fragment.

A38. A method for making antibody, or an antigen-binding fragment thereof, the method comprising steps of:
i) providing an antibody or a fragment that comprises a heavy chain variable region having an amino acid sequence set forth in SEQ ID NO: 88; and
ii) subjecting the antibody or fragment of step (i) to affinity maturation and/or optimization, so as to provide an affinity matured and/or optimized antibody or fragment.

A39. A method for making an antibody, or an antigen-binding fragment thereof, the method comprising steps of:
i) providing an antibody or a fragment that comprises a heavy chain variable region having an amino acid sequence set forth in SEQ ID NO: 106; and
ii) subjecting the antibody or fragment of step (i) to affinity maturation and/or optimization, so as to provide an affinity matured and/or optimized antibody or fragment.

A40. The method of any one of embodiments A34-A39, wherein step (ii) comprises mutagenesis.

A41. The method of embodiment A40, wherein the mutagenesis is within a CDR.

A42. The method of embodiment A40, wherein the mutagenesis is within a variable region.

A43. The method of embodiment A40, wherein the mutagenesis is within a constant region.

A44. The method of any one of embodiments A34-A43, wherein step (ii) comprises light-chain shuffling.

What is claimed is:

1. A method of inhibiting transforming growth factor β1 (TGFβ1) signaling in a subject, the method comprising administering to the subject an antibody, or an antigen-binding fragment thereof, that specifically binds a human latent transforming growth factor beta binding protein 1 (LTBP1)-proTGFβ1 complex or a human latent transforming growth factor beta binding protein 3 (LTBP3)-proTGFβ1 complex, comprising a heavy chain variable domain and a light chain variable domain,
wherein the heavy chain variable domain comprises:
a heavy chain complementary determining region 1 (CDRH1) comprising an amino acid sequence set forth as SEQ ID NO: 166,
a heavy chain complementary determining region 2 (CDRH2) comprising an amino acid sequence set forth as SEQ ID NO: 167, and
a heavy chain complementary determining region 3 (CDRH3) comprising an amino acid sequence set forth as SEQ ID NO: 168; and
wherein the light chain variable domain comprises:
a light chain complementary determining region 1 (CDRL1) comprising an amino acid sequence set forth as SEQ ID NO: 169,
a light chain complementary determining region 2 (CDRL2) comprising an amino acid sequence set forth as SEQ ID NO: 170, and,
a light chain complementary determining region 3 (CDRL3) comprising an amino acid sequence set forth as SEQ ID NO: 171,
wherein the TGFβ1 is presented by LTBP1 or LTBP3.

2. The method of claim 1, wherein the heavy chain variable domain comprises an amino acid sequence set forth as SEQ ID NO: 318 and the light chain variable domain comprises an amino acid sequence set forth as SEQ ID NO: 319.

3. The method of claim 1, wherein the heavy chain variable domain consists of an amino acid sequence set forth as SEQ ID NO: 318 and the light chain variable domain consists of an amino acid sequence set forth as SEQ ID NO: 319.

4. The method of claim 1, wherein the subject has a fibrotic condition.

5. The method of claim 4, wherein the fibrotic condition is an organ fibrosis.

6. The method of claim 5, wherein the organ fibrosis is selected from the group consisting of kidney fibrosis, liver fibrosis, lung fibrosis, cardiac fibrosis, pancreatic fibrosis, skin fibrosis, muscle fibrosis, and uterine fibroids.

7. The method of claim 4, wherein the fibrotic condition is a fibrotic disorder comprising chronic inflammation.

8. The method of claim 7, wherein the fibrotic disorder comprising chronic inflammation is muscular dystrophy, multiple sclerosis, or cystic fibrosis.

9. The method of claim 8, wherein the muscular dystrophy is Duechenne muscular dystrophy (DMD).

10. The method of claim 4, wherein the fibrotic condition is Alport syndrome.

11. The method of claim 4, wherein the fibrotic condition is fibrosis, fibroids, desmoplasia, or amyotrophic lateral sclerosis (ALS).

12. The method of claim 4, wherein the fibrotic condition is a liver disease.

13. The method of claim 12, wherein the liver disease is selected from the group consisting of non-alcoholic fatty liver disease (NAFLD), stage 2 and 3 liver fibrosis, stage 4 fibrosis, primary biliary cholangitis (PBC), and primary sclerosing cholangitis (PSC).

14. The method of claim 13, wherein the NAFLD is non-alcoholic fatty liver (NAFL) or non-alcoholic steatohepatitis (NASH).

15. The method of claim 14, wherein the NASH is noncirrhotic NASH with liver fibrosis, liver cirrhosis, NASH with compensated cirrhosis, NASH with decompensated cirrhosis, or liver inflammation with fibrosis.

16. The method of claim 12, further comprising administering a myostatin inhibitor to the subject.

17. The method of claim 4, wherein the fibrotic condition is a kidney disease.

18. The method of claim 17, wherein the kidney disease is selected from the group consisting of IgA nephropathy, focal and segmental glomerulosclerosis, crescentic glomerulonephritis, lupus nephritis, and diabetic nephropathy.

19. The method of claim 1, wherein the administering is subcutaneous administration.

20. The method of claim 1, wherein the heavy chain variable domain comprises an amino acid sequence having at least 95% identity to SEQ ID NO: 318 and the light chain variable domain comprises an amino acid sequence having at least 95% identity to SEQ ID NO: 319.

* * * * *

SEQUENCE LISTING

```
<160> NUMBER OF SEQ ID NOS: 401

<210> SEQ ID NO 1
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Tyr Thr Phe Thr Ser Tyr Gly
1               5

<210> SEQ ID NO 2
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Ile Ser Ala Tyr Asn Gly Asn Thr
1               5

<210> SEQ ID NO 3
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Ala Arg Ala Pro Leu Gly Asn Phe Asp Ser
1               5                   10

<210> SEQ ID NO 4
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 4

Ser Gly Ser Ile Ala Ser Asn Tyr
1               5

<210> SEQ ID NO 5
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Glu Asp Asn
1

<210> SEQ ID NO 6
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gln Ser Tyr Asp Ser Ser Asn His Pro Val Val
1               5                   10

<210> SEQ ID NO 7
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Pro Leu Gly Asn Phe Asp Ser Trp Gly Gln Gly Thr Met
            100                 105                 110

Val Thr Val Ser Ser
        115

<210> SEQ ID NO 8
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 8

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn His Pro Val Val Phe Gly Gly Gly Thr Lys Leu Thr Val Leu
            100                 105                 110
```

<210> SEQ ID NO 9
<211> LENGTH: 361
<212> TYPE: PRT
<213> ORGANISM: Homo sapiens

<400> SEQUENCE: 9

```
Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Arg Asp Asn Thr Leu Gln Val Asp Ile Asn
        195                 200                 205

Gly Phe Thr Thr Gly Arg Arg Gly Asp Leu Ala Thr Ile His Gly Met
    210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg Ala Leu Asp Thr Asn Tyr Cys
```

```
                         245                 250                 255
Phe Ser Ser Thr Glu Lys Asn Cys Cys Val Arg Gln Leu Tyr Ile Asp
                260                 265                 270

Phe Arg Lys Asp Leu Gly Trp Lys Trp Ile His Glu Pro Lys Gly Tyr
            275                 280                 285

His Ala Asn Phe Cys Leu Gly Pro Cys Pro Tyr Ile Trp Ser Leu Asp
        290                 295                 300

Thr Gln Tyr Ser Lys Val Leu Ala Leu Tyr Asn Gln His Asn Pro Gly
305                 310                 315                 320

Ala Ser Ala Ala Pro Cys Cys Val Pro Gln Ala Leu Glu Pro Leu Pro
                325                 330                 335

Ile Val Tyr Tyr Val Gly Arg Lys Pro Lys Val Glu Gln Leu Ser Asn
            340                 345                 350

Met Ile Val Arg Ser Cys Lys Cys Ser
            355                 360

<210> SEQ ID NO 10
<211> LENGTH: 395
<212> TYPE: PRT
<213> ORGANISM: Homo sapiens

<400> SEQUENCE: 10

Ser Leu Ser Thr Cys Ser Thr Leu Asp Met Asp Gln Phe Met Arg Lys
1               5                   10                  15

Arg Ile Glu Ala Ile Arg Gly Gln Ile Leu Ser Lys Leu Lys Leu Thr
            20                  25                  30

Ser Pro Pro Glu Asp Tyr Pro Glu Pro Glu Glu Val Pro Pro Glu Val
        35                  40                  45

Ile Ser Ile Tyr Asn Ser Thr Arg Asp Leu Leu Gln Glu Lys Ala Ser
    50                  55                  60

Arg Arg Ala Ala Ala Cys Glu Arg Glu Arg Ser Asp Glu Glu Tyr Tyr
65                  70                  75                  80

Ala Lys Glu Val Tyr Lys Ile Asp Met Pro Pro Phe Phe Pro Ser Glu
                85                  90                  95

Asn Ala Ile Pro Pro Thr Phe Tyr Arg Pro Tyr Phe Arg Ile Val Arg
            100                 105                 110

Phe Asp Val Ser Ala Met Glu Lys Asn Ala Ser Asn Leu Val Lys Ala
        115                 120                 125

Glu Phe Arg Val Phe Arg Leu Gln Asn Pro Lys Ala Arg Val Pro Glu
    130                 135                 140

Gln Arg Ile Glu Leu Tyr Gln Ile Leu Lys Ser Lys Asp Leu Thr Ser
145                 150                 155                 160

Pro Thr Gln Arg Tyr Ile Asp Ser Lys Val Val Lys Thr Arg Ala Glu
                165                 170                 175

Gly Glu Trp Leu Ser Phe Asp Val Thr Asp Ala Val His Glu Trp Leu
            180                 185                 190

His His Lys Asp Arg Asn Leu Gly Phe Lys Ile Ser Leu His Cys Pro
        195                 200                 205

Cys Cys Thr Phe Val Pro Ser Asn Asn Tyr Ile Ile Pro Asn Lys Ser
    210                 215                 220

Glu Glu Leu Glu Ala Arg Phe Ala Gly Ile Asp Gly Thr Ser Thr Tyr
225                 230                 235                 240

Thr Ser Gly Asp Gln Lys Thr Ile Lys Ser Thr Arg Lys Lys Asn Ser
                245                 250                 255
```

```
Gly Lys Thr Pro His Leu Leu Leu Met Leu Leu Pro Ser Tyr Arg Leu
            260                 265                 270

Glu Ser Gln Gln Thr Asn Arg Arg Lys Lys Arg Ala Leu Asp Ala Ala
        275                 280                 285

Tyr Cys Phe Arg Asn Val Gln Asp Asn Cys Cys Leu Arg Pro Leu Tyr
    290                 295                 300

Ile Asp Phe Lys Arg Asp Leu Gly Trp Lys Trp Ile His Glu Pro Lys
305                 310                 315                 320

Gly Tyr Asn Ala Asn Phe Cys Ala Gly Ala Cys Pro Tyr Leu Trp Ser
                325                 330                 335

Ser Asp Thr Gln His Ser Arg Val Leu Ser Leu Tyr Asn Thr Ile Asn
            340                 345                 350

Pro Glu Ala Ser Ala Ser Pro Cys Cys Val Ser Gln Asp Leu Glu Pro
        355                 360                 365

Leu Thr Ile Leu Tyr Tyr Ile Gly Lys Thr Pro Lys Ile Glu Gln Leu
    370                 375                 380

Ser Asn Met Ile Val Lys Ser Cys Lys Cys Ser
385                 390                 395

<210> SEQ ID NO 11
<211> LENGTH: 392
<212> TYPE: PRT
<213> ORGANISM: Homo sapiens

<400> SEQUENCE: 11

Ser Leu Ser Leu Ser Thr Cys Thr Thr Leu Asp Phe Gly His Ile Lys
1               5                   10                  15

Lys Lys Arg Val Glu Ala Ile Arg Gly Gln Ile Leu Ser Lys Leu Arg
            20                  25                  30

Leu Thr Ser Pro Pro Glu Pro Thr Val Met Thr His Val Pro Tyr Gln
        35                  40                  45

Val Leu Ala Leu Tyr Asn Ser Thr Arg Glu Leu Leu Glu Glu Met His
    50                  55                  60

Gly Glu Arg Glu Glu Gly Cys Thr Gln Glu Asn Thr Glu Ser Glu Tyr
65                  70                  75                  80

Tyr Ala Lys Glu Ile His Lys Phe Asp Met Ile Gln Gly Leu Ala Glu
                85                  90                  95

His Asn Glu Leu Ala Val Cys Pro Lys Gly Ile Thr Ser Lys Val Phe
            100                 105                 110

Arg Phe Asn Val Ser Ser Val Glu Lys Asn Arg Thr Asn Leu Phe Arg
        115                 120                 125

Ala Glu Phe Arg Val Leu Arg Val Pro Asn Pro Ser Ser Lys Arg Asn
    130                 135                 140

Glu Gln Arg Ile Glu Leu Phe Gln Ile Leu Arg Pro Asp Glu His Ile
145                 150                 155                 160

Ala Lys Gln Arg Tyr Ile Gly Gly Lys Asn Leu Pro Thr Arg Gly Thr
                165                 170                 175

Ala Glu Trp Leu Ser Phe Asp Val Thr Asp Thr Val Arg Glu Trp Leu
            180                 185                 190

Leu Arg Arg Glu Ser Asn Leu Gly Leu Glu Ile Ser Ile His Cys Pro
        195                 200                 205

Cys His Thr Phe Gln Pro Asn Gly Asp Ile Leu Glu Asn Ile His Glu
    210                 215                 220

Val Met Glu Ile Lys Phe Lys Gly Val Asp Asn Glu Asp Asp His Gly
225                 230                 235                 240
```

```
Arg Gly Asp Leu Gly Arg Leu Lys Lys Gln Lys Asp His His Asn Pro
                245                 250                 255

His Leu Ile Leu Met Met Ile Pro Pro His Arg Leu Asp Asn Pro Gly
            260                 265                 270

Gln Gly Gly Gln Arg Lys Lys Arg Ala Leu Asp Thr Asn Tyr Cys Phe
            275                 280                 285

Arg Asn Leu Glu Glu Asn Cys Cys Val Arg Pro Leu Tyr Ile Asp Phe
            290                 295                 300

Arg Gln Asp Leu Gly Trp Lys Trp Val His Glu Pro Lys Gly Tyr Tyr
305                 310                 315                 320

Ala Asn Phe Cys Ser Gly Pro Cys Pro Tyr Leu Arg Ser Ala Asp Thr
                325                 330                 335

Thr His Ser Thr Val Leu Gly Leu Tyr Asn Thr Leu Asn Pro Glu Ala
            340                 345                 350

Ser Ala Ser Pro Cys Cys Val Pro Gln Asp Leu Glu Pro Leu Thr Ile
            355                 360                 365

Leu Tyr Tyr Val Gly Arg Thr Pro Lys Val Glu Gln Leu Ser Asn Met
370                 375                 380

Val Val Lys Ser Cys Lys Cys Ser
385                 390

<210> SEQ ID NO 12
<211> LENGTH: 361
<212> TYPE: PRT
<213> ORGANISM: Homo sapiens

<400> SEQUENCE: 12

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Arg Asp Asn Thr Leu Gln Val Asp Ile Asn
        195                 200                 205

Gly Phe Thr Thr Gly Arg Arg Gly Asp Leu Ala Thr Ile His Gly Met
```

```
                210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg Ala Leu Asp Thr Asn Tyr Cys
            245                 250                 255

Phe Ser Ser Thr Glu Lys Asn Cys Cys Val Arg Gln Leu Tyr Ile Asp
                260                 265                 270

Phe Arg Lys Asp Leu Gly Trp Lys Trp Ile His Glu Pro Lys Gly Tyr
            275                 280                 285

His Ala Asn Phe Cys Leu Gly Pro Cys Pro Tyr Ile Trp Ser Leu Asp
        290                 295                 300

Thr Gln Tyr Ser Lys Val Leu Ala Leu Tyr Asn Gln His Asn Pro Gly
305                 310                 315                 320

Ala Ser Ala Ala Pro Cys Cys Val Pro Gln Ala Leu Glu Pro Leu Pro
                325                 330                 335

Ile Val Tyr Tyr Val Gly Arg Lys Pro Lys Val Glu Gln Leu Ser Asn
            340                 345                 350

Met Ile Val Arg Ser Cys Lys Cys Ser
        355                 360

<210> SEQ ID NO 13
<211> LENGTH: 361
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Arg Asp Asn Thr Leu Gln Val Asp Ile Asn
        195                 200                 205
```

```
Gly Phe Thr Thr Gly Arg Arg Gly Asp Leu Ala Thr Ile His Gly Met
        210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg Ala Leu Asp Thr Asn Tyr Cys
                245                 250                 255

Phe Ser Ser Thr Glu Lys Asn Cys Cys Val Arg Gln Leu Tyr Ile Asp
            260                 265                 270

Phe Arg Lys Asp Leu Gly Trp Lys Trp Ile His Glu Pro Lys Gly Tyr
        275                 280                 285

His Ala Asn Phe Cys Leu Gly Pro Cys Pro Tyr Ile Trp Ser Leu Asp
    290                 295                 300

Thr Gln Tyr Ser Lys Val Leu Ala Leu Tyr Asn Gln His Asn Pro Gly
305                 310                 315                 320

Ala Ser Ala Ala Pro Cys Cys Val Pro Gln Ala Leu Glu Pro Leu Pro
                325                 330                 335

Ile Val Tyr Tyr Val Gly Arg Lys Pro Lys Val Glu Gln Leu Ser Asn
            340                 345                 350

Met Ile Val Arg Ser Cys Lys Cys Ser
        355                 360

<210> SEQ ID NO 14
<211> LENGTH: 360
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190
```

```
His Cys Ser Cys Asp Ser Arg Asp Asn Thr Leu Gln Val Asp Ile Asn
            195                 200                 205

Gly Phe Thr Thr Gly Arg Arg Gly Asp Leu Ala Thr Ile His Gly Met
210                 215                 220

Asn Arg Pro Phe Leu Leu Leu Met Ala Thr Pro Leu Glu Arg Ala Gln
225                 230                 235                 240

His Leu Gln Ser Ser Arg His Gly Ala Leu Asp Thr Asn Tyr Cys Phe
            245                 250                 255

Ser Ser Thr Glu Lys Asn Cys Cys Val Arg Gln Leu Tyr Ile Asp Phe
                260                 265                 270

Arg Lys Asp Leu Gly Trp Lys Trp Ile His Glu Pro Lys Gly Tyr His
            275                 280                 285

Ala Asn Phe Cys Leu Gly Pro Cys Pro Tyr Ile Trp Ser Leu Asp Thr
290                 295                 300

Gln Tyr Ser Lys Val Leu Ala Leu Tyr Asn Gln His Asn Pro Gly Ala
305                 310                 315                 320

Ser Ala Ala Pro Cys Cys Val Pro Gln Ala Leu Glu Pro Leu Pro Ile
                325                 330                 335

Val Tyr Tyr Val Gly Arg Lys Pro Lys Val Glu Gln Leu Ser Asn Met
            340                 345                 350

Ile Val Arg Ser Cys Lys Cys Ser
            355                 360

<210> SEQ ID NO 15
<211> LENGTH: 360
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
```

```
                    180                 185                 190
His Cys Ser Cys Asp Ser Arg Asp Asn Thr Leu Gln Val Asp Ile Asn
                195                 200                 205

Gly Phe Thr Thr Gly Arg Arg Gly Asp Leu Ala Thr Ile His Gly Met
        210                 215                 220

Asn Arg Pro Phe Leu Leu Leu Met Ala Thr Pro Leu Glu Arg Ala Gln
225                 230                 235                 240

His Leu Gln Ser Ser Arg His Gly Ala Leu Asp Thr Asn Tyr Cys Phe
                245                 250                 255

Ser Ser Thr Glu Lys Asn Cys Cys Val Arg Gln Leu Tyr Ile Asp Phe
            260                 265                 270

Arg Lys Asp Leu Gly Trp Lys Trp Ile His Glu Pro Lys Gly Tyr His
        275                 280                 285

Ala Asn Phe Cys Leu Gly Pro Cys Pro Tyr Ile Trp Ser Leu Asp Thr
        290                 295                 300

Gln Tyr Ser Lys Val Leu Ala Leu Tyr Asn Gln His Asn Pro Gly Ala
305                 310                 315                 320

Ser Ala Ala Pro Cys Cys Val Pro Gln Ala Leu Glu Pro Leu Pro Ile
                325                 330                 335

Val Tyr Tyr Val Gly Arg Lys Pro Lys Val Glu Gln Leu Ser Asn Met
            340                 345                 350

Ile Val Arg Ser Cys Lys Cys Ser
                355                 360

<210> SEQ ID NO 16
<211> LENGTH: 395
<212> TYPE: PRT
<213> ORGANISM: Homo sapiens

<400> SEQUENCE: 16

Ser Leu Ser Thr Cys Ser Thr Leu Asp Met Asp Gln Phe Met Arg Lys
1               5                   10                  15

Arg Ile Glu Ala Ile Arg Gly Gln Ile Leu Ser Lys Leu Lys Leu Thr
                20                  25                  30

Ser Pro Pro Glu Asp Tyr Pro Glu Pro Glu Glu Val Pro Pro Glu Val
            35                  40                  45

Ile Ser Ile Tyr Asn Ser Thr Arg Asp Leu Leu Gln Glu Lys Ala Ser
        50                  55                  60

Arg Arg Ala Ala Ala Cys Glu Arg Glu Arg Ser Asp Glu Glu Tyr Tyr
65              70                  75                  80

Ala Lys Glu Val Tyr Lys Ile Asp Met Pro Pro Phe Phe Pro Ser Glu
                85                  90                  95

Asn Ala Ile Pro Pro Thr Phe Tyr Arg Pro Tyr Phe Arg Ile Val Arg
            100                 105                 110

Phe Asp Val Ser Ala Met Glu Lys Asn Ala Ser Asn Leu Val Lys Ala
        115                 120                 125

Glu Phe Arg Val Phe Arg Leu Gln Asn Pro Lys Ala Arg Val Pro Glu
    130                 135                 140

Gln Arg Ile Glu Leu Tyr Gln Ile Leu Lys Ser Lys Asp Leu Thr Ser
145                 150                 155                 160

Pro Thr Gln Arg Tyr Ile Asp Ser Lys Val Val Lys Thr Arg Ala Glu
                165                 170                 175

Gly Glu Trp Leu Ser Phe Asp Val Thr Asp Ala Val His Glu Trp Leu
            180                 185                 190
```

His His Lys Asp Arg Asn Leu Gly Phe Lys Ile Ser Leu His Cys Pro
            195                 200                 205

Cys Cys Thr Phe Val Pro Ser Asn Asn Tyr Ile Ile Pro Asn Lys Ser
210                 215                 220

Glu Glu Leu Glu Ala Arg Phe Ala Gly Ile Asp Gly Thr Ser Thr Tyr
225                 230                 235                 240

Thr Ser Gly Asp Gln Lys Thr Ile Lys Ser Thr Arg Lys Lys Asn Ser
            245                 250                 255

Gly Lys Thr Pro His Leu Leu Leu Met Leu Leu Pro Ser Tyr Arg Leu
            260                 265                 270

Glu Ser Gln Gln Thr Asn Arg Arg Lys Lys Arg Ala Leu Asp Ala Ala
            275                 280                 285

Tyr Cys Phe Arg Asn Val Gln Asp Asn Cys Cys Leu Arg Pro Leu Tyr
290                 295                 300

Ile Asp Phe Lys Arg Asp Leu Gly Trp Lys Trp Ile His Glu Pro Lys
305                 310                 315                 320

Gly Tyr Asn Ala Asn Phe Cys Ala Gly Ala Cys Pro Tyr Leu Trp Ser
            325                 330                 335

Ser Asp Thr Gln His Ser Arg Val Leu Ser Leu Tyr Asn Thr Ile Asn
            340                 345                 350

Pro Glu Ala Ser Ala Ser Pro Cys Cys Val Ser Gln Asp Leu Glu Pro
            355                 360                 365

Leu Thr Ile Leu Tyr Tyr Ile Gly Lys Thr Pro Lys Ile Glu Gln Leu
            370                 375                 380

Ser Asn Met Ile Val Lys Ser Cys Lys Cys Ser
385                 390                 395

<210> SEQ ID NO 17
<211> LENGTH: 395
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Ser Leu Ser Thr Ser Thr Leu Asp Met Asp Gln Phe Met Arg Lys
1               5                   10                  15

Arg Ile Glu Ala Ile Arg Gly Gln Ile Leu Ser Lys Leu Lys Leu Thr
                20                  25                  30

Ser Pro Pro Glu Asp Tyr Pro Glu Pro Glu Glu Val Pro Pro Glu Val
            35                  40                  45

Ile Ser Ile Tyr Asn Ser Thr Arg Asp Leu Leu Gln Glu Lys Ala Ser
50                  55                  60

Arg Arg Ala Ala Ala Cys Glu Arg Glu Arg Ser Asp Glu Glu Tyr Tyr
65                  70                  75                  80

Ala Lys Glu Val Tyr Lys Ile Asp Met Pro Pro Phe Phe Pro Ser Glu
                85                  90                  95

Asn Ala Ile Pro Pro Thr Phe Tyr Arg Pro Tyr Phe Arg Ile Val Arg
            100                 105                 110

Phe Asp Val Ser Ala Met Glu Lys Asn Ala Ser Asn Leu Val Lys Ala
            115                 120                 125

Glu Phe Arg Val Phe Arg Leu Gln Asn Pro Lys Ala Arg Val Pro Glu
130                 135                 140

Gln Arg Ile Glu Leu Tyr Gln Ile Leu Lys Ser Lys Asp Leu Thr Ser

```
145                 150                 155                 160
Pro Thr Gln Arg Tyr Ile Asp Ser Lys Val Val Lys Thr Arg Ala Glu
                165                 170                 175

Gly Glu Trp Leu Ser Phe Asp Val Thr Asp Ala Val His Glu Trp Leu
                180                 185                 190

His His Lys Asp Arg Asn Leu Gly Phe Lys Ile Ser Leu His Cys Pro
                195                 200                 205

Cys Cys Thr Phe Val Pro Ser Asn Asn Tyr Ile Ile Pro Asn Lys Ser
210                 215                 220

Glu Glu Leu Glu Ala Arg Phe Ala Gly Ile Asp Gly Thr Ser Thr Tyr
225                 230                 235                 240

Thr Ser Gly Asp Gln Lys Thr Ile Lys Ser Thr Arg Lys Lys Asn Ser
                245                 250                 255

Gly Lys Thr Pro His Leu Leu Leu Met Leu Leu Pro Ser Tyr Arg Leu
                260                 265                 270

Glu Ser Gln Gln Thr Asn Arg Arg Lys Lys Arg Ala Leu Asp Ala Ala
                275                 280                 285

Tyr Cys Phe Arg Asn Val Gln Asp Asn Cys Cys Leu Arg Pro Leu Tyr
290                 295                 300

Ile Asp Phe Lys Arg Asp Leu Gly Trp Lys Trp Ile His Glu Pro Lys
305                 310                 315                 320

Gly Tyr Asn Ala Asn Phe Cys Ala Gly Ala Cys Pro Tyr Leu Trp Ser
                325                 330                 335

Ser Asp Thr Gln His Ser Arg Val Leu Ser Leu Tyr Asn Thr Ile Asn
                340                 345                 350

Pro Glu Ala Ser Ala Ser Pro Cys Cys Val Ser Gln Asp Leu Glu Pro
                355                 360                 365

Leu Thr Ile Leu Tyr Tyr Ile Gly Lys Thr Pro Lys Ile Glu Gln Leu
                370                 375                 380

Ser Asn Met Ile Val Lys Ser Cys Lys Cys Ser
385                 390                 395

<210> SEQ ID NO 18
<211> LENGTH: 394
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Ser Leu Ser Thr Ser Ser Thr Leu Asp Met Asp Gln Phe Met Arg Lys
1               5                   10                  15

Arg Ile Glu Ala Ile Arg Gly Gln Ile Leu Ser Lys Leu Lys Leu Thr
                20                  25                  30

Ser Pro Pro Glu Asp Tyr Pro Glu Pro Glu Glu Val Pro Pro Glu Val
            35                  40                  45

Ile Ser Ile Tyr Asn Ser Thr Arg Asp Leu Leu Gln Glu Lys Ala Ser
        50                  55                  60

Arg Arg Ala Ala Ala Cys Glu Arg Glu Arg Ser Asp Glu Glu Tyr Tyr
65                  70                  75                  80

Ala Lys Glu Val Tyr Lys Ile Asp Met Pro Pro Phe Phe Pro Ser Glu
                85                  90                  95

Asn Ala Ile Pro Pro Thr Phe Tyr Arg Pro Tyr Phe Arg Ile Val Arg
            100                 105                 110
```

```
Phe Asp Val Ser Ala Met Glu Lys Asn Ala Ser Asn Leu Val Lys Ala
        115                 120                 125

Glu Phe Arg Val Phe Arg Leu Gln Asn Pro Lys Ala Arg Val Pro Glu
130                 135                 140

Gln Arg Ile Glu Leu Tyr Gln Ile Leu Lys Ser Lys Asp Leu Thr Ser
145                 150                 155                 160

Pro Thr Gln Arg Tyr Ile Asp Ser Lys Val Lys Thr Arg Ala Glu
            165                 170                 175

Gly Glu Trp Leu Ser Phe Asp Val Thr Asp Ala Val His Glu Trp Leu
                180                 185                 190

His His Lys Asp Arg Asn Leu Gly Phe Lys Ile Ser Leu His Cys Pro
        195                 200                 205

Cys Cys Thr Phe Val Pro Ser Asn Asn Tyr Ile Ile Pro Asn Lys Ser
    210                 215                 220

Glu Glu Leu Glu Ala Arg Phe Ala Gly Ile Asp Gly Thr Ser Thr Tyr
225                 230                 235                 240

Thr Ser Gly Asp Gln Lys Thr Ile Lys Ser Thr Arg Lys Lys Asn Ser
                245                 250                 255

Gly Lys Thr Pro His Leu Leu Leu Met Leu Leu Pro Ser Tyr Arg Leu
            260                 265                 270

Glu Ser Gln Gln Thr Asn Arg Arg Lys Gly Ala Leu Asp Ala Ala Tyr
        275                 280                 285

Cys Phe Arg Asn Val Gln Asp Asn Cys Cys Leu Arg Pro Leu Tyr Ile
    290                 295                 300

Asp Phe Lys Arg Asp Leu Gly Trp Lys Trp Ile His Glu Pro Lys Gly
305                 310                 315                 320

Tyr Asn Ala Asn Phe Cys Ala Gly Ala Cys Pro Tyr Leu Trp Ser Ser
                325                 330                 335

Asp Thr Gln His Ser Arg Val Leu Ser Leu Tyr Asn Thr Ile Asn Pro
            340                 345                 350

Glu Ala Ser Ala Ser Pro Cys Cys Val Ser Gln Asp Leu Glu Pro Leu
        355                 360                 365

Thr Ile Leu Tyr Tyr Ile Gly Lys Thr Pro Lys Ile Glu Gln Leu Ser
    370                 375                 380

Asn Met Ile Val Lys Ser Cys Lys Cys Ser
385                 390

<210> SEQ ID NO 19
<211> LENGTH: 394
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Ser Leu Ser Thr Cys Ser Thr Leu Asp Met Asp Gln Phe Met Arg Lys
1               5                   10                  15

Arg Ile Glu Ala Ile Arg Gly Gln Ile Leu Ser Lys Leu Lys Leu Thr
            20                  25                  30

Ser Pro Pro Glu Asp Tyr Pro Glu Pro Glu Glu Val Pro Pro Glu Val
        35                  40                  45

Ile Ser Ile Tyr Asn Ser Thr Arg Asp Leu Leu Gln Glu Lys Ala Ser
    50                  55                  60
```

Arg Arg Ala Ala Ala Cys Glu Arg Glu Arg Ser Asp Glu Glu Tyr Tyr
65                  70                  75                  80

Ala Lys Glu Val Tyr Lys Ile Asp Met Pro Pro Phe Phe Pro Ser Glu
                85                  90                  95

Asn Ala Ile Pro Pro Thr Phe Tyr Arg Pro Tyr Phe Arg Ile Val Arg
            100                 105                 110

Phe Asp Val Ser Ala Met Glu Lys Asn Ala Ser Asn Leu Val Lys Ala
        115                 120                 125

Glu Phe Arg Val Phe Arg Leu Gln Asn Pro Lys Ala Arg Val Pro Glu
    130                 135                 140

Gln Arg Ile Glu Leu Tyr Gln Ile Leu Lys Ser Lys Asp Leu Thr Ser
145                 150                 155                 160

Pro Thr Gln Arg Tyr Ile Asp Ser Lys Val Val Lys Thr Arg Ala Glu
                165                 170                 175

Gly Glu Trp Leu Ser Phe Asp Val Thr Asp Ala Val His Glu Trp Leu
            180                 185                 190

His His Lys Asp Arg Asn Leu Gly Phe Lys Ile Ser Leu His Cys Pro
        195                 200                 205

Cys Cys Thr Phe Val Pro Ser Asn Asn Tyr Ile Ile Pro Asn Lys Ser
    210                 215                 220

Glu Glu Leu Glu Ala Arg Phe Ala Gly Ile Asp Gly Thr Ser Thr Tyr
225                 230                 235                 240

Thr Ser Gly Asp Gln Lys Thr Ile Lys Ser Thr Arg Lys Lys Asn Ser
                245                 250                 255

Gly Lys Thr Pro His Leu Leu Leu Met Leu Leu Pro Ser Tyr Arg Leu
            260                 265                 270

Glu Ser Gln Gln Thr Asn Arg Arg Lys Gly Ala Leu Asp Ala Ala Tyr
        275                 280                 285

Cys Phe Arg Asn Val Gln Asp Asn Cys Cys Leu Arg Pro Leu Tyr Ile
    290                 295                 300

Asp Phe Lys Arg Asp Leu Gly Trp Lys Trp Ile His Glu Pro Lys Gly
305                 310                 315                 320

Tyr Asn Ala Asn Phe Cys Ala Gly Ala Cys Pro Tyr Leu Trp Ser Ser
                325                 330                 335

Asp Thr Gln His Ser Arg Val Leu Ser Leu Tyr Asn Thr Ile Asn Pro
            340                 345                 350

Glu Ala Ser Ala Ser Pro Cys Cys Val Ser Gln Asp Leu Glu Pro Leu
        355                 360                 365

Thr Ile Leu Tyr Tyr Ile Gly Lys Thr Pro Lys Ile Glu Gln Leu Ser
    370                 375                 380

Asn Met Ile Val Lys Ser Cys Lys Cys Ser
385                 390

<210> SEQ ID NO 20
<211> LENGTH: 392
<212> TYPE: PRT
<213> ORGANISM: Homo sapiens

<400> SEQUENCE: 20

Ser Leu Ser Leu Ser Thr Cys Thr Thr Leu Asp Phe Gly His Ile Lys
1               5                   10                  15

Lys Lys Arg Val Glu Ala Ile Arg Gly Gln Ile Leu Ser Lys Leu Arg
            20                  25                  30

Leu Thr Ser Pro Pro Glu Pro Thr Val Met Thr His Val Pro Tyr Gln
        35                  40                  45

Val Leu Ala Leu Tyr Asn Ser Thr Arg Glu Leu Leu Glu Glu Met His
 50                  55                  60

Gly Glu Arg Glu Glu Gly Cys Thr Gln Glu Asn Thr Glu Ser Glu Tyr
 65                  70                  75                  80

Tyr Ala Lys Glu Ile His Lys Phe Asp Met Ile Gln Gly Leu Ala Glu
                 85                  90                  95

His Asn Glu Leu Ala Val Cys Pro Lys Gly Ile Thr Ser Lys Val Phe
            100                 105                 110

Arg Phe Asn Val Ser Ser Val Glu Lys Asn Arg Thr Asn Leu Phe Arg
        115                 120                 125

Ala Glu Phe Arg Val Leu Arg Val Pro Asn Pro Ser Ser Lys Arg Asn
    130                 135                 140

Glu Gln Arg Ile Glu Leu Phe Gln Ile Leu Arg Pro Asp Glu His Ile
145                 150                 155                 160

Ala Lys Gln Arg Tyr Ile Gly Gly Lys Asn Leu Pro Thr Arg Gly Thr
                165                 170                 175

Ala Glu Trp Leu Ser Phe Asp Val Thr Asp Thr Val Arg Glu Trp Leu
            180                 185                 190

Leu Arg Arg Glu Ser Asn Leu Gly Leu Glu Ile Ser Ile His Cys Pro
        195                 200                 205

Cys His Thr Phe Gln Pro Asn Gly Asp Ile Leu Glu Asn Ile His Glu
    210                 215                 220

Val Met Glu Ile Lys Phe Lys Gly Val Asp Asn Glu Asp Asp His Gly
225                 230                 235                 240

Arg Gly Asp Leu Gly Arg Leu Lys Lys Gln Lys Asp His His Asn Pro
                245                 250                 255

His Leu Ile Leu Met Met Ile Pro Pro His Arg Leu Asp Asn Pro Gly
            260                 265                 270

Gln Gly Gly Gln Arg Lys Lys Arg Ala Leu Asp Thr Asn Tyr Cys Phe
        275                 280                 285

Arg Asn Leu Glu Glu Asn Cys Cys Val Arg Pro Leu Tyr Ile Asp Phe
    290                 295                 300

Arg Gln Asp Leu Gly Trp Lys Trp Val His Glu Pro Lys Gly Tyr Tyr
305                 310                 315                 320

Ala Asn Phe Cys Ser Gly Pro Cys Pro Tyr Leu Arg Ser Ala Asp Thr
                325                 330                 335

Thr His Ser Thr Val Leu Gly Leu Tyr Asn Thr Leu Asn Pro Glu Ala
            340                 345                 350

Ser Ala Ser Pro Cys Cys Val Pro Gln Asp Leu Glu Pro Leu Thr Ile
        355                 360                 365

Leu Tyr Tyr Val Gly Arg Thr Pro Lys Val Glu Gln Leu Ser Asn Met
    370                 375                 380

Val Val Lys Ser Cys Lys Cys Ser
385                 390

<210> SEQ ID NO 21
<211> LENGTH: 392
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Ser Leu Ser Leu Ser Thr Ser Thr Thr Leu Asp Phe Gly His Ile Lys
1               5                   10                  15

Lys Lys Arg Val Glu Ala Ile Arg Gly Gln Ile Leu Ser Lys Leu Arg
            20                  25                  30

Leu Thr Ser Pro Pro Glu Pro Thr Val Met Thr His Val Pro Tyr Gln
        35                  40                  45

Val Leu Ala Leu Tyr Asn Ser Thr Arg Glu Leu Leu Glu Glu Met His
50                  55                  60

Gly Glu Arg Glu Glu Gly Cys Thr Gln Glu Asn Thr Glu Ser Glu Tyr
65                  70                  75                  80

Tyr Ala Lys Glu Ile His Lys Phe Asp Met Ile Gln Gly Leu Ala Glu
                85                  90                  95

His Asn Glu Leu Ala Val Cys Pro Lys Gly Ile Thr Ser Lys Val Phe
                100                 105                 110

Arg Phe Asn Val Ser Ser Val Glu Lys Asn Arg Thr Asn Leu Phe Arg
            115                 120                 125

Ala Glu Phe Arg Val Leu Arg Val Pro Asn Pro Ser Ser Lys Arg Asn
            130                 135                 140

Glu Gln Arg Ile Glu Leu Phe Gln Ile Leu Arg Pro Asp Glu His Ile
145                 150                 155                 160

Ala Lys Gln Arg Tyr Ile Gly Gly Lys Asn Leu Pro Thr Arg Gly Thr
                165                 170                 175

Ala Glu Trp Leu Ser Phe Asp Val Thr Asp Thr Val Arg Glu Trp Leu
            180                 185                 190

Leu Arg Arg Glu Ser Asn Leu Gly Leu Glu Ile Ser Ile His Cys Pro
            195                 200                 205

Cys His Thr Phe Gln Pro Asn Gly Asp Ile Leu Glu Asn Ile His Glu
210                 215                 220

Val Met Glu Ile Lys Phe Lys Gly Val Asp Asn Glu Asp Asp His Gly
225                 230                 235                 240

Arg Gly Asp Leu Gly Arg Leu Lys Lys Gln Lys Asp His His Asn Pro
                245                 250                 255

His Leu Ile Leu Met Met Ile Pro Pro His Arg Leu Asp Asn Pro Gly
                260                 265                 270

Gln Gly Gly Gln Arg Lys Lys Arg Ala Leu Asp Thr Asn Tyr Cys Phe
            275                 280                 285

Arg Asn Leu Glu Glu Asn Cys Cys Val Arg Pro Leu Tyr Ile Asp Phe
            290                 295                 300

Arg Gln Asp Leu Gly Trp Lys Trp Val His Glu Pro Lys Gly Tyr Tyr
305                 310                 315                 320

Ala Asn Phe Cys Ser Gly Pro Cys Pro Tyr Leu Arg Ser Ala Asp Thr
                325                 330                 335

Thr His Ser Thr Val Leu Gly Leu Tyr Asn Thr Leu Asn Pro Glu Ala
            340                 345                 350

Ser Ala Ser Pro Cys Cys Val Pro Gln Asp Leu Glu Pro Leu Thr Ile
            355                 360                 365

Leu Tyr Tyr Val Gly Arg Thr Pro Lys Val Glu Gln Leu Ser Asn Met
370                 375                 380

Val Val Lys Ser Cys Lys Cys Ser
385                 390

<210> SEQ ID NO 22
<211> LENGTH: 391
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Ser Leu Ser Leu Ser Thr Ser Thr Thr Leu Asp Phe Gly His Ile Lys
1               5                   10                  15

Lys Lys Arg Val Glu Ala Ile Arg Gly Gln Ile Leu Ser Lys Leu Arg
            20                  25                  30

Leu Thr Ser Pro Pro Glu Pro Thr Val Met Thr His Val Pro Tyr Gln
            35                  40                  45

Val Leu Ala Leu Tyr Asn Ser Thr Arg Glu Leu Leu Glu Glu Met His
    50                  55                  60

Gly Glu Arg Glu Glu Gly Cys Thr Gln Glu Asn Thr Glu Ser Glu Tyr
65                  70                  75                  80

Tyr Ala Lys Glu Ile His Lys Phe Asp Met Ile Gln Gly Leu Ala Glu
                85                  90                  95

His Asn Glu Leu Ala Val Cys Pro Lys Gly Ile Thr Ser Lys Val Phe
            100                 105                 110

Arg Phe Asn Val Ser Ser Val Glu Lys Asn Arg Thr Asn Leu Phe Arg
        115                 120                 125

Ala Glu Phe Arg Val Leu Arg Val Pro Asn Pro Ser Ser Lys Arg Asn
    130                 135                 140

Glu Gln Arg Ile Glu Leu Phe Gln Ile Leu Arg Pro Asp Glu His Ile
145                 150                 155                 160

Ala Lys Gln Arg Tyr Ile Gly Gly Lys Asn Leu Pro Thr Arg Gly Thr
                165                 170                 175

Ala Glu Trp Leu Ser Phe Asp Val Thr Asp Thr Val Arg Glu Trp Leu
            180                 185                 190

Leu Arg Arg Glu Ser Asn Leu Gly Leu Glu Ile Ser Ile His Cys Pro
        195                 200                 205

Cys His Thr Phe Gln Pro Asn Gly Asp Ile Leu Glu Asn Ile His Glu
    210                 215                 220

Val Met Glu Ile Lys Phe Lys Gly Val Asp Asn Glu Asp Asp His Gly
225                 230                 235                 240

Arg Gly Asp Leu Gly Arg Leu Lys Lys Gln Lys Asp His His Asn Pro
                245                 250                 255

His Leu Ile Leu Met Met Ile Pro Pro His Arg Leu Asp Asn Pro Gly
            260                 265                 270

Gln Gly Gly Gln Arg Lys Gly Ala Leu Asp Thr Asn Tyr Cys Phe Arg
        275                 280                 285

Asn Leu Glu Glu Asn Cys Cys Val Arg Pro Leu Tyr Ile Asp Phe Arg
    290                 295                 300

Gln Asp Leu Gly Trp Lys Trp Val His Glu Pro Lys Gly Tyr Tyr Ala
305                 310                 315                 320

Asn Phe Cys Ser Gly Pro Cys Pro Tyr Leu Arg Ser Ala Asp Thr Thr
                325                 330                 335

His Ser Thr Val Leu Gly Leu Tyr Asn Thr Leu Asn Pro Glu Ala Ser
            340                 345                 350

Ala Ser Pro Cys Cys Val Pro Gln Asp Leu Glu Pro Leu Thr Ile Leu
        355                 360                 365

Tyr Tyr Val Gly Arg Thr Pro Lys Val Glu Gln Leu Ser Asn Met Val
    370                 375                 380
```

Val Lys Ser Cys Lys Cys Ser
385                 390

<210> SEQ ID NO 23
<211> LENGTH: 391
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Ser Leu Ser Leu Ser Thr Cys Thr Thr Leu Asp Phe Gly His Ile Lys
1               5                   10                  15

Lys Lys Arg Val Glu Ala Ile Arg Gly Gln Ile Leu Ser Lys Leu Arg
                20                  25                  30

Leu Thr Ser Pro Pro Glu Pro Thr Val Met Thr His Val Pro Tyr Gln
            35                  40                  45

Val Leu Ala Leu Tyr Asn Ser Thr Arg Glu Leu Leu Glu Glu Met His
        50                  55                  60

Gly Glu Arg Glu Glu Gly Cys Thr Gln Glu Asn Thr Glu Ser Glu Tyr
65                  70                  75                  80

Tyr Ala Lys Glu Ile His Lys Phe Asp Met Ile Gln Gly Leu Ala Glu
                85                  90                  95

His Asn Glu Leu Ala Val Cys Pro Lys Gly Ile Thr Ser Lys Val Phe
            100                 105                 110

Arg Phe Asn Val Ser Ser Val Glu Lys Asn Arg Thr Asn Leu Phe Arg
        115                 120                 125

Ala Glu Phe Arg Val Leu Arg Val Pro Asn Pro Ser Ser Lys Arg Asn
    130                 135                 140

Glu Gln Arg Ile Glu Leu Phe Gln Ile Leu Arg Pro Asp Glu His Ile
145                 150                 155                 160

Ala Lys Gln Arg Tyr Ile Gly Gly Lys Asn Leu Pro Thr Arg Gly Thr
                165                 170                 175

Ala Glu Trp Leu Ser Phe Asp Val Thr Asp Thr Val Arg Glu Trp Leu
            180                 185                 190

Leu Arg Arg Glu Ser Asn Leu Gly Leu Glu Ile Ser Ile His Cys Pro
        195                 200                 205

Cys His Thr Phe Gln Pro Asn Gly Asp Ile Leu Glu Asn Ile His Glu
    210                 215                 220

Val Met Glu Ile Lys Phe Lys Gly Val Asp Asn Glu Asp Asp His Gly
225                 230                 235                 240

Arg Gly Asp Leu Gly Arg Leu Lys Lys Gln Lys Asp His His Asn Pro
                245                 250                 255

His Leu Ile Leu Met Met Ile Pro Pro His Arg Leu Asp Asn Pro Gly
            260                 265                 270

Gln Gly Gly Gln Arg Lys Gly Ala Leu Asp Thr Asn Tyr Cys Phe Arg
        275                 280                 285

Asn Leu Glu Glu Asn Cys Cys Val Arg Pro Leu Tyr Ile Asp Phe Arg
    290                 295                 300

Gln Asp Leu Gly Trp Lys Trp Val His Glu Pro Lys Gly Tyr Tyr Ala
305                 310                 315                 320

Asn Phe Cys Ser Gly Pro Cys Pro Tyr Leu Arg Ser Ala Asp Thr Thr
                325                 330                 335

```
His Ser Thr Val Leu Gly Leu Tyr Asn Thr Leu Asn Pro Glu Ala Ser
                340                 345                 350

Ala Ser Pro Cys Cys Val Pro Gln Asp Leu Glu Pro Leu Thr Ile Leu
            355                 360                 365

Tyr Tyr Val Gly Arg Thr Pro Lys Val Glu Gln Leu Ser Asn Met Val
        370                 375                 380

Val Lys Ser Cys Lys Cys Ser
385                 390

<210> SEQ ID NO 24
<211> LENGTH: 361
<212> TYPE: PRT
<213> ORGANISM: Mus sp.

<400> SEQUENCE: 24

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Asp Pro Glu Pro Glu Pro Glu Ala Asp Tyr Tyr Ala Lys Glu Val Thr
65                  70                  75                  80

Arg Val Leu Met Val Asp Arg Asn Asn Ala Ile Tyr Glu Lys Thr Lys
                85                  90                  95

Asp Ile Ser His Ser Ile Tyr Met Phe Phe Asn Thr Ser Asp Ile Arg
            100                 105                 110

Glu Ala Val Pro Glu Pro Leu Leu Ser Arg Ala Glu Leu Arg Leu
        115                 120                 125

Gln Arg Leu Lys Ser Ser Val Glu Gln His Val Glu Leu Tyr Gln Lys
    130                 135                 140

Tyr Ser Asn Asn Ser Trp Arg Tyr Leu Gly Asn Arg Leu Leu Thr Pro
145                 150                 155                 160

Thr Asp Thr Pro Glu Trp Leu Ser Phe Asp Val Thr Gly Val Val Arg
                165                 170                 175

Gln Trp Leu Asn Gln Gly Asp Gly Ile Gln Gly Phe Arg Phe Ser Ala
            180                 185                 190

His Cys Ser Cys Asp Ser Lys Asp Asn Lys Leu His Val Glu Ile Asn
        195                 200                 205

Gly Ile Ser Pro Lys Arg Arg Gly Asp Leu Gly Thr Ile His Asp Met
    210                 215                 220

Asn Arg Pro Phe Leu Leu Leu Met Ala Thr Pro Leu Glu Arg Ala Gln
225                 230                 235                 240

His Leu His Ser Ser Arg His Arg Arg Ala Leu Asp Thr Asn Tyr Cys
                245                 250                 255

Phe Ser Ser Thr Glu Lys Asn Cys Cys Val Arg Gln Leu Tyr Ile Asp
            260                 265                 270

Phe Arg Lys Asp Leu Gly Trp Lys Trp Ile His Glu Pro Lys Gly Tyr
        275                 280                 285

His Ala Asn Phe Cys Leu Gly Pro Cys Pro Tyr Ile Trp Ser Leu Asp
    290                 295                 300

Thr Gln Tyr Ser Lys Val Leu Ala Leu Tyr Asn Gln His Asn Pro Gly
305                 310                 315                 320
```

Ala Ser Ala Ser Pro Cys Cys Val Pro Gln Ala Leu Glu Pro Leu Pro
            325                 330                 335

Ile Val Tyr Tyr Val Gly Arg Lys Pro Lys Val Glu Gln Leu Ser Asn
            340                 345                 350

Met Ile Val Arg Ser Cys Lys Cys Ser
        355                 360

<210> SEQ ID NO 25
<211> LENGTH: 361
<212> TYPE: PRT
<213> ORGANISM: Macaca fascicularis

<400> SEQUENCE: 25

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Lys Asp Asn Thr Leu Gln Val Asp Ile Asn
        195                 200                 205

Gly Phe Thr Thr Gly Arg Arg Gly Asp Leu Ala Thr Ile His Gly Met
210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg Ala Leu Asp Thr Asn Tyr Cys
                245                 250                 255

Phe Ser Ser Thr Glu Lys Asn Cys Cys Val Arg Gln Leu Tyr Ile Asp
            260                 265                 270

Phe Arg Lys Asp Leu Gly Trp Lys Trp Ile His Glu Pro Lys Gly Tyr
        275                 280                 285

His Ala Asn Phe Cys Leu Gly Pro Cys Pro Tyr Ile Trp Ser Leu Asp
290                 295                 300

Thr Gln Tyr Ser Lys Val Leu Ala Leu Tyr Asn Gln His Asn Pro Gly
305                 310                 315                 320

Ala Ser Ala Ala Pro Cys Cys Val Pro Gln Ala Leu Glu Pro Leu Pro

```
                     325                 330                 335

Ile Val Tyr Tyr Val Gly Arg Lys Pro Lys Val Glu Gln Leu Ser Asn
            340                 345                 350

Met Ile Val Arg Ser Lys Cys Ser
            355                 360

<210> SEQ ID NO 26
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Asp Pro Glu Pro Glu Pro Glu Ala Asp Tyr Tyr Ala Lys Glu Val Thr
65                  70                  75                  80

Arg Val Leu Met Val Asp Arg Asn Asn Ala Ile Tyr Glu Lys Thr Lys
                85                  90                  95

Asp Ile Ser His Ser Ile Tyr Met Phe Phe Asn Thr Ser Asp Ile Arg
            100                 105                 110

Glu Ala Val Pro Glu Pro Pro Leu Leu Ser Arg Ala Glu Leu Arg Leu
        115                 120                 125

Gln Arg Leu Lys Ser Ser Val Glu Gln His Val Glu Leu Tyr Gln Lys
    130                 135                 140

Tyr Ser Asn Asn Ser Trp Arg Tyr Leu Gly Asn Arg Leu Leu Thr Pro
145                 150                 155                 160

Thr Asp Thr Pro Glu Trp Leu Ser Phe Asp Val Thr Gly Val Val Arg
                165                 170                 175

Gln Trp Leu Asn Gln Gly Asp Gly Ile Gln Gly Phe Arg Phe Ser Ala
            180                 185                 190

His Cys Ser Cys Asp Ser Lys Asp Asn Lys Leu His Val Glu Ile Asn
        195                 200                 205

Gly Ile Ser Pro Lys Arg Arg Gly Asp Leu Gly Thr Ile His Asp Met
    210                 215                 220

Asn Arg Pro Phe Leu Leu Leu Met Ala Thr Pro Leu Glu Arg Ala Gln
225                 230                 235                 240

His Leu His Ser Ser Arg His Arg Arg
                245

<210> SEQ ID NO 27
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27
```

```
Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
                100                 105                 110

Glu Ala Val Pro Glu Pro Val Leu Leu Ser Arg Ala Glu Leu Arg Leu
            115                 120                 125

Leu Arg Leu Lys Leu Lys Val Glu Gln His Val Glu Leu Tyr Gln Lys
    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Lys Asp Asn Thr Leu Gln Val Asp Ile Asn
        195                 200                 205

Gly Phe Thr Thr Gly Arg Arg Gly Asp Leu Ala Thr Ile His Gly Met
    210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg
                245

<210> SEQ ID NO 28
<211> LENGTH: 360
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Asp Pro Glu Pro Glu Pro Glu Ala Asp Tyr Tyr Ala Lys Glu Val Thr
65                  70                  75                  80

Arg Val Leu Met Val Asp Arg Asn Asn Ala Ile Tyr Glu Lys Thr Lys
                85                  90                  95
```

Asp Ile Ser His Ser Ile Tyr Met Phe Phe Asn Thr Ser Asp Ile Arg
                100                 105                 110

Glu Ala Val Pro Glu Pro Pro Leu Leu Ser Arg Ala Glu Leu Arg Leu
            115                 120                 125

Gln Arg Leu Lys Ser Ser Val Glu Gln His Val Glu Leu Tyr Gln Lys
        130                 135                 140

Tyr Ser Asn Asn Ser Trp Arg Tyr Leu Gly Asn Arg Leu Leu Thr Pro
145                 150                 155                 160

Thr Asp Thr Pro Glu Trp Leu Ser Phe Asp Val Thr Gly Val Val Arg
                165                 170                 175

Gln Trp Leu Asn Gln Gly Asp Gly Ile Gln Gly Phe Arg Phe Ser Ala
            180                 185                 190

His Cys Ser Cys Asp Ser Lys Asp Asn Lys Leu His Val Glu Ile Asn
        195                 200                 205

Gly Ile Ser Pro Lys Arg Arg Gly Asp Leu Gly Thr Ile His Asp Met
210                 215                 220

Asn Arg Pro Phe Leu Leu Leu Met Ala Thr Pro Leu Glu Arg Ala Gln
225                 230                 235                 240

His Leu His Ser Ser Arg His Gly Ala Leu Asp Thr Asn Tyr Cys Phe
            245                 250                 255

Ser Ser Thr Glu Lys Asn Cys Cys Val Arg Gln Leu Tyr Ile Asp Phe
        260                 265                 270

Arg Lys Asp Leu Gly Trp Lys Trp Ile His Glu Pro Lys Gly Tyr His
            275                 280                 285

Ala Asn Phe Cys Leu Gly Pro Cys Pro Tyr Ile Trp Ser Leu Asp Thr
290                 295                 300

Gln Tyr Ser Lys Val Leu Ala Leu Tyr Asn Gln His Asn Pro Gly Ala
305                 310                 315                 320

Ser Ala Ser Pro Cys Cys Val Pro Gln Ala Leu Glu Pro Leu Pro Ile
                325                 330                 335

Val Tyr Tyr Val Gly Arg Lys Pro Lys Val Glu Gln Leu Ser Asn Met
            340                 345                 350

Ile Val Arg Ser Cys Lys Cys Ser
            355                 360

<210> SEQ ID NO 29
<211> LENGTH: 361
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Asp Pro Glu Pro Glu Pro Glu Ala Asp Tyr Tyr Ala Lys Glu Val Thr
65                  70                  75                  80

Arg Val Leu Met Val Asp Arg Asn Asn Ala Ile Tyr Glu Lys Thr Lys

```
                85                  90                  95
Asp Ile Ser His Ser Ile Tyr Met Phe Phe Asn Thr Ser Asp Ile Arg
            100                 105                 110

Glu Ala Val Pro Glu Pro Leu Leu Ser Arg Ala Glu Leu Arg Leu
            115                 120                 125

Gln Arg Leu Lys Ser Ser Val Glu Gln His Val Glu Leu Tyr Gln Lys
130                 135                 140

Tyr Ser Asn Asn Ser Trp Arg Tyr Leu Gly Asn Arg Leu Leu Thr Pro
145                 150                 155                 160

Thr Asp Thr Pro Glu Trp Leu Ser Phe Asp Val Thr Gly Val Val Arg
            165                 170                 175

Gln Trp Leu Asn Gln Gly Asp Gly Ile Gln Gly Phe Arg Phe Ser Ala
            180                 185                 190

His Cys Ser Cys Asp Ser Lys Asp Asn Lys Leu His Val Glu Ile Asn
            195                 200                 205

Gly Ile Ser Pro Lys Arg Arg Gly Asp Leu Gly Thr Ile His Asp Met
        210                 215                 220

Asn Arg Pro Phe Leu Leu Leu Met Ala Thr Pro Leu Glu Arg Ala Gln
225                 230                 235                 240

His Leu His Ser Ser Arg His Arg Arg Ala Leu Asp Thr Asn Tyr Cys
            245                 250                 255

Phe Ser Ser Thr Glu Lys Asn Cys Cys Val Arg Gln Leu Tyr Ile Asp
            260                 265                 270

Phe Arg Lys Asp Leu Gly Trp Lys Trp Ile His Glu Pro Lys Gly Tyr
        275                 280                 285

His Ala Asn Phe Cys Leu Gly Pro Cys Pro Tyr Ile Trp Ser Leu Asp
        290                 295                 300

Thr Gln Tyr Ser Lys Val Leu Ala Leu Tyr Asn Gln His Asn Pro Gly
305                 310                 315                 320

Ala Ser Ala Ser Pro Cys Cys Val Pro Gln Ala Leu Glu Pro Leu Pro
            325                 330                 335

Ile Val Tyr Tyr Val Gly Arg Lys Pro Lys Val Glu Gln Leu Ser Asn
            340                 345                 350

Met Ile Val Arg Ser Cys Lys Cys Ser
            355                 360

<210> SEQ ID NO 30
<211> LENGTH: 361
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80
```

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
            115                 120                 125

Leu Arg Leu Lys Leu Lys Val Glu Gln His Val Glu Leu Tyr Gln Lys
        130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
            165                 170                 175

Gln Trp Leu Ser Arg Gly Gly Glu Ile Glu Gly Phe Arg Leu Ser Ala
            180                 185                 190

His Cys Ser Cys Asp Ser Lys Asp Asn Thr Leu Gln Val Asp Ile Asn
            195                 200                 205

Gly Phe Thr Thr Gly Arg Arg Gly Asp Leu Ala Thr Ile His Gly Met
        210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg Ala Leu Asp Thr Asn Tyr Cys
            245                 250                 255

Phe Ser Ser Thr Glu Lys Asn Cys Cys Val Arg Gln Leu Tyr Ile Asp
            260                 265                 270

Phe Arg Lys Asp Leu Gly Trp Lys Trp Ile His Glu Pro Lys Gly Tyr
            275                 280                 285

His Ala Asn Phe Cys Leu Gly Pro Cys Pro Tyr Ile Trp Ser Leu Asp
        290                 295                 300

Thr Gln Tyr Ser Lys Val Leu Ala Leu Tyr Asn Gln His Asn Pro Gly
305                 310                 315                 320

Ala Ser Ala Ala Pro Cys Cys Val Pro Gln Ala Leu Glu Pro Leu Pro
            325                 330                 335

Ile Val Tyr Tyr Val Gly Arg Lys Pro Lys Val Glu Gln Leu Ser Asn
        340                 345                 350

Met Ile Val Arg Ser Cys Lys Cys Ser
        355                 360

<210> SEQ ID NO 31
<211> LENGTH: 360
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Lys Asp Asn Thr Leu Gln Val Asp Ile Asn
        195                 200                 205

Gly Phe Thr Thr Gly Arg Arg Gly Asp Leu Ala Thr Ile His Gly Met
210                 215                 220

Asn Arg Pro Phe Leu Leu Leu Met Ala Thr Pro Leu Glu Arg Ala Gln
225                 230                 235                 240

His Leu Gln Ser Ser Arg His Gly Ala Leu Asp Thr Asn Tyr Cys Phe
                245                 250                 255

Ser Ser Thr Glu Lys Asn Cys Cys Val Arg Gln Leu Tyr Ile Asp Phe
            260                 265                 270

Arg Lys Asp Leu Gly Trp Lys Trp Ile His Glu Pro Lys Gly Tyr His
        275                 280                 285

Ala Asn Phe Cys Leu Gly Pro Cys Pro Tyr Ile Trp Ser Leu Asp Thr
    290                 295                 300

Gln Tyr Ser Lys Val Leu Ala Leu Tyr Asn Gln His Asn Pro Gly Ala
305                 310                 315                 320

Ser Ala Ala Pro Cys Cys Val Pro Gln Ala Leu Glu Pro Leu Pro Ile
                325                 330                 335

Val Tyr Tyr Val Gly Arg Lys Pro Lys Val Glu Gln Leu Ser Asn Met
            340                 345                 350

Ile Val Arg Ser Cys Lys Cys Ser
        355                 360

<210> SEQ ID NO 32
<211> LENGTH: 1375
<212> TYPE: PRT
<213> ORGANISM: Homo sapiens

<400> SEQUENCE: 32

Asn His Thr Gly Arg Ile Lys Val Val Phe Thr Pro Ser Ile Cys Lys
1               5                   10                  15

Val Thr Cys Thr Lys Gly Ser Cys Gln Asn Ser Cys Glu Lys Gly Asn
                20                  25                  30

Thr Thr Thr Leu Ile Ser Glu Asn Gly His Ala Ala Asp Thr Leu Thr
            35                  40                  45

Ala Thr Asn Phe Arg Val Val Ile Cys His Leu Pro Cys Met Asn Gly
    50                  55                  60

Gly Gln Cys Ser Ser Arg Asp Lys Cys Gln Cys Pro Pro Asn Phe Thr
65                  70                  75                  80

```
Gly Lys Leu Cys Gln Ile Pro Val His Gly Ala Ser Val Pro Lys Leu
                 85                  90                  95

Tyr Gln His Ser Gln Gln Pro Gly Lys Ala Leu Gly Thr His Val Ile
                100                 105                 110

His Ser Thr His Thr Leu Pro Leu Thr Val Thr Ser Gln Gln Gly Val
                115                 120                 125

Lys Val Lys Phe Pro Pro Asn Ile Val Asn Ile His Val Lys His Pro
130                 135                 140

Pro Glu Ala Ser Val Gln Ile His Gln Val Ser Arg Ile Asp Gly Pro
145                 150                 155                 160

Thr Gly Gln Lys Thr Lys Glu Ala Gln Pro Gly Gln Ser Gln Val Ser
                165                 170                 175

Tyr Gln Gly Leu Pro Val Gln Lys Thr Gln Thr Ile His Ser Thr Tyr
                180                 185                 190

Ser His Gln Gln Val Ile Pro His Val Tyr Pro Val Ala Ala Lys Thr
                195                 200                 205

Gln Leu Gly Arg Cys Phe Gln Glu Thr Ile Gly Ser Gln Cys Gly Lys
                210                 215                 220

Ala Leu Pro Gly Leu Ser Lys Gln Glu Asp Cys Cys Gly Thr Val Gly
225                 230                 235                 240

Thr Ser Trp Gly Phe Asn Lys Cys Gln Lys Cys Pro Lys Lys Pro Ser
                245                 250                 255

Tyr His Gly Tyr Asn Gln Met Met Glu Cys Leu Pro Gly Tyr Lys Arg
                260                 265                 270

Val Asn Asn Thr Phe Cys Gln Asp Ile Asn Glu Cys Gln Leu Gln Gly
                275                 280                 285

Val Cys Pro Asn Gly Glu Cys Leu Asn Thr Met Gly Ser Tyr Arg Cys
                290                 295                 300

Thr Cys Lys Ile Gly Phe Gly Pro Asp Pro Thr Phe Ser Ser Cys Val
305                 310                 315                 320

Pro Asp Pro Pro Val Ile Ser Glu Glu Lys Gly Pro Cys Tyr Arg Leu
                325                 330                 335

Val Ser Ser Gly Arg Gln Cys Met His Pro Leu Ser Val His Leu Thr
                340                 345                 350

Lys Gln Leu Cys Cys Cys Ser Val Gly Lys Ala Trp Gly Pro His Cys
                355                 360                 365

Glu Lys Cys Pro Leu Pro Gly Thr Ala Ala Phe Lys Glu Ile Cys Pro
                370                 375                 380

Gly Gly Met Gly Tyr Thr Val Ser Gly Val His Arg Arg Arg Pro Ile
385                 390                 395                 400

His His His Val Gly Lys Gly Pro Val Phe Val Lys Pro Lys Asn Thr
                405                 410                 415

Gln Pro Val Ala Lys Ser Thr His Pro Pro Leu Pro Ala Lys Glu
                420                 425                 430

Glu Pro Val Glu Ala Leu Thr Phe Ser Arg Glu His Gly Pro Gly Val
                435                 440                 445

Ala Glu Pro Glu Val Ala Thr Ala Pro Pro Glu Lys Glu Ile Pro Ser
450                 455                 460

Leu Asp Gln Glu Lys Thr Lys Leu Glu Pro Gly Gln Pro Gln Leu Ser
465                 470                 475                 480

Pro Gly Ile Ser Thr Ile His Leu His Pro Gln Phe Pro Val Val Ile
                485                 490                 495
```

```
Glu Lys Thr Ser Pro Pro Val Pro Val Ala Pro Glu Ala Ser
            500             505             510
Thr Ser Ser Ala Ser Gln Val Ile Ala Pro Thr Gln Val Thr Glu Ile
            515             520                 525
Asn Glu Cys Thr Val Asn Pro Asp Ile Cys Gly Ala Gly His Cys Ile
            530             535                 540
Asn Leu Pro Val Arg Tyr Thr Cys Ile Cys Tyr Glu Gly Tyr Arg Phe
545             550                 555                     560
Ser Glu Gln Gln Arg Lys Cys Val Asp Ile Asp Glu Cys Thr Gln Val
                565             570                 575
Gln His Leu Cys Ser Gln Gly Arg Cys Glu Asn Thr Glu Gly Ser Phe
            580             585                 590
Leu Cys Ile Cys Pro Ala Gly Phe Met Ala Ser Glu Glu Gly Thr Asn
            595             600                 605
Cys Ile Asp Val Asp Glu Cys Leu Arg Pro Asp Val Cys Gly Glu Gly
            610             615                 620
His Cys Val Asn Thr Val Gly Ala Phe Arg Cys Glu Tyr Cys Asp Ser
625             630                 635                     640
Gly Tyr Arg Met Thr Gln Arg Gly Arg Cys Glu Asp Ile Asp Glu Cys
                645             650                 655
Leu Asn Pro Ser Thr Cys Pro Asp Glu Gln Cys Val Asn Ser Pro Gly
            660             665                 670
Ser Tyr Gln Cys Val Pro Cys Thr Glu Gly Phe Arg Gly Trp Asn Gly
            675             680                 685
Gln Cys Leu Asp Val Asp Glu Cys Leu Glu Pro Asn Val Cys Ala Asn
            690             695                 700
Gly Asp Cys Ser Asn Leu Glu Gly Ser Tyr Met Cys Ser Cys His Lys
705             710                 715                     720
Gly Tyr Thr Arg Thr Pro Asp His Lys His Cys Arg Asp Ile Asp Glu
                725             730                 735
Cys Gln Gln Gly Asn Leu Cys Val Asn Gly Gln Cys Lys Asn Thr Glu
            740             745                 750
Gly Ser Phe Arg Cys Thr Cys Gly Gln Gly Tyr Gln Leu Ser Ala Ala
            755             760                 765
Lys Asp Gln Cys Glu Asp Ile Asp Glu Cys Gln His Arg His Leu Cys
770             775                 780
Ala His Gly Gln Cys Arg Asn Thr Glu Gly Ser Phe Gln Cys Val Cys
785             790                 795                     800
Asp Gln Gly Tyr Arg Ala Ser Gly Leu Gly Asp His Cys Glu Asp Ile
                805             810                 815
Asn Glu Cys Leu Glu Asp Lys Ser Val Cys Gln Arg Gly Asp Cys Ile
            820             825                 830
Asn Thr Ala Gly Ser Tyr Asp Cys Thr Cys Pro Asp Gly Phe Gln Leu
            835             840                 845
Asp Asp Asn Lys Thr Cys Gln Asp Ile Asn Glu Cys Glu His Pro Gly
850             855                 860
Leu Cys Gly Pro Gln Gly Glu Cys Leu Asn Thr Glu Gly Ser Phe His
865             870                 875                     880
Cys Val Cys Gln Gln Gly Phe Ser Ile Ser Ala Asp Gly Arg Thr Cys
                885             890                 895
Glu Asp Ile Asp Glu Cys Val Asn Asn Thr Val Cys Asp Ser His Gly
            900             905                 910
Phe Cys Asp Asn Thr Ala Gly Ser Phe Arg Cys Leu Cys Tyr Gln Gly
```

```
                915                 920                 925
Phe Gln Ala Pro Gln Asp Gly Gln Gly Cys Val Asp Val Asn Glu Cys
    930                 935                 940
Glu Leu Leu Ser Gly Val Cys Gly Glu Ala Phe Cys Glu Asn Val Glu
945                 950                 955                 960
Gly Ser Phe Leu Cys Val Cys Ala Asp Glu Asn Gln Glu Tyr Ser Pro
                965                 970                 975
Met Thr Gly Gln Cys Arg Ser Arg Thr Ser Thr Asp Leu Asp Val Asp
            980                 985                 990
Val Asp Gln Pro Lys Glu Glu Lys Lys Glu Cys Tyr Tyr Asn Leu Asn
                995                 1000                1005
Asp Ala Ser Leu Cys Asp Asn Val Leu Ala Pro Asn Val Thr Lys
        1010                1015                1020
Gln Glu Cys Cys Cys Thr Ser Gly Val Gly Trp Gly Asp Asn Cys
        1025                1030                1035
Glu Ile Phe Pro Cys Pro Val Leu Gly Thr Ala Glu Phe Thr Glu
        1040                1045                1050
Met Cys Pro Lys Gly Lys Gly Phe Val Pro Ala Gly Glu Ser Ser
        1055                1060                1065
Ser Glu Ala Gly Gly Glu Asn Tyr Lys Asp Ala Asp Glu Cys Leu
        1070                1075                1080
Leu Phe Gly Gln Glu Ile Cys Lys Asn Gly Phe Cys Leu Asn Thr
        1085                1090                1095
Arg Pro Gly Tyr Glu Cys Tyr Cys Lys Gln Gly Thr Tyr Tyr Asp
        1100                1105                1110
Pro Val Lys Leu Gln Cys Phe Asp Met Asp Glu Cys Gln Asp Pro
        1115                1120                1125
Ser Ser Cys Ile Asp Gly Gln Cys Val Asn Thr Glu Gly Ser Tyr
        1130                1135                1140
Asn Cys Phe Cys Thr His Pro Met Val Leu Asp Ala Ser Glu Lys
        1145                1150                1155
Arg Cys Ile Arg Pro Ala Glu Ser Asn Glu Gln Ile Glu Glu Thr
        1160                1165                1170
Asp Val Tyr Gln Asp Leu Cys Trp Glu His Leu Ser Asp Glu Tyr
        1175                1180                1185
Val Cys Ser Arg Pro Leu Val Gly Lys Gln Thr Thr Tyr Thr Glu
        1190                1195                1200
Cys Cys Cys Leu Tyr Gly Glu Ala Trp Gly Met Gln Cys Ala Leu
        1205                1210                1215
Cys Pro Leu Lys Asp Ser Asp Asp Tyr Ala Gln Leu Cys Asn Ile
        1220                1225                1230
Pro Val Thr Gly Arg Arg Gln Pro Tyr Gly Arg Asp Ala Leu Val
        1235                1240                1245
Asp Phe Ser Glu Gln Tyr Thr Pro Glu Ala Asp Pro Tyr Phe Ile
        1250                1255                1260
Gln Asp Arg Phe Leu Asn Ser Phe Glu Glu Leu Gln Ala Glu Glu
        1265                1270                1275
Cys Gly Ile Leu Asn Gly Cys Glu Asn Gly Arg Cys Val Arg Val
        1280                1285                1290
Gln Glu Gly Tyr Thr Cys Asp Cys Phe Asp Gly Tyr His Leu Asp
        1295                1300                1305
Thr Ala Lys Met Thr Cys Val Asp Val Asn Glu Cys Asp Glu Leu
        1310                1315                1320
```

```
Asn Asn Arg Met Ser Leu Cys Lys Asn Ala Lys Cys Ile Asn Thr
    1325                1330                1335

Asp Gly Ser Tyr Lys Cys Leu Cys Leu Pro Gly Tyr Val Pro Ser
    1340                1345                1350

Asp Lys Pro Asn Tyr Cys Thr Pro Leu Asn Thr Ala Leu Asn Leu
    1355                1360                1365

Glu Lys Asp Ser Asp Leu Glu
    1370                1375

<210> SEQ ID NO 33
<211> LENGTH: 1373
<212> TYPE: PRT
<213> ORGANISM: Macaca fascicularis

<400> SEQUENCE: 33

Asn His Thr Gly Arg Ile Lys Val Val Phe Thr Pro Ser Ile Cys Lys
1               5                   10                  15

Val Thr Cys Thr Lys Gly Ser Cys Gln Asn Ser Cys Glu Lys Gly Asn
            20                  25                  30

Thr Thr Thr Leu Ile Ser Glu Asn Gly His Ala Ala Asp Thr Leu Thr
        35                  40                  45

Ala Thr Asn Phe Arg Val Val Leu Cys His Leu Pro Cys Met Asn Gly
50                  55                  60

Gly Gln Cys Ser Ser Arg Asp Lys Cys Gln Cys Pro Pro Asn Phe Thr
65                  70                  75                  80

Gly Lys Leu Cys Gln Ile Pro Val His Gly Ala Ser Val Pro Lys Leu
                85                  90                  95

Tyr Gln His Ser Gln Gln Pro Gly Lys Ala Leu Gly Thr His Val Ile
            100                 105                 110

His Ser Thr His Thr Leu Pro Leu Thr Val Thr Ser Gln Gln Gly Val
        115                 120                 125

Lys Val Lys Phe Pro Pro Asn Ile Val Asn Ile His Val Lys His Pro
130                 135                 140

Pro Glu Ala Ser Val Gln Ile His Gln Val Ser Arg Ile Asp Gly Pro
145                 150                 155                 160

Thr Gly Gln Lys Thr Lys Glu Ala Gln Pro Gly Gln Ser Gln Val Ser
                165                 170                 175

Tyr Gln Gly Leu Pro Val Gln Lys Thr Gln Thr Ile His Ser Thr Tyr
            180                 185                 190

Ser His Gln Gln Val Ile Pro His Val Tyr Pro Val Ala Ala Lys Thr
        195                 200                 205

Gln Leu Gly Arg Cys Phe Gln Glu Thr Ile Gly Ser Gln Cys Gly Lys
210                 215                 220

Ala Leu Pro Gly Leu Ser Lys Gln Glu Asp Cys Cys Gly Thr Val Gly
225                 230                 235                 240

Thr Ser Trp Gly Phe Asn Lys Cys Gln Lys Cys Pro Lys Lys Pro Ser
                245                 250                 255

Tyr His Gly Tyr Asn Gln Met Met Glu Cys Leu Pro Gly Tyr Lys Arg
            260                 265                 270

Val Asn Asn Thr Phe Cys Gln Asp Ile Asn Glu Cys Gln Leu Gln Gly
        275                 280                 285

Val Cys Pro Asn Gly Glu Cys Leu Asn Thr Met Gly Ser Tyr Arg Cys
290                 295                 300

Thr Cys Lys Ile Gly Phe Gly Pro Asp Pro Thr Phe Ser Ser Cys Val
```

```
            305                 310                 315                 320
        Pro Asp Pro Pro Val Ile Ser Glu Glu Lys Gly Pro Cys Tyr Arg Leu
                        325                 330                 335
        Val Ser Ser Gly Arg Gln Cys Met His Pro Leu Ser Val His Leu Thr
                        340                 345                 350
        Lys Gln Leu Cys Cys Ser Val Gly Lys Ala Trp Gly Pro His Cys
                        355                 360                 365
        Glu Lys Cys Pro Leu Pro Gly Thr Ala Ala Phe Lys Glu Ile Cys Pro
                370                 375                 380
        Gly Gly Met Gly Tyr Thr Val Ser Gly Val His Arg Arg Pro Ile
        385                 390                 395                 400
        His His His Val Gly Lys Gly Pro Val Phe Val Lys Pro Lys Asn Thr
                        405                 410                 415
        Gln Pro Val Ala Lys Ser Thr His Pro Pro Leu Pro Ala Lys Glu
                        420                 425                 430
        Glu Pro Val Glu Ala Leu Thr Phe Ser Arg Glu His Gly Pro Gly Val
                        435                 440                 445
        Ala Glu Pro Glu Val Ala Thr Ala Pro Pro Glu Lys Glu Ile Pro Ser
                        450                 455                 460
        Leu Asp Gln Glu Lys Thr Lys Leu Glu Pro Gly Gln Pro Gln Leu Ser
        465                 470                 475                 480
        Pro Gly Ile Ser Thr Ile His Leu His Pro Gln Phe Pro Val Val Ile
                        485                 490                 495
        Glu Lys Thr Ser Pro Pro Val Pro Val Glu Val Ala Pro Glu Ala Ser
                        500                 505                 510
        Thr Ser Ser Ala Ser Gln Val Ile Ala Pro Thr Gln Val Thr Glu Ile
                        515                 520                 525
        Asn Glu Cys Thr Val Asn Pro Asp Ile Cys Gly Ala Gly His Cys Ile
                530                 535                 540
        Asn Leu Pro Val Arg Tyr Thr Cys Ile Cys Tyr Glu Gly Tyr Lys Phe
        545                 550                 555                 560
        Ser Glu Gln Gln Arg Lys Cys Val Asp Ile Asp Glu Cys Thr Gln Val
                        565                 570                 575
        Gln His Leu Cys Ser Gln Gly Arg Cys Glu Asn Thr Glu Gly Ser Phe
                        580                 585                 590
        Leu Cys Ile Cys Pro Ala Gly Phe Met Ala Ser Glu Glu Gly Thr Asn
                        595                 600                 605
        Cys Ile Asp Val Asp Glu Cys Leu Arg Pro Asp Val Cys Gly Glu Gly
                610                 615                 620
        His Cys Val Asn Thr Val Gly Ala Phe Arg Cys Glu Tyr Cys Asp Ser
        625                 630                 635                 640
        Gly Tyr Arg Met Thr Gln Arg Gly Arg Cys Glu Asp Ile Asp Glu Cys
                        645                 650                 655
        Leu Asn Pro Ser Thr Cys Pro Asp Glu Gln Cys Val Asn Ser Pro Gly
                        660                 665                 670
        Ser Tyr Gln Cys Val Pro Cys Thr Glu Gly Phe Arg Gly Trp Asn Gly
                        675                 680                 685
        Gln Cys Leu Asp Val Asp Glu Cys Leu Glu Pro Asn Val Cys Thr Asn
                        690                 695                 700
        Gly Asp Cys Ser Asn Leu Glu Gly Ser Tyr Met Cys Ser Cys His Lys
        705                 710                 715                 720
        Gly Tyr Thr Arg Thr Pro Asp His Lys His Cys Lys Asp Ile Asp Glu
                        725                 730                 735
```

-continued

Cys Gln Gln Gly Asn Leu Cys Val Asn Gly Gln Cys Lys Asn Thr Glu
        740                 745                 750

Gly Ser Phe Arg Cys Thr Cys Gly Gln Gly Tyr Gln Leu Ser Ala Ala
        755                 760                 765

Lys Asp Gln Cys Glu Asp Ile Asp Glu Cys Gln His His His Leu Cys
        770                 775                 780

Ala His Gly Gln Cys Arg Asn Thr Glu Gly Ser Phe Gln Cys Val Cys
785             790                 795                     800

Asp Gln Gly Tyr Arg Ala Ser Gly Leu Gly Asp His Cys Glu Asp Ile
            805                 810                 815

Asn Glu Cys Leu Glu Asp Lys Ser Val Cys Gln Arg Gly Asp Cys Ile
        820                 825                 830

Asn Thr Ala Gly Ser Tyr Asp Cys Thr Cys Pro Asp Gly Phe Gln Leu
            835                 840                 845

Asp Asp Asn Lys Thr Cys Gln Asp Ile Asn Glu Cys Glu His Pro Gly
        850                 855                 860

Leu Cys Gly Pro Gln Gly Glu Cys Leu Asn Thr Glu Gly Ser Phe His
865             870                 875                     880

Cys Val Cys Gln Gln Gly Phe Ser Ile Ser Ala Asp Gly Arg Thr Cys
                885                 890                 895

Glu Asp Ile Asp Glu Cys Val Asn Asn Thr Val Cys Asp Ser His Gly
            900                 905                 910

Phe Cys Asp Asn Thr Ala Gly Ser Phe Arg Cys Leu Cys Tyr Gln Gly
        915                 920                 925

Phe Gln Ala Pro Gln Asp Gly Gln Gly Cys Val Asp Val Asn Glu Cys
        930                 935                 940

Glu Leu Leu Ser Gly Val Cys Gly Glu Ala Phe Cys Glu Asn Val Glu
945             950                 955                     960

Gly Ser Phe Leu Cys Val Cys Ala Asp Glu Asn Gln Glu Tyr Ser Pro
            965                 970                 975

Met Thr Gly Gln Cys Arg Ser Arg Thr Ser Thr Asp Leu Asp Val Glu
        980                 985                 990

Gln Pro Lys Glu Glu Lys Lys Glu Cys Tyr Tyr Asn Leu Asn Asp Ala
        995                 1000                1005

Ser Leu Cys Asp Asn Val Leu Ala Pro Asn Val Thr Lys Gln Glu
        1010                1015                1020

Cys Cys Cys Thr Ser Gly Ala Gly Trp Gly Asp Asn Cys Glu Ile
        1025                1030                1035

Phe Pro Cys Pro Val Leu Gly Thr Ala Glu Phe Thr Glu Met Cys
        1040                1045                1050

Pro Lys Gly Lys Gly Phe Val Pro Ala Gly Glu Ser Ser Ser Glu
        1055                1060                1065

Ala Gly Gly Glu Asn Tyr Lys Asp Ala Asp Glu Cys Leu Leu Phe
        1070                1075                1080

Gly Gln Glu Ile Cys Lys Asn Gly Phe Cys Leu Asn Thr Arg Pro
        1085                1090                1095

Gly Tyr Glu Cys Tyr Cys Lys Gln Gly Thr Tyr Tyr Asp Pro Val
        1100                1105                1110

Lys Leu Gln Cys Phe Asp Met Asp Glu Cys Gln Asp Pro Ser Ser
        1115                1120                1125

Cys Ile Asp Gly Gln Cys Val Asn Thr Glu Gly Ser Tyr Asn Cys
        1130                1135                1140

-continued

```
Phe Cys Thr His Pro Met Val Leu Asp Ala Ser Glu Lys Arg Cys
1145                1150                1155

Ile Arg Pro Ala Glu Ser Asn Glu Gln Ile Glu Thr Asp Val
1160                1165                1170

Tyr Gln Asp Leu Cys Trp Glu His Leu Ser Asp Glu Tyr Val Cys
1175                1180                1185

Ser Arg Pro Leu Val Gly Lys Gln Thr Thr Tyr Thr Glu Cys Cys
1190                1195                1200

Cys Leu Tyr Gly Glu Ala Trp Gly Met Gln Cys Ala Leu Cys Pro
1205                1210                1215

Met Lys Asp Ser Asp Tyr Ala Gln Leu Cys Asn Ile Pro Val
1220                1225                1230

Thr Gly Arg Arg Gln Pro Tyr Gly Arg Asp Ala Leu Val Asp Phe
1235                1240                1245

Ser Glu Gln Tyr Ala Pro Glu Ala Asp Pro Tyr Phe Ile Gln Asp
1250                1255                1260

Arg Phe Leu Asn Ser Phe Glu Glu Leu Gln Ala Glu Glu Cys Gly
1265                1270                1275

Ile Leu Asn Gly Cys Glu Asn Gly Arg Cys Val Arg Val Gln Glu
1280                1285                1290

Gly Tyr Thr Cys Asp Cys Phe Asp Gly Tyr His Leu Asp Thr Ala
1295                1300                1305

Lys Met Thr Cys Val Asp Val Asn Glu Cys Asp Glu Leu Asn Asn
1310                1315                1320

Arg Met Ser Leu Cys Lys Asn Ala Lys Cys Ile Asn Thr Glu Gly
1325                1330                1335

Ser Tyr Lys Cys Leu Cys Leu Pro Gly Tyr Val Pro Ser Asp Lys
1340                1345                1350

Pro Asn Tyr Cys Thr Pro Leu Asn Thr Ala Leu Asn Leu Glu Lys
1355                1360                1365

Asp Ser Asp Leu Glu
1370

<210> SEQ ID NO 34
<211> LENGTH: 1374
<212> TYPE: PRT
<213> ORGANISM: Mus sp.

<400> SEQUENCE: 34

Asn His Thr Gly Arg Ile Lys Val Val Phe Thr Pro Ser Ile Cys Lys
1               5                   10                  15

Val Thr Cys Thr Lys Gly Asn Cys Gln Asn Ser Cys Gln Lys Gly Asn
                20                  25                  30

Thr Thr Thr Leu Ile Ser Glu Asn Gly His Ala Ala Asp Thr Leu Thr
            35                  40                  45

Ala Thr Asn Phe Arg Val Val Ile Cys His Leu Pro Cys Met Asn Gly
        50                  55                  60

Gly Gln Cys Ser Ser Arg Asp Lys Cys Gln Cys Pro Pro Asn Phe Thr
65                  70                  75                  80

Gly Lys Leu Cys Gln Ile Pro Val Leu Gly Ala Ser Met Pro Lys Leu
                85                  90                  95

Tyr Gln His Ala Gln Gln Gln Gly Lys Ala Leu Gly Ser His Val Ile
            100                 105                 110

His Ser Thr His Thr Leu Pro Leu Thr Met Thr Ser Gln Gln Gly Val
        115                 120                 125
```

```
Lys Val Lys Phe Pro Pro Asn Ile Val Asn Ile His Val Lys His Pro
130                 135                 140

Pro Glu Ala Ser Val Gln Ile His Gln Val Ser Arg Ile Asp Ser Pro
145                 150                 155                 160

Gly Gly Gln Lys Val Lys Glu Ala Gln Pro Gly Gln Ser Gln Val Ser
                165                 170                 175

Tyr Gln Gly Leu Pro Val Gln Lys Thr Gln Thr Val His Ser Thr Tyr
                180                 185                 190

Ser His Gln Gln Leu Ile Pro His Val Tyr Pro Val Ala Ala Lys Thr
                195                 200                 205

Gln Leu Gly Arg Cys Phe Gln Glu Thr Ile Gly Ser Gln Cys Gly Lys
210                 215                 220

Ala Leu Pro Gly Leu Ser Lys Gln Glu Asp Cys Cys Gly Thr Val Gly
225                 230                 235                 240

Thr Ser Trp Gly Phe Asn Lys Cys Gln Lys Cys Pro Lys Lys Gln Ser
                245                 250                 255

Tyr His Gly Tyr Thr Gln Met Met Glu Cys Leu Gln Gly Tyr Lys Arg
                260                 265                 270

Val Asn Asn Thr Phe Cys Gln Asp Ile Asn Glu Cys Gln Leu Gln Gly
                275                 280                 285

Val Cys Pro Asn Gly Glu Cys Leu Asn Thr Met Gly Ser Tyr Arg Cys
290                 295                 300

Ser Cys Lys Met Gly Phe Gly Pro Asp Pro Thr Phe Ser Ser Cys Val
305                 310                 315                 320

Pro Asp Pro Pro Val Ile Ser Glu Glu Lys Gly Pro Cys Tyr Arg Leu
                325                 330                 335

Val Ser Pro Gly Arg His Cys Met His Pro Leu Ser Val His Leu Thr
                340                 345                 350

Lys Gln Ile Cys Cys Cys Ser Val Gly Lys Ala Trp Gly Pro His Cys
                355                 360                 365

Glu Lys Cys Pro Leu Pro Gly Thr Ala Ala Phe Lys Glu Ile Cys Pro
370                 375                 380

Gly Gly Met Gly Tyr Thr Val Ser Gly Val His Arg Arg Arg Pro Ile
385                 390                 395                 400

His Gln His Ile Gly Lys Glu Ala Val Tyr Val Lys Pro Lys Asn Thr
                405                 410                 415

Gln Pro Val Ala Lys Ser Thr His Pro Pro Leu Pro Ala Lys Glu
                420                 425                 430

Glu Pro Val Glu Ala Leu Thr Ser Ser Trp Glu His Gly Pro Arg Gly
                435                 440                 445

Ala Glu Pro Glu Val Val Thr Ala Pro Pro Glu Lys Glu Ile Pro Ser
450                 455                 460

Leu Asp Gln Glu Lys Thr Arg Leu Glu Pro Gly Gln Pro Gln Leu Ser
465                 470                 475                 480

Pro Gly Val Ser Thr Ile His Leu His Pro Gln Phe Pro Val Val Val
                485                 490                 495

Glu Lys Thr Ser Pro Pro Val Pro Val Glu Val Ala Pro Glu Ala Ser
                500                 505                 510

Thr Ser Ser Ala Ser Gln Val Ile Ala Pro Thr Gln Val Thr Glu Ile
                515                 520                 525

Asn Glu Cys Thr Val Asn Pro Asp Ile Cys Gly Ala Gly His Cys Ile
530                 535                 540
```

-continued

```
Asn Leu Pro Val Arg Tyr Thr Cys Ile Cys Tyr Glu Gly Tyr Lys Phe
545                 550                 555                 560
Ser Glu Gln Leu Arg Lys Cys Val Asp Ile Asp Glu Cys Ala Gln Val
            565                 570                 575
Arg His Leu Cys Ser Gln Gly Arg Cys Glu Asn Thr Glu Gly Ser Phe
        580                 585                 590
Leu Cys Val Cys Pro Ala Gly Phe Met Ala Ser Glu Glu Gly Thr Asn
    595                 600                 605
Cys Ile Asp Val Asp Glu Cys Leu Arg Pro Asp Met Cys Arg Asp Gly
610                 615                 620
Arg Cys Ile Asn Thr Ala Gly Ala Phe Arg Cys Glu Tyr Cys Asp Ser
625                 630                 635                 640
Gly Tyr Arg Met Ser Arg Arg Gly Tyr Cys Glu Asp Ile Asp Glu Cys
            645                 650                 655
Leu Lys Pro Ser Thr Cys Pro Glu Glu Gln Cys Val Asn Thr Pro Gly
        660                 665                 670
Ser Tyr Gln Cys Val Pro Cys Thr Glu Gly Phe Arg Gly Trp Asn Gly
    675                 680                 685
Gln Cys Leu Asp Val Asp Glu Cys Leu Gln Pro Lys Val Cys Thr Asn
690                 695                 700
Gly Ser Cys Thr Asn Leu Glu Gly Ser Tyr Met Cys Ser Cys His Arg
705                 710                 715                 720
Gly Tyr Ser Pro Thr Pro Asp His Arg His Cys Gln Asp Ile Asp Glu
            725                 730                 735
Cys Gln Gln Gly Asn Leu Cys Met Asn Gly Gln Cys Arg Asn Thr Asp
        740                 745                 750
Gly Ser Phe Arg Cys Thr Cys Gly Gln Gly Tyr Gln Leu Ser Ala Ala
    755                 760                 765
Lys Asp Gln Cys Glu Asp Ile Asp Glu Cys Glu His His Leu Cys
770                 775                 780
Ser His Gly Gln Cys Arg Asn Thr Glu Gly Ser Phe Gln Cys Val Cys
785                 790                 795                 800
Asn Gln Gly Tyr Arg Ala Ser Val Leu Gly Asp His Cys Glu Asp Ile
            805                 810                 815
Asn Glu Cys Leu Glu Asp Ser Ser Val Cys Gln Gly Gly Asp Cys Ile
        820                 825                 830
Asn Thr Ala Gly Ser Tyr Asp Cys Thr Cys Pro Asp Gly Phe Gln Leu
    835                 840                 845
Asn Asp Asn Lys Gly Cys Gln Asp Ile Asn Glu Cys Ala Gln Pro Gly
850                 855                 860
Leu Cys Gly Ser His Gly Glu Cys Leu Asn Thr Gln Gly Ser Phe His
865                 870                 875                 880
Cys Val Cys Glu Gln Gly Phe Ser Ile Ser Ala Asp Gly Arg Thr Cys
            885                 890                 895
Glu Asp Ile Asp Glu Cys Val Asn Asn Thr Val Cys Asp Ser His Gly
        900                 905                 910
Phe Cys Asp Asn Thr Ala Gly Ser Phe Arg Cys Leu Cys Tyr Gln Gly
    915                 920                 925
Phe Gln Ala Pro Gln Asp Gly Gln Gly Cys Val Asp Val Asn Glu Cys
930                 935                 940
Glu Leu Leu Ser Gly Val Cys Gly Glu Ala Phe Cys Glu Asn Val Glu
945                 950                 955                 960
Gly Ser Phe Leu Cys Val Cys Ala Asp Glu Asn Gln Glu Tyr Ser Pro
```

-continued

```
                965                 970                 975
Met Thr Gly Gln Cys Arg Ser Arg Val Thr Glu Asp Ser Gly Val Asp
            980                 985                 990
Arg Gln Pro Arg Glu Glu Lys Lys  Glu Cys Tyr Tyr Asn  Leu Asn Asp
        995                 1000                1005
Ala Ser  Leu Cys Asp Asn Val  Leu Ala Pro Asn Val  Thr Lys Gln
    1010                1015                1020
Glu Cys  Cys Cys Thr Ser Gly  Ala Gly Trp Gly Asp  Asn Cys Glu
    1025                1030                1035
Ile Phe  Pro Cys Pro Val Gln  Gly Thr Ala Glu Phe  Thr Glu Met
    1040                1045                1050
Cys Pro  Arg Gly Lys Gly Leu  Val Pro Ala Gly Glu  Ser Ser Tyr
    1055                1060                1065
Asp Thr  Gly Gly Glu Asn Tyr  Lys Asp Ala Asp Glu  Cys Leu Leu
    1070                1075                1080
Phe Gly  Glu Glu Ile Cys Lys  Asn Gly Tyr Cys Leu  Asn Thr Gln
    1085                1090                1095
Pro Gly  Tyr Glu Cys Tyr Cys  Lys Gln Gly Thr Tyr  Tyr Asp Pro
    1100                1105                1110
Val Lys  Leu Gln Cys Phe Asp  Met Asp Glu Cys Gln  Asp Pro Asn
    1115                1120                1125
Ser Cys  Ile Asp Gly Gln Cys  Val Asn Thr Glu Gly  Ser Tyr Asn
    1130                1135                1140
Cys Phe  Cys Thr His Pro Met  Val Leu Asp Ala Ser  Glu Lys Arg
    1145                1150                1155
Cys Val  Gln Pro Thr Glu Ser  Asn Glu Gln Ile Glu  Glu Thr Asp
    1160                1165                1170
Val Tyr  Gln Asp Leu Cys Trp  Glu His Leu Ser Glu  Glu Tyr Val
    1175                1180                1185
Cys Ser  Arg Pro Leu Val Gly  Lys Gln Thr Thr Tyr  Thr Glu Cys
    1190                1195                1200
Cys Cys  Leu Tyr Gly Glu Ala  Trp Gly Met Gln Cys  Ala Leu Cys
    1205                1210                1215
Pro Met  Lys Asp Ser Asp Asp  Tyr Ala Gln Leu Cys  Asn Ile Pro
    1220                1225                1230
Val Thr  Gly Arg Arg Arg Pro  Tyr Gly Arg Asp Ala  Leu Val Asp
    1235                1240                1245
Phe Ser  Glu Gln Tyr Gly Pro  Glu Thr Asp Pro Tyr  Phe Ile Gln
    1250                1255                1260
Asp Arg  Phe Leu Asn Ser Phe  Glu Glu Leu Gln Ala  Glu Glu Cys
    1265                1270                1275
Gly Ile  Leu Asn Gly Cys Glu  Asn Gly Arg Cys Val  Arg Val Gln
    1280                1285                1290
Glu Gly  Tyr Thr Cys Asp Cys  Phe Asp Gly Tyr His  Leu Asp Met
    1295                1300                1305
Ala Lys  Met Thr Cys Val Asp  Val Asn Glu Cys Ser  Glu Leu Asn
    1310                1315                1320
Asn Arg  Met Ser Leu Cys Lys  Asn Ala Lys Cys Ile  Asn Thr Glu
    1325                1330                1335
Gly Ser  Tyr Lys Cys Leu Cys  Leu Pro Gly Tyr Ile  Pro Ser Asp
    1340                1345                1350
Lys Pro  Asn Tyr Cys Thr Pro  Leu Asn Ser Ala Leu  Asn Leu Asp
    1355                1360                1365
```

Lys Glu Ser Asp Leu Glu
        1370

<210> SEQ ID NO 35
<211> LENGTH: 1260
<212> TYPE: PRT
<213> ORGANISM: Homo sapiens

<400> SEQUENCE: 35

Gly Pro Ala Gly Glu Arg Gly Ala Gly Gly Gly Ala Leu Ala Arg
1               5                   10                  15

Glu Arg Phe Lys Val Val Phe Ala Pro Val Ile Cys Lys Arg Thr Cys
            20                  25                  30

Leu Lys Gly Gln Cys Arg Asp Ser Cys Gln Gln Gly Ser Asn Met Thr
            35                  40                  45

Leu Ile Gly Glu Asn Gly His Ser Thr Asp Thr Leu Thr Gly Ser Gly
        50                  55                  60

Phe Arg Val Val Val Cys Pro Leu Pro Cys Met Asn Gly Gly Gln Cys
65              70                  75                  80

Ser Ser Arg Asn Gln Cys Leu Cys Pro Pro Asp Phe Thr Gly Arg Phe
                85                  90                  95

Cys Gln Val Pro Ala Gly Gly Ala Gly Gly Thr Gly Gly Ser Gly
                100                 105                 110

Pro Gly Leu Ser Arg Thr Gly Ala Leu Ser Thr Gly Ala Leu Pro Pro
            115                 120                 125

Leu Ala Pro Glu Gly Asp Ser Val Ala Ser Lys His Ala Ile Tyr Ala
        130                 135                 140

Val Gln Val Ile Ala Asp Pro Pro Gly Pro Gly Glu Gly Pro Pro Ala
145             150                 155                 160

Gln His Ala Ala Phe Leu Val Pro Leu Gly Pro Gly Gln Ile Ser Ala
                165                 170                 175

Glu Val Gln Ala Pro Pro Val Val Asn Val Arg Val His His Pro
            180                 185                 190

Pro Glu Ala Ser Val Gln Val His Arg Ile Glu Ser Ser Asn Ala Glu
        195                 200                 205

Ser Ala Ala Pro Ser Gln His Leu Leu Pro His Pro Lys Pro Ser His
        210                 215                 220

Pro Arg Pro Pro Thr Gln Lys Pro Leu Gly Arg Cys Phe Gln Asp Thr
225                 230                 235                 240

Leu Pro Lys Gln Pro Cys Gly Ser Asn Pro Leu Pro Gly Leu Thr Lys
                245                 250                 255

Gln Glu Asp Cys Cys Gly Ser Ile Gly Thr Ala Trp Gly Gln Ser Lys
            260                 265                 270

Cys His Lys Cys Pro Gln Leu Gln Tyr Thr Gly Val Gln Lys Pro Gly
        275                 280                 285

Pro Val Arg Gly Glu Val Gly Ala Asp Cys Pro Gln Gly Tyr Lys Arg
    290                 295                 300

Leu Asn Ser Thr His Cys Gln Asp Ile Asn Glu Cys Ala Met Pro Gly
305                 310                 315                 320

Val Cys Arg His Gly Asp Cys Leu Asn Asn Pro Gly Ser Tyr Arg Cys
                325                 330                 335

Val Cys Pro Pro Gly His Ser Leu Gly Pro Ser Arg Thr Gln Cys Ile
            340                 345                 350

Ala Asp Lys Pro Glu Glu Lys Ser Leu Cys Phe Arg Leu Val Ser Pro

-continued

```
            355                 360                 365
Glu His Gln Cys Gln His Pro Leu Thr Thr Arg Leu Thr Arg Gln Leu
    370                 375                 380
Cys Cys Cys Ser Val Gly Lys Ala Trp Gly Ala Arg Cys Gln Arg Cys
385                 390                 395                 400
Pro Thr Asp Gly Thr Ala Ala Phe Lys Glu Ile Cys Pro Ala Gly Lys
                405                 410                 415
Gly Tyr His Ile Leu Thr Ser His Gln Thr Leu Thr Ile Gln Gly Glu
            420                 425                 430
Ser Asp Phe Ser Leu Phe Leu His Pro Asp Gly Pro Pro Lys Pro Gln
        435                 440                 445
Gln Leu Pro Glu Ser Pro Ser Gln Ala Pro Pro Glu Asp Thr Glu
    450                 455                 460
Glu Glu Arg Gly Val Thr Thr Asp Ser Pro Val Ser Glu Glu Arg Ser
465                 470                 475                 480
Val Gln Gln Ser His Pro Thr Ala Thr Thr Pro Ala Arg Pro Tyr
                485                 490                 495
Pro Glu Leu Ile Ser Arg Pro Ser Pro Thr Met Arg Trp Phe Leu
            500                 505                 510
Pro Asp Leu Pro Pro Ser Arg Ser Ala Val Glu Ile Ala Pro Thr Gln
        515                 520                 525
Val Thr Glu Thr Asp Glu Cys Arg Leu Asn Gln Asn Ile Cys Gly His
    530                 535                 540
Gly Glu Cys Val Pro Gly Pro Pro Asp Tyr Ser Cys His Cys Asn Pro
545                 550                 555                 560
Gly Tyr Arg Ser His Pro Gln His Arg Tyr Cys Val Asp Val Asn Glu
                565                 570                 575
Cys Glu Ala Glu Pro Cys Gly Pro Gly Arg Gly Ile Cys Met Asn Thr
            580                 585                 590
Gly Gly Ser Tyr Asn Cys His Cys Asn Arg Gly Tyr Arg Leu His Val
        595                 600                 605
Gly Ala Gly Gly Arg Ser Cys Val Asp Leu Asn Glu Cys Ala Lys Pro
    610                 615                 620
His Leu Cys Gly Asp Gly Gly Phe Cys Ile Asn Phe Pro Gly His Tyr
625                 630                 635                 640
Lys Cys Asn Cys Tyr Pro Gly Tyr Arg Leu Lys Ala Ser Arg Pro Pro
                645                 650                 655
Val Cys Glu Asp Ile Asp Glu Cys Arg Asp Pro Ser Ser Cys Pro Asp
            660                 665                 670
Gly Lys Cys Glu Asn Lys Pro Gly Ser Phe Lys Cys Ile Ala Cys Gln
        675                 680                 685
Pro Gly Tyr Arg Ser Gln Gly Gly Gly Ala Cys Arg Asp Val Asn Glu
    690                 695                 700
Cys Ala Glu Gly Ser Pro Cys Ser Pro Gly Trp Cys Glu Asn Leu Pro
705                 710                 715                 720
Gly Ser Phe Arg Cys Thr Cys Ala Gln Gly Tyr Ala Pro Ala Pro Asp
                725                 730                 735
Gly Arg Ser Cys Leu Asp Val Asp Glu Cys Glu Ala Gly Asp Val Cys
                740                 745                 750
Asp Asn Gly Ile Cys Ser Asn Thr Pro Gly Ser Phe Gln Cys Gln Cys
            755                 760                 765
Leu Ser Gly Tyr His Leu Ser Arg Asp Arg Ser His Cys Glu Asp Ile
        770                 775                 780
```

```
Asp Glu Cys Asp Phe Pro Ala Ala Cys Ile Gly Gly Asp Cys Ile Asn
785                 790                 795                 800

Thr Asn Gly Ser Tyr Arg Cys Leu Cys Pro Gln Gly His Arg Leu Val
            805                 810                 815

Gly Gly Arg Lys Cys Gln Asp Ile Asp Glu Cys Ser Gln Asp Pro Ser
        820                 825                 830

Leu Cys Leu Pro His Gly Ala Cys Lys Asn Leu Gln Gly Ser Tyr Val
    835                 840                 845

Cys Val Cys Asp Glu Gly Phe Thr Pro Thr Gln Asp Gln His Gly Cys
850                 855                 860

Glu Glu Val Glu Gln Pro His His Lys Lys Glu Cys Tyr Leu Asn Phe
865                 870                 875                 880

Asp Asp Thr Val Phe Cys Asp Ser Val Leu Ala Thr Asn Val Thr Gln
                885                 890                 895

Gln Glu Cys Cys Cys Ser Leu Gly Ala Gly Trp Gly Asp His Cys Glu
            900                 905                 910

Ile Tyr Pro Cys Pro Val Tyr Ser Ser Ala Glu Phe His Ser Leu Cys
        915                 920                 925

Pro Asp Gly Lys Gly Tyr Thr Gln Asp Asn Asn Ile Val Asn Tyr Gly
    930                 935                 940

Ile Pro Ala His Arg Asp Ile Asp Glu Cys Met Leu Phe Gly Ser Glu
945                 950                 955                 960

Ile Cys Lys Glu Gly Lys Cys Val Asn Thr Gln Pro Gly Tyr Glu Cys
                965                 970                 975

Tyr Cys Lys Gln Gly Phe Tyr Tyr Asp Gly Asn Leu Leu Glu Cys Val
            980                 985                 990

Asp Val Asp Glu Cys Leu Asp Glu  Ser Asn Cys Arg Asn  Gly Val Cys
        995                 1000                1005

Glu Asn  Thr Arg Gly Gly Tyr  Arg Cys Ala Cys Thr  Pro Pro Ala
    1010                1015                1020

Glu Tyr  Ser Pro Ala Gln Arg  Gln Cys Leu Ser Pro  Glu Glu Met
    1025                1030                1035

Asp Val  Asp Glu Cys Gln Asp  Pro Ala Ala Cys Arg  Pro Gly Arg
    1040                1045                1050

Cys Val  Asn Leu Pro Gly Ser  Tyr Arg Cys Glu Cys  Arg Pro Pro
    1055                1060                1065

Trp Val  Pro Gly Pro Ser Gly  Arg Asp Cys Gln Leu  Pro Glu Ser
    1070                1075                1080

Pro Ala  Glu Arg Ala Pro Glu  Arg Arg Asp Val Cys  Trp Ser Gln
    1085                1090                1095

Arg Gly  Glu Asp Gly Met Cys  Ala Gly Pro Leu Ala  Gly Pro Ala
    1100                1105                1110

Leu Thr  Phe Asp Asp Cys Cys  Cys Arg Gln Gly Arg  Gly Trp Gly
    1115                1120                1125

Ala Gln  Cys Arg Pro Cys Pro  Pro Arg Gly Ala Gly  Ser His Cys
    1130                1135                1140

Pro Thr  Ser Gln Ser Glu Ser  Asn Ser Phe Trp Asp  Thr Ser Pro
    1145                1150                1155

Leu Leu  Leu Gly Lys Pro Pro  Arg Asp Glu Asp Ser  Ser Glu Glu
    1160                1165                1170

Asp Ser  Asp Glu Cys Arg Cys  Val Ser Gly Arg Cys  Val Pro Arg
    1175                1180                1185
```

```
Pro Gly Gly Ala Val Cys Glu Cys Pro Gly Gly Phe Gln Leu Asp
    1190            1195                1200

Ala Ser Arg Ala Arg Cys Val Asp Ile Asp Glu Cys Arg Glu Leu
    1205            1210                1215

Asn Gln Arg Gly Leu Leu Cys Lys Ser Glu Arg Cys Val Asn Thr
    1220            1225                1230

Ser Gly Ser Phe Arg Cys Val Cys Lys Ala Gly Phe Ala Arg Ser
    1235            1240                1245

Arg Pro His Gly Ala Cys Val Pro Gln Arg Arg
    1250            1255                1260

<210> SEQ ID NO 36
<211> LENGTH: 1260
<212> TYPE: PRT
<213> ORGANISM: Macaca fascicularis

<400> SEQUENCE: 36

Gly Pro Ala Gly Glu Arg Gly Ala Gly Gly Gly Ala Leu Ala Arg
1               5                   10                  15

Glu Arg Phe Lys Val Val Phe Ala Pro Val Ile Cys Lys Arg Thr Cys
                20                  25                  30

Leu Lys Gly Gln Cys Arg Asp Ser Cys Gln Gln Gly Ser Asn Met Thr
                35                  40                  45

Leu Ile Gly Glu Asn Gly His Ser Thr Asp Thr Leu Thr Gly Ser Gly
50                  55                  60

Phe Arg Val Val Cys Pro Leu Pro Cys Met Asn Gly Gly Gln Cys
65                  70                  75                  80

Ser Ser Arg Asn Gln Cys Leu Cys Pro Pro Asp Phe Thr Gly Arg Phe
                85                  90                  95

Cys Gln Val Pro Ala Gly Gly Ala Gly Gly Thr Gly Ser Gly
                100                 105                 110

Pro Gly Leu Ser Arg Ala Gly Ala Leu Ser Thr Gly Ala Leu Pro Pro
                115                 120                 125

Leu Ala Pro Glu Gly Asp Ser Val Ala Ser Lys His Ala Ile Tyr Ala
    130                 135                 140

Val Gln Val Ile Ala Asp Pro Pro Gly Pro Gly Glu Gly Pro Pro Ala
145                 150                 155                 160

Gln His Ala Ala Phe Leu Val Pro Leu Gly Pro Gly Gln Ile Ser Ala
                165                 170                 175

Glu Val Gln Ala Pro Pro Val Val Asn Val Arg Val His His Pro
                180                 185                 190

Pro Glu Ala Ser Val Gln Val His Arg Ile Glu Ser Ser Asn Ala Glu
    195                 200                 205

Gly Ala Ala Pro Ser Gln His Leu Leu Pro His Pro Lys Pro Ser His
    210                 215                 220

Pro Arg Pro Pro Thr Gln Lys Pro Leu Gly Arg Cys Phe Gln Asp Thr
225                 230                 235                 240

Leu Pro Lys Gln Pro Cys Gly Ser Asn Pro Leu Pro Gly Leu Thr Lys
                245                 250                 255

Gln Glu Asp Cys Cys Gly Ser Ile Gly Thr Ala Trp Gly Gln Ser Lys
                260                 265                 270

Cys His Lys Cys Pro Gln Leu Gln Tyr Thr Gly Val Gln Lys Pro Gly
                275                 280                 285

Pro Val Arg Gly Glu Val Gly Ala Asp Cys Pro Gln Gly Tyr Lys Arg
                290                 295                 300
```

-continued

```
Leu Asn Ser Thr His Cys Gln Asp Ile Asn Glu Cys Ala Met Pro Gly
305                 310                 315                 320
Val Cys Arg His Gly Asp Cys Leu Asn Asn Pro Gly Ser Tyr Arg Cys
                325                 330                 335
Val Cys Pro Pro Gly His Ser Leu Gly Pro Ser Arg Thr Gln Cys Ile
            340                 345                 350
Ala Asp Lys Pro Glu Glu Lys Ser Leu Cys Phe Arg Leu Val Ser Pro
            355                 360                 365
Glu His Gln Cys Gln His Pro Leu Thr Thr Arg Leu Thr Arg Gln Leu
        370                 375                 380
Cys Cys Cys Ser Val Gly Lys Ala Trp Gly Ala Arg Cys Gln Arg Cys
385                 390                 395                 400
Pro Ala Asp Gly Thr Ala Ala Phe Lys Glu Ile Cys Pro Ala Gly Lys
                405                 410                 415
Gly Tyr His Ile Leu Thr Ser His Gln Thr Leu Thr Ile Gln Gly Glu
                420                 425                 430
Ser Asp Phe Ser Leu Phe Leu His Pro Asp Gly Pro Pro Lys Pro Gln
            435                 440                 445
Gln Leu Pro Glu Ser Pro Ser Gln Ala Pro Pro Glu Asp Thr Glu
        450                 455                 460
Glu Glu Arg Gly Val Thr Thr Asp Ser Pro Val Ser Glu Glu Arg Ser
465                 470                 475                 480
Val Gln Gln Ser His Pro Thr Ala Thr Thr Ser Pro Ala Arg Pro Tyr
                485                 490                 495
Pro Glu Leu Ile Ser Arg Pro Ser Pro Thr Met Arg Trp Phe Leu
                500                 505                 510
Pro Asp Leu Pro Pro Ser Arg Ser Ala Val Glu Ile Ala Pro Thr Gln
            515                 520                 525
Val Thr Glu Thr Asp Glu Cys Arg Leu Asn Gln Asn Ile Cys Gly His
        530                 535                 540
Gly Glu Cys Val Pro Gly Pro Pro Asp Tyr Ser Cys His Cys Asn Pro
545                 550                 555                 560
Gly Tyr Arg Ser His Pro Gln His Arg Tyr Cys Val Asp Val Asn Glu
                565                 570                 575
Cys Glu Ala Glu Pro Cys Gly Pro Gly Arg Gly Ile Cys Met Asn Thr
            580                 585                 590
Gly Gly Ser Tyr Asn Cys His Cys Asn Arg Gly Tyr Arg Leu His Val
            595                 600                 605
Gly Ala Gly Gly Arg Ser Cys Val Asp Leu Asn Glu Cys Ala Lys Pro
        610                 615                 620
His Leu Cys Gly Asp Gly Gly Phe Cys Ile Asn Phe Pro Gly His Tyr
625                 630                 635                 640
Lys Cys Asn Cys Tyr Pro Gly Tyr Arg Leu Lys Ala Ser Arg Pro Pro
                645                 650                 655
Val Cys Glu Asp Ile Asp Glu Cys Arg Asp Pro Ser Ser Cys Pro Asp
            660                 665                 670
Gly Lys Cys Glu Asn Lys Pro Gly Ser Phe Lys Cys Ile Ala Cys Gln
            675                 680                 685
Pro Gly Tyr Arg Ser Gln Gly Gly Gly Ala Cys Arg Asp Val Asn Glu
        690                 695                 700
Cys Ala Glu Gly Ser Pro Cys Ser Pro Gly Trp Cys Glu Asn Leu Pro
705                 710                 715                 720
```

-continued

```
Gly Ser Phe Arg Cys Thr Cys Ala Gln Gly Tyr Ala Pro Ala Pro Asp
            725                 730                 735

Gly Arg Ser Cys Val Asp Val Asp Glu Cys Glu Ala Gly Asp Val Cys
            740                 745                 750

Asp Asn Gly Ile Cys Thr Asn Thr Pro Gly Ser Phe Gln Cys Gln Cys
            755                 760                 765

Leu Ser Gly Tyr His Leu Ser Arg Asp Arg Ser His Cys Glu Asp Ile
            770                 775                 780

Asp Glu Cys Asp Phe Ala Ala Cys Ile Gly Asp Cys Ile Asn
785                 790                 795                 800

Thr Asn Gly Ser Tyr Arg Cys Leu Cys Pro Gln Gly His Arg Leu Val
            805                 810                 815

Gly Gly Arg Lys Cys Gln Asp Ile Asp Glu Cys Thr Gln Asp Pro Gly
            820                 825                 830

Leu Cys Leu Pro His Gly Ala Cys Lys Asn Leu Gln Gly Ser Tyr Val
            835                 840                 845

Cys Val Cys Asp Glu Gly Phe Thr Pro Thr Gln Asp Gln His Gly Cys
850                 855                 860

Glu Glu Val Glu Gln Pro His His Lys Lys Glu Cys Tyr Leu Asn Phe
865                 870                 875                 880

Asp Asp Thr Val Phe Cys Asp Ser Val Leu Ala Thr Asn Val Thr Gln
                885                 890                 895

Gln Glu Cys Cys Cys Ser Leu Gly Ala Gly Trp Gly Asp His Cys Glu
                900                 905                 910

Ile Tyr Pro Cys Pro Val Tyr Ser Ser Ala Glu Phe His Ser Leu Cys
            915                 920                 925

Pro Asp Gly Lys Gly Tyr Thr Gln Asp Asn Asn Ile Val Asn Tyr Gly
            930                 935                 940

Ile Pro Ala His Arg Asp Ile Asp Glu Cys Met Leu Phe Gly Ala Glu
945                 950                 955                 960

Ile Cys Lys Glu Gly Lys Cys Val Asn Thr Pro Gly Tyr Glu Cys
            965                 970                 975

Tyr Cys Lys Gln Gly Phe Tyr Tyr Asp Gly Asn Leu Leu Glu Cys Val
            980                 985                 990

Asp Val Asp Glu Cys Leu Asp Glu  Ser Asn Cys Arg Asn  Gly Val Cys
            995                1000                1005

Glu Asn  Thr Arg Gly Gly Tyr  Arg Cys Ala Cys Thr  Pro Pro Ala
           1010                1015                1020

Glu Tyr  Ser Pro Ala Gln Arg  Gln Cys Leu Ser Pro  Glu Glu Met
           1025                1030                1035

Asp Val  Asp Glu Cys Gln Asp  Pro Ala Ala Cys Arg  Pro Gly Arg
           1040                1045                1050

Cys Val  Asn Leu Pro Gly Ser  Tyr Arg Cys Glu Cys  Arg Pro Pro
           1055                1060                1065

Trp Val  Pro Gly Pro Ser Gly  Arg Asp Cys Gln Leu  Pro Glu Ser
           1070                1075                1080

Pro Ala  Glu Arg Ala Pro Glu  Arg Arg Asp Val Cys  Trp Ser Gln
           1085                1090                1095

Arg Gly  Glu Asp Gly Met Cys  Ala Gly Pro Gln Ala  Gly Pro Ala
           1100                1105                1110

Leu Thr  Phe Asp Asp Cys Cys  Cys Arg Gln Gly Arg  Gly Trp Gly
           1115                1120                1125

Ala Gln  Cys Arg Pro Cys Pro  Pro Arg Gly Ala Gly  Ser Gln Cys
```

```
                    1130                1135                1140
Pro Thr Ser Gln Ser Glu Ser Asn Ser Phe Trp Asp Thr Ser Pro
            1145                1150                1155

Leu Leu Leu Gly Lys Pro Arg Arg Asp Glu Asp Ser Ser Glu Glu
        1160                1165                1170

Asp Ser Asp Glu Cys Arg Cys Val Ser Gly Arg Cys Val Pro Arg
    1175                1180                1185

Pro Gly Gly Ala Val Cys Glu Cys Pro Gly Gly Phe Gln Leu Asp
1190                1195                1200

Ala Ser Arg Ala Arg Cys Val Asp Ile Asp Glu Cys Arg Glu Leu
        1205                1210                1215

Asn Gln Arg Gly Leu Leu Cys Lys Ser Glu Arg Cys Val Asn Thr
    1220                1225                1230

Ser Gly Ser Phe Arg Cys Val Cys Lys Ala Gly Phe Ala Arg Ser
1235                1240                1245

Arg Pro His Gly Ala Cys Val Pro Gln Arg Arg Arg
        1250                1255                1260

<210> SEQ ID NO 37
<211> LENGTH: 1228
<212> TYPE: PRT
<213> ORGANISM: Mus sp.

<400> SEQUENCE: 37

Gly Pro Ala Gly Glu Arg Gly Thr Gly Gly Gly Ala Leu Ala Arg
1               5                   10                  15

Glu Arg Phe Lys Val Val Phe Ala Pro Val Ile Cys Lys Arg Thr Cys
            20                  25                  30

Leu Lys Gly Gln Cys Arg Asp Ser Cys Gln Gln Gly Ser Asn Met Thr
        35                  40                  45

Leu Ile Gly Glu Asn Gly His Ser Thr Asp Thr Leu Thr Gly Ser Ala
    50                  55                  60

Phe Arg Val Val Val Cys Pro Leu Pro Cys Met Asn Gly Gly Gln Cys
65                  70                  75                  80

Ser Ser Arg Asn Gln Cys Leu Cys Pro Pro Asp Phe Thr Gly Arg Phe
                85                  90                  95

Cys Gln Val Pro Ala Ala Gly Thr Gly Ala Gly Thr Gly Ser Ser Gly
            100                 105                 110

Pro Gly Leu Ala Arg Thr Gly Ala Met Ser Thr Gly Pro Leu Pro Pro
        115                 120                 125

Leu Ala Pro Glu Gly Glu Ser Val Ala Ser Lys His Ala Ile Tyr Ala
    130                 135                 140

Val Gln Val Ile Ala Asp Pro Pro Gly Pro Gly Glu Gly Pro Pro Ala
145                 150                 155                 160

Gln His Ala Ala Phe Leu Val Pro Leu Gly Pro Gly Gln Ile Ser Ala
                165                 170                 175

Glu Val Gln Ala Pro Pro Pro Val Asn Val Arg Val His His Pro
            180                 185                 190

Pro Glu Ala Ser Val Gln Val His Arg Ile Glu Gly Pro Asn Ala Glu
        195                 200                 205

Gly Pro Ala Ser Ser Gln His Leu Leu Pro His Pro Lys Pro Pro His
    210                 215                 220

Pro Arg Pro Pro Thr Gln Lys Pro Leu Gly Arg Cys Phe Gln Asp Thr
225                 230                 235                 240
```

```
Leu Pro Lys Gln Pro Cys Gly Ser Asn Pro Leu Pro Gly Leu Thr Lys
            245                 250                 255

Gln Glu Asp Cys Cys Gly Ser Ile Gly Thr Ala Trp Gly Gln Ser Lys
            260                 265                 270

Cys His Lys Cys Pro Gln Leu Gln Tyr Thr Gly Val Gln Lys Pro Val
            275                 280                 285

Pro Val Arg Gly Glu Val Gly Ala Asp Cys Pro Gln Gly Tyr Lys Arg
            290                 295                 300

Leu Asn Ser Thr His Cys Gln Asp Ile Asn Glu Cys Ala Met Pro Gly
305                 310                 315                 320

Asn Val Cys His Gly Asp Cys Leu Asn Asn Pro Gly Ser Tyr Arg Cys
                325                 330                 335

Val Cys Pro Pro Gly His Ser Leu Gly Pro Leu Ala Ala Gln Cys Ile
            340                 345                 350

Ala Asp Lys Pro Glu Glu Lys Ser Leu Cys Phe Arg Leu Val Ser Thr
            355                 360                 365

Glu His Gln Cys Gln His Pro Leu Thr Thr Arg Leu Thr Arg Gln Leu
            370                 375                 380

Cys Cys Cys Ser Val Gly Lys Ala Trp Gly Ala Arg Cys Gln Arg Cys
385                 390                 395                 400

Pro Ala Asp Gly Thr Ala Ala Phe Lys Glu Ile Cys Pro Gly Lys Gly
            405                 410                 415

Tyr His Ile Leu Thr Ser His Gln Thr Leu Thr Ile Gln Gly Glu Ser
            420                 425                 430

Asp Phe Ser Leu Phe Leu His Pro Asp Gly Pro Pro Lys Pro Gln Gln
            435                 440                 445

Leu Pro Glu Ser Pro Ser Arg Ala Pro Pro Leu Glu Asp Thr Glu Glu
            450                 455                 460

Glu Arg Gly Val Thr Met Asp Pro Pro Val Ser Glu Glu Arg Ser Val
465                 470                 475                 480

Gln Gln Ser His Pro Thr Thr Thr Thr Ser Pro Pro Arg Pro Tyr Pro
            485                 490                 495

Glu Leu Ile Ser Arg Pro Ser Pro Pro Thr Phe His Arg Phe Leu Pro
            500                 505                 510

Asp Leu Pro Pro Ser Arg Ser Ala Val Glu Ile Ala Pro Thr Gln Val
            515                 520                 525

Thr Glu Thr Asp Glu Cys Arg Leu Asn Gln Asn Ile Cys Gly His Gly
            530                 535                 540

Gln Cys Val Pro Gly Pro Ser Asp Tyr Ser Cys His Cys Asn Ala Gly
545                 550                 555                 560

Tyr Arg Ser His Pro Gln His Arg Tyr Cys Val Asp Val Asn Glu Cys
            565                 570                 575

Glu Ala Glu Pro Cys Gly Pro Gly Lys Gly Ile Cys Met Asn Thr Gly
            580                 585                 590

Gly Ser Tyr Asn Cys His Cys Asn Arg Gly Tyr Arg Leu His Val Gly
            595                 600                 605

Ala Gly Gly Arg Ser Cys Val Asp Leu Asn Glu Cys Ala Lys Pro His
            610                 615                 620

Leu Cys Gly Asp Gly Gly Phe Cys Ile Asn Phe Pro Gly His Tyr Lys
625                 630                 635                 640

Cys Asn Cys Tyr Pro Gly Tyr Arg Leu Lys Ala Ser Arg Pro Pro Ile
            645                 650                 655

Cys Glu Asp Ile Asp Glu Cys Arg Asp Pro Ser Thr Cys Pro Asp Gly
```

```
                660             665             670
Lys Cys Glu Asn Lys Pro Gly Ser Phe Lys Cys Ile Ala Cys Gln Pro
            675             680             685

Gly Tyr Arg Ser Gln Gly Gly Ala Cys Arg Asp Val Asn Glu Cys
690             695             700

Ser Glu Gly Thr Pro Cys Ser Pro Gly Trp Cys Glu Asn Leu Pro Gly
705             710             715             720

Ser Tyr Arg Cys Thr Cys Ala Gln Tyr Glu Pro Ala Gln Asp Gly Leu
            725             730             735

Ser Cys Ile Asp Val Asp Glu Cys Glu Ala Gly Lys Val Cys Gln Asp
            740             745             750

Gly Ile Cys Thr Asn Thr Pro Gly Ser Phe Gln Cys Gln Cys Leu Ser
            755             760             765

Gly Tyr His Leu Ser Arg Asp Arg Ser Arg Cys Glu Asp Ile Asp Glu
            770             775             780

Cys Asp Phe Pro Ala Ala Cys Ile Gly Gly Asp Cys Ile Asn Thr Asn
785             790             795             800

Gly Ser Tyr Arg Cys Leu Cys Pro Leu Gly His Arg Leu Val Gly Gly
            805             810             815

Arg Lys Cys Lys Lys Asp Ile Asp Glu Cys Ser Gln Asp Pro Gly Leu
            820             825             830

Cys Leu Pro His Ala Cys Glu Asn Leu Gln Gly Ser Tyr Val Cys Val
            835             840             845

Cys Asp Glu Gly Phe Thr Leu Thr Gln Asp Gln His Gly Cys Glu Glu
850             855             860

Val Glu Gln Pro His His Lys Lys Glu Cys Tyr Leu Asn Phe Asp Asp
865             870             875             880

Thr Val Phe Cys Asp Ser Val Leu Ala Thr Asn Val Thr Gln Gln Glu
            885             890             895

Cys Cys Cys Ser Leu Gly Ala Gly Trp Gly Asp His Cys Glu Ile Tyr
            900             905             910

Pro Cys Pro Val Tyr Ser Ser Ala Glu Phe His Ser Leu Val Pro Asp
            915             920             925

Gly Lys Arg Leu His Ser Gly Gln Gln His Cys Glu Leu Cys Ile Pro
            930             935             940

Ala His Arg Asp Ile Asp Glu Cys Ile Leu Phe Gly Ala Glu Ile Cys
945             950             955             960

Lys Glu Gly Lys Cys Val Asn Thr Gln Pro Gly Tyr Glu Cys Tyr Cys
            965             970             975

Lys Gln Gly Phe Tyr Tyr Asp Gly Asn Leu Leu Glu Cys Val Asp Val
            980             985             990

Asp Glu Cys Leu Asp Glu Ser Asn Cys Arg Asn Gly Val Cys Glu Asn
            995             1000            1005

Thr Arg Gly Gly Tyr Arg Cys Ala Cys Thr Pro Pro Ala Glu Tyr
            1010            1015            1020

Ser Pro Ala Gln Ala Gln Cys Leu Ile Pro Glu Arg Trp Ser Thr
            1025            1030            1035

Pro Gln Arg Asp Val Lys Cys Ala Gly Ala Ser Glu Glu Arg Thr
            1040            1045            1050

Ala Cys Val Trp Gly Pro Trp Ala Gly Pro Ala Leu Thr Phe Asp
            1055            1060            1065

Asp Cys Cys Cys Arg Gln Pro Arg Leu Gly Thr Gln Cys Arg Pro
            1070            1075            1080
```

```
Cys Pro Pro Arg Gly Thr Gly Ser Gln Cys Pro Thr Ser Gln Ser
    1085                1090                1095

Glu Ser Asn Ser Phe Trp Asp Thr Ser Pro Leu Leu Leu Gly Lys
    1100                1105                1110

Ser Pro Arg Asp Glu Asp Ser Glu Glu Asp Ser Asp Glu Cys
    1115                1120                1125

Arg Cys Val Ser Gly Arg Cys Val Pro Arg Pro Gly Gly Ala Val
    1130                1135                1140

Cys Glu Cys Pro Gly Gly Phe Gln Leu Asp Ala Ser Arg Ala Arg
    1145                1150                1155

Cys Val Asp Ile Asp Glu Cys Arg Glu Leu Asn Gln Arg Gly Leu
    1160                1165                1170

Leu Cys Lys Ser Glu Arg Cys Val Asn Thr Ser Gly Ser Phe Arg
    1175                1180                1185

Cys Val Cys Lys Ala Gly Phe Thr Arg Ser Arg Pro His Gly Pro
    1190                1195                1200

Ala Cys Leu Ser Ala Ala Ala Asp Asp Ala Ala Ile Ala His Thr
    1205                1210                1215

Ser Val Ile Asp His Arg Gly Tyr Phe His
    1220                1225

<210> SEQ ID NO 38
<211> LENGTH: 645
<212> TYPE: PRT
<213> ORGANISM: Homo sapiens

<400> SEQUENCE: 38

Ala Gln His Gln Asp Lys Val Pro Cys Lys Met Val Asp Lys Lys Val
1               5                   10                  15

Ser Cys Gln Val Leu Gly Leu Leu Gln Val Pro Ser Val Leu Pro Pro
                20                  25                  30

Asp Thr Glu Thr Leu Asp Leu Ser Gly Asn Gln Leu Arg Ser Ile Leu
            35                  40                  45

Ala Ser Pro Leu Gly Phe Tyr Thr Ala Leu Arg His Leu Asp Leu Ser
    50                  55                  60

Thr Asn Glu Ile Ser Phe Leu Gln Pro Gly Ala Phe Gln Ala Leu Thr
65                  70                  75                  80

His Leu Glu His Leu Ser Leu Ala His Asn Arg Leu Ala Met Ala Thr
                85                  90                  95

Ala Leu Ser Ala Gly Gly Leu Gly Pro Leu Pro Arg Val Thr Ser Leu
                100                 105                 110

Asp Leu Ser Gly Asn Ser Leu Tyr Ser Gly Leu Leu Glu Arg Leu Leu
            115                 120                 125

Gly Glu Ala Pro Ser Leu His Thr Leu Ser Leu Ala Glu Asn Ser Leu
    130                 135                 140

Thr Arg Leu Thr Arg His Thr Phe Arg Asp Met Pro Ala Leu Glu Gln
145                 150                 155                 160

Leu Asp Leu His Ser Asn Val Leu Met Asp Ile Glu Asp Gly Ala Phe
                165                 170                 175

Glu Gly Leu Pro Arg Leu Thr His Leu Asn Leu Ser Arg Asn Ser Leu
                180                 185                 190

Thr Cys Ile Ser Asp Phe Ser Leu Gln Gln Leu Arg Val Leu Asp Leu
            195                 200                 205

Ser Cys Asn Ser Ile Glu Ala Phe Gln Thr Ala Ser Gln Pro Gln Ala
```

```
            210                 215                 220
Glu Phe Gln Leu Thr Trp Leu Asp Leu Arg Glu Asn Lys Leu Leu His
225                 230                 235                 240

Phe Pro Asp Leu Ala Ala Leu Pro Arg Leu Ile Tyr Leu Asn Leu Ser
                245                 250                 255

Asn Asn Leu Ile Arg Leu Pro Thr Gly Pro Pro Gln Asp Ser Lys Gly
                260                 265                 270

Ile His Ala Pro Ser Glu Gly Trp Ser Ala Leu Pro Leu Ser Ala Pro
                275                 280                 285

Ser Gly Asn Ala Ser Gly Arg Pro Leu Ser Gln Leu Leu Asn Leu Asp
        290                 295                 300

Leu Ser Tyr Asn Glu Ile Glu Leu Ile Pro Asp Ser Phe Leu Glu His
305                 310                 315                 320

Leu Thr Ser Leu Cys Phe Leu Asn Leu Ser Arg Asn Cys Leu Arg Thr
                325                 330                 335

Phe Glu Ala Arg Arg Leu Gly Ser Leu Pro Cys Leu Met Leu Leu Asp
                340                 345                 350

Leu Ser His Asn Ala Leu Glu Thr Leu Glu Leu Gly Ala Arg Ala Leu
                355                 360                 365

Gly Ser Leu Arg Thr Leu Leu Leu Gln Gly Asn Ala Leu Arg Asp Leu
        370                 375                 380

Pro Pro Tyr Thr Phe Ala Asn Leu Ala Ser Leu Gln Arg Leu Asn Leu
385                 390                 395                 400

Gln Gly Asn Arg Val Ser Pro Cys Gly Gly Pro Asp Glu Pro Gly Pro
                405                 410                 415

Ser Gly Cys Val Ala Phe Ser Gly Ile Thr Ser Leu Arg Ser Leu Ser
                420                 425                 430

Leu Val Asp Asn Glu Ile Glu Leu Leu Arg Ala Gly Ala Phe Leu His
                435                 440                 445

Thr Pro Leu Thr Glu Leu Asp Leu Ser Ser Asn Pro Gly Leu Glu Val
                450                 455                 460

Ala Thr Gly Ala Leu Gly Gly Leu Glu Ala Ser Leu Glu Val Leu Ala
465                 470                 475                 480

Leu Gln Gly Asn Gly Leu Met Val Leu Gln Val Asp Leu Pro Cys Phe
                485                 490                 495

Ile Cys Leu Lys Arg Leu Asn Leu Ala Glu Asn Arg Leu Ser His Leu
                500                 505                 510

Pro Ala Trp Thr Gln Ala Val Ser Leu Glu Val Leu Asp Leu Arg Asn
                515                 520                 525

Asn Ser Phe Ser Leu Leu Pro Gly Ser Ala Met Gly Gly Leu Glu Thr
        530                 535                 540

Ser Leu Arg Arg Leu Tyr Leu Gln Gly Asn Pro Leu Ser Cys Cys Gly
545                 550                 555                 560

Asn Gly Trp Leu Ala Ala Gln Leu His Gln Gly Arg Val Asp Val Asp
                565                 570                 575

Ala Thr Gln Asp Leu Ile Cys Arg Phe Ser Ser Gln Glu Glu Val Ser
                580                 585                 590

Leu Ser His Val Arg Pro Glu Asp Cys Glu Lys Gly Gly Leu Lys Asn
                595                 600                 605

Ile Asn Leu Ile Ile Ile Leu Thr Phe Ile Leu Val Ser Ala Ile Leu
                610                 615                 620

Leu Thr Thr Leu Ala Ala Cys Cys Cys Val Arg Arg Gln Lys Phe Asn
625                 630                 635                 640
```

```
Gln Gln Tyr Lys Ala
            645

<210> SEQ ID NO 39
<211> LENGTH: 610
<212> TYPE: PRT
<213> ORGANISM: Homo sapiens

<400> SEQUENCE: 39

Ala Gln His Gln Asp Lys Val Pro Cys Lys Met Val Asp Lys Lys Val
1               5                   10                  15

Ser Cys Gln Val Leu Gly Leu Leu Gln Val Pro Ser Val Leu Pro Pro
            20                  25                  30

Asp Thr Glu Thr Leu Asp Leu Ser Gly Asn Gln Leu Arg Ser Ile Leu
        35                  40                  45

Ala Ser Pro Leu Gly Phe Tyr Thr Ala Leu Arg His Leu Asp Leu Ser
    50                  55                  60

Thr Asn Glu Ile Ser Phe Leu Gln Pro Gly Ala Phe Gln Ala Leu Thr
65                  70                  75                  80

His Leu Glu His Leu Ser Leu Ala His Asn Arg Leu Ala Met Ala Thr
                85                  90                  95

Ala Leu Ser Ala Gly Gly Leu Gly Pro Leu Pro Arg Val Thr Ser Leu
            100                 105                 110

Asp Leu Ser Gly Asn Ser Leu Tyr Ser Gly Leu Leu Glu Arg Leu Leu
        115                 120                 125

Gly Glu Ala Pro Ser Leu His Thr Leu Ser Leu Ala Glu Asn Ser Leu
130                 135                 140

Thr Arg Leu Thr Arg His Thr Phe Arg Asp Met Pro Ala Leu Glu Gln
145                 150                 155                 160

Leu Asp Leu His Ser Asn Val Leu Met Asp Ile Glu Asp Gly Ala Phe
                165                 170                 175

Glu Gly Leu Pro Arg Leu Thr His Leu Asn Leu Ser Arg Asn Ser Leu
            180                 185                 190

Thr Cys Ile Ser Asp Phe Ser Leu Gln Gln Leu Arg Val Leu Asp Leu
        195                 200                 205

Ser Cys Asn Ser Ile Glu Ala Phe Gln Thr Ala Ser Gln Pro Gln Ala
    210                 215                 220

Glu Phe Gln Leu Thr Trp Leu Asp Leu Arg Glu Asn Lys Leu Leu His
225                 230                 235                 240

Phe Pro Asp Leu Ala Ala Leu Pro Arg Leu Ile Tyr Leu Asn Leu Ser
                245                 250                 255

Asn Asn Leu Ile Arg Leu Pro Thr Gly Pro Pro Gln Asp Ser Lys Gly
            260                 265                 270

Ile His Ala Pro Ser Glu Gly Trp Ser Ala Leu Pro Leu Ser Ala Pro
        275                 280                 285

Ser Gly Asn Ala Ser Gly Arg Pro Leu Ser Gln Leu Leu Asn Leu Asp
    290                 295                 300

Leu Ser Tyr Asn Glu Ile Glu Leu Ile Pro Asp Ser Phe Leu Glu His
305                 310                 315                 320

Leu Thr Ser Leu Cys Phe Leu Asn Leu Ser Arg Asn Cys Leu Arg Thr
                325                 330                 335

Phe Glu Ala Arg Arg Leu Gly Ser Leu Pro Cys Leu Met Leu Leu Asp
            340                 345                 350

Leu Ser His Asn Ala Leu Glu Thr Leu Glu Leu Gly Ala Arg Ala Leu
```

```
                355                 360                 365
Gly Ser Leu Arg Thr Leu Leu Leu Gln Gly Asn Ala Leu Arg Asp Leu
    370                 375                 380

Pro Pro Tyr Thr Phe Ala Asn Leu Ala Ser Leu Gln Arg Leu Asn Leu
385                 390                 395                 400

Gln Gly Asn Arg Val Ser Pro Cys Gly Pro Asp Glu Pro Gly Pro
                405                 410                 415

Ser Gly Cys Val Ala Phe Ser Gly Ile Thr Ser Leu Arg Ser Leu Ser
                420                 425                 430

Leu Val Asp Asn Glu Ile Glu Leu Leu Arg Ala Gly Ala Phe Leu His
                435                 440                 445

Thr Pro Leu Thr Glu Leu Asp Leu Ser Ser Asn Pro Gly Leu Glu Val
        450                 455                 460

Ala Thr Gly Ala Leu Gly Gly Leu Glu Ala Ser Leu Glu Val Leu Ala
465                 470                 475                 480

Leu Gln Gly Asn Gly Leu Met Val Leu Gln Val Asp Leu Pro Cys Phe
                485                 490                 495

Ile Cys Leu Lys Arg Leu Asn Leu Ala Glu Asn Arg Leu Ser His Leu
            500                 505                 510

Pro Ala Trp Thr Gln Ala Val Ser Leu Glu Val Leu Asp Leu Arg Asn
            515                 520                 525

Asn Ser Phe Ser Leu Leu Pro Gly Ser Ala Met Gly Gly Leu Glu Thr
    530                 535                 540

Ser Leu Arg Arg Leu Tyr Leu Gln Gly Asn Pro Leu Ser Cys Cys Gly
545                 550                 555                 560

Asn Gly Trp Leu Ala Ala Gln Leu His Gln Gly Arg Val Asp Val Asp
                565                 570                 575

Ala Thr Gln Asp Leu Ile Cys Arg Phe Ser Ser Gln Glu Glu Val Ser
            580                 585                 590

Leu Ser His Val Arg Pro Glu Asp Cys Glu Lys Gly Gly Leu Lys Asn
        595                 600                 605

Ile Asn
    610

<210> SEQ ID NO 40
<211> LENGTH: 646
<212> TYPE: PRT
<213> ORGANISM: Mus sp.

<400> SEQUENCE: 40

Ile Ser Gln Arg Arg Glu Gln Val Pro Cys Arg Thr Val Asn Lys Glu
1               5                   10                  15

Ala Leu Cys His Gly Leu Gly Leu Leu Gln Val Pro Ser Val Leu Ser
                20                  25                  30

Leu Asp Ile Gln Ala Leu Tyr Leu Ser Gly Asn Gln Leu Gln Ser Ile
            35                  40                  45

Leu Val Ser Pro Leu Gly Phe Tyr Thr Ala Leu Arg His Leu Asp Leu
        50                  55                  60

Ser Asp Asn Gln Ile Ser Phe Leu Gln Ala Gly Val Phe Gln Ala Leu
65                  70                  75                  80

Pro Tyr Leu Glu His Leu Asn Leu Ala His Asn Arg Leu Ala Thr Gly
                85                  90                  95

Met Ala Leu Asn Ser Gly Gly Leu Gly Arg Leu Pro Leu Leu Val Ser
                100                 105                 110
```

-continued

```
Leu Asp Leu Ser Gly Asn Ser Leu His Gly Asn Leu Val Glu Arg Leu
            115                 120                 125

Leu Gly Glu Thr Pro Arg Leu Arg Thr Leu Ser Leu Ala Glu Asn Ser
        130                 135                 140

Leu Thr Arg Leu Ala Arg His Thr Phe Trp Gly Met Pro Ala Val Glu
145                 150                 155                 160

Gln Leu Asp Leu His Ser Asn Val Leu Met Asp Ile Glu Asp Gly Ala
                165                 170                 175

Phe Glu Ala Leu Pro His Leu Thr His Leu Asn Leu Ser Arg Asn Ser
            180                 185                 190

Leu Thr Cys Ile Ser Asp Phe Ser Leu Gln Gln Leu Gln Val Leu Asp
        195                 200                 205

Leu Ser Cys Asn Ser Ile Glu Ala Phe Gln Thr Ala Pro Glu Pro Gln
210                 215                 220

Ala Gln Phe Gln Leu Ala Trp Leu Asp Leu Arg Glu Asn Lys Leu Leu
225                 230                 235                 240

His Phe Pro Asp Leu Ala Val Phe Pro Arg Leu Ile Tyr Leu Asn Val
                245                 250                 255

Ser Asn Asn Leu Ile Gln Leu Pro Ala Gly Leu Pro Arg Gly Ser Glu
            260                 265                 270

Asp Leu His Ala Pro Ser Glu Gly Trp Ser Ala Ser Pro Leu Ser Asn
        275                 280                 285

Pro Ser Arg Asn Ala Ser Thr His Pro Leu Ser Gln Leu Leu Asn Leu
290                 295                 300

Asp Leu Ser Tyr Asn Glu Ile Glu Leu Val Pro Ala Ser Phe Leu Glu
305                 310                 315                 320

His Leu Thr Ser Leu Arg Phe Leu Asn Leu Ser Arg Asn Cys Leu Arg
                325                 330                 335

Ser Phe Glu Ala Arg Gln Val Asp Ser Leu Pro Cys Leu Val Leu Leu
            340                 345                 350

Asp Leu Ser His Asn Val Leu Glu Ala Leu Glu Leu Gly Thr Lys Val
        355                 360                 365

Leu Gly Ser Leu Gln Thr Leu Leu Leu Gln Asp Asn Ala Leu Gln Glu
370                 375                 380

Leu Pro Pro Tyr Thr Phe Ala Ser Leu Ala Ser Leu Gln Arg Leu Asn
385                 390                 395                 400

Leu Gln Gly Asn Gln Val Ser Pro Cys Gly Gly Pro Ala Glu Pro Gly
                405                 410                 415

Pro Pro Gly Cys Val Asp Phe Ser Gly Ile Pro Thr Leu His Val Leu
            420                 425                 430

Asn Met Ala Gly Asn Ser Met Gly Met Leu Arg Ala Gly Ser Phe Leu
        435                 440                 445

His Thr Pro Leu Thr Glu Leu Asp Leu Ser Thr Asn Pro Gly Leu Asp
450                 455                 460

Val Ala Thr Gly Ala Leu Val Gly Leu Glu Ala Ser Leu Glu Val Leu
465                 470                 475                 480

Glu Leu Gln Gly Asn Gly Leu Thr Val Leu Arg Val Asp Leu Pro Cys
                485                 490                 495

Phe Leu Arg Leu Lys Arg Leu Asn Leu Ala Glu Asn Gln Leu Ser His
            500                 505                 510

Leu Pro Ala Trp Thr Arg Ala Val Ser Leu Glu Val Leu Asp Leu Arg
        515                 520                 525

Asn Asn Ser Phe Ser Leu Leu Pro Gly Asn Ala Met Gly Gly Leu Glu
```

```
            530                 535                 540
Thr Ser Leu Arg Arg Leu Tyr Leu Gln Gly Asn Pro Leu Ser Cys Cys
545                 550                 555                 560

Gly Asn Gly Trp Leu Ala Ala Gln Leu His Gln Gly Arg Val Asp Val
                565                 570                 575

Asp Ala Thr Gln Asp Leu Ile Cys Arg Phe Gly Ser Gln Glu Leu
                580                 585                 590

Ser Leu Ser Leu Val Arg Pro Glu Asp Cys Glu Lys Gly Gly Leu Lys
                595                 600                 605

Asn Val Asn Leu Ile Leu Leu Ser Phe Thr Leu Val Ser Ala Ile
                610                 615                 620

Val Leu Thr Thr Leu Ala Thr Ile Cys Phe Leu Arg Arg Gln Lys Leu
625                 630                 635                 640

Ser Gln Gln Tyr Lys Ala
                645

<210> SEQ ID NO 41
<211> LENGTH: 611
<212> TYPE: PRT
<213> ORGANISM: Mus sp.

<400> SEQUENCE: 41

Ile Ser Gln Arg Arg Glu Gln Val Pro Cys Arg Thr Val Asn Lys Glu
1               5                   10                  15

Ala Leu Cys His Gly Leu Gly Leu Leu Gln Val Pro Ser Val Leu Ser
                20                  25                  30

Leu Asp Ile Gln Ala Leu Tyr Leu Ser Gly Asn Gln Leu Gln Ser Ile
            35                  40                  45

Leu Val Ser Pro Leu Gly Phe Tyr Thr Ala Leu Arg His Leu Asp Leu
        50                  55                  60

Ser Asp Asn Gln Ile Ser Phe Leu Gln Ala Gly Val Phe Gln Ala Leu
65                  70                  75                  80

Pro Tyr Leu Glu His Leu Asn Leu Ala His Asn Arg Leu Ala Thr Gly
                85                  90                  95

Met Ala Leu Asn Ser Gly Gly Leu Gly Arg Leu Pro Leu Leu Val Ser
                100                 105                 110

Leu Asp Leu Ser Gly Asn Ser Leu His Gly Asn Leu Val Glu Arg Leu
            115                 120                 125

Leu Gly Glu Thr Pro Arg Leu Arg Thr Leu Ser Leu Ala Glu Asn Ser
        130                 135                 140

Leu Thr Arg Leu Ala Arg His Thr Phe Trp Gly Met Pro Ala Val Glu
145                 150                 155                 160

Gln Leu Asp Leu His Ser Asn Val Leu Met Asp Ile Glu Asp Gly Ala
                165                 170                 175

Phe Glu Ala Leu Pro His Leu Thr His Leu Asn Leu Ser Arg Asn Ser
                180                 185                 190

Leu Thr Cys Ile Ser Asp Phe Ser Leu Gln Gln Leu Gln Val Leu Asp
            195                 200                 205

Leu Ser Cys Asn Ser Ile Glu Ala Phe Gln Thr Ala Pro Glu Pro Gln
        210                 215                 220

Ala Gln Phe Gln Leu Ala Trp Leu Asp Leu Arg Glu Asn Lys Leu Leu
225                 230                 235                 240

His Phe Pro Asp Leu Ala Val Phe Pro Arg Leu Ile Tyr Leu Asn Val
                245                 250                 255
```

```
Ser Asn Asn Leu Ile Gln Leu Pro Ala Gly Leu Pro Arg Gly Ser Glu
            260                 265                 270

Asp Leu His Ala Pro Ser Glu Gly Trp Ser Ala Ser Pro Leu Ser Asn
        275                 280                 285

Pro Ser Arg Asn Ala Ser Thr His Pro Leu Ser Gln Leu Leu Asn Leu
    290                 295                 300

Asp Leu Ser Tyr Asn Glu Ile Glu Leu Val Pro Ala Ser Phe Leu Glu
305                 310                 315                 320

His Leu Thr Ser Leu Arg Phe Leu Asn Leu Ser Arg Asn Cys Leu Arg
                325                 330                 335

Ser Phe Glu Ala Arg Gln Val Asp Ser Leu Pro Cys Leu Val Leu Leu
            340                 345                 350

Asp Leu Ser His Asn Val Leu Glu Ala Leu Glu Leu Gly Thr Lys Val
        355                 360                 365

Leu Gly Ser Leu Gln Thr Leu Leu Leu Gln Asp Asn Ala Leu Gln Glu
    370                 375                 380

Leu Pro Pro Tyr Thr Phe Ala Ser Leu Ala Ser Leu Gln Arg Leu Asn
385                 390                 395                 400

Leu Gln Gly Asn Gln Val Ser Pro Cys Gly Gly Pro Ala Glu Pro Gly
                405                 410                 415

Pro Pro Gly Cys Val Asp Phe Ser Gly Ile Pro Thr Leu His Val Leu
            420                 425                 430

Asn Met Ala Gly Asn Ser Met Gly Met Leu Arg Ala Gly Ser Phe Leu
        435                 440                 445

His Thr Pro Leu Thr Glu Leu Asp Leu Ser Thr Asn Pro Gly Leu Asp
450                 455                 460

Val Ala Thr Gly Ala Leu Val Gly Leu Glu Ala Ser Leu Glu Val Leu
465                 470                 475                 480

Glu Leu Gln Gly Asn Gly Leu Thr Val Leu Arg Val Asp Leu Pro Cys
                485                 490                 495

Phe Leu Arg Leu Lys Arg Leu Asn Leu Ala Glu Asn Gln Leu Ser His
            500                 505                 510

Leu Pro Ala Trp Thr Arg Ala Val Ser Leu Glu Val Leu Asp Leu Arg
        515                 520                 525

Asn Asn Ser Phe Ser Leu Leu Pro Gly Asn Ala Met Gly Gly Leu Glu
    530                 535                 540

Thr Ser Leu Arg Arg Leu Tyr Leu Gln Gly Asn Pro Leu Ser Cys Cys
545                 550                 555                 560

Gly Asn Gly Trp Leu Ala Ala Gln Leu His Gln Gly Arg Val Asp Val
                565                 570                 575

Asp Ala Thr Gln Asp Leu Ile Cys Arg Phe Gly Ser Gln Glu Glu Leu
            580                 585                 590

Ser Leu Ser Leu Val Arg Pro Glu Asp Cys Glu Lys Gly Gly Leu Lys
        595                 600                 605

Asn Val Asn
    610

<210> SEQ ID NO 42
<211> LENGTH: 692
<212> TYPE: PRT
<213> ORGANISM: Homo sapiens

<400> SEQUENCE: 42

Met Glu Leu Leu Pro Leu Trp Leu Cys Leu Gly Phe His Phe Leu Thr
1               5                   10                  15
```

```
Val Gly Trp Arg Asn Arg Ser Gly Thr Ala Thr Ala Ala Ser Gln Gly
             20                  25                  30

Val Cys Lys Leu Val Gly Gly Ala Ala Asp Cys Arg Gly Gln Ser Leu
         35                  40                  45

Ala Ser Val Pro Ser Ser Leu Pro Pro His Ala Arg Met Leu Thr Leu
 50                  55                  60

Asp Ala Asn Pro Leu Lys Thr Leu Trp Asn His Ser Leu Gln Pro Tyr
 65                  70                  75                  80

Pro Leu Leu Glu Ser Leu Ser Leu His Ser Cys His Leu Glu Arg Ile
                 85                  90                  95

Ser Arg Gly Ala Phe Gln Glu Gln Gly His Leu Arg Ser Leu Val Leu
            100                 105                 110

Gly Asp Asn Cys Leu Ser Glu Asn Tyr Glu Glu Thr Ala Ala Ala Leu
        115                 120                 125

His Ala Leu Pro Gly Leu Arg Arg Leu Asp Leu Ser Gly Asn Ala Leu
130                 135                 140

Thr Glu Asp Met Ala Ala Leu Met Leu Gln Asn Leu Ser Ser Leu Arg
145                 150                 155                 160

Ser Val Ser Leu Ala Gly Asn Thr Ile Met Arg Leu Asp Asp Ser Val
                165                 170                 175

Phe Glu Gly Leu Glu Arg Leu Arg Glu Leu Asp Leu Gln Arg Asn Tyr
            180                 185                 190

Ile Phe Glu Ile Glu Gly Gly Ala Phe Asp Gly Leu Ala Glu Leu Arg
        195                 200                 205

His Leu Asn Leu Ala Phe Asn Asn Leu Pro Cys Ile Val Asp Phe Gly
210                 215                 220

Leu Thr Arg Leu Arg Val Leu Asn Val Ser Tyr Asn Val Leu Glu Trp
225                 230                 235                 240

Phe Leu Ala Thr Gly Gly Glu Ala Ala Phe Glu Leu Glu Thr Leu Asp
                245                 250                 255

Leu Ser His Asn Gln Leu Leu Phe Phe Pro Leu Leu Pro Gln Tyr Ser
            260                 265                 270

Lys Leu Arg Thr Leu Leu Leu Arg Asp Asn Asn Met Gly Phe Tyr Arg
        275                 280                 285

Asp Leu Tyr Asn Thr Ser Ser Pro Arg Glu Met Val Ala Gln Phe Leu
290                 295                 300

Leu Val Asp Gly Asn Val Thr Asn Ile Thr Thr Val Ser Leu Trp Glu
305                 310                 315                 320

Glu Phe Ser Ser Ser Asp Leu Ala Asp Leu Arg Phe Leu Asp Met Ser
                325                 330                 335

Gln Asn Gln Phe Gln Tyr Leu Pro Asp Gly Phe Leu Arg Lys Met Pro
            340                 345                 350

Ser Leu Ser His Leu Asn Leu His Gln Asn Cys Leu Met Thr Leu His
        355                 360                 365

Ile Arg Glu His Glu Pro Pro Gly Ala Leu Thr Glu Leu Asp Leu Ser
370                 375                 380

His Asn Gln Leu Ser Glu Leu His Leu Ala Pro Gly Leu Ala Ser Cys
385                 390                 395                 400

Leu Gly Ser Leu Arg Leu Phe Asn Leu Ser Ser Asn Gln Leu Leu Gly
                405                 410                 415

Val Pro Pro Gly Leu Phe Ala Asn Ala Arg Asn Ile Thr Thr Leu Asp
            420                 425                 430
```

```
Met Ser His Asn Gln Ile Ser Leu Cys Pro Leu Pro Ala Ala Ser Asp
            435                 440                 445

Arg Val Gly Pro Pro Ser Cys Val Asp Phe Arg Asn Met Ala Ser Leu
450                 455                 460

Arg Ser Leu Ser Leu Glu Gly Cys Gly Leu Gly Ala Leu Pro Asp Cys
465                 470                 475                 480

Pro Phe Gln Gly Thr Ser Leu Thr Tyr Leu Asp Leu Ser Ser Asn Trp
                485                 490                 495

Gly Val Leu Asn Gly Ser Leu Ala Pro Leu Gln Asp Val Ala Pro Met
                500                 505                 510

Leu Gln Val Leu Ser Leu Arg Asn Met Gly Leu His Ser Ser Phe Met
            515                 520                 525

Ala Leu Asp Phe Ser Gly Phe Gly Asn Leu Arg Asp Leu Asp Leu Ser
        530                 535                 540

Gly Asn Cys Leu Thr Thr Phe Pro Arg Phe Gly Ser Leu Ala Leu
545                 550                 555                 560

Glu Thr Leu Asp Leu Arg Arg Asn Ser Leu Thr Ala Leu Pro Gln Lys
                565                 570                 575

Ala Val Ser Glu Gln Leu Ser Arg Gly Leu Arg Thr Ile Tyr Leu Ser
                580                 585                 590

Gln Asn Pro Tyr Asp Cys Cys Gly Val Asp Gly Trp Gly Ala Leu Gln
            595                 600                 605

His Gly Gln Thr Val Ala Asp Trp Ala Met Val Thr Cys Asn Leu Ser
        610                 615                 620

Ser Lys Ile Ile Arg Val Thr Glu Leu Pro Gly Gly Val Pro Arg Asp
625                 630                 635                 640

Cys Lys Trp Glu Arg Leu Asp Leu Gly Leu Leu Tyr Leu Val Leu Ile
                645                 650                 655

Leu Pro Ser Cys Leu Thr Leu Leu Val Ala Cys Thr Val Ile Val Leu
            660                 665                 670

Thr Phe Lys Lys Pro Leu Leu Gln Val Ile Lys Ser Arg Cys His Trp
        675                 680                 685

Ser Ser Val Tyr
    690

<210> SEQ ID NO 43
<211> LENGTH: 660
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Met Asp Met Arg Val Pro Ala Gln Leu Leu Gly Leu Leu Leu Leu Trp
1               5                   10                  15

Phe Ser Gly Val Leu Gly Trp Arg Asn Arg Ser Gly Thr Ala Thr Ala
                20                  25                  30

Ala Ser Gln Gly Val Cys Lys Leu Val Gly Gly Ala Ala Asp Cys Arg
            35                  40                  45

Gly Gln Ser Leu Ala Ser Val Pro Ser Ser Leu Pro Pro His Ala Arg
        50                  55                  60

Met Leu Thr Leu Asp Ala Asn Pro Leu Lys Thr Leu Trp Asn His Ser
65                  70                  75                  80

Leu Gln Pro Tyr Pro Leu Leu Glu Ser Leu Ser Leu His Ser Cys His
```

```
                      85                  90                  95
Leu Glu Arg Ile Ser Arg Gly Ala Phe Gln Glu Gln Gly His Leu Arg
                100                 105                 110

Ser Leu Val Leu Gly Asp Asn Cys Leu Ser Glu Asn Tyr Glu Glu Thr
            115                 120                 125

Ala Ala Ala Leu His Ala Leu Pro Gly Leu Arg Arg Leu Asp Leu Ser
        130                 135                 140

Gly Asn Ala Leu Thr Glu Asp Met Ala Ala Leu Met Leu Gln Asn Leu
145                 150                 155                 160

Ser Ser Leu Arg Ser Val Ser Leu Ala Gly Asn Thr Ile Met Arg Leu
                165                 170                 175

Asp Asp Ser Val Phe Glu Gly Leu Glu Arg Leu Arg Glu Leu Asp Leu
            180                 185                 190

Gln Arg Asn Tyr Ile Phe Glu Ile Glu Gly Ala Phe Asp Gly Leu
        195                 200                 205

Ala Glu Leu Arg His Leu Asn Leu Ala Phe Asn Asn Leu Pro Cys Ile
        210                 215                 220

Val Asp Phe Gly Leu Thr Arg Leu Arg Val Leu Asn Val Ser Tyr Asn
225                 230                 235                 240

Val Leu Glu Trp Phe Leu Ala Thr Gly Gly Glu Ala Ala Phe Glu Leu
                245                 250                 255

Glu Thr Leu Asp Leu Ser His Asn Gln Leu Leu Phe Phe Pro Leu Leu
            260                 265                 270

Pro Gln Tyr Ser Lys Leu Arg Thr Leu Leu Leu Arg Asp Asn Asn Met
        275                 280                 285

Gly Phe Tyr Arg Asp Leu Tyr Asn Thr Ser Ser Pro Arg Glu Met Val
        290                 295                 300

Ala Gln Phe Leu Leu Val Asp Gly Asn Val Thr Asn Ile Thr Thr Val
305                 310                 315                 320

Ser Leu Trp Glu Glu Phe Ser Ser Ser Asp Leu Ala Asp Leu Arg Phe
                325                 330                 335

Leu Asp Met Ser Gln Asn Gln Phe Gln Tyr Leu Pro Asp Gly Phe Leu
            340                 345                 350

Arg Lys Met Pro Ser Leu Ser His Leu Asn Leu His Gln Asn Cys Leu
        355                 360                 365

Met Thr Leu His Ile Arg Glu His Glu Pro Pro Gly Ala Leu Thr Glu
        370                 375                 380

Leu Asp Leu Ser His Asn Gln Leu Ser Glu Leu His Leu Ala Pro Gly
385                 390                 395                 400

Leu Ala Ser Cys Leu Gly Ser Leu Arg Leu Phe Asn Leu Ser Ser Asn
                405                 410                 415

Gln Leu Leu Gly Val Pro Pro Gly Leu Phe Ala Asn Ala Arg Asn Ile
            420                 425                 430

Thr Thr Leu Asp Met Ser His Asn Gln Ile Ser Leu Cys Pro Leu Pro
        435                 440                 445

Ala Ala Ser Asp Arg Val Gly Pro Pro Ser Cys Val Asp Phe Arg Asn
        450                 455                 460

Met Ala Ser Leu Arg Ser Leu Ser Leu Glu Gly Cys Gly Leu Gly Ala
465                 470                 475                 480

Leu Pro Asp Cys Pro Phe Gln Gly Thr Ser Leu Thr Tyr Leu Asp Leu
                485                 490                 495

Ser Ser Asn Trp Gly Val Leu Asn Gly Ser Leu Ala Pro Leu Gln Asp
            500                 505                 510
```

```
Val Ala Pro Met Leu Gln Val Leu Ser Leu Arg Asn Met Gly Leu His
            515                 520                 525

Ser Ser Phe Met Ala Leu Asp Phe Ser Gly Phe Gly Asn Leu Arg Asp
    530                 535                 540

Leu Asp Leu Ser Gly Asn Cys Leu Thr Thr Phe Pro Arg Phe Gly Gly
545                 550                 555                 560

Ser Leu Ala Leu Glu Thr Leu Asp Leu Arg Arg Asn Ser Leu Thr Ala
                565                 570                 575

Leu Pro Gln Lys Ala Val Ser Glu Gln Leu Ser Arg Gly Leu Arg Thr
                580                 585                 590

Ile Tyr Leu Ser Gln Asn Pro Tyr Asp Cys Cys Gly Val Asp Gly Trp
            595                 600                 605

Gly Ala Leu Gln His Gly Gln Thr Val Ala Asp Trp Ala Met Val Thr
            610                 615                 620

Cys Asn Leu Ser Ser Lys Ile Ile Arg Val Thr Glu Leu Pro Gly Gly
625                 630                 635                 640

Val Pro Arg Asp Cys Lys Trp Glu Arg Leu Asp Leu Gly Leu His His
                645                 650                 655

His His His His
        660

<210> SEQ ID NO 44
<211> LENGTH: 689
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Met Asp Met Arg Val Pro Ala Gln Leu Leu Gly Leu Leu Leu Leu Trp
1               5                  10                  15

Phe Ser Gly Val Leu Gly Trp Arg Asn Arg Ser Gly Thr Ala Thr Ala
            20                  25                  30

Ala Ser Gln Gly Val Cys Lys Leu Val Gly Gly Ala Ala Asp Cys Arg
        35                  40                  45

Gly Gln Ser Leu Ala Ser Val Pro Ser Ser Leu Pro Pro His Ala Arg
    50                  55                  60

Met Leu Thr Leu Asp Ala Asn Pro Leu Lys Thr Leu Trp Asn His Ser
65                  70                  75                  80

Leu Gln Pro Tyr Pro Leu Leu Glu Ser Leu Ser Leu His Ser Cys His
                85                  90                  95

Leu Glu Arg Ile Ser Arg Gly Ala Phe Gln Glu Gln Gly His Leu Arg
            100                 105                 110

Ser Leu Val Leu Gly Asp Asn Cys Leu Ser Glu Asn Tyr Glu Glu Thr
        115                 120                 125

Ala Ala Ala Leu His Ala Leu Pro Gly Leu Arg Arg Leu Asp Leu Ser
    130                 135                 140

Gly Asn Ala Leu Thr Glu Asp Met Ala Ala Leu Met Leu Gln Asn Leu
145                 150                 155                 160

Ser Ser Leu Arg Ser Val Ser Leu Ala Gly Asn Thr Ile Met Arg Leu
                165                 170                 175

Asp Asp Ser Val Phe Glu Gly Leu Glu Arg Leu Arg Glu Leu Asp Leu
            180                 185                 190
```

-continued

```
Gln Arg Asn Tyr Ile Phe Glu Ile Glu Gly Gly Ala Phe Asp Gly Leu
        195                 200                 205

Ala Glu Leu Arg His Leu Asn Leu Ala Phe Asn Asn Leu Pro Cys Ile
210                 215                 220

Val Asp Phe Gly Leu Thr Arg Leu Arg Val Leu Asn Val Ser Tyr Asn
225                 230                 235                 240

Val Leu Glu Trp Phe Leu Ala Thr Gly Gly Glu Ala Ala Phe Glu Leu
                245                 250                 255

Glu Thr Leu Asp Leu Ser His Asn Gln Leu Leu Phe Phe Pro Leu Leu
                260                 265                 270

Pro Gln Tyr Ser Lys Leu Arg Thr Leu Leu Leu Arg Asp Asn Asn Met
            275                 280                 285

Gly Phe Tyr Arg Asp Leu Tyr Asn Thr Ser Ser Pro Arg Glu Met Val
290                 295                 300

Ala Gln Phe Leu Leu Val Asp Gly Asn Val Thr Asn Ile Thr Thr Val
305                 310                 315                 320

Ser Leu Trp Glu Glu Phe Ser Ser Ser Asp Leu Ala Asp Leu Arg Phe
                325                 330                 335

Leu Asp Met Ser Gln Asn Gln Phe Gln Tyr Leu Pro Asp Gly Phe Leu
                340                 345                 350

Arg Lys Met Pro Ser Leu Ser His Leu Asn Leu His Gln Asn Cys Leu
            355                 360                 365

Met Thr Leu His Ile Arg Glu His Glu Pro Pro Gly Ala Leu Thr Glu
370                 375                 380

Leu Asp Leu Ser His Asn Gln Leu Ser Glu Leu His Leu Ala Pro Gly
385                 390                 395                 400

Leu Ala Ser Cys Leu Gly Ser Leu Arg Leu Phe Asn Leu Ser Ser Asn
                405                 410                 415

Gln Leu Leu Gly Val Pro Pro Gly Leu Phe Ala Asn Ala Arg Asn Ile
                420                 425                 430

Thr Thr Leu Asp Met Ser His Asn Gln Ile Ser Leu Cys Pro Leu Pro
            435                 440                 445

Ala Ala Ser Asp Arg Val Gly Pro Pro Ser Cys Val Asp Phe Arg Asn
450                 455                 460

Met Ala Ser Leu Arg Ser Leu Ser Leu Glu Gly Cys Gly Leu Gly Ala
465                 470                 475                 480

Leu Pro Asp Cys Pro Phe Gln Gly Thr Ser Leu Thr Tyr Leu Asp Leu
                485                 490                 495

Ser Ser Asn Trp Gly Val Leu Asn Gly Ser Leu Ala Pro Leu Gln Asp
            500                 505                 510

Val Ala Pro Met Leu Gln Val Leu Ser Leu Arg Asn Met Gly Leu His
            515                 520                 525

Ser Ser Phe Met Ala Leu Asp Phe Ser Gly Phe Gly Asn Leu Arg Asp
530                 535                 540

Leu Asp Leu Ser Gly Asn Cys Leu Thr Thr Phe Pro Arg Phe Gly Gly
545                 550                 555                 560

Ser Leu Ala Leu Glu Thr Leu Asp Leu Arg Arg Asn Ser Leu Thr Ala
                565                 570                 575

Leu Pro Gln Lys Ala Val Ser Glu Gln Leu Ser Arg Gly Leu Arg Thr
            580                 585                 590

Ile Tyr Leu Ser Gln Asn Pro Tyr Asp Cys Cys Gly Val Asp Gly Trp
            595                 600                 605

Gly Ala Leu Gln His Gly Gln Thr Val Ala Asp Trp Ala Met Val Thr
```

```
        610                 615                 620
Cys Asn Leu Ser Ser Lys Ile Ile Arg Val Thr Glu Leu Pro Gly Gly
625                 630                 635                 640

Val Pro Arg Asp Cys Lys Trp Glu Arg Leu Asp Leu Gly Leu Leu Ile
                645                 650                 655

Ile Ile Leu Thr Phe Ile Leu Val Ser Ala Ile Leu Leu Thr Thr Leu
            660                 665                 670

Ala Ala Cys Cys Cys Val Arg Arg Gln Lys Phe Asn Gln Gln Tyr Lys
        675                 680                 685

Ala
```

```
<210> SEQ ID NO 45
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Cys Pro Pro Cys Pro
1               5

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52

<400> SEQUENCE: 52

000
```

-continued

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

-continued

```
<400> SEQUENCE: 74

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asn Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Asp Tyr Tyr Tyr Gly Met Asp Val Trp Gly Gln Gly
            100                 105                 110

Thr Leu Val Thr Val Ser Ser
        115

<210> SEQ ID NO 75
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Gln Ser Gly Leu Thr Gln Pro Ala Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Ala Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Tyr Val Phe Gly Thr Gly Thr Lys Leu Thr Val Leu
            100                 105                 110

<210> SEQ ID NO 76
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 76

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45
```

Gly Glu Ile Ile His Ser Gly Ser Thr Asn Tyr Asn Pro Ser Leu Lys
            50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Arg Gly Val Gly Leu Gly Arg Phe Asp Pro Trp Gly Gln Gly Thr Leu
            100                 105                 110

Val Thr Val Ser Ser
            115

<210> SEQ ID NO 77
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Gln Ser Glu Leu Thr Gln Ser Pro Ser Ala Ser Gly Thr Pro Gly Gln
1               5                   10                  15

Arg Val Thr Ile Ser Cys Ser Gly Ser Asn Ser Asn Ile Gly Thr Asn
            20                  25                  30

Thr Val Asn Trp Tyr Gln Gln Phe Pro Gly Thr Ala Pro Lys Leu Leu
        35                  40                  45

Ile Tyr Tyr Asn Asp Gln Arg Pro Ser Gly Val Ser Asp Arg Phe Ser
 50                  55                  60

Gly Ser Arg Ser Gly Thr Ser Ala Ser Leu Ala Ile Asn Gly Leu Gln
 65                  70                  75                  80

Ser Glu Asp Glu Ala Asp Tyr Tyr Cys Ala Thr Trp Asp Asp Ser Leu
                85                  90                  95

Ser Gly Val Val Phe Gly Gly Gly Thr Lys Leu Thr Val Leu
            100                 105                 110

<210> SEQ ID NO 78
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

```
Arg Gly Val Gly Leu Gly Arg Phe Asp Pro Trp Gly Gln Gly Thr Leu
                100                 105                 110

Val Thr Val Ser Ser
        115

<210> SEQ ID NO 79
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Gln Ser Glu Leu Thr Gln Ser Pro Ser Ala Ser Gly Thr Pro Gly Gln
1               5                   10                  15

Arg Val Thr Ile Ser Cys Ser Gly Ser Asn Ser Asn Ile Gly Thr Asn
            20                  25                  30

Thr Val Asn Trp Tyr Gln Gln Phe Pro Gly Thr Ala Pro Lys Leu Leu
        35                  40                  45

Ile Tyr Tyr Asn Asp Gln Arg Pro Ser Gly Val Ser Asp Arg Phe Ser
50                  55                  60

Gly Ser Arg Ser Gly Thr Ser Ala Ser Leu Ala Ile Asn Gly Leu Gln
65                  70                  75                  80

Ser Glu Asp Glu Ala Asp Tyr Tyr Cys Ala Thr Trp Asp Asp Ser Leu
                85                  90                  95

Ser Gly Val Val Phe Gly Gly Gly Thr Lys Leu Thr Val Leu
            100                 105                 110

<210> SEQ ID NO 80
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Gln Val Gln Leu Gln Gln Ser Gly Pro Gly Leu Val Arg Pro Ser Gln
1               5                   10                  15

Thr Leu Ser Leu Thr Cys Ala Ile Ser Gly Asp Ser Val Ser Ser Asn
            20                  25                  30

Gly Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
50                  55                  60

Val Ser Val Lys Ser Arg Ile Thr Ile Asn Pro Asp Thr Ser Lys Asn
65                  70                  75                  80

Gln Phe Ser Leu Lys Leu Thr Ser Val Thr Pro Glu Asp Thr Ala Val
                85                  90                  95

Tyr Tyr Cys Ala Arg Gly Glu Asp Trp Gly Tyr Ala Phe Asp Ile Trp
            100                 105                 110

Gly Gln Gly Thr Leu Val Thr Val Ser Ser
        115                 120

<210> SEQ ID NO 81
<211> LENGTH: 110
<212> TYPE: PRT
```

<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Asp Asp Lys Gln Arg Pro Ser Gly Ile Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn Val Val Phe Gly Gly Gly Thr Lys Val Thr Val Leu
            100                 105                 110

<210> SEQ ID NO 82
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asp Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Asn Pro Tyr Tyr Tyr Met Asp Val Trp Gly Gln Gly Thr
            100                 105                 110

Thr Val Thr Val Ser Ser
        115

<210> SEQ ID NO 83
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

Gln Ser Glu Leu Thr Gln Ala Pro Ser Val Ser Val Ala Pro Gly Gln
1               5                   10                  15

```
Thr Ala Arg Ile Thr Cys Gly Gly Asn Asn Ile Gly Gly Arg Ser Lys
            20                  25                  30

Ser Val His Trp Tyr Gln His Lys Leu Gly Gln Ala Pro Val Leu Ile
            35                  40                  45

Val Tyr Asp Asn Thr Asp Arg Pro Ser Gly Ile Ser Glu Arg Phe Ser
 50                  55                  60

Gly Ser Ser Ser Val Asn Ala Ala Thr Leu Thr Ile Thr Thr Ala Glu
 65                  70                  75                  80

Ala Gly Asp Glu Gly Asp Tyr Tyr Cys Gln Val Trp Asp Val Ser Thr
                85                  90                  95

Asp His Val Val Phe Gly Gly Gly Thr Lys Val Thr Val Leu
            100                 105                 110

<210> SEQ ID NO 84
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Gln Val Gln Leu Val Glu Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
            35                  40                  45

Gly Trp Ile Asn Pro Asn Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                85                  90                  95

Ala Asn Arg Arg Arg Gly Ser Ala Phe Asp Ile Trp Gly Gln Gly Thr
            100                 105                 110

Leu Val Thr Val Ser Ser
        115

<210> SEQ ID NO 85
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Asn Phe Met Leu Thr Gln Pro His Ser Val Ser Glu Ser Pro Gly Lys
 1               5                  10                  15

Thr Val Thr Ile Ser Cys Thr Gly Ser Ser Gly Ser Ile Ala Ser Asn
            20                  25                  30

Tyr Val Gln Trp Tyr Gln Gln Arg Pro Gly Ser Ser Pro Thr Thr Val
            35                  40                  45

Ile Tyr Glu Asp Asn Gln Arg Pro Ser Gly Val Pro Asp Arg Phe Ser
 50                  55                  60
```

Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Asp
                 85                  90                  95

Asn Tyr His Val Ile Phe Gly Gly Gly Thr Lys Leu Thr Val Leu
            100                 105                 110

<210> SEQ ID NO 86
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

Gln Val Gln Leu Val Glu Ser Gly Gly Ala Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Thr Gly Tyr Gly Phe Gly Leu Phe Trp Gly Gln Gly Thr
            100                 105                 110

Met Val Thr Val Ser Ser
            115

<210> SEQ ID NO 87
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

Asn Phe Met Leu Thr Gln Pro His Ser Val Ser Glu Ser Pro Gly Arg
 1               5                  10                  15

Thr Leu Thr Ile Pro Cys Phe Arg Ser Ser Gly Asn Ile Gly Asp Ser
             20                  25                  30

Tyr Val His Trp Tyr Gln Gln Arg Pro Gly Ser Ala Pro Thr Thr Val
         35                  40                  45

Ile Tyr Arg Asp Ser Gln Arg Pro Ser Gly Val Pro Asp Arg Phe Ser
     50                  55                  60

Gly Ser Ile Asp Phe Ser Ser Asn Ser Ala Ser Leu Thr Ile Ser Gly
 65                  70                  75                  80

Leu Lys Thr Glu Asp Glu Ala Ala Tyr Tyr Cys Gln Ser Tyr Asp Arg
                 85                  90                  95

Ser Asn Gln Trp Val Phe Gly Gly Gly Thr Lys Leu Thr Val Leu
            100                 105                 110

-continued

```
<210> SEQ ID NO 88
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88

Gln Leu Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Asn Asn Tyr
            20                  25                  30

Pro Ile His Trp Val Arg Gln Ala Pro Gly Lys Gly Leu Glu Trp Val
        35                  40                  45

Ala Val Met Ser Tyr Asp Gly Ile Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Arg Ile Ala Ala Arg Arg Gly Gly Phe Asp Tyr Trp Gly
            100                 105                 110

Gln Gly Thr Leu Val Thr Val Ser Ser
        115                 120

<210> SEQ ID NO 89
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 89

Asn Phe Met Leu Thr Gln Pro His Ser Val Ser Glu Ser Pro Gly Lys
1               5                   10                  15

Thr Val Thr Ile Ser Cys Thr Arg Ser Ser Gly Asn Ile Asp Asn Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asp Asn Gln Gly Val Val Phe Gly Gly Gly Thr Lys Leu Thr Val Leu
            100                 105                 110

<210> SEQ ID NO 90
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 90
```

```
Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asp Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Gly Leu Arg Ser Asp Asp Thr Ala Val Tyr Tyr Cys
                85                  90                  95

Ala Arg Ala Pro Leu Gly Asn Phe Asp Ser Trp Gly Gln Gly Thr Leu
            100                 105                 110

Val Thr Val Ser Ser
            115
```

<210> SEQ ID NO 91
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 91

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn His Val Val Phe Gly Gly Gly Thr Lys Val Thr Val Leu
            100                 105                 110
```

<210> SEQ ID NO 92
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 92

```
Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Pro Asn Tyr
            20                  25                  30

Ala Met Ser Trp Val Arg Gln Ala Pro Gly Lys Gly Leu Glu Trp Val
        35                  40                  45
```

```
Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Leu Glu Gly Gly Tyr Tyr Trp Asp Tyr Tyr Tyr Gly
            100                 105                 110

Met Asp Val Trp Gly Gln Gly Thr Leu Val Thr Val Ser Ser
            115                 120                 125

<210> SEQ ID NO 93
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 93

Asn Phe Met Leu Thr Gln Pro His Ser Val Ser Glu Ser Pro Gly Lys
 1               5                  10                  15

Thr Val Thr Ile Ser Cys Thr Arg Ser Ser Gly Ser Ile Ala Ser Asn
                20                  25                  30

Tyr Val Gln Trp Tyr Gln Gln Arg Pro Gly Ser Ser Pro Thr Thr Val
             35                  40                  45

Ile Tyr Glu Asp Asn Gln Arg Pro Ser Gly Val Pro Asp Arg Phe Ser
 50                  55                  60

Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                 85                  90                  95

Ser Ile Val Val Phe Gly Gly Gly Thr Gln Leu Thr Val Leu
            100                 105                 110

<210> SEQ ID NO 94
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Phe Thr Phe Asn Asn Tyr Pro Ile His
 1               5

<210> SEQ ID NO 95
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Val Met Ser Tyr Asp Gly Ile Asn Lys Tyr Tyr Ala Asp Ser Val Lys
 1               5                  10                  15

Gly
```

```
<210> SEQ ID NO 96
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Ala Arg Pro Arg Ile Ala Ala Arg Arg Gly Gly Phe Asp Tyr
1               5                   10

<210> SEQ ID NO 97
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Thr Arg Ser Ser Gly Asn Ile Asp Asn Asn Tyr Val Gln
1               5                   10

<210> SEQ ID NO 98
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Glu Asp Asn Gln Arg Pro Ser
1               5

<210> SEQ ID NO 99
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Gln Ser Tyr Asp Ser Asp Asn Gln Gly Val Val
1               5                   10

<210> SEQ ID NO 100
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Gly Ser Ile Ser Ser Ser Ser Tyr Tyr Trp Gly
1               5                   10

<210> SEQ ID NO 101
<211> LENGTH: 10
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Ser Ile Ser Tyr Ser Gly Ser Thr Tyr Tyr
1               5                   10

<210> SEQ ID NO 102
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Ala Arg Asp Pro Ser Tyr Asp Ser Ile Ala Gly Met Asp Val
1               5                   10

<210> SEQ ID NO 103
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Arg Ala Ser Gln Ser Ile Ser Ser Tyr Leu Asn
1               5                   10

<210> SEQ ID NO 104
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Ala Ala Ser Asn Leu Gln Ser
1               5

<210> SEQ ID NO 105
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Gln Gln Ser Phe Asp Phe Pro Phe Thr
1               5

<210> SEQ ID NO 106
<211> LENGTH: 122
<212> TYPE: PRT
<213> ORGANISM: Artificial Sequence
<220> FEATURE:
<221> NAME/KEY: source
```

<223> OTHER INFORMATION: /note="Description of Artificial Sequence:
    Synthetic polypeptide"

<400> SEQUENCE: 106

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Ser Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Pro Ser Tyr Asp Ser Ile Ala Gly Met Asp Val Trp
            100                 105                 110

Gly Gln Gly Thr Thr Val Thr Val Ser Ser
        115                 120

<210> SEQ ID NO 107
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 107

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Asp Phe Pro Phe
                85                  90                  95

Thr Phe Gly Gly Gly Thr Lys Val Glu Ile Lys
            100                 105

<210> SEQ ID NO 108
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 108

Phe Thr Phe Arg Ser Tyr Val Met His
1               5

<210> SEQ ID NO 109

```
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Val Ile Ser His Glu Gly Ser Leu Lys Tyr Tyr Ala Asp Ser Val Lys
1               5                   10                  15
Gly

<210> SEQ ID NO 110
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

Ala Val Pro Arg Ile Ala Ala Arg Arg Gly Gly Phe Gly Tyr
1               5                   10

<210> SEQ ID NO 111
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 111

Thr Arg Ser Ser Gly Asn Ile Asp Asn Asn Tyr Val Gln
1               5                   10

<210> SEQ ID NO 112
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Glu Asp Asn Gln Arg Pro Ser
1               5

<210> SEQ ID NO 113
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 113

Gln Ser Tyr Asp Ser Asp Asn Gln Gly Val Val
1               5                   10

<210> SEQ ID NO 114
<211> LENGTH: 121
<212> TYPE: PRT
```

<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 114

```
Gln Val Gln Leu Val Glu Ser Gly Gly Val Val Gln Pro Gly Arg
1               5                  10                  15

Ser Leu Arg Leu Ser Cys Ala Ala Ser Gly Phe Thr Phe Arg Ser Tyr
            20                  25                  30

Val Met His Trp Val Arg Gln Ala Pro Gly Lys Gly Leu Glu Trp Val
        35                  40                  45

Ala Val Ile Ser His Glu Gly Ser Leu Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Val Pro Arg Ile Ala Ala Arg Arg Gly Gly Phe Gly Tyr Trp Gly
            100                 105                 110

Gln Gly Thr Leu Val Thr Val Ser Ser
        115                 120
```

<210> SEQ ID NO 115
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 115

```
Asn Phe Met Leu Thr Gln Pro His Ser Val Ser Glu Ser Pro Gly Lys
1               5                  10                  15

Thr Val Thr Ile Ser Cys Thr Arg Ser Ser Gly Asn Ile Asp Asn Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asp Asn Gln Gly Val Val Phe Gly Gly Gly Thr Lys Leu Thr Val Leu
            100                 105                 110
```

<210> SEQ ID NO 116
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

```
Phe Thr Phe Arg Ser Tyr Val Met His
1               5
```

```
<210> SEQ ID NO 117
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

Val Ile Ser His Glu Gly Ser Leu Lys Tyr Tyr Ala Asp Ser Val Lys
1               5                   10                  15

Gly

<210> SEQ ID NO 118
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Ala Arg Pro Arg Ile Ala Ala Arg Arg Gly Gly Phe Gly Tyr
1               5                   10

<210> SEQ ID NO 119
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119

Thr Arg Ser Ser Gly Asn Ile Asp Asn Asn Tyr Val Gln
1               5                   10

<210> SEQ ID NO 120
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 120

Glu Asp Asn Gln Arg Pro Ser
1               5

<210> SEQ ID NO 121
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Gln Ser Tyr Asp Ser Asp Asn Gln Gly Val Val
1               5                   10
```

-continued

<210> SEQ ID NO 122
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 122

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
                20                  25                  30

Val Met His Trp Val Arg Gln Ala Pro Gly Lys Gly Leu Glu Trp Val
            35                  40                  45

Ala Val Ile Ser His Glu Gly Ser Leu Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Arg Ile Ala Ala Arg Arg Gly Gly Phe Gly Tyr Trp Gly
            100                 105                 110

Gln Gly Thr Leu Val Thr Val Ser Ser
        115                 120

<210> SEQ ID NO 123
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 123

Asn Phe Met Leu Thr Gln Pro His Ser Val Ser Glu Ser Pro Gly Lys
1               5                   10                  15

Thr Val Thr Ile Ser Cys Thr Arg Ser Ser Gly Asn Ile Asp Asn Asn
                20                  25                  30

Tyr Val Gln Trp Tyr Gln Gln Arg Pro Gly Ser Ser Pro Thr Thr Val
            35                  40                  45

Ile Tyr Glu Asp Asn Gln Arg Pro Ser Gly Val Pro Asp Arg Phe Ser
        50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asp Asn Gln Gly Val Val Phe Gly Gly Gly Thr Lys Leu Thr Val Leu
            100                 105                 110

<210> SEQ ID NO 124
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 124

```
Phe Thr Phe Arg Ser Tyr Val Met His
1               5
```

<210> SEQ ID NO 125
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

```
Val Ile Ser His Glu Gly Ser Leu Lys Tyr Tyr Ala Asp Ser Val Lys
1               5                   10                  15

Gly
```

<210> SEQ ID NO 126
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 126

```
Ala Val Pro Arg Ile Ala Ala Arg Arg Gly Gly Phe Gly Tyr
1               5                   10
```

<210> SEQ ID NO 127
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 127

```
Thr Arg Ser Ser Gly Asn Ile Asp Asn Asn Tyr Val Gln
1               5                   10
```

<210> SEQ ID NO 128
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 128

```
Glu Asp Asn Gln Arg Pro Ser
1               5
```

<210> SEQ ID NO 129
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 129

```
Gln Ser Tyr Asp Phe Asn Asn Gln Gly Val Val
```

```
1               5                    10
```

<210> SEQ ID NO 130
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 130

```
Phe Thr Phe Arg Ser Tyr Val Met His
1               5
```

<210> SEQ ID NO 131
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 131

```
Val Ile Ser His Glu Gly Ser Leu Lys Tyr Tyr Ala Asp Ser Val Lys
1               5                   10                  15
Gly
```

<210> SEQ ID NO 132
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 132

```
Ala Val Pro Arg Ile Ala Ala Arg Arg Gly Gly Phe Gly Tyr
1               5                   10
```

<210> SEQ ID NO 133
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 133

```
Thr Arg Ser Ser Gly Asn Ile Asp Asn Asn Tyr Val Gln
1               5                   10
```

<210> SEQ ID NO 134
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 134

```
Glu Asp Asn Gln Arg Pro Ser
1               5
```

```
<210> SEQ ID NO 135
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 135

Gln Ser Tyr Asp Tyr Asp Ala Gln Gly Val Val
1               5                   10

<210> SEQ ID NO 136
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 136

Phe Thr Phe Arg Ser Tyr Val Met His
1               5

<210> SEQ ID NO 137
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 137

Val Ile Ser His Glu Gly Ser Leu Lys Tyr Tyr Ala Asp Ser Val Lys
1               5                   10                  15
Gly

<210> SEQ ID NO 138
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 138

Ala Val Pro Arg Ile Ala Ala Arg Arg Gly Gly Phe Gly Tyr
1               5                   10

<210> SEQ ID NO 139
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 139

Thr Arg Ser Ser Gly Leu Ile Asp Asp Asn Tyr Val Gln
1               5                   10

<210> SEQ ID NO 140
```

<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 140

Glu Asp Asn Gln Arg Pro Ser
1               5

<210> SEQ ID NO 141
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 141

Gln Ser Tyr Asp Ser Asp Leu Gln Arg Val Val
1               5                   10

<210> SEQ ID NO 142
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 142

Phe Thr Phe Arg Ser Tyr Val Met His
1               5

<210> SEQ ID NO 143
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 143

Val Ile Ser His Glu Gly Ser Leu Lys Tyr Tyr Ala Asp Ser Val Lys
1               5                   10                  15

Gly

<210> SEQ ID NO 144
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 144

Ala Val Pro Arg Ile Ala Ala Arg Arg Gly Gly Phe Gly Tyr
1               5                   10

<210> SEQ ID NO 145
<211> LENGTH: 13
<212> TYPE: PRT

<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 145

Thr Arg Ser Ser Gly Ser Ile Asp Asn Asn Tyr Val Gln
1               5                   10

<210> SEQ ID NO 146
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 146

Glu Asp Phe Ile Arg Pro Ser
1               5

<210> SEQ ID NO 147
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 147

Gln Ser Tyr Asp Asp Asp Leu Gln Gly Val Val
1               5                   10

<210> SEQ ID NO 148
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 148

Phe Thr Phe Arg Ser Tyr Val Met His
1               5

<210> SEQ ID NO 149
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 149

Val Ile Ser His Glu Gly Ser Leu Lys Tyr Tyr Ala Asp Ser Val Lys
1               5                   10                  15

Gly

<210> SEQ ID NO 150
<211> LENGTH: 14
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 150

Ala Val Pro Arg Ile Ala Ala Arg Arg Gly Gly Phe Gly Tyr
1               5                   10

<210> SEQ ID NO 151
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 151

Thr Arg Ser Ser Gly Leu Ile Asp Asp Asn Tyr Val Gln
1               5                   10

<210> SEQ ID NO 152
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 152

Glu Asp Ala Gln Arg Pro Ser
1               5

<210> SEQ ID NO 153
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 153

Gln Ser Tyr Asp His Asp Glu Gln Gly Val Val
1               5                   10

<210> SEQ ID NO 154
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 154

Phe Thr Phe Arg Ser Tyr Val Met His
1               5

<210> SEQ ID NO 155
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 155

Val Ile Ser His Glu Gly Ser Leu Lys Tyr Tyr Ala Asp Ser Val Lys
1               5                   10                  15
Gly

<210> SEQ ID NO 156
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 156

Ala Arg Pro Arg Ile Ala Ala Arg Arg Gly Gly Phe Gly Tyr
1               5                   10

<210> SEQ ID NO 157
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 157

Thr Arg Ser Ser Gly Asn Ile Asp Asn Asn Tyr Val Gln
1               5                   10

<210> SEQ ID NO 158
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 158

Glu Asp Asn Gln Arg Pro Ser
1               5

<210> SEQ ID NO 159
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 159

Gln Ser Tyr Asp Tyr Ser Asn Gln Gly Val Val
1               5                   10

<210> SEQ ID NO 160
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 160

```
Phe Thr Phe Arg Ser Tyr Val Met His
1               5

<210> SEQ ID NO 161
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 161

Val Ile Ser His Glu Gly Ser Leu Lys Tyr Tyr Ala Asp Ser Val Lys
1               5                   10                  15

Gly

<210> SEQ ID NO 162
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 162

Ala Arg Pro Arg Ile Ala Ala Arg Arg Gly Gly Phe Gly Tyr
1               5                   10

<210> SEQ ID NO 163
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 163

Thr Arg Ser Ser Gly Asn Ile Asp Asn Asn Tyr Val Gln
1               5                   10

<210> SEQ ID NO 164
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 164

Glu Asp Asn Gln Arg Pro Ser
1               5

<210> SEQ ID NO 165
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 165

Gln Ser Tyr Asp Tyr Asp Asn Gln Ala Val Val
1               5                   10
```

```
<210> SEQ ID NO 166
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 166

Phe Thr Phe Arg Ser Tyr Val Met His
1               5

<210> SEQ ID NO 167
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 167

Val Ile Ser His Glu Gly Ser Leu Lys Tyr Tyr Ala Asp Ser Val Lys
1               5                   10                  15
Gly

<210> SEQ ID NO 168
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 168

Ala Arg Pro Arg Ile Ala Ala Arg Arg Gly Gly Phe Gly Tyr
1               5                   10

<210> SEQ ID NO 169
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 169

Thr Arg Ser Ser Gly Asn Ile Asp Asn Asn Tyr Val Gln
1               5                   10

<210> SEQ ID NO 170
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 170

Glu Asp Asn Gln Arg Pro Ser
1               5
```

```
<210> SEQ ID NO 171
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 171

Gln Ser Tyr Asp Tyr Asp Thr Gln Gly Val Val
1               5                   10

<210> SEQ ID NO 172
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 172

Phe Thr Phe Arg Ser Tyr Val Met His
1               5

<210> SEQ ID NO 173
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 173

Val Ile Ser His Glu Gly Ser Leu Lys Tyr Tyr Ala Asp Ser Val Lys
1               5                   10                  15

Gly

<210> SEQ ID NO 174
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 174

Ala Arg Pro Arg Ile Ala Ala Arg Arg Gly Gly Phe Gly Tyr
1               5                   10

<210> SEQ ID NO 175
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 175

Thr Arg Ser Ser Gly Asn Ile Asp Tyr Asn Tyr Val Gln
1               5                   10

<210> SEQ ID NO 176
<211> LENGTH: 7
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 176

Glu Asp Asn Val Arg Pro Ser
1               5

<210> SEQ ID NO 177
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 177

Gln Ser Tyr Asp Ser Asp Asn Gln Arg Val Val
1               5                   10

<210> SEQ ID NO 178
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 178

Phe Thr Phe Arg Ser Tyr Val Met His
1               5

<210> SEQ ID NO 179
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 179

Val Ile Ser His Glu Gly Ser Leu Lys Tyr Tyr Ala Asp Ser Val Lys
1               5                   10                  15

Gly

<210> SEQ ID NO 180
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 180

Ala Arg Pro Arg Ile Ala Ala Arg Arg Gly Gly Phe Gly Tyr
1               5                   10

<210> SEQ ID NO 181
<211> LENGTH: 13
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 181

Thr Arg Ser His Gly Asn Ile Asp Asp Asn Tyr Val Gln
1               5                   10

<210> SEQ ID NO 182
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 182

Glu Asp Asn Val Arg Pro Ser
1               5

<210> SEQ ID NO 183
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 183

Gln Ser Tyr Asp Ser Asp Asn Gln Leu Val Val
1               5                   10

<210> SEQ ID NO 184
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 184

Phe Thr Phe Arg Ser Tyr Val Met His
1               5

<210> SEQ ID NO 185
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 185

Val Ile Ser His Glu Gly Ser Leu Lys Tyr Tyr Ala Asp Ser Val Lys
1               5                   10                  15

Gly

<210> SEQ ID NO 186
<211> LENGTH: 14
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 186

Ala Arg Pro Arg Ile Ala Ala Arg Arg Gly Gly Phe Gly Tyr
1               5                   10

<210> SEQ ID NO 187
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 187

Thr Arg Ser Ser Gly Ala Ile Asp Asp Asn Tyr Val Gln
1               5                   10

<210> SEQ ID NO 188
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 188

Glu Asp Phe Gln Arg Pro Ser
1               5

<210> SEQ ID NO 189
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 189

Gln Ser Tyr Asp Asp Asp Leu Gln Gly Val Val
1               5                   10

<210> SEQ ID NO 190
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 190

Phe Thr Phe Arg Ser Tyr Val Met His
1               5

<210> SEQ ID NO 191
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 191
```

```
Val Ile Ser His Glu Gly Ser Gly Lys Tyr Tyr Ala Asp Ser Val Lys
1               5                   10                  15

Gly

<210> SEQ ID NO 192
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 192

Ala Arg Pro Arg Ile Ala Ala Arg Arg Gly Gly Phe Gly Ser
1               5                   10

<210> SEQ ID NO 193
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 193

Thr Arg Ser Ser Gly Asn Ile Asp Tyr Asn Tyr Val Gln
1               5                   10

<210> SEQ ID NO 194
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 194

Glu Asp Asn Val Arg Pro Ser
1               5

<210> SEQ ID NO 195
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 195

Gln Ser Tyr Asp Ser Asp Asn Gln Arg Val Val
1               5                   10

<210> SEQ ID NO 196
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 196

Phe Thr Phe Arg Ser Tyr Val Met His
```

<210> SEQ ID NO 197
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 197

Val Ile Ser His Glu Gly Ser Gly Lys Tyr Tyr Ala Asp Ser Val Lys
1               5                   10                  15
Gly

<210> SEQ ID NO 198
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 198

Ala Arg Pro Arg Ile Ala Ala Arg Arg Gly Gly Phe Gly Ser
1               5                   10

<210> SEQ ID NO 199
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 199

Thr Arg Ser Ser Gly Asn Ile Asp Tyr Asn Tyr Val Gln
1               5                   10

<210> SEQ ID NO 200
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 200

Glu Asp Asn Val Arg Pro Ser
1               5

<210> SEQ ID NO 201
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 201

Gln Ser Tyr Asp Tyr Asp Asn Gln Ala Val Val
1               5                   10

```
<210> SEQ ID NO 202
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 202

Phe Thr Phe Arg Ser Tyr Val Met His
1               5

<210> SEQ ID NO 203
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 203

Val Ile Ser His Glu Gly Ser Gly Lys Tyr Tyr Ala Asp Ser Val Lys
1               5                   10                  15

Gly

<210> SEQ ID NO 204
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 204

Ala Arg Pro Arg Ile Ala Ala Arg Arg Gly Gly Phe Gly Ser
1               5                   10

<210> SEQ ID NO 205
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 205

Thr Arg Ser Ser Gly Asn Ile Asp Tyr Asn Tyr Val Gln
1               5                   10

<210> SEQ ID NO 206
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 206

Glu Asp Asn Val Arg Pro Ser
1               5

<210> SEQ ID NO 207
```

-continued

```
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 207

Gln Ser Tyr Asp Tyr Asp Thr Gln Gly Val Val
1               5                   10

<210> SEQ ID NO 208
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 208

Phe Thr Phe Arg Ser Tyr Val Met His
1               5

<210> SEQ ID NO 209
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 209

Val Ile Ser His Glu Gly Ser Gly Lys Tyr Tyr Ala Asp Ser Val Lys
1               5                   10                  15

Gly

<210> SEQ ID NO 210
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 210

Ala Arg Pro Arg Ile Ala Ala Arg Arg Gly Gly Phe Gly Ser
1               5                   10

<210> SEQ ID NO 211
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 211

Thr Arg Ser Ser Gly Asn Ile Asp Tyr Asn Tyr Val Gln
1               5                   10

<210> SEQ ID NO 212
<211> LENGTH: 7
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 212

Glu Asp Asn Val Arg Pro Ser
1               5

<210> SEQ ID NO 213
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 213

Gln Gly Tyr Asp Trp Asp Thr Gln Gly Val Val
1               5                   10

<210> SEQ ID NO 214
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 214

Phe Thr Phe Arg Ser Tyr Val Met His
1               5

<210> SEQ ID NO 215
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 215

Val Ile Ser His Glu Gly Ser Gly Lys Tyr Tyr Ala Asp Ser Val Lys
1               5                   10                  15
Gly

<210> SEQ ID NO 216
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 216

Ala Arg Pro Arg Ile Ala Ala Arg Arg Gly Gly Phe Gly Thr
1               5                   10

<210> SEQ ID NO 217
<211> LENGTH: 13
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 217

Thr Arg Ser Ser Gly Asn Ile Asp Tyr Asn Tyr Val Gln
1               5                   10

<210> SEQ ID NO 218
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 218

Glu Asp Asn Val Arg Pro Ser
1               5

<210> SEQ ID NO 219
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 219

Gln Ser Tyr Asp Ser Asp Asn Gln Arg Val Val
1               5                   10

<210> SEQ ID NO 220
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 220

Phe Thr Phe Arg Ser Tyr Val Met His
1               5

<210> SEQ ID NO 221
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 221

Val Ile Ser His Glu Gly Ser Gly Lys Tyr Tyr Ala Asp Ser Val Lys
1               5                   10                  15

Gly

<210> SEQ ID NO 222
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
```

```
              Synthetic peptide"

<400> SEQUENCE: 222

Ala Arg Pro Arg Ile Ala Ala Arg Arg Gly Gly Phe Gly Thr
1               5                   10

<210> SEQ ID NO 223
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 223

Thr Arg Ser Ser Gly Asn Ile Asp Tyr Asn Tyr Val Gln
1               5                   10

<210> SEQ ID NO 224
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 224

Glu Asp Asn Val Arg Pro Ser
1               5

<210> SEQ ID NO 225
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 225

Gln Ser Tyr Asp Tyr Asp Asn Gln Ala Val Val
1               5                   10

<210> SEQ ID NO 226
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 226

Phe Thr Phe Arg Ser Tyr Val Met His
1               5

<210> SEQ ID NO 227
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 227
```

Val Ile Ser His Glu Gly Ser Gly Lys Tyr Tyr Ala Asp Ser Val Lys
1               5                   10                  15

Gly

<210> SEQ ID NO 228
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 228

Ala Arg Pro Arg Ile Ala Ala Arg Arg Gly Gly Phe Gly Thr
1               5                   10

<210> SEQ ID NO 229
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 229

Thr Arg Ser Ser Gly Asn Ile Asp Tyr Asn Tyr Val Gln
1               5                   10

<210> SEQ ID NO 230
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 230

Glu Asp Asn Val Arg Pro Ser
1               5

<210> SEQ ID NO 231
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 231

Gln Ser Tyr Asp Tyr Asp Thr Gln Gly Val Val
1               5                   10

<210> SEQ ID NO 232
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 232

Phe Thr Phe Arg Ser Tyr Val Met His
1               5

<210> SEQ ID NO 233
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 233

Val Ile Ser His Glu Gly Ser Gly Lys Tyr Tyr Ala Asp Ser Val Lys
1               5                   10                  15
Gly

<210> SEQ ID NO 234
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 234

Ala Arg Pro Arg Ile Ala Ala Arg Arg Gly Gly Phe Gly Thr
1               5                   10

<210> SEQ ID NO 235
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 235

Thr Arg Ser Ser Gly Asn Ile Asp Tyr Asn Tyr Val Gln
1               5                   10

<210> SEQ ID NO 236
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 236

Glu Asp Asn Val Arg Pro Ser
1               5

<210> SEQ ID NO 237
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 237

Gln Gly Tyr Asp Trp Asp Thr Gln Gly Val Val
1               5                   10

```
<210> SEQ ID NO 238
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 238

Phe Thr Phe Arg Ser Tyr Val Met His
1               5

<210> SEQ ID NO 239
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 239

Val Ile Ser His Glu Gly Ser Gly Lys Tyr Tyr Ala Asp Ser Val Lys
1               5                   10                  15

Gly

<210> SEQ ID NO 240
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 240

Ala Leu Pro Arg Ile Ala Ala Arg Arg Gly Gly Phe Gly Ser
1               5                   10

<210> SEQ ID NO 241
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 241

Thr Arg Ser Ser Gly Asn Ile Asp Tyr Asn Tyr Val Gln
1               5                   10

<210> SEQ ID NO 242
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 242

Glu Asp Asn Val Arg Pro Ser
1               5

<210> SEQ ID NO 243
<211> LENGTH: 11
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 243

Gln Ser Tyr Asp Ser Asp Asn Gln Arg Val Val
1               5                   10

<210> SEQ ID NO 244
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 244

Phe Thr Phe Arg Ser Tyr Val Met His
1               5

<210> SEQ ID NO 245
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 245

Val Ile Ser His Glu Gly Ser Gly Lys Tyr Tyr Ala Asp Ser Val Lys
1               5                   10                  15

Gly

<210> SEQ ID NO 246
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 246

Ala Leu Pro Arg Ile Ala Ala Arg Arg Gly Gly Phe Gly Ser
1               5                   10

<210> SEQ ID NO 247
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 247

Thr Arg Ser Ser Gly Asn Ile Asp Tyr Asn Tyr Val Gln
1               5                   10

<210> SEQ ID NO 248
<211> LENGTH: 7
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 248

Glu Asp Asn Val Arg Pro Ser
1               5

<210> SEQ ID NO 249
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 249

Gln Ser Tyr Asp Tyr Asp Asn Gln Ala Val Val
1               5                   10

<210> SEQ ID NO 250
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 250

Phe Thr Phe Arg Ser Tyr Val Met His
1               5

<210> SEQ ID NO 251
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 251

Val Ile Ser His Glu Gly Ser Gly Lys Tyr Tyr Ala Asp Ser Val Lys
1               5                   10                  15

Gly

<210> SEQ ID NO 252
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 252

Ala Leu Pro Arg Ile Ala Ala Arg Arg Gly Gly Phe Gly Ser
1               5                   10

<210> SEQ ID NO 253
<211> LENGTH: 13
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 253

Thr Arg Ser Ser Gly Asn Ile Asp Tyr Asn Tyr Val Gln
1               5                   10

<210> SEQ ID NO 254
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 254

Glu Asp Asn Val Arg Pro Ser
1               5

<210> SEQ ID NO 255
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 255

Gln Ser Tyr Asp Tyr Asp Thr Gln Gly Val Val
1               5                   10

<210> SEQ ID NO 256
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 256

Phe Thr Phe Arg Ser Tyr Val Met His
1               5

<210> SEQ ID NO 257
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 257

Val Ile Ser His Glu Gly Ser Gly Lys Tyr Tyr Ala Asp Ser Val Lys
1               5                   10                  15

Gly

<210> SEQ ID NO 258
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 258

Ala Leu Pro Arg Ile Ala Ala Arg Arg Gly Gly Phe Gly Ser
1               5                   10

<210> SEQ ID NO 259
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 259

Thr Arg Ser Ser Gly Asn Ile Asp Tyr Asn Tyr Val Gln
1               5                   10

<210> SEQ ID NO 260
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 260

Glu Asp Asn Val Arg Pro Ser
1               5

<210> SEQ ID NO 261
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 261

Gln Gly Tyr Asp Trp Asp Thr Gln Gly Val Val
1               5                   10

<210> SEQ ID NO 262
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 262

Phe Thr Phe Arg Ser Tyr Val Met His
1               5

<210> SEQ ID NO 263
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 263

Val Ile Ser His Glu Gly Ser Gly Lys Tyr Tyr Ala Asp Ser Val Lys
1               5                   10                  15
```

-continued

```
1               5                   10                  15

Gly

<210> SEQ ID NO 264
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 264

Ala Leu Pro Arg Ile Ala Ala Arg Arg Gly Gly Phe Gly Thr
1               5                   10

<210> SEQ ID NO 265
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 265

Thr Arg Ser Ser Gly Asn Ile Asp Tyr Asn Tyr Val Gln
1               5                   10

<210> SEQ ID NO 266
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 266

Glu Asp Asn Val Arg Pro Ser
1               5

<210> SEQ ID NO 267
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 267

Gln Ser Tyr Asp Ser Asp Asn Gln Arg Val Val
1               5                   10

<210> SEQ ID NO 268
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 268

Phe Thr Phe Arg Ser Tyr Val Met His
1               5
```

```
<210> SEQ ID NO 269
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 269

Val Ile Ser His Glu Gly Ser Gly Lys Tyr Tyr Ala Asp Ser Val Lys
1               5                   10                  15

Gly

<210> SEQ ID NO 270
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 270

Ala Leu Pro Arg Ile Ala Ala Arg Arg Gly Gly Phe Gly Thr
1               5                   10

<210> SEQ ID NO 271
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 271

Thr Arg Ser Ser Gly Asn Ile Asp Tyr Asn Tyr Val Gln
1               5                   10

<210> SEQ ID NO 272
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 272

Glu Asp Asn Val Arg Pro Ser
1               5

<210> SEQ ID NO 273
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 273

Gln Ser Tyr Asp Tyr Asp Asn Gln Ala Val Val
1               5                   10

<210> SEQ ID NO 274
```

```
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 274

Phe Thr Phe Arg Ser Tyr Val Met His
1               5

<210> SEQ ID NO 275
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 275

Val Ile Ser His Glu Gly Ser Gly Lys Tyr Tyr Ala Asp Ser Val Lys
1               5                   10                  15

Gly

<210> SEQ ID NO 276
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 276

Ala Leu Pro Arg Ile Ala Ala Arg Arg Gly Gly Phe Gly Thr
1               5                   10

<210> SEQ ID NO 277
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 277

Thr Arg Ser Ser Gly Asn Ile Asp Tyr Asn Tyr Val Gln
1               5                   10

<210> SEQ ID NO 278
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 278

Glu Asp Asn Val Arg Pro Ser
1               5

<210> SEQ ID NO 279
<211> LENGTH: 11
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 279

Gln Ser Tyr Asp Tyr Asp Thr Gln Gly Val Val
1               5                   10

<210> SEQ ID NO 280
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 280

Phe Thr Phe Arg Ser Tyr Val Met His
1               5

<210> SEQ ID NO 281
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 281

Val Ile Ser His Glu Gly Ser Gly Lys Tyr Tyr Ala Asp Ser Val Lys
1               5                   10                  15

Gly

<210> SEQ ID NO 282
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 282

Ala Leu Pro Arg Ile Ala Ala Arg Arg Gly Gly Phe Gly Thr
1               5                   10

<210> SEQ ID NO 283
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 283

Thr Arg Ser Ser Gly Asn Ile Asp Tyr Asn Tyr Val Gln
1               5                   10

<210> SEQ ID NO 284
<211> LENGTH: 7
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 284

Glu Asp Asn Val Arg Pro Ser
1               5

<210> SEQ ID NO 285
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 285

Gln Gly Tyr Asp Trp Asp Thr Gln Gly Val Val
1               5                   10

<210> SEQ ID NO 286
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 286

Gly Ser Ile Arg Ser Ser Ser Tyr Tyr Trp Gly
1               5                   10

<210> SEQ ID NO 287
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 287

Ser Ile Ser Tyr Ser Ala Thr Thr Tyr Tyr
1               5                   10

<210> SEQ ID NO 288
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 288

Ala Ser Asp Pro Ser Tyr Asp Ser Ala Ala Gly Met Asp Val
1               5                   10

<210> SEQ ID NO 289
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 289

Arg Ala Ser Lys Val Ile Ser Ser Tyr Leu Asn
1               5                   10

<210> SEQ ID NO 290
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 290

Tyr Ala Ser Ser Leu Gln Ser
1               5

<210> SEQ ID NO 291
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 291

Gln Gln Ser Asn Asp Trp Pro Phe Thr
1               5

<210> SEQ ID NO 292
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 292

Gly Ser Ile Arg Ser Ser Ser Tyr Tyr Trp Gly
1               5                   10

<210> SEQ ID NO 293
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 293

Ser Ile Ser Tyr Ser Ala Thr Thr Tyr Tyr
1               5                   10

<210> SEQ ID NO 294
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 294

Ala Gly Asp Pro Ser Tyr Asp Ser Ile Ala Gly Met Gln Val
1               5                   10
```

<210> SEQ ID NO 295
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 295

Arg Ala Ser Gln Ser Ile Ser Ser Tyr Leu Asn
1               5                   10

<210> SEQ ID NO 296
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 296

Ala Ala Ser Asn Leu Gln Ser
1               5

<210> SEQ ID NO 297
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 297

Gln Gln Ser Phe Asp Trp Pro Leu Thr
1               5

<210> SEQ ID NO 298
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 298

Gly Ser Ile Arg Ser Ser Ser Tyr Tyr Trp Gly
1               5                   10

<210> SEQ ID NO 299
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 299

Ser Ile Ser Tyr Ser Ala Thr Thr Tyr Tyr
1               5                   10

<210> SEQ ID NO 300
<211> LENGTH: 14

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 300

Ala Gly Asp Pro Ser Tyr Asp Ser Ile Ala Gly Met Gln Val
1               5                   10

<210> SEQ ID NO 301
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 301

Arg Ala Ser Gln Ser Ile Ser Tyr Tyr Leu Asn
1               5                   10

<210> SEQ ID NO 302
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 302

Ser Ala Ser Ser Arg Gln Ser
1               5

<210> SEQ ID NO 303
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 303

Gln Gln Gly Phe Asp Phe Pro Leu Thr
1               5

<210> SEQ ID NO 304
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 304

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Val Met His Trp Val Arg Gln Ala Pro Gly Lys Gly Leu Glu Trp Val
        35                  40                  45

Ala Val Ile Ser His Glu Gly Ser Leu Lys Tyr Tyr Ala Asp Ser Val
```

```
                   50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Val Pro Arg Ile Ala Ala Arg Arg Gly Gly Phe Gly Tyr Trp Gly
                    100                 105                 110

Gln Gly Thr Leu Val Thr Val Ser Ser
                    115                 120

<210> SEQ ID NO 305
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 305

Asn Phe Met Leu Thr Gln Pro His Ser Val Ser Glu Ser Pro Gly Lys
 1               5                  10                  15

Thr Val Thr Ile Ser Cys Thr Arg Ser Ser Gly Asn Ile Asp Asn Asn
                20                  25                  30

Tyr Val Gln Trp Tyr Gln Gln Arg Pro Gly Ser Ser Pro Thr Thr Val
            35                  40                  45

Ile Tyr Glu Asp Asn Gln Arg Pro Ser Gly Val Pro Asp Arg Phe Ser
        50                  55                  60

Gly Ser Ile Asp Ser Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Phe
                     85                  90                  95

Asn Asn Gln Gly Val Val Phe Gly Gly Gly Thr Lys Leu Thr Val Leu
                    100                 105                 110

<210> SEQ ID NO 306
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 306

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Arg Ser Tyr
                20                  25                  30

Val Met His Trp Val Arg Gln Ala Pro Gly Lys Gly Leu Glu Trp Val
            35                  40                  45

Ala Val Ile Ser His Glu Gly Ser Leu Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Val Pro Arg Ile Ala Ala Arg Arg Gly Gly Phe Gly Tyr Trp Gly
                    100                 105                 110
```

```
Gln Gly Thr Leu Val Thr Val Ser Ser
        115                 120
```

<210> SEQ ID NO 307
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 307

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Asn Ile Asp Asn Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Tyr
                85                  90                  95

Asp Ala Gln Gly Val Val Phe Gly Gly Gly Thr Lys Leu Thr Val Leu
            100                 105                 110
```

<210> SEQ ID NO 308
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 308

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Val Met His Trp Val Arg Gln Ala Pro Gly Lys Gly Leu Glu Trp Val
        35                  40                  45

Ala Val Ile Ser His Glu Gly Ser Leu Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Val Pro Arg Ile Ala Ala Arg Arg Gly Gly Phe Gly Tyr Trp Gly
            100                 105                 110

Gln Gly Thr Leu Val Thr Val Ser Ser
        115                 120
```

<210> SEQ ID NO 309
<211> LENGTH: 112
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic polypeptide"

<400> SEQUENCE: 309

Asn Phe Met Leu Thr Gln Pro His Ser Val Ser Glu Ser Pro Gly Lys
1               5                   10                  15

Thr Val Thr Ile Ser Cys Thr Arg Ser Ser Gly Leu Ile Asp Asp Asn
            20                  25                  30

Tyr Val Gln Trp Tyr Gln Arg Pro Gly Ser Ser Pro Thr Thr Val
        35                  40                  45

Ile Tyr Glu Asp Asn Gln Arg Pro Ser Gly Val Pro Asp Arg Phe Ser
50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asp Leu Gln Arg Val Val Phe Gly Gly Gly Thr Lys Leu Thr Val Leu
            100                 105                 110

<210> SEQ ID NO 310
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 310

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Val Met His Trp Val Arg Gln Ala Pro Gly Lys Gly Leu Glu Trp Val
        35                  40                  45

Ala Val Ile Ser His Glu Gly Ser Leu Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Val Pro Arg Ile Ala Ala Arg Gly Gly Phe Gly Tyr Trp Gly
            100                 105                 110

Gln Gly Thr Leu Val Thr Val Ser Ser
        115                 120

<210> SEQ ID NO 311
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 311

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Asp Asn Asn

```
            20                  25                  30

Tyr Val Gln Trp Tyr Gln Gln Arg Pro Gly Ser Ser Pro Thr Thr Val
            35                  40                  45

Ile Tyr Glu Asp Phe Ile Arg Pro Ser Gly Val Pro Asp Arg Phe Ser
50                      55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Asp
                85                  90                  95

Asp Leu Gln Gly Val Val Phe Gly Gly Gly Thr Lys Leu Thr Val Leu
                100                 105                 110

<210> SEQ ID NO 312
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 312

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Val Met His Trp Val Arg Gln Ala Pro Gly Lys Gly Leu Glu Trp Val
            35                  40                  45

Ala Val Ile Ser His Glu Gly Ser Leu Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Val Pro Arg Ile Ala Ala Arg Arg Gly Gly Phe Gly Tyr Trp Gly
                100                 105                 110

Gln Gly Thr Leu Val Thr Val Ser Ser
            115                 120

<210> SEQ ID NO 313
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 313

Asn Phe Met Leu Thr Gln Pro His Ser Val Ser Glu Ser Pro Gly Lys
1               5                   10                  15

Thr Val Thr Ile Ser Cys Thr Arg Ser Ser Gly Leu Ile Asp Asp Asn
            20                  25                  30

Tyr Val Gln Trp Tyr Gln Gln Arg Pro Gly Ser Ser Pro Thr Thr Val
            35                  40                  45

Ile Tyr Glu Asp Ala Gln Arg Pro Ser Gly Val Pro Asp Arg Phe Ser
        50                  55                  60

Gly Ser Ile Asp Ser Ser Ser Asn Ser Ala Ser Leu Thr Ile Ser Gly
65                  70                  75                  80
```

Leu Lys Thr Glu Asp Glu Ala Asp Tyr Tyr Cys Gln Ser Tyr Asp His
                85                  90                  95

Asp Glu Gln Gly Val Val Phe Gly Gly Gly Thr Lys Leu Thr Val Leu
            100                 105                 110

<210> SEQ ID NO 314
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 314

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Val Met His Trp Val Arg Gln Ala Pro Gly Lys Gly Leu Glu Trp Val
        35                  40                  45

Ala Val Ile Ser His Glu Gly Ser Leu Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Arg Ile Ala Ala Arg Arg Gly Gly Phe Gly Tyr Trp Gly
            100                 105                 110

Gln Gly Thr Leu Val Thr Val Ser Ser
        115                 120

<210> SEQ ID NO 315
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 315

Asn Phe Met Leu Thr Gln Pro His Ser Val Ser Glu Ser Pro Gly Lys
1               5                   10                  15

Thr Val Thr Ile Ser Cys Thr Arg Ser Ser Gly Asn Ile Asp Asn Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Tyr
                85                  90                  95

Ser Asn Gln Gly Val Val Phe Gly Gly Gly Thr Lys Leu Thr Val Leu
            100                 105                 110

<210> SEQ ID NO 316
<211> LENGTH: 121

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 316

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Val Met His Trp Val Arg Gln Ala Pro Gly Lys Gly Leu Glu Trp Val
        35                  40                  45

Ala Val Ile Ser His Glu Gly Ser Leu Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Arg Ile Ala Ala Arg Arg Gly Gly Phe Gly Tyr Trp Gly
            100                 105                 110

Gln Gly Thr Leu Val Thr Val Ser Ser
        115                 120

<210> SEQ ID NO 317
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 317

Asn Phe Met Leu Thr Gln Pro His Ser Val Ser Glu Ser Pro Gly Lys
1               5                   10                  15

Thr Val Thr Ile Ser Cys Thr Arg Ser Ser Gly Asn Ile Asp Asn Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Tyr
                85                  90                  95

Asp Asn Gln Ala Val Val Phe Gly Gly Gly Thr Lys Leu Thr Val Leu
            100                 105                 110

<210> SEQ ID NO 318
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 318

Gln Val Gln Leu Val Glu Ser Gly Gly Gly Val Val Gln Pro Gly Arg

```
                1               5                   10                  15
Ser Leu Arg Leu Ser Cys Ala Ala Ser Gly Phe Thr Phe Arg Ser Tyr
                    20                  25                  30

Val Met His Trp Val Arg Gln Ala Pro Gly Lys Gly Leu Glu Trp Val
            35                  40                  45

Ala Val Ile Ser His Glu Gly Ser Leu Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Arg Pro Arg Ile Ala Ala Arg Arg Gly Gly Phe Gly Tyr Trp Gly
                100                 105                 110

Gln Gly Thr Leu Val Thr Val Ser Ser
                115                 120
```

<210> SEQ ID NO 319
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 319

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Asn Ile Asp Asn Asn
                20                  25                  30

Tyr Val Gln Trp Tyr Gln Gln Arg Pro Gly Ser Ser Pro Thr Thr Val
            35                  40                  45

Ile Tyr Glu Asp Asn Gln Arg Pro Ser Gly Val Pro Asp Arg Phe Ser
        50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Tyr
                85                  90                  95

Asp Thr Gln Gly Val Val Phe Gly Gly Gly Thr Lys Leu Thr Val Leu
                100                 105                 110
```

<210> SEQ ID NO 320
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 320

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
                    20                  25                  30

Val Met His Trp Val Arg Gln Ala Pro Gly Lys Gly Leu Glu Trp Val
            35                  40                  45

Ala Val Ile Ser His Glu Gly Ser Leu Lys Tyr Tyr Ala Asp Ser Val
        50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Pro Arg Ile Ala Ala Arg Gly Gly Phe Tyr Trp Gly
            100                 105                 110

Gln Gly Thr Leu Val Thr Val Ser Ser
        115                 120
```

<210> SEQ ID NO 321
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 321

```
Asn Phe Met Leu Thr Gln Pro His Ser Val Ser Glu Ser Pro Gly Lys
  1               5                  10                  15

Thr Val Thr Ile Ser Cys Thr Arg Ser Ser Gly Asn Ile Asp Tyr Asn
             20                  25                  30

Tyr Val Gln Trp Tyr Gln Gln Arg Pro Gly Ser Ser Pro Thr Thr Val
         35                  40                  45

Ile Tyr Glu Asp Asn Val Arg Pro Ser Gly Val Pro Asp Arg Phe Ser
     50                  55                  60

Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                 85                  90                  95

Asp Asn Gln Arg Val Val Phe Gly Gly Gly Thr Lys Leu Thr Val Leu
            100                 105                 110
```

<210> SEQ ID NO 322
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 322

```
Gln Val Gln Leu Val Glu Ser Gly Gly Val Val Gln Pro Gly Arg
  1               5                  10                  15

Ser Leu Arg Leu Ser Cys Ala Ala Ser Gly Phe Thr Phe Arg Ser Tyr
             20                  25                  30

Val Met His Trp Val Arg Gln Ala Pro Gly Lys Gly Leu Glu Trp Val
         35                  40                  45

Ala Val Ile Ser His Glu Gly Ser Leu Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Pro Arg Ile Ala Ala Arg Gly Gly Phe Tyr Trp Gly
            100                 105                 110
```

```
Gln Gly Thr Leu Val Thr Val Ser Ser
        115                 120
```

<210> SEQ ID NO 323
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 323

```
Asn Phe Met Leu Thr Gln Pro His Ser Val Ser Glu Ser Pro Gly Lys
1               5                   10                  15

Thr Val Thr Ile Ser Cys Thr Arg Ser His Gly Asn Ile Asp Asp Asn
            20                  25                  30

Tyr Val Gln Trp Tyr Gln Gln Arg Pro Gly Ser Ser Pro Thr Thr Val
        35                  40                  45

Ile Tyr Glu Asp Asn Val Arg Pro Ser Gly Val Pro Asp Arg Phe Ser
    50                  55                  60

Gly Ser Ile Asp Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asp Asn Gln Leu Val Val Phe Gly Gly Gly Thr Lys Leu Thr Val Leu
                100                 105                 110
```

<210> SEQ ID NO 324
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 324

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Val Met His Trp Val Arg Gln Ala Pro Gly Lys Gly Leu Glu Trp Val
        35                  40                  45

Ala Val Ile Ser His Glu Gly Ser Leu Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Arg Ile Ala Ala Arg Gly Gly Phe Tyr Trp Gly
                100                 105                 110

Gln Gly Thr Leu Val Thr Val Ser Ser
        115                 120
```

<210> SEQ ID NO 325
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 325

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ala Ile Asp Asp Asn
            20                  25                  30

Tyr Val Gln Trp Tyr Gln Gln Arg Pro Gly Ser Ser Pro Thr Thr Val
        35                  40                  45

Ile Tyr Glu Asp Phe Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Asp
                85                  90                  95

Asp Leu Gln Gly Val Val Phe Gly Gly Gly Thr Lys Leu Thr Val Leu
            100                 105                 110

<210> SEQ ID NO 326
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 326

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Val Met His Trp Val Arg Gln Ala Pro Gly Lys Gly Leu Glu Trp Val
        35                  40                  45

Ala Val Ile Ser His Glu Gly Ser Gly Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Arg Ile Ala Ala Arg Arg Gly Gly Phe Gly Ser Trp Gly
            100                 105                 110

Gln Gly Thr Leu Val Thr Val Ser Ser
        115                 120

<210> SEQ ID NO 327
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 327

Asn Phe Met Leu Thr Gln Pro His Ser Val Ser Glu Ser Pro Gly Lys
1               5                   10                  15

Thr Val Thr Ile Ser Cys Thr Arg Ser Ser Gly Asn Ile Asp Tyr Asn
            20                  25                  30

```
Tyr Val Gln Trp Tyr Gln Gln Arg Pro Gly Ser Ser Pro Thr Thr Val
            35                  40                  45

Ile Tyr Glu Asp Asn Val Arg Pro Ser Gly Val Pro Asp Arg Phe Ser
 50                  55                  60

Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                85                  90                  95

Asp Asn Gln Arg Val Val Phe Gly Gly Gly Thr Lys Leu Thr Val Leu
                100                 105                 110
```

<210> SEQ ID NO 328
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 328

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Arg Ser Tyr
                20                  25                  30

Val Met His Trp Val Arg Gln Ala Pro Gly Lys Gly Leu Glu Trp Val
            35                  40                  45

Ala Val Ile Ser His Glu Gly Ser Gly Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Pro Arg Ile Ala Ala Arg Arg Gly Gly Phe Gly Ser Trp Gly
                100                 105                 110

Gln Gly Thr Leu Val Thr Val Ser Ser
            115                 120
```

<210> SEQ ID NO 329
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 329

```
Asn Phe Met Leu Thr Gln Pro His Ser Val Ser Glu Ser Pro Gly Lys
 1               5                  10                  15

Thr Val Thr Ile Ser Cys Thr Arg Ser Ser Gly Asn Ile Asp Tyr Asn
                20                  25                  30

Tyr Val Gln Trp Tyr Gln Gln Arg Pro Gly Ser Ser Pro Thr Thr Val
            35                  40                  45

Ile Tyr Glu Asp Asn Val Arg Pro Ser Gly Val Pro Asp Arg Phe Ser
 50                  55                  60

Gly Ser Ile Asp Ser Ser Asn Ser Ala Ser Leu Thr Ile Ser Gly
 65                  70                  75                  80
```

```
Leu Lys Thr Glu Asp Glu Ala Asp Tyr Tyr Cys Gln Ser Tyr Asp Tyr
                85                  90                  95

Asp Asn Gln Ala Val Val Phe Gly Gly Gly Thr Lys Leu Thr Val Leu
            100                 105                 110

<210> SEQ ID NO 330
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 330

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
                20                  25                  30

Val Met His Trp Val Arg Gln Ala Pro Gly Lys Gly Leu Glu Trp Val
            35                  40                  45

Ala Val Ile Ser His Glu Gly Ser Gly Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Arg Ile Ala Ala Arg Gly Gly Phe Gly Ser Trp Gly
            100                 105                 110

Gln Gly Thr Leu Val Thr Val Ser Ser
            115                 120

<210> SEQ ID NO 331
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 331

Asn Phe Met Leu Thr Gln Pro His Ser Val Ser Glu Ser Pro Gly Lys
1               5                   10                  15

Thr Val Thr Ile Ser Cys Thr Arg Ser Ser Gly Asn Ile Asp Tyr Asn
                20                  25                  30

Tyr Val Gln Trp Tyr Gln Gln Arg Pro Gly Ser Pro Thr Thr Val
            35                  40                  45

Ile Tyr Glu Asp Asn Val Arg Pro Ser Gly Val Pro Asp Arg Phe Ser
        50                  55                  60

Gly Ser Ile Asp Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Tyr
                85                  90                  95

Asp Thr Gln Gly Val Val Phe Gly Gly Gly Thr Lys Leu Thr Val Leu
            100                 105                 110

<210> SEQ ID NO 332
<211> LENGTH: 121
<212> TYPE: PRT
```

<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 332

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Val Met His Trp Val Arg Gln Ala Pro Gly Lys Gly Leu Glu Trp Val
        35                  40                  45

Ala Val Ile Ser His Glu Gly Ser Gly Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Arg Ile Ala Ala Arg Arg Gly Gly Phe Gly Ser Trp Gly
            100                 105                 110

Gln Gly Thr Leu Val Thr Val Ser Ser
        115                 120

<210> SEQ ID NO 333
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 333

Asn Phe Met Leu Thr Gln Pro His Ser Val Ser Glu Ser Pro Gly Lys
1               5                   10                  15

Thr Val Thr Ile Ser Cys Thr Arg Ser Ser Gly Asn Ile Asp Tyr Asn
            20                  25                  30

Tyr Val Gln Trp Tyr Gln Gln Arg Pro Gly Ser Ser Pro Thr Thr Val
        35                  40                  45

Ile Tyr Glu Asp Asn Val Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Gly Tyr Asp Trp
                85                  90                  95

Asp Thr Gln Gly Val Val Phe Gly Gly Gly Thr Lys Leu Thr Val Leu
            100                 105                 110

<210> SEQ ID NO 334
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 334

Gln Val Gln Leu Val Glu Ser Gly Gly Gly Val Val Gln Pro Gly Arg
1               5                   10                  15

```
Ser Leu Arg Leu Ser Cys Ala Ala Ser Gly Phe Thr Phe Arg Ser Tyr
            20                  25                  30

Val Met His Trp Val Arg Gln Ala Pro Gly Lys Gly Leu Glu Trp Val
            35                  40                  45

Ala Val Ile Ser His Glu Gly Ser Gly Lys Tyr Tyr Ala Asp Ser Val
50                      55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Arg Ile Ala Ala Arg Arg Gly Gly Phe Gly Thr Trp Gly
            100                 105                 110

Gln Gly Thr Leu Val Thr Val Ser Ser
            115                 120

<210> SEQ ID NO 335
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 335

Asn Phe Met Leu Thr Gln Pro His Ser Val Ser Glu Ser Pro Gly Lys
1               5                   10                  15

Thr Val Thr Ile Ser Cys Thr Arg Ser Ser Gly Asn Ile Asp Tyr Asn
            20                  25                  30

Tyr Val Gln Trp Tyr Gln Gln Arg Pro Gly Ser Ser Pro Thr Thr Val
            35                  40                  45

Ile Tyr Glu Asp Asn Val Arg Pro Ser Gly Val Pro Asp Arg Phe Ser
            50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asp Asn Gln Arg Val Val Phe Gly Gly Gly Thr Lys Leu Thr Val Leu
            100                 105                 110

<210> SEQ ID NO 336
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 336

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Val Met His Trp Val Arg Gln Ala Pro Gly Lys Gly Leu Glu Trp Val
            35                  40                  45

Ala Val Ile Ser His Glu Gly Ser Gly Lys Tyr Tyr Ala Asp Ser Val
            50                  55                  60
```

-continued

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Arg Ile Ala Ala Arg Arg Gly Gly Phe Gly Thr Trp Gly
            100                 105                 110

Gln Gly Thr Leu Val Thr Val Ser Ser
            115                 120

<210> SEQ ID NO 337
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 337

Asn Phe Met Leu Thr Gln Pro His Ser Val Ser Glu Ser Pro Gly Lys
1               5                   10                  15

Thr Val Thr Ile Ser Cys Thr Arg Ser Ser Gly Asn Ile Asp Tyr Asn
            20                  25                  30

Tyr Val Gln Trp Tyr Gln Gln Arg Pro Gly Ser Ser Pro Thr Thr Val
        35                  40                  45

Ile Tyr Glu Asp Asn Val Arg Pro Ser Gly Val Pro Asp Arg Phe Ser
    50                  55                  60

Gly Ser Ile Asp Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Tyr
                85                  90                  95

Asp Asn Gln Ala Val Val Phe Gly Gly Gly Thr Lys Leu Thr Val Leu
            100                 105                 110

<210> SEQ ID NO 338
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 338

Gln Val Gln Leu Val Glu Ser Gly Gly Gly Val Gln Pro Gly Arg
1               5                   10                  15

Ser Leu Arg Leu Ser Cys Ala Ala Ser Gly Phe Thr Phe Arg Ser Tyr
            20                  25                  30

Val Met His Trp Val Arg Gln Ala Pro Gly Lys Gly Leu Glu Trp Val
        35                  40                  45

Ala Val Ile Ser His Glu Gly Ser Gly Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Arg Ile Ala Ala Arg Arg Gly Gly Phe Gly Thr Trp Gly
            100                 105                 110

Gln Gly Thr Leu Val Thr Val Ser Ser
            115                 120

```
                115                 120

<210> SEQ ID NO 339
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 339

Asn Phe Met Leu Thr Gln Pro His Ser Val Ser Glu Ser Pro Gly Lys
1               5                  10                  15

Thr Val Thr Ile Ser Cys Thr Arg Ser Ser Gly Asn Ile Asp Tyr Asn
            20                  25                  30

Tyr Val Gln Trp Tyr Gln Arg Pro Gly Ser Ser Pro Thr Thr Val
        35                  40                  45

Ile Tyr Glu Asp Asn Val Arg Pro Ser Gly Val Pro Asp Arg Phe Ser
    50                  55                  60

Gly Ser Ile Asp Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Tyr
                85                  90                  95

Asp Thr Gln Gly Val Val Phe Gly Gly Gly Thr Lys Leu Thr Val Leu
            100                 105                 110

<210> SEQ ID NO 340
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 340

Gln Val Gln Leu Val Glu Ser Gly Gly Val Val Gln Pro Gly Arg
1               5                  10                  15

Ser Leu Arg Leu Ser Cys Ala Ala Ser Gly Phe Thr Phe Arg Ser Tyr
            20                  25                  30

Val Met His Trp Val Arg Gln Ala Pro Gly Lys Gly Leu Glu Trp Val
        35                  40                  45

Ala Val Ile Ser His Glu Gly Ser Gly Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Arg Ile Ala Ala Arg Gly Gly Phe Gly Thr Trp Gly
            100                 105                 110

Gln Gly Thr Leu Val Thr Val Ser Ser
            115                 120

<210> SEQ ID NO 341
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 341

Asn Phe Met Leu Thr Gln Pro His Ser Val Ser Glu Ser Pro Gly Lys
1               5                   10                  15

Thr Val Thr Ile Ser Cys Thr Arg Ser Ser Gly Asn Ile Asp Tyr Asn
            20                  25                  30

Tyr Val Gln Trp Tyr Gln Gln Arg Pro Gly Ser Ser Pro Thr Thr Val
        35                  40                  45

Ile Tyr Glu Asp Asn Val Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Gly Tyr Asp Trp
                85                  90                  95

Asp Thr Gln Gly Val Val Phe Gly Gly Gly Thr Lys Leu Thr Val Leu
            100                 105                 110

<210> SEQ ID NO 342
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 342

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Val Met His Trp Val Arg Gln Ala Pro Gly Lys Gly Leu Glu Trp Val
        35                  40                  45

Ala Val Ile Ser His Glu Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Pro Arg Ile Ala Ala Arg Arg Gly Gly Phe Gly Ser Trp Gly
            100                 105                 110

Gln Gly Thr Leu Val Thr Val Ser Ser
            115                 120

<210> SEQ ID NO 343
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 343

Asn Phe Met Leu Thr Gln Pro His Ser Val Ser Glu Ser Pro Gly Lys
1               5                   10                  15

Thr Val Thr Ile Ser Cys Thr Arg Ser Ser Gly Asn Ile Asp Tyr Asn
            20                  25                  30

Tyr Val Gln Trp Tyr Gln Gln Arg Pro Gly Ser Ser Pro Thr Thr Val
             35                  40                  45

Ile Tyr Glu Asp Asn Val Arg Pro Ser Gly Val Pro Asp Arg Phe Ser
 50                  55                  60

Gly Ser Ile Asp Ser Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                 85                  90                  95

Asp Asn Gln Arg Val Val Phe Gly Gly Gly Thr Lys Leu Thr Val Leu
            100                 105                 110

<210> SEQ ID NO 344
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 344

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Arg Ser Tyr
             20                  25                  30

Val Met His Trp Val Arg Gln Ala Pro Gly Lys Gly Leu Glu Trp Val
             35                  40                  45

Ala Val Ile Ser His Gly Gly Ser Gly Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Leu Pro Arg Ile Ala Ala Arg Gly Gly Phe Gly Ser Trp Gly
            100                 105                 110

Gln Gly Thr Leu Val Thr Val Ser Ser
        115                 120

<210> SEQ ID NO 345
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 345

Asn Phe Met Leu Thr Gln Pro His Ser Val Ser Glu Ser Pro Gly Lys
1               5                   10                  15

Thr Val Thr Ile Ser Cys Thr Arg Ser Ser Gly Asn Ile Asp Tyr Asn
             20                  25                  30

Tyr Val Gln Trp Tyr Gln Gln Arg Pro Gly Ser Ser Pro Thr Thr Val
             35                  40                  45

Ile Tyr Glu Asp Asn Val Arg Pro Ser Gly Val Pro Asp Arg Phe Ser
 50                  55                  60

Gly Ser Ile Asp Ser Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Tyr

```
                85                  90                  95

Asp Asn Gln Ala Val Val Phe Gly Gly Gly Thr Lys Leu Thr Val Leu
            100                 105                 110

<210> SEQ ID NO 346
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 346

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Val Met His Trp Val Arg Gln Ala Pro Gly Lys Gly Leu Glu Trp Val
        35                  40                  45

Ala Val Ile Ser His Glu Gly Ser Gly Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Pro Arg Ile Ala Ala Arg Arg Gly Gly Phe Gly Ser Trp Gly
            100                 105                 110

Gln Gly Thr Leu Val Thr Val Ser Ser
        115                 120

<210> SEQ ID NO 347
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 347

Asn Phe Met Leu Thr Gln Pro His Ser Val Ser Glu Ser Pro Gly Lys
1               5                   10                  15

Thr Val Thr Ile Ser Cys Thr Arg Ser Ser Gly Asn Ile Asp Tyr Asn
            20                  25                  30

Tyr Val Gln Trp Tyr Gln Gln Arg Pro Gly Ser Ser Pro Thr Thr Val
        35                  40                  45

Ile Tyr Glu Asp Asn Val Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Tyr
                85                  90                  95

Asp Thr Gln Gly Val Val Phe Gly Gly Gly Thr Lys Leu Thr Val Leu
            100                 105                 110

<210> SEQ ID NO 348
<211> LENGTH: 121
<212> TYPE: PRT
<213> ORGANISM: Artificial Sequence
```

<220> FEATURE:
<221> NAME/KEY: source
<223> OTHER INFORMATION: /note="Description of Artificial Sequence:
      Synthetic polypeptide"

<400> SEQUENCE: 348

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Val Met His Trp Val Arg Gln Ala Pro Gly Lys Gly Leu Glu Trp Val
        35                  40                  45

Ala Val Ile Ser His Glu Gly Ser Gly Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Pro Arg Ile Ala Ala Arg Arg Gly Gly Phe Gly Ser Trp Gly
            100                 105                 110

Gln Gly Thr Leu Val Thr Val Ser Ser
            115                 120
```

<210> SEQ ID NO 349
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 349

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Asn Ile Asp Tyr Asn
            20                  25                  30

Tyr Val Gln Trp Tyr Gln Arg Pro Gly Ser Ser Pro Thr Thr Val
        35                  40                  45

Ile Tyr Glu Asp Asn Val Arg Pro Ser Gly Val Pro Asp Arg Phe Ser
    50                  55                  60

Gly Ser Ile Asp Ser Ser Asn Ser Ala Ser Leu Thr Ile Ser Gly
65                  70                  75                  80

Leu Lys Thr Glu Asp Glu Ala Asp Tyr Tyr Cys Gln Gly Tyr Asp Trp
                85                  90                  95

Asp Thr Gln Gly Val Val Phe Gly Gly Gly Thr Lys Leu Thr Val Leu
            100                 105                 110
```

<210> SEQ ID NO 350
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 350

```
Gln Val Gln Leu Val Glu Ser Gly Gly Gly Val Val Gln Pro Gly Arg
1               5                   10                  15
```

```
Ser Leu Arg Leu Ser Cys Ala Ala Ser Gly Phe Thr Phe Arg Ser Tyr
            20                  25                  30

Val Met His Trp Val Arg Gln Ala Pro Gly Lys Gly Leu Glu Trp Val
        35                  40                  45

Ala Val Ile Ser His Glu Gly Ser Gly Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Pro Arg Ile Ala Ala Arg Gly Gly Phe Gly Thr Trp Gly
                100                 105                 110

Gln Gly Thr Leu Val Thr Val Ser Ser
            115                 120
```

<210> SEQ ID NO 351
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 351

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Asn Ile Asp Tyr Asn
            20                  25                  30

Tyr Val Gln Trp Tyr Gln Gln Arg Pro Gly Ser Ser Pro Thr Thr Val
        35                  40                  45

Ile Tyr Glu Asp Asn Val Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asp Asn Gln Arg Val Val Phe Gly Gly Gly Thr Lys Leu Thr Val Leu
                100                 105                 110
```

<210> SEQ ID NO 352
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 352

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Val Met His Trp Val Arg Gln Ala Pro Gly Lys Gly Leu Glu Trp Val
        35                  40                  45

Ala Val Ile Ser His Glu Gly Ser Gly Lys Tyr Tyr Ala Asp Ser Val
    50                  55                  60

Lys Gly Arg Phe Thr Ile Ser Arg Asp Asn Ser Lys Asn Thr Leu Tyr
```

```
             65                  70                  75                  80

Leu Gln Met Asn Ser Leu Arg Ala Glu Asp Thr Ala Val Tyr Tyr Cys
                85                  90                  95

Ala Leu Pro Arg Ile Ala Ala Arg Arg Gly Gly Phe Gly Thr Trp Gly
               100                 105                 110

Gln Gly Thr Leu Val Thr Val Ser Ser
               115                 120

<210> SEQ ID NO 353
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 353

Asn Phe Met Leu Thr Gln Pro His Ser Val Ser Glu Ser Pro Gly Lys
1               5                  10                  15

Thr Val Thr Ile Ser Cys Thr Arg Ser Ser Gly Asn Ile Asp Tyr Asn
                20                  25                  30

Tyr Val Gln Trp Tyr Gln Gln Arg Pro Gly Ser Ser Pro Thr Thr Val
            35                  40                  45

Ile Tyr Glu Asp Asn Val Arg Pro Ser Gly Val Pro Asp Arg Phe Ser
50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Tyr
                85                  90                  95

Asp Asn Gln Ala Val Val Phe Gly Gly Gly Thr Lys Leu Thr Val Leu
               100                 105                 110

<210> SEQ ID NO 354
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 354

Gln Val Gln Leu Val Glu Ser Gly Gly Gly Val Val Gln Pro Gly Arg
1               5                  10                  15

Ser Leu Arg Leu Ser Cys Ala Ala Ser Gly Phe Thr Phe Arg Ser Tyr
                20                  25                  30

Val Met His Trp Val Arg Gln Ala Pro Gly Lys Gly Leu Glu Trp Val
            35                  40                  45

Ala Val Ile Ser His Glu Gly Ser Gly Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Pro Arg Ile Ala Ala Arg Arg Gly Gly Phe Gly Thr Trp Gly
               100                 105                 110

Gln Gly Thr Leu Val Thr Val Ser Ser
               115                 120
```

<210> SEQ ID NO 355
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 355

Asn Phe Met Leu Thr Gln Pro His Ser Val Ser Glu Ser Pro Gly Lys
1               5                   10                  15

Thr Val Thr Ile Ser Cys Thr Arg Ser Ser Gly Asn Ile Asp Tyr Asn
            20                  25                  30

Tyr Val Gln Trp Tyr Gln Gln Arg Pro Gly Ser Ser Pro Thr Thr Val
        35                  40                  45

Ile Tyr Glu Asp Asn Val Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Tyr
                85                  90                  95

Asp Thr Gln Gly Val Val Phe Gly Gly Gly Thr Lys Leu Thr Val Leu
            100                 105                 110

<210> SEQ ID NO 356
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 356

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Val Met His Trp Val Arg Gln Ala Pro Gly Lys Gly Leu Glu Trp Val
        35                  40                  45

Ala Val Ile Ser His Glu Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Pro Arg Ile Ala Ala Arg Arg Gly Gly Phe Gly Thr Trp Gly
            100                 105                 110

Gln Gly Thr Leu Val Thr Val Ser Ser
            115                 120

<210> SEQ ID NO 357
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 357

Asn Phe Met Leu Thr Gln Pro His Ser Val Ser Glu Ser Pro Gly Lys
1               5                   10                  15

Thr Val Thr Ile Ser Cys Thr Arg Ser Ser Gly Asn Ile Asp Tyr Asn
            20                  25                  30

Tyr Val Gln Trp Tyr Gln Gln Arg Pro Gly Ser Ser Pro Thr Thr Val
        35                  40                  45

Ile Tyr Glu Asp Asn Val Arg Pro Ser Gly Val Pro Asp Arg Phe Ser
    50                  55                  60

Gly Ser Ile Asp Ser Ser Asn Ser Ala Ser Leu Thr Ile Ser Gly
65                  70                  75                  80

Leu Lys Thr Glu Asp Glu Ala Asp Tyr Tyr Cys Gln Gly Tyr Asp Trp
                85                  90                  95

Asp Thr Gln Gly Val Val Phe Gly Gly Thr Lys Leu Thr Val Leu
            100                 105                 110

<210> SEQ ID NO 358
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 358

Gln Leu Gln Leu Gln Glu Ser Gly Pro Gly Leu Ala Lys Pro Ser Glu
1               5                   10                  15

Thr Leu Ser Leu Thr Cys Thr Val Ser Gly Gly Ser Ile Arg Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Ser Tyr Ser Ala Thr Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Ser Asp Pro Ser Tyr Asp Ser Ala Ala Gly Met Asp Val Trp
            100                 105                 110

Gly Gln Gly Thr Thr Val Thr Val Ser Ser
        115                 120

<210> SEQ ID NO 359
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 359

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Val Ile Ser Ser Tyr
            20                  25                  30

Leu Asn Trp Tyr Gln Gln Lys Pro Gly Lys Ala Pro Lys Leu Leu Ile

```
            35                  40                  45
Tyr Tyr Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Asp Trp Pro Phe
                 85                  90                  95

Thr Phe Gly Gly Gly Thr Lys Val Glu Ile Lys
            100                 105

<210> SEQ ID NO 360
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 360

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Ser Tyr Ser Ala Thr Thr Tyr Tyr Asn Pro Ser
 50                 55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Gly Asp Pro Ser Tyr Asp Ser Ile Ala Gly Met Gln Val Trp
            100                 105                 110

Gly Gln Gly Thr Thr Val Thr Val Ser Ser
        115                 120

<210> SEQ ID NO 361
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 361

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
 50                 55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Asp Trp Pro Leu
                85                  90                  95
```

Thr Phe Gly Gly Gly Thr Lys Val Glu Ile Lys
            100                 105

<210> SEQ ID NO 362
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 362

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Ser Tyr Ser Ala Thr Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Gly Asp Pro Ser Tyr Asp Ser Ile Ala Gly Met Gln Val Trp
            100                 105                 110

Gly Gln Gly Thr Thr Val Thr Val Ser Ser
        115                 120

<210> SEQ ID NO 363
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 363

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Tyr Tyr
            20                  25                  30

Leu Asn Trp Tyr Gln Gln Lys Pro Gly Lys Ala Pro Lys Leu Leu Ile
        35                  40                  45

Tyr Ser Ala Ser Arg Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Phe Asp Phe Pro Leu
                85                  90                  95

Thr Phe Gly Gly Gly Thr Lys Val Glu Ile Lys
            100                 105

<210> SEQ ID NO 364
<211> LENGTH: 503
<212> TYPE: PRT
<213> ORGANISM: Homo sapiens -continued

```
<400> SEQUENCE: 364

Glu Thr Asp Glu Cys Arg Leu Asn Gln Asn Ile Cys Gly His Gly Glu
1               5                   10                  15

Cys Val Pro Gly Pro Pro Asp Tyr Ser Cys His Cys Asn Pro Gly Tyr
            20                  25                  30

Arg Ser His Pro Gln His Arg Tyr Cys Val Asp Val Asn Glu Cys Glu
        35                  40                  45

Ala Glu Pro Cys Gly Pro Gly Arg Gly Ile Cys Met Asn Thr Gly Gly
    50                  55                  60

Ser Tyr Asn Cys His Cys Asn Arg Gly Tyr Arg Leu His Val Gly Ala
65                  70                  75                  80

Gly Gly Arg Ser Cys Val Asp Leu Asn Glu Cys Ala Lys Pro His Leu
                85                  90                  95

Cys Gly Asp Gly Gly Phe Cys Ile Asn Phe Pro Gly His Tyr Lys Cys
            100                 105                 110

Asn Cys Tyr Pro Gly Tyr Arg Leu Lys Ala Ser Arg Pro Pro Val Cys
        115                 120                 125

Glu Asp Ile Asp Glu Cys Arg Asp Pro Ser Ser Cys Pro Asp Gly Lys
    130                 135                 140

Cys Glu Asn Lys Pro Gly Ser Phe Lys Cys Ile Ala Cys Gln Pro Gly
145                 150                 155                 160

Tyr Arg Ser Gln Gly Gly Gly Ala Cys Arg Asp Val Asn Glu Cys Ala
                165                 170                 175

Glu Gly Ser Pro Cys Ser Pro Gly Trp Cys Glu Asn Leu Pro Gly Ser
            180                 185                 190

Phe Arg Cys Thr Cys Ala Gln Gly Tyr Ala Pro Ala Pro Asp Gly Arg
        195                 200                 205

Ser Cys Leu Asp Val Asp Glu Cys Glu Ala Gly Asp Val Cys Asp Asn
    210                 215                 220

Gly Ile Cys Ser Asn Thr Pro Gly Ser Phe Gln Cys Gln Cys Leu Ser
225                 230                 235                 240

Gly Tyr His Leu Ser Arg Asp Arg Ser His Cys Glu Asp Ile Asp Glu
                245                 250                 255

Cys Asp Phe Pro Ala Ala Cys Ile Gly Gly Asp Cys Ile Asn Thr Asn
            260                 265                 270

Gly Ser Tyr Arg Cys Leu Cys Pro Gln Gly His Arg Leu Val Gly Gly
        275                 280                 285

Arg Lys Cys Gln Asp Ile Asp Glu Cys Ser Gln Asp Pro Ser Leu Cys
    290                 295                 300

Leu Pro His Gly Ala Cys Lys Asn Leu Gln Gly Ser Tyr Val Cys Val
305                 310                 315                 320

Cys Asp Glu Gly Phe Thr Pro Thr Gln Asp Gln His Gly Cys Glu Glu
                325                 330                 335

Val Glu Gln Pro His His Lys Lys Glu Cys Tyr Leu Asn Phe Asp Asp
            340                 345                 350

Thr Val Phe Cys Asp Ser Val Leu Ala Thr Asn Val Thr Gln Gln Glu
        355                 360                 365

Cys Cys Cys Ser Leu Gly Ala Gly Trp Gly Asp His Cys Glu Ile Tyr
    370                 375                 380

Pro Cys Pro Val Tyr Ser Ser Ala Glu Phe His Ser Leu Cys Pro Asp
385                 390                 395                 400

Gly Lys Gly Tyr Thr Gln Asp Asn Asn Ile Val Asn Tyr Gly Ile Pro
                405                 410                 415
```

```
Ala His Arg Asp Ile Asp Glu Cys Met Leu Phe Gly Ser Glu Ile Cys
            420                 425                 430

Lys Glu Gly Lys Cys Val Asn Thr Gln Pro Gly Tyr Glu Cys Tyr Cys
            435                 440                 445

Lys Gln Gly Phe Tyr Tyr Asp Gly Asn Leu Leu Glu Cys Val Asp Val
            450                 455                 460

Asp Glu Cys Leu Asp Glu Ser Asn Cys Arg Asn Gly Val Cys Glu Asn
465                 470                 475                 480

Thr Arg Gly Gly Tyr Arg Cys Ala Cys Thr Pro Pro Ala Glu Tyr Ser
                485                 490                 495

Pro Ala Gln Arg Gln Cys Leu
            500

<210> SEQ ID NO 365
<211> LENGTH: 503
<212> TYPE: PRT
<213> ORGANISM: Mus sp.

<400> SEQUENCE: 365

Glu Thr Asp Glu Cys Arg Leu Asn Gln Asn Ile Cys Gly His Gly Gln
1               5                   10                  15

Cys Val Pro Gly Pro Ser Asp Tyr Ser Cys His Cys Asn Ala Gly Tyr
            20                  25                  30

Arg Ser His Pro Gln His Arg Tyr Cys Val Asp Val Asn Glu Cys Glu
            35                  40                  45

Ala Glu Pro Cys Gly Pro Gly Lys Gly Ile Cys Met Asn Thr Gly Gly
        50                  55                  60

Ser Tyr Asn Cys His Cys Asn Arg Gly Tyr Arg Leu His Val Gly Ala
65                  70                  75                  80

Gly Gly Arg Ser Cys Val Asp Leu Asn Glu Cys Thr Lys Pro His Leu
                85                  90                  95

Cys Gly Asp Gly Gly Phe Cys Ile Asn Phe Pro Gly His Tyr Lys Cys
            100                 105                 110

Asn Cys Tyr Pro Gly Tyr Arg Leu Lys Ala Ser Arg Pro Pro Ile Cys
            115                 120                 125

Glu Asp Ile Asp Glu Cys Arg Asp Pro Ser Thr Cys Pro Asp Gly Lys
        130                 135                 140

Cys Glu Asn Lys Pro Gly Ser Phe Lys Cys Ile Ala Cys Gln Pro Gly
145                 150                 155                 160

Tyr Arg Ser Gln Gly Gly Gly Ala Cys Arg Asp Val Asn Glu Cys Ser
                165                 170                 175

Glu Gly Thr Pro Cys Ser Pro Gly Trp Cys Glu Asn Leu Pro Gly Ser
            180                 185                 190

Tyr Arg Cys Thr Cys Ala Gln Gly Tyr Glu Pro Ala Gln Asp Gly Leu
            195                 200                 205

Ser Cys Ile Asp Val Asp Glu Cys Glu Ala Gly Lys Val Cys Gln Asp
        210                 215                 220

Gly Ile Cys Thr Asn Thr Pro Gly Ser Phe Gln Cys Gln Cys Leu Ser
225                 230                 235                 240

Gly Tyr His Leu Ser Arg Asp Arg Ser Arg Cys Glu Asp Ile Asp Glu
                245                 250                 255

Cys Asp Phe Pro Ala Ala Cys Ile Gly Gly Asp Cys Ile Asn Thr Asn
            260                 265                 270

Gly Ser Tyr Arg Cys Leu Cys Pro Gln Gly His Arg Leu Val Gly Gly
```

```
                275                 280                 285
Arg Lys Cys Gln Asp Ile Asp Glu Cys Ser Gln Asp Pro Gly Leu Cys
    290                 295                 300

Leu Pro His Gly Ala Cys Glu Asn Leu Gln Gly Ser Tyr Val Cys Val
305                 310                 315                 320

Cys Asp Glu Gly Phe Thr Leu Thr Gln Asp Gln His Gly Cys Glu Glu
                325                 330                 335

Val Glu Gln Pro His His Lys Lys Glu Cys Tyr Leu Asn Phe Asp Asp
            340                 345                 350

Thr Val Phe Cys Asp Ser Val Leu Ala Thr Asn Val Thr Gln Gln Glu
        355                 360                 365

Cys Cys Cys Ser Leu Gly Ala Gly Trp Gly Asp His Cys Glu Ile Tyr
    370                 375                 380

Pro Cys Pro Val Tyr Ser Ser Ala Glu Phe His Ser Leu Cys Pro Asp
385                 390                 395                 400

Gly Lys Gly Tyr Thr Gln Asp Asn Asn Ile Val Asn Tyr Gly Ile Pro
                405                 410                 415

Ala His Arg Asp Ile Asp Glu Cys Ile Leu Phe Gly Ala Glu Ile Cys
            420                 425                 430

Lys Glu Gly Lys Cys Val Asn Thr Gln Pro Gly Tyr Glu Cys Tyr Cys
        435                 440                 445

Lys Gln Gly Phe Tyr Tyr Asp Gly Asn Leu Leu Glu Cys Val Asp Val
    450                 455                 460

Asp Glu Cys Leu Asp Glu Ser Asn Cys Arg Asn Gly Val Cys Glu Asn
465                 470                 475                 480

Thr Arg Gly Gly Tyr Arg Cys Ala Cys Thr Pro Pro Ala Glu Tyr Ser
                485                 490                 495

Pro Ala Gln Arg Gln Cys Leu
            500

<210> SEQ ID NO 366
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (8)..(8)
<223> OTHER INFORMATION: /replace="Gly"
<220> FEATURE:
<221> NAME/KEY: SITE
<222> LOCATION: (1)..(17)
<223> OTHER INFORMATION: /note="Variant residues given in the sequence
      have no preference with respect to those in the annotations
      for variant positions"

<400> SEQUENCE: 366

Val Ile Ser His Glu Gly Ser Leu Lys Tyr Tyr Ala Asp Ser Val Lys
1               5                   10                  15

Gly

<210> SEQ ID NO 367
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
```

```
        Synthetic peptide"
<220> FEATURE:
<221> NAME/KEY: VARIANT
<222> LOCATION: (2)..(2)
<223> OTHER INFORMATION: /replace="Arg" or "Leu"
<220> FEATURE:
<221> NAME/KEY: VARIANT
<222> LOCATION: (14)..(14)
<223> OTHER INFORMATION: /replace="Ser" or "Thr"
<220> FEATURE:
<221> NAME/KEY: SITE
<222> LOCATION: (1)..(14)
<223> OTHER INFORMATION: /note="Variant residues given in the sequence
      have no preference with respect to those in the annotations
      for variant positions"

<400> SEQUENCE: 367

Ala Val Pro Arg Ile Ala Ala Arg Arg Gly Gly Phe Gly Tyr
1               5                   10

<210> SEQ ID NO 368
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (4)..(4)
<223> OTHER INFORMATION: /replace="His"
<220> FEATURE:
<221> NAME/KEY: VARIANT
<222> LOCATION: (6)..(6)
<223> OTHER INFORMATION: /replace="Leu" or "Ser" or "Ala"
<220> FEATURE:
<221> NAME/KEY: VARIANT
<222> LOCATION: (9)..(9)
<223> OTHER INFORMATION: /replace="Asp" or "Tyr"
<220> FEATURE:
<221> NAME/KEY: SITE
<222> LOCATION: (1)..(13)
<223> OTHER INFORMATION: /note="Variant residues given in the sequence
      have no preference with respect to those in the annotations
      for variant positions"

<400> SEQUENCE: 368

Thr Arg Ser Ser Gly Asn Ile Asp Asn Asn Tyr Val Gln
1               5                   10

<210> SEQ ID NO 369
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(3)
<223> OTHER INFORMATION: /replace="Phe" or "Ala"
<220> FEATURE:
<221> NAME/KEY: VARIANT
<222> LOCATION: (4)..(4)
<223> OTHER INFORMATION: /replace="Ile" or "Val"
<220> FEATURE:
<221> NAME/KEY: SITE
<222> LOCATION: (1)..(7)
<223> OTHER INFORMATION: /note="Variant residues given in the sequence
      have no preference with respect to those in the annotations
      for variant positions"

<400> SEQUENCE: 369
```

```
Glu Asp Asn Gln Arg Pro Ser
1               5

<210> SEQ ID NO 370
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Gly"
<220> FEATURE:
<221> NAME/KEY: VARIANT
<222> LOCATION: (5)..(5)
<223> OTHER INFORMATION: /replace="Phe" or "Tyr" or "Asp" or "His" or
      "Trp"
<220> FEATURE:
<221> NAME/KEY: VARIANT
<222> LOCATION: (6)..(6)
<223> OTHER INFORMATION: /replace="Asp" or "Ser"
<220> FEATURE:
<221> NAME/KEY: VARIANT
<222> LOCATION: (7)..(7)
<223> OTHER INFORMATION: /replace="Ala" or "Leu" or "Glu" or "Thr"
<220> FEATURE:
<221> NAME/KEY: VARIANT
<222> LOCATION: (9)..(9)
<223> OTHER INFORMATION: /replace="Arg" or "Ala" or "Leu"
<220> FEATURE:
<221> NAME/KEY: SITE
<222> LOCATION: (1)..(11)
<223> OTHER INFORMATION: /note="Variant residues given in the sequence
      have no preference with respect to those in the annotations
      for variant positions"

<400> SEQUENCE: 370

Gln Ser Tyr Asp Ser Asn Asn Gln Gly Val Val
1               5                   10

<210> SEQ ID NO 371
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Gly"
<220> FEATURE:
<221> NAME/KEY: VARIANT
<222> LOCATION: (9)..(9)
<223> OTHER INFORMATION: /replace="Ile"
<220> FEATURE:
<221> NAME/KEY: VARIANT
<222> LOCATION: (13)..(13)
<223> OTHER INFORMATION: /replace="Gln"
<220> FEATURE:
<221> NAME/KEY: SITE
<222> LOCATION: (1)..(14)
<223> OTHER INFORMATION: /note="Variant residues given in the sequence
      have no preference with respect to those in the annotations
      for variant positions"

<400> SEQUENCE: 371

Ala Ser Asp Pro Ser Tyr Asp Ser Ala Ala Gly Met Asp Val
1               5                   10
```

```
<210> SEQ ID NO 372
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: Any amino acid, and optionally Lys or Gln
<220> FEATURE:
<221> NAME/KEY: MOD_RES
<222> LOCATION: (5)..(5)
<223> OTHER INFORMATION: Any amino acid, and optionally Val or Ser
<220> FEATURE:
<221> NAME/KEY: MOD_RES
<222> LOCATION: (8)..(8)
<223> OTHER INFORMATION: Any amino acid, and optionally Ser or Tyr

<400> SEQUENCE: 372

Arg Ala Ser Xaa Xaa Ile Ser Xaa Tyr Leu Asn
1               5                   10

<210> SEQ ID NO 373
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Any amino acid, and optionally Tyr, Ala or Ser
<220> FEATURE:
<221> NAME/KEY: MOD_RES
<222> LOCATION: (4)..(4)
<223> OTHER INFORMATION: Any amino acid, and optionally Ser or Asn
<220> FEATURE:
<221> NAME/KEY: MOD_RES
<222> LOCATION: (5)..(5)
<223> OTHER INFORMATION: Any amino acid, and optionally Leu or Arg

<400> SEQUENCE: 373

Xaa Ala Ser Xaa Xaa Gln Ser
1               5

<210> SEQ ID NO 374
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any amino acid, and optionally Ser or Gly
<220> FEATURE:
<221> NAME/KEY: MOD_RES
<222> LOCATION: (4)..(4)
<223> OTHER INFORMATION: Any amino acid, and optionally Phe or Asn
<220> FEATURE:
<221> NAME/KEY: MOD_RES
<222> LOCATION: (6)..(6)
<223> OTHER INFORMATION: Any amino acid, and optionally Trp or Phe
<220> FEATURE:
<221> NAME/KEY: MOD_RES
<222> LOCATION: (8)..(8)
<223> OTHER INFORMATION: Any amino acid, and optionally Phe or Leu
```

```
<400> SEQUENCE: 374

Gln Gln Xaa Xaa Asp Xaa Pro Xaa Thr
1               5

<210> SEQ ID NO 375
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: Any amino acid, and optionally Ser or Arg
<220> FEATURE:
<221> NAME/KEY: MOD_RES
<222> LOCATION: (5)..(5)
<223> OTHER INFORMATION: Any amino acid, and optionally Gly or Ser

<400> SEQUENCE: 375

Phe Thr Phe Xaa Xaa Tyr Val Met His
1               5

<210> SEQ ID NO 376
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Any amino acid, and optionally Val or Ser
<220> FEATURE:
<221> NAME/KEY: MOD_RES
<222> LOCATION: (7)..(7)
<223> OTHER INFORMATION: Any amino acid, and optionally Ser or Gly
<220> FEATURE:
<221> NAME/KEY: MOD_RES
<222> LOCATION: (8)..(8)
<223> OTHER INFORMATION: Any amino acid, and optionally Phe or Leu

<400> SEQUENCE: 376

Xaa Ile Ser His Glu Gly Xaa Xaa Lys Tyr Tyr Ala Asp Ser Val Lys
1               5                   10                  15

Gly

<210> SEQ ID NO 377
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Any amino acid, and optionally Ala or Val
<220> FEATURE:
<221> NAME/KEY: MOD_RES
<222> LOCATION: (2)..(2)
<223> OTHER INFORMATION: Any amino acid, and optionally Arg, Val, Gly or
      Lys
<220> FEATURE:
<221> NAME/KEY: MOD_RES
<222> LOCATION: (4)..(4)
```

```
<223> OTHER INFORMATION: Any amino acid, and optionally Arg, His or Leu
<220> FEATURE:
<221> NAME/KEY: MOD_RES
<222> LOCATION: (5)..(5)
<223> OTHER INFORMATION: Any amino acid, and optionally Ile, Val or Gly
<220> FEATURE:
<221> NAME/KEY: MOD_RES
<222> LOCATION: (6)..(6)
<223> OTHER INFORMATION: Any amino acid, and optionally Ala, Ser or Leu
<220> FEATURE:
<221> NAME/KEY: MOD_RES
<222> LOCATION: (7)..(7)
<223> OTHER INFORMATION: Any amino acid, and optionally Ala or Val
<220> FEATURE:
<221> NAME/KEY: MOD_RES
<222> LOCATION: (12)..(12)
<223> OTHER INFORMATION: Any amino acid, and optionally Phe or Tyr
<220> FEATURE:
<221> NAME/KEY: MOD_RES
<222> LOCATION: (13)..(13)
<223> OTHER INFORMATION: Any amino acid, and optionally Asp, Gly, Arg or
      Ser
<220> FEATURE:
<221> NAME/KEY: MOD_RES
<222> LOCATION: (14)..(14)
<223> OTHER INFORMATION: Any amino acid, and optionally Tyr, Gly, Arg,
      Leu, Val, Ala or Lys

<400> SEQUENCE: 377

Xaa Xaa Pro Xaa Xaa Xaa Xaa Arg Arg Gly Gly Xaa Xaa Xaa
1               5                   10

<210> SEQ ID NO 378
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Any amino acid, and optionally Ser or Pro
<220> FEATURE:
<221> NAME/KEY: MOD_RES
<222> LOCATION: (4)..(4)
<223> OTHER INFORMATION: Any amino acid, and optionally Ser, His or Arg
<220> FEATURE:
<221> NAME/KEY: MOD_RES
<222> LOCATION: (6)..(6)
<223> OTHER INFORMATION: Any amino acid, and optionally Ser or Gly
<220> FEATURE:
<221> NAME/KEY: MOD_RES
<222> LOCATION: (11)..(11)
<223> OTHER INFORMATION: Any amino acid, and optionally Gly, Ile, Asn or
      Val

<400> SEQUENCE: 378

Gly Xaa Ile Xaa Ser Xaa Ser Tyr Tyr Trp Xaa
1               5                   10

<210> SEQ ID NO 379
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: Any amino acid, and optionally Ser or Thr
```

<400> SEQUENCE: 379

Ser Ile Ser Tyr Ser Ala Xaa Thr Tyr Tyr Asn Pro Ser Leu Lys Ser
1               5                   10                  15

<210> SEQ ID NO 380
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Any amino acid, and optionally Ala or Val
<220> FEATURE:
<221> NAME/KEY: MOD_RES
<222> LOCATION: (2)..(2)
<223> OTHER INFORMATION: Any amino acid, and optionally Arg, Ser or Gly
<220> FEATURE:
<221> NAME/KEY: MOD_RES
<222> LOCATION: (4)..(4)
<223> OTHER INFORMATION: Any amino acid, and optionally Pro, Tyr, Arg,
      Val, Ile, His, Thr or Glu
<220> FEATURE:
<221> NAME/KEY: MOD_RES
<222> LOCATION: (5)..(5)
<223> OTHER INFORMATION: Any amino acid, and optionally Ser, Asp, Glu or
      Asn
<220> FEATURE:
<221> NAME/KEY: MOD_RES
<222> LOCATION: (7)..(7)
<223> OTHER INFORMATION: Any amino acid, and optionally Asp, Ala or Thr
<220> FEATURE:
<221> NAME/KEY: MOD_RES
<222> LOCATION: (8)..(8)
<223> OTHER INFORMATION: Any amino acid, and optionally Ser, Gly, Thr or
      Ala
<220> FEATURE:
<221> NAME/KEY: MOD_RES
<222> LOCATION: (9)..(9)
<223> OTHER INFORMATION: Any amino acid, and optionally Ile, Ala, Arg,
      Gln or Val
<220> FEATURE:
<221> NAME/KEY: MOD_RES
<222> LOCATION: (10)..(10)
<223> OTHER INFORMATION: Any amino acid, and optionally Ala, Glu, Lys,
      Gly or Thr
<220> FEATURE:
<221> NAME/KEY: MOD_RES
<222> LOCATION: (12)..(12)
<223> OTHER INFORMATION: Any amino acid, and optionally Met or Ile
<220> FEATURE:
<221> NAME/KEY: MOD_RES
<222> LOCATION: (13)..(13)
<223> OTHER INFORMATION: Any amino acid, and optionally Asp, Leu, Gln,
      Val, Asn or Gly
<220> FEATURE:
<221> NAME/KEY: MOD_RES
<222> LOCATION: (14)..(14)
<223> OTHER INFORMATION: Any amino acid, and optionally Val, Arg, Asn,
      Glu or Lys

<400> SEQUENCE: 380

Xaa Xaa Asp Xaa Xaa Tyr Xaa Xaa Xaa Xaa Gly Xaa Xaa Xaa
1               5                   10

<210> SEQ ID NO 381
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:

```
            Synthetic peptide"
<220> FEATURE:
<221> NAME/KEY: MOD_RES
<222> LOCATION: (6)..(6)
<223> OTHER INFORMATION: Any amino acid, and optionally Gly or Ala
<220> FEATURE:
<221> NAME/KEY: MOD_RES
<222> LOCATION: (7)..(7)
<223> OTHER INFORMATION: Any amino acid, and optionally Ser or Thr

<400> SEQUENCE: 381

Ser Ile Ser Tyr Ser Xaa Xaa Thr Tyr Tyr
1               5                   10

<210> SEQ ID NO 382
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Ser"
<220> FEATURE:
<221> NAME/KEY: VARIANT
<222> LOCATION: (8)..(8)
<223> OTHER INFORMATION: /replace="Leu"
<220> FEATURE:
<221> NAME/KEY: SITE
<222> LOCATION: (1)..(17)
<223> OTHER INFORMATION: /note="Variant residues given in the sequence
      have no preference with respect to those in the annotations
      for variant positions"

<400> SEQUENCE: 382

Val Ile Ser His Glu Gly Ser Phe Lys Tyr Tyr Ala Asp Ser Val Lys
1               5                   10                  15

Gly

<210> SEQ ID NO 383
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Val"
<220> FEATURE:
<221> NAME/KEY: VARIANT
<222> LOCATION: (6)..(6)
<223> OTHER INFORMATION: /replace="Leu"
<220> FEATURE:
<221> NAME/KEY: SITE
<222> LOCATION: (1)..(14)
<223> OTHER INFORMATION: /note="Variant residues given in the sequence
      have no preference with respect to those in the annotations
      for variant positions"

<400> SEQUENCE: 383

Ala Arg Pro Arg Ile Ala Ala Arg Arg Gly Gly Phe Gly Tyr
1               5                   10

<210> SEQ ID NO 384
<211> LENGTH: 11
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Pro"
<220> FEATURE:
<221> NAME/KEY: VARIANT
<222> LOCATION: (4)..(4)
<223> OTHER INFORMATION: /replace="Arg"
<220> FEATURE:
<221> NAME/KEY: VARIANT
<222> LOCATION: (11)..(11)
<223> OTHER INFORMATION: /replace="Ile" or "Asn"
<220> FEATURE:
<221> NAME/KEY: SITE
<222> LOCATION: (1)..(11)
<223> OTHER INFORMATION: /note="Variant residues given in the sequence
      have no preference with respect to those in the annotations
      for variant positions"

<400> SEQUENCE: 384

Gly Ser Ile His Ser Ser Ser Tyr Tyr Trp Gly
1               5                   10

<210> SEQ ID NO 385
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Ser" or "Gly"
<220> FEATURE:
<221> NAME/KEY: VARIANT
<222> LOCATION: (4)..(4)
<223> OTHER INFORMATION: /replace="Val"
<220> FEATURE:
<221> NAME/KEY: VARIANT
<222> LOCATION: (8)..(8)
<223> OTHER INFORMATION: /replace="Ala"
<220> FEATURE:
<221> NAME/KEY: VARIANT
<222> LOCATION: (9)..(9)
<223> OTHER INFORMATION: /replace="Arg" or "Ile" or "Val"
<220> FEATURE:
<221> NAME/KEY: VARIANT
<222> LOCATION: (13)..(13)
<223> OTHER INFORMATION: /replace="Gln" or "Gly"
<220> FEATURE:
<221> NAME/KEY: VARIANT
<222> LOCATION: (14)..(14)
<223> OTHER INFORMATION: /replace="Arg"
<220> FEATURE:
<221> NAME/KEY: SITE
<222> LOCATION: (1)..(14)
<223> OTHER INFORMATION: /note="Variant residues given in the sequence
      have no preference with respect to those in the annotations
      for variant positions"

<400> SEQUENCE: 385

Ala Arg Asp Pro Ser Tyr Asp Ser Ala Ala Gly Met Asp Val
1               5                   10

<210> SEQ ID NO 386
<211> LENGTH: 11
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (4)..(4)
<223> OTHER INFORMATION: /replace="His" or "Arg"
<220> FEATURE:
<221> NAME/KEY: VARIANT
<222> LOCATION: (6)..(6)
<223> OTHER INFORMATION: /replace="Gly"
<220> FEATURE:
<221> NAME/KEY: VARIANT
<222> LOCATION: (11)..(11)
<223> OTHER INFORMATION: /replace="Ile" or "Asn" or "Val"
<220> FEATURE:
<221> NAME/KEY: SITE
<222> LOCATION: (1)..(11)
<223> OTHER INFORMATION: /note="Variant residues given in the sequence
      have no preference with respect to those in the annotations
      for variant positions"

<400> SEQUENCE: 386

Gly Ser Ile Ser Ser Ser Ser Tyr Tyr Trp Gly
1               5                   10

<210> SEQ ID NO 387
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Ser" or "Gly"
<220> FEATURE:
<221> NAME/KEY: VARIANT
<222> LOCATION: (9)..(9)
<223> OTHER INFORMATION: /replace="Ile"
<220> FEATURE:
<221> NAME/KEY: VARIANT
<222> LOCATION: (13)..(13)
<223> OTHER INFORMATION: /replace="Gln"
<220> FEATURE:
<221> NAME/KEY: SITE
<222> LOCATION: (1)..(14)
<223> OTHER INFORMATION: /note="Variant residues given in the sequence
      have no preference with respect to those in the annotations
      for variant positions"

<400> SEQUENCE: 387

Ala Arg Asp Pro Ser Tyr Asp Ser Ala Ala Gly Met Asp Val
1               5                   10

<210> SEQ ID NO 388
<211> LENGTH: 6
<212> TYPE: PRT
<213> ORGANISM: Unknown
<220> FEATURE:
<221> NAME/KEY: source
<223> OTHER INFORMATION: /note="Description of Unknown:
      TGFbeta1 sequence"

<400> SEQUENCE: 388

Leu Ser Lys Leu Arg Leu
1               5

<210> SEQ ID NO 389
<211> LENGTH: 11
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (4)..(4)
<223> OTHER INFORMATION: /replace="Gln"
<220> FEATURE:
<221> NAME/KEY: VARIANT
<222> LOCATION: (5)..(5)
<223> OTHER INFORMATION: /replace="Ser"
<220> FEATURE:
<221> NAME/KEY: VARIANT
<222> LOCATION: (8)..(8)
<223> OTHER INFORMATION: /replace="Tyr"
<220> FEATURE:
<221> NAME/KEY: SITE
<222> LOCATION: (1)..(11)
<223> OTHER INFORMATION: /note="Variant residues given in the sequence
      have no preference with respect to those in the annotations
      for variant positions"

<400> SEQUENCE: 389

Arg Ala Ser Lys Val Ile Ser Ser Tyr Leu Asn
1               5                   10

<210> SEQ ID NO 390
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Ala" or "Ser"
<220> FEATURE:
<221> NAME/KEY: VARIANT
<222> LOCATION: (4)..(4)
<223> OTHER INFORMATION: /replace="Asn"
<220> FEATURE:
<221> NAME/KEY: VARIANT
<222> LOCATION: (5)..(5)
<223> OTHER INFORMATION: /replace="Arg"
<220> FEATURE:
<221> NAME/KEY: SITE
<222> LOCATION: (1)..(7)
<223> OTHER INFORMATION: /note="Variant residues given in the sequence
      have no preference with respect to those in the annotations
      for variant positions"

<400> SEQUENCE: 390

Tyr Ala Ser Ser Leu Gln Ser
1               5

<210> SEQ ID NO 391
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(3)
<223> OTHER INFORMATION: /replace="Gly"
<220> FEATURE:
<221> NAME/KEY: VARIANT
<222> LOCATION: (4)..(4)
```

```
<223> OTHER INFORMATION: /replace="Asn"
<220> FEATURE:
<221> NAME/KEY: VARIANT
<222> LOCATION: (6)..(6)
<223> OTHER INFORMATION: /replace="Phe"
<220> FEATURE:
<221> NAME/KEY: VARIANT
<222> LOCATION: (8)..(8)
<223> OTHER INFORMATION: /replace="Leu"
<220> FEATURE:
<221> NAME/KEY: SITE
<222> LOCATION: (1)..(9)
<223> OTHER INFORMATION: /note="Variant residues given in the sequence
      have no preference with respect to those in the annotations
      for variant positions"

<400> SEQUENCE: 391

Gln Gln Ser Phe Asp Trp Pro Phe Thr
1               5

<210> SEQ ID NO 392
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (4)..(4)
<223> OTHER INFORMATION: /replace="Arg"
<220> FEATURE:
<221> NAME/KEY: VARIANT
<222> LOCATION: (5)..(5)
<223> OTHER INFORMATION: /replace="Ser"
<220> FEATURE:
<221> NAME/KEY: SITE
<222> LOCATION: (1)..(9)
<223> OTHER INFORMATION: /note="Variant residues given in the sequence
      have no preference with respect to those in the annotations
      for variant positions"

<400> SEQUENCE: 392

Phe Thr Phe Ser Gly Tyr Val Met His
1               5

<210> SEQ ID NO 393
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Ser"
<220> FEATURE:
<221> NAME/KEY: VARIANT
<222> LOCATION: (7)..(7)
<223> OTHER INFORMATION: /replace="Gly"
<220> FEATURE:
<221> NAME/KEY: VARIANT
<222> LOCATION: (8)..(8)
<223> OTHER INFORMATION: /replace="Leu"
<220> FEATURE:
<221> NAME/KEY: SITE
<222> LOCATION: (1)..(17)
<223> OTHER INFORMATION: /note="Variant residues given in the sequence
      have no preference with respect to those in the annotations
      for variant positions"

<400> SEQUENCE: 393
```

```
Val Ile Ser His Glu Gly Ser Phe Lys Tyr Tyr Ala Asp Ser Val Lys
1               5                   10                  15

Gly

<210> SEQ ID NO 394
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Val"
<220> FEATURE:
<221> NAME/KEY: VARIANT
<222> LOCATION: (2)..(2)
<223> OTHER INFORMATION: /replace="Val" or "Gly" or "Lys"
<220> FEATURE:
<221> NAME/KEY: VARIANT
<222> LOCATION: (4)..(4)
<223> OTHER INFORMATION: /replace="His" or "Leu"
<220> FEATURE:
<221> NAME/KEY: VARIANT
<222> LOCATION: (5)..(5)
<223> OTHER INFORMATION: /replace="Val" or "Gly"
<220> FEATURE:
<221> NAME/KEY: VARIANT
<222> LOCATION: (6)..(6)
<223> OTHER INFORMATION: /replace="Ser" or "Leu"
<220> FEATURE:
<221> NAME/KEY: VARIANT
<222> LOCATION: (7)..(7)
<223> OTHER INFORMATION: /replace="Val"
<220> FEATURE:
<221> NAME/KEY: VARIANT
<222> LOCATION: (12)..(12)
<223> OTHER INFORMATION: /replace="Tyr"
<220> FEATURE:
<221> NAME/KEY: VARIANT
<222> LOCATION: (13)..(13)
<223> OTHER INFORMATION: /replace="Gly" or "Arg" or "Ser"
<220> FEATURE:
<221> NAME/KEY: VARIANT
<222> LOCATION: (14)..(14)
<223> OTHER INFORMATION: /replace="Gly" or "Arg" or "Leu" or "Val" or
      "Ala" or "Lys"
<220> FEATURE:
<221> NAME/KEY: SITE
<222> LOCATION: (1)..(14)
<223> OTHER INFORMATION: /note="Variant residues given in the sequence
      have no preference with respect to those in the annotations
      for variant positions"

<400> SEQUENCE: 394

Ala Arg Pro Arg Ile Ala Ala Arg Arg Gly Gly Phe Asp Tyr
1               5                   10

<210> SEQ ID NO 395
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Pro"
<220> FEATURE:
<221> NAME/KEY: VARIANT
```

```
<222> LOCATION: (4)..(4)
<223> OTHER INFORMATION: /replace="His" or "Arg"
<220> FEATURE:
<221> NAME/KEY: VARIANT
<222> LOCATION: (6)..(6)
<223> OTHER INFORMATION: /replace="Gly"
<220> FEATURE:
<221> NAME/KEY: VARIANT
<222> LOCATION: (11)..(11)
<223> OTHER INFORMATION: /replace="Ile" or "Asn" or "Val"
<220> FEATURE:
<221> NAME/KEY: SITE
<222> LOCATION: (1)..(11)
<223> OTHER INFORMATION: /note="Variant residues given in the sequence
      have no preference with respect to those in the annotations
      for variant positions"

<400> SEQUENCE: 395

Gly Ser Ile Ser Ser Ser Ser Tyr Tyr Trp Gly
1               5                   10

<210> SEQ ID NO 396
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (7)..(7)
<223> OTHER INFORMATION: /replace="Thr"
<220> FEATURE:
<221> NAME/KEY: SITE
<222> LOCATION: (1)..(16)
<223> OTHER INFORMATION: /note="Variant residues given in the sequence
      have no preference with respect to those in the annotations
      for variant positions"

<400> SEQUENCE: 396

Ser Ile Ser Tyr Ser Ala Ser Thr Tyr Tyr Asn Pro Ser Leu Lys Ser
1               5                   10                  15

<210> SEQ ID NO 397
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Val"
<220> FEATURE:
<221> NAME/KEY: VARIANT
<222> LOCATION: (2)..(2)
<223> OTHER INFORMATION: /replace="Ser" or "Gly"
<220> FEATURE:
<221> NAME/KEY: VARIANT
<222> LOCATION: (4)..(4)
<223> OTHER INFORMATION: /replace="Tyr" or "Arg" or "Val" or "Ile" or
      "His" or "Thr" or "Glu"
<220> FEATURE:
<221> NAME/KEY: VARIANT
<222> LOCATION: (5)..(5)
<223> OTHER INFORMATION: /replace="Asp" or "Glu" or "Asn"
<220> FEATURE:
<221> NAME/KEY: VARIANT
<222> LOCATION: (7)..(7)
<223> OTHER INFORMATION: /replace="Ala" or "Thr"
<220> FEATURE:
<221> NAME/KEY: VARIANT
```

```
<222> LOCATION: (8)..(8)
<223> OTHER INFORMATION: /replace="Gly" or "Thr" or "Ala"
<220> FEATURE:
<221> NAME/KEY: VARIANT
<222> LOCATION: (9)..(9)
<223> OTHER INFORMATION: /replace="Ala" or "Arg" or "Gln" or "Val"
<220> FEATURE:
<221> NAME/KEY: VARIANT
<222> LOCATION: (10)..(10)
<223> OTHER INFORMATION: /replace="Glu" or "Lys" or "Gly" or "Thr"
<220> FEATURE:
<221> NAME/KEY: VARIANT
<222> LOCATION: (12)..(12)
<223> OTHER INFORMATION: /replace="Ile"
<220> FEATURE:
<221> NAME/KEY: VARIANT
<222> LOCATION: (13)..(13)
<223> OTHER INFORMATION: /replace="Leu" or "Gln" or "Val" or "Asn" or
      "Gly"
<220> FEATURE:
<221> NAME/KEY: VARIANT
<222> LOCATION: (14)..(14)
<223> OTHER INFORMATION: /replace="Arg" or "Asn" or "Glu" or "Lys"
<220> FEATURE:
<221> NAME/KEY: SITE
<222> LOCATION: (1)..(14)
<223> OTHER INFORMATION: /note="Variant residues given in the sequence
      have no preference with respect to those in the annotations
      for variant positions"

<400> SEQUENCE: 397

Ala Arg Asp Pro Ser Tyr Asp Ser Ile Ala Gly Met Asp Val
1               5                   10

<210> SEQ ID NO 398
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (6)..(6)
<223> OTHER INFORMATION: /replace="Ala"
<220> FEATURE:
<221> NAME/KEY: VARIANT
<222> LOCATION: (7)..(7)
<223> OTHER INFORMATION: /replace="Thr"
<220> FEATURE:
<221> NAME/KEY: SITE
<222> LOCATION: (1)..(10)
<223> OTHER INFORMATION: /note="Variant residues given in the sequence
      have no preference with respect to those in the annotations
      for variant positions"

<400> SEQUENCE: 398

Ser Ile Ser Tyr Ser Gly Ser Thr Tyr Tyr
1               5                   10

<210> SEQ ID NO 399
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Ala"
<220> FEATURE:
<221> NAME/KEY: VARIANT
```

```
<222> LOCATION: (4)..(4)
<223> OTHER INFORMATION: /replace="Ala" or "Tyr" or "Asp" or "Ser" or
      "Arg" or "His"
<220> FEATURE:
<221> NAME/KEY: VARIANT
<222> LOCATION: (5)..(5)
<223> OTHER INFORMATION: /replace="Gln" or "Ser" or "Gly" or "Lys" or
      "Glu" or "Arg" or "His"
<220> FEATURE:
<221> NAME/KEY: VARIANT
<222> LOCATION: (6)..(6)
<223> OTHER INFORMATION: /replace="Arg"
<220> FEATURE:
<221> NAME/KEY: VARIANT
<222> LOCATION: (7)..(7)
<223> OTHER INFORMATION: /replace="Gly" or "Ala" or "Leu" or "Ser" or
      "Asn" or "Val" or "Asp" or "Gln"
<220> FEATURE:
<221> NAME/KEY: VARIANT
<222> LOCATION: (8)..(8)
<223> OTHER INFORMATION: /replace="Met" or "Leu"
<220> FEATURE:
<221> NAME/KEY: VARIANT
<222> LOCATION: (9)..(9)
<223> OTHER INFORMATION: /replace="Phe" or "Tyr" or "Asn" or "Ser"
<220> FEATURE:
<221> NAME/KEY: SITE
<222> LOCATION: (1)..(9)
<223> OTHER INFORMATION: /note="Variant residues given in the sequence
      have no preference with respect to those in the annotations
      for variant positions"

<400> SEQUENCE: 399

Phe Thr Phe Asn Asn Tyr Pro Ile His
1               5

<210> SEQ ID NO 400
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (4)..(4)
<223> OTHER INFORMATION: /replace="His"
<220> FEATURE:
<221> NAME/KEY: VARIANT
<222> LOCATION: (7)..(7)
<223> OTHER INFORMATION: /replace="Ala" or "Gly"
<220> FEATURE:
<221> NAME/KEY: VARIANT
<222> LOCATION: (11)..(11)
<223> OTHER INFORMATION: /replace="Thr" or "Ser" or "His" or "Leu" or
      "Ile" or "Asn" or "Val" or "Ala"
<220> FEATURE:
<221> NAME/KEY: SITE
<222> LOCATION: (1)..(11)
<223> OTHER INFORMATION: /note="Variant residues given in the sequence
      have no preference with respect to those in the annotations
      for variant positions"

<400> SEQUENCE: 400

Gly Ser Ile Ser Ser Ser Ser Tyr Tyr Trp Gly
1               5                   10

<210> SEQ ID NO 401
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
```

```
                 Synthetic peptide"
<220> FEATURE:
<221> NAME/KEY: VARIANT
<222> LOCATION: (3)..(3)
<223> OTHER INFORMATION: /replace="Ala"
<220> FEATURE:
<221> NAME/KEY: VARIANT
<222> LOCATION: (6)..(6)
<223> OTHER INFORMATION: /replace="Ala" or "Ser"
<220> FEATURE:
<221> NAME/KEY: VARIANT
<222> LOCATION: (7)..(7)
<223> OTHER INFORMATION: /replace="Thr"
<220> FEATURE:
<221> NAME/KEY: SITE
<222> LOCATION: (1)..(10)
<223> OTHER INFORMATION: /note="Variant residues given in the sequence
      have no preference with respect to those in the annotations
      for variant positions"

<400> SEQUENCE: 401

Ser Ile Ser Tyr Ser Gly Ser Thr Tyr Tyr
1               5                   10
```